United States Patent
Kabakibi et al.

(10) Patent No.: US 11,504,367 B2
(45) Date of Patent: Nov. 22, 2022

(54) COMPOUNDS AND METHODS FOR TREATING OXALATE-RELATED DISEASES

(71) Applicant: OxaluRx, Inc., St. Louis, MO (US)

(72) Inventors: Ayman Kabakibi, San Diego, CA (US); Mehmet Kahraman, La Jolla, CA (US); Michael Clare, Skokie, IL (US); Thomas Leedom, Escondido, CA (US)

(73) Assignee: OxaluRx, Inc., St. Louis, MO (US)

( * ) Notice: Subject to any disclaimer, the term of this patent is extended or adjusted under 35 U.S.C. 154(b) by 0 days.

(21) Appl. No.: 17/000,301

(22) Filed: Aug. 22, 2020

(65) Prior Publication Data

US 2021/0052586 A1 Feb. 25, 2021

Related U.S. Application Data

(60) Provisional application No. 62/890,378, filed on Aug. 22, 2019.

(51) Int. Cl.
| | | |
|---|---|---|
| *A61K 31/506* | (2006.01) | |
| *C07D 249/04* | (2006.01) | |
| *C07D 405/12* | (2006.01) | |
| *A61K 31/4192* | (2006.01) | |
| *C07D 401/12* | (2006.01) | |
| *C07D 401/14* | (2006.01) | |
| *A61K 31/4439* | (2006.01) | |
| *A61K 31/501* | (2006.01) | |
| *A61K 31/497* | (2006.01) | |
| *C07D 405/14* | (2006.01) | |
| *A61K 31/454* | (2006.01) | |

(52) U.S. Cl.
CPC ........ *A61K 31/506* (2013.01); *A61K 31/4192* (2013.01); *A61K 31/4439* (2013.01); *A61K 31/454* (2013.01); *A61K 31/497* (2013.01); *A61K 31/501* (2013.01); *C07D 249/04* (2013.01); *C07D 401/12* (2013.01); *C07D 401/14* (2013.01); *C07D 405/12* (2013.01); *C07D 405/14* (2013.01)

(58) Field of Classification Search
CPC .................................................. A61K 31/506
See application file for complete search history.

(56) References Cited

U.S. PATENT DOCUMENTS

| | | |
|---|---|---|
| 4,248,879 A | 2/1981 | Buckle |
| 2006/0160794 A1 | 7/2006 | Amegadzie |
| 2020/0390778 A1 | 12/2020 | Keller |

FOREIGN PATENT DOCUMENTS

| | | |
|---|---|---|
| WO | 2017100266 | 6/2017 |
| WO | 2017100268 | 6/2017 |
| WO | 2019133770 | 7/2019 |
| WO | 2019133813 | 7/2019 |
| WO | 2019165159 | 8/2019 |
| WO | 2020257487 | 12/2020 |
| WO | 2021035196 | 2/2021 |

OTHER PUBLICATIONS

Cox, J. et al., "Discovery of CHK-336: A First-in-Class, Liver-Targeted, Small Molecule Inhibitor of Lactate Dehydrogenase for the Treatment of Primary Hyperoxaluria", Chinook Therapeutics presentation, 9 pages, (2020).
International Application No. PCT/US2019/019070; International Preliminary Report on Patentability, dated Sep. 3, 2020; 8 pages.
International Application No. PCT/US2019/019070; International Search Report and Written Opinion of the International Searching Authority, dated Jun. 27, 2019; 11 pages.
International Application No. PCT/US2020/047548; International Search Report and Written Opinion of the International Searching Authority, dated Nov. 24, 2020; 8 pages.
OXLUMO™ (Lumasiran) Product Label, Highlights of Prescribing Information, Manufactured for Alnylam Pharmaceuticals, Inc., 10 pages, (revised Nov. 2020).
U.S. Appl. No. 16/971,825; Notice of Allowance, dated Mar. 15, 2022; 22 pages.
International Application No. PCT/US2020/047548; International Preliminary Report on Patentability, dated Mar. 3, 2022; 6 pages.

*Primary Examiner* — Yong S. Chong
(74) *Attorney, Agent, or Firm* — Dennis A. Bennett; Cynthia Hathaway; C A Schlect

(57) ABSTRACT

Disclosed herein are compounds and compositions for modulating glycolate oxidase, useful for treating oxalate-related diseases, such as hyperoxaluria, where modulating glycolate oxidase is expected to be therapeutic to a patent in need thereof. Methods of modulating glycolate oxidase activity in a human or animal subject are also provided.

25 Claims, 6 Drawing Sheets

COMPOUNDS AND METHODS FOR TREATING OXALATE-RELATED DISEASES

This application claims the benefit of priority of U.S. Provisional Patent Application Ser. No. 62/890,378 filed Aug. 22, 2019, the disclosure of which is incorporated by reference in its entirety for all purposes.

The present disclosure relates to new compounds and compositions and their application as pharmaceuticals for treating disease. Methods of treating oxalate-related diseases, including hyperoxaluria and related conditions, in a human or animal subject, are also provided.

Oxalate-related diseases are characterized by oxalate accumulation or dysregulation of glyoxylate metabolism in the subject. Hyperoxaluria is an oxalate-related disease characterized by elevated urinary excretion of oxalate. Primary and secondary hyperoxaluria are two distinct clinical manifestations of hyperoxaluria. Primary hyperoxaluria is an inherited error of metabolism due to mutations in at least one of several different hepatic enzymes involved in glyoxylate and hydroxyproline (HYP) metabolism. Oxalate is endogenously generated by a pathway in which human glycolate oxidase (GO or hGOX) oxidizes glycolate to glyoxylate. Then glyoxylate is subsequently converted to oxalate by lactate dehydrogenase (LDH). Mutations in hepatic enzymes involved in these related metabolic pathways result in excess oxalate being formed and excreted through the kidneys.

In contrast, secondary hyperoxaluria is caused by increased dietary ingestion or absorption of oxalate, precursors of oxalate, or alteration in intestinal microflora. Dietary oxalate comes from spinach, bran, rhubarb, beets, potatoes, nuts, nut butter, and other foods. As urinary oxalate levels increase in hyperoxaluria, insoluble crystals of calcium oxalate begin to form in the urinary tract and deposit in the renal tubules causing kidney function to decline. The disease spectrum of hyperoxaluria extends from recurrent kidney stones (nephrolithiasis), nephrocalcinosis, and urinary tract infections to chronic kidney disease and eventually end-stage renal disease. When calcium oxalate burden exceeds the renal excretory capacity, calcium oxalate also deposits in various organ systems via systemic oxalosis.

Increased urinary oxalate levels help establish an initial diagnosis for hyperoxaluria, while elevated plasma oxalate levels are likely to be more indicative of when patients develop chronic kidney disease. A definitive diagnosis of primary hyperoxaluria is best achieved by genetic analysis, and if genetic studies prove inconclusive, liver biopsy is undertaken to establish the diagnosis. Diagnostic clues pointing towards secondary hyperoxaluria are a supportive dietary history and tests to detect increased intestinal absorption of oxalate.

Conservative treatment for both types of hyperoxaluria includes vigorous hydration and administration of crystallization inhibitors to decrease calcium oxalate precipitation. Pyridoxine is also found to help about 30% of patients with primary hyperoxaluria type 1. The onset of the disease can occur at any point from infancy through adulthood and is typically fatal with early onset in the absence of an organ transplant. Liver-kidney and isolated kidney transplantation are the treating choice in primary hyperoxaluria type 1 and type 2, respectively. Data are scarce on the role of transplantation in primary hyperoxaluria type 3.

Currently, there are no broadly effective treatment options for primary hyperoxaluria. More and better options are needed, for example, compounds that inhibit glycolate oxidase, thus reducing the concentration of glyoxylate available for conversion to oxalate. Early treatment to inhibit GO (often referred to as "substrate depletion therapy") would decrease urinary oxalate concentrations before organ function is compromised.

Accordingly, disclosed herein are new compositions and methods for targeting glycolate oxidase inhibition and treating hyperoxaluria.

DETAILED DESCRIPTION

Figure 1:
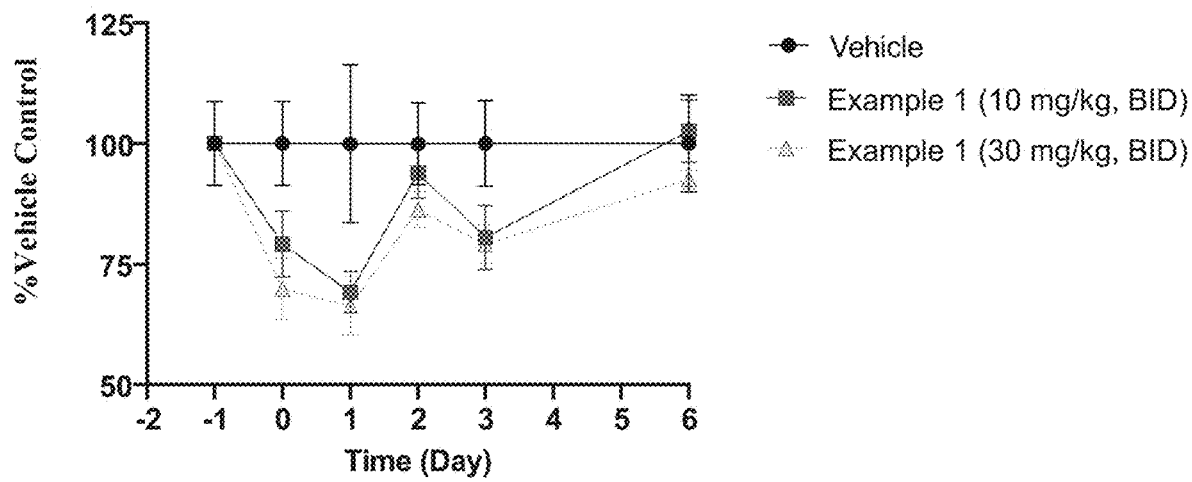
FIG. 1 shows urine oxalate as a percentage of the vehicle-treated control group over time in days for compound 1 dosed at 10 and 30 mg/kg in the alanine-glyoxylate aminotransferase knockout (Agxt−/−) mouse model of primary hyperoxaluria 1 (PH-1).

Novel compounds and pharmaceutical compositions, certain of which have been found to treat oxalate-related diseases, including all types of hyperoxaluria, have been discovered, together with methods of synthesizing and using the compounds, including methods for treating hyperoxaluria in a patient by administering the compounds.

Certain compounds disclosed herein possess useful glycolate oxidase inhibitory activity and may be used to treat or in the prophylaxis of oxalate-related diseases. Thus, in a broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating glycolate oxidase. Other embodiments provide methods for treating an oxalate-related disease in a patient in need of such treatment, comprising administering to the patient a therapeutically effective amount of a compound or composition as disclosed herein. Also provided is the use of certain compounds disclosed herein for use in manufacturing a medicament for treating a disease or condition ameliorated by modulating glycolate oxidase.

Provided herein are the following specific embodiments:

Embodiment 1: A compound of structural Formula I

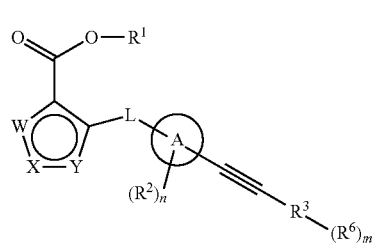

(I)

Embodiment 3: The compound of Embodiment 2, wherein W is N, X is N, and Y is NH.

Embodiment 4: The compound of any one of Embodiments 1 to 3, wherein each $R^2$ is independently chosen from 5-10-membered heteroaryl, $C_1$-$C_6$ alkoxy, $C_1$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, $C_6$-$C_{10}$ aryl, cyano, and halogen;

Embodiment 5: The compound of any one of Embodiments 1 to 4, wherein $R^3$ is chosen from 3-10-membered heterocycloalkyl, 5-10-membered heteroaryl, $C_1$-$C_6$ alkyl, $C_1$-$C_6$ sulfonyl, $C_3$-$C_6$ cycloalkyl, $C_3$-$C_6$ cycloalkylalkyl, $C_6$-$C_{10}$ aryl, and $C_6$-$C_{10}$ arylalkyl.

Embodiment 6: A compound of Embodiment 1, having structural Formula II

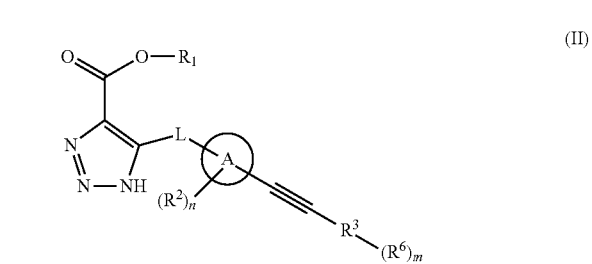

(II)

or a salt, polymorph, or tautomer thereof, wherein:
W is chosen from N, NH, S, O), and $CCH_3$;
X is chosen from NH, S, O), and CH;
Y is N or NH;
$R^1$ is chosen from hydrogen, $C_1$-$C_6$ alkyl, $C_1$-$C_6$ haloalkyl, and $C_1$-$C_6$ cycloalkyl;
L is chosen from O, S, $CH_2$, NH, $NR^4$, S(O), $SO_2$, and $CR^4$=$CR^5$;
A is chosen from monocyclic or bicyclic aryl, and monocyclic or bicyclic heteroaryl;
each $R^2$ is independently chosen from $C_6$-$C_{10}$ aryl, 5-10-membered heteroaryl, $C_1$-$C_6$ alkoxy, $C_1$-$C_6$ alkyl, $C_3$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, cyano, and halogen;
n is 0, 1, or 2;
$R^3$ is chosen from 3-10-membered heterocycloalkyl, 5-10-membered heteroaryl, $C_6$-$C_{10}$ aryl, $C_1$-$C_6$ alkyl, $C_1$-$C_6$ sulfonyl, $C_3$-$C_6$ cycloalkyl, 3-10-membered heterocycloalkylalkyl, 5-10-membered heteroarylalkyl, $C_6$-$C_{10}$ arylalkyl, and $C_3$-$C_6$ cycloalkylalkyl;
$R^4$ and $R^5$ are each independently chosen from hydrogen and $C_1$-$C_6$ alkyl, or $R^4$ and $R^5$, together with the atoms to which they are attached, form a cycloalkenyl; and
each $R^6$ is independently chosen from 4-6-membered heterocycloalkyl, 5-10-membered heteroaryl, amino, $C_1$-$C_6$ alkoxy, $C_1$-$C_6$ alkyl, $C_1$-$C_6$ alkylsulfonyl, $C_1$-$C_6$ haloalkyl, $C_3$-$C_6$ cycloalkyl, $C_3$-$C_6$ cycloalkylalkyl, carboxyl, cyano, halogen, hydroxyl, methyl-4-6-membered heterocycloalkyl, and phenyl; and
m is 0, 1, 2, or 3.

Embodiment 2: The compound of Embodiment 1, wherein:
W is N, X is N, and Y is NH;
W is $CCH_3$, X is NH, and Y is N;
W is $CCH_3$, X is O and Y is N;
W is N, X is O, and Y is N; or
W is N, X is CH and Y is NH.

or a salt, polymorph, or tautomer thereof, wherein:
$R^1$ is chosen from hydrogen, $C_1$-$C_6$ alkyl, and $C_1$-$C_6$ cycloalkyl;
L is chosen from O, S, $CH_2$, NH, $NR^4$, S(O), $SO_2$, and $CR^4$=$CR^5$;
A is chosen from monocyclic or bicyclic aryl, and monocyclic or bicyclic heteroaryl;
each $R^2$ is independently chosen from 5-10-membered heteroaryl, $C_1$-$C_6$ alkoxy, $C_1$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, $C_6$-$C_{10}$ aryl, cyano, and halogen;
n is 0, 1, or 2;
$R^3$ is chosen from 3-10-membered heterocycloalkyl, 5-10-membered heteroaryl, $C_1$-$C_6$ alkyl, $C_1$-$C_6$ sulfonyl, $C_3$-$C_6$ cycloalkyl, $C_3$-$C_6$ cycloalkylalkyl, $C_6$-$C_{10}$ aryl, and $C_6$-$C_{10}$ arylalkyl;
$R^4$ and $R^5$ are each independently chosen from hydrogen and $C_1$-$C_6$ alkyl, or $R^4$ and $R^5$, together with the atoms to which they are attached, form a cycloalkenyl; and
each $R^6$ is independently chosen from 4-6-membered heterocycloalkyl, 5-10-membered heteroaryl, amino, $C_1$-$C_6$ alkoxy, $C_1$-$C_6$ alkyl, $C_1$-$C_6$ alkylsulfonyl, $C_1$-$C_6$ haloalkyl, $C_3$-$C_6$ cycloalkyl, $C_3$-$C_6$ cycloalkylalkyl, carboxyl, cyano, halogen, hydroxyl, methyl-4-6-membered heterocycloalkyl, and phenyl; and
m is 0, 1, 2, or 3.

Embodiment 7: The compound of any one of Embodiments 1 to 6, wherein A is chosen from indazolyl, indolyl, naphthalenyl, oxazolyl, oxodihydropyridinyl, phenyl, pyridazinyl, pyridinyl, and thiazolyl.

Embodiment 8: The compound of any one of Embodiments 1 to 6, wherein A is monocyclic aryl.

Embodiment 9: The compound of Embodiment 8, wherein A is phenyl.

Embodiment 10: A compound of Embodiment 6, having structural Formula III,

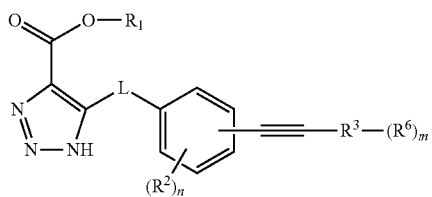

or a salt, polymorph, or tautomer thereof, wherein:

$R^1$ is chosen from hydrogen, $C_1$-$C_6$ alkyl, and $C_1$-$C_6$ cycloalkyl;

L is chosen from O, S, $CH_2$, NH, $NR^4$, S(O), $SO_2$, and $CR^4$=$CR^5$;

each $R^2$ is independently chosen from 5-10-membered heteroaryl, $C_1$-$C_6$ alkoxy, $C_1$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, $C_6$-$C_{10}$ aryl, cyano, and halogen;

n is 0, 1, or 2;

$R^3$ is chosen from 3-10-membered heterocycloalkyl, 5-10-membered heteroaryl, $C_1$-$C_6$ alkyl, $C_1$-$C_6$ sulfonyl, $C_3$-$C_6$ cycloalkyl, $C_3$-$C_6$ cycloalkylalkyl, $C_6$-$C_{10}$ aryl, and $C_6$-$C_{10}$ arylalkyl;

$R^4$ and $R^5$ are each independently chosen from hydrogen and $C_1$-$C_6$ alkyl, or $R^4$ and $R^5$, together with the atoms to which they are attached, form a cycloalkenyl; and each $R^6$ is independently chosen from 4-6-membered heterocycloalkyl, 5-10-membered heteroaryl, amino, $C_1$-$C_6$ alkoxy, $C_1$-$C_6$ alkyl, $C_1$-$C_6$ alkylsulfonyl, $C_1$-$C_6$ haloalkyl, $C_3$-$C_6$ cycloalkyl, $C_3$-$C_6$ cycloalkylalkyl, carboxyl, cyano, halogen, hydroxyl, methyl-4-6-membered heterocycloalkyl, and phenyl; and m is 0, 1, 2, or 3.

Embodiment 11: The compound of any one of Embodiments 1 to 10, wherein $R^3$ is chosen from methyl, propyl, cyclopropyl, cyclobutyl, cyclopentyl, tetrahydrofuranyl, cyclohexyl, tetrahydropyranyl, piperidinyl, dihydropyranyl, indazolyl, benzodioxolyl, phenyl, pyridinyl, pyrimidinyl, pyridazinyl, pyrazolyl, oxazolyl, thiazolyl, imidazolyl, triazolyl, benzoxazolyl, oxodihydropyridinyl, thiazolyl, tetrazolyl, cyclopropylmethyl, cyclobutylmethyl, cyclopentylmethyl, cyclohexylmethyl, benzyl, dioxaspirodecanyl, oxocyclohexyl, and bicyclo[1.1.1]pentyl, any of which is optionally substituted with 1, 2, or 3 $R^6$ groups.

Embodiment 12: The compound of any one of Embodiments 1 to 10, wherein $R^3$ is chosen from $C_1$-$C_6$ alkyl, $C_3$-$C_6$ cycloalkyl, and $C_3$-$C_6$ cycloalkylalkyl, any of which is optionally substituted with 1, 2, or 3 $R^6$ groups.

Embodiment 13: The compound of any one of Embodiments 1 to 10, wherein $R^3$ is chosen from propyl and cyclopropylmethyl.

Embodiment 14: The compound of any one of Embodiments 1 to 13, wherein $R^6$ is chosen from methyl, hydroxyl, amino, dimethylamino, propyl, cyclopropylmethyl, indazolyl, benzodioxolyl, cyclopropyl, tetrahydrofuranyl, cyclohexyl, tetrahydropyranyl, piperidinyl, methylpiperidinyl, phenyl, fluoro, chloro, methylsulfonyl, cyano, trifluoromethyl, methoxy, carboxyl, and fluoromethyl.

Embodiment 15: The compound of Embodiment 14, wherein $R^6$ is chosen from chloro, methyl, cyano, fluoro, methylsulfonyl, methoxy, carboxyl, trifluoromethyl.

Embodiment 16: The compound of any one of Embodiments 1 to 15, wherein m is 0.

Embodiment 17: A compound of Embodiment 4, having structural Formula IV,

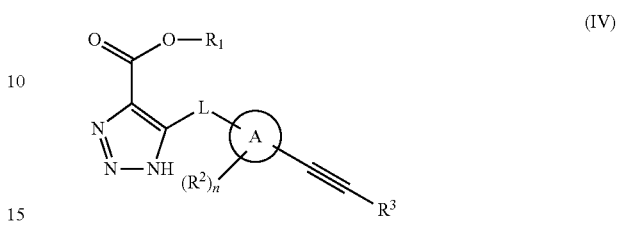

or a salt, polymorph, or tautomer thereof, wherein:

$R^1$ is chosen from hydrogen, $C_1$-$C_6$ alkyl, and $C_1$-$C_6$ cycloalkyl;

L is chosen from O, S, $CH_2$, NH, $NR^4$, S(O), $SO_2$, and $CR^4$=$CR^5$;

A is chosen from monocyclic or bicyclic aryl, and monocyclic or bicyclic heteroaryl;

each $R^2$ is independently chosen from 5-10-membered heteroaryl, $C_1$-$C_6$ alkoxy, $C_1$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, $C_6$-$C_{10}$ aryl, cyano, and halogen;

n is 0, 1, or 2;

$R^3$ is chosen from $C_1$-$C_6$ alkyl, $C_3$-$C_6$ cycloalkyl, and $C_3$-$C_6$ cycloalkylalkyl; and $R^4$ and $R^5$ are each independently chosen from hydrogen and $C_1$-$C_6$ alkyl, or $R^4$ and $R^5$, together with the atoms to which they are attached, form a cycloalkenyl.

Embodiment 18: The compound of any one of Embodiments 1 to 17, wherein L is chosen from O, S, $CH_2$, and NH.

Embodiment 19: The compound of Embodiment 18, wherein L is O or S.

Embodiment 20: The compound of any one of Embodiments 15 to 19, wherein A is chosen from indazolyl, indolyl, naphthalenyl, oxazolyl, oxodihydropyridinyl, phenyl, pyridazinyl, pyridinyl, and thiazolyl.

Embodiment 21: The compound of Embodiment 20, wherein A is monocyclic aryl.

Embodiment 22: The compound of Embodiment 21, wherein A is phenyl.

Embodiment 23: The compound of any one of Embodiments 1 to 22, wherein each $R^2$ is independently chosen from fluoro, chloro, methyl, methoxy, trifluoromethyl, methylthio, methylsulfonyl, trifluoromethoxy, trifluoroethoxy, phenyl, and pyrazolyl.

Embodiment 24: The compound of Embodiment 23, wherein each $R^2$ is independently chosen from fluoro, chloro, methyl, trifluoromethyl, methylsulfonyl, and methoxy.

Embodiment 25: The compound of any one of Embodiments 1 to 24, wherein n is 0.

Embodiment 26: The compound of any one of Embodiments 17 to 25, wherein $R^3$ is chosen from isobutyl and cyclopropylmethyl.

Embodiment 27: A compound of Embodiment 10, having structural Formula V,

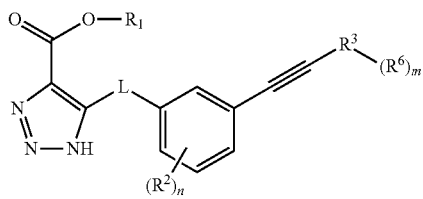

or a salt, polymorph, or tautomer thereof, wherein:
$R^1$ is chosen from hydrogen, $C_1$-$C_6$ alkyl, and $C_1$-$C_6$ cycloalkyl;
L is chosen from O and S;
each $R^2$ is independently chosen from 5-10-membered heteroaryl, $C_1$-$C_6$ alkoxy, $C_1$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, $C_6$-$C_{10}$ aryl, cyano, and halogen;
n is 0, 1, or 2;
$R^3$ is chosen from $C_2$-$C_6$ alkyl, $C_3$-$C_6$ cycloalkyl, and $C_3$-$C_6$ cycloalkylalkyl;
and
each $R^6$ is $C_1$-$C_6$ alkoxy, $C_1$-$C_6$ alkyl, $C_1$-$C_6$ haloalkyl, $C_3$-$C_6$ cycloalkyl, cyano, halogen, and hydroxyl; and
m is 0, 1, 2, or 3.

Embodiment 28: The compound of Embodiment 27, wherein $R^1$ is hydrogen.

Embodiment 29: The compound of Embodiment 27 or 28, wherein n is 0.

Embodiment 30: The compound of any one of Embodiments 27-29, wherein n is 0 or 1; and $R^6$, if present, is halogen.

Embodiment 31: The compound of any one of Embodiments 27-30, wherein $R^3$ is chosen from $C_2$-$C_6$ alkyl, $C_3$-$C_6$ cycloalkyl, and $C_3$-$C_6$ cycloalkylmethyl.

Embodiment 32: The compound of any of Embodiments 27-31, wherein $R^3$ is chosen from ethyl, propyl, isopropyl, isobutyl, sec-butyl, tert-butyl, cyclopropyl, cyclobutyl, cyclopentyl, cyclohexyl, bicyclo[1.1.1]pentyl, cyclopropylmethyl, cyclobutylmethyl, cyclopentylmethyl, cyclohexylmethyl, and bicyclo[1.1.1]pentylmethyl.

Embodiment 33: The compound of any of Embodiments 27-31, wherein $R^3$ is chosen from ethyl, propyl, isopropyl, isobutyl, sec-butyl, tert-butyl, cyclopropyl, cyclobutyl, cyclopentyl, cyclohexyl, cyclopropylmethyl, cyclobutylmethyl, cyclopentylmethyl, and cyclohexylmethyl.

Embodiment 34: The compound of any one of Embodiments 26 to 33, wherein $R^3$ is chosen from isobutyl and cyclopropylmethyl.

Embodiment 35: A compound of Embodiment 17, having structural Formula VI,

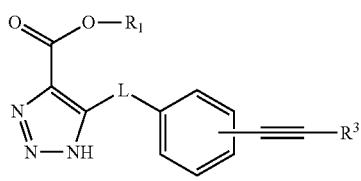

or a salt, polymorph, or tautomer thereof, wherein:
$R^1$ is chosen from hydrogen, $C_1$-$C_6$ alkyl, and $C_1$-$C_6$ cycloalkyl;

L is chosen from O, S, $CH_2$, and NH; and
$R^3$ is chosen from $C_2$-$C_6$ alkyl, $C_3$-$C_6$ cycloalkyl, and $C_3$-$C_6$ cycloalkylalkyl.

Embodiment 36: The compound of any one of Embodiments 1 to 35, wherein $R^1$ is chosen from methyl, ethyl, isopropyl, t-butyl, and hydrogen.

Embodiment 37: The compound of Embodiment 36, wherein $R^1$ is hydrogen.

Embodiment 38: The compound of Embodiment 35, wherein L is O or S.

Embodiment 39: The compound of Embodiment 35, wherein $R^3$ is chosen from isobutyl and cyclopropylmethyl.

Embodiment 40: A compound chosen from Examples 3-414 or a salt, polymorph, or tautomer thereof.

Embodiment 41: A compound chosen from

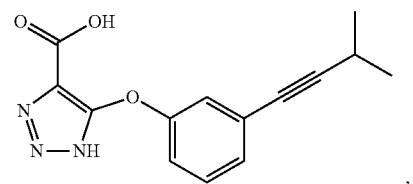

,

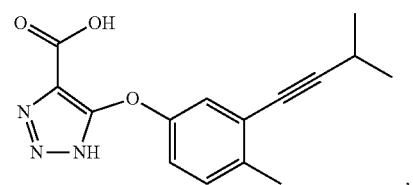

,

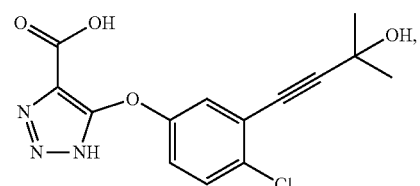

,

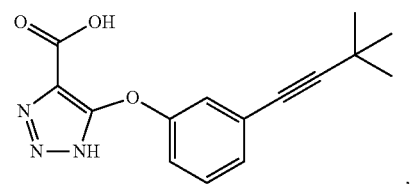

,

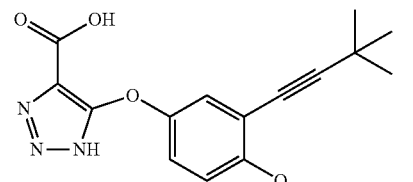

,

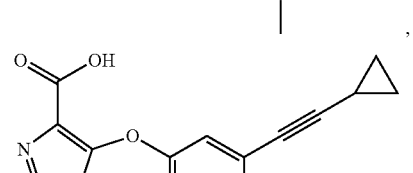

,

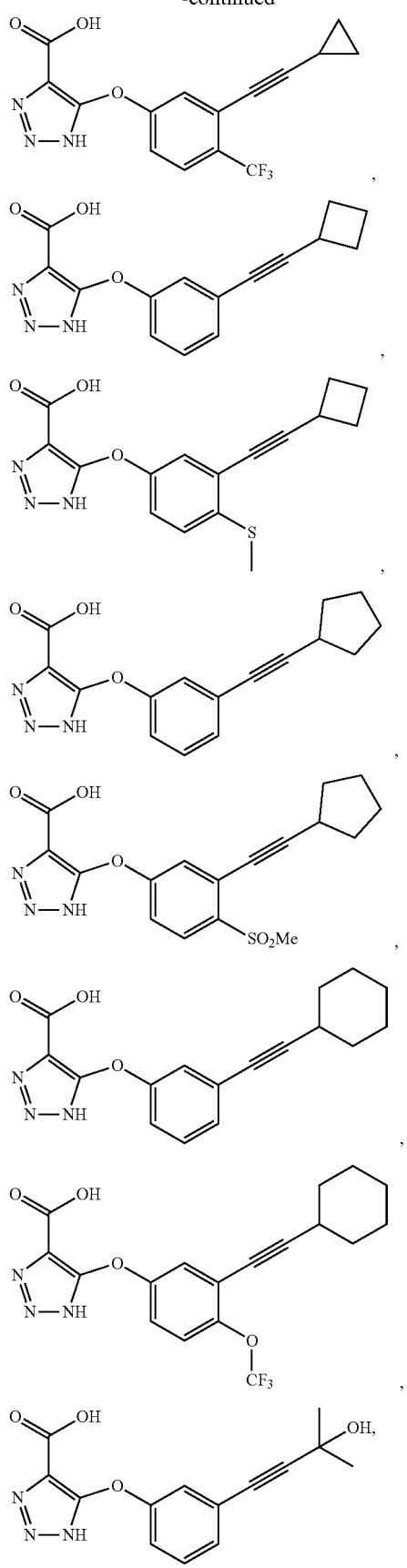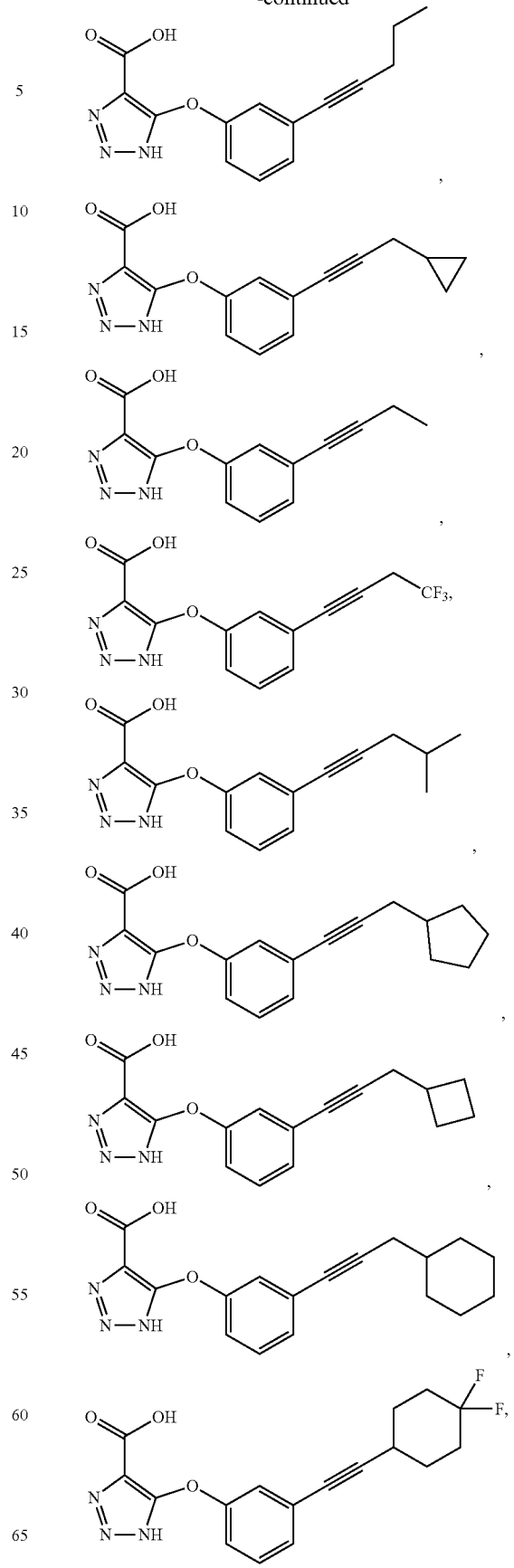

11
-continued
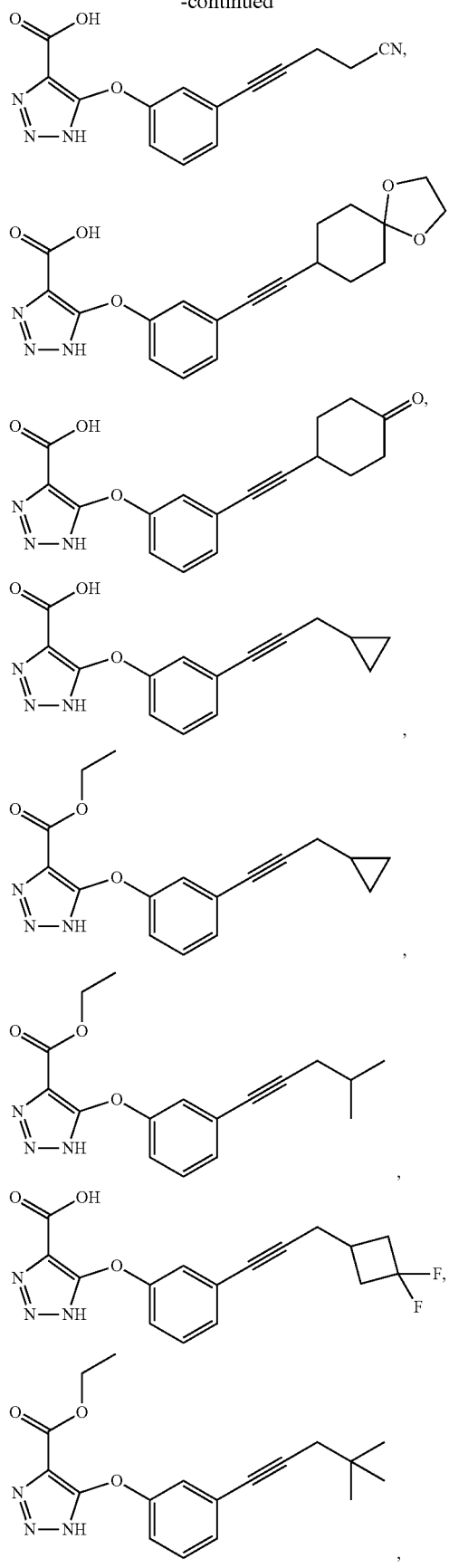
12
-continued
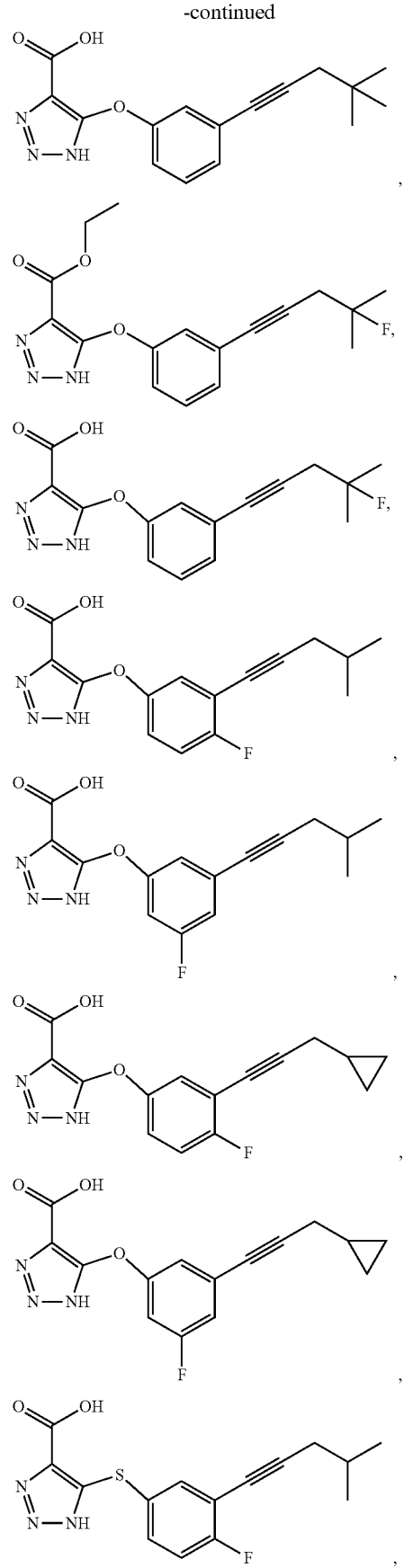

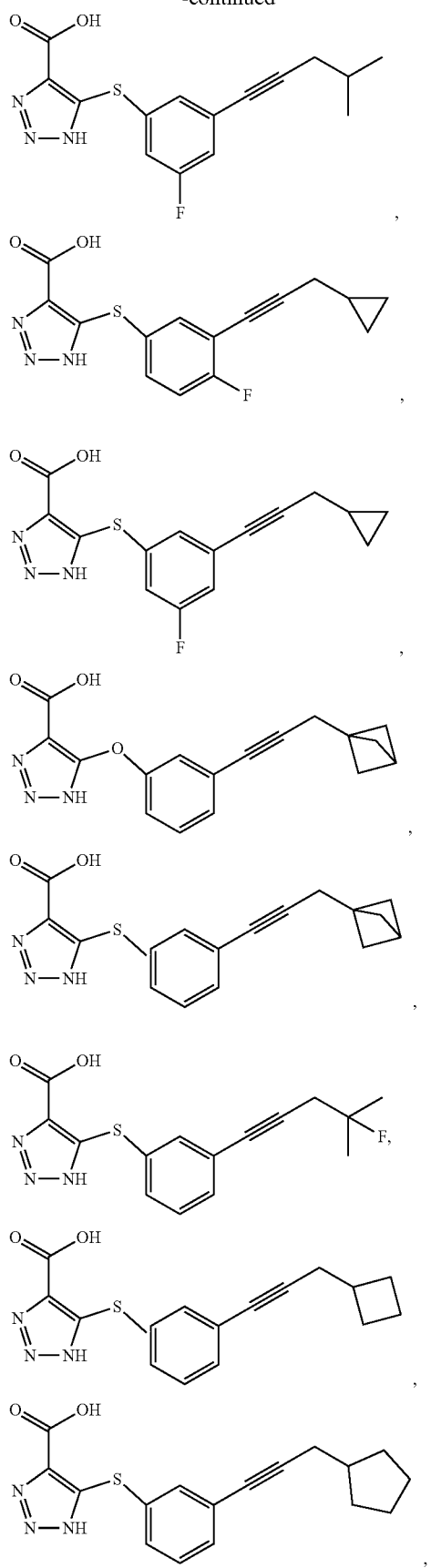
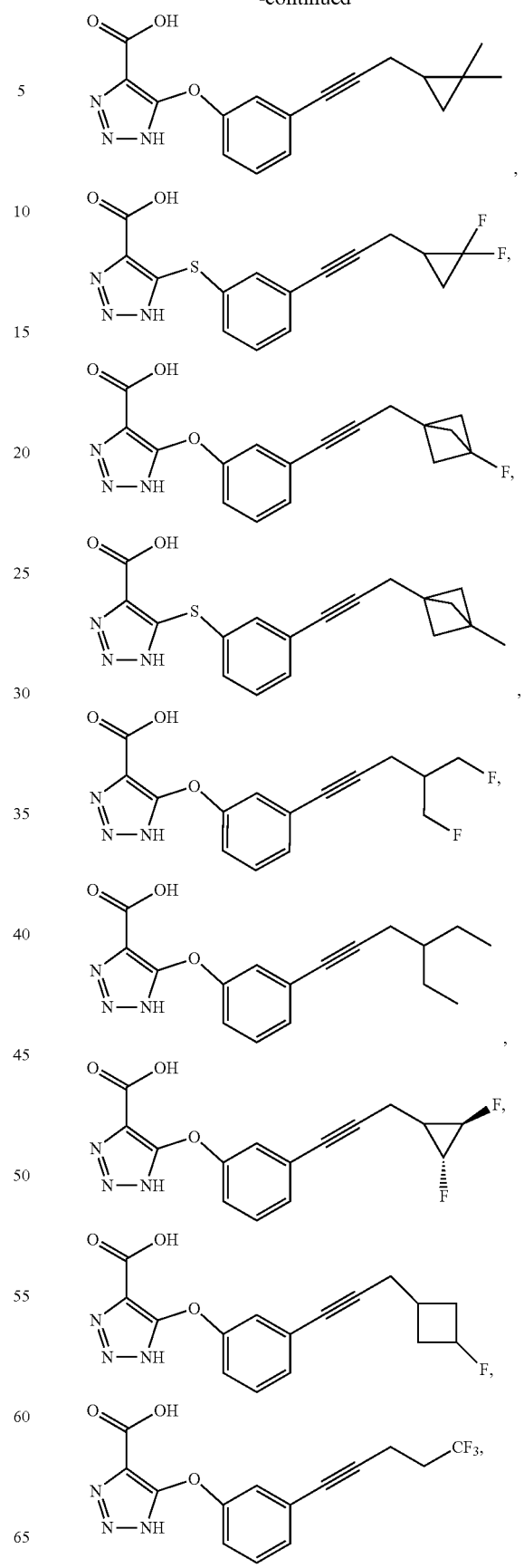

-continued

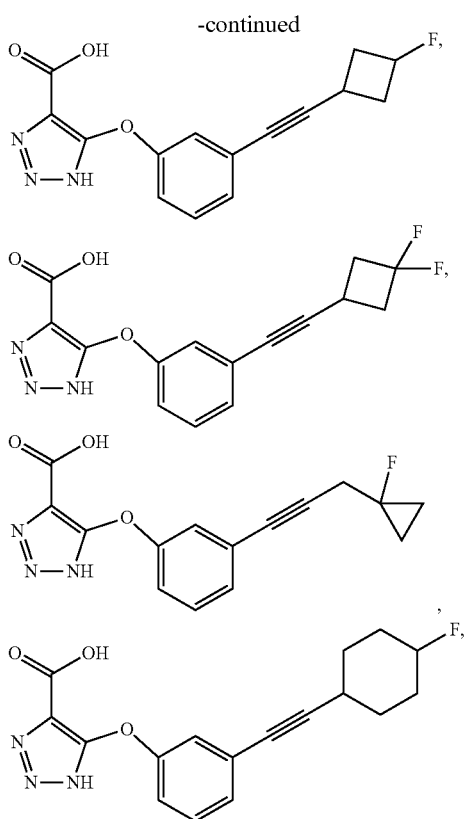

or a salt, polymorph, or tautomer thereof.

Embodiment 42: A compound of any of Embodiments 1-41, or a salt, polymorph, or tautomer thereof, for use as a medicament.

Embodiment 43: A compound of any of Embodiments 1-41, or a salt, polymorph, or tautomer thereof, for use in manufacturing a medicament for preventing or treating an oxalate-related disease.

Embodiment 44: A pharmaceutical composition comprising a compound of any of Embodiments 1-41, or a salt, polymorph, or tautomer thereof together with a pharmaceutically acceptable carrier.

Embodiment 45: The pharmaceutical composition of any of Embodiments 1-41, formulated for oral administration.

Embodiment 46: The pharmaceutical composition of any of Embodiments 1-41, additionally comprising another therapeutic agent.

Embodiment 47: A method of inhibiting glycolate oxidase (GOX) activity in a biological sample comprising contacting the biological sample with a pharmaceutical composition as recited in any of Embodiments 44-46, or a compound of any of Embodiments 1-41, or a salt, polymorph, or tautomer thereof.

Embodiment 48: A method of treating an oxalate-related disease in a subject in need thereof, comprising the step of administering to the subject a pharmaceutical composition as recited in any of Embodiments 44-46, or a compound of any of Embodiments 1-41 or a salt, polymorph, or tautomer thereof.

Embodiment 49: The method of Embodiment 48, wherein the subject is human.

Embodiment 50: The method of Embodiment 49, wherein the oxalate-related disease is hyperoxaluria.

Embodiment 51: The method of Embodiment 50, wherein the oxalate-related disease is primary hyperoxaluria.

Embodiment 52: The method of Embodiment 50, wherein the oxalate-related disease is enteric hyperoxaluria.

Embodiment 53: The method of Embodiment 48, wherein the oxalate-related disease is calcium oxalate kidney stones.

Embodiment 54: The method of Embodiment 48, wherein the oxalate-related disease is idiopathic calcium oxalate stone former (ICSF).

Embodiment 55: The method of Embodiment 48, wherein the oxalate-related disease is calcium oxalate kidney stones after bariatric surgery.

Embodiment 56: The method of Embodiment 48, wherein the oxalate-related disease is urolithiasis or nephrolithiasis for gastrointestinal diseases such as Crohn's disease and ulcerative colitis.

Embodiment 57: A method of treating an oxalate-related disease in a subject in need thereof, comprising the sequential or co-administration of a pharmaceutical composition as recited in any of Embodiments 44-46, or a compound of any of Embodiments 1-41 and a second therapeutic agent.

Embodiment 58: A pharmaceutical composition as recited in any of Embodiments 44-46, or a compound of any of Embodiments 1-41 or a salt, polymorph, or tautomer thereof, for use in human therapy.

Embodiment 59: A pharmaceutical composition as recited in any of Embodiments 44-46, or a compound of any of Embodiments 1-41 or a salt, polymorph, or tautomer thereof, for use in treating an oxalate-related disease.

Embodiment 60: Use of a compound of any of Embodiments 1-41 or a salt, polymorph, or tautomer thereof, for manufacturing a medicament to treat an oxalate-related disease.

Provided herein are compounds of Formula Ia:

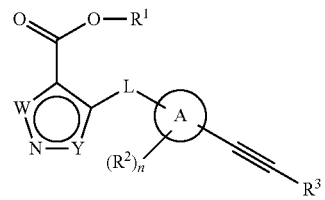

(Ia)

or a salt or prodrug thereof, wherein:

W is chosen from N, NH, S, and CCH$_3$;

X is chosen from N, NH, S, and O;

Y is N if W is NH, S, or CH$_3$; Y is NH if W is N;

R$^1$ is chosen from hydrogen, C$_1$-C$_6$ alkyl, and C$_1$-C$_6$ cycloalkyl;

L is chosen from CH$_2$, NH, NR$^4$, O, S, S(O), SO$_2$, and CR$^4$=CR$^5$;

A is chosen from monocyclic or bicyclic aryl, monocyclic or bicyclic heteroaryl, biaryl, and biheteroaryl;

each R$^2$ is independently chosen from hydrogen, halogen, C$_1$-C$_6$ alkyl, C$_2$-C$_6$ alkenyl, C$_2$-C$_6$ alkynyl, C$_3$-C$_6$ cycloalkyl, 3-6-membered heterocycloalkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ alkylsulfonyl, C$_1$-C$_6$ haloalkylsulfonyl, pentafluorosulfaneyl, sulfamoyl, C$_1$-C$_6$ alkylsulfamoyl, C$_1$-C$_6$ dialkylsulfamoyl, cyano, amino, N-acetylamino, C$_1$-C$_6$ alkylamino, C$_1$-C$_6$ dialkylamino, hydroxy, and C$_1$-C$_6$ hydroxyalkyl;

n is 0, 1, 2, or 3;

R$^3$ is chosen from hydrogen, C$_1$-C$_6$ alkyl, C$_2$-C$_6$ alkenyl, C$_2$-C$_6$ alkynyl, C$_3$-C$_6$ cycloalkyl, 3-10-membered heterocycloalkyl, C$_6$-C$_{10}$ aryl, 5-10-membered heteroaryl, C$_1$-C$_6$ haloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ alkylsulfonyl, $C_3$-$C_6$ cycloalkyl $C_1$-$C_6$ alkylsulfonyl, $C_3$-$C_6$ heterocycloalkyl $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl, any of which that comprises a cyclic group is optionally substituted with 1, 2, or 3 $R^6$ groups;

$R^4$ and $R^5$ are each independently chosen from hydrogen and $C_1$-$C_6$ alkyl; and each $R^6$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 4-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl.

In certain embodiments,

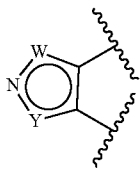

is chosen from

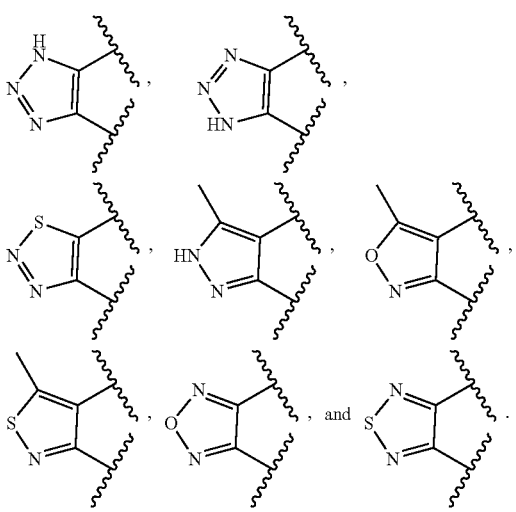

In certain embodiments, X is N.

Also provided is a compound of structural Formula IIa

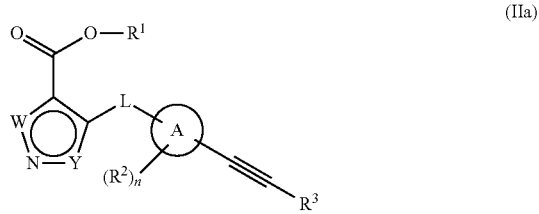

or a salt or prodrug thereof, wherein:
W is chosen from N, NH, S, and $CCH_3$;
Y is N if W is NH, S, or $CH_3$; Y is NH if W is N;

$R^1$ is chosen from hydrogen, $C_1$-$C_6$ alkyl, and $C_1$-$C_6$ cycloalkyl;

L is chosen from $CH_2$, NH, $NR^4$, O, S, S(O), $SO_2$, and $CR^4$=$CR^5$;

A is chosen from monocyclic or bicyclic aryl, monocyclic or bicyclic heteroaryl, biaryl, and biheteroaryl;

each $R^2$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 3-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, C alkylamino, C dialkylamino, hydroxy, and $C_1$-$C_6$ hydroxyalkyl;

n is 0, 1, 2, or 3;

$R^3$ is chosen from hydrogen, $C_1$-$C_6$ alkyl, $C_2$-$C_6$ alkenyl, $C_2$-$C_6$ alkynyl, $C_3$-$C_6$ cycloalkyl, 3-10-membered heterocycloalkyl, $C_6$-$C_{10}$ aryl, 5-10-membered heteroaryl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_3$-$C_6$ cycloalkyl $C_1$-$C_6$ alkylsulfonyl, $C_3$-$C_6$ heterocycloalkyl $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl, any of which that comprises a cyclic group is optionally substituted with 1, 2, or 3 $R^6$ groups;

$R^4$ and $R^5$ are each independently chosen from hydrogen and $C_1$-$C_6$ alkyl; and each $R^6$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 4-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl.

In certain embodiments, W is N or NH.

In certain embodiments, W is NH, and Y is N.

In certain embodiments,

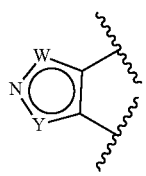

is chosen from

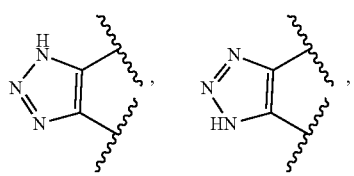

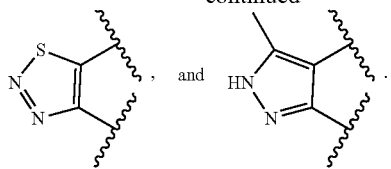

In certain embodiments,

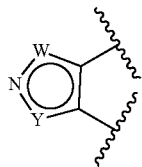

is chosen from

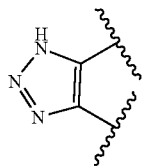 and 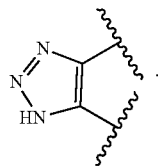.

In certain embodiments, L is O.

In certain embodiments, R¹ is hydrogen.

In certain embodiments, A is chosen from phenyl and C₆ monocyclic heteroaryl.

In certain embodiments, A is chosen from phenyl, pyridinyl, pyridazinyl, pyrimidinyl, and pyridinonyl.

In certain embodiments, A is monocyclic aryl optionally substituted with one or more R² groups. In certain embodiments, A is biaryl optionally substituted with one or more R² groups. In certain embodiments, A is bicyclic aryl optionally substituted with one or more R² groups. In certain embodiments, A is monocyclic heteroaryl optionally substituted with one or more R² groups. In certain embodiments, A is bicyclic heteroaryl optionally substituted with one or more R² groups.

In certain embodiments, A is chosen from phenyl, biphenyl, naphthyl, pyridinylphenyl, phenylpyridinyl, and bipyridinyl, any of which is optionally substituted with one or more R² groups.

In certain embodiments, A is phenyl optionally substituted with one or more R² groups. In certain embodiments, A is biphenyl optionally substituted with one or more R² groups. In certain embodiments, A is naphthyl optionally substituted with one or more R² groups. In certain embodiments, A is pyridinylphenyl optionally substituted with one or more R² groups. In certain embodiments, A is phenylpyridinyl optionally substituted with one or more R² groups. In certain embodiments, A is bipyridinyl optionally substituted with one or more R² groups.

In certain embodiments, n is chosen from 0, 1, or 2.

In certain embodiments, R³ is chosen from phenyl, 5-10-membered heteroaryl, $C_3$-$C_6$ cycloalkyl, and 3-10-membered heterocycloalkyl.

In certain embodiments, R³ is chosen from phenyl, pyridinyl, pyridazinyl, pyrimidinyl, pyridinonyl, pyrrolyl, pyrazolyl, imidazolyl, isoxazolyl, thiazolyl, triazolyl, cyclopropyl, cyclobutyl, cyclopentyl, cyclohexyl, furanyl, pyranyl, and piperidinyl.

Also provided is a compound of structural Formula IIIa

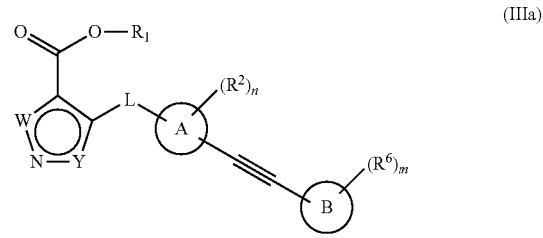

(IIIa)

or a salt or prodrug thereof, wherein:
W is chosen from N, NH, S, and CCH₃;
Y is N if W is NH, S, or CH₃; Y is NH if W is N;
R¹ is chosen from hydrogen, $C_1$-$C_6$ alkyl, and $C_1$-$C_6$ cycloalkyl;
L is chosen from CH₂, NH, NR⁴, O, S, S(O), SO₂, and CR⁴=CR⁵;
A is chosen from monocyclic or bicyclic aryl, monocyclic or bicyclic heteroaryl, biaryl, and biheteroaryl, optionally substituted with one or more R² groups;
B is chosen from $C_3$-$C_6$ cycloalkyl, 3-12-membered heterocycloalkyl, $C_6$-$C_{10}$ aryl, and 5-10-membered heteroaryl;
each R² is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl;
n is 0, 1, 2, or 3;
R⁴ and R⁵ are each independently chosen from hydrogen or $C_1$-$C_6$ alkyl;
each R⁶ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 4-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl; and
m is 0, 1, 2, or 3.

In certain embodiments, W is N or NH; Y is N if W is NH; and Y is NH if W is N.

In certain embodiments, W is N or NH.

In certain embodiments, W is NH, and Y is N.

In certain embodiments,

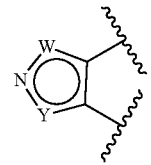

is chosen from

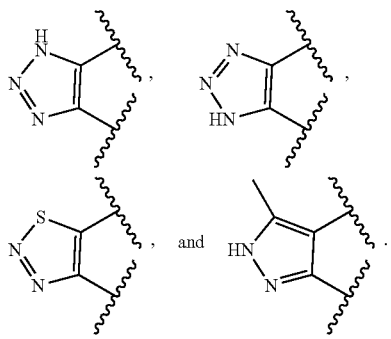

In certain embodiments,

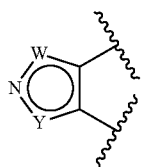

is chosen from

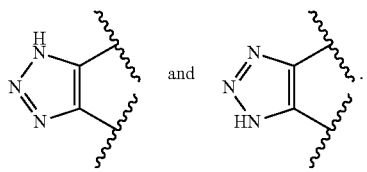 [SMILES: *c1nn[nH]c1* ; *c1nn[nH]c1*]

In certain embodiments, L is O.

In certain embodiments, $R^1$ is hydrogen.

In certain embodiments, A is chosen from phenyl and $C_6$ monocyclic heteroaryl.

In certain embodiments, A is chosen from phenyl, pyridinyl, pyridazinyl, pyrimidinyl, and pyridinonyl.

In certain embodiments, A is monocyclic aryl optionally substituted with one or more $R^2$ groups. In certain embodiments, A is biaryl optionally substituted with one or more $R^2$ groups. In certain embodiments, A is bicyclic aryl optionally substituted with one or more $R^2$ groups. In certain embodiments, A is monocyclic heteroaryl optionally substituted with one or more $R^2$ groups. In certain embodiments, A is bicyclic heteroaryl optionally substituted with one or more $R^2$ groups.

In certain embodiments, A is chosen from phenyl, biphenyl, naphthyl, pyridinylphenyl, phenylpyridinyl, and bipyridinyl, any of which is optionally substituted with one or more $R^2$ groups.

In certain embodiments, A is phenyl optionally substituted with one or more $R^2$ groups. In certain embodiments, A is biphenyl optionally substituted with one or more $R^2$ groups. In certain embodiments, A is naphthyl optionally substituted with one or more $R^2$ groups. In certain embodiments, A is pyridinylphenyl optionally substituted with one or more $R^2$ groups. In certain embodiments, A is phenylpyridinyl optionally substituted with one or more $R^2$ groups. In certain embodiments, A is bipyridinyl optionally substituted with one or more $R^2$ groups.

In certain embodiments, n is chosen from 0, 1, or 2.

In certain embodiments, B is chosen from phenyl, 5-10-membered heteroaryl, $C_3$-$C_6$ cycloalkyl, and 3-10-membered heterocycloalkyl.

In certain embodiments, B is chosen from phenyl, pyridinyl, pyridazinyl, pyrimidinyl, pyridinonyl, pyrrolyl, pyrazolyl, imidazolyl, isoxazolyl, thiazolyl, triazolyl, cyclopropyl, cyclobutyl, cyclopentyl, cyclohexyl, furanyl, pyranyl, and piperidinyl.

Also provided is a compound chosen from Examples 3-231 or a salt or prodrug thereof.

In certain embodiments, the compound is chosen from:

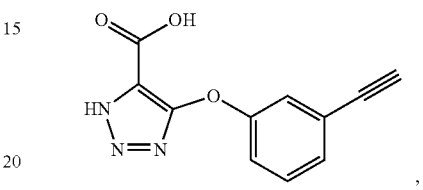

,

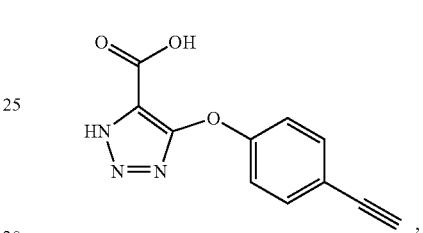

,

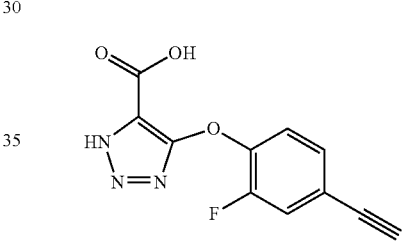

,

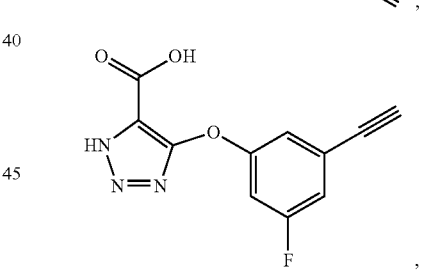

,

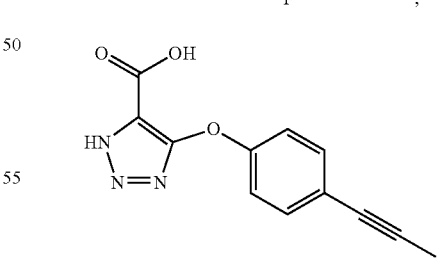

,

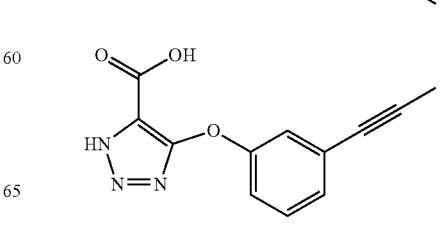

,

-continued
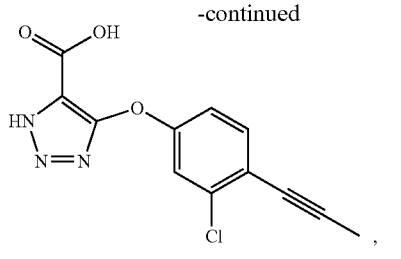
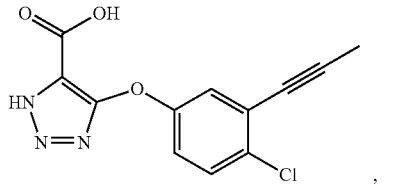
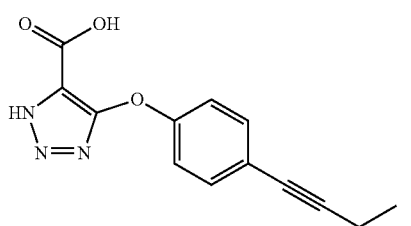
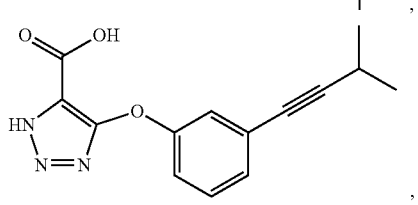
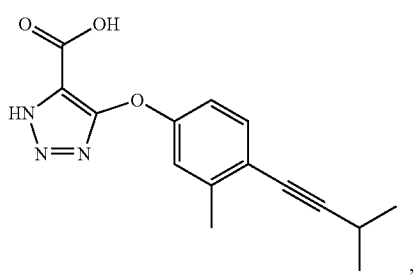
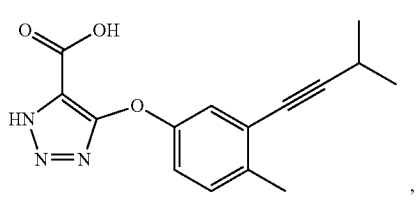
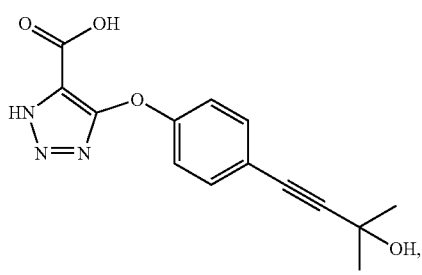
-continued
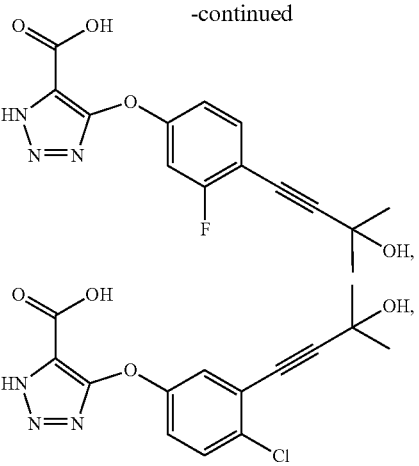
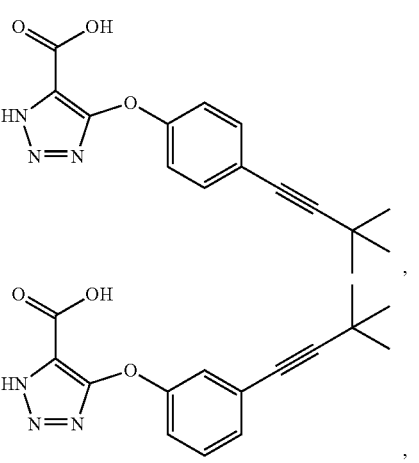
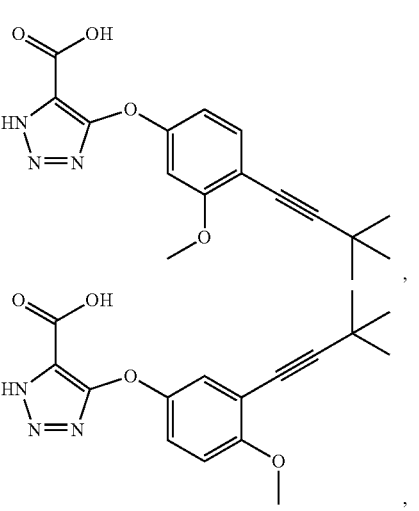
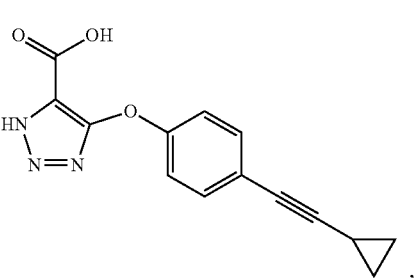

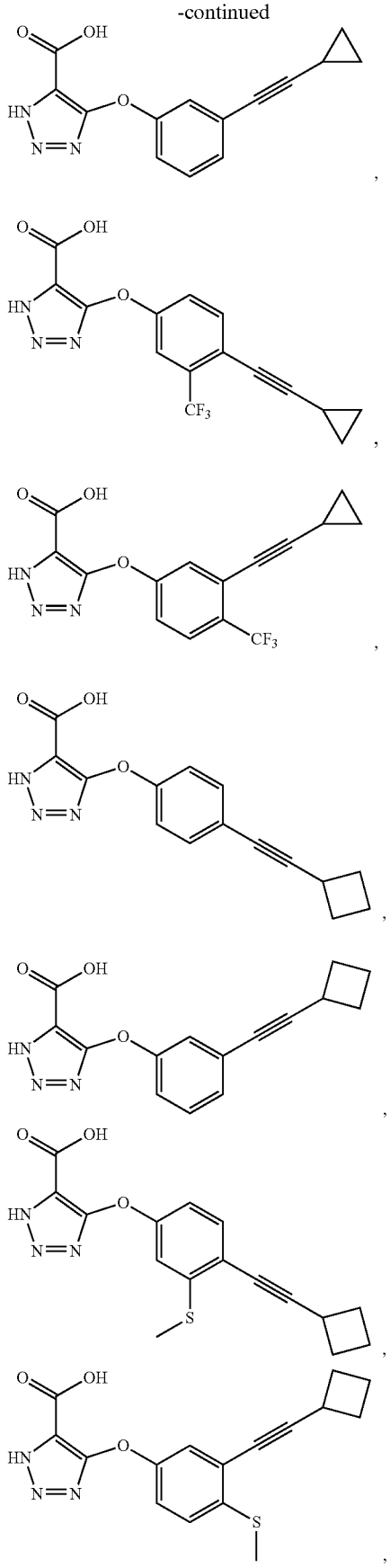
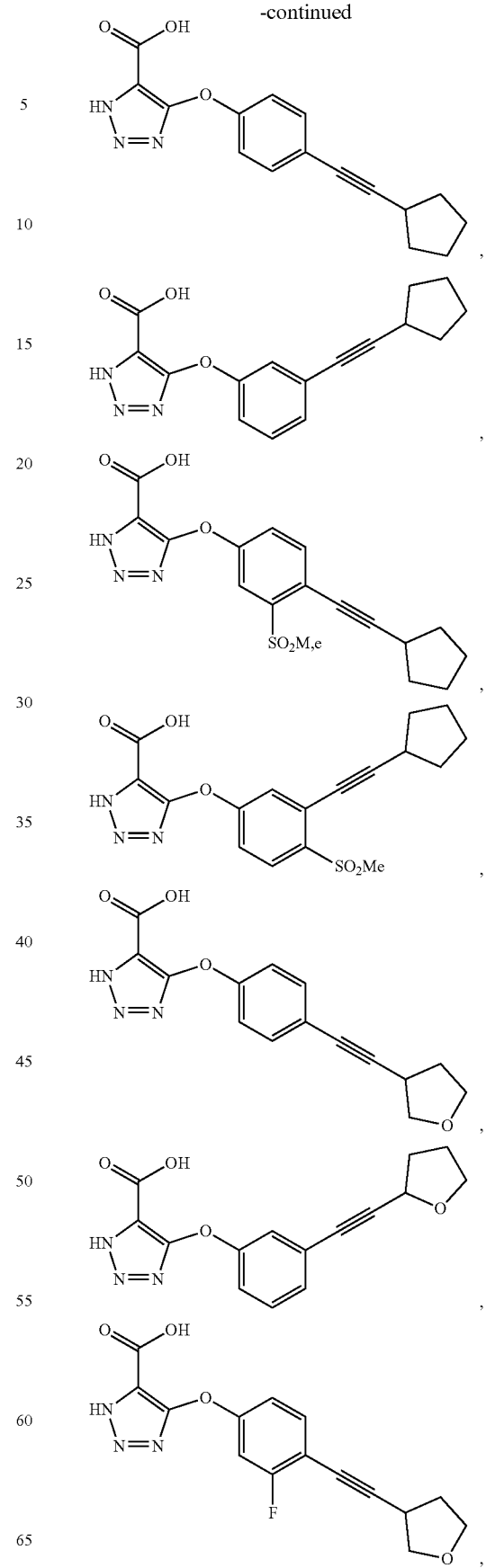

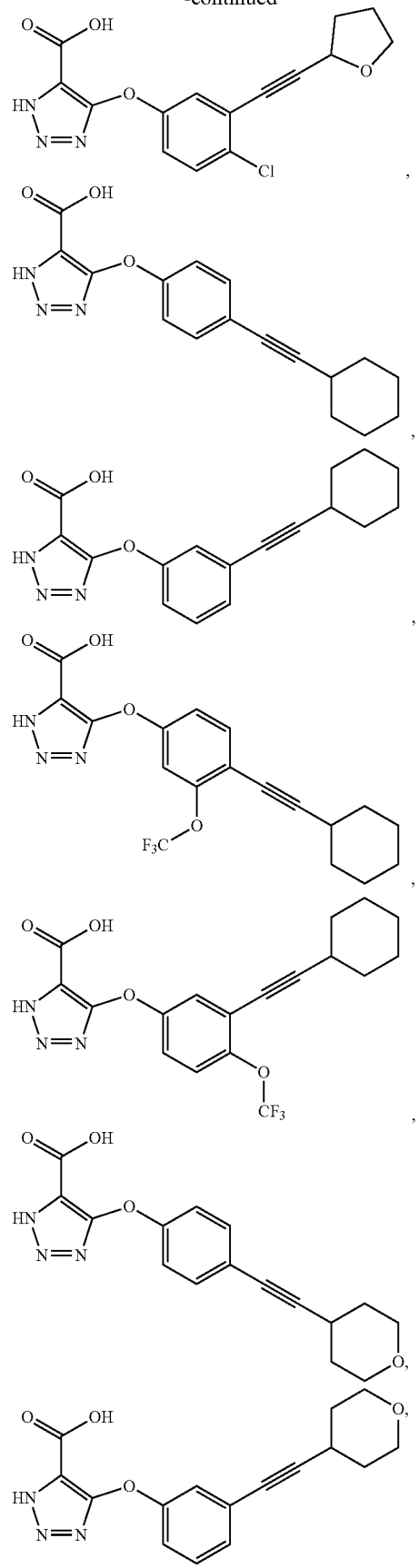
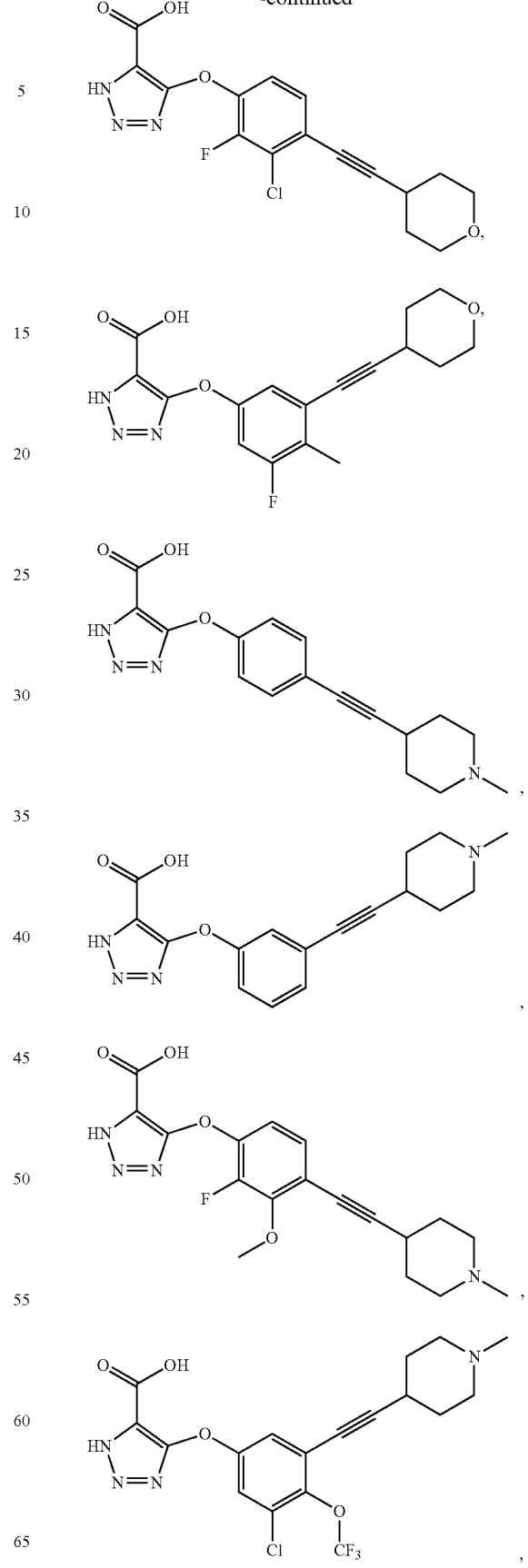

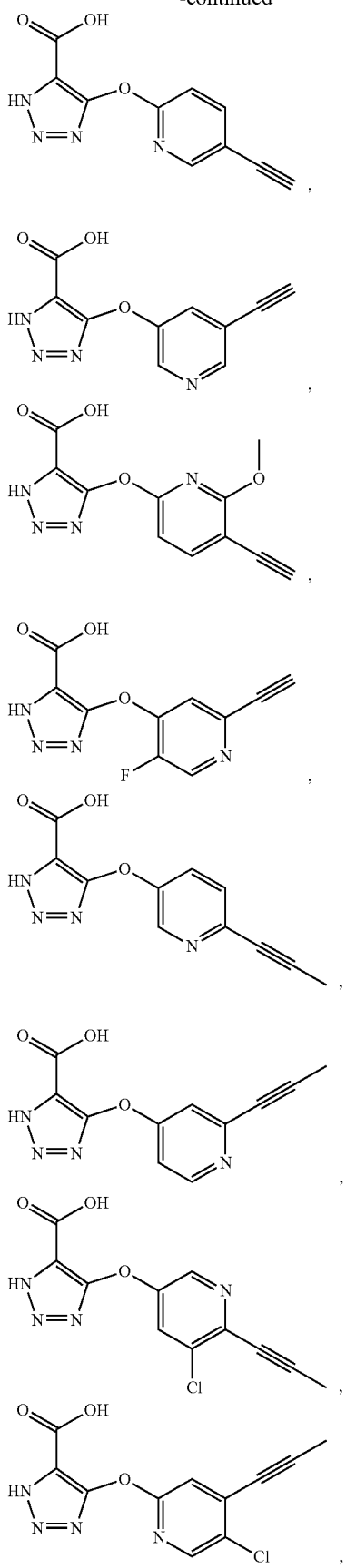
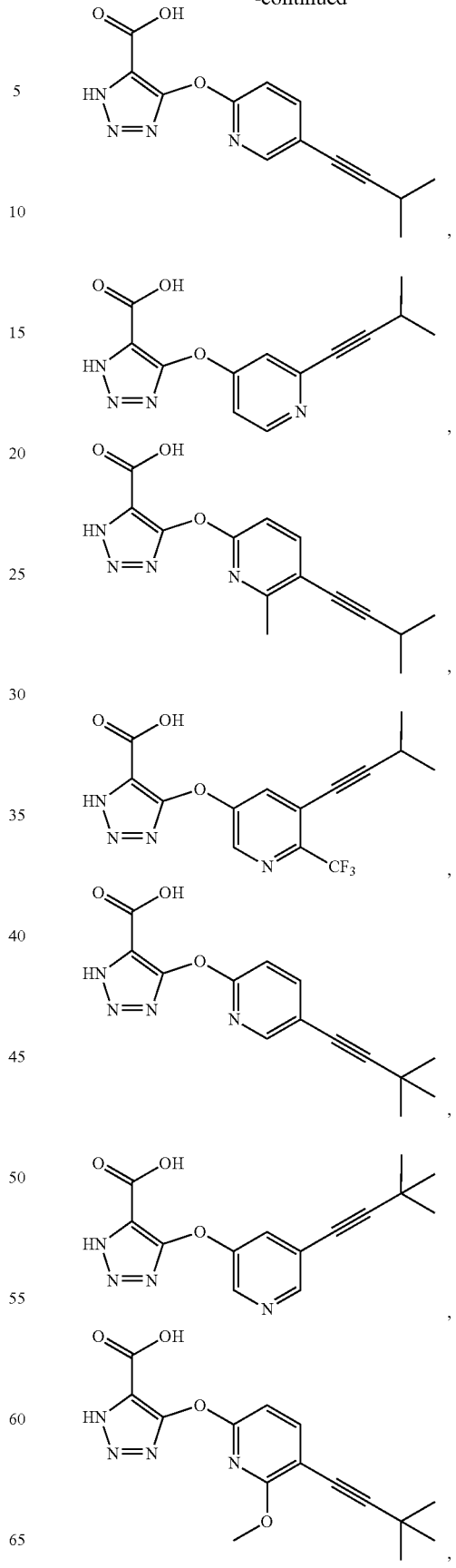

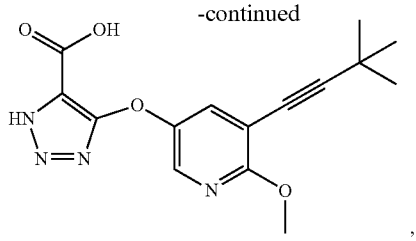,
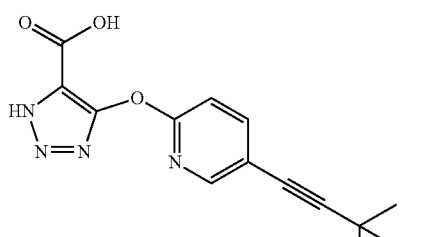
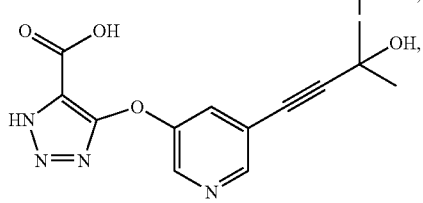,
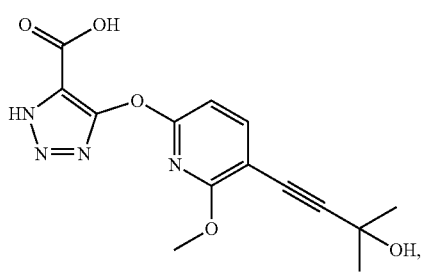
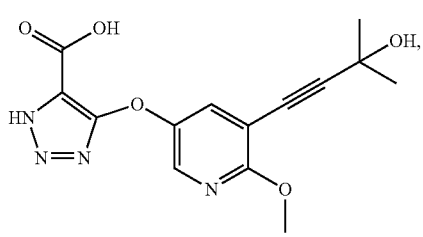,
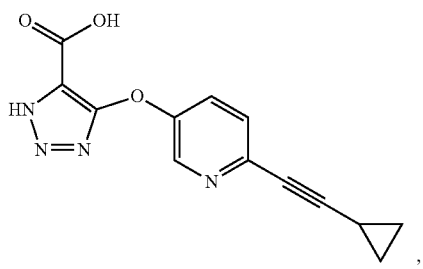
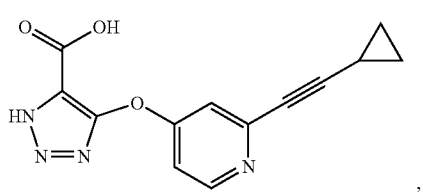,
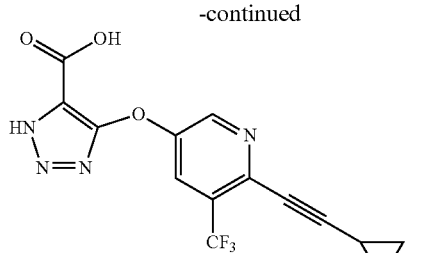,
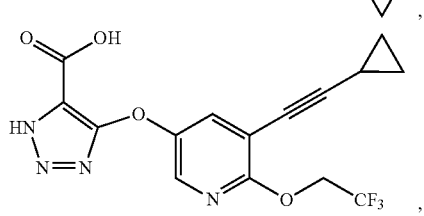,
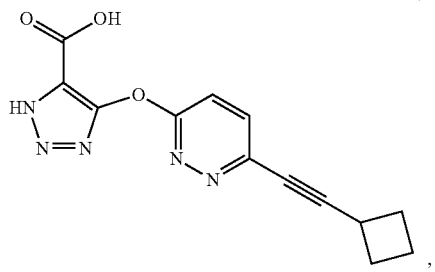,
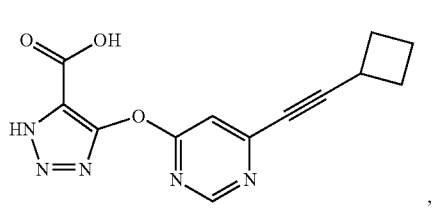,
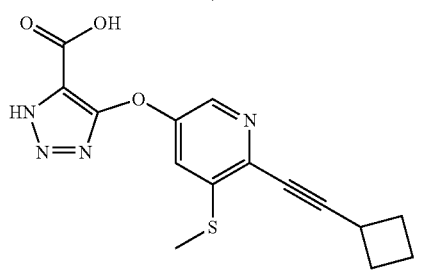,
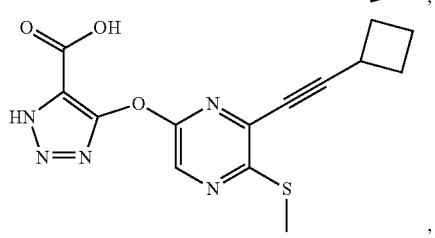,
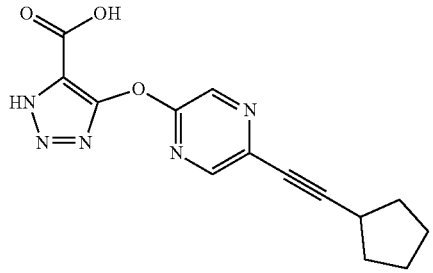,

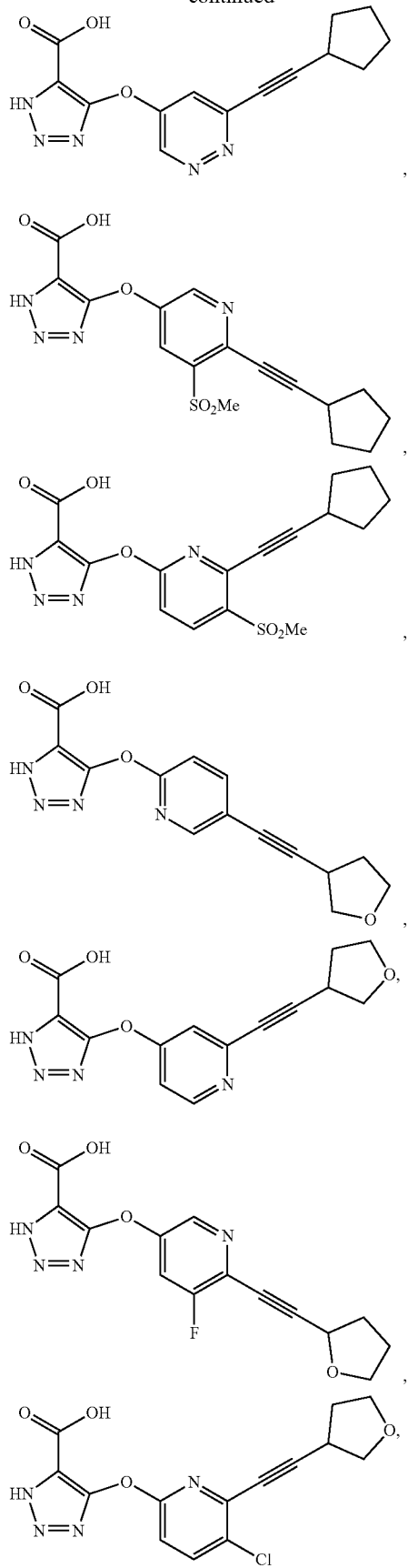
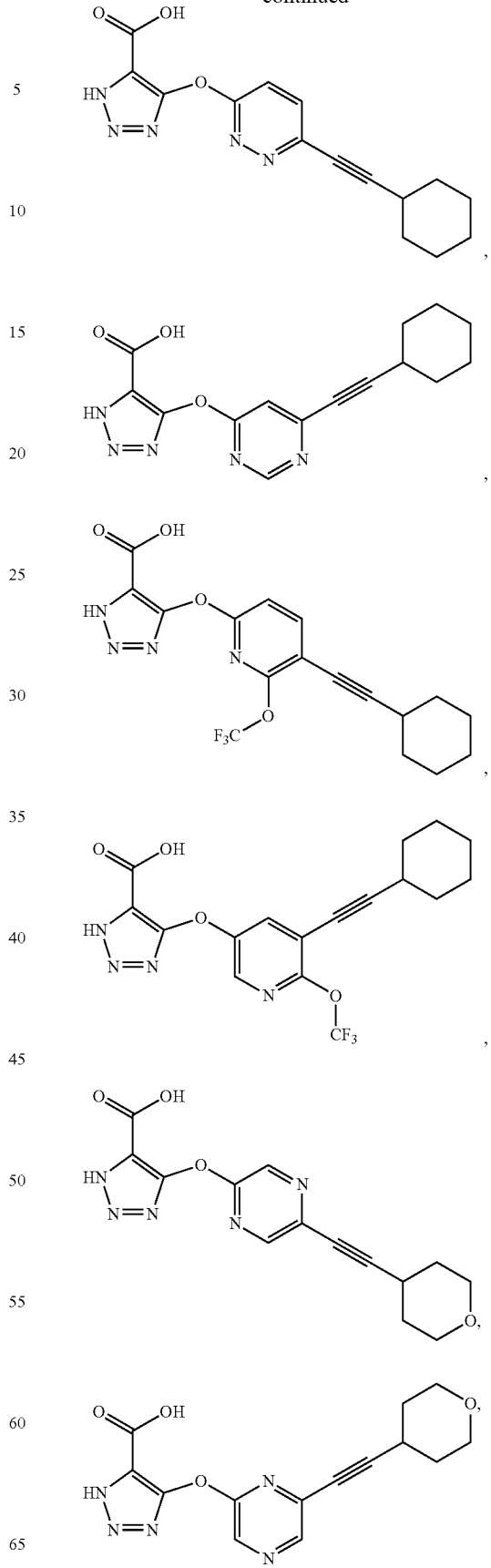

35
-continued
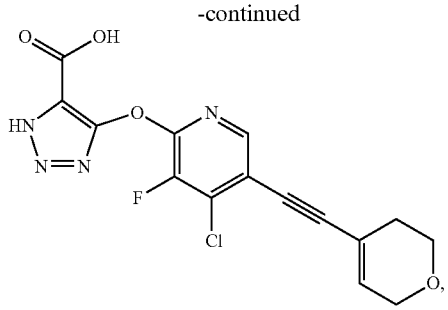
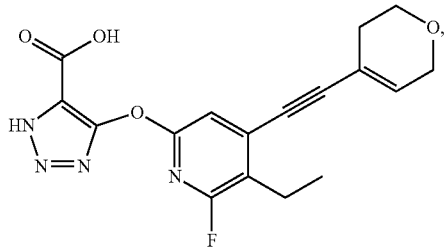
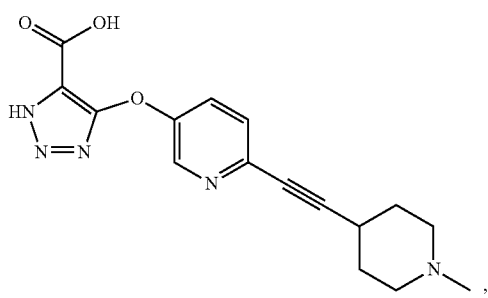
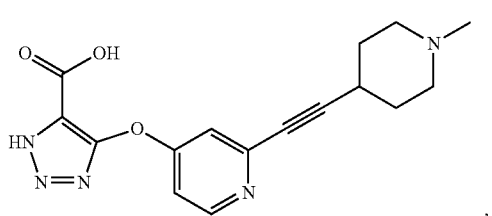
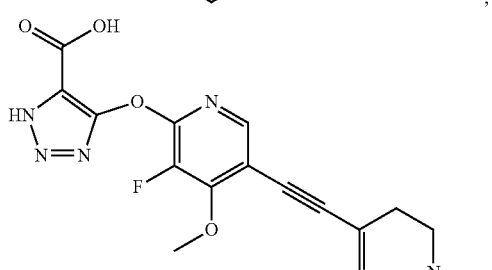
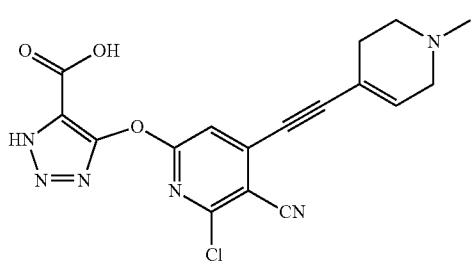
36
-continued
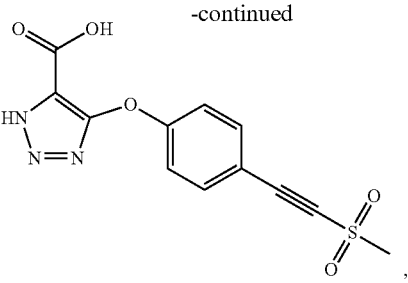
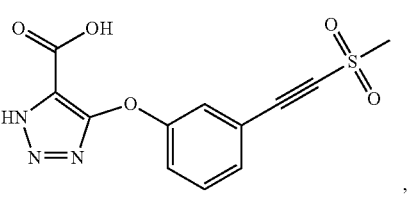
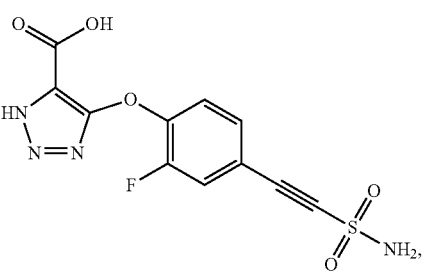
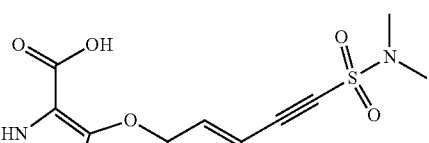
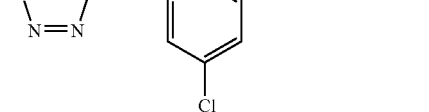
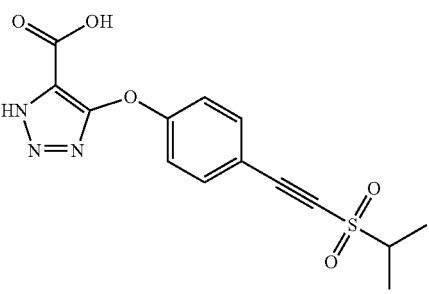
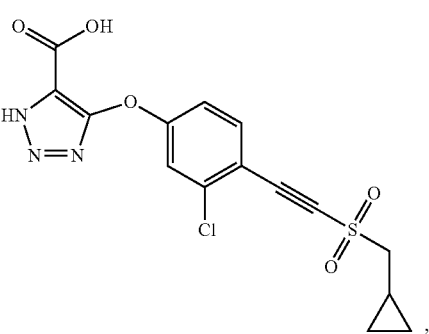

37
-continued
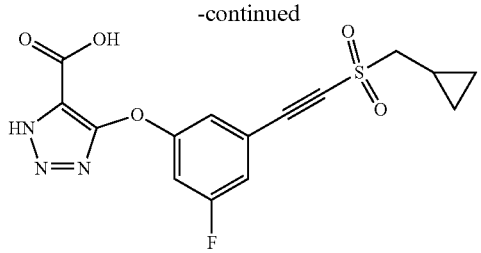
,
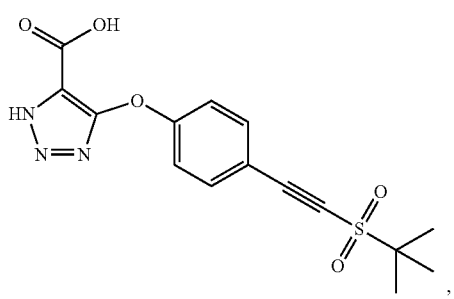
,
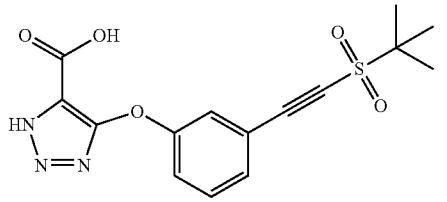
,
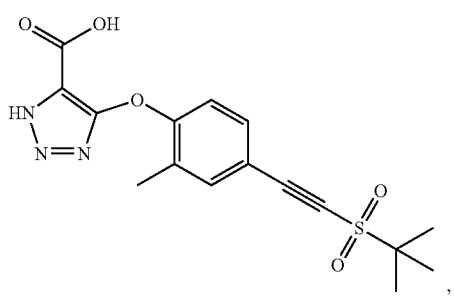
,
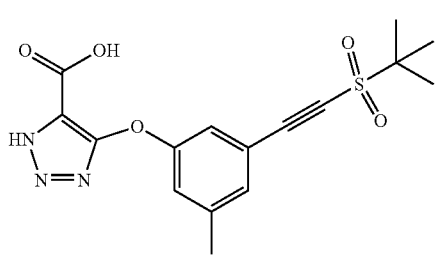
,
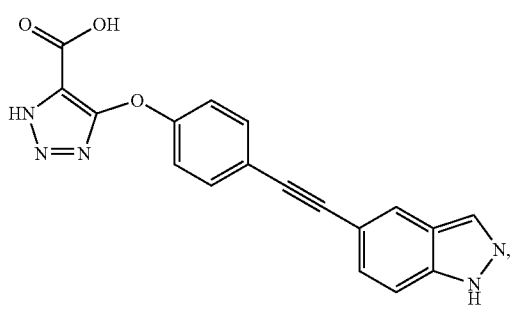
,
38
-continued
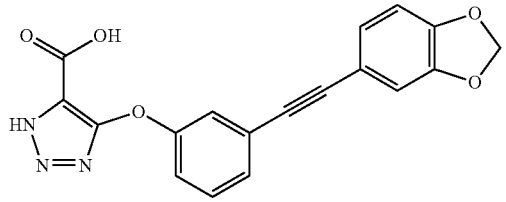
,
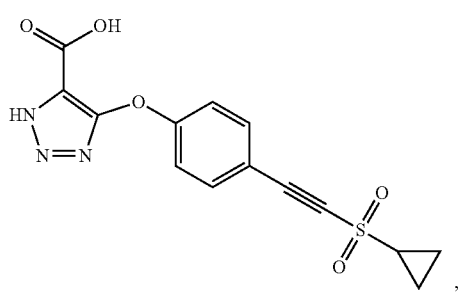
,
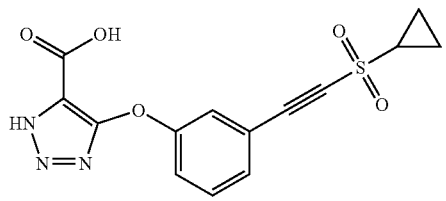
,
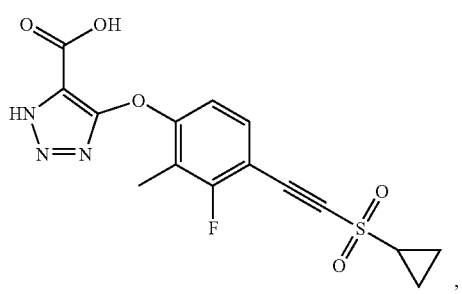
,
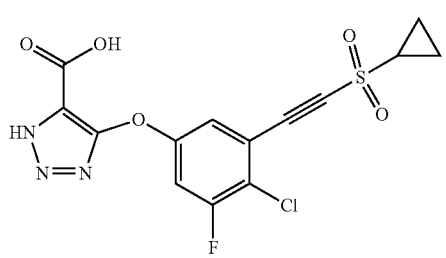
,
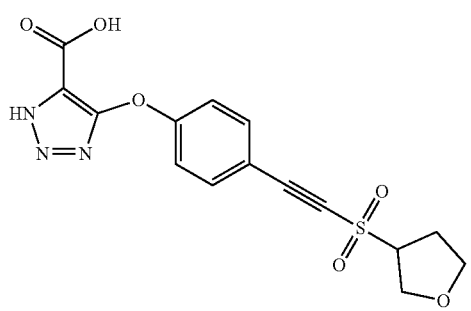
,

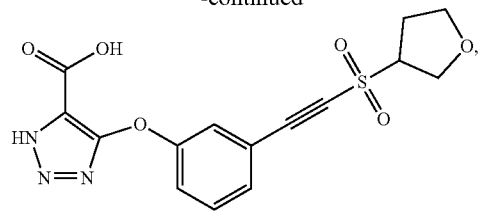
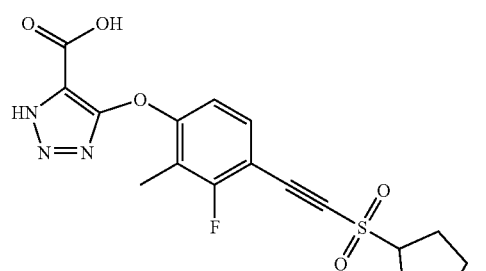
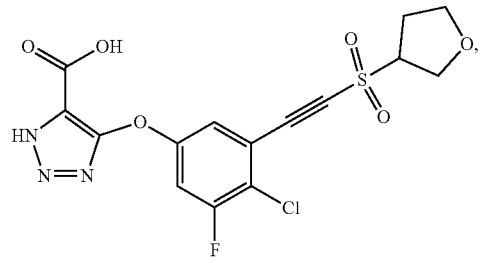
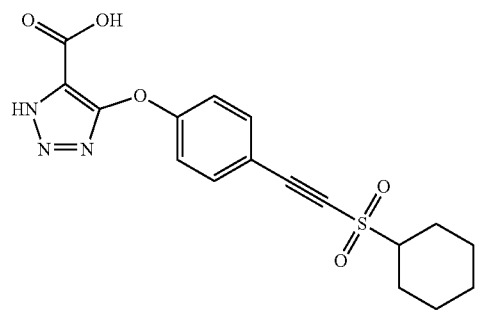
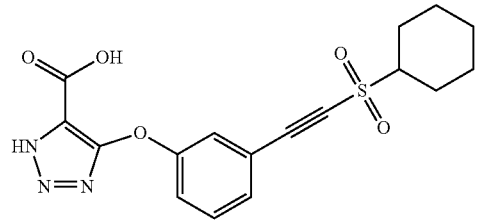
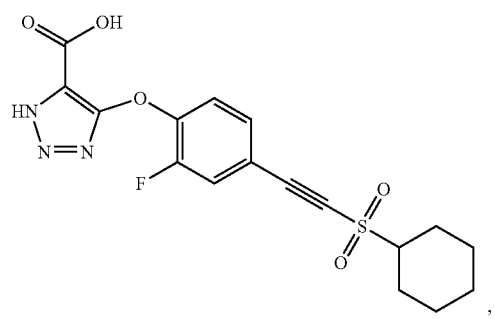
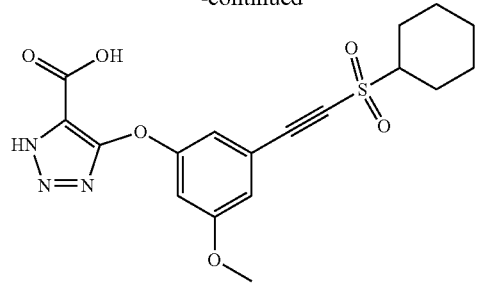
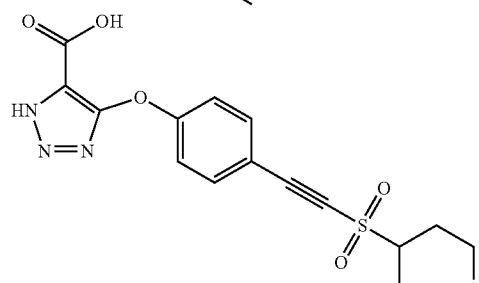
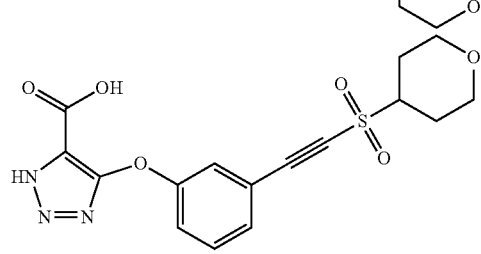
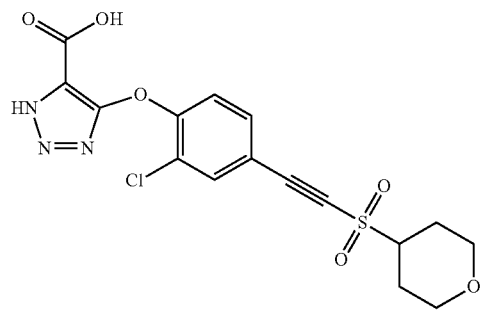
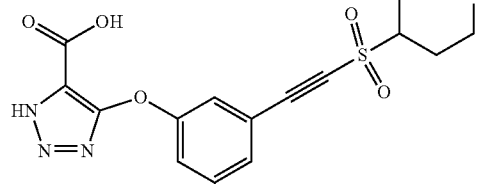
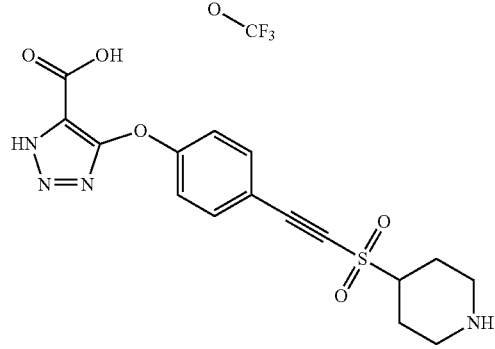

41
-continued
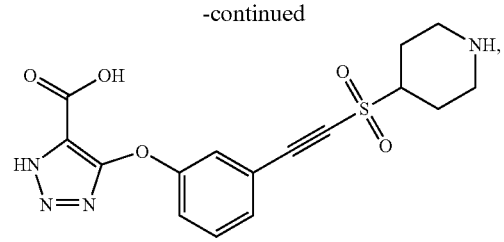
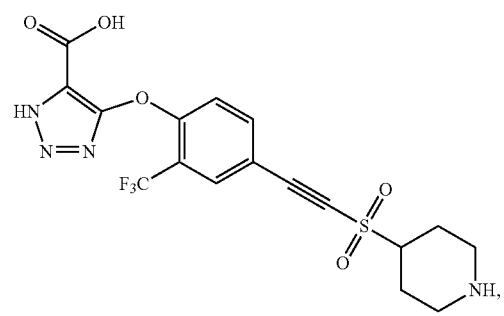
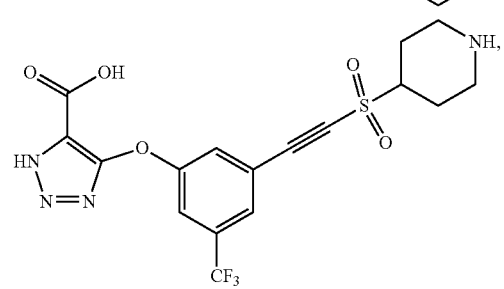
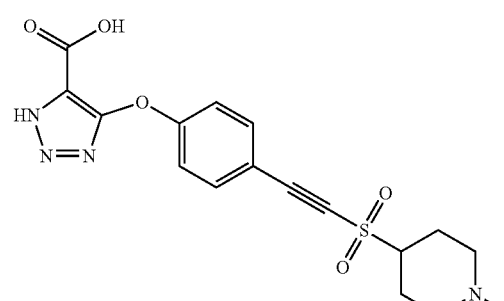
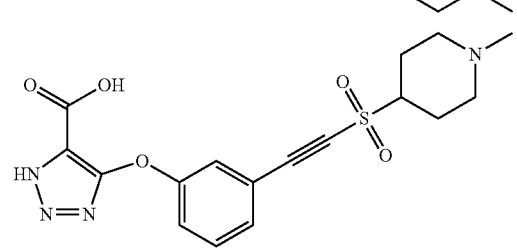
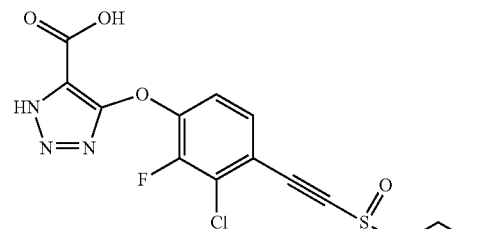
42
-continued
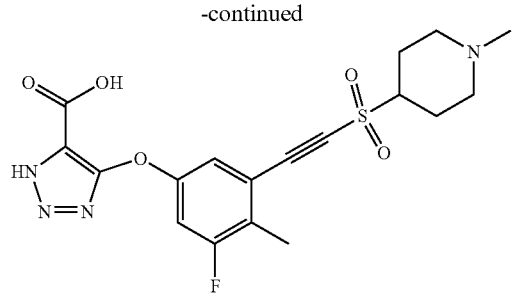
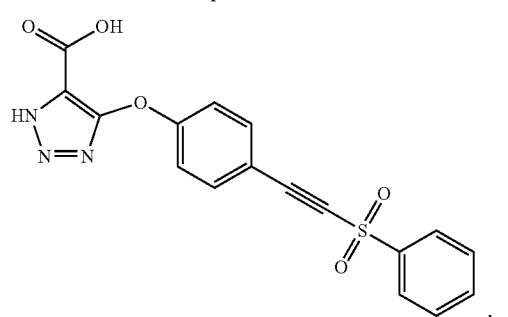
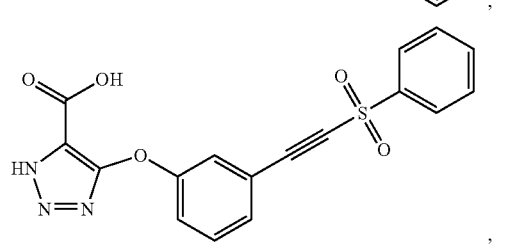
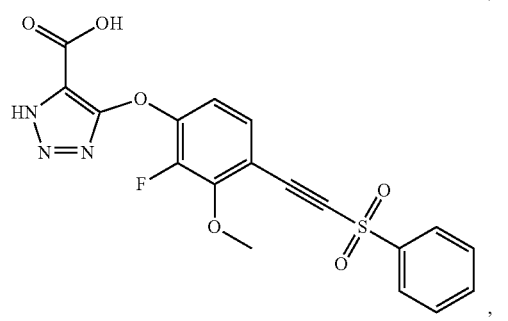
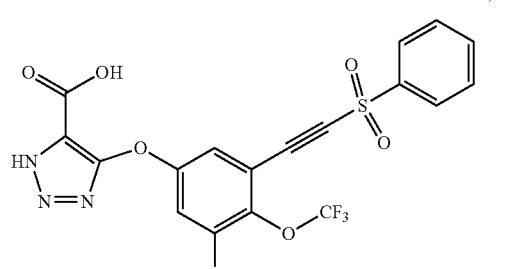
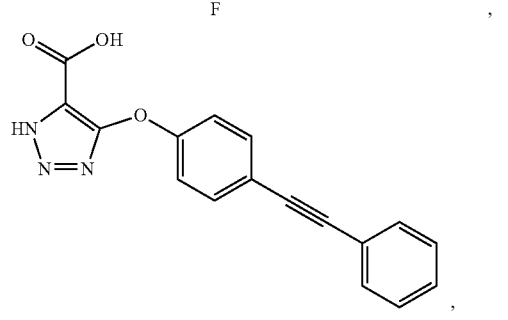

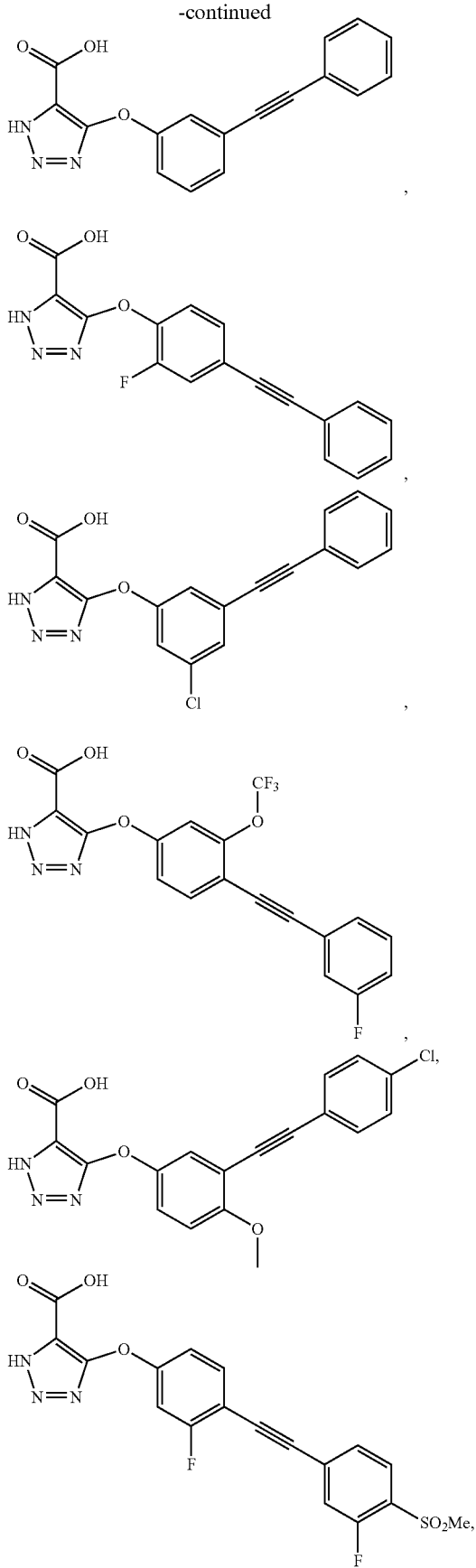
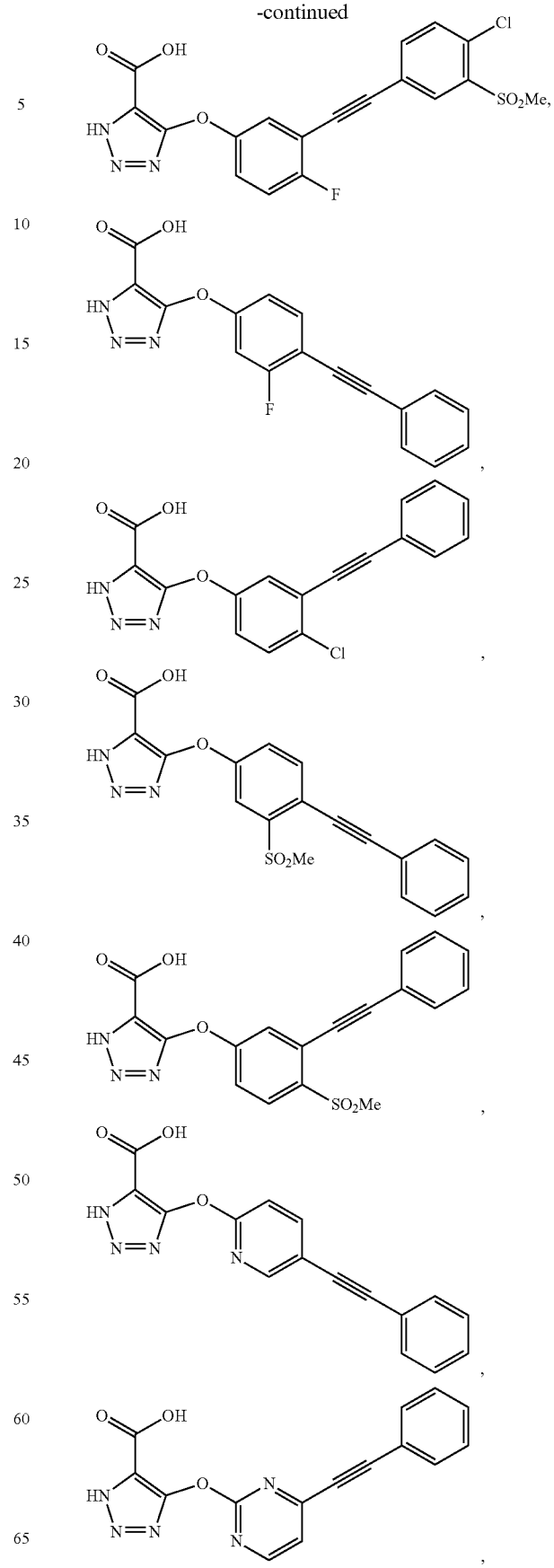

-continued
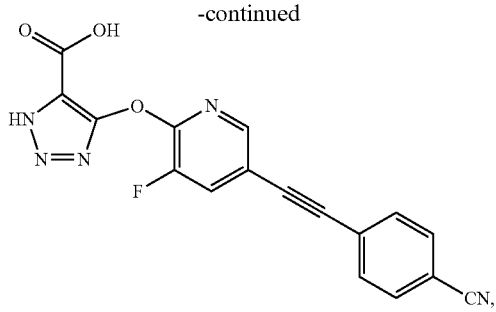
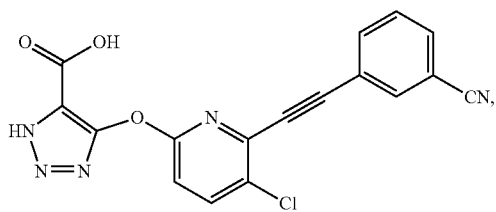
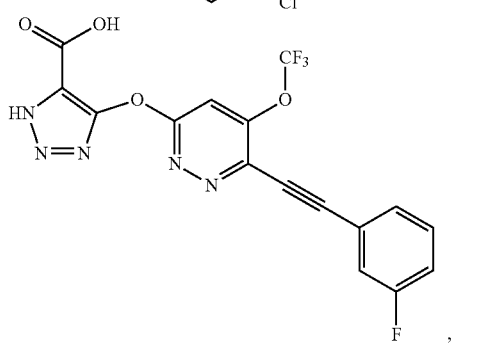
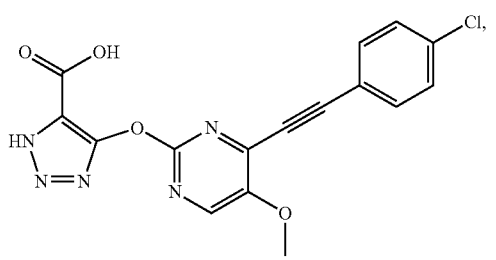
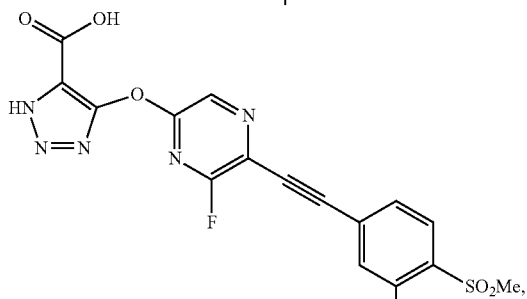
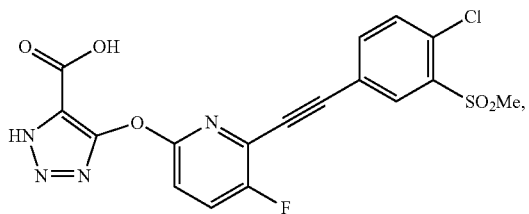
-continued
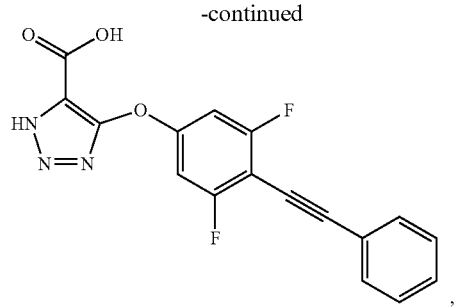
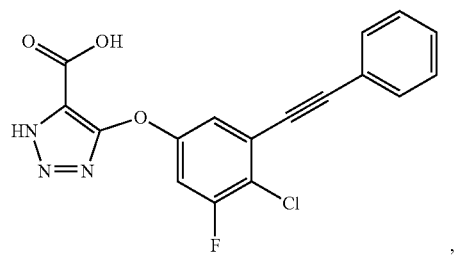
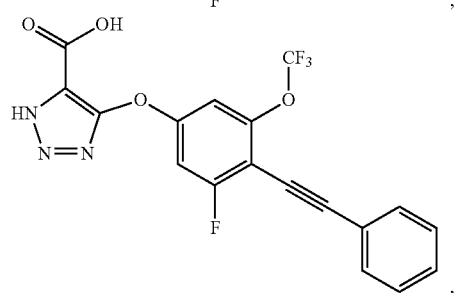
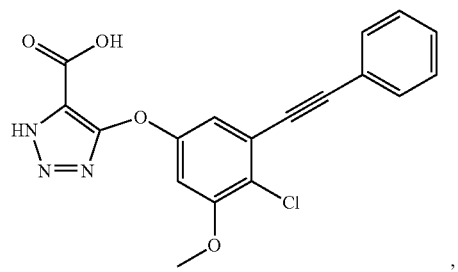
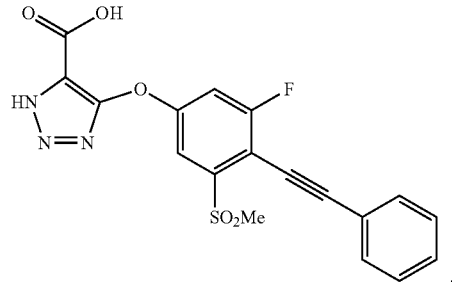
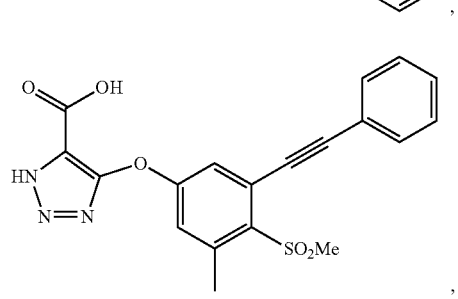

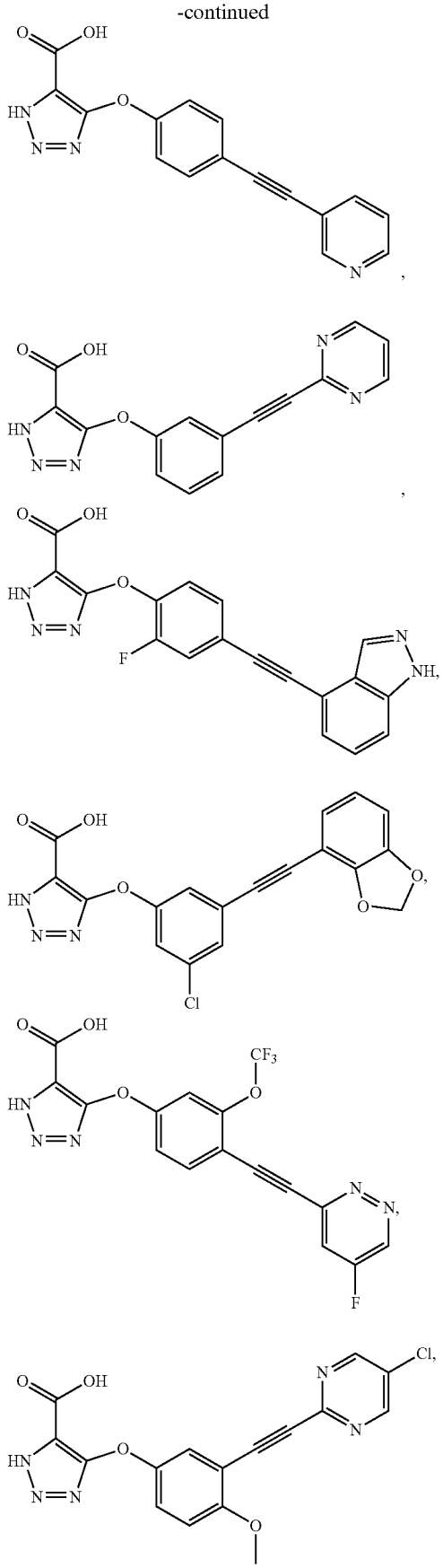
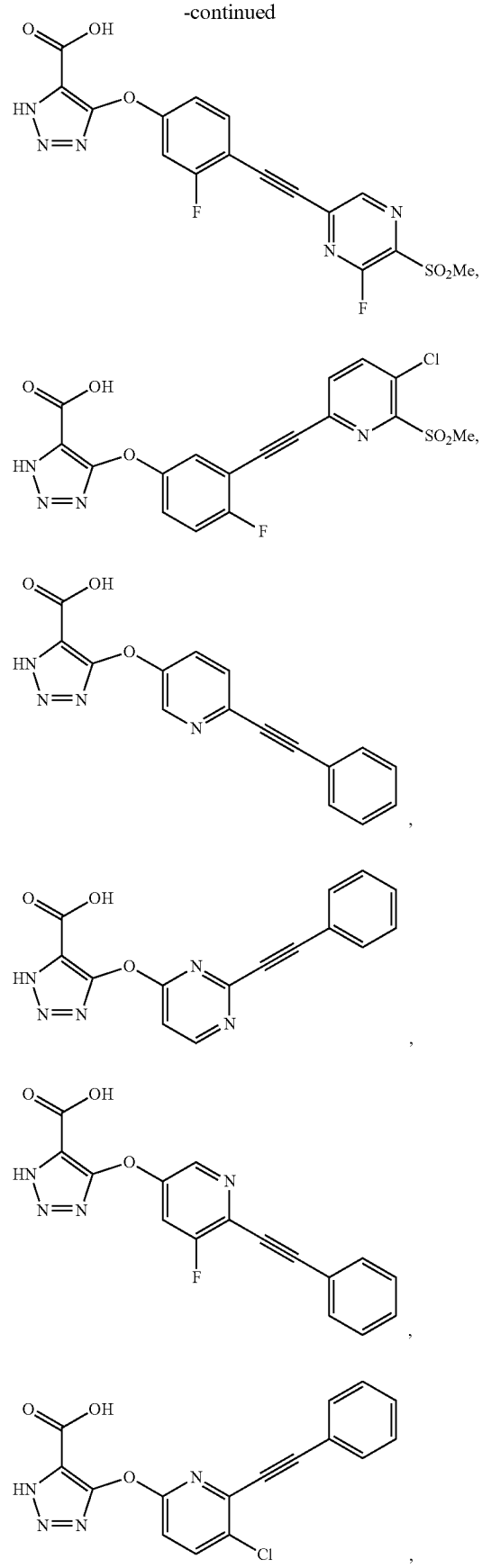

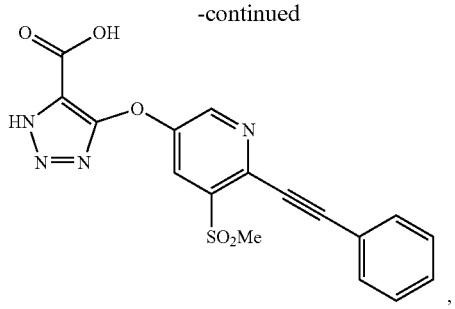
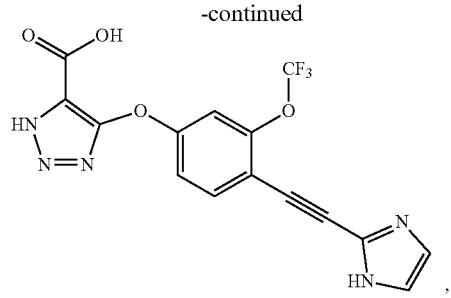
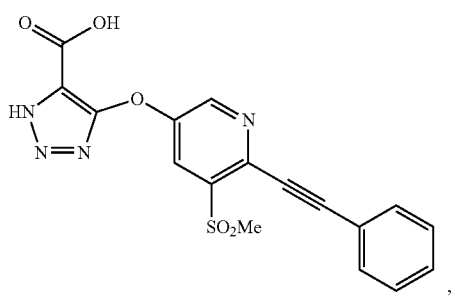
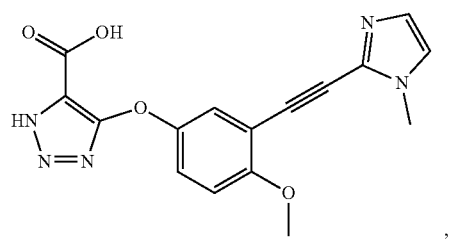
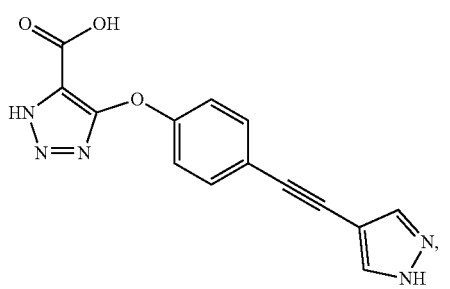
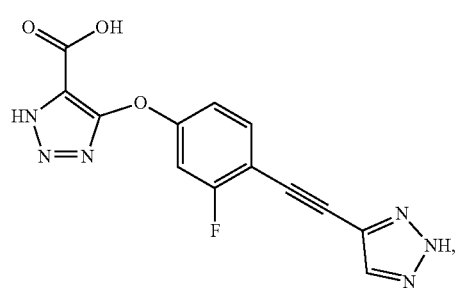
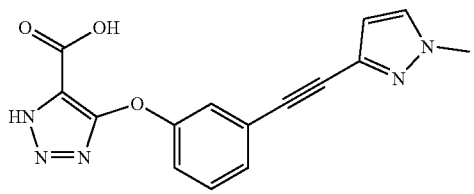
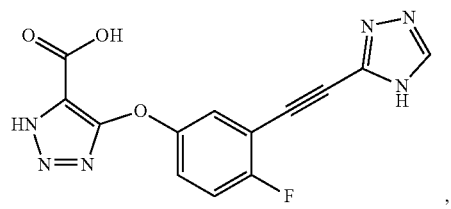
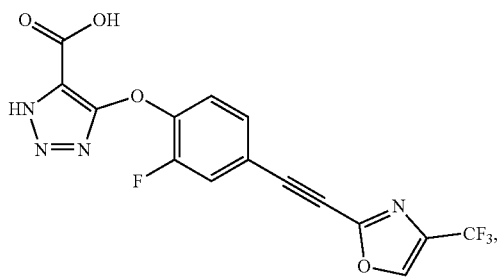
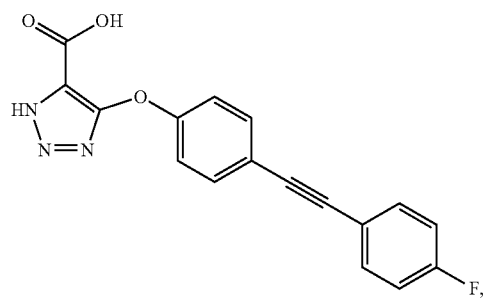
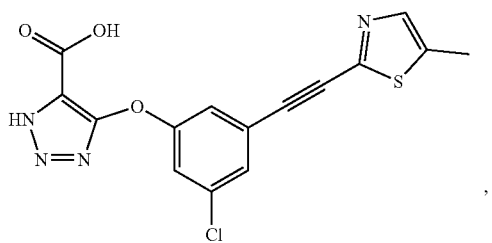
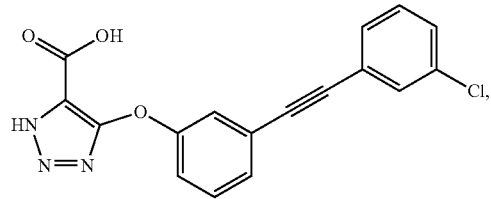

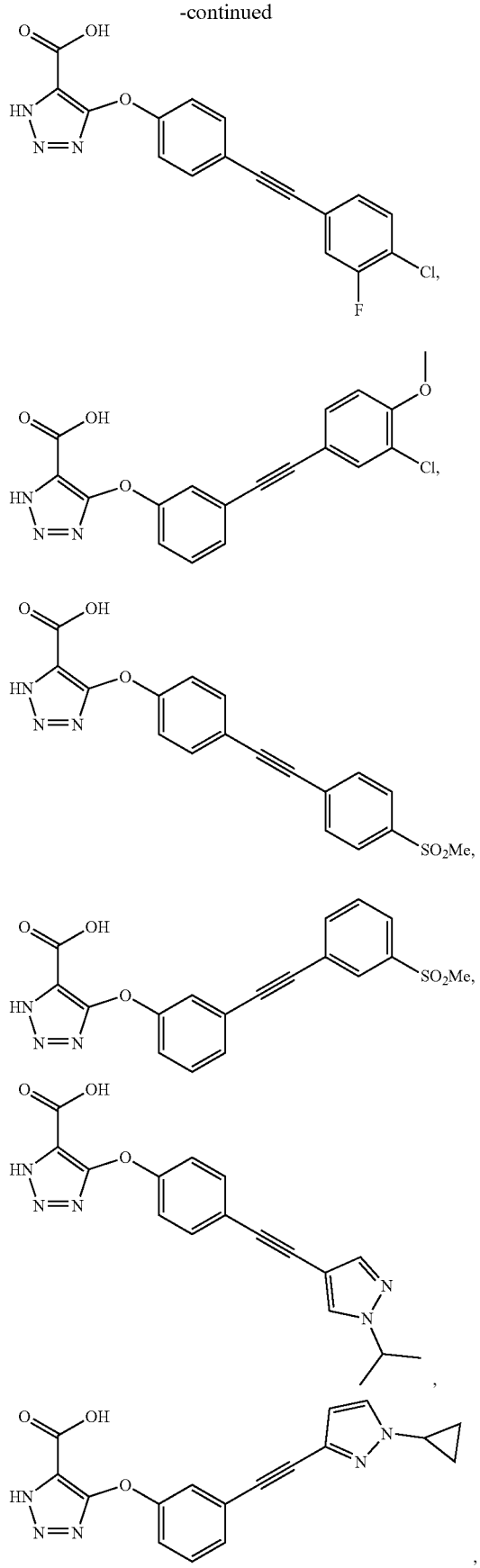
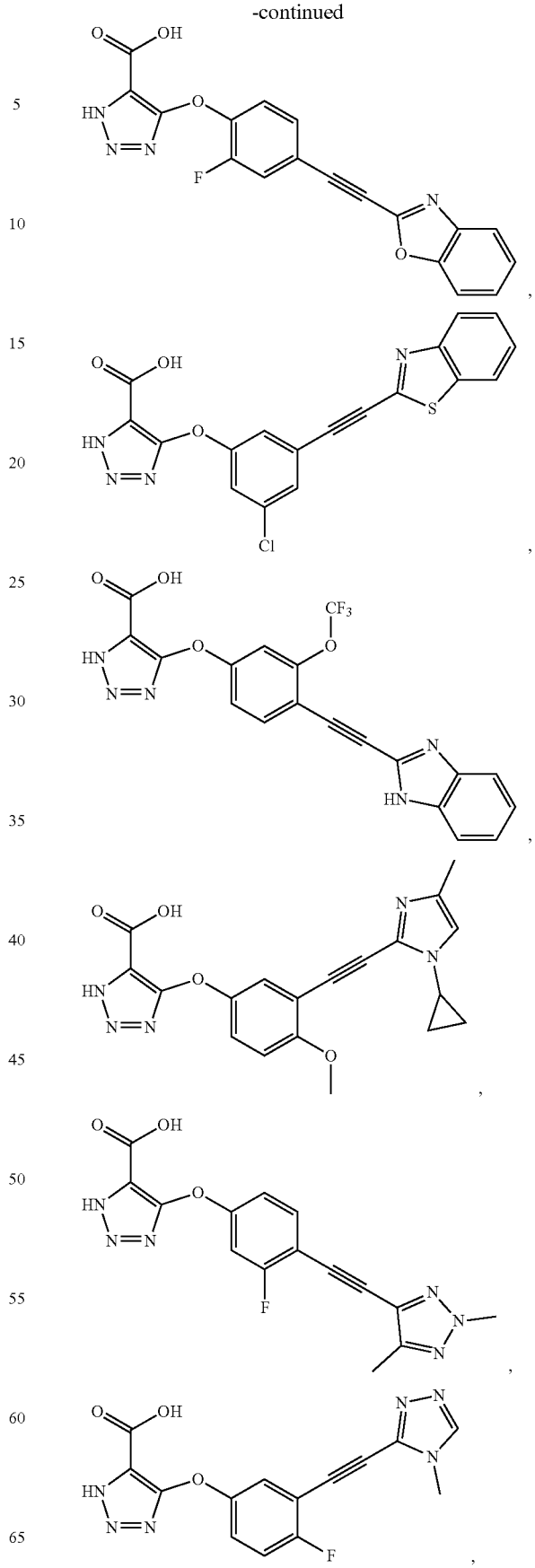

-continued
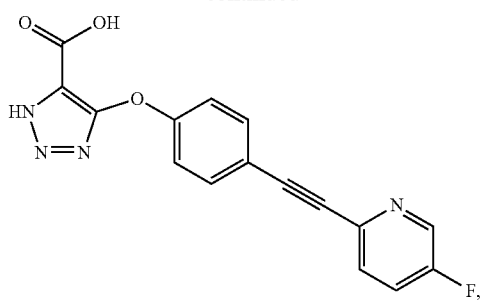
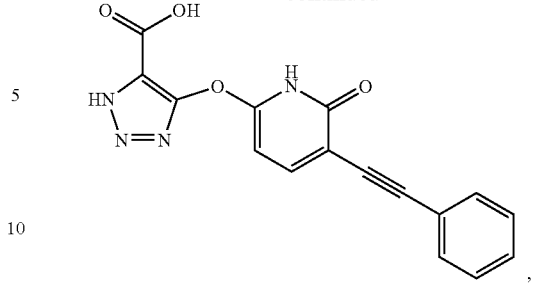
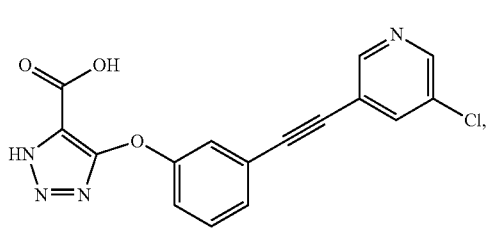
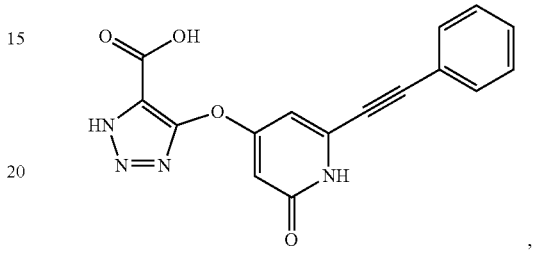
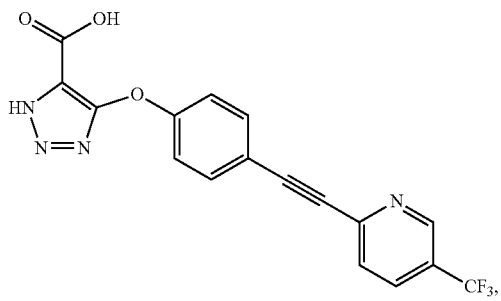
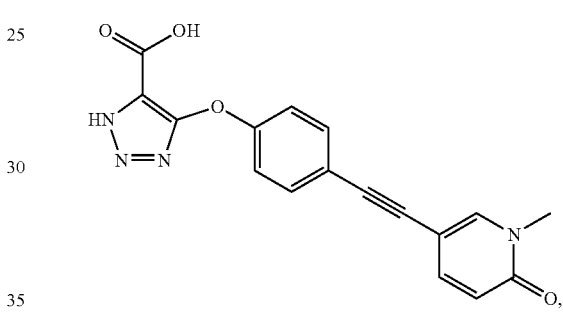
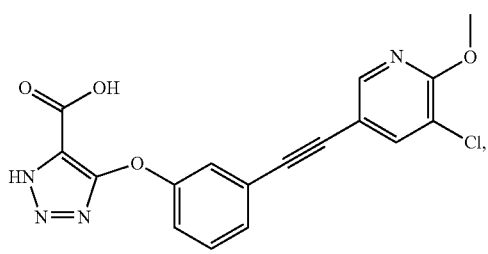
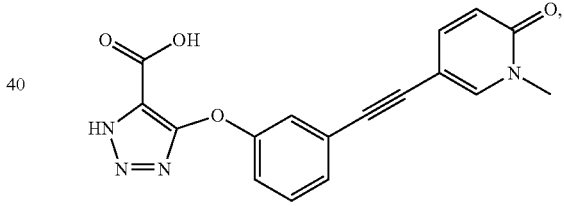
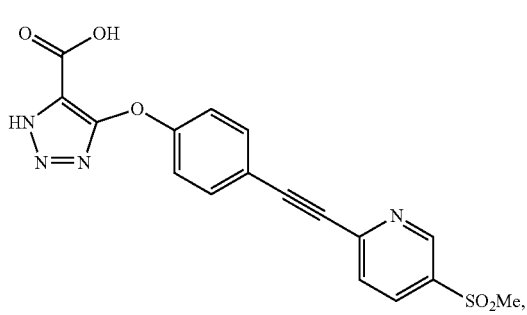
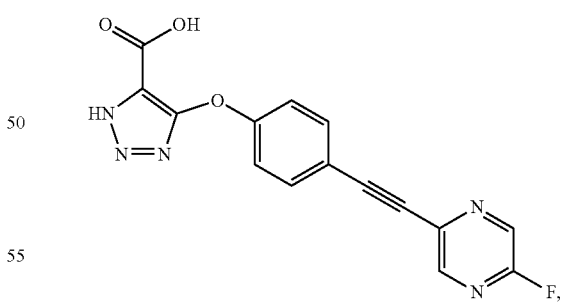
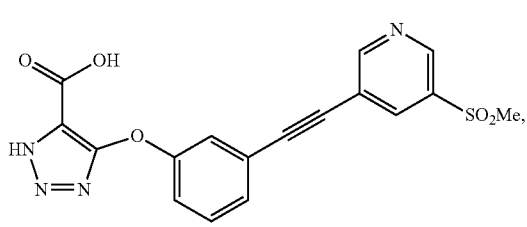
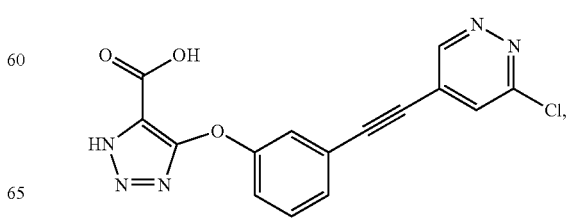

55
-continued
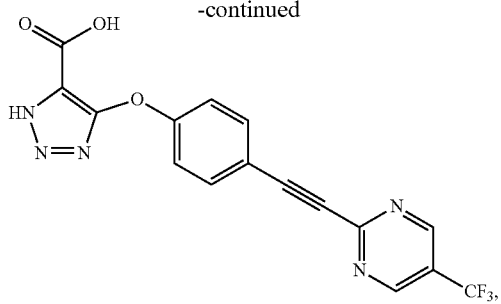
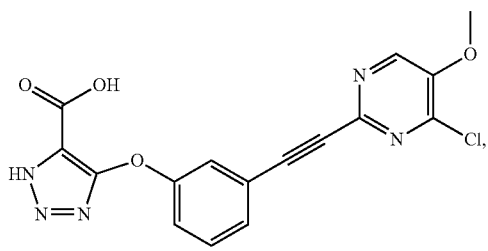
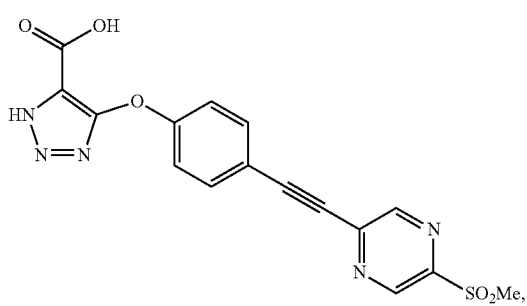
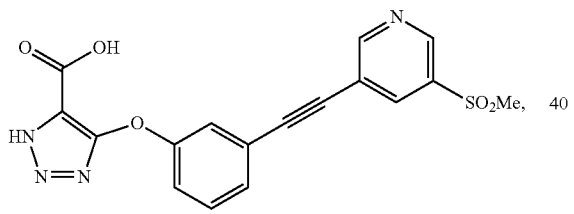
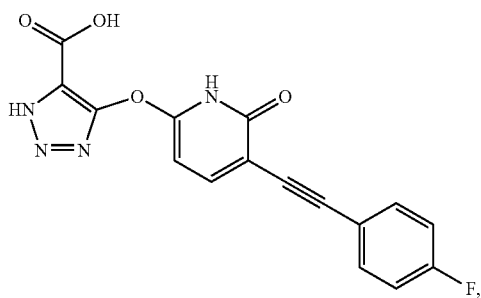
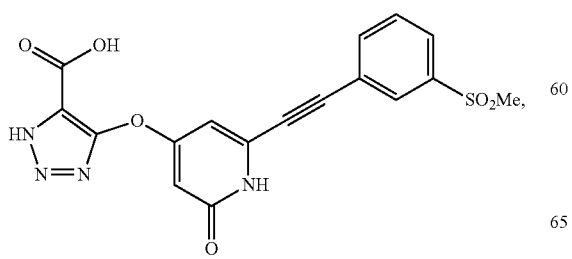
56
-continued
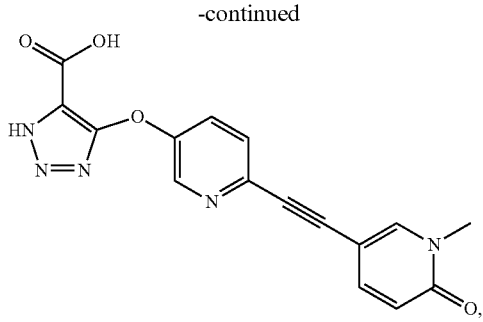
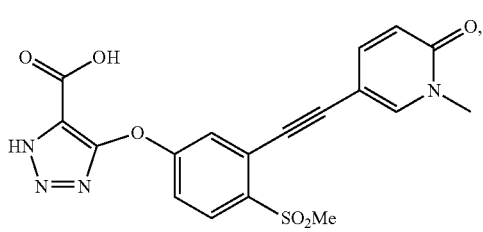
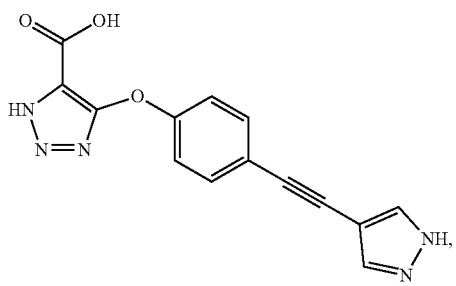
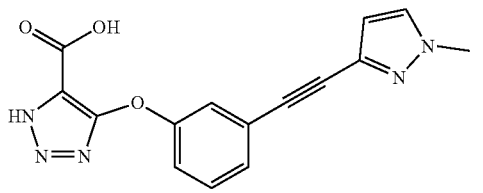
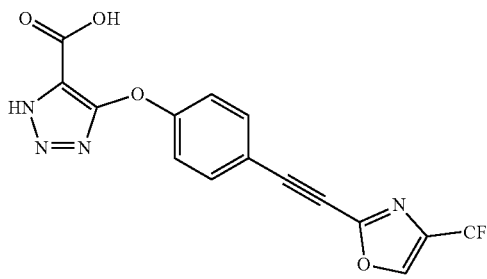
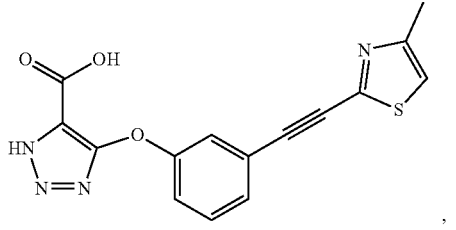

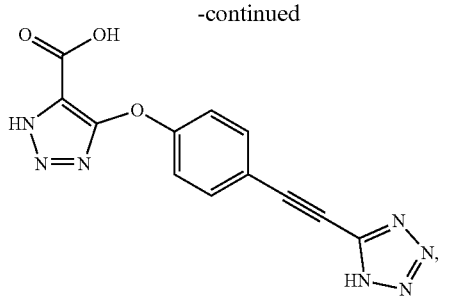,
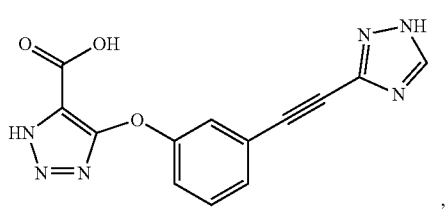,
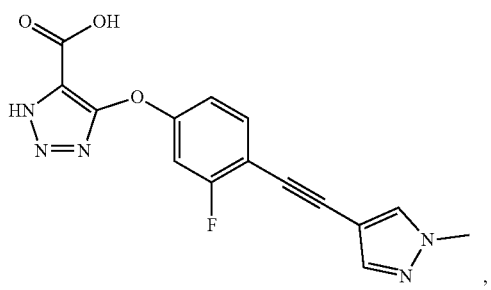,
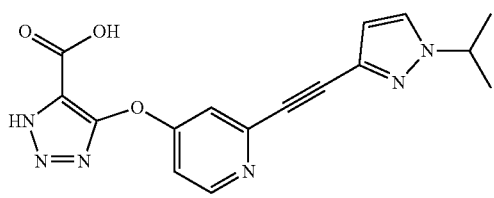,
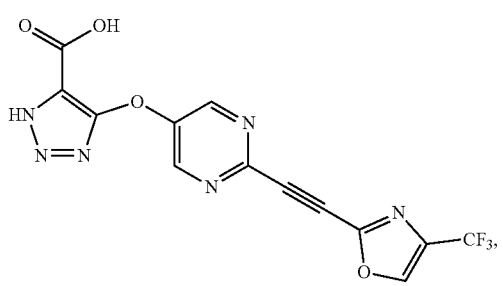,
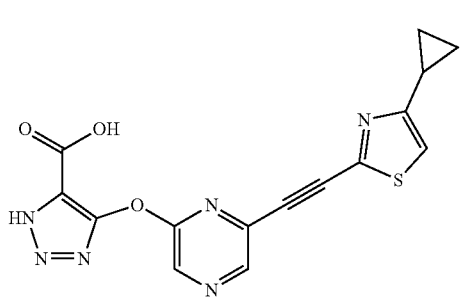,
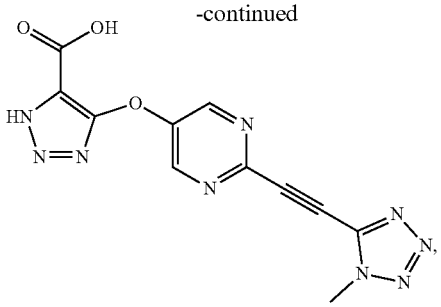,
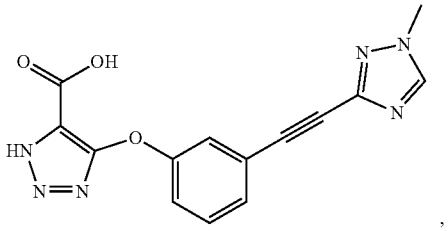,
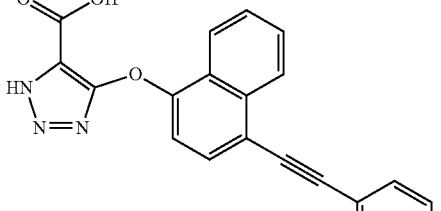,
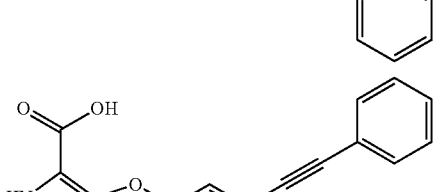,
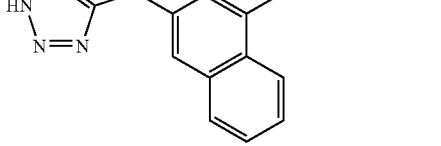,
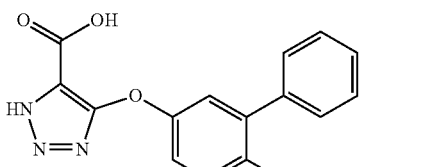,
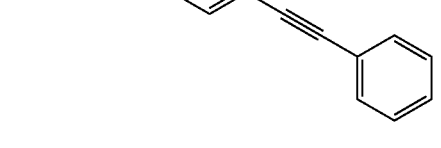,
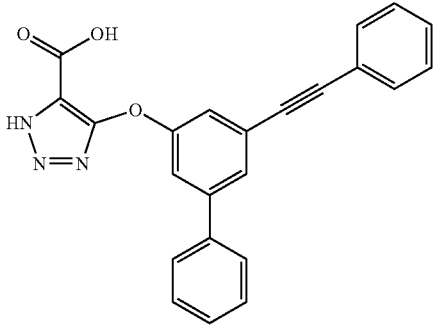,

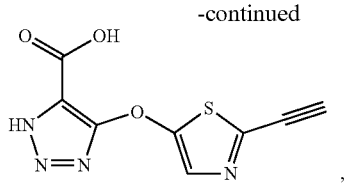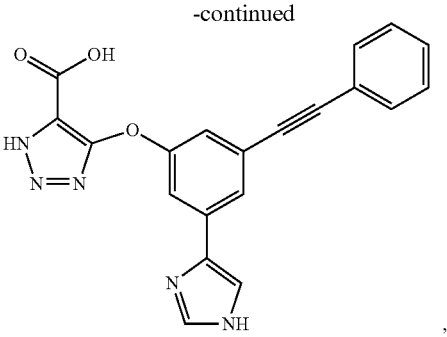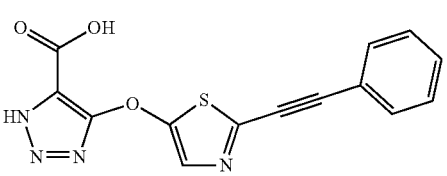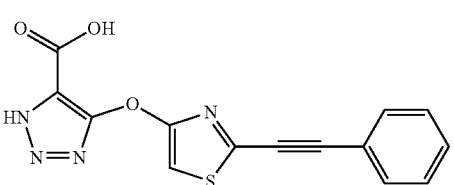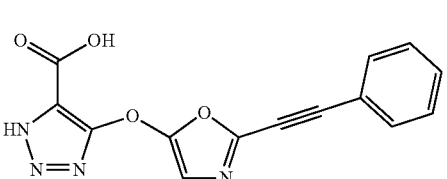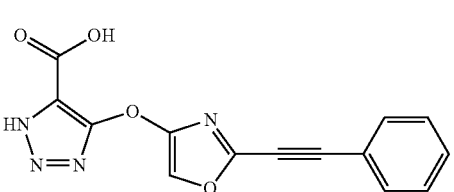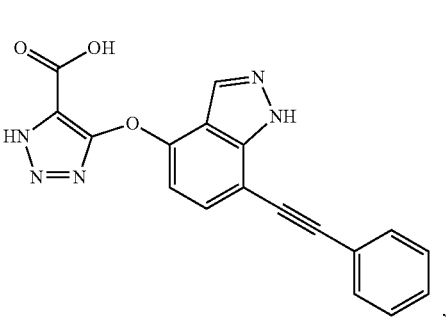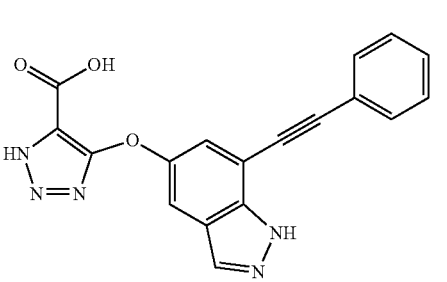

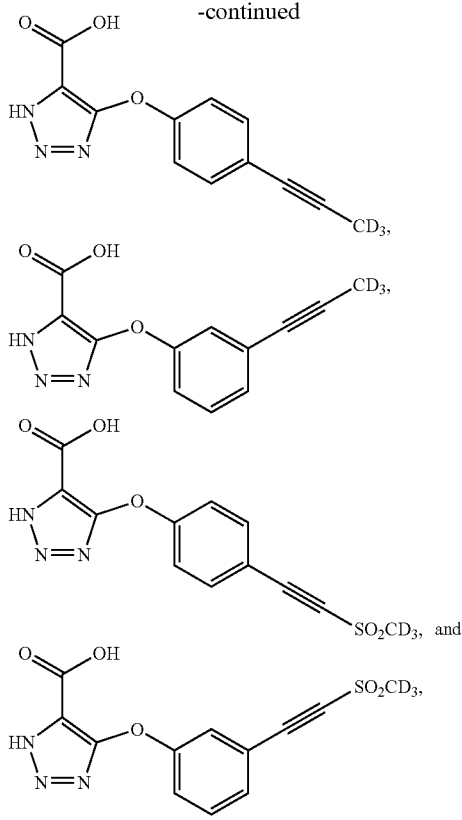

and/or a salt or ester thereof.

In certain embodiments, provided herein are compounds as disclosed herein in which one or more carbon-bound hydrogens may be replaced with deuterium. Such compounds are useful for, among other things, monitoring in assays, metabolic studies, and internal standards.

Also provided herein is a compound as disclosed herein, or a salt or prodrug thereof, for use as a medicament.

Also provided herein is a compound as disclosed herein, or a salt or prodrug thereof, for use in the manufacture of a medicament for preventing or treating an oxalate-related disease.

Also provided herein is a pharmaceutical composition comprising a compound as disclosed herein, or a salt or prodrug thereof, together with a pharmaceutically acceptable carrier.

In certain embodiments, the pharmaceutical composition is formulated for oral administration.

In certain embodiments, the pharmaceutical composition additionally comprises another therapeutic agent.

Also provided herein is a method of inhibiting glycolate oxidase (GOX) activity in a biological sample comprising contacting the biological sample with a pharmaceutical composition as disclosed herein, or a compound as disclosed herein, or a salt or prodrug thereof.

Also provided herein is a method of treating an oxalate-related disease in a subject in need thereof, comprising the step of administering to the subject a pharmaceutical composition as disclosed herein, or a compound as disclosed herein, or a salt or prodrug thereof.

In certain embodiments, the subject is a human.

In certain embodiments, the oxalate-related disease is hyperoxaluria.

In certain embodiments, the oxalate-related disease is primary hyperoxaluria.

In certain embodiments, the oxalate-related disease is primary hyperoxaluria type 1 (PH1).

In certain embodiments, the oxalate-related disease is enteric/secondary hyperoxaluria.

In certain embodiments, the oxalate-related disease is systemic oxalosis.

In certain embodiments, the oxalate-related disease is nephrolithiasis.

In certain embodiments, the oxalate-related disease is ureterolithiasis.

In certain embodiments, the oxalate-related disease is calcium oxalate kidney stones.

Also provided herein is a method of treating an oxalate-related disease in a subject in need thereof, comprising the sequential or co-administration of a pharmaceutical composition as disclosed herein, or a compound disclosed herein; and a second therapeutic agent.

Also provided herein is a pharmaceutical composition as disclosed herein, or a compound as disclosed herein, or a salt or prodrug thereof, for use in human therapy.

Also provided herein is a pharmaceutical composition as disclosed herein, or a compound as disclosed herein, or a salt or prodrug thereof, for use in treating an oxalate-related disease.

Also provided herein is the use of a compound as disclosed herein, or a salt or prodrug thereof, for the manufacture of a medicament to treat an oxalate-related disease.

Also provided herein are the following exemplary embodiments:

Embodiment P1: a compound of Formula I:

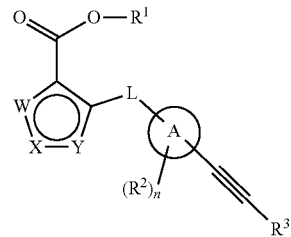

or a salt or prodrug thereof, wherein:

W is chosen from N, NH, S, and CCH$_3$;

X is chosen from N, NH, S, and O;

Y is N if W is NH, S, or CH$_3$; Y is NH if W is N;

R$^1$ is chosen from hydrogen, C$_1$-C$_6$ alkyl, and C$_1$-C$_6$ cycloalkyl;

L is chosen from CH$_2$, NH, NR$^4$, O, S, S(O), SO$_2$, and CR$^4$=CR$^5$;

A is chosen from monocyclic or bicyclic aryl, monocyclic or bicyclic heteroaryl, biaryl, and biheteroaryl;

each R$^2$ is independently chosen from hydrogen, halogen, C$_1$-C$_6$ alkyl, C$_2$-C$_6$ alkenyl, C$_2$-C$_6$ alkynyl, C$_3$-C$_6$ cycloalkyl, 3-6-membered heterocycloalkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ alkylsulfonyl, C$_1$-C$_6$ haloalkylsulfonyl, pentafluorosulfaneyl, sulfamoyl, C$_1$-C$_6$ alkylsulfamoyl, C$_1$-C$_6$ dialkylsulfamoyl, cyano, amino, N-acetylamino, C$_1$-C$_6$ alkylamino, C$_1$-C$_6$ dialkylamino, hydroxy, and C$_1$-C$_6$ hydroxyalkyl;

n is 0, 1, 2, or 3;

R$^3$ is chosen from hydrogen, C$_1$-C$_6$ alkyl, C$_2$-C$_6$ alkenyl, C$_2$-C$_6$ alkynyl, C$_3$-C$_6$ cycloalkyl, 3-10-membered heterocycloalkyl, $C_6$-$C_{10}$ aryl, 5-10-membered heteroaryl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_3$-$C_6$ cycloalkyl $C_1$-$C_6$ alkylsulfonyl, $C_3$-$C_6$ heterocycloalkyl $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl, any of which that comprises a cyclic group is optionally substituted with 1, 2, or 3 $R^6$ groups;

$R^4$ and $R^5$ are each independently chosen from hydrogen and $C_1$-$C_6$ alkyl; and each $R^6$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 4-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl.

Embodiment P2: a compound as recited in Embodiment P1, wherein:

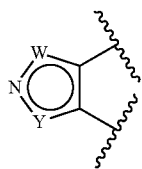

is chosen from

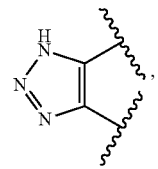 , 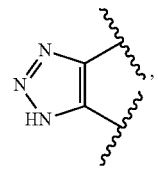 , 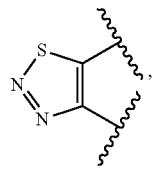 ,

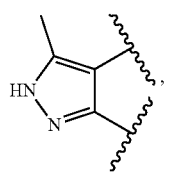 , 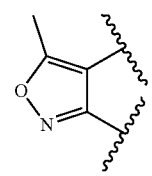 , 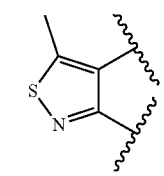 ,

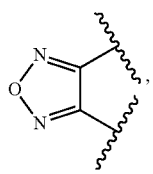 and 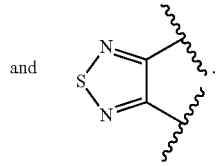 .

Embodiment P3: a compound as recited in Embodiment P1, wherein X is N.

Embodiment P4: a compound as recited in any of Embodiments P1-P3, having structural formula II

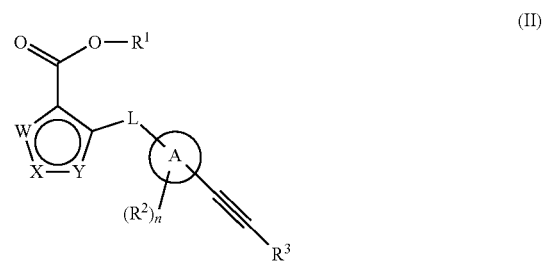

or a salt or prodrug thereof, wherein:

W is chosen from N, NH, S, and $CCH_3$;

Y is N if W is NH, S, or $CH_3$; Y is NH if W is N;

$R^1$ is chosen from hydrogen, $C_1$-$C_6$ alkyl, and $C_1$-$C_6$ cycloalkyl;

L is chosen from $CH_2$, NH, $NR^4$, O, S, S(O), $SO_2$, and $CR^4$=$CR^5$;

A is chosen from monocyclic or bicyclic aryl, monocyclic or bicyclic heteroaryl, biaryl, and biheteroaryl;

each $R^2$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 3-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl;

n is 0, 1, 2, or 3;

$R^3$ is chosen from hydrogen, $C_1$-$C_6$ alkyl, $C_2$-$C_6$ alkenyl, $C_2$-$C_6$ alkynyl, $C_3$-$C_6$ cycloalkyl, 3-10-membered heterocycloalkyl, $C_6$-$C_{10}$ aryl, 5-10-membered heteroaryl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_3$-$C_6$ cycloalkyl $C_1$-$C_6$ alkylsulfonyl, $C_3$-$C_6$ heterocycloalkyl $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl, any of which that comprises a cyclic group is optionally substituted with 1, 2, or 3 $R^6$ groups;

$R^4$ and $R^5$ are each independently chosen from hydrogen and $C_1$-$C_6$ alkyl; and each $R^6$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 4-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl.

Embodiment P5: a compound as recited in any of Embodiments P1-P4, wherein W is N or NH.

Embodiment P6: a compound as recited in any of Embodiments P1-P5, wherein W is NH, and Y is N.

Embodiment P7: a compound as recited in any of Embodiments P1-P5, wherein

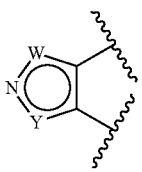

is chosen from

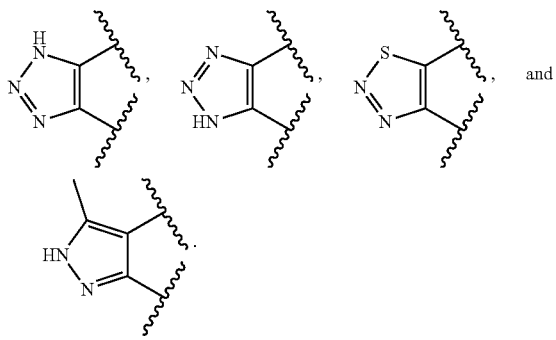

Embodiment P8: a compound as recited in Embodiment P7, wherein

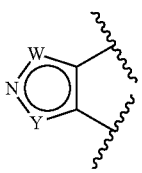

is chosen from

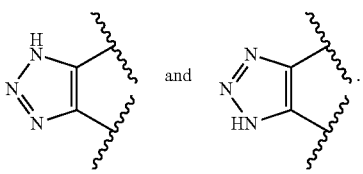 [SMILES: *c1nn[nH]c1* ; *c1nn[nH]c1*]

Embodiment P9: a compound as recited in any of Embodiments P1-P8, wherein L is O.

Embodiment P10: a compound as recited in any of Embodiments P1-P9, wherein $R^1$ is hydrogen.

Embodiment P11: a compound as recited in any of Embodiments P1-P10, wherein A is chosen from phenyl and $C_6$ monocyclic heteroaryl.

Embodiment P12: a compound as recited in Embodiment P11, wherein A is chosen from phenyl, pyridinyl, pyridazinyl, pyrimidinyl, and pyridinonyl.

Embodiment P13: a compound as recited in any of Embodiments P1-P10, wherein A is monocyclic aryl optionally substituted with one or more $R^2$ groups.

Embodiment P14: a compound as recited in any of Embodiments P1-P10, wherein A is biaryl optionally substituted with one or more $R^2$ groups.

Embodiment P15: a compound as recited in any of Embodiments P1-P10, wherein A is bicyclic aryl optionally substituted with one or more $R^2$ groups.

Embodiment P16: a compound as recited in any of Embodiments P1-P10, wherein A is monocyclic heteroaryl optionally substituted with one or more $R^2$ groups.

Embodiment P17: a compound as recited in any of Embodiments P1-P10, wherein A is bicyclic heteroaryl optionally substituted with one or more $R^2$ groups.

Embodiment P18: a compound as recited in any of Embodiments P1-P10, wherein A is chosen from phenyl, biphenyl, naphthyl, pyridinylphenyl, phenylpyridinyl, and bipyridinyl any of which is optionally substituted with one or more $R^2$ groups.

Embodiment P19: a compound as recited in any of Embodiments P1-P10, wherein A is phenyl optionally substituted with one or more $R^2$ groups.

Embodiment P20: a compound as recited in any of Embodiments P1-P10, wherein A is biphenyl optionally substituted with one or more $R^2$ groups.

Embodiment P21: a compound as recited in any of Embodiments P1-P10, wherein A is naphthyl optionally substituted with one or more $R^2$ groups.

Embodiment P22: a compound as recited in any of Embodiments P1-P10, wherein A is pyridinylphenyl optionally substituted with one or more $R^2$ groups.

Embodiment P23: a compound as recited in any of Embodiments P1-P10, wherein A is phenylpyridinyl optionally substituted with one or more $R^2$ groups.

Embodiment P24: a compound as recited in any of Embodiments P1-P10, wherein A is bipyridinyl optionally substituted with one or more $R^2$ groups.

Embodiment P25: a compound as recited in any of Embodiments P1-P24, wherein n is chosen from 0, 1, or 2.

Embodiment P26: a compound as recited in any of Embodiments P1-P25, wherein $R^3$ is chosen from phenyl, 5-10-membered heteroaryl, $C_3$-$C_6$ cycloalkyl, and 3-10-membered heterocycloalkyl.

Embodiment P27: a compound as recited in Embodiment P26, wherein $R^3$ is chosen from phenyl, pyridinyl, pyridazinyl, pyrimidinyl, pyridinonyl, pyrrolyl, pyrazolyl, imidazolyl, isoxazolyl, thiazolyl, triazolyl, cyclopropyl, cyclobutyl, cyclopentyl, cyclohexyl, furanyl, pyranyl, and piperidinyl.

Embodiment P28: a compound of structural Formula III

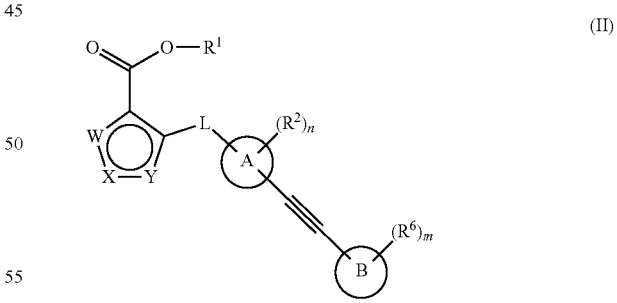

(II)

or a salt or prodrug thereof, wherein:
W is chosen from N, NH, S, and $CCH_3$;
Y is N if W is NH, S, or $CH_3$; Y is NH if W is N;
$R^1$ is chosen from hydrogen, $C_1$-$C_6$ alkyl, and $C_1$-$C_6$ cycloalkyl;
L is chosen from $CH_2$, NH, $NR^4$, O, S, S(O), $SO_2$, and $CR^4$=$CR^5$;
A is chosen from monocyclic or bicyclic aryl, monocyclic or bicyclic heteroaryl, biaryl, and biheteroaryl, optionally substituted with one or more $R^2$ groups;

B is chosen from $C_3$-$C_6$ cycloalkyl, 3-12-membered heterocycloalkyl, $C_6$-$C_{10}$ aryl, and 5-10-membered heteroaryl;

each $R^2$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl;

n is 0, 1, 2, or 3;

$R^4$ and $R^5$ are each independently chosen from hydrogen or $C_1$-$C_6$ alkyl;

each $R^6$ is independently chosen from hydrogen, halogen, $C_1$-$C_6$ alkyl, $C_2$-$C_6$ alkenyl, $C_2$-$C_6$ alkynyl, $C_3$-$C_6$ cycloalkyl, 4-6-membered heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ haloalkylsulfonyl, pentafluorosulfaneyl, sulfamoyl, $C_1$-$C_6$ alkylsulfamoyl, $C_1$-$C_6$ dialkylsulfamoyl, cyano, amino, N-acetylamino, $C_1$-$C_6$ alkylamino, $C_1$-$C_6$ dialkylamino, hydroxy, and $C_1$-$C_6$ hydroxyalkyl; and m is 0, 1, 2, or 3.

Embodiment P29: a compound as recited in Embodiment P28, wherein W is N or NH; Y is N if W is NH; and Y is NH if W is N.

Embodiment P30: a compound as recited in any of Embodiments P28-P29, wherein W is N or NH.

Embodiment P31: a compound as recited in Embodiment P30, wherein W is NH, and Y is N.

Embodiment P32: a compound as recited in any of Embodiments P28-P31, wherein

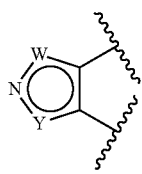

is chosen from

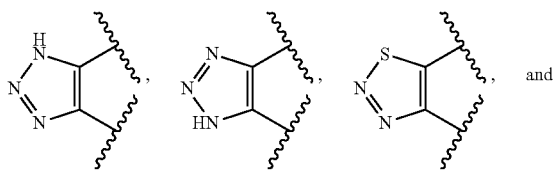

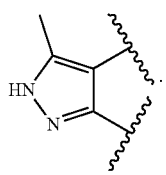

Embodiment P33: a compound as recited in Embodiment P32, wherein

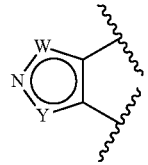

is chosen from

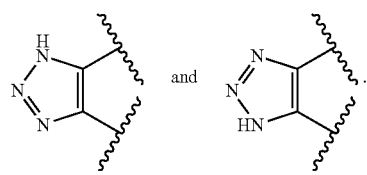 [SMILES: *c1nn[nH]c1* ; *c1nn[nH]c1*]

Embodiment P34: a compound as recited in any of Embodiments P28-P33, wherein L is O.

Embodiment P35: a compound as recited in any of Embodiments P28-P34, wherein $R^1$ is hydrogen.

Embodiment P36: a compound as recited in any of Embodiments P28-P35, wherein A is chosen from phenyl and $C_6$ monocyclic heteroaryl.

Embodiment P37: a compound as recited in Embodiment P36, wherein A is chosen from phenyl, pyridinyl, pyridazinyl, pyrimidinyl, and pyridinonyl.

Embodiment P38: a compound as recited in any of Embodiments P28-P35, wherein A is monocyclic aryl optionally substituted with one or more $R^2$ groups.

Embodiment P39: a compound as recited in any of Embodiments P28-P35, wherein A is biaryl optionally substituted with one or more $R^2$ groups.

Embodiment P40: a compound as recited in any of Embodiments P28-P35, wherein A is bicyclic aryl optionally substituted with one or more $R^2$ groups.

Embodiment P41: a compound as recited in any of Embodiments P28-P35, wherein A is monocyclic heteroaryl optionally substituted with one or more $R^2$ groups.

Embodiment P42: a compound as recited in any of Embodiments P28-P35, wherein A is bicyclic heteroaryl optionally substituted with one or more $R^2$ groups.

Embodiment P43: a compound as recited in Embodiment P42, wherein A is chosen from phenyl, biphenyl, naphthyl, pyridinylphenyl, phenylpyridinyl, and bipyridinyl any of which is optionally substituted with one or more $R^2$ groups.

Embodiment P44: a compound as recited in any of Embodiments P28-P35, wherein A is phenyl optionally substituted with one or more $R^2$ groups.

Embodiment P45: a compound as recited in any of Embodiments P28-P35, wherein A is biphenyl optionally substituted with one or more $R^2$ groups.

Embodiment P46: a compound as recited in any of Embodiments P28-P35, wherein A is naphthyl optionally substituted with one or more $R^2$ groups.

Embodiment P47: a compound as recited in any of Embodiments P28-P35, wherein A is pyridinylphenyl optionally substituted with one or more $R^2$ groups.

Embodiment P48: a compound as recited in any of Embodiments P28-P35, wherein A is phenylpyridinyl optionally substituted with one or more $R^2$ groups.

Embodiment P49: a compound as recited in any of Embodiments P28-P35, wherein A is bipyridinyl optionally substituted with one or more $R^2$ groups.

Embodiment P50: a compound as recited in any of Embodiments P28-P49, wherein n is chosen from 0, 1, or 2.

Embodiment P51: a compound as recited in any of Embodiments P28-P50, wherein B is chosen from phenyl, 5-10-membered heteroaryl, $C_3$-$C_6$ cycloalkyl, and 3-10-membered heterocycloalkyl.

Embodiment P52: a compound as recited in Embodiment P51, wherein B is chosen from phenyl, pyridinyl, pyridazinyl, pyrimidinyl, pyridinonyl, pyrrolyl, pyrazolyl, imidazolyl, isoxazolyl, thiazolyl, triazolyl, cyclopropyl, cyclobutyl, cyclopentyl, cyclohexyl, furanyl, pyranyl, and piperidinyl.

Embodiment P53: a compound chosen from Examples 3-231, or a salt or prodrug thereof.

Embodiment P54: a compound as recited in any of Embodiments P1-P53, or a salt or prodrug thereof, for use as a medicament.

Embodiment P55: a compound as recited in any of Embodiments P1-P53, or a salt or prodrug thereof, for use in the manufacture of a medicament for preventing or treating an oxalate-related disease.

Embodiment P56: a pharmaceutical composition comprising a compound as recited in any of Embodiments P1-P53, a salt or prodrug thereof together with a pharmaceutically acceptable carrier.

Embodiment P57: the pharmaceutical composition as recited in Embodiment P56, formulated for oral administration.

Embodiment P58: the pharmaceutical composition as recited in any of Embodiments P56-P57, additionally comprises another therapeutic agent.

Embodiment P59: a method of inhibiting glycolate oxidase (GOX) activity in a biological sample comprising contacting the biological sample with a pharmaceutical composition as recited in any of Embodiments P56P58, or a compound as recited in any of Embodiments P1-P53, or a salt or prodrug thereof.

Embodiment P60: a method of treating an oxalate-related disease in a subject in need thereof, comprising the step of administering to the subject a pharmaceutical composition as recited in any of Embodiments 56-58, or a compound as recited in any of Embodiments P1-P53, or a salt or prodrug thereof.

Embodiment P61: the method as recited in Embodiment P60, wherein the subject is a human.

Embodiment P62: the method as recited in any of Embodiments P59P60, wherein the oxalate-related disease is hyperoxaluria.

Embodiment P63: the method as recited in any of Embodiments P59P60, wherein the oxalate-related disease is primary hyperoxaluria.

Embodiment P64: the method as recited in Embodiment P63, wherein the oxalate-related disease is primary hyperoxaluria type 1 (PH1).

Embodiment P65: the method as recited in any of Embodiments P59P60, wherein the oxalate-related disease is enteric/secondary hyperoxaluria.

Embodiment P66: the method as recited in any of Embodiments P59P60, wherein the oxalate-related disease is systemic oxalosis.

Embodiment P67: the method as recited in any of Embodiments P59P60, wherein the oxalate-related disease is nephrolithiasis.

Embodiment P68: the method as recited in any of Embodiments P59P60, wherein the oxalate-related disease is ureterolithiasis.

Embodiment P69: the method as recited in any of Embodiments P59P60, wherein the oxalate-related disease is calcium oxalate kidney stones.

Embodiment P70: a method of treating an oxalate-related disease in a subject in need thereof, comprising the sequential or co-administration of a pharmaceutical composition as recited in any of Embodiments P56P58, or a compound as recited in any of Embodiments P1-P53, or a salt or prodrug thereof; and a second therapeutic agent.

Embodiment P71: a pharmaceutical composition as recited in any of Embodiments P56-P58, or a compound as recited in any of Embodiments P1-P53, or a salt or prodrug thereof, for use in human therapy.

Embodiment P72: a pharmaceutical composition as recited in any of Embodiments 56-58, or a compound as recited in any of Embodiments P1-P53, or a salt or prodrug thereof, for use in treating an oxalate-related disease.

Embodiment P73: the use of a compound as recited in any of Embodiments P1-P53, or a salt or prodrug thereof for the manufacture of a medicament to treat an oxalate-related disease.

In certain embodiments provided are compounds as disclosed herein in which one or more carbon-bound hydrogens may be replaced with deuterium. Such compounds are useful for, among other things, monitoring in assays, metabolic studies, and internal standards.

Definitions

As used herein, the terms below have the meanings indicated.

When introducing elements of the present disclosure or the embodiment(s) thereof, the articles "a," "an," "the" and "said" are intended to mean that there are one or more of the elements. The terms "comprising," "including" and "having" are inclusive and mean that there may be additional elements other than the listed elements.

The term "and/or" when in a list of two or more items, means that any of the listed items can be employed by itself or in combination with one or more of the listed items. For example, the expression "A and/or B" means either or both of A and B, i.e., A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about" qualifies the numerical values that it modifies, denoting such a value as a variable within a margin of error. When no margin of error, such as a standard deviation to a mean value given in a chart or table of data, is recited, the term "about" means that range which would encompass the recited value and the range which would be included by rounding up or down to that figure, considering significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl, and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl comprises from 2 to 6 carbon atoms. The term "alkenylene" refers to a carbon-carbon double bond system attached at two or more positions such as ethenylene (—CH═CH—, —C::C—). Examples of suitable alkenyl radicals include ethenyl, propenyl, 2-methylpropenyl, 1,4-butadienyl, and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl comprises between 1 and 10 carbon atoms. In further embodiments, the alkyl comprises between 1 and 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "straight-chain alkyl" refers to an alkyl radical containing from 1 to 20 carbon atoms in a linear sequence without branches. Examples of straight-chain alkyl radicals include n-octyl (—CH$_2$CH$_2$CH$_2$CH$_2$CH$_2$CH$_2$CH$_2$CH$_2$—), n-butyl (—CH$_2$CH$_2$CH$_2$CH$_2$—), and ethyl (—CH$_2$CH$_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like. Additionally, the alkyl groups of a dialkylamino may combine to form heterocycloalkyl, either of which is optionally substituted.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butynyl, butyn-2-yl, pentynyl, 3-methylbutynyl, hexyn-2-yl, and the like. Unless otherwise specified, the term "alkynyl" may include "alkynylene" groups.

The terms "amido" and "carbamoyl" refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to an RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which is optionally substituted.

The term "aryl," as used herein, alone or in combination, means a carbocyclic aromatic system containing one, two or three rings wherein such polycyclic ring systems are fused. The term "aryl" embraces aromatic groups such as phenyl, naphthyl, anthracenyl, and phenanthryl.

The term "arylene," as used herein, alone or in combination, refers to an aryl group attached at two or more positions, such as phenylene (—C$_6$H$_4$—, which encompasses

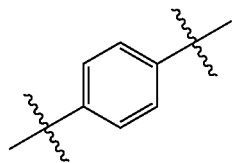 [SMILES: *c1ccc(*)cc1]

and the corresponding meta- and para-isomers). Unless otherwise specified, the term "aryl" may include "arylene" groups.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "biaryl," as used herein, refers to a first aryl group attached to the parent molecular moiety, with the first aryl group substituted with a second aryl group. Examples of biaryl groups include biphenyl, 2-(2-pyridyl)phenyl, and 5-(2-naphthyl)-thien-1-yl.

The term "biheteroaryl," as used herein, refers to a first heteroaryl group attached to the parent molecular moiety, with the first heteroaryl group substituted with a second heteroaryl group. Examples of biaryl groups include 3,3'-bipyridinyl.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to an —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl (—C(O)H]) and, in combination, is a —C(O)— group.

The term "carboxyl" or "carboxy," as used herein, refers to —C(O)OH or the corresponding "carboxylate" anion, such as is in a carboxylic acid salt. An "O-carboxy" group refers to an RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl comprises from 5 to 7 carbon atoms. When the cycloalkyl is partially saturated, it is partially unsaturated and may be referred to as a "cycloalkenyl," comprising at least on C=C. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like.

"Bicyclic" and "tricyclic" as used herein are intended to include both fused ring systems, such as decahydronaphtha-lene, octahydronaphthalene, as well as the multicyclic (multicentered) saturated or partially unsaturated type. The latter type of isomer is exemplified in general by bicyclo[1.1.1]pentane, camphor, adamantane, and bicyclo[3,2,1]octane.

The term "cycloalkylene," refers to a cycloalkyl group attached at two or more positions, such as cyclohexylene (—$C_6H_{10}$—, which encompasses,

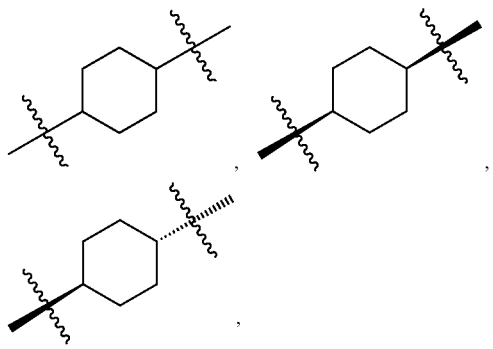

and the corresponding 1,2- and 1,4-isomers). Unless otherwise specified, the term "cycloalkyl" may include "cycloalkylene" groups.

The term "diazanaphthalene," as used herein, alone or in combination, refers to analogs of naphthalene, having formula $C_8H_6N_2$, in which two >CH groups have been replaced with two >N groups. Examples of diazanaphthalene include cinnoline, phthalazine, and 1,8-diazanaphthalene.

The term "bicyclic ring system" as used herein refers to a group which contains two distinct rings of atoms. In certain embodiments, bicyclic ring systems contain a single atom common to both ring systems. In certain embodiments, bicyclic ring systems contain two or more atoms common to both ring systems. Examples of compounds with bicyclic ring systems include decalin, norbornane, and pinene. Further examples of compounds with bicyclic ring systems are bicyclo[1.1.1]pentane, bicyclo[3.1.0]hexane, 1,4-diazabicyclo[2.2.2]octane, 1,5-diazabicyclo[4.3.0]non-5-ene, and 7-oxabicyclo[2.2.1]heptadiene. In certain embodiments, the bicyclic ring system is

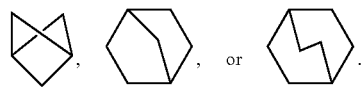

The term "tricyclic ring system," as used herein, refers to a group that contains three distinct rings of atoms. In certain embodiments, bicyclic ring systems contain a single atom common to two rings. In certain embodiments, bicyclic ring systems contain two or more atoms common to two rings. Examples of compounds with tricyclic ring systems include perhydroanthracene, cedrene, and taxadiene. Further examples of compounds with tricyclic ring systems are tricyclo[3.1.0.0$^{2,4}$]hexane, tricyclo[3.3.1.1$^{3,7}$]decane, and cyclopentadiene diepoxide.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods, such as mass spectrometry and nuclear magnetic resonance spectroscopy.

The term "is/are deuterium," when used to describe a given position in a molecule such as $R_1$, $R_2$, $R_3$, $R_4$, $R_5$, $R_6$, $R_7$, $R_8$, $R_9$, $R_{10}$, and $R_{11}$ or the symbol "D," when used to represent a given position in a drawing of a molecular structure, means that the specified position is enriched with deuterium above the naturally occurring distribution of deuterium. In an embodiment, deuterium enrichment is of no less than about 1%, in another no less than about 5%, in another no less than about 10%, in another no less than about 20%, in another no less than about 50%, in another no less than about 70%, in another no less than about 80%, in another no less than about 90%, or another no less than about 98% of deuterium at the specified position.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo" or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl, and polyhaloalkyl radicals. A monohaloalkyl radical, for one example, may have an iodo, bromo, chloro, or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "halocycloalkyl," as used herein, alone or in combination, refers to a cycloalkyl radical having the meaning as defined above wherein one or more hydrogens are replaced with a halogen. The halocycloalkyl may be saturated, or partially saturated monocyclic, bicyclic or tricyclic alkyl group wherein each cyclic moiety contains from 3 to 12 carbon atom ring members and which may optionally be a benzo fused ring system which is optionally substituted as defined herein. Specifically embraced are monohalocycloalkyl, dihalocycloalkyl, and polyhalocycloalkyl radicals. A monocyclohaloalkyl radical, for one example, may have an iodo, bromo, chloro, or fluoro atom within the radical. Dihalo and polyhalocycloalkyl radicals may have two or more of the same halo atoms or a combination of different halo radicals. Examples of halocycloalkyl radicles include fluorocyclopropyl, fluorocyclobutyl, difluorocyclobutyl, fluorocyclohexyl, difluorocyclohexyl.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms chosen from O, N, and S, and wherein the N and S atoms may optionally be oxidized. The N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one fused rings is aromatic, which contains at least one atom chosen from O, S, and N. In certain embodiments, the heteroaryl comprises from 1 to 4 heteroatoms as ring members. In further embodiments, the heteroaryl comprises from 1 to 2 heteroatoms as ring members. In certain embodiments, the heteroaryl comprises from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, benzothiazolyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heteroarylene," as used herein, alone or in combination, refers to a heteroaryl group attached at two or more positions, such as pyrimidinylene (—C$_5$H$_3$N—, which encompasses the 2,3 isomer:

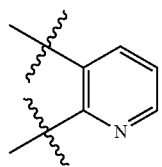 [SMILES: *c1cccnc1*]

as well as the 2,4-, 2,5-, 2,6-, 3,4-, and 3,5-isomers). Unless otherwise specified, the term "heteroaryl" may include "heteroarylene" groups.

The terms "heterocycloalkyl" and, interchangeably, "heterocycle," as used herein, alone or in combination, each refers to a saturated, partially unsaturated, or fully unsaturated (but nonaromatic) monocyclic, bicyclic, or tricyclic heterocyclic group containing at least one heteroatom as a ring member, wherein each the heteroatom may be independently chosen from nitrogen, oxygen, and sulfur. In certain embodiments, the heterocycloalkyl comprises a spirocycle ring system. In certain embodiments, the heterocycloalkyl comprises from 1 to 4 heteroatoms as ring members. In further embodiments, the heterocycloalkyl comprises from 1 to 2 heteroatoms as ring members. In certain embodiments, the heterocycloalkyl comprises from 3 to 8 ring members in each ring. In further embodiments, the heterocycloalkyl comprises from 3 to 7 ring members in each ring. In yet further embodiments, the heterocycloalkyl comprises from 5 to 6 ring members in each ring. In further embodiments, the heterocycle comprises a bicyclic ring system. In further embodiments, the heterocycle comprises a tricyclic ring system. In further embodiments, the heterocycle comprises a bicyclic ring system, the bicyclic ring system comprising a ring of three atoms. In further embodiments, the heterocycle comprises a bicyclic ring system, the bicyclic ring system comprising a ring of four atoms. In further embodiments, the heterocycle comprises a bicyclic ring system, the bicyclic ring system comprising a ring of five atoms. In further embodiments, the heterocycle comprises a bicyclic ring system, the bicyclic ring system comprising a pyrrolidine ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein or an additional heterocycle group. Examples of heterocycle groups include 3-azabicyclo[3.1.0]hexan-6-yl, aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups are optionally substituted unless specifically prohibited.

The term "heterocycloalkylene" refers to a heterocycloalkyl group attached at two or more positions, such as piperazinylene ($-C_4H_8N_2-$). Unless otherwise specified, the term "heterocycloalkyl" may include "heterocycloalkylene" groups.

The term "hydrazinyl" as used herein, alone or in combination, refers to two amino groups joined by a single bond, i.e., $-N-N-$.

The term "hydroxy," as used herein, alone or in combination, refers to $-OH$.

The term "hydroxyalkyl," as used herein, alone or in combination, refers to a hydroxy group attached to the parent molecular moiety through an alkyl group.

The term "imino," as used herein, alone or in combination, refers to $=N-$.

The term "iminohydroxy," as used herein, alone or in combination, refers to $=N(OH)$ and $=N-O-$.

The phrase "in the main chain" refers to the longest contiguous or adjacent chain of carbon atoms starting at the point of attachment of a group to the compounds of any one formulas disclosed herein.

The term "isocyanato" refers to a $-NCO$ group.

The term "isothiocyanato" refers to a $-NCS$ group.

The phrase "linear chain of atoms" refers to the longest straight chain of atoms independently chosen from carbon, nitrogen, oxygen, and sulfur.

The term "lower," as used herein, alone or in a combination, where not otherwise specifically defined, means containing from 1 to and including 6 carbon atoms (i.e., $C_1$-$C_8$ alkyl).

The term "lower aryl," as used herein, alone or in combination, means phenyl or naphthyl, either of which is optionally substituted as provided.

The term "lower heteroaryl," as used herein, alone or in combination, means either 1) monocyclic heteroaryl comprising five or six ring members, of which between one and four the members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to $-NRR'$, wherein R and R' are independently chosen from hydrogen, alkyl, and lower heteroalkyl, any of which is optionally substituted. Additionally, the R and R' of a lower amino group may combine to form a five- or six-membered heterocycloalkyl, either of which may be optionally substituted.

The term "mercapto" as used herein, alone or in combination, refers to an RS— group, where R is as defined herein.

The term "nitro," as used herein, alone or in combination, refers to $-NO_2$.

The terms "oxy" or "oxa," as used herein, alone or in combination, refer to $-O-$.

The term "oxo," as used herein, alone or in combination, refers to $=O$.

The term "perhaloalkoxy" refers to an alkoxy group where halogen atoms replace all the hydrogen atoms.

The term "perhaloalkyl" as used herein, alone or in combination, refers to an alkyl group where halogen atoms replace all the hydrogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the $-SO_3H$ group and its anion as the sulfonic acid is used in salt formation.

The term "sulfanyl," as used herein, alone or in combination, refers to $-S-$.

The term "sulfinyl," as used herein, alone or in combination, refers to $-S(O)-$.

The term "sulfonyl," as used herein, alone or in combination, refers to $-S(O)_2-$.

The term "N-sulfonamido" or "sulfamoyl" refers to an $RS(=O)_2NR'-$ group with R and R' as defined herein.

The term "S-sulfonamido" refers to an $-S(=O)_2NRR'$, group, with R and R' as defined herein.

The terms "thia" and "thio," as used herein, alone or in combination, refer to a $-S-$ group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an $-SH$ group.

The term "thiocarbonyl," as used herein, when alone includes thioformyl $-C(S)H$ and in combination, is a $-C(S)-$ group.

The term "N-thiocarbamyl" refers to a ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to an $X_3CS(O)_2NR$— group with X is a halogen and R as defined herein.

The term "trihalomethanesulfonyl" refers to an $X_3CS(O)_2$— group where X is a halogen.

The term "trihalomethoxy" refers to an $X_3CO$— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl, and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted, and unsubstituted forms are encompassed. Where a substituent is qualified as "substituted," the substituted form is specifically intended. Additionally, different sets of optional substituents to a moiety may be defined as needed; in these cases, the optional substitution IS as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. The disclosure encompasses all isomeric stereochemical forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof.

Compounds may exist as tautomers. This disclosure provides all tautomeric isomers. For example, many embodiments contain a triazole ring substituted with a carboxylate group and a second moiety. In one tautomer, the hydrogen is on the nitrogen adjacent to the carboxylate group, as shown in Formula IIc:

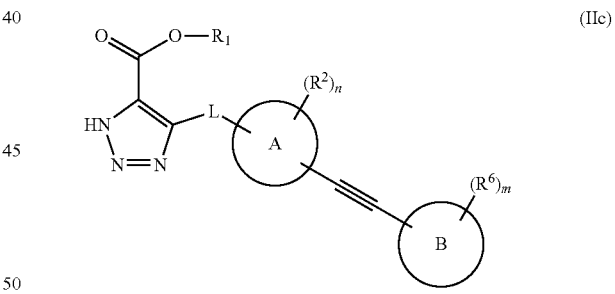

(IIc)

In another tautomer, the hydrogen is on the nitrogen adjacent to the second moiety, as shown in Formula IIb:

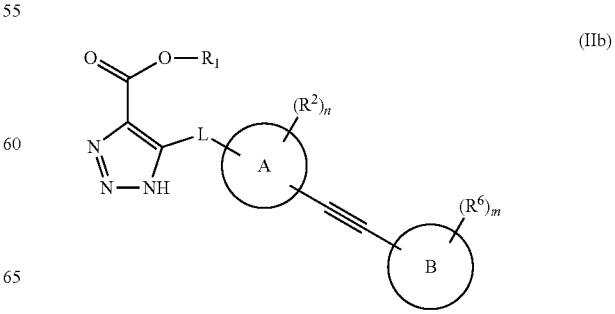

(IIb)

Crystallography studies captured the tautomer of Formula IIb, with the hydrogen on the nitrogen adjacent to the second moiety. As such, figures and schema in this disclosure have been depicted with this as the dominant tautomer. One of skill in the art would recognize, however, that both tautomers are equivalents and that each compound, figure, and scheme can be written with either isomer depicted.

Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are part of larger substructure. A bond may be single, double, or triple unless otherwise specified. A dashed line between two atoms in a drawing of a molecule indicates that an additional bond may be present or absent at that position.

The term "disease" as used herein is generally synonymous with and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms and causes the human or animal to have a reduced duration or quality of life.

The term "combination therapy" means administering two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. Also, such administration encompasses the use of each type of therapeutic agent in a sequential manner. In either case, the treatment regimen provides beneficial effects of the drug combination in treating the conditions or disorders described herein.

The phrase "therapeutically effective" is intended to qualify the amount of active ingredients used for treating a disease or disorder or on the effecting of a clinical endpoint.

The term "therapeutically acceptable" refers to those compounds (or salts, prodrugs, tautomers, zwitterionic forms, etc.) suitable for use in contact with the tissues of patients without undue toxicity, irritation, and allergic response, are commensurate with a reasonable benefit/risk ratio and are effective for their intended use.

As used herein, "treatment" of a patient is intended to include prophylaxis. Treatment may also be preemptive, i.e., it may include prevention of disease. Prevention of disease may involve complete protection from disease, for example, as in the case of prevention of infection with a pathogen, or may involve prevention of disease progression. For example, the prevention of a disease may not mean complete foreclosure of any effect related to the diseases at any level. Instead, it may mean the prevention of the symptoms of a disease to a clinically significant or detectable level. Prevention of diseases may also mean the prevention of the progression of a disease to a later stage of the disease.

The term "patient" is generally synonymous with the term "subject" and includes all mammals, including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration, whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example of a prodrug, without limitation, would be a compound which is administered as an ester (the "prodrug"), but then is metabolically hydrolyzed to the carboxylic acid, the active entity. Additional examples include peptidyl derivatives of a compound.

Salts and Polymorphs

The compounds disclosed herein can exist as therapeutically acceptable salts. The present disclosure includes compounds listed above in the form of salts, including acid addition salts. Suitable salts include those formed with both organic and inorganic acids. Such acid addition salts are normally pharmaceutically acceptable. However, salts of non-pharmaceutically acceptable salts may be used for preparing and purifying the compound in question. Basic addition salts may also be formed and be pharmaceutically acceptable.

The term "therapeutically acceptable salt," as used herein, represents salts or zwitterionic forms of the compounds disclosed herein, which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordinating the compounds with an alkali metal or alkaline earth ion. Hence, the present disclosure contemplates sodium, potassium, magnesium, and calcium salts of the compounds disclosed herein and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Formulations

While the disclosed compounds may be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers/excipients thereof and optionally one or more other therapeutic ingredients. The carrier(s) must be "acceptable" in the sense of being compatible with the other ingredients of the formulation and not deleterious to the recipient thereof. Proper formulation depends on the route of administration chosen. Any of the well-known techniques, carriers, and excipients may be used as suitable and as understood in the art. The pharmaceutical compositions disclosed herein may be manufactured in any manner known in the art, e.g., through conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration. However, the most suitable route may depend upon, for example, the condition and disorder of the recipient. The formulations may conveniently be presented in unit dosage form and may be prepared by any of the methods well known in the art of pharmacy. Typically, these methods include the step of bringing into association a compound disclosed herein or a pharmaceutically acceptable salt, ester, amide, prodrug, or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface-active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. Also, stabilizers may be added. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example, sealed ampoules and vials and may be stored in powder form or in a freeze-dried (lyophilized) condition requiring only the addition of the sterile liquid carrier, for example, saline or sterile pyrogen-free water, immediately before use. Extemporaneous injection solutions and suspensions may be prepared from sterile powders, granules, and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated conventionally. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration, which includes applying a compound disclosed herein externally to the epidermis or the buccal cavity and the instillation of such a compound into the ear, eye, and nose, such that the compound does not significantly enter the bloodstream. In contrast, systemic administration refers to oral, intravenous, intraperitoneal, and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 01% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds may be a dry powder composition, for example, a powder mix of the compound and a suitable powder base such as lactose or starch. The powder composition may be presented in unit dosage form, in, for example, capsules, cartridges, gelatin or blister packs from which the powder may be administered with the aid of an inhalator or insufflator.

Unit dosage formulations are those containing an effective dose, as herein below recited, or an appropriate fraction thereof, of the active ingredient.

In addition to the ingredients particularly mentioned above, the formulations described above may include other agents conventional in the art having regard to the type of formulation in question, for example, those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form varies depending upon the host treated and the particular mode of administration.

The compounds can be administered in various modes, e.g., orally, topically, or by injection. The precise amount of compound administered to a patient is the responsibility of the attendant physician. The specific dose level for any particular patient depends upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combination Therapies

In certain instances, it may be appropriate to administer at least one of the compounds described herein (or a pharmaceutically acceptable salt, ester, or prodrug thereof) in combination with another therapeutic agent. By way of example only, if one side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for primary hyperoxaluria involving administration of one of the compounds described herein, increased therapeutic benefit may result by also providing the patient with another therapeutic agent for primary hyperoxaluria. In any case, regardless of the disease, disorder or condition being treated, the overall benefit experienced by the patient may simply be additive of the two therapeutic agents or the patient may experience a synergistic benefit.

Therapies that treat glycolate oxidase-mediated disorders may be combined with the compounds described herein include vitamin B-6, bacterial or recombinant enzyme degraders of dietary oxalate, and supplements of calcium, potassium phosphate, and citrate. Other therapies which may benefit from combination with the compounds described herein include those which take time to take effect, such as treatments that focus on knocking out glycolate oxidase by oligonucleotides (e.g., Alnylam, Dicerna), knocking out lactate dehydrogenase A (LDHA) enzyme (e.g., Dicerna) or CRISPR-Cas9-mediated glycolate oxidase disruption (e.g., Intellia, Precision Biosciences), as well as treatments with oxalate-metabolizing bacteria such as *Oxalobacter formigenes* to degrade oxalate in the GI tract (e.g., OxThera).

In any case, the multiple therapeutic agents (at least one of which is a compound disclosed herein) may be administered in any order or even simultaneously. If simultaneously, the multiple therapeutic agents may be provided in a single, unified form, or multiple forms (by way of example only, either as a single pill or as two separate pills). One of the therapeutic agents may be given in multiple doses, or both may be given as multiple doses. If not simultaneous, the timing between the multiple doses may be any duration of time, ranging from a few minutes to four weeks.

Indications

Thus, in another aspect, certain embodiments provide methods for treating glycolate oxidase-mediated disorders in a human or animal subject in need of such treatment comprising administering to the subject an amount of a compound disclosed herein effective to reduce or prevent the disorder in the subject, in combination with at least one additional agent for the treating the disorder that is known in the art. In a related aspect, certain embodiments provide therapeutic compositions comprising at least one compound disclosed herein in combination with one or more additional agents for the treating glycolate oxidase-mediated disorders.

Specific diseases to be treated by the compounds, compositions, and methods disclosed herein include oxalate-related diseases, such as hyperoxaluria, for example, primary hyperoxaluria, enteric hyperoxaluria, idiopathic hyperoxaluria, oxalate poisoning, and kidney stones. The disease may be primary hyperoxaluria. The primary hyperoxaluria may be Type 1 (PH-1). The primary hyperoxaluria may be Type 2 (PH2). The primary hyperoxaluria may be Type 3 (PH3). The disease may be enteric hyperoxaluria. The disease may be idiopathic hyperoxaluria. The disease may be oxalate poisoning. The condition may be kidney stones.

Hyperoxaluria involves an excessive urinary excretion of oxalate. Individuals with hyperoxaluria often have calcium oxalate kidney stones. It is sometimes called Bird's disease, after Golding Bird, who first described the condition.

There are three known types of primary hyperoxaluria. Without wishing to be bound by theory, type I primary hyperoxaluria (PH-1) is caused by alanine-glyoxylate aminotransferase (AGXT), a key enzyme involved in the breakdown of oxalate. The AGXT is expressed only in the liver, and the encoded protein is localized mostly in the peroxisomes, where it is involved in glyoxylate detoxification. Mutations in this gene, some of which alter subcellular targeting, have been for type I primary hyperoxaluria. PH-1 is an example of a protein mistargeting disease, wherein AGXT shows a trafficking defect. Instead of being trafficked to peroxisomes, it is targeted to mitochondria, where it is metabolically deficient despite being catalytically active.

Without wishing to be bound by theory, type II primary hyperoxaluria (PH2) is for glyoxylate reductase/hydroxypyruvate reductase (GRHPR). Mutations in this GRHPR gene cause type II hyperoxaluria. PH2 is a complication of a jejunoileal bypass, or in any patient who has lost much of the ileum with an intact colon, thus causing the excessive absorption of oxalate from the colon.

Without wishing to be bound by theory, type III primary hyperoxaluria (PH3) is for mutations in the mitochondrial dihydrodipicolinate synthase-like (DHDPSL) gene on chromosome 10, which encodes 4-hydroxy-2-oxoglutarate aldolase (HOGA1). This enzyme catalyzes the last step in the metabolic pathway of hydroxyproline. Using heterozygosity mapping, which searched for long heterozygous patterns unique to all patients in each family and overlapped between families, and reconstructed haplotypes, an allelic fragment was determined to be shared by all patients of Ashkenazi Jewish descent and bearing a three-base pair deletion in DHDPSL. Overall, six mutations were detected: four missense mutations, one in-frame deletion, and one splice-site mutation.

The term "systemic oxalosis" refers to significantly elevated levels of oxalate in the systemic circulation of a subject. Systemic oxalosis occurs when the kidneys stop eliminating calcium oxalate crystals from the body through the urine, such as in subjects who have primary and intestinal causes of hyperoxaluria. Because the kidneys stop functioning, oxalate crystals are deposited elsewhere in the body, such as the blood vessels, bones and body organs, liver, kidney, skin, nails, teeth, eyes, etc.

Before the present disclosure, the main therapeutic approach to primary hyperoxaluria has been restricted to symptomatic treatment, i.e., liver-kidney transplantation once the disease has already reached mature or terminal stages. Genomics and proteomics approaches have been reported to elucidate some kinetics of AGXT folding, which directly bears on its targeting to appropriate subcellular localization. Secondary hyperoxaluria is much more common than primary hyperoxaluria and has been treated by limiting dietary oxalate and providing calcium supplementation. A child with primary hyperoxaluria had to be treated with a liver and kidney transplant. A favorable outcome was more likely if a kidney transplant was complemented by a liver transplant, given the disease originates in the liver.

As such, the present disclosure supplies a long-felt but unmet need for treating hyperoxaluria, including Types I, II, and III primary hyperoxaluria and secondary, especially in children. The disclosed compounds and compositions can treat hyperoxaluria before the disease destroys the kidneys and liver, mandating transplantation.

Besides being useful for human treatment, certain compounds and formulations disclosed herein may also be useful for the veterinary treatment of companion animals, exotic animals and farm animals, including mammals, rodents, and the like. More examples of suitable animals include horses, dogs, and cats.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; Bu=butyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; dppf=1,1'-bis(diphenylphosphino)ferrocene; EDC.HCl=EDCI.HCl=1-ethyl-3-(3-dimethylaminopropyl)carbodiimide hydrochloride; Et=ethyl; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyl-disilazane; HOBT=1-hydroxybenzotriazole; iPr=i-Pr=isopropyl=2-propyl; iPrOH=i-PrOH=isopropanol; LAH=lithium aluminiumhydride; LDA=lithium diisopropyl amide; LiHMDS=Lithium bis(trimethylsilyl)amide; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tert-butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide;

NBS=N-bromosuccinimide; NCS=N-chlorosuccinimide; NIS=N-iodosuccinimide; NMP=N-Methyl-2-pyrrolidone; Pd(Ph₃)₄=tetrakis(triphenylphosphine)palladium(0); Pd₂(dba)₃=tris(dibenzylideneacetone)dipalladium(0); PdCl₂(PPh₃)₂=bis(triphenylphosphine)palladium(II) dichloride; PG=protecting group; Ph=phenyl; prep-HPLC=preparative high-performance liquid chromatography; PMBCl=para-methoxybenzyl; PMBCl=para-methoxybenzyl chloride; PMBOH=para-methoxybenzyl alcohol; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; t-BuOH=tBuOH=tert-butanol; T3P=Propylphosphonic Anhydride; TEA=Et₃N=triethylamine; TFA=trifluoroacetic acid; TFAA=trifluoroacetic anhydride; THF=tetrahydrofuran; TIPS=triisopropylsilyl; Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

All experiments were conducted under an atmosphere of dry argon in oven-dried glassware using standard Schlenk techniques unless noted otherwise. Experiments performed in an oil bath were done using Fisher Scientific silicone oil in a Pyrex crystallizing dish on top of an IKA RCT basic model magnetic hotplate stirrer with an ETS-D5 electronic contact thermometer. Glovebox manipulations were performed in an MBraun Unilab glove-box under an atmosphere of dry argon. All reagents were purchased from Sigma-Aldrich or Alfa Aesar and were used without further purification unless noted otherwise. Pre-catalysts were acquired from Total Synthesis Ltd., Toronto, Canada. All reaction vials (screw-cap threaded, caps attached, 15×45 mm) were purchased from Fisher Scientific. Analytical thin-layer chromatography (TLC) was performed on EMD 60 F254 pre-coated glass plates, and spots were visualized with UV light (254 nm). Column chromatography purifications were carried out using the flash technique on ZEOprep 60 silica gel (40-63 μm).

The following schemes can generally be used to practice the present disclosure.

Scheme I

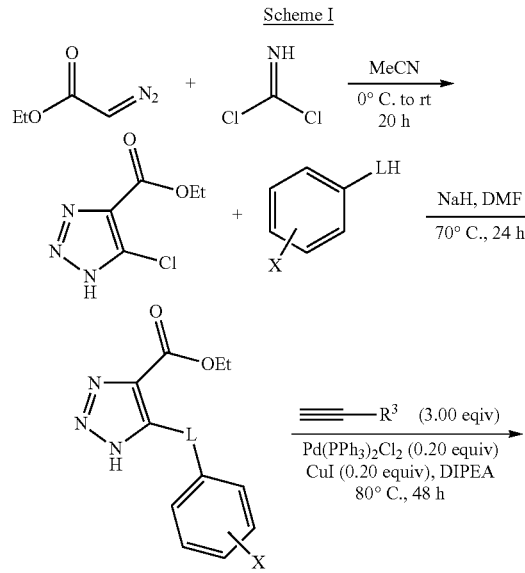

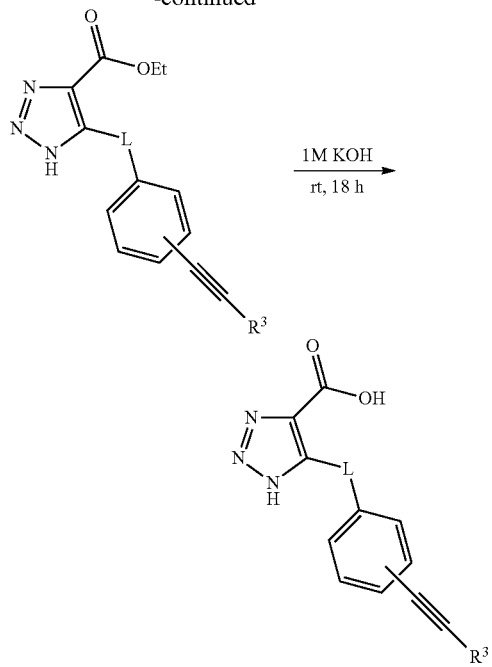

Scheme I depicts the formation of a chlorotriazole formed from reacting ethyl diazoacetate and carbonimidic dichloride. The chlorotriazole is then reacted with a halogen-substituted aryl group (where L is oxygen, nitrogen, or sulfur) under basic conditions to yield a bromophenyl linked triazole. The bromine is then reacted in the presence of palladium and copper catalysts and an alkynyl reagent in a Sonogashira cross-coupling.

Scheme II

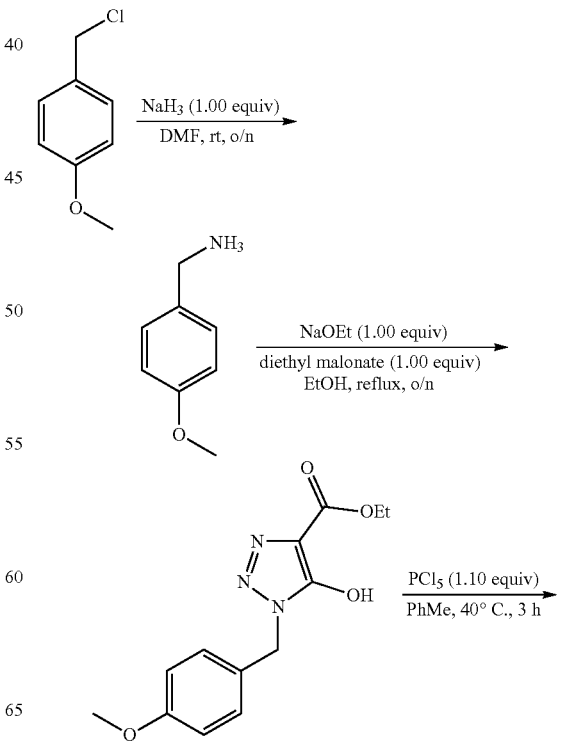

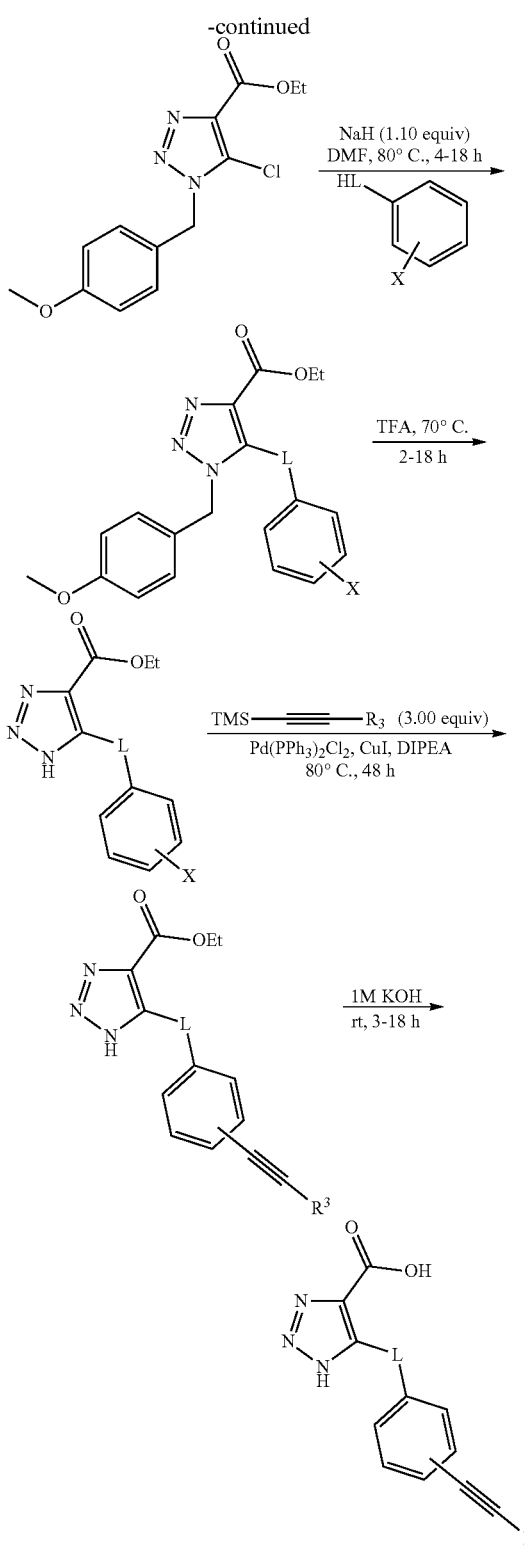

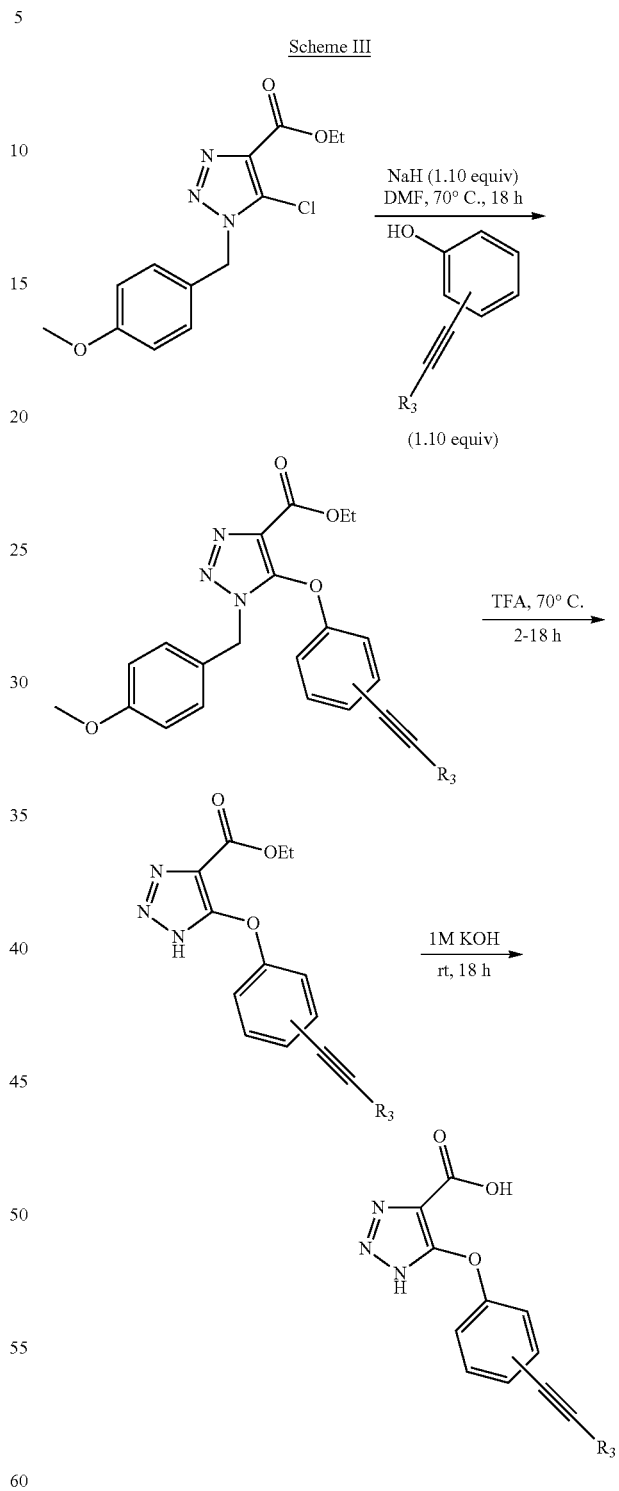

Scheme I, the bromine is then reacted in the presence of palladium and copper catalysts and an alkynyl reagent in a Sonogashira cross-coupling.

Scheme II depicts an alternative route to triazole formation. Here, benzyl chloride is converted to an azide via nucleophilic substitution. Cycloaddition between the azide and diethyl malonate yields hydroxytriazole that is converted to chlorotriazole. The chlorotriazole is further reacted with a halogen-substituted aryl group (where L is oxygen, nitrogen, or sulfur) to yield bromophenoxytriazole. As in Scheme III depicts the reaction of a chlorotriazole with an acetylene-substituted phenol under basic conditions to yield an alkynylphenoxytriazole. The method above can be modified to accommodate an alternate reagent in the first step, for example, a substituted or unsubstituted monocyclic or bicyclic aryl, monocyclic or bicyclic heteroaryl, biaryl, and biheteroaryl, such as biphenyl, naphthyl, pyridinylphenyl, phenylpyridinyl, or bipyridinyl.

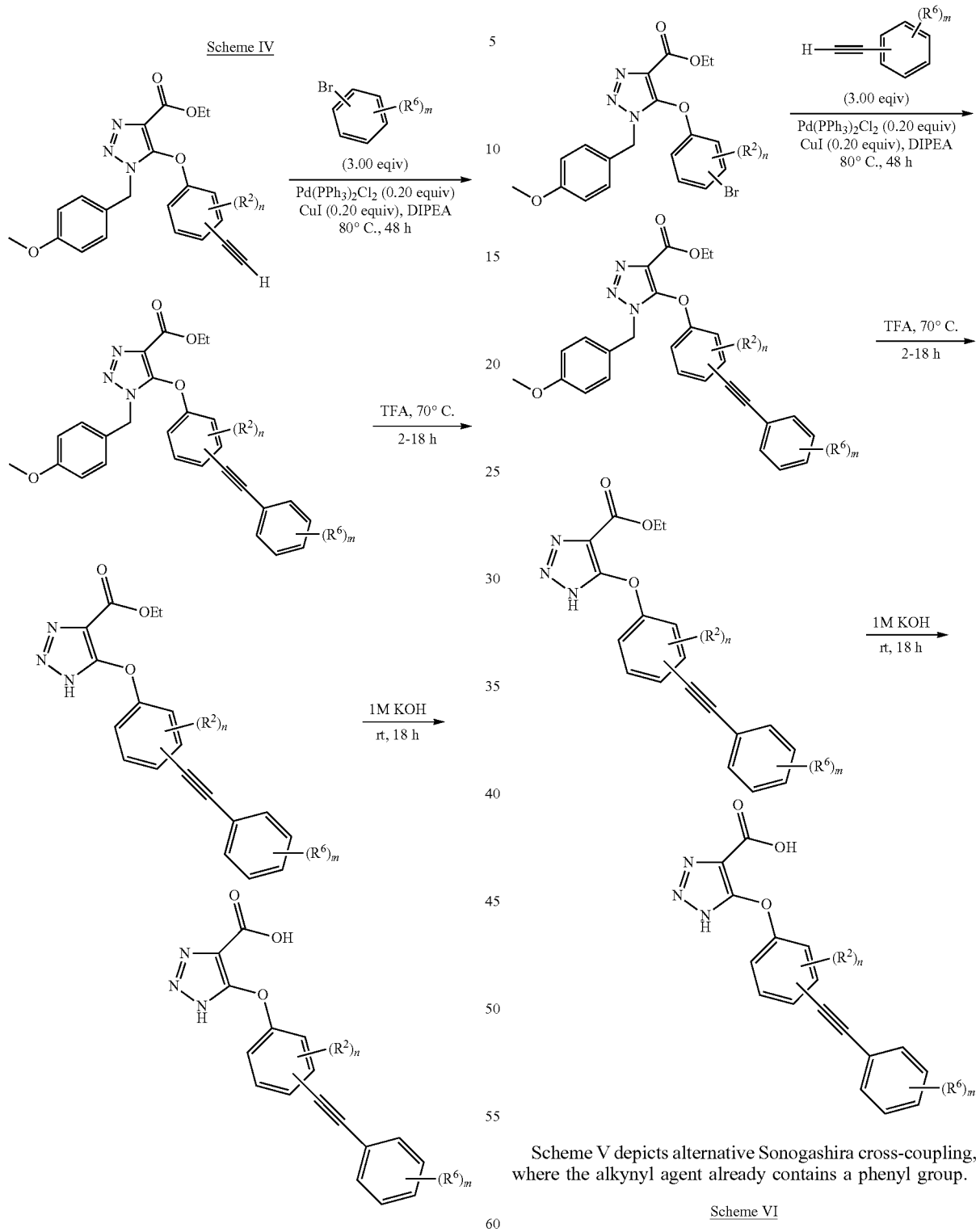

Scheme IV depicts a synthetic method for preparing O-linked 1H-1,2,3-triazole-4-carboxylic acids with Sonogashira cross-coupling. The bromine is replaced with a protected ethynyl group, which is then deprotected to a terminal alkyne. This terminal alkyne is coupled to bromo or iodo aryl groups in a second Sonogashira cross-coupling.

Scheme V depicts alternative Sonogashira cross-coupling, where the alkynyl agent already contains a phenyl group.

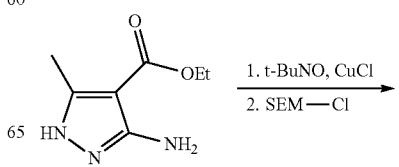

-continued

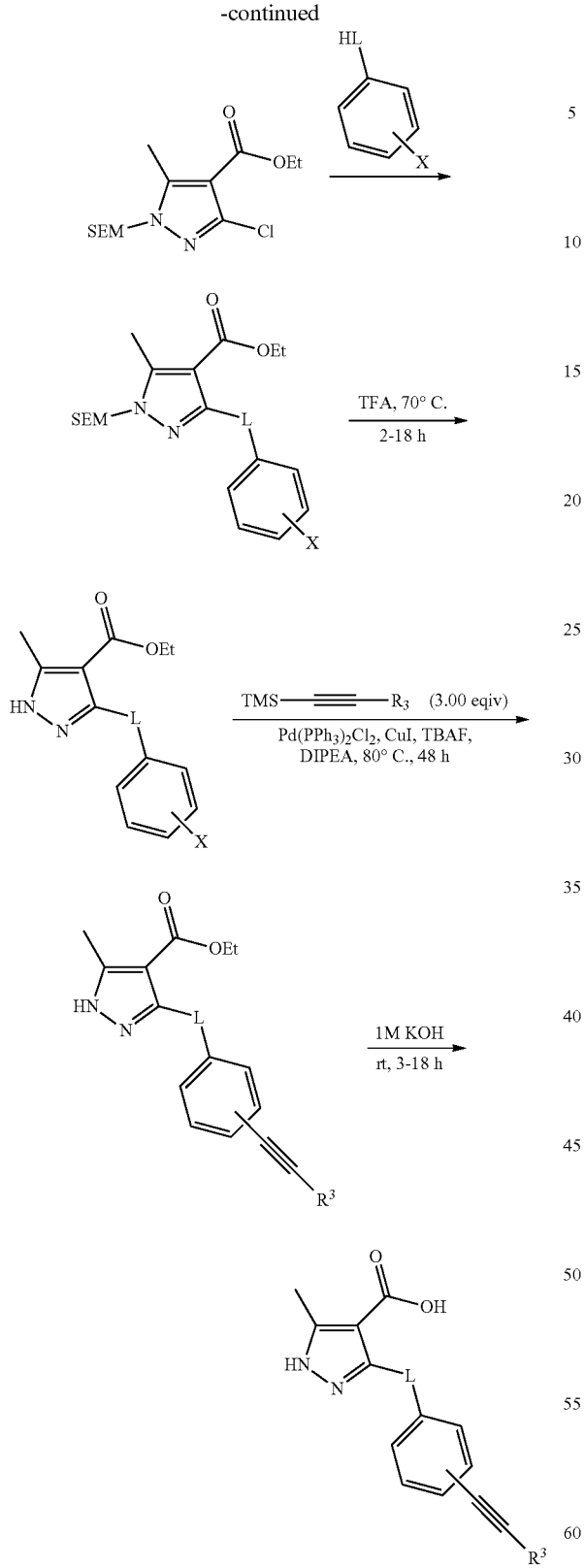

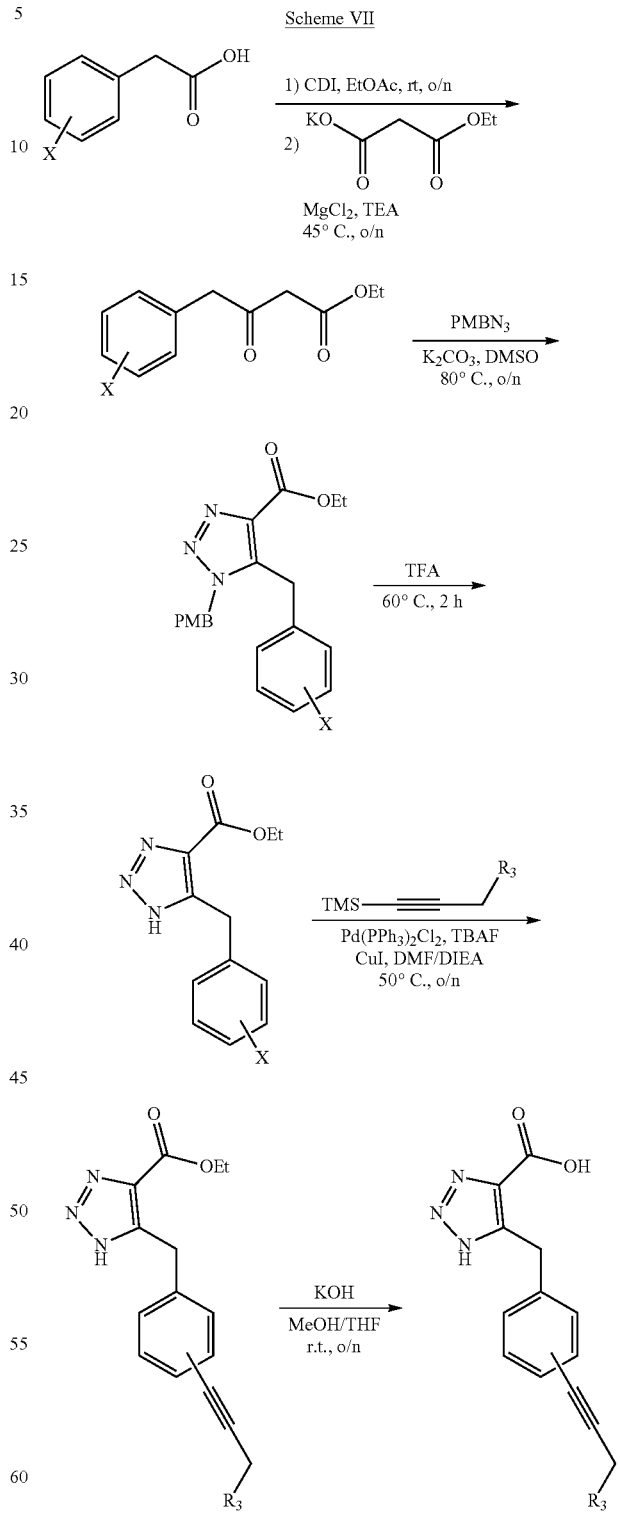

nated phenyl linked pyrazole that is converted to final compounds as described in Scheme II.

Scheme VII

Scheme VI depicts the chlorination of aminopyrazole, followed by protection. Then, the chloropyrazole is displaced with a halogenated aryl group where L is oxygen, nitrogen, or sulfur under basic conditions to yield halogenated phenyl linked pyrazole that is converted to final compounds as described in Scheme II.

Scheme VII depicts the conversion of phenylacetic acid to ethyl 3-oxo-4-phenylbutanoate that is cyclized in the presence of an azide to form a triazole. The triazole is first deprotected. Then, the aryl halide is coupled with substituted trimethylsilylacetylene under Sonogashira coupling condition to yield desired compounds after hydrolysis as in Scheme II.

Scheme VIII

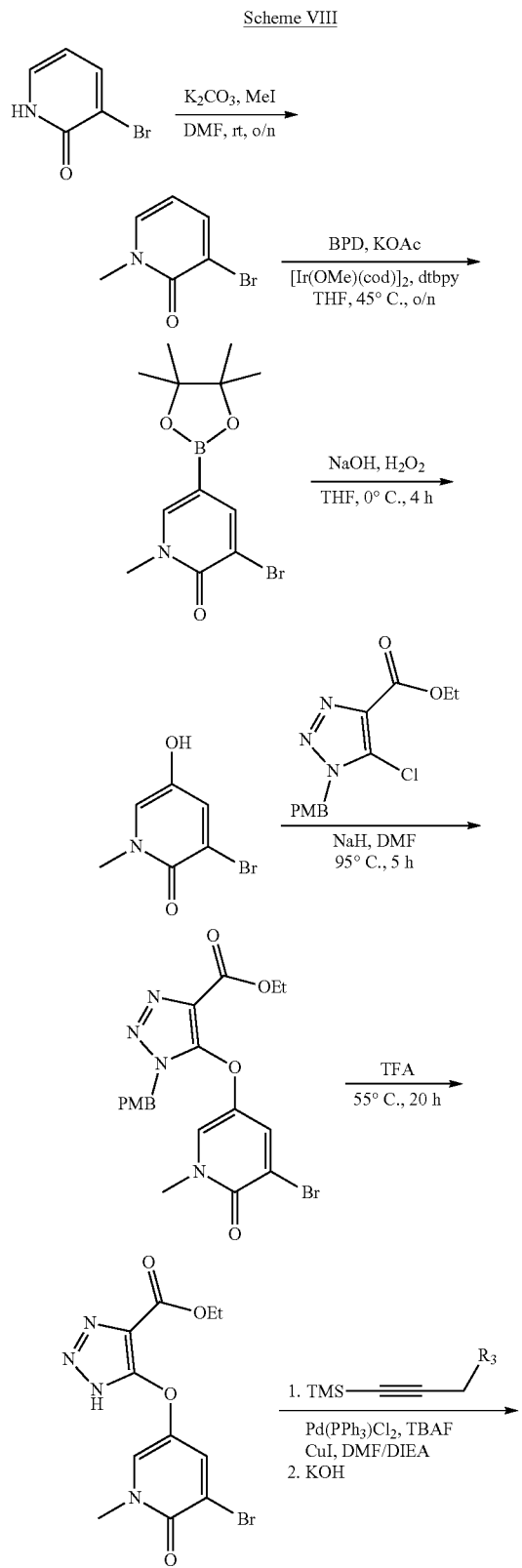

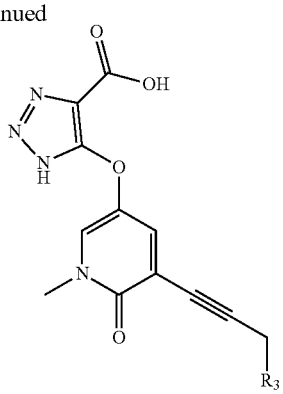

Scheme VIII depicts the alkylation of 3-bromopyridin-2(1H)-one with iodomethane under basic condition. Then, 3-bromo-1-methylpyridin-2(1H)-one is converted to boronic ester in the presence of an iridium catalyst. Boronic ester is then oxidized to 3-bromo-5-hydroxy-1-methylpyridin-2(1H)-one that is used to displace chlorotriazole to afford substituted triazole. This triazole is then converted to final compounds using the methods described in Scheme II.

Scheme IX

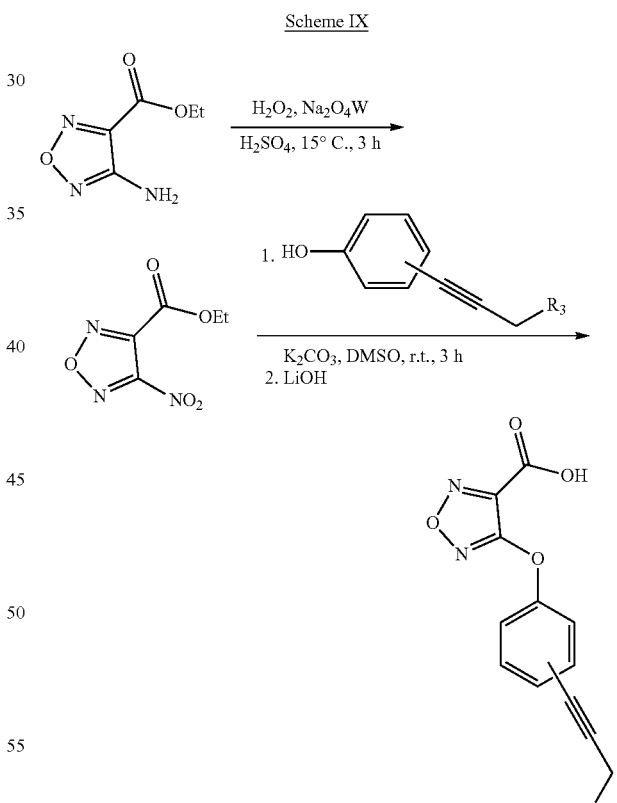

Scheme IX depicts the conversion of aminooxadiazole to nitrooxadiazole. The nitrodiazole was displaced with an acetylene-substituted phenol to provide final compounds.

General Sulfination Procedure by $S_NAr$

An oven-dried argon-filled vial (A) (8 mL) containing a magnetic stir bar was charged with 36 mg sodium hydride (0.75 mmol, 1.1 equivalents), and a thiophenol (0.780 mmol, 1.15 equivalents). The vial was sealed with a screw cap and backfilled with argon three times. N,N-Dimethylformamide (3 mL) was then added via syringe, and the solution stirred for 10 min. A second oven-dried argon-filled vial (B) (8 mL) containing a magnetic stir bar was then charged with an aryl halide (0.68 mmol, 1.0 equivalents), sealed with a screw cap and backfilled with argon three times. The contents of vial A were then transferred to vial B via syringe. Vial B was then placed in a pre-heated oil bath at 70° C. and stirred for 24 h. The reaction mixture was then cooled to room temperature, diluted with ethyl acetate (150 mL), washed with water (5×20 mL), brine (20 mL), and the filtrate concentrated in vacuo. The crude product was purified via flash chromatography on silica gel to yield the desired product.

General Sulfination Procedure by Cross-Coupling

An oven-dried argon-filled vial (A) (8 mL) containing a magnetic stir bar was charged with 52.7 mg potassium tert-butoxide (0.470 mmol, 1.10 equivalents) and a thiophenol (0.490 mmol, 1.15 equivalents). The vial was sealed with a screw cap and backfilled with argon three times. Toluene (1 mL) was then added via syringe, and the solution stirred for 10 min. A second oven-dried argon-filled vial (B) (8 mL) containing a magnetic stir bar was then charged with an aryl halide (0.43 mmol, 1.0 equivalents), 2.8 mg lithium isopropoxide (0.043 mmol, 0.1 equivalents), and 10.8 mg Pd-PEPPSI™-IPent$^{Cl}$-o-picoline (0.0129 mmol, 0.03 equivalents). Vial B was then sealed with a screw cap, backfilled with argon three times, and toluene (3 mL) was added via syringe. The contents of vial B were then transferred to vial A via syringe and stirred for 24 h. The reaction mixture was then cooled to room temperature and passed through a plug of silica with ethyl acetate. The filtrate was concentrated in vacuo, and the crude product was purified via flash chromatography on silica gel to yield the desired product.

General S$_N$Ar Procedure with Phenoxides

An oven-dried argon-filled vial (A) (8 mL) containing a magnetic stir bar was charged with 36 mg sodium hydride (0.75 mmol, 1.1 equivalents) and a phenol (0.780 mmol, 1.15 equivalents). The vial was sealed with a screw cap and backfilled with argon three times. N,N-Dimethylformamide (3 mL) was then added via syringe, and the solution stirred for 30 min. A second oven-dried argon-filled vial (B) (8 mL) containing a magnetic stir bar was then charged with an aryl halide (0.68 mmol, 1.0 equivalents), sealed with a screw cap and backfilled with argon three times. The contents of vial A were then transferred to vial B via syringe. Vial B was then placed in a pre-heated oil bath at 80° C. and stirred for 24 h. The reaction mixture was then cooled to room temperature, diluted with ethyl acetate (150 mL), washed with water (5×20 mL), brine (20 mL), and the filtrate concentrated in vacuo. The crude product was purified via flash chromatography on silica gel to yield the desired product.

General PMB Group Removal Procedure

A vial (8 mL) containing a magnetic stir bar was charged with the molecule containing the PMB group (50 mg to 200 mg) and 3 mL trifluoroacetic acid. The vial was sealed with a screw cap, placed in a pre-heated oil bath at 70° C. and stirred for 24 h. The reaction mixture was then cooled to room temperature, diluted with ethyl acetate (150 mL), washed with 5% sodium bicarbonate (2×50 mL), brine (20 mL), and the filtrate concentrated in vacuo. The crude product was purified via flash chromatography on silica gel to yield the desired product.

General Ethyl Ester Hydrolysis Procedure

A vial (8 mL) containing a magnetic stir bar was charged with the ethyl ester (20 mg to 150 mg) and 5 mL 1 N KOH. The vial was then sealed with a screw cap and stirred at room temperature for 6 h. The pH was adjusted to between 2 and 3 using 0.1 N HCl, and the contents of the vial were extracted with ethyl acetate (3×50 mL). The organic layers were combined, dried over anhydrous magnesium sulfate, filtered, and concentrated in vacuo. The crude product was purified by trituration in diethyl ether to yield the desired product.

The following compounds are prepared by the methods of Schemes I-V:

Intermediate 1: Synthesis of Ethyl 5-chloro-1-(4-methoxybenzyl)-1H-1,2,3-triazole-4-carboxylate Step 1—Ethyl 5-chloro-1,2,3-triazole-4-carboxylate

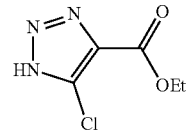

A 100-mL round bottom flask with a stir bar was charged with 6.2 mL ethyl diazoacetate (58 mmol, 2.0 equivalents), sealed with a rubber septum, and backfilled with argon three times. Acetonitrile (35 mL) was transferred to the flask via a syringe, and the flask was then cooled to 0° C. Next, 2.2 mL phosgene (29 mmol, 1.0 equivalents) was added dropwise, and the reaction mixture was stirred at room temperature for 20 h. The solvent was removed in vacuo, and the crude product was purified by silica gel column chromatography (4% ethyl acetate/hexanes) to give the title compound as a colorless oil (1.6 g, 26%).

Step 2-4-Methoxybenzyl Chloride

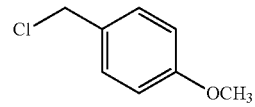

A 250-mL round bottom flask with a stir bar was charged with 4-methoxybenzyl alcohol (8.34 g, 6.00 mmol, 1.00 equivalents), sealed with a rubber septum and backfilled with argon three times. The alcohol was then dissolved in 100 mL diethyl ether transferred via syringe, followed by 8.9 mL thionyl chloride (12 mmol, 2.0 equivalents) added dropwise via syringe. The reaction mixture was stirred at room temperature for 5 h. The reaction mixture was then quenched by slowly adding water (50 mL). (Caution: HCl gas was developed). The aqueous and organic phases were separated, and the aqueous layer was extracted with dichloromethane (2×50 mL). The organic layers were combined and washed with saturated sodium bicarbonate (2×50 mL), water (2×50 mL), dried with anhydrous magnesium sulfate, filtered, and the solvent removed in vacuo to give 4-methoxybenzyl chloride (8.9 g, 94%) as a colorless oil. $^1$H-NMR (300 MHz, CDCl$_3$) δ: 7.32 (d, 2H), 6.89 (d, 2H), 4.57 (s, 2H), 3.81 (s, 3H).

Step 3-4-Methoxybenzyl Azide

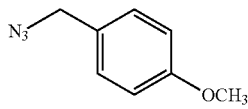

A 50-mL round bottom flask (A) with a stir bar was charged with 2.10 g sodium azide (31.8 mmol, 1.00 equivalents), sealed with a rubber septum and backfilled with argon three times. A 50-mL round bottom flask (B) was charged with 5.00 g 4-methoxybenzyl chloride (31.8 mmol, 1.00 equivalents), sealed with a rubber septum, and backfilled with argon three times. N,N-dimethylformamide (20 mL) was added to flask B to dissolve 4-methoxybenzyl chloride, then transferred to flask A and stirred for 24 hours at room temperature. The mixture was then diluted with water (200 mL) and extracted with diethyl ether (3×50 mL), the combined extracts were washed with water (5×50 mL), dried with anhydrous sodium sulfate, filtered and the solvent removed in vacuo to give the title compound (4.94 g, 95%) as a colorless oil. $^1$H-NMR (400 MHz, CDCl$_3$) δ: 7.25 (d, 2H), 6.91 (d, 2H), 4.26 (s, 2H), 3.81 (s, 3H).

Step 4—Ethyl 5-hydroxy-1-(4-methoxybenzyl)-1H-1,2,3-triazole-4-carboxylate

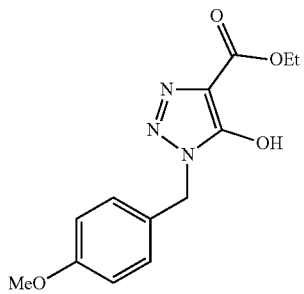 [SMILES: CCOC(=O)c1nnn(Cc2ccc(OC)cc2)c1O]

A 100-mL round bottom flask with a stir bar was charged with 4.19 g diethyl malonate (26.0 mmol, 1.00 equivalents), 10.0 mL 30% sodium ethoxide in ethanol (26.0 mmol, 1.00 equivalents) and ethanol (30 mL). The flask was sealed with a rubber septum and backfilled with argon three times. After 30 min of stirring, a solution of 4.25 g 4-methoxybenzyl azide (26.0 mmol, 1.00 equivalents) in ethanol (10 mL) was added dropwise with stirring. The mixture was then refluxed for 18 h. After cooling, the ethanol was removed in vacuo and water was added. The pH was adjusted to 2 with dilute hydrochloric acid to give a crystalline precipitate, which was filtered, washed with water, and dried in vacuo with P4O10 desiccant. Recrystallization from chloroform-pentanes gave the title compound (4.6 g, 67%) as an off-white solid. $^1$H-NMR (400 MHz, DMSO-d$_6$) δ: 7.20 (d, 2H), 6.90 (d, 2H), 5.25 (s, 2H), 4.23 (q, 2H), 3.72 (s, 3H), 1.26 (t, 3H).

Step 5—Synthesis of ethyl 5-chloro-1-(4-methoxybenzyl)-1H-1,2,3-triazole-4-carboxylate

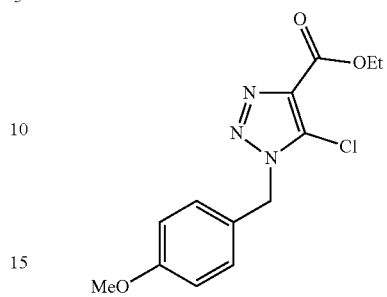

A 100-mL round bottom flask with a stir bar was charged with 3.70 g ethyl 5-hydroxy-1-(4-methoxybenzyl)-1H-1,2,3-triazole-4-carboxylate (13.3 mmol, 1.00 equivalents) and toluene (40 mL). With stirring, 3.0 g phosphorus pentachloride (14 mmol, 1.1 equivalents) was added slowly to the round bottom flask. The mixture was stirred at 40° C. for 90 min under argon. The solvent was removed in vacuo, and the residue dissolved in diethyl ether and washed with saturated sodium bicarbonate (3×50 mL), water (2×50 mL), dried with anhydrous magnesium sulfate, filtered and the solvent removed in vacuo. Recrystallization from diethyl ether-pentane gave pure the title compound (2.53 g, 65%) as an off-white solid. $^1$HNMR (300 MHz, CDCl$_3$) δ: 7.26 (d, 2H), 6.87 (d, 2H), 5.50 (s, 2H), 4.42 (q, 2H), 3.79 (s, 3H), 1.40 (t, 3H).

Example 1: 5-(3-Ethynylphenoxy)-1H-1,2,3-triazole-4-carboxylic Acid

Step 1: Ethyl 5-(3-((triisopropylsilyl)ethynyl)phenoxy)-1H-1,2,3-triazole-4-carboxylate

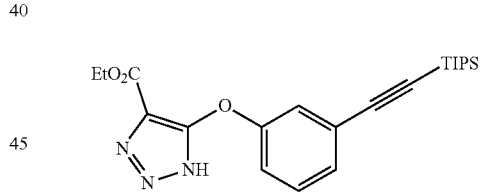

A 10-mL round bottom flask with a stir bar was charged with ethyl 5-(3-bromophenoxy)-1H-1,2,3-triazole-4-carboxylate (265 mg, 0.85 mmol, 1.00 equivalents.), ethynyltriisopropylsilane (0.25 mL, 2.55 mmol, 3.00 equivalents), (Ph$_3$P)$_2$PdCl$_2$ (120 mg, 0.17 mmol, 0.20 equivalents.), and CuI (34.0 mg, 0.17 mmol, 0.20 equivalents.) sealed with a rubber septum and backfilled with argon three times. The diisopropylamine (4 mL) was added at room temperature, and the flask was heated to 80° C. for 48 hours. Cooled to room temperature and diluted with ethyl acetate (50 mL) and filtered through a pad of Celite. The filtrate was washed with water (3×25 mL), brine (25 mL), dried over anhydrous Na$_2$SO$_4$, filtered, and concentrated under reduced pressure. The crude was purified by silica gel column chromatography with 5% diethyl ether/dichloromethane to yield ethyl 5-(3-((triisopropylsilyl)ethynyl)phenoxy)-1H-1,2,3-triazole-4-carboxylate as a yellow oil (105 mg, 30%). $^1$H-NMR (400 MHz, CDCl$_3$) δ: 7.33 (m, 3H), 7.09 (s, 1H), 4.38 (q, 2H), 1.27 (m, 6H), 1.10 (s, 18H).

Step 2: Ethyl 5-(3-ethynylphenoxy)-1H-1,2,3-triazole-4-carboxylate

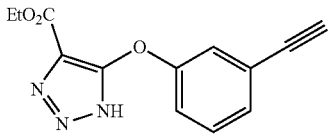 [SMILES: C#Cc1cccc(Oc2[nH]nnc2C(=O)O)c1]

A 10-mL round bottom flask with a stir bar was charged with ethyl 5-(3-((triisopropylsilyl)ethynyl)phenoxy)-1H-1,2,3-triazole-4-carboxylate as a yellow oil (98.0 mg, 0.24 mmol, 1.00 equivalents), sealed with a rubber septum and backfilled with argon three times. THF (1 mL) was added followed by TBAF (0.48 mL, 0.48 mmol, 2.00 equivalents) in THF. Stirred at room temperature for 2 h. Diluted with ethyl acetate (50 mL) and washed with water (3×25 mL), brine (25 mL), dried over anhydrous $Na_2SO_4$, filtered and concentrated under reduced pressure. The crude was purified by silica gel column chromatography with 5% diethyl ether/dichloromethane to yield ethyl 5-(3-ethynylphenoxy)-1H-1,2,3-triazole-4-carboxylate as a yellow oil (44.0 mg, 71%). The crude was used without purification in the next step.

Step 3: 5-(3-Ethynylphenoxy)-1H-1,2,3-triazole-4-carboxylic Acid

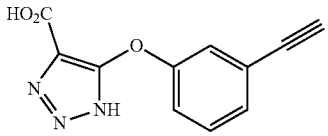

A vial (8 mL) containing a magnetic stir bar was charged with the ethyl 5-(3-ethynylphenoxy)-1H-1,2,3-triazole-4-carboxylate as a yellow oil (40 mg, 0.16 mmol) and 3 mL of 1 N KOH. The vial was then sealed with a screw cap and stirred at room temperature for 18 hours. The pH was adjusted to between 2 and 3 using 1 N HCl, and the contents of the vial were extracted with ethyl acetate (3×50 mL). The organic layers were combined, dried over anhydrous $MgSO_4$, filtered, and concentrated in vacuo. The crude product was purified by trituration in dichloromethane/pentane mixture to yield 5-(3-ethynylphenoxy)-1H-1,2,3-triazole-4-carboxylic acid as a light-yellow solid (19.2 mg, 55%). $^1$H-NMR (400 MHz, Acetone-$d_6$) δ: 7.42 (d, 1H), 7.30-7.21 (m, 3H), 3.72 (s, 1H).

Example 2: 5-(4-Ethynylphenoxy)-1H-1,2,3-triazole-4-carboxylic Acid

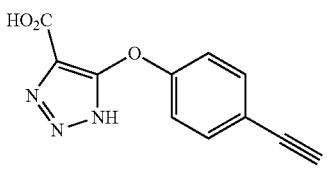 [SMILES: C#Cc1ccc(Oc2[nH]nnc2C(=O)O)cc1]

The title compound was prepared by the method described in Example I using ethyl 5-(4-bromophenoxy)-1H-1,2,3-triazole-4-carboxylate (265 mg, 0.85 mmol, 1.00 equivalents.) and ethynyltriisopropylsilane (0.25 mL, 2.55 mmol, 3.00 equivalents) as reagents in Step 1, to give 5-(4-ethynylphenoxy)-1H-1,2,3-triazole-4-carboxylic acid as a light-yellow solid (19.9 mg, 12%). $^1$H-NMR (400 MHz, DMSO-$d_6$) δ: 7.61 (d, 2H), 7.11 (d, 2H). 3.33 (s, 1H).

Example 5: 5-(4-(Prop-1-ynyl)phenoxy)-1H-1,2,3-triazole-4-carboxylic Acid

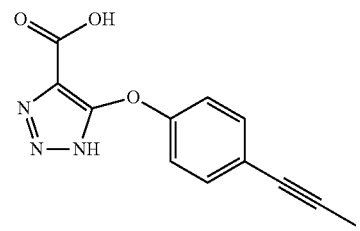 [SMILES: CC#Cc1ccc(Oc2[nH]nnc2C(=O)O)cc1]

Step 1: 4-Methoxybenzyl Azide

To a mixture of sodium azide (31.1 g, 479 mmol, 1.0 eq) in DMF (300 mL) was added PMBCl (75.0 g, 479 mmol, 1.0 eq) dropwise at room temperature under $N_2$. The resulting mixture was stirred at room temperature overnight. The reaction mixture was diluted with water (1 L) and extracted with $Et_2O$ (3×500 mL). The combined organic layers were washed with brine (3×1 L), dried over anhydrous $Na_2SO_4$, and concentrated to give the title compound (100 g, crude) as a colorless oil. $^1$H-NMR (400 MHz, $CDCl_3$) δ: 7.25 (d, 2H), 6.91 (d, 2H), 4.26 (s, 2H), 3.81 (s, 3H).

Step 2: Ethyl 5-hydroxy-1-(4-methoxybenzyl)-1H-1,2,3-triazole-4-carboxylate

To a solution of sodium ethoxide (32.6 g, 479 mmol, 1.0 eq) in dry-EtOH (780 mL) was added diethyl malonate (76.6 g, 479 mmol, 1.0 eq) at room temperature under $N_2$. The resulting mixture was stirred at room temperature for 0.5 h. A solution of 1-(azidomethyl)-4-methoxybenzene (100 g crude, 479 mmol, 1.0 eq) was added slowly. The reaction mixture was refluxed overnight. After removal of the most of solvent, the residue was diluted with water (500 mL) and adjusted to pH 2 by 4N HCl. The resulting precipitate was collected and recrystallized from $Et_2O$ to give the title compound (60.0 g, yield: 45%) as a white solid. $^1$H-NMR (400 MHz, DMSO-$d_6$) δ: 7.20 (d, 2H), 6.90 (d, 2H), 5.25 (s, 2H), 4.23 (q, 2H), 3.72 (s, 3H), 1.26 (t, 3H).

Step 3: Ethyl 5-chloro-1-(4-methoxybenzyl)-1H-1,2,3-triazole-4-carboxylate

To a mixture of ethyl 5-hydroxy-1-(4-methoxybenzyl)-1H-1,2,3-triazole-4-carboxylate (26.0 g, 93.5 mmol, 1.0 eq) in toluene (580 mL) was added $PCl_5$ (49.0 g, 234 mmol, 2.5 eq) portion-wise. The reaction mixture was stirred at 40° C. for under $N_2$ for 3 h. The solvent was removed in vacuo, and the residue was dissolved in diethyl ether (500 mL), washed with saturated sodium bicarbonate (3×100 mL), dried over anhydrous sodium sulfate, filtered and the solvent removed in vacuo. The residue was purified by silica gel column chromatography (PE:EtOAc=15:1) to give the title compound (24.0 g, yield: 63%) as a pale-yellow solid. $^1$H-NMR (400 MHz, CDCl$_3$) δ: 7.26 (d, 2H), 6.87 (d, 2H), 5.50 (s, 2H), 4.42 (q, 2H), 3.79 (s, 3H), 1.40 (t, 3H).

Step 4: 5-(4-Bromophenoxy)-1-(4-methoxybenzyl)-1H-1,2,3-triazole-4-carboxylate

To a mixture of NaH (60% in mineral oil, 1.62 g, 40.6 mmol, 1.5 eq) in DMF (240 mL) was added 4-bromophenol (7.03 g, 40.6 mmol, 1.5 eq) at 0° C. The resulting mixture was stirred at room temperature for 1 h. Ethyl 5-chloro-1-(4-methoxybenzyl)-1H-1,2,3-triazole-4-carboxylate (8 g, 27.1 mmol, 1.0 eq) was added into the mixture and stirred at 80° C. for 4 h. The reaction was quenched with saturated NH$_4$Cl aqueous solution and extracted with EtOAc (100 mL). The separated organic layer was dried over anhydrous sodium sulfate and concentrated. The residue was recrystallized from (PE:EtOAc=10:1) to give the title compound (8.70 g, yield: 74%) as a white solid. MS (ESI) m/z 432.1 [M+H]$^+$.

Step 5: Ethyl 5-(4-bromophenoxy)-1H-1,2,3-triazole-4-carboxylate

A solution of ethyl 5-(4-bromophenoxy)-1-(4-methoxybenzyl)-1H-1,2,3-triazole-4-carboxylate (8.70 g, 20.1 mmol) in TFA (110 mL) was heated at 60° C. for 2 h. The reaction mixture was concentrated under reduced pressure, and the residue was washed with (PE:EtOAc=3:1, 150 mL) to give the title compound (5.00 g, yield: 80%) as a white solid. MS (ESI) m/z 312.0 [M+H]$^+$.

Step 6: Ethyl 5-(4-(prop-1-ynyl)phenoxy)-1H-1,2,3-triazole-4-carboxylate

A mixture of ethyl 5-(4-bromophenoxy)-1H-1,2,3-triazole-4-carboxylate (260 mg, 0.83 mmol, 1.0 eq), prop-1-yne (1M in THF, 14.2 mL, 14.2 mmol, 17 eq), Pd(PPh$_3$)$_2$Cl$_2$ (167 mg, 0.24 mmol, 0.29 eq) and CuI (67 mg, 0.36 mmol, 0.43 eq) in diisopropylamine (4 mL) in a sealed tube was heated at 80° C. under N$_2$ for 6 h. The reaction mixture was concentrated and the residue was purified by prep-HPLC (5-95% CH$_3$CN in water) to give the title compound (80 mg, yield: 36%) as a yellow oil. MS (ESI) m/z 272.2 [M+H]$^+$.

Step 7: 4-(4-(Prop-1-ynyl)phenoxy)-1H-1,2,3-triazole-5-carboxylic acid

A mixture of ethyl 5-(4-(prop-1-ynyl)phenoxy)-1H-1,2,3-triazole-4-carboxylate (80.0 mg, 0.294 mmol, 1.0 eq) in 1N KOH (4 mL, 4 mmol, 13.6 eq) was stirred at room temperature for 3 h. The reaction was adjusted to pH about 3 and extracted with EtOAc (3×30 mL). The organic layers were combined, dried over anhydrous magnesium sulfate, filtered, and concentrated in vacuo. The crude product was purified by prep-HPLC (10-95% CH$_3$CN in water) to give the title compound (29.1 mg, yield: 40%) as a white solid. $^1$H-NMR (400 MHz, DMSO-d$_6$) δ: 13.34 (brs, 1H), 7.37 (d, J=8.8 Hz, 2H), 7.02 (d, J=8.4 Hz, 2H), 2.02 (s, 3H). MS (ESI) m/z 244.1 [M+H]$^+$.

Example 6: 5-(3-(Prop-1-ynyl)phenoxy)-1H-1,2,3-triazole-4-carboxylic Acid

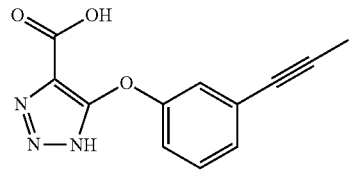 [SMILES: CC#Cc1cccc(Oc2[nH]nnc2C(=O)O)c1]

Step 1: 5-(3-bromophenoxy)-1-(4-methoxybenzyl)-1H-1,2,3-triazole-4-carboxylate

To a mixture of NaH (60% in mineral oil, 1.62 g, 40.6 mmol, 1.5 eq) in DMF (240 mL) was added 3-bromophenol (7.03 g, 40.6 mmol, 1.5 eq) at 0° C. The resulting mixture was stirred at room temperature for 1 h. Ethyl 5-chloro-1-(4-methoxybenzyl)-1H-1,2,3-triazole-4-carboxylate (8 g, 27.1 mmol, 1.0 eq, Example 1, Step 3) was added into the mixture and stirred at 80° C. for 4 h. The reaction was quenched with saturated NH$_4$Cl aqueous solution and extracted with EtOAc (100 mL). The separated organic layer was dried over anhydrous sodium sulfate and concentrated. The residue was recrystallized from (PE:EtOAc=20:1) to give the title compound (8.50 g, yield: 73%) as a white solid. MS (ESI) m/z 432.1 [M+H]$^+$.

Step 2: Ethyl 1-(4-methoxybenzyl)-5-(3-(prop-1-ynyl)phenoxy)-1H-1,2,3-triazole-4-carboxylate A mixture of ethyl 5-(3-bromophenoxy)-1-(4-methoxybenzyl)-1H-1,2,3-triazole-4-carboxylate (750 mg, 1.74 mmol, 1.0 eq), prop-1-yne (1M in THF, 5.22 mL, 5.22 mmol, 3.0 eq), Pd(PPh$_3$)$_2$Cl$_2$ (244 mg, 0.35 mmol, 0.2 eq) and CuI (99 mg, 0.52 mmol, 0.3 eq) in diisopropylamine (8 mL) in a sealed tube was heated at 80° C. under N$_2$ for 4 h. The reaction mixture was concentrated and the residue was purified by prep-HPLC (10-95% CH$_3$CN in water) to give the title compound (600 mg, yield: 88%) as a yellow oil. MS (ESI) m/z 392.2 [M+H]$^+$.

Step 3: Ethyl 5-(3-(prop-1-ynyl)phenoxy)-1H-1,2,3-triazole-4-carboxylate

A solution of ethyl 1-(4-methoxybenzyl)-5-(3-(prop-1-ynyl)phenoxy)-1H-1,2,3-triazole-4-carboxylate (600 mg, 1.53 mmol) in TFA (6 mL) was stirred at room temperature overnight. The reaction mixture was concentrated under reduced pressure. The residue was treated with sat. aqueous NaHCO$_3$ solution (100 mL) and extracted with EtOAc (3×200 mL). The combined organic layers were dried over anhydrous sodium sulfate and concentrated to give a crude, which was purified by prep-HPLC (5-65% CH$_3$CN in water) to give the title compound (180 mg, yield: 43%) as a white solid. MS (ESI) m/z 272.1 [M+H]$^+$.

Step 4: 4-(3-(prop-1-ynyl)phenoxy)-1H-1,2,3-triazole-5-carboxylic Acid

A mixture of ethyl 5-(3-(prop-1-ynyl)phenoxy)-1H-1,2,3-triazole-4-carboxylate (180 mg, 0.664 mmol, 1.0 eq) in 1N KOH (10 mL, 10 mmol, 15.0 eq) was stirred at room temperature for 3 h. The reaction was adjusted to pH ~3 and extracted with EtOAc (3×100 mL). The organic layers were combined, dried over anhydrous magnesium sulfate, filtered, and concentrated in vacuo. The crude product was purified by prep-HPLC (10-65% CH₃CN in water) to give the title compound (108 mg, yield: 67%) as a white solid. ¹H-NMR (400 MHz, DMSO-d₆) δ: 13.28 (brs, 1H), 7.34 (t, J=8.0 Hz, 1H), 7.15 (d, J=7.6 Hz, 1H), 7.06-7.03 (m, 2H), 2.03 (s, 3H). MS (ESI) m/z 244.1 [M+H]⁺.

Example 9: 5-(4-(3-Methylbut-1-ynyl)phenoxy)-1H-1,2,3-triazole-4-carboxylic Acid

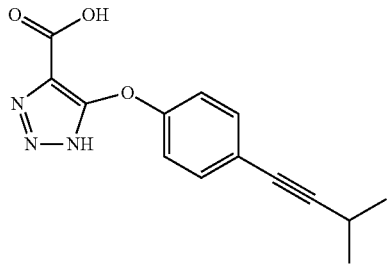 [SMILES: CC(C)C#Cc1ccc(Oc2[nH]nnc2C(=O)O)cc1]

The title compound was prepared following procedures described for Example 5 using ethyl 5-(4-bromophenoxy)-1H-1,2,3-triazole-4-carboxylate and 3-methylbut-1-yne to afford 5-(4-(3-methylbut-1-ynyl)phenoxy)-1H-1,2,3-triazole-4-carboxylic acid. ¹H-NMR (400 MHz, DMSO-d₆) δ: 13.23 (brs, 1H), 7.35 (d, J=8.8 Hz, 2H), 7.01 (d, J=8.8 Hz, 2H), 2.82-2.75 (m, 1H), 1.20 (d, J=6.8 Hz, 6H). MS (ESI) m/z 272.1 [M+H]⁺.

Example 10: 5-(3-(3-Methylbut-1-ynyl)phenoxy)-1H-1,2,3-triazole-4-carboxylic Acid

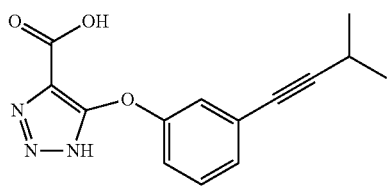 [SMILES: CC(C)C#Cc1cccc(Oc2[nH]nnc2C(=O)O)c1]

The title compound was prepared following procedures described for Example 6 using ethyl 5-(3-bromophenoxy)-1-(4-methoxybenzyl)-1H-1,2,3-triazole-4-carboxylate and 3-methylbut-1-yne to afford 5-(3-(3-methylbut-1-ynyl)phenoxy)-1H-1,2,3-triazole-4-carboxylic acid. ¹H-NMR (400 MHz, DMSO-d₆) δ: 13.30 (brs, 1H), 7.34 (t, J=8.0 Hz, 1H), 7.14 (d, J=7.6 Hz, 1H), 7.06-7.00 (m, 2H), 2.81-2.77 (m, 1H), 1.20 (d, J=6.8 Hz, 6H). MS (ESI) m/z 272.1 [M+H]⁺.

Example 13: 5-(4-(3-Hydroxy-3-methylbut-1-ynyl)phenoxy)-1H-1,2,3-triazole-4-carboxylic Acid

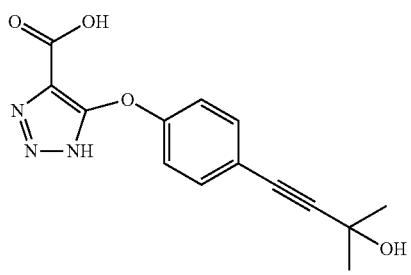 [SMILES: CC(C)(O)C#Cc1ccc(Oc2[nH]nnc2C(=O)O)cc1]

The title compound was prepared following procedures described for Example 5 using ethyl 5-(4-bromophenoxy)-1H-1,2,3-triazole-4-carboxylate and 2-methylbut-3-yn-2-ol to afford 5-(4-(2-cyclopropylethynyl)phenoxy)-1H-1,2,3-triazole-4-carboxylic acid. ¹H-NMR (400 MHz, DMSO-d₆) δ: 7.29 (d, J=8.8 Hz, 2H), 6.86 (d, J=8.8 Hz, 2H), 1.44-1.50 (s, 6H). MS (ESI) m/z 286.0 [M−H]⁻.

Example 16: 5-(4-(3,3-Dimethylbut-1-ynyl)phenoxy)-1H-1,2,3-triazole-4-carboxylic Acid

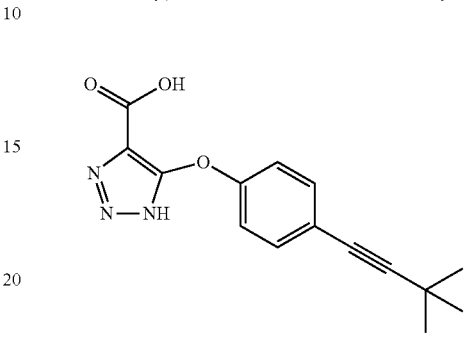

The title compound was prepared following procedures described for Example 5 using ethyl 5-chloro-1-(4-methoxybenzyl)-1H-1,2,3-triazole-4-carboxylate, 4-iodophenol and 3,3-dimethylbut-1-yne to afford 5-(4-(3,3-dimethylbut-1-ynyl)phenoxy)-1H-1,2,3-triazole-4-carboxylic acid. ¹H-NMR (400 MHz, DMSO-d₆) δ: 7.36-7.32 (m, 2H), 7.03-6.99 (m, 2H), 1.28 (s, 9H). MS (ESI) m/z 286.1 [M+H]⁺.

Example 17: 5-(3-(3,3-Dimethylbut-1-ynyl)phenoxy)-1H-1,2,3-triazole-4-carboxylic Acid

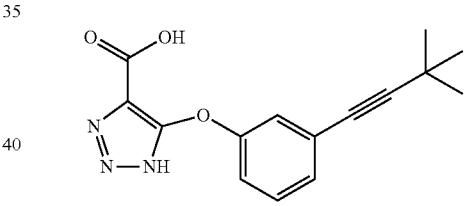

The title compound was prepared following procedures described for Example 6 using ethyl 5-chloro-1-(4-methoxybenzyl)-1H-1,2,3-triazole-4-carboxylate, 3-iodophenol and 3,3-dimethylbut-1-yne to afford 5-(3-(3,3-dimethylbut-1-ynyl)phenoxy)-1H-1,2,3-triazole-4-carboxylic acid. ¹H-NMR (400 MHz, DMSO-d₆) δ: 15.26 (brs, 1H), 13.20 (brs, 1H), 7.33 (t, J=8.0 Hz, 1H), 7.13 (d, J=7.6 Hz, 1H), 7.06-7.03 (m, 4H), 6.98 (s, 1H), 1.27 (s, 9H). MS (ESI) m/z 286.1 [M+H]⁺.

Example 20: 5-(4-(2-Cyclopropylethynyl)phenoxy)-1H-1,2,3-triazole-4-carboxylic Acid

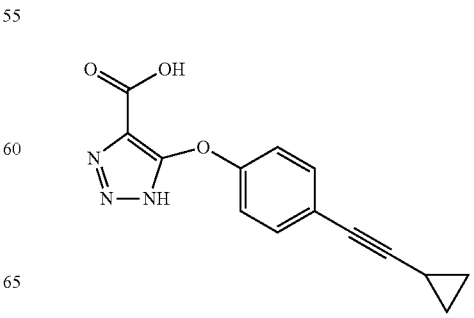

The title compound was prepared following procedures described for Example 5 using ethyl 5-(4-bromophenoxy)-1H-1,2,3-triazole-4-carboxylate and ethynylcyclopropane to afford 5-(4-(2-cyclopropylethynyl)phenoxy)-1H-1,2,3-triazole-4-carboxylic acid. $^1$H-NMR (400 MHz, DMSO-$d_6$) δ: 13.49 (brs, 1H), 7.35 (d, J=8.8 Hz, 2H), 7.01 (d, J=8.8 Hz, 2H), 1.54-1.50 (m, 1H), 0.89-0.84 (m, 2H), 0.73-0.69 (m, 2H). MS (ESI) m/z 270.1 [M+H]$^+$.

Example 21: 5-(3-(2-Cyclopropylethynyl)phenoxy)-1H-1,2,3-triazole-4-carboxylic Acid

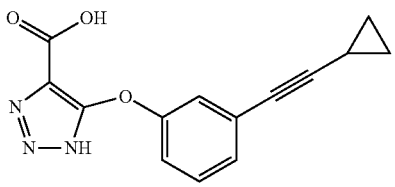 [SMILES: O=C(O)c1nn[nH]c1Oc1cccc(C#CC2CC2)c1]

The title compound was prepared following procedures described for Example 5 using ethyl 5-(3-bromophenoxy)-1H-1,2,3-triazole-4-carboxylate and ethynylcyclopropane to afford 5-(3-(2-cyclopropylethynyl)phenoxy)-1H-1,2,3-triazole-4-carboxylic acid. $^1$H-NMR (400 MHz, DMSO-$d_6$) δ: 7.31 (t, J=8.0 Hz, 1H), 7.12 (d, J=7.2 Hz, 1H), 7.03-6.98 (m, 2H), 1.54-1.50 (m, 1H), 0.89-0.85 (m, 2H), 0.75-0.71 (m, 2H). MS (ESI) m/z 270.1 [M+H]$^+$.

Example 24: 5-(4-(2-Cyclobutylethynyl)phenoxy)-1H-1,2,3-triazole-4-carboxylic Acid

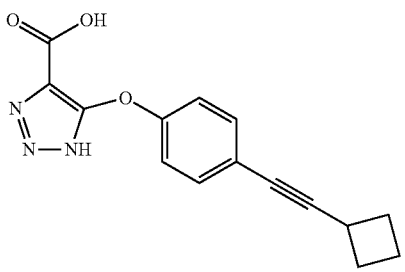 [SMILES: O=C(O)c1nn[nH]c1Oc1ccc(C#CC2CCC2)cc1]

The title compound was prepared following procedures described for Example 5 using ethyl 5-chloro-1-(4-methoxybenzyl)-1H-1,2,3-triazole-4-carboxylate, 4-iodophenol and ethynylcyclobutane to afford 5-(4-(2-cyclobutylethynyl)phenoxy)-1H-1,2,3-triazole-4-carboxylic acid. $^1$H-NMR (400 MHz, DMSO-$d_6$) δ: 7.29 (d, J=8.8 Hz, 2H), 6.83 (d, J=8.4 Hz, 2H), 3.29-3.16 (m, 1H), 2.32-2.24 (m, 2H), 2.13-2.08 (m, 2H), 1.96-1.82 (m, 2H). MS (ESI) m/z 284.1 [M+H]$^+$.

Example 25: 5-(3-(2-Cyclobutylethynyl)phenoxy)-1H-1,2,3-triazole-4-carboxylic Acid

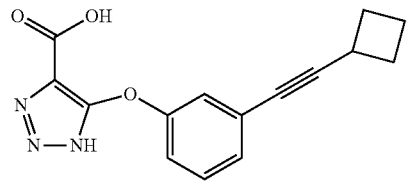 [SMILES: O=C(O)c1nn[nH]c1Oc1cccc(C#CC2CCC2)c1]

The title compound was prepared following procedures described for Example 6 using ethyl 5-chloro-1-(4-methoxybenzyl)-1H-1,2,3-triazole-4-carboxylate, 3-iodophenol and ethynylcyclobutane to afford 5-(3-(2-cyclobutylethynyl)phenoxy)-1H-1,2,3-triazole-4-carboxylic acid. $^1$H-NMR (400 MHz, DMSO-$d_6$) δ: 15.28 (brs, 1H), 13.26 (brs, 1H), 7.34 (t, J=8.0 Hz, 1H), 7.15 (d, J=7.6 Hz, 1H), 7.06-7.02 (m, 2H), 3.34-3.24 (m, 1H), 2.32-2.24 (m, 2H), 2.14-2.07 (m, 2H), 1.96-1.83 (m, 2H). MS (ESI) m/z 284.1 [M+H]$^+$ Example 28: 5-(4-(2-Cyclopentylethynyl)phenoxy)-1H-1,2,3-triazole-4-carboxylic Acid

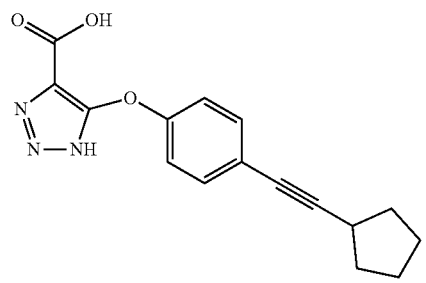 [SMILES: O=C(O)c1nn[nH]c1Oc1ccc(C#CC2CCCC2)cc1]

The title compound was prepared following procedures described for Example 5 using ethyl 5-chloro-1-(4-methoxybenzyl)-1H-1,2,3-triazole-4-carboxylate, 4-iodophenol and ethynylcyclopentane to afford 5-(4-(2-cyclopentylethynyl)phenoxy)-1H-1,2,3-triazole-4-carboxylic acid. $^1$H-NMR (400 MHz, DMSO-$d_6$) δ: 7.36-7.34 (m, 2H), 7.02-7.00 (m, 2H), 2.86-2.82 (m, 1H), 1.97-1.94 (m, 2H), 1.71-1.54 (m, 6H). MS (ESI) m/z 296.0 [M−H]$^-$.

Example 29: 5-(3-(2-Cyclopentylethynyl)phenoxy)-1H-1,2,3-triazole-4-carboxylic Acid

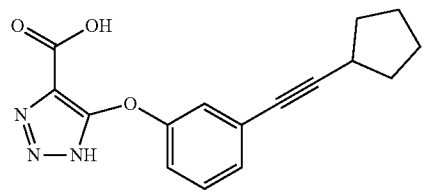 [SMILES: O=C(O)c1nn[nH]c1Oc1cccc(C#CC2CCCC2)c1]

The title compound was prepared following procedures described for Example 6 using ethyl 5-chloro-1-(4-methoxybenzyl)-1H-1,2,3-triazole-4-carboxylate, 3-iodophenol and ethynylcyclopentane to afford 5-(3-(2-cyclopentylethynyl)phenoxy)-1H-1,2,3-triazole-4-carboxylic acid. ¹H-NMR (400 MHz, DMSO-d₆) δ: 15.24 (brs, 1H), 13.26 (brs, 1H), 7.33 (t, J=8.0 Hz, 1H), 7.14 (dd, J=7.6 Hz, 0.8 Hz, 1H), 7.06-7.00 (m, 2H), 2.86-2.80 (m, 1H), 1.99-1.92 (m, 2H), 1.71-1.54 (m, 6H). MS (ESI) m/z 298.1 [M+H]⁺

Example 36: 5-(4-(2-Cyclohexylethynyl)phenoxy)-1H-1,2,3-triazole-4-carboxylic Acid

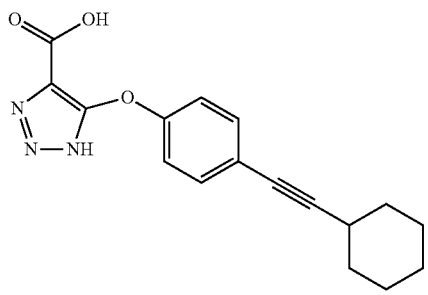 [SMILES: O=C(O)c1nn[nH]c1Oc1ccc(C#CC2CCCCC2)cc1]

The title compound was prepared following procedures described for Example 5 using ethyl 5-chloro-1-(4-methoxybenzyl)-1H-1,2,3-triazole-4-carboxylate, 4-iodophenol and ethynylcyclohexane to afford 5-(4-(2-cyclohexylethynyl)phenoxy)-1H-1,2,3-triazole-4-carboxylic acid. ¹H-NMR (400 MHz, DMSO-d₆) δ: 13.22 (brs, 1H), 7.36 (d, J=8.4 Hz, 2H), 7.01 (d, J=8.8 Hz, 2H), 2.64-2.58 (m, 1H), 1.83-1.79 (m, 2H), 1.68-1.67 (m, 2H), 1.50-1.45 (m, 2H), 1.35-1.31 (m, 2H). MS (ESI) m/z 312.1 [M+H]⁺.

Example 37: 5-(3-(2-Cyclohexylethynyl)phenoxy)-1H-1,2,3-triazole-4-carboxylic Acid

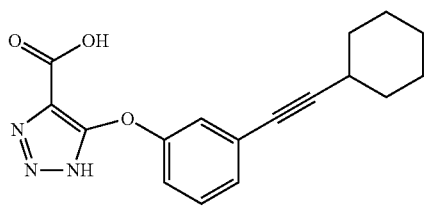 [SMILES: O=C(O)c1nn[nH]c1Oc1cccc(C#CC2CCCCC2)c1]

The title compound was prepared following procedures described for Example 6 using ethyl 5-chloro-1-(4-methoxybenzyl)-1H-1,2,3-triazole-4-carboxylate, 3-iodophenol and ethynylcyclohexane to afford 5-(3-(2-cyclohexylethynyl)phenoxy)-1H-1,2,3-triazole-4-carboxylic acid. ¹H-NMR (400 MHz, DMSO-d₆) δ: 15.25 (brs, 1H), 13.27 (brs, 1H), 7.33 (t, J=8.0 Hz, 1H), 7.14 (dd, J=7.6 Hz, 0.8 Hz, 1H), 7.06-7.01 (m, 2H), 2.64-2.60 (m, 1H), 1.82-1.79 (m, 2H), 1.69-1.65 (m, 2H), 1.50-1.44 (m, 2H), 1.35-1.30 (m, 2H). MS (ESI) m/z 312.2 [M+H]⁺.

Example 40: 5-(4-(2-(Tetrahydro-2H-pyran-4-yl)ethynyl)phenoxy)-1H-1,2,3-triazole-4-carboxylic Acid

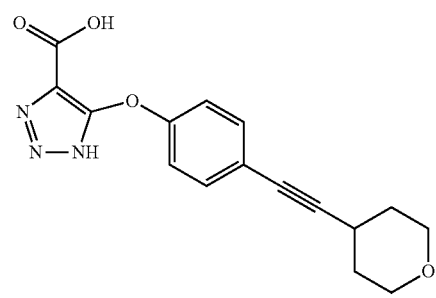 [SMILES: O=C(O)c1nn[nH]c1Oc1ccc(C#CC2CCOCC2)cc1]

The title compound was prepared following procedures described for Example 5 using ethyl 5-chloro-1-(4-methoxybenzyl)-1H-1,2,3-triazole-4-carboxylate, 4-bromophenol and ethynyl-tetrahydro-2H-pyran to afford 5-(4-(2-(tetrahydro-2H-pyran-4-yl)ethynyl)phenoxy)-1H-1,2,3-triazole-4-carboxylic acid. MS (ESI) m/z 314.2 [M+H]⁺

Example 41: 5-(3-(2-(Tetrahydro-2H-pyran-4-yl)ethynyl)phenoxy)-1H-1,2,3-triazole-4-carboxylic Acid

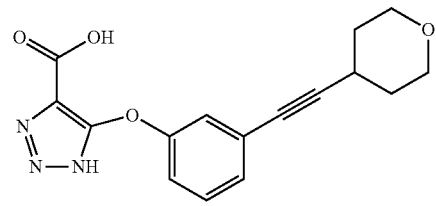 [SMILES: O=C(O)c1nn[nH]c1Oc1cccc(C#CC2CCOCC2)c1]

The title compound was prepared following procedures described for Example 5 using ethyl 5-chloro-1-(4-methoxybenzyl)-1H-1,2,3-triazole-4-carboxylate, 3-bromophenol and ethynyl-tetrahydro-2H-pyran to afford 5-(3-(2-(tetrahydro-2H-pyran-4-yl)ethynyl)phenoxy)-1H-1,2,3-triazole-4-carboxylic acid. MS (ESI) m/z 314.2 [M+H]⁺

Example 108: 5-(4-(2-(1H-Indazol-5-yl)ethynyl)phenoxy)-1H-1,2,3-triazole-4-carboxylic Acid

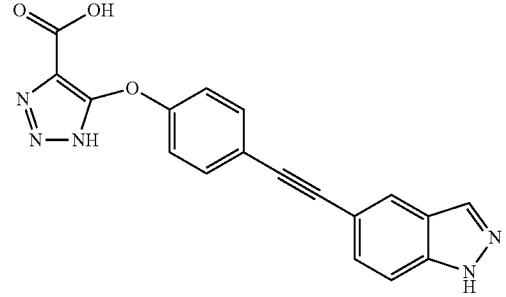 [SMILES: O=C(O)c1nn[nH]c1Oc1ccc(C#Cc2ccc3[nH]ncc3c2)cc1]

The title compound was prepared following procedures described for Example 282 using ethyl 5-(4-ethynylphenoxy)-1H-1,2,3-triazole-4-carboxylate and 5-bromo-1H-indazole to afford 5-(4-(2-(1H-Indazol-5-yl)ethynyl)phenoxy)-1H-1,2,3-triazole-4-carboxylic acid. ¹H-NMR (400 MHz, DMSO-d₆) δ: 15.32 (brs, 1H), 13.26 (brs, 1H), 8.12 (s, 1H), 8.01 (s, 1H), 7.59-7.46 (m, 4H), 7.11 (d, J=8.8 Hz, 2H). MS (ESI) m/z 346.1 [M+H]⁺

Example 138: 5-(4-(2-Phenylethynyl)phenoxy)-1H-1,2,3-triazole-4-carboxylic Acid

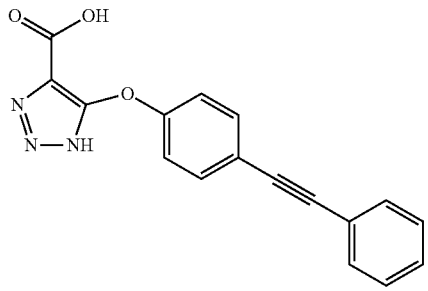 [SMILES: O=C(O)c1nn[nH]c1Oc1ccc(C#Cc2ccccc2)cc1]

Step 1: Ethyl 5-(4-((trimethylsilyl)ethynyl)phenoxy)-1H-1,2,3-triazole-4-carboxylate A mixture of ethyl 5-(4-bromophenoxy)-1H-1,2,3-triazole-4-carboxylate (2.0 g, 6.40 mmol, 1.0 eq), ethynyltrimethylsilane (6.60 g, 67.3 mmol, 10.5 eq), Pd(PPh₃)₂Cl₂ (950 mg, 1.35 mmol, 0.21 eq) and CuI (384 mg, 2.02 mmol, 0.32 eq) in diisopropylamine (30 mL) in a sealed tube was heated at 80° C. under N₂ for 4 h. The reaction mixture was concentrated and the residue was purified by prep-HPLC (10-95% CH₃CN in water) to give the title compound (1.99 g, yield: 94%) as a brown solid. MS (ESI) m/z 330.1 [M+H]⁺.

Step 2: 5-(4-ethynylphenoxy)-1H-1,2,3-triazole-4-carboxylic Acid

A mixture of ethyl 5-(4-((trimethylsilyl)ethynyl)phenoxy)-1H-1,2,3-triazole-4-carboxylate (600 mg, 1.82 mmol, 1.0 eq) in 1N KOH (20 mL, 20 mmol, 11 eq) was stirred at room temperature for 3 h. The reaction was adjusted to pH ~3 by 1N HCl and extracted with EtOAc (3×50 mL). The organic layers were combined, dried over anhydrous sodium sulfate, filtered, and concentrated in vacuo. The crude product was purified by prep-HPLC (5-95% CH₃CN in water) to give the desired (220 mg, yield: 53%) as a white solid. MS (ESI) m/z 230.1 [M+H]⁺.

Step 3: 4-(4-(Phenylethynyl)phenoxy)-1H-1,2,3-triazole-5-carboxylic Acid

A mixture of ethyl 5-(4-ethynylphenoxy)-1H-1,2,3-triazole-4-carboxylic acid (150 mg, 0.65 mmol, 1.0 eq), iodobenzene (265 mg, 1.30 mmol, 2.0 eq), Pd(PPh₃)₂Cl₂ (91 mg, 0.13 mmol, 0.2 eq) and CuI (25 mg, 0.13 mmol, 0.2 eq) in diisopropylamine (6 mL) in a sealed tube was heated at 50° C. under N₂ for 6 h. The reaction mixture was concentrated and the residue was purified by prep-HPLC (5-95% CH₃CN in water) to give the desired (30.1 mg, yield: 15%) as a yellow solid. ¹H-NMR (400 MHz, DMSO-d₆) δ: 13.41 (brs, 1H), 7.57-7.53 (m, 4H), 7.44-7.41 (m, 3H), 7.10 (dd, J=6.8, 2.0 Hz, 2H). MS (ESI) m/z 304.1 [M−H]⁻.

Example 139: 5-(3-(2-Phenylethynyl)phenoxy)-1H-1,2,3-triazole-4-carboxylic Acid

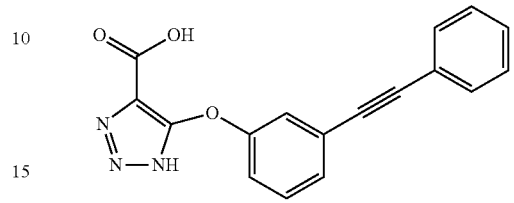

The title compound was prepared following procedures described for Example 6 using ethyl 5-(3-bromophenoxy)-1-(4-methoxybenzyl)-1H-1,2,3-triazole-4-carboxylate and ethynylbenzene to afford 5-(3-(3-methylbut-1-ynyl)phenoxy)-1H-1,2,3-triazole-4-carboxylic acid. ¹H-NMR (400 MHz, DMSO-d₆) δ: 13.40 (brs, 1H), 7.58-7.55 (m, 2H), 7.45-7.41 (m, 4H), 7.34 (d, J=7.6 Hz, 1H), 7.22 (d, J=2.0 Hz, 1H), 7.16-7.13 (m, 1H). MS (ESI) m/z 306.1 [M+H]⁺.

Example 146: 5-(3-Fluoro-4-(2-phenylethynyl)phenoxy)-1H-1,2,3-triazole-4-carboxylic Acid

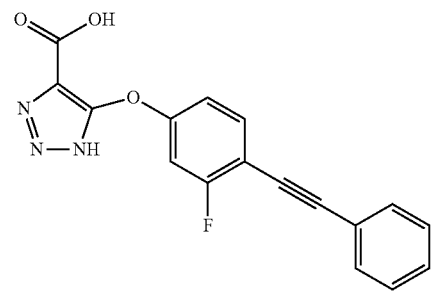 [SMILES: O=C(O)c1nn[nH]c1Oc1ccc(C#Cc2ccccc2)c(F)c1]

The title compound was prepared following procedures described for Example 6 using ethyl 5-chloro-1-(4-methoxybenzyl)-1H-1,2,3-triazole-4-carboxylate, 4-bromo-3-fluorophenol and ethynylbenzene to afford 5-(3-fluoro-4-(2-phenylethynyl)phenoxy)-1H-1,2,3-triazole-4-carboxylic acid. ¹H-NMR (400 MHz, DMSO-d₆) δ: 7.57-7.42 (m, 5H), 6.90 (dd, J=11.2, 2.0 Hz, 1H), 6.78 (dd, J=8.4, 2.0 Hz, 1H). MS (ESI) m/z 324.1 [M+H]⁺.

Example 147: 5-(4-Chloro-3-(2-phenylethynyl)phenoxy)-1H-1,2,3-triazole-4-carboxylic Acid

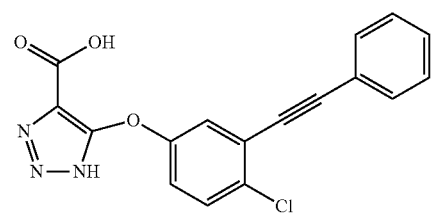 [SMILES: O=C(O)c1nn[nH]c1Oc1ccc(Cl)c(C#Cc2ccccc2)c1]

The title compound was prepared following procedures described for Example 5 using ethyl 5-chloro-1-(4-methoxybenzyl)-1H-1,2,3-triazole-4-carboxylate, 3-bromo-4-chlorophenol and ethynylbenzene to afford 5-(4-chloro-3-(2-phenylethynyl)phenoxy)-1H-1,2,3-triazole-4-carboxylic acid. $^1$H-NMR (400 MHz, DMSO-d$_6$) δ: 7.60-7.57 (m, 3H), 7.47-7.44 (m, 3H), 7.39 (d, J=3.2 Hz, 1H), 7.18 (dd, J=8.8, 3.2 Hz, 1H). MS (ESI) m/z 337.9 [M−H]$^-$.

Example 149: 5-(4-(Methylsulfonyl)-3-(2-phenylethynyl)phenoxy)-1H-1,2,3-triazole-4-carboxylic Acid

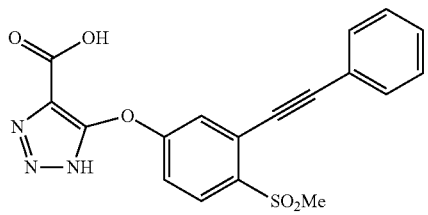 [SMILES: CS(=O)(=O)c1ccc(Oc2[nH]nnc2C(=O)O)cc1C#Cc1ccccc1]

The title compound was prepared following procedures described for Example 5 using ethyl 5-chloro-1-(4-methoxybenzyl)-1H-1,2,3-triazole-4-carboxylate, 3-bromo-4-(methylsulfonyl)phenol and ethynylbenzene to afford 5-(4-(methylsulfonyl)-3-(2-phenylethynyl)phenoxy)-1H-1,2,3-triazole-4-carboxylic acid. $^1$H-NMR (400 MHz, DMSO-d$_6$) δ: 7.95 (d, J=8.8 Hz, 1H), 7.62-7.61 (m, 2H), 7.51-7.42 (m, 3H), 7.24-7.20 (m, 1H), 7.14 (dd, J=8.8, 2.4 Hz, 1H), 3.36 (s, 3H). MS (ESI) m/z 384.1 [M+H]$^+$.

Example 165: 5-(3-(2-(Pyrimidin-2-yl)ethynyl)phenoxy)-1H-1,2,3-triazole-4-carboxylic Acid

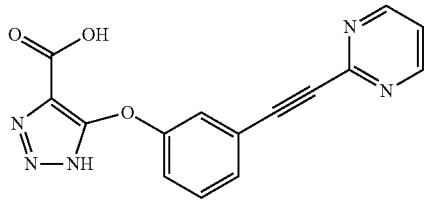 [SMILES: O=C(O)c1nn[nH]c1Oc1cccc(C#Cc2ncccn2)c1]

The title compound was prepared following procedures described for Example 282 using ethyl 5-(3-ethynylphenoxy)-1H-1,2,3-triazole-4-carboxylate and 2-bromopyrimidine to afford 5-(3-(2-(pyrimidin-2-yl)ethynyl)phenoxy)-1H-1,2,3-triazole-4-carboxylic acid. $^1$H-NMR (400 MHz, DMSO-d$_6$) δ: 13.30 (brs, 1H), 8.85 (d, J=4.8 Hz, 2H), 7.55-7.44 (m, 3H), 7.34 (d, J=2.4 Hz, 1H), 7.26-7.23 (m, 1H). MS (ESI) m/z 308.1 [M+H]$^+$.

Example 178: 5-(4-(2-(1H-Pyrazol-4-yl)ethynyl)phenoxy)-1H-1,2,3-triazole-4-carboxylic Acid

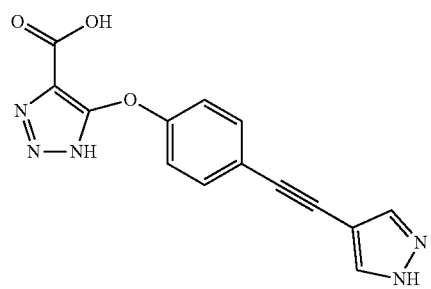 [SMILES: O=C(O)c1nn[nH]c1Oc1ccc(C#Cc2cn[nH]c2)cc1]

The title compound was prepared following procedures described for Example 282 using ethyl 5-(4-ethynylphenoxy)-1H-1,2,3-triazole-4-carboxylate and 4-iodo-1H-pyrazole to afford 5-(4-(2-(1H-pyrazol-4-yl)ethynyl)phenoxy)-1H-1,2,3-triazole-4-carboxylic acid. $^1$H-NMR (400 MHz, DMSO-d$_6$) δ: 13.28 (brs, 1H), 7.93 (s, 2H), 7.47 (d, J=8.4 Hz, 2H), 7.07 (d, J=8.4 Hz, 2H). MS (ESI) m/z 296.1 [M+H]$^+$.

Example 187: 5-(3-(2-(3-Chlorophenyl)ethynyl)phenoxy)-1H-1,2,3-triazole-4-carboxylic Acid

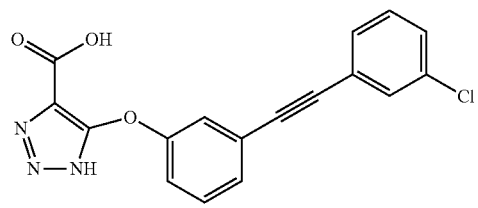 [SMILES: O=C(O)c1nn[nH]c1Oc1cccc(C#Cc2cccc(Cl)c2)c1]

The title compound was prepared following procedures described for Example 5 using ethyl 5-chloro-1-(4-methoxybenzyl)-1H-1,2,3-triazole-4-carboxylate, 3-iodophenol, and 1-chloro-3-ethynylbenzene to afford 5-(3-(2-(3-chlorophenyl)ethynyl)phenoxy)-1H-1,2,3-triazole-4-carboxylic acid. $^1$H-NMR (400 MHz, DMSO-d$_6$) δ: 15.30 (brs, 1H), 13.27 (brs, 1H), 7.66 (t, J=1.2 Hz, 1H), 7.55-7.43 (m, 4H), 7.37-7.35 (m, 1H), 7.25 (t, J=1.2 Hz, 1H), 7.19-7.16 (m, 1H). MS (ESI) m/z 339.8 [M+H]$^+$.

Example 190: 5-(4-(2-(4-(Methylsulfonyl)phenyl)ethynyl)phenoxy)-1H-1,2,3-triazole-4-carboxylic Acid

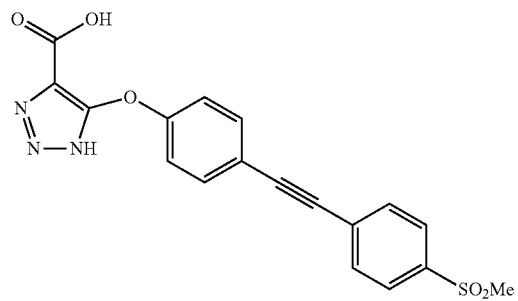 [SMILES: CS(=O)(=O)c1ccc(C#Cc2ccc(Oc3[nH]nnc3C(=O)O)cc2)cc1]

The title compound was prepared following procedures described for Example 138 using 5-(4-ethynylphenoxy)-1H-1,2,3-triazole-4-carboxylic acid and 1-bromo-4-(methylsulfonyl)benzene to afford 5-(4-(2-(4-(Methylsulfonyl)phenyl)ethynyl)phenoxy)-1H-1,2,3-triazole-4-carboxylic acid. $^1$H-NMR (400 MHz, DMSO-d$_6$) δ: 15.33 (brs, 1H), 13.28 (brs, 1H), 7.96 (d, J=8.4 Hz, 2H), 7.80 (d, J=8.4 Hz, 2H), 7.61 (d, J=8.8 Hz, 2H), 7.14 (d, J=8.8 Hz, 2H), 3.26 (s, 3H). MS (ESI) m/z 382.0 [M−H]$^-$.

Example 191: 5-(3-(2-(3-(Methylsulfonyl)phenyl)ethynyl)phenoxy)-1H-1,2,3-triazole-4-carboxylic Acid

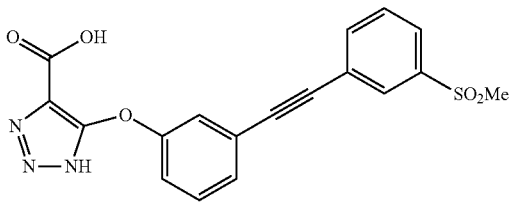 [SMILES: CS(=O)(=O)c1cccc(C#Cc2cccc(Oc3[nH]nnc3C(=O)O)c2)c1]

The title compound was prepared following procedures described for Example 138 using ethyl 5-(3-ethynylphenoxy)-1H-1,2,3-triazole-4-carboxylate and 1-bromo-3-(methylsulfonyl)benzene to afford 5-(3-(2-(3-(methylsulfonyl)phenyl)ethynyl)phenoxy)-1H-1,2,3-triazole-4-carboxylic acid. $^1$H-NMR (400 MHz, DMSO-d$_6$) δ: 15.30 (brs, 1H), 13.23 (brs, 1H), 8.10 (t, J=1.2 Hz, 1H), 7.97-7.90 (m, 2H), 7.72 (t, J=8.0 Hz, 1H), 7.46 (t, J=8.0 Hz, 1H), 7.41-7.39 (m, 1H), 7.29 (t, J=1.6 Hz, 1H), 7.21-7.18 (m, 1H), 3.28 (s, 3H). MS (ESI) m/z 382.0 [M−H]$^-$.

Example 208: 4-(4-((1-Methyl-6-oxo-1,6-dihydropyridin-3-yl)ethynyl)phenoxy)-1H-1,2,3-triazole-5-carboxylic Acid

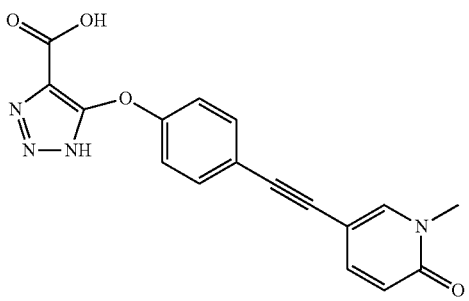 [SMILES: Cn1cc(C#Cc2ccc(Oc3[nH]nnc3C(=O)O)cc2)ccc1=O]

The title compound was prepared following procedures described for Example 138 using ethyl 5-(4-ethynylphenoxy)-1H-1,2,3-triazole-4-carboxylate and 5-bromo-1-methylpyridin-2(1H)-one to afford 4-(4-((1-methyl-6-oxo-1,6-dihydropyridin-3-yl)ethynyl)phenoxy)-1H-1,2,3-triazole-5-carboxylic acid. $^1$H-NMR (400 MHz, DMSO-d$_6$) δ: 15.36 (brs, 1H), 8.14 (d, J=2.0 Hz, 1H), 7.53-7.47 (m, 3H), 7.09 (d, J=8.8 Hz, 2H), 6.41 (d, J=9.6 Hz, 1H), 3.45 (s, 3H). MS (ESI) m/z 337.1 [M+H]$^+$.

Example 209: 4-(3-((1-Methyl-6-oxo-1,6-dihydropyridin-3-yl)ethynyl)phenoxy)-1H-1,2,3-triazole-5-carboxylic Acid

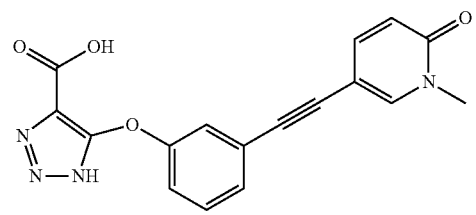 [SMILES: Cn1cc(C#Cc2cccc(Oc3[nH]nnc3C(=O)O)c2)ccc1=O]

The title compound was prepared following procedures described for Example 138 using ethyl 5-(3-ethynylphenoxy)-1H-1,2,3-triazole-4-carboxylate and 5-bromo-1-methylpyridin-2(1H)-one to afford 4-(3-((1-methyl-6-oxo-1,6-dihydropyridin-3-yl)ethynyl)phenoxy)-1H-1,2,3-triazole-5-carboxylic acid. $^1$H-NMR (400 MHz, DMSO-d$_6$) δ: 8.17 (d, J=2.4 Hz, 1H), 7.52 (dd, J=2.4, 9.2 Hz, 1H), 7.33 (t, J=8.0 Hz, 1H), 7.13 (d, J=7.6 Hz, 1H), 6.99 (dd, J=2.0, 8.4 Hz, 1H), 6.86 (s, 1H), 6.38 (d, J=9.2 Hz, 1H), 3.43 (s, 3H). MS (ESI) m/z 337.1 [M+H]$^+$.

Example 215: 5-(3-(3-Hydroxy-3-methylbut-1-ynyl)phenoxy)-1H-1,2,3-triazole-4-carboxylic Acid

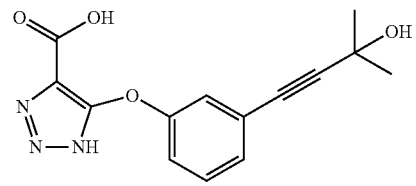 [SMILES: CC(C)(O)C#Cc1cccc(Oc2[nH]nnc2C(=O)O)c1]

The title compound was prepared following procedures described for Example 5 using ethyl 5-(3-bromophenoxy)-1H-1,2,3-triazole-4-carboxylate and 2-methylbut-3-yn-2-ol to afford 5-(4-(2-cyclopropylethynyl)phenoxy)-1H-1,2,3-triazole-4-carboxylic acid. $^1$H-NMR (400 MHz, DMSO-d$_6$) δ: 15.30 (brs, 1H), 7.37 (t, J=8.0 Hz, 1H), 7.17 (d, J=7.6 Hz, 1H), 7.09 (d, J=8.0 Hz, 1H), 7.01 (s, 1H), 1.45 (s, 6H). MS (ESI) m/z 286.1 [M−H]$^-$.

Example 220: 5-(4-(2-(1-Methyl-1H-pyrazol-4-yl)ethynyl)phenoxy)-1H-1,2,3-triazole-4-carboxylic Acid

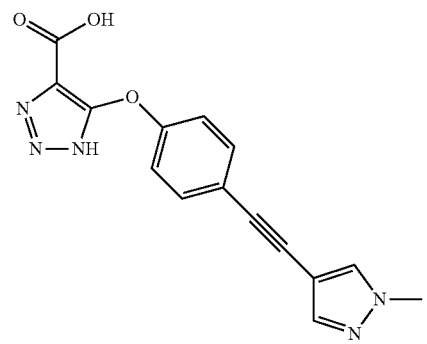 [SMILES: Cn1cc(C#Cc2ccc(Oc3[nH]nnc3C(=O)O)cc2)cn1]

The title compound was prepared following procedures described for Example 282 using ethyl 5-(4-ethynylphenoxy)-1H-1,2,3-triazole-4-carboxylate and 4-iodo-1-methyl-1H-pyrazole to afford 5-(4-(2-(1-methyl-1H-pyrazol-4-yl)ethynyl)phenoxy)-1H-1,2,3-triazole-4-carboxylic acid. $^1$H-NMR (400 MHz, CD$_3$OD) δ: 13.32 (brs, 1H), 8.05 (s, 1H), 7.67 (s, 1H), 7.49-7.45 (m, 2H), 7.09-7.05 (m, 2H), 3.85 (s, 3H). MS (ESI) m/z 310.1 [M+H]$^+$.

Example 221: 5-(3-(2-(1-Methyl-1H-pyrazol-4-yl)ethynyl)phenoxy)-1H-1,2,3-triazole-4-carboxylic Acid

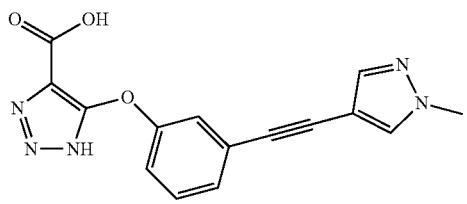 [SMILES: Cn1cc(C#Cc2cccc(Oc3[nH]nnc3C(=O)O)c2)cn1]

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 4-iodo-1-methyl-1H-pyrazole to afford 5-(3-(2-(1-methyl-1H-pyrazol-4-yl)ethynyl)phenoxy)-1H-1,2,3-triazole-4-carboxylic acid. $^1$H-NMR (400 MHz, DMSO-d$_6$) δ: 8.08 (s, 1H), 7.69 (s, 1H), 7.39 (t, J=8.0 Hz, 1H), 7.25 (d, J=7.6 Hz, 1H), 7.12-7.09 (m, 2H), 3.85 (s, 3H). MS (ESI) m/z 310.1 [M+H]$^+$.

Example 254: 5-(4-(2-(3-(Methylsulfonyl)phenyl)ethynyl)phenoxy)-1H-1,2,3-triazole-4-carboxylic Acid

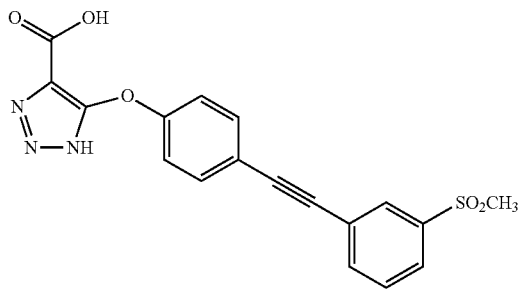 [SMILES: CS(=O)(=O)c1cccc(C#Cc2ccc(Oc3[nH]nnc3C(=O)O)cc2)c1]

The title compound was prepared following procedures described for Example 138 using 5-(4-ethynylphenoxy)-1H-1,2,3-triazole-4-carboxylate and 1-bromo-3-(methylsulfonyl)benzene to afford 5-(4-(2-(3-(methylsulfonyl)phenyl)ethynyl)phenoxy)-1H-1,2,3-triazole-4-carboxylic acid. $^1$H-NMR (400 MHz, DMSO-d$_6$) δ: 15.33 (brs, 1H), 13.28 (brs, 1H), 8.07 (t, J=1.6 Hz, 1H), 7.95-7.88 (m, 2H), 7.71 (t, J=8.0 Hz, 1H), 7.61 (d, J=9.2 Hz, 2H), 7.13 (d, J=8.8 Hz, 2H), 3.28 (s, 3H). MS (ESI) m/z 382.0 [M−H]$^−$.

Example 255: 5-(3-(2-(4-(Methylsulfonyl)phenyl)ethynyl)phenoxy)-1H-1,2,3-triazole-4-carboxylic Acid

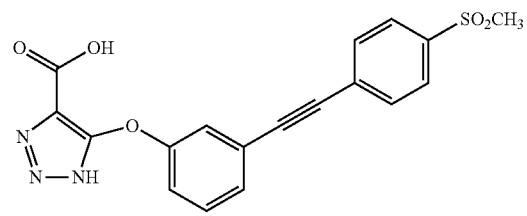 [SMILES: CS(=O)(=O)c1ccc(C#Cc2cccc(Oc3[nH]nnc3C(=O)O)c2)cc1]

The title compound was prepared following procedures described for Example 138 using ethyl 5-(3-ethynylphenoxy)-1H-1,2,3-triazole-4-carboxylate and 1-bromo-4-(methylsulfonyl)benzene to afford 5-(3-(2-(4-(Methylsulfonyl)phenyl)ethynyl)phenoxy)-1H-1,2,3-triazole-4-carboxylic acid. $^1$H-NMR (400 MHz, DMSO-d$_6$) δ: 7.96 (d, J=8.4 Hz, 2H), 7.83 (d, J=8.4 Hz, 2H), 7.45 (t, J=7.6 Hz, 1H), 7.39 (d, J=7.6 Hz, 1H), 7.26 (s, 1H), 7.18 (d, J=8.0 Hz, 1H), 3.26 (s, 3H). MS (ESI) m/z 382.0 [M−H]$^−$.

Example 256: 4-(4-((1-Methyl-2-oxo-1,2-dihydropyridin-4-yl)ethynyl)phenoxy)-1H-1,2,3-triazole-5-carboxylic Acid

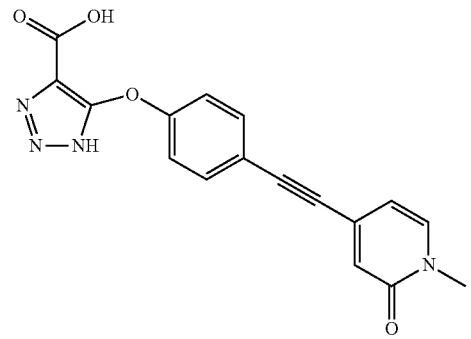 [SMILES: Cn1ccc(C#Cc2ccc(Oc3[nH]nnc3C(=O)O)cc2)cc1=O]

The title compound was prepared following procedures described for Example 138 using ethyl 5-(4-ethynylphenoxy)-1H-1,2,3-triazole-4-carboxylate and 4-bromo-1-methylpyridin-2(1H)-one to afford 4-(4-((1-methyl-2-oxo-1,2-dihydropyridin-4-yl)ethynyl)phenoxy)-1H-1,2,3-triazole-5-carboxylic acid. $^1$H-NMR (400 MHz, DMSO-d$_6$) δ: 7.73 (d, J=6.8 Hz, 1H), 7.58 (dd, J=2.4, 6.8 Hz, 2H), 7.11 (dd, J=2.0, 6.8 Hz, 2H), 6.53 (d, J=2.0 Hz, 1H), 6.29 (dd, J=1.6, 6.8 Hz, 1H), 3.42 (s, 3H). MS (ESI) m/z 337.1 [M+H]$^+$.

Example 257: 4-(3-((1-Methyl-2-oxo-1,2-dihydropyridin-4-yl)ethynyl)phenoxy)-1H-1,2,3-triazole-5-carboxylic Acid

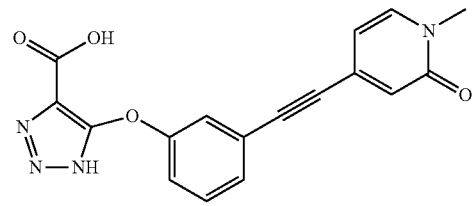 [SMILES: Cn1ccc(C#Cc2cccc(Oc3[nH]nnc3C(=O)O)c2)cc1=O]

The title compound was prepared following procedures described for Example 138 using 5-(3-ethynylphenoxy)-1H-1,2,3-triazole-4-carboxylate and 4-bromo-1-methylpyridin-2(1H)-one to afford 4-(3-((1-methyl-2-oxo-1,2-dihydropyridin-4-yl)ethynyl)phenoxy)-1H-1,2,3-triazole-5-carboxylic acid. $^1$H-NMR (400 MHz, DMSO-$d_6$) δ: 7.71 (d, J=7.2 Hz, 1H), 7.38 (t, J=8.0 Hz, 1H), 7.24 (d, J=7.6 Hz, 1H), 7.06-7.00 (m, 2H), 6.55 (d, J=2.0 Hz, 1H), 6.31 (dd, J=2.0, 7.2 Hz, 1H), 3.42 (s, 3H). MS (ESI) m/z 337.1 [M+H]$^+$.

Example 258: 5-(3-Fluoro-5-(2-phenylethynyl)phenoxy)-1H-1,2,3-triazole-4-carboxylic Acid

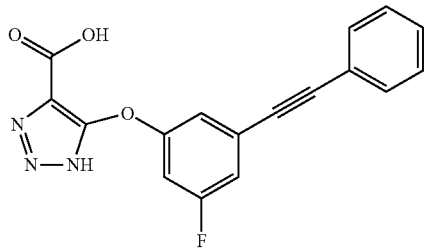 [SMILES: O=C(O)c1nn[nH]c1Oc1cc(F)cc(C#Cc2ccccc2)c1]

The title compound was prepared following procedures described for Example 5 using ethyl 5-chloro-1-(4-methoxybenzyl)-1H-1,2,3-triazole-4-carboxylate, 3-bromo-5-fluorophenol and ethynylbenzene to afford 5-(3-fluoro-5-(2-phenylethynyl)phenoxy)-1H-1,2,3-triazole-4-carboxylic acid. $^1$H-NMR (400 MHz, DMSO-$d_6$) δ: 15.35 (brs, 1H), 13.28 (brs, 1H), 7.59-7.56 (m, 2H), 7.46-7.42 (m, 3H), 7.29-7.23 (m, 1H), 7.15-7.11 (m, 1H), 7.08 (s, 1H). MS (ESI) m/z 321.9 [M–H]$^-$.

Example 259: 5-(4-Fluoro-3-(2-phenylethynyl)phenoxy)-1H-1,2,3-triazole-4-carboxylic Acid

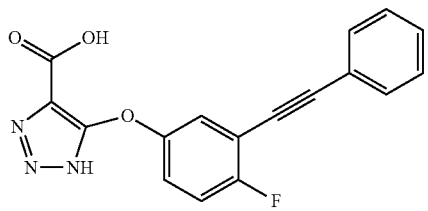 [SMILES: O=C(O)c1nn[nH]c1Oc1ccc(F)c(C#Cc2ccccc2)c1]

The title compound was prepared following procedures described for Example 5 using ethyl 5-chloro-1-(4-methoxybenzyl)-1H-1,2,3-triazole-4-carboxylate, 3-bromo-4-fluorophenol and ethynylbenzene to afford 5-(4-fluoro-3-(2-phenylethynyl)phenoxy)-1H-1,2,3-triazole-4-carboxylic acid. $^1$H-NMR (400 MHz, DMSO-$d_6$) δ: 13.35 (brs, 1H), 7.59-7.56 (m, 2H), 7.46-7.42 (m, 3H), 7.38-7.34 (m, 2H), 7.25-7.21 (m, 1H). MS (ESI) m/z 324.1 [M+H]$^+$.

Example 260: 5-(2-Fluoro-4-(2-phenylethynyl)phenoxy)-1H-1,2,3-triazole-4-carboxylic Acid

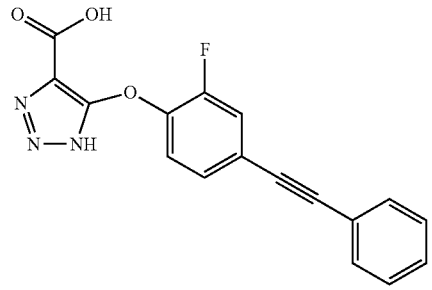 [SMILES: O=C(O)c1nn[nH]c1Oc1ccc(C#Cc2ccccc2)cc1F]

The title compound was prepared following procedures described for Example 5 using ethyl 5-chloro-1-(4-methoxybenzyl)-1H-1,2,3-triazole-4-carboxylate, 2-fluoro-4-iodophenol and ethynylbenzene to afford 5-(2-fluoro-4-(2-phenylethynyl)phenoxy)-1H-1,2,3-triazole-4-carboxylic acid. $^1$H-NMR (400 MHz, DMSO-$d_6$) δ: 13.44 (brs, 1H), 7.64 (dd, J=11.2, 2.0 Hz, 1H), 7.58-7.55 (m, 2H), 7.45-7.43 (m, 3H), 7.40-7.37 (m, 1H), 7.26 (t, J=8.4 Hz, 1H). MS (ESI) m/z 321.9 [M–H]$^-$.

Example 261: 5-(2-Fluoro-5-(2-phenylethynyl)phenoxy)-1H-1,2,3-triazole-4-carboxylic Acid

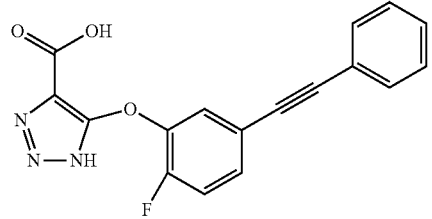 [SMILES: O=C(O)c1nn[nH]c1Oc1cc(C#Cc2ccccc2)ccc1F]

The title compound was prepared following procedures described for Example 6 using ethyl 5-chloro-1-(4-methoxybenzyl)-1H-1,2,3-triazole-4-carboxylate, 5-bromo-2-fluorophenol and ethynylbenzene to afford 5-(2-fluoro-5-(2-phenylethynyl)phenoxy)-1H-1,2,3-triazole-4-carboxylic acid. $^1$H-NMR (400 MHz, DMSO-$d_6$) δ: 7.56-7.54 (m, 2H), 7.47-7.42 (m, 6H). MS (ESI) m/z 321.9 [M–H]$^-$.

Example 262: 5-(4-Methyl-3-(2-phenylethynyl)phenoxy)-1H-1,2,3-triazole-4-carboxylic Acid

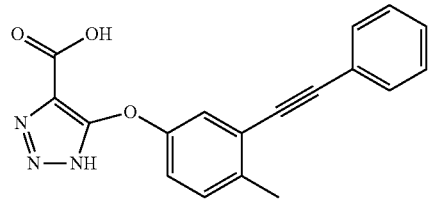 [SMILES: Cc1ccc(Oc2[nH]nnc2C(=O)O)cc1C#Cc1ccccc1]

The title compound was prepared following procedures described for Example 5 using ethyl 5-chloro-1-(4-methoxybenzyl)-1H-1,2,3-triazole-4-carboxylate, 3-bromo-4-methylphenol and ethynylbenzene to afford 5-(4-methyl-3-(2-phenylethynyl)phenoxy)-1H-1,2,3-triazole-4-carboxylic acid. ¹H-NMR (400 MHz, DMSO-d₆) δ: 15.27 (brs, 1H), 13.27 (brs, 1H), 7.58-7.56 (m, 2H), 7.44-7.42 (m, 3H), 7.32 (d, J=8.4 Hz, 1H), 7.18 (d, J=2.8 Hz, 1H), 7.05 (dd, J=8.4, 2.8 Hz, 1H), 2.44 (s, 3H). MS (ESI) m/z 318.0 [M−H]⁻.

Example 263: 5-(4-(Trifluoromethyl)-3-(2-phenylethynyl)phenoxy)-1H-1,2,3-triazole-4-carboxylic Acid

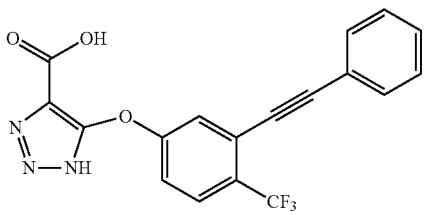

The title compound was prepared following procedures described for Example 5 using ethyl 5-chloro-1-(4-methoxybenzyl)-1H-1,2,3-triazole-4-carboxylate, 3-bromo-4-(trifluoromethyl)phenol and ethynylbenzene to afford 5-(4-(trifluoromethyl)-3-(2-phenylethynyl)phenoxy)-1H-1,2,3-triazole-4-carboxylic acid. ¹H-NMR (400 MHz, DMSO-d₆) δ: 15.46 (brs, 1H), 13.36 (brs, 1H), 7.82 (d, J=8.8 Hz, 1H), 7.57-7.54 (m, 2H), 7.49-7.45 (m, 4H), 7.26 (dd, J=8.4, 2.0 Hz, 1H). MS (ESI) m/z 374.1 [M+H]⁺.

Example 264: 5-(4-Methoxy-3-(2-phenylethynyl)phenoxy)-1H-1,2,3-triazole-4-carboxylic Acid

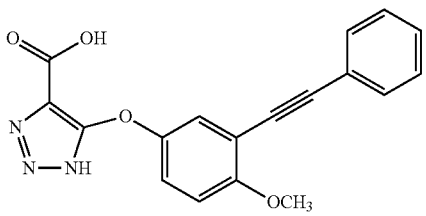

The title compound was prepared following procedures described for Example 5 using ethyl 5-chloro-1-(4-methoxybenzyl)-1H-1,2,3-triazole-4-carboxylate, 3-bromo-4-methoxyphenol and ethynylbenzene to afford 5-(4-methoxy-3-(2-phenylethynyl)phenoxy)-1H-1,2,3-triazole-4-carboxylic acid. ¹H-NMR (400 MHz, DMSO-d₆) δ: 15.13 (brs, 1H), 13.19 (brs, 1H), 7.53-7.51 (m, 2H), 7.43-7.41 (m, 3H), 7.24 (d, J=2.8 Hz, 1H), 7.17 (dd, J=8.8, 2.8 Hz, 1H), 7.08 (d, J=9.2 Hz, 1H), 3.86 (s, 3H). MS (ESI) m/z 333.9 [M−H]⁻.

Example 265: 5-(3-Fluoro-5-(2-(4-carboxyphenyl)ethynyl)phenoxy)-1H-1,2,3-triazole-4-carboxylic Acid

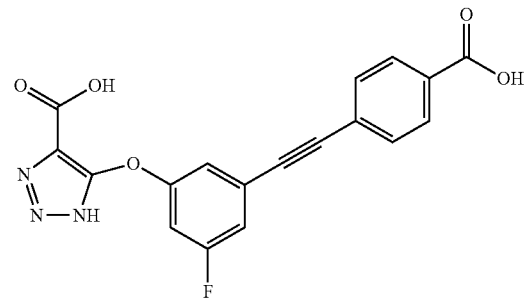 [SMILES: O=C(O)c1ccc(C#Cc2cc(F)cc(Oc3[nH]nnc3C(=O)O)c2)cc1]

The title compound was prepared following procedures described for Example 5 using ethyl 5-chloro-1-(4-methoxybenzyl)-1H-1,2,3-triazole-4-carboxylate, 3-bromo-5-fluorophenol and ethyl 4-ethynylbenzoate to afford 5-(3-fluoro-5-(2-(4-carboxyphenyl)ethynyl)phenoxy)-1H-1,2,3-triazole-4-carboxylic acid. MS (ESI) m/z 366.6[M−H]⁻.

Example 266: 5-(4-Fluoro-3-(2-(4-(methylsulfonyl)phenyl)ethynyl)phenoxy)-1H-1,2,3-triazole-4-carboxylic Acid

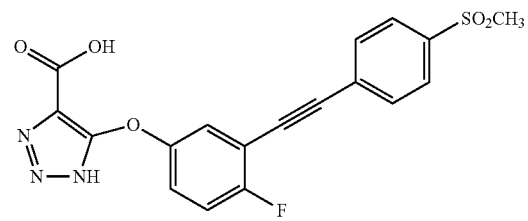 [SMILES: CS(=O)(=O)c1ccc(C#Cc2cc(Oc3[nH]nnc3C(=O)O)ccc2F)cc1]

The title compound was prepared following procedures described for Example 5 using ethyl 5-chloro-1-(4-methoxybenzyl)-1H-1,2,3-triazole-4-carboxylate, 3-bromo-4-fluorophenol and 1-ethynyl-4-(methylsulfonyl)benzene to afford 5-(4-fluoro-3-(2-(4-(methylsulfonyl)phenyl)ethynyl)phenoxy)-1H-1,2,3-triazole-4-carboxylic acid. ¹H-NMR (400 MHz, DMSO-d₆) δ: 7.98 (d, J=8.8 Hz, 2H), 7.84 (d, J=8.8 Hz, 2H), 7.44-7.37 (m, 2H), 7.30-7.26 (m, 1H), 3.27 (s, 3H). MS (ESI) m/z 402.1 [M+H]⁺.

Example 267: 5-(4-Fluoro-3-(2-(3-(methylsulfonyl)phenyl)ethynyl)phenoxy)-1H-1,2,3-triazole-4-carboxylic Acid

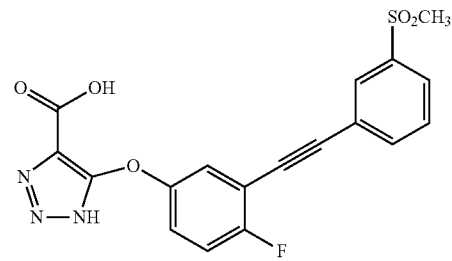 [SMILES: CS(=O)(=O)c1cccc(C#Cc2cc(Oc3[nH]nnc3C(=O)O)ccc2F)c1]

The title compound was prepared following procedures described for Example 5 using ethyl 5-chloro-1-(4-methoxybenzyl)-1H-1,2,3-triazole-4-carboxylate, 3-bromo-4-fluorophenol and 1-ethynyl-3-(methylsulfonyl)benzene to 5-(4-fluoro-3-(2-(3-(methylsulfonyl)phenyl)ethynyl)phenoxy)-1H-1,2,3-triazole-4-carboxylic acid. $^1$H-NMR (400 MHz, DMSO-d$_6$) δ: 8.11 (t, J=1.6 Hz, 1H), 8.00-7.91 (m, 2H), 7.73 (t, J=8.0 Hz, 1H), 7.45-7.37 (m, 2H), 7.30-7.26 (m, 1H), 3.29 (s, 3H). MS (ESI) m/z 399.9 [M–H]$^-$.

Example 268: 4-(3-((4-Cyanophenyl)ethynyl)-4-fluorophenoxy)-1H-1,2,3-triazole-5-carboxylic Acid

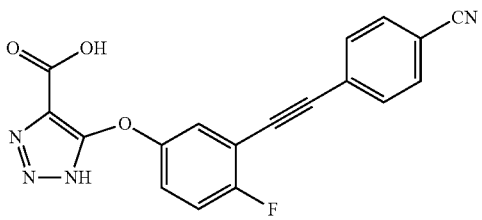 [SMILES: N#Cc1ccc(C#Cc2cc(Oc3[nH]nnc3C(=O)O)ccc2F)cc1]

The title compound was prepared following procedures described for Example 5 using ethyl 5-chloro-1-(4-methoxybenzyl)-1H-1,2,3-triazole-4-carboxylate, 3-bromo-4-fluorophenol and 4-ethynylbenzonitrile to afford 4-(3-((4-cyanophenyl)ethynyl)-4-fluorophenoxy)-1H-1,2,3-triazole-5-carboxylic acid. $^1$H-NMR (400 MHz, DMSO-d$_6$) δ: 7.91 (d, J=8.0 Hz, 2H), 7.77 (d, J=8.4 Hz, 2H), 7.36 (t, J=9.2 Hz, 1H), 7.32-7.20 (m, 2H). MS (ESI) m/z 349.1 [M+H]$^+$.

Example 269: 5-(4-((4-Cyanophenyl)ethynyl)-3-fluorophenoxy)-1H-1,2,3-triazole-4-carboxylic Acid

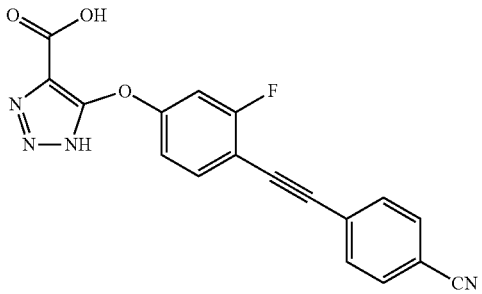 [SMILES: N#Cc1ccc(C#Cc2ccc(Oc3[nH]nnc3C(=O)O)cc2F)cc1]

The title compound was prepared following procedures described for Example 5 using ethyl 5-chloro-1-(4-methoxybenzyl)-1H-1,2,3-triazole-4-carboxylate, 4-bromo-3-fluorophenol and 3-ethynylbenzonitrile to afford 5-(4-((4-cyanophenyl)ethynyl)-3-fluorophenoxy)-1H-1,2,3-triazole-4-carboxylic acid. $^1$H-NMR (400 MHz, DMSO-d$_6$) δ: 7.91 (d, J=8.8 Hz, 2H), 7.74 (d, J=8.4 Hz, 2H), 7.70 (t, J=8.4 Hz, 1H), 7.20 (dd, J=10.8, 2.4 Hz, 1H), 6.97 (dd, J=8.8, 2.4 Hz, 1H). MS (ESI) m/z 349.1 [M+H]$^+$.

Example 270: 5-(4-((3-Cyanophenyl)ethynyl)-3-fluorophenoxy)-1H-1,2,3-triazole-4-carboxylic Acid

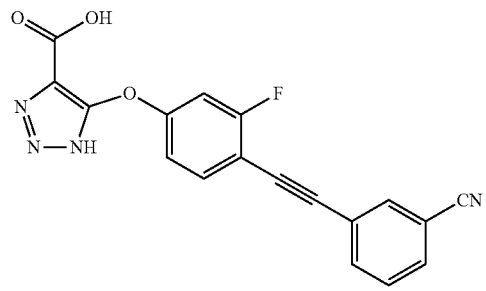 [SMILES: N#Cc1cccc(C#Cc2ccc(Oc3[nH]nnc3C(=O)O)cc2F)c1]

The title compound was prepared following procedures described for Example 5 using ethyl 5-chloro-1-(4-methoxybenzyl)-1H-1,2,3-triazole-4-carboxylate, 4-bromo-3-fluorophenol and 3-ethynylbenzonitrile to afford 5-(4-((3-cyanophenyl)ethynyl)-3-fluorophenoxy)-1H-1,2,3-triazole-4-carboxylic acid. $^1$H-NMR (400 MHz, DMSO-d$_6$) δ: 8.07 (t, J=1.6 Hz, 1H), 7.92-7.88 (m, 2H), 7.65 (t, J=8.0 Hz, 2H), 7.74 (d, J=8.4 Hz, 2H), 7.70 (t, J=8.4 Hz, 1H), 7.20 (dd, J=10.8, 2.4 Hz, 1H), 6.97 (dd, J=8.4, 2.4 Hz, 1H). MS (ESI) m/z 349.1 [M+H]$^+$.

Example 271: 5-(4-((3-Cyanophenyl)ethynyl)-3-fluorophenoxy)-1H-1,2,3-triazole-4-carboxylic Acid

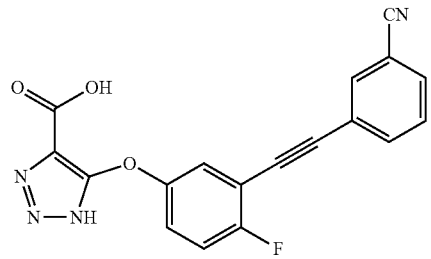 [SMILES: N#Cc1cccc(C#Cc2cc(Oc3[nH]nnc3C(=O)O)ccc2F)c1]

The title compound was prepared following procedures described for Example 5 using ethyl 5-chloro-1-(4-methoxybenzyl)-1H-1,2,3-triazole-4-carboxylate, 3-bromo-4-fluorophenol and 3-ethynylbenzonitrile to afford 5-(4-((3-cyanophenyl)ethynyl)-3-fluorophenoxy)-1H-1,2,3-triazole-4-carboxylic acid. $^1$H-NMR (400 MHz, DMSO-d$_6$) δ: 8.09 (s, 1H), 7.93-7.90 (m, 1H), 7.65 (t, J=8.0 Hz, 1H), 7.40-7.36 (m, 2H), 7.29-7.25 (m, 1H). MS (ESI) m/z 349.1 [M+H]$^+$.

Example 272: 5-(3-Fluoro-4-(2-(4-(methylsulfonyl)phenyl)ethynyl)phenoxy)-1H-1,2,3-triazole-4-carboxylic Acid

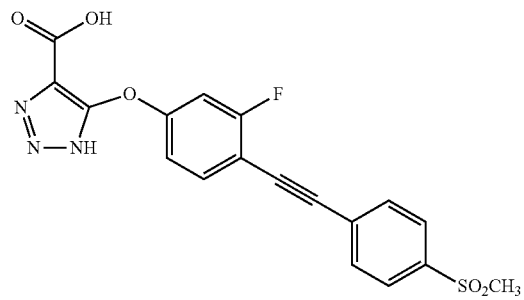 [SMILES: CS(=O)(=O)c1ccc(C#Cc2ccc(Oc3[nH]nnc3C(=O)O)cc2F)cc1]

The title compound was prepared following procedures described for Example 5 using ethyl 5-chloro-1-(4-methoxybenzyl)-1H-1,2,3-triazole-4-carboxylate, 4-bromo-3-fluorophenol and 1-ethynyl-4-(methylsulfonyl)benzene to afford 5-(3-fluoro-4-(2-(4-(methylsulfonyl)phenyl)ethynyl)phenoxy)-1H-1,2,3-triazole-4-carboxylic acid. $^1$H-NMR (400 MHz, DMSO-d$_6$) δ: 7.97 (d, J=8.4 Hz, 2H), 7.82 (d, J=8.8 Hz, 2H), 7.68 (t, J=8.4 Hz, 1H), 7.21 (dd, J=10.8, 2.4 Hz, 1H), 6.98 (dd, J=8.4, 2.4 Hz, 1H). MS (ESI) m/z 402.1 [M+H]$^+$.

Example 273: 5-(3-Fluoro-4-(2-(3-(methylsulfonyl)phenyl)ethynyl)phenoxy)-1H-1,2,3-triazole-4-carboxylic Acid

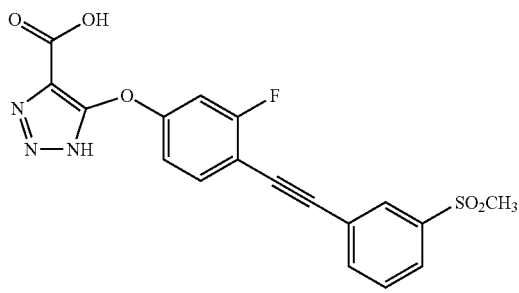

The title compound was prepared following procedures described for Example 5 using ethyl 5-chloro-1-(4-methoxybenzyl)-1H-1,2,3-triazole-4-carboxylate, 4-bromo-3-fluorophenol and 1-ethynyl-3-(methylsulfonyl)benzene to afford 5-(3-fluoro-4-(2-(3-(methylsulfonyl)phenyl)ethynyl)phenoxy)-1H-1,2,3-triazole-4-carboxylic acid. $^1$H-NMR (400 MHz, DMSO-d$_6$) δ: 8.08 (s, 1H), 7.97 (d, J=7.6 Hz, 1H), 7.91 (d, J=8.0 Hz, 1H), 7.75-7.66 (m, 2H), 7.21 (dd, J=10.8, 2.4 Hz, 1H), 6.98 (dd, J=8.8, 2.4 Hz, 1H). MS (ESI) m/z 402.1 [M+H]$^+$.

Example 274: 5-(3-Fluoro-5-(2-(4-(methylsulfonyl)phenyl)ethynyl)phenoxy)-1H-1,2,3-triazole-4-carboxylic Acid

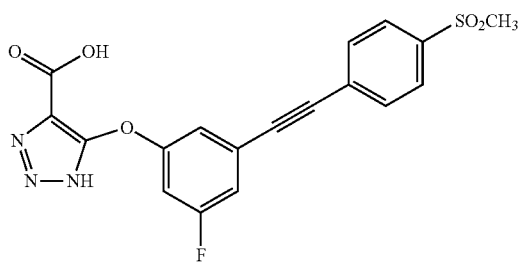 [SMILES: CS(=O)(=O)c1ccc(C#Cc2cc(F)cc(Oc3[nH]nnc3C(=O)O)c2)cc1]

The title compound was prepared following procedures described for Example 5 using ethyl 5-chloro-1-(4-methoxybenzyl)-1H-1,2,3-triazole-4-carboxylate, 3-bromo-5-fluorophenol and 1-ethynyl-4-(methylsulfonyl)benzene to afford 5-(3-fluoro-5-(2-(4-(methylsulfonyl)phenyl)ethynyl)phenoxy)-1H-1,2,3-triazole-4-carboxylic acid. $^1$H-NMR (400 MHz, DMSO-d$_6$) δ: 7.98 (d, J=8.8 Hz, 2H), 7.83 (d, J=8.8 Hz, 2H), 7.31 (d, J=8.0 Hz, 1H), 7.22-7.18 (m, 1H), 7.15 (s, 1H), 3.27 (s, 3H). MS (ESI) m/z 399.9 [M–H]$^-$.

Example 275: 5-(3-Fluoro-5-(2-(3-(methylsulfonyl)phenyl)ethynyl)phenoxy)-1H-1,2,3-triazole-4-carboxylic Acid

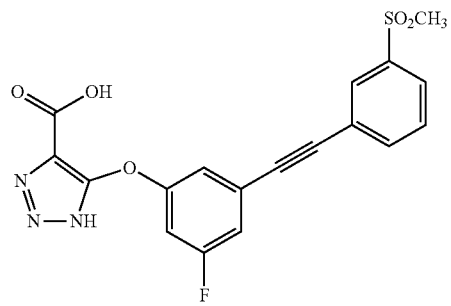 [SMILES: CS(=O)(=O)c1cccc(C#Cc2cc(F)cc(Oc3[nH]nnc3C(=O)O)c2)c1]

The title compound was prepared following procedures described for Example 5 using ethyl 5-chloro-1-(4-methoxybenzyl)-1H-1,2,3-triazole-4-carboxylate, 3-bromo-5-fluorophenol and 1-ethynyl-3-(methylsulfonyl)benzene to afford 5-(3-fluoro-5-(2-(3-(methylsulfonyl)phenyl)ethynyl)phenoxy)-1H-1,2,3-triazole-4-carboxylic acid. $^1$H-NMR (400 MHz, DMSO-d$_6$) δ: 15.37 (brs, 1H), 13.27 (brs, 1H), 8.12 (s, 1H), 8.11-7.90 (m, 2H), 7.72 (t, J=8.0 Hz, 1H), 7.30 (d, J=8.8 Hz, 1H), 7.19-7.15 (m, 2H), 3.28 (s, 3H). MS (ESI) m/z 399.9 [M–H]$^-$.

Example 276: 4-(3-((4-Cyanophenyl)ethynyl)-5-fluorophenoxy)-1H-1,2,3-triazole-5-carboxylic Acid

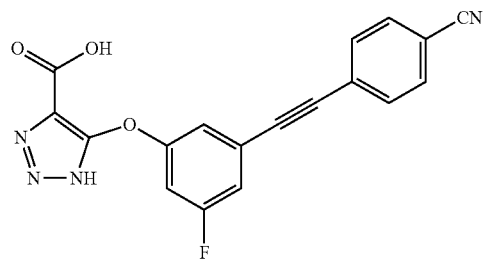 [SMILES: N#Cc1ccc(C#Cc2cc(F)cc(Oc3[nH]nnc3C(=O)O)c2)cc1]

The title compound was prepared following procedures described for Example 5 using ethyl 5-chloro-1-(4-methoxybenzyl)-1H-1,2,3-triazole-4-carboxylate, 3-bromo-5-fluorophenol and 4-ethynylbenzonitrile to afford 4-(3-((4-cyanophenyl)ethynyl)-5-fluorophenoxy)-1H-1,2,3-triazole-5-carboxylic acid. $^1$H-NMR (400 MHz, DMSO-d$_6$) δ: 7.91 (d, J=8.4 Hz, 2H), 7.76 (d, J=8.4 Hz, 2H), 7.29 (d, J=8.0 Hz, 1H), 7.72 (t, J=8.0 Hz, 1H), 7.21-7.17 (m, 1H), 7.14 (s, 1H). MS (ESI) m/z 346.9 [M–H]$^-$.

Example 277: 4-(3-((3-Cyanophenyl)ethynyl)-5-fluorophenoxy)-1H-1,2,3-triazole-5-carboxylic Acid

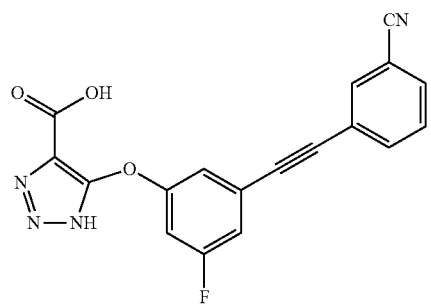 [SMILES: N#Cc1cccc(C#Cc2cc(F)cc(Oc3[nH]nnc3C(=O)O)c2)c1]

The title compound was prepared following procedures described for Example 5 using ethyl 5-chloro-1-(4-methoxybenzyl)-1H-1,2,3-triazole-4-carboxylate, 3-bromo-5-fluorophenol and 3-ethynylbenzonitrile to afford 4-(3-((3-cyanophenyl)ethynyl)-5-fluorophenoxy)-1H-1,2,3-triazole-5-carboxylic acid. ¹H-NMR (400 MHz, DMSO-d₆) δ: 8.09 (t, J=1.2 Hz, 1H), 7.93-7.89 (m, 2H), 7.65 (t, J=8.0 Hz, 1H), 7.29-7.26 (m, 1H), 7.21-7.17 (m, 1H), 7.11 (s, 1H). MS (ESI) m/z 346.9 [M−H]⁻.

Example 278: 5-(4-(2-(3-Fluorophenyl)ethynyl)phenoxy)-1H-1,2,3-triazole-4-carboxylic Acid

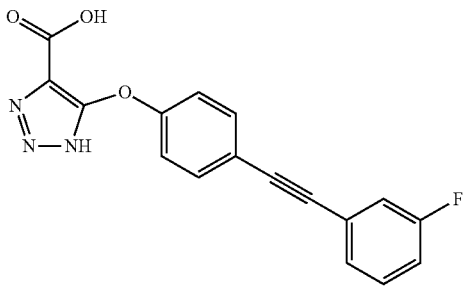 [SMILES: O=C(O)c1nn[nH]c1Oc1ccc(C#Cc2cccc(F)c2)cc1]

The title compound was prepared following procedures described for Example 5 using ethyl 5-chloro-1-(4-methoxybenzyl)-1H-1,2,3-triazole-4-carboxylate, 4-iodophenol and 1-ethynyl-3-fluorobenzene to afford 5-(4-(2-(3-fluorophenyl)ethynyl)phenoxy)-1H-1,2,3-triazole-4-carboxylic acid. ¹H-NMR (400 MHz, DMSO-d₆) δ: 7.59-7.56 (m, 2H), 7.50-7.39 (m, 3H), 7.30-7.25 (m, 1H), 7.14-7.10 (m, 2H). MS (ESI) m/z 322.0 [M−H]⁻.

Example 279: 5-(3-(2-(3-Fluorophenyl)ethynyl)phenoxy)-1H-1,2,3-triazole-4-carboxylic Acid

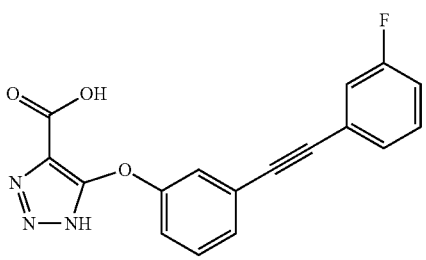 [SMILES: O=C(O)c1nn[nH]c1Oc1cccc(C#Cc2cccc(F)c2)c1]

The title compound was prepared following procedures described for Example 5 using ethyl 5-chloro-1-(4-methoxybenzyl)-1H-1,2,3-triazole-4-carboxylate, 3-iodophenol and 1-ethynyl-3-fluorobenzene to afford 5-(3-(2-(3-fluorophenyl)ethynyl)phenoxy)-1H-1,2,3-triazole-4-carboxylic acid. ¹H-NMR (400 MHz, DMSO-d₆) δ: 15.31 (brs, 1H), 13.30 (brs, 1H), 7.49-7.16 (m, 8H). MS (ESI) m/z 322.0 [M−H]⁻.

Example 280: 5-(4-(2-(4-Methoxyphenyl)ethynyl)phenoxy)-1H-1,2,3-triazole-4-carboxylic Acid

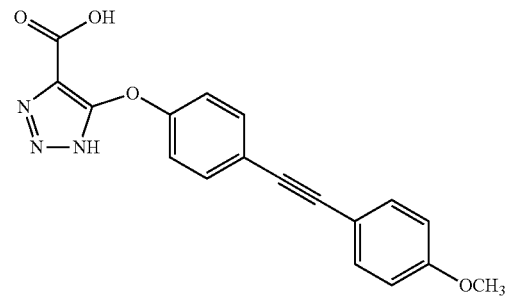 [SMILES: COc1ccc(C#Cc2ccc(Oc3[nH]nnc3C(=O)O)cc2)cc1]

The title compound was prepared following procedures described for Example 5 using ethyl 5-chloro-1-(4-methoxybenzyl)-1H-1,2,3-triazole-4-carboxylate, 4-iodophenol and 1-ethynyl-4-methoxybenzene to afford 5-(4-(2-(4-methoxyphenyl)ethynyl)phenoxy)-1H-1,2,3-triazole-4-carboxylic acid. ¹H-NMR (400 MHz, DMSO-d₆) δ: 7.52-7.47 (m, 4H), 7.10-7.08 (m, 2H), 6.99-6.97 (m, 2H), 3.79 (s, 3H). MS (ESI) m/z 334.0 [M−H]⁻.

Example 281: 5-(4-(2-(3-Methoxyphenyl)ethynyl)phenoxy)-1H-1,2,3-triazole-4-carboxylic Acid

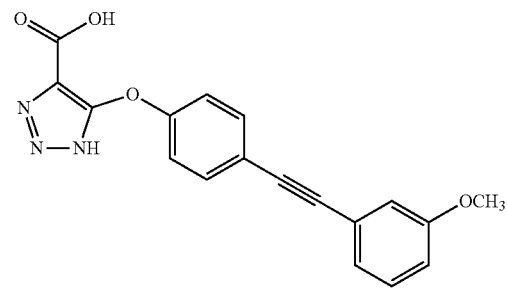 [SMILES: COc1cccc(C#Cc2ccc(Oc3[nH]nnc3C(=O)O)cc2)c1]

The title compound was prepared following procedures described for Example 5 using ethyl 5-chloro-1-(4-methoxybenzyl)-1H-1,2,3-triazole-4-carboxylate, 4-iodophenol and 1-ethynyl-3-methoxybenzene to afford 5-(4-(2-(3-methoxyphenyl)ethynyl)phenoxy)-1H-1,2,3-triazole-4-carboxylic acid. ¹H-NMR (400 MHz, DMSO-d₆) δ: 15.28 (brs, 1H), 13.20 (brs, 1H), 7.51-7.49 (m, 2H), 7.41 (t, J=8.0 Hz, 1H), 7.30 (d, J=7.6 Hz, 1H), 7.18 (s, 1H), 7.13-7.10 (m, 1H), 6.99-6.97 (m, 2H). MS (ESI) m/z 334.0 [M−H]⁻.

Example 282: 5-(4-(2-(6-Methoxypyridin-3-yl)ethynyl)phenoxy)-1H-1,2,3-triazole-4-carboxylic Acid

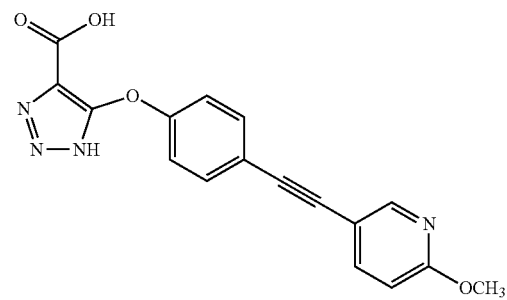

Step 1: Ethyl 5-(4-((trimethylsilyl)ethynyl)phenoxy)-1H-1,2,3-triazole-4-carboxylate A mixture of ethyl 5-(4-bromophenoxy)-1H-1,2,3-triazole-4-carboxylate (2.0 g, 6.40 mmol, 1.0 eq), ethynyltrimethylsilane (6.60 g, 67.3 mmol, 10.5 eq), Pd(PPh₃)₂Cl₂ (950 mg, 1.35 mmol, 0.21 eq) and CuI (384 mg, 2.02 mmol, 0.32 eq) in diisopropylamine (30 mL) in a sealed tube was heated at 80° C. under N₂ for 4 h. The reaction mixture was concentrated and the residue was purified by prep-HPLC (10-95% CH₃CN in water) to give the desired (1.99 g, crude) as a brown solid. MS (ESI) m/z 330.1 [M+H]⁺

Step 2: Ethyl 5-(4-ethynylphenoxy)-1H-1,2,3-triazole-4-carboxylate

To a solution of ethyl 5-(4-((trimethylsilyl)ethynyl)phenoxy)-1H-1,2,3-triazole-4-carboxylate (1.99 g, crude, 6.40 mmol, 1.0 eq) in THF (20 mL) was added TBAF (1M in THF, 12 mL, 12 mmol, 1.9 eq) at room temperature. The reaction mixture was stirred at room temperature for 1 h. The reaction was concentrated and the residue was adjusted to pH 2 by 1N HCl. The aqueous layer was extracted with EtOAc (3×150 mL). The combined organic layers were dried over anhydrous sodium sulfate and concentrated. The residue was purified by prep-HPLC (5-95% CH₃CN in water) to give the desired (600 mg, yield: 37% over two steps) as a yellow solid. MS (ESI) m/z 258.2 [M+H]⁺

Step 3: Ethyl 5-(4-((6-methoxypyridin-3-yl)ethynyl)phenoxy)-1H-1,2,3-triazole-4-carboxylate A mixture of ethyl 5-(4-ethynylphenoxy)-1H-1,2,3-triazole-4-carboxylate (310 mg, 1.20 mmol, 1.0 eq), 5-iodo-2-methoxypyridine (564 mg, 2.40 mmol, 2.0 eq), Pd(PPh₃)₂Cl₂ (84 mg, 0.12 mmol, 0.1 eq) and CuI (23 mg, 0.12 mmol, 0.1 eq) in DMF/DIEA (3 mL/1.5 mL) in a sealed tube was heated at 50° C. under N₂ for 2 h. The reaction mixture was concentrated and the residue was purified by silica gel column chromatography (DCM:methanol=50:1) to give the desired (360 mg, yield: 82%) as a brown gel. MS (ESI) m/z 365.1 [M+H]⁺

Step 4: 5-(4-((6-methoxypyridin-3-yl)ethynyl)phenoxy)-1H-1,2,3-triazole-4-carboxylic Acid A mixture of ethyl 5-(4-((6-methoxypyridin-3-yl)ethynyl)phenoxy)-1H-1,2,3-triazole-4-carboxylate (360 mg, 1.0 mmol, 1.0 eq) in 1N KOH (4 mL, 4 mmol, 4.0 eq) and THF/methanol (4 mL/4 mL) was stirred at room temperature overnight. The reaction was adjusted to pH ~3 and extracted with EtOAc (3×50 mL). The organic layers were combined, dried over anhydrous sodium sulfate, filtered and concentrated in vacuo. The crude product was purified by prep-HPLC (5-95% CH₃CN in water) to give the desired (105 mg, yield: 31%) as a yellow solid. ¹H-NMR (400 MHz, DMSO-d₆) δ: 8.39 (d, J=2.0 Hz, 1H), 7.86 (dd, J=8.4 Hz, 2.0 Hz, 1H), 7.56-7.53 (m, 2H), 7.10-7.08 (m, 2H), 6.88 (d, J=8.8 Hz, 1H), 3.89 (s, 3H). MS (ESI) m/z 336.8 [M+H]⁺

Example 283: 5-(4-(2-(2-Methoxypyridin-4-yl)ethynyl)phenoxy)-1H-1,2,3-triazole-4-carboxylic Acid

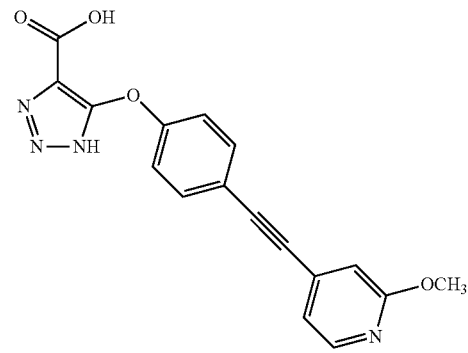 [SMILES: COc1cc(C#Cc2ccc(Oc3[nH]nnc3C(=O)O)cc2)ccn1]

The title compound was prepared following procedures described for Example 282 using ethyl 5-(4-((trimethylsilyl)ethynyl)phenoxy)-1H-1,2,3-triazole-4-carboxylate, 5-iodo-2-methoxypyridine to afford 5-(4-(2-(2-methoxypyridin-4-yl)ethynyl)phenoxy)-1H-1,2,3-triazole-4-carboxylic acid. ¹H-NMR (400 MHz, DMSO-d₆) δ: 8.19 (d, J=5.2 Hz, 1H), 7.56-7.54 (m, 2H), 7.08 (dd, J=5.2 Hz, 1.2 Hz, 1H), 6.99-6.97 (m, 2H), 6.94 (s, 1H), 3.86 (s, 3H). MS (ESI) m/z 336.8 [M+H]⁺

Example 284: 5-(3-(2-(6-Methoxypyridin-3-yl)ethynyl)phenoxy)-1H-1,2,3-triazole-4-carboxylic Acid

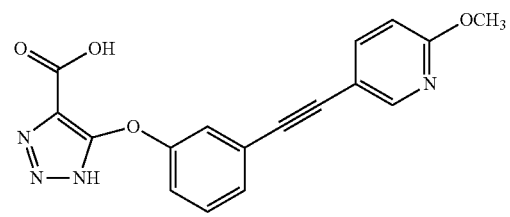 [SMILES: COc1ccc(C#Cc2cccc(Oc3[nH]nnc3C(=O)O)c2)cn1]

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 5-iodo-2-methoxypyridine to afford 5-(3-(2-(6-methoxypyridin-3-yl)ethynyl)phenoxy)-1H-1,2,3-triazole-4-carboxylic acid. ¹H-NMR (400 MHz, DMSO-d₆) δ: 15.28 (brs, 1H), 13.25 (brs, 1H), 8.40 (d, J=1.6 Hz, 1H), 7.88 (dd, J=8.4 Hz, 2.4 Hz, 1H), 7.43 (t, J=8.0 Hz, '1H), 7.30 (d, J=7.6 Hz, 1H), 7.21 (t, J=2.4 Hz, 1H), 7.16-7.13 (m, 1H), 6.88 (d, J=8.8 Hz, 1H), 3.89 (s, 3H). MS (ESI) m/z 336.9 [M+H]⁺.

Example 285: 5-(3-(2-(2-Methoxypyridin-4-yl)ethynyl)phenoxy)-1H-1,2,3-triazole-4-carboxylic Acid

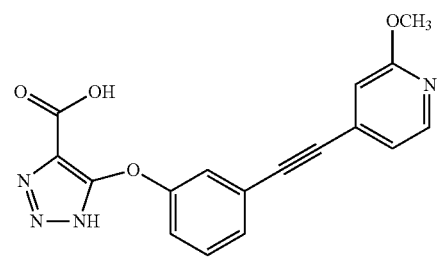 [SMILES: COc1cc(C#Cc2cccc(Oc3[nH]nnc3C(=O)O)c2)ccn1]

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 4-iodo-2-methoxypyridine to afford 5-(3-(2-(2-Methoxypyridin-4-yl)ethynyl)phenoxy)-1H-1,2,3-triazole-4-carboxylic acid. $^1$H-NMR (400 MHz, DMSO-$d_6$) δ: 15.29 (brs, 1H), 13.23 (brs, 1H), 8.21 (d, J=5.2 Hz, 1H), 7.46 (t, J=8.4 Hz, 1H), 7.39 (d, J=7.6 Hz, 1H), 7.28 (s, 1H), 7.22-7.19 (m, 1H), 7.11 (dd, J=5.2 Hz, 1.2 Hz, 1H), 6.98 (s, 1H), 3.87 (s, 3H). MS (ESI) m/z 336.9 [M+H]$^+$.

Example 286: 5-(4-(2-(3-Methoxyphenyl)ethynyl)phenoxy)-1H-1,2,3-triazole-4-carboxylic Acid

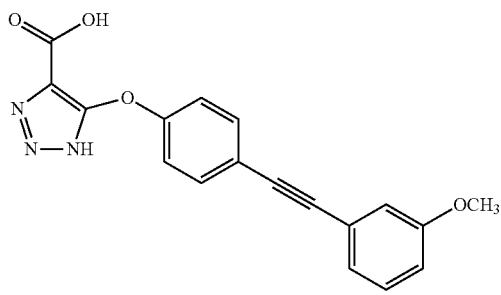 [SMILES: COc1cccc(C#Cc2ccc(Oc3[nH]nnc3C(=O)O)cc2)c1]

The title compound was prepared following procedures described for Example 5 using ethyl 5-chloro-1-(4-methoxybenzyl)-1H-1,2,3-triazole-4-carboxylate, 4-iodophenol, and 1-ethynyl-3-methoxybenzene to afford 5-(4-(2-(3-methoxyphenyl)ethynyl)phenoxy)-1H-1,2,3-triazole-4-carboxylic acid. $^1$H-NMR (400 MHz, DMSO-$d_6$) δ: 7.58-7.54 (m, 2H), 7.33 (t, J=8.0 Hz, 1H), 7.13-7.09 (m, 4H), 7.00-6.97 (m, 1H), 3.79 (s, 3H). MS (ESI) m/z 335.8 [M+H]$^+$ Example 287: 5-(3-(2-(3-Methoxyphenyl)ethynyl)phenoxy)-1H-1,2,3-triazole-4-carboxylic Acid

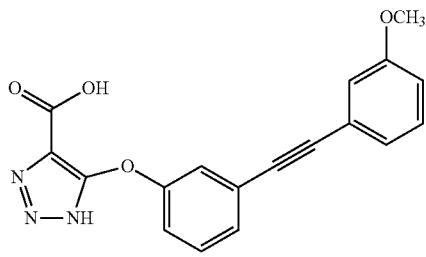 [SMILES: COc1cccc(C#Cc2cccc(Oc3[nH]nnc3C(=O)O)c2)c1]

The title compound was prepared following procedures described for Example 5 using ethyl 5-chloro-1-(4-methoxybenzyl)-1H-1,2,3-triazole-4-carboxylate, 3-iodophenol, and 1-ethynyl-3-methoxybenzene to afford 5-(3-(2-(3-methoxyphenyl)ethynyl)phenoxy)-1H-1,2,3-triazole-4-carboxylic acid. $^1$H-NMR (400 MHz, DMSO-$d_6$) δ: 15.29 (brs, 1H), 13.23 (brs, 1H), 7.43 (t, J=8.0 Hz, 1H), 7.33 (t, J=8.0 Hz, 2H), 7.22 (t, J=2.0 Hz, 1H), 7.17-7.12 (m, 3H), 7.02-6.99 (m, 1H). MS (ESI) m/z 335.9 [M+H]$^+$.

Example 288: 5-(4-(2-(4-Fluorophenyl)ethynyl)phenoxy)-1H-1,2,3-triazole-4-carboxylic Acid

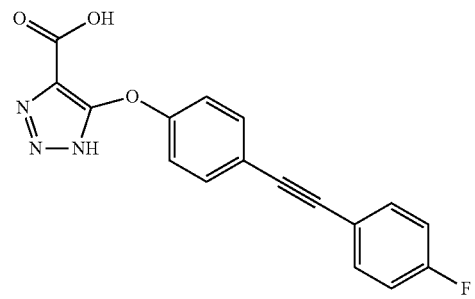 [SMILES: O=C(O)c1nn[nH]c1Oc1ccc(C#Cc2ccc(F)cc2)cc1]

The title compound was prepared following procedures described for Example 5 using ethyl 5-chloro-1-(4-methoxybenzyl)-1H-1,2,3-triazole-4-carboxylate, 4-iodophenol, and 1-ethynyl-4-fluorobenzene to afford 5-(4-(2-(4-fluorophenyl)ethynyl)phenoxy)-1H-1,2,3-triazole-4-carboxylic acid. $^1$H-NMR (400 MHz, DMSO-$d_6$) δ: 7.63-7.54 (m, 4H), 7.30-7.25 (m, 2H), 7.11 (dd, J=6.8, 2.0 Hz, 2H). MS (ESI) m/z 321.9 [M–H]$^-$.

Example 289: 5-(3-(2-(4-Fluorophenyl)ethynyl)phenoxy)-1H-1,2,3-triazole-4-carboxylic Acid

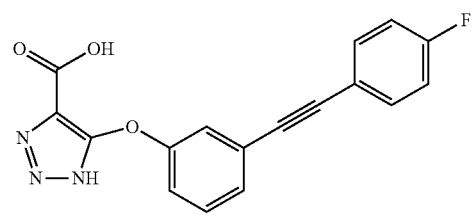 [SMILES: O=C(O)c1nn[nH]c1Oc1cccc(C#Cc2ccc(F)cc2)c1]

The title compound was prepared following procedures described for Example 5 using ethyl 5-chloro-1-(4-methoxybenzyl)-1H-1,2,3-triazole-4-carboxylate, 3-iodophenol, and 1-ethynyl-4-fluorobenzene to afford 5-(3-(2-(4-fluorophenyl)ethynyl)phenoxy)-1H-1,2,3-triazole-4-carboxylic acid. $^1$H-NMR (400 MHz, DMSO-$d_6$) δ: 7.85-7.61 (m, 2H), 7.43 (t, J=8.0 Hz, 1H), 7.35-7.21 (m, 4H), 7.16-7.13 (m, 1H). MS (ESI) m/z 321.9 [M–H]$^-$.

Example 290: 5-(4-(2-(4-Chlorophenyl)ethynyl)phenoxy)-1H-1,2,3-triazole-4-carboxylic Acid

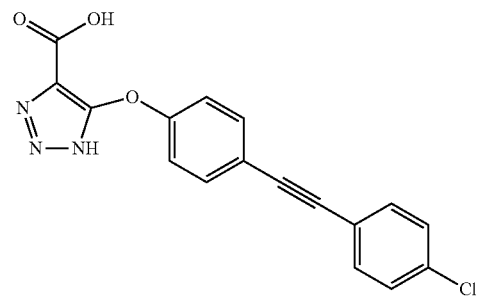 [SMILES: O=C(O)c1nn[nH]c1Oc1ccc(C#Cc2ccc(Cl)cc2)cc1]

The title compound was prepared following procedures described for Example 5 using ethyl 5-chloro-1-(4-methoxybenzyl)-1H-1,2,3-triazole-4-carboxylate, 4-iodophenol, and 1-chloro-4-ethynylbenzene to afford 5-(4-(2-(4-chlorophenyl)ethynyl)phenoxy)-1H-1,2,3-triazole-4-carboxylic acid. $^1$H-NMR (400 MHz, DMSO-$d_6$) δ: 7.58-7.55 (m, 4H), 7.50-7.48 (m, 2H), 7.12-7.10 (m, 2H). MS (ESI) m/z 337.9 [M−H]$^−$.

Example 291: 5-(4-(2-(3-Chlorophenyl)ethynyl)phenoxy)-1H-1,2,3-triazole-4-carboxylic Acid

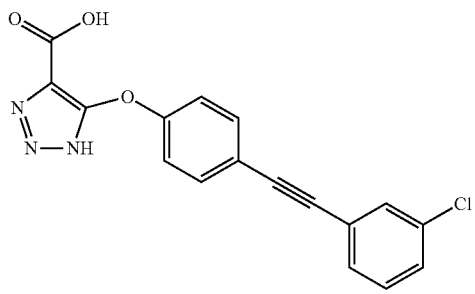 [SMILES: O=C(O)c1nn[nH]c1Oc1ccc(C#Cc2cccc(Cl)c2)cc1]

The title compound was prepared following procedures described for Example 5 using ethyl 5-chloro-1-(4-methoxybenzyl)-1H-1,2,3-triazole-4-carboxylate, 4-iodophenol, and 1-chloro-3-ethynylbenzene to afford 5-(4-(2-(3-chlorophenyl)ethynyl)phenoxy)-1H-1,2,3-triazole-4-carboxylic acid. $^1$H-NMR (400 MHz, DMSO-$d_6$) δ: 7.63-7.47 (m, 6H), 7.13-7.11 (m, 2H). MS (ESI) m/z 337.8 [M−H]$^−$.

Example 292: 5-(3-(2-(4-Chlorophenyl)ethynyl)phenoxy)-1H-1,2,3-triazole-4-carboxylic Acid

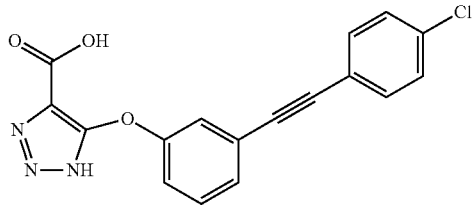 [SMILES: O=C(O)c1nn[nH]c1Oc1cccc(C#Cc2ccc(Cl)cc2)c1]

The title compound was prepared following procedures described for Example 5 using ethyl 5-chloro-1-(4-methoxybenzyl)-1H-1,2,3-triazole-4-carboxylate, 3-iodophenol, and 1-chloro-4-ethynylbenzene to afford 5-(3-(2-(4-chlorophenyl)ethynyl)phenoxy)-1H-1,2,3-triazole-4-carboxylic acid. $^1$H-NMR (400 MHz, DMSO-$d_6$) δ: 7.85-7.61 (m, 2H), 7.43 (t, J=8.0 Hz, 1H), 7.35-7.21 (m, 4H), 7.16-7.13 (m, 1H). MS (ESI) m/z 339.8 [M+H]$^+$.

Example 293: 5-(4-(2-(6-Methylpyridin-2-yl)ethynyl)phenoxy)-1H-1,2,3-triazole-4-carboxylic Acid

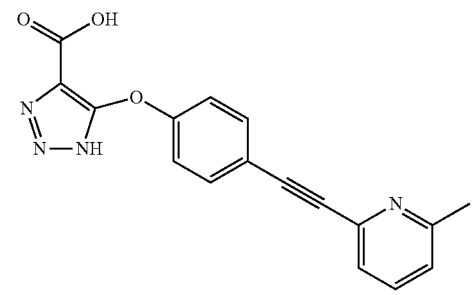 [SMILES: Cc1cccc(C#Cc2ccc(Oc3[nH]nnc3C(=O)O)cc2)n1]

The title compound was prepared following procedures described for Example 282 using ethyl 5-(4-ethynylphenoxy)-1H-1,2,3-triazole-4-carboxylate, 2-bromo-6-methylpyridine to afford 5-(4-(2-(6-methylpyridin-2-yl)ethynyl)phenoxy)-1H-1,2,3-triazole-4-carboxylic acid. $^1$H-NMR (400 MHz, CD$_3$OD) δ: 8.05 (t, J=8.0 Hz, 1H), 7.70-7.69 (m, 3H), 7.53 (d, J=8.0 Hz, 1H), 7.22-7.19 (m, 2H), 2.66 (s, 3H). MS (ESI) m/z 320.9 [M+H]$^+$.

Example 294: 5-(3-(2-(6-Methylpyridin-2-yl)ethynyl)phenoxy)-1H-1,2,3-triazole-4-carboxylic Acid

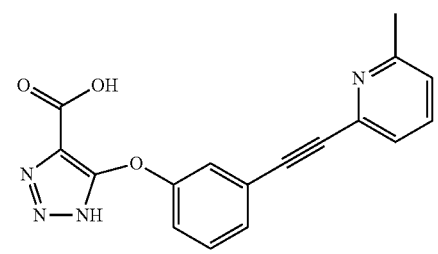 [SMILES: Cc1cccc(C#Cc2cccc(Oc3[nH]nnc3C(=O)O)c2)n1]

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 4-bromo-2-methylpyridine to afford 5-(3-(2-(6-methylpyridin-2-yl)ethynyl)phenoxy)-1H-1,2,3-triazole-4-carboxylic acid. $^1$H-NMR (400 MHz, DMSO-$d_6$) δ: 7.80-7.78 (m, 1H), 7.53-7.34 (m, 4H), 7.28 (s, 1H), 7.20 (dd, J=8.4 Hz, 2.0 Hz, 1H), 2.50 (s, 3H). MS (ESI) m/z 320.9 [M+H]$^+$.

Example 295: 5-(3-(2-(6-Methylpyridin-3-yl)ethynyl)phenoxy)-1H-1,2,3-triazole-4-carboxylic Acid

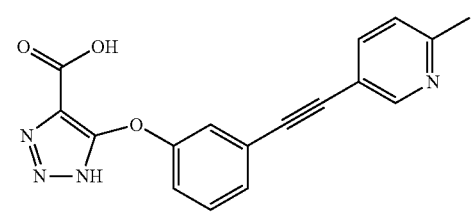 [SMILES: Cc1ccc(C#Cc2cccc(Oc3[nH]nnc3C(=O)O)c2)cn1]

The title compound was prepared following procedures described for Example 282 using ethyl 5-chloro-1-(4- methoxybenzyl)-1H-1,2,3-triazole-4-carboxylate, 3-bromophenol, ethynyltrimethylsilane and 5-bromo-2-methylpyridine to afford 5-(3-(2-(6-methylpyridin-3-yl)ethynyl)phenoxy)-1H-1,2,3-triazole-4-carboxylic acid. $^1$H-NMR (400 MHz, DMSO-d$_6$) δ: 15.31 (brs, 1H), 13.30 (brs, 1H), 8.64 (d, J=2.0 Hz, 1H), 7.80 (dd, J=8.0 Hz, 2.4 Hz, 1H), 7.45 (t, J=8.0 Hz, 1H), 7.37-7.33 (m, 2H), 7.24 (t, J=2.0 Hz, 1H), 7.18-7.15 (m, 1H), 2.50 (s, 3H). MS (ESI) m/z 320.9 [M+H]$^+$.

Example 296: 5-(3-(2-(2-Methylpyridin-4-yl)ethynyl)phenoxy)-1H-1,2,3-triazole-4-carboxylic Acid

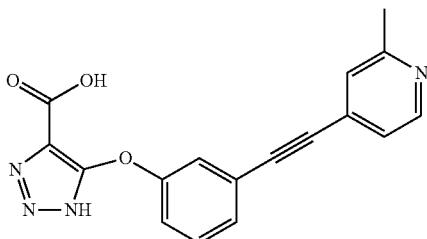

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 4-bromo-2-methylpyridine to afford 5-(3-(2-(2-methylpyridin-4-yl)ethynyl)phenoxy)-1H-1,2,3-triazole-4-carboxylic acid. $^1$H-NMR (400 MHz, CD$_3$OD) δ: 8.63 (d, J=6.0 Hz, 1H), 7.92 (s, 1H), 7.82 (dd, J=6.0 Hz, 1.2 Hz, 1H), 7.52-7.41 (m, 3H), 7.32-7.29 (m, 1H), 2.74 (s, 3H). MS (ESI) m/z 320.9 [M+H]$^+$ Example 297: 5-(4-(2-(6-Methylpyridin-3-yl)ethynyl)phenoxy)-1H-1,2,3-triazole-4-carboxylic Acid

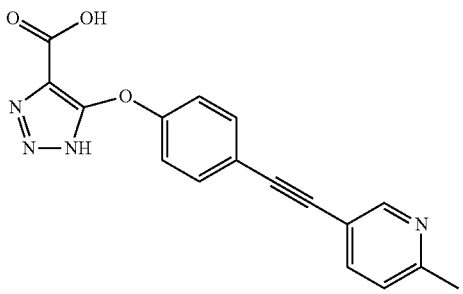 [SMILES: Cc1ccc(C#Cc2ccc(Oc3[nH]nnc3C(=O)O)cc2)cn1]

The title compound was prepared following procedures described for Example 282 using ethyl 5-chloro-1-(4-methoxybenzyl)-1H-1,2,3-triazole-4-carboxylate, 4-bromophenol, ethynyltrimethylsilane and 5-bromo-2-methylpyridine to afford 5-(4-(2-(6-methylpyridin-3-yl)ethynyl)phenoxy)-1H-1,2,3-triazole-4-carboxylic acid. $^1$H-NMR (400 MHz, DMSO-d$_6$) δ: 15.32 (brs, 1H), 13.33 (brs, 1H), 8.65 (s, 1H), 7.88 (dd, J=8.0, 2.0 Hz, 1H), 7.58 (d, J=8.8 Hz, 2H), 7.35 (d, J=8.4 Hz, 1H), 7.12 (d, J=8.8 Hz, 2H), 2.51 (s, 3H). MS (ESI) m/z 321.1 [M+H]$^+$ Example 298: 5-(4-(2-(2-Methylpyridin-4-yl)ethynyl)phenoxy)-1H-1,2,3-triazole-4-carboxylic Acid

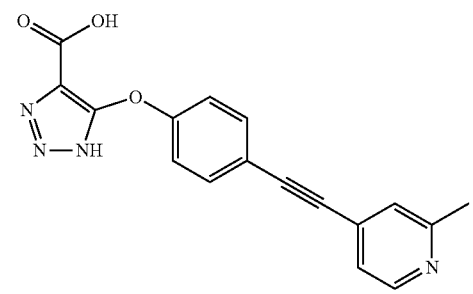 [SMILES: Cc1cc(C#Cc2ccc(Oc3[nH]nnc3C(=O)O)cc2)ccn1]

The title compound was prepared following procedures described for Example 282 using ethyl 5-chloro-1-(4-methoxybenzyl)-1H-1,2,3-triazole-4-carboxylate, 4-bromophenol, ethynyltrimethylsilane and 4-bromo-2-methylpyridine to afford 5-(4-(2-(2-methylpyridin-4-yl)ethynyl)phenoxy)-1H-1,2,3-triazole-4-carboxylic acid. $^1$H-NMR (400 MHz, DMSO-d$_6$) δ: 13.36 (brs, 1H), 7.57 (d, J=5.6 Hz, 1H), 7.64-7.62 (m, 2H), 7.59 (s, 1H), 7.48 (d, J=5.2 Hz, 1H), 7.17-7.14 (m, 2H), 2.54 (s, 3H). MS (ESI) m/z 321.1 [M+H]$^+$ Example 299: 5-(4-(Pent-1-ynyl)phenoxy)-1H-1,2,3-triazole-4-carboxylic Acid

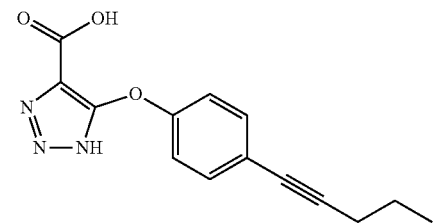 [SMILES: CCCC#Cc1ccc(Oc2[nH]nnc2C(=O)O)cc1]

The title compound was prepared following procedures described for Example 5 using ethyl 5-chloro-1-(4-methoxybenzyl)-1H-1,2,3-triazole-4-carboxylate, 4-iodophenol and pent-1-yne to afford 5-(4-(pent-1-ynyl)phenoxy)-1H-1,2,3-triazole-4-carboxylic acid. $^1$H-NMR (400 MHz, DMSO-d$_6$) δ: 13.32 (brs, 1H), 7.39-7.36 (m, 2H), 7.04-7.00 (m, 2H), 2.38 (t, J=6.8 Hz, 2H), 1.60-1.51 (m, 2H), 0.99 (t, J=7.2 Hz, 3H). MS (ESI) m/z 272.1 [M+H]$^+$ Example 300: 5-(3-(Pent-1-ynyl)phenoxy)-1H-1,2,3-triazole-4-carboxylic Acid

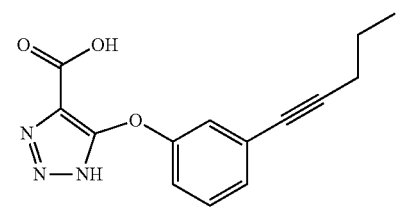 [SMILES: CCCC#Cc1cccc(Oc2[nH]nnc2C(=O)O)c1]

The title compound was prepared following procedures described for Example 6 using ethyl 5-chloro-1-(4-methoxybenzyl)-1H-1,2,3-triazole-4-carboxylate, 3-iodophenol and pent-1-yne to afford 5-(3-(pent-1-ynyl)phenoxy)-1H-1,2,3-triazole-4-carboxylic acid. $^1$H-NMR (400 MHz, DMSO-d$_6$) δ: 7.25 (t, J=8.0 Hz, 1H), 7.02 (d, J=7.6 Hz, 1H), 6.92-6.89 (m, 1H), 6.80 (t, J=2.0 Hz, 1H), 2.38 (t, J=6.8 Hz, 2H), 1.60-1.51 (m, 2H), 0.99 (t, J=7.2 Hz, 3H). MS (ESI) m/z 272.1 [M+H]$^+$

Example 301: 5-(4-(3-Cyclopropylprop-1-ynyl)phenoxy)-1H-1,2,3-triazole-4-carboxylic Acid

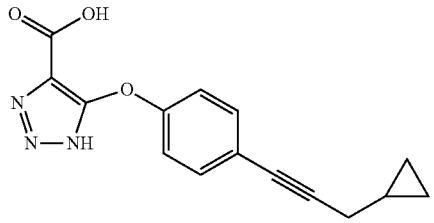

The title compound was prepared following procedures described for Example 3 using ethyl 5-chloro-1-(4-methoxybenzyl)-1H-1,2,3-triazole-4-carboxylate, 4-iodophenol and (3-cyclopropylprop-1-ynyl)trimethylsilane to afford 5-(4-(3-cyclopropylprop-1-ynyl)phenoxy)-1H-1,2,3-triazole-4-carboxylic acid. $^1$H-NMR (400 MHz, DMSO-d$_6$) δ: 7.29 (d, J=8.8 Hz, 2H), 6.83 (d, J=8.4 Hz, 2H), 2.44 (d, J=6.0 Hz, 2H), 1.01-0.95 (m, 1H), 0.49-0.44 (m, 2H), 0.26-0.22 (m, 2H). MS (ESI) m/z 284.1 [M+H]$^+$.

Example 302: 5-(3-(3-Cyclopropylprop-1-ynyl)phenoxy)-1H-1,2,3-triazole-4-carboxylic Acid

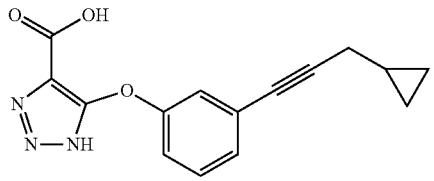 [SMILES: O=C(O)c1nn[nH]c1Oc1cccc(C#CCC2CC2)c1]

Step 1: Ethyl 5-(3-iodophenoxy)-1-(4-methoxybenzyl)-1H-1,2,3-triazole-4-carboxylate To a mixture of NaH (60% in mineral oil, 1.85 g, 46.2 mmol, 1.5 eq) in DMF (375 mL) was added 3-iodophenol (12.0 g, 54.5 mmol, 1.5 eq) at 0° C. The resulting mixture was stirred at room temperature for 1 h. Ethyl 5-chloro-1-(4-methoxybenzyl)-1H-1,2,3-triazole-4-carboxylate (12.4 g, 42.0 mmol, 1.0 eq) was added into the mixture and stirred at 85° C. overnight. The reaction was quenched with saturated NH$_4$Cl aqueous solution and extracted with EtOAc (3×200 mL). The combined organic layers were dried over anhydrous sodium sulfate and concentrated. The residue was purified by silica gel column chromatography (PE:EtOAc=4:1) to give the desired (18.0 g, yield: 89%) as a brown oil. MS (ESI) m/z 480.0 [M+H]$^+$.

Step 2: Ethyl 5-(3-iodophenoxy)-1H-1,2,3-triazole-4-carboxylate

A solution of ethyl 5-(3-iodophenoxy)-1-(4-methoxybenzyl)-1H-1,2,3-triazole-4-carboxylate (18.0 g, 37.5 mmol) in TFA (200 mL) was heated at 65° C. for 2 h. The reaction mixture was concentrated under reduced pressure, and the residue was purified by silica gel column chromatography (PE:EtOAc=3:1) to give the desired (12.3 g, yield: 91%) as a brown solid. MS (ESI) m/z 360.0 [M+H]$^+$.

Step 4: (3-cyclopropylprop-1-ynyl)trimethylsilane

To a solution of ethynyltrimethylsilane (5 g, 51.0 mmol) in dry-THF (25 mL) was added n-BuLi (2.5 M in hexane, 25 mL, 62.5 mmol, 1.2 eq) drop-wise at −78° C. under N$_2$. After the resulting mixture was stirred at 0° C. for 10 minutes, HMPA (13.9 g, 77.5 mmol, 1.5 eq) was added slowly at −78° C. The reaction mixture was stirred at room temperature overnight. The reaction was diluted with Et$_2$O (80 mL) and washed with brine. The separated organic layer was dried over anhydrous sodium sulfate and concentrated to give the crude desired (8 g) as a pale yellow liquid, which was used directly for next step without further purification.

Step 5: Ethyl 5-(3-(3-cyclopropylprop-1-ynyl)phenoxy)-1H-1,2,3-triazole-4-carboxylate A mixture of ethyl 5-(3-iodophenoxy)-1H-1,2,3-triazole-4-carboxylate (324 mg, 0.9 mmol, 1.0 eq), (3-cyclopropylprop-1-ynyl)trimethylsilane (1.8 g, crude), Pd(PPh$_3$)$_2$Cl$_2$ (63.2 mg, 0.09 mmol, 0.1 eq), CuI (17.1 mg, 0.09 mmol, 0.1 eq) and TBAF (1M in THF, 16.2 mL, 16.2 mmol, 18.0 eq) in DIEA (12 mL) in a sealed tube was heated at 70° C. under N$_2$ for 2 h. The reaction mixture was concentrated and the residue was purified by silica gel column chromatography (PE:EtOAc=5:1) to give the desired (167 mg, yield: 59%) as a brown solid. MS (ESI) m/z 312.1 [M+H]$^+$.

Step 6: 5-(3-(3-cyclopropylprop-1-ynyl)phenoxy)-1H-1,2,3-triazole-4-carboxylic Acid A mixture of ethyl 5-(3-(3-cyclopropylprop-1-ynyl)phenoxy)-1H-1,2,3-triazole-4-carboxylate (167 mg, 0.53 mmol) and 3N KOH (2 mL, 4 mmol, 7.5 eq) in methanol/THF (2 mL/2 mL) was stirred at room temperature overnight. The reaction was adjusted to pH ~3 by 1 HCl and extracted with EtOAc (3×50 mL). The organic layers were combined, dried over anhydrous sodium sulfate, filtered and concentrated in vacuo. The crude product was purified by prep-HPLC (5-95% CH$_3$CN in water) to give the desired (50 mg, yield: 33%) as a white solid. $^1$H-NMR (400 MHz, DMSO-d$_6$) δ: 13.2 (br, 1H), 7.34 (t, J=7.6 Hz, 1H), 7.16 (d, J=8.0, 1H), 7.06-7.03 (m, 2H), 2.45 (d, J=6.0 Hz, 2H), 1.01-0.94 (m, 1H), 0.49-0.44 (m, 2H), 0.24-0.20 (m, 2H). MS (ESI) m/z 284.1 [M+H]$^+$

Example 303: 5-(4-(But-1-ynyl)phenoxy)-1H-1,2,3-triazole-4-carboxylic Acid

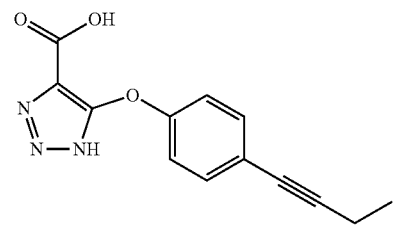 [SMILES: CCC#Cc1ccc(Oc2[nH]nnc2C(=O)O)cc1]

The title compound was prepared following procedures described for Example 5 using ethyl 5-chloro-1-(4-methoxybenzyl)-1H-1,2,3-triazole-4-carboxylate, 4-iodophenol and but-1-ynyltrimethylsilane to afford 5-(4-(but-1-ynyl)phenoxy)-1H-1,2,3-triazole-4-carboxylic acid. $^1$H-NMR (400 MHz, DMSO-d$_6$) δ: 7.29 (d, J=8.8 Hz, 2H), 6.83 (d, J=8.4 Hz, 2H), 2.39 (q, J=7.6 Hz, 2H), 1.15 (t, J=7.6 Hz, 3H). MS (ESI) m/z 258.1 [M+H]$^+$.

Example 304: 5-(3-(But-1-ynyl)phenoxy)-1H-1,2,3-triazole-4-carboxylic Acid

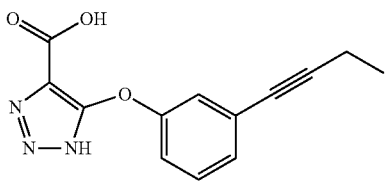 [SMILES: CCC#Cc1cccc(Oc2[nH]nnc2C(=O)O)c1]

The title compound was prepared following procedures described for Example 6 using ethyl 5-chloro-1-(4-methoxybenzyl)-1H-1,2,3-triazole-4-carboxylate, 3-iodophenol and but-1-ynyltrimethylsilane to afford 5-(3-(but-1-ynyl)phenoxy)-1H-1,2,3-triazole-4-carboxylic acid. $^1$H-NMR (400 MHz, DMSO-d$_6$) δ: 7.34 (t, J=8.0 Hz, 1H), 7.15 (d, J=8.0 Hz, 1H), 7.06-7.02 (m, 2H), 2.40 (q, J=7.6 Hz, 2H), 1.15 (t, J=7.6 Hz, 3H). MS (ESI) m/z 258.1 [M+H]$^+$.

Example 305: 5-(4-(4,4,4-Trifluorobut-1-ynyl)phenoxy)-1H-1,2,3-triazole-4-carboxylic Acid

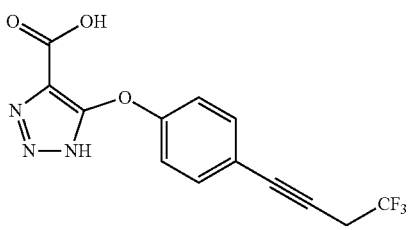 [SMILES: O=C(O)c1nn[nH]c1Oc1ccc(C#CCC(F)(F)F)cc1]

A mixture of ethyl 5-(4-ethynylphenoxy)-1H-1,2,3-triazole-4-carboxylic acid (320 mg, 1.40 mmol, 1.0 eq), 1,1,1-trifluoro-2-iodoethane (1.47 g, 7.00 mmol, 5.0 eq), DABCO (940 mg, 8.40 mmol, 6.0 eq), Pd$_2$(dba)$_3$ (128 mg, 0.14 mmol, 0.1 eq) and DPE-Phos (151 mg, 0.28 mmol, 0.2 eq) in toluene (6 mL) was heated at 80° C. under N$_2$ for 2.5 h. The reaction mixture was concentrated and the residue was purified by prep-HPLC (10-95% CH$_3$CN in water) to give the desired (10.2 mg, yield: 2%) as a white solid. $^1$H-NMR (400 MHz, DMSO-d$_6$) δ: 7.45 (d, J=8.8 Hz, 2H), 7.05 (d, J=8.8 Hz, 2H), 3.76 (q, J=10.4 Hz, 2H). MS (ESI) m/z 310.0 [M–H]$^-$.

Example 306: 5-(3-(4,4,4-Trifluorobut-1-ynyl)phenoxy)-1H-1,2,3-triazole-4-carboxylic Acid

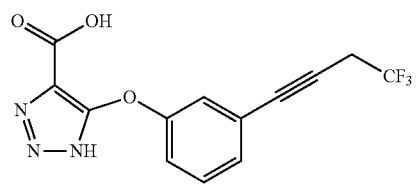 [SMILES: O=C(O)c1nn[nH]c1Oc1cccc(C#CCC(F)(F)F)c1]

The title compound was prepared following procedures described for Example 305 using 5-(3-ethynylphenoxy)-1H-1,2,3-triazole-4-carboxylic acid and 1,1,1-trifluoro-2-iodoethane to afford 5-(3-(4,4,4-trifluorobut-1-ynyl)phenoxy)-1H-1,2,3-triazole-4-carboxylic acid. $^1$H-NMR (400 MHz, DMSO-d$_6$) δ: 7.40 (t, J=8.0 Hz, 1H), 7.24 (d, J=7.6 Hz, 1H), 7.14-7.12 (m, 2H), 3.79 (q, J=10.4 Hz, 2H). MS (ESI) m/z 312.0 [M+H]$^+$.

Example 307: 5-(3-(2-(1H-Indazol-5-yl)ethynyl)phenoxy)-1H-1,2,3-triazole-4-carboxylic Acid

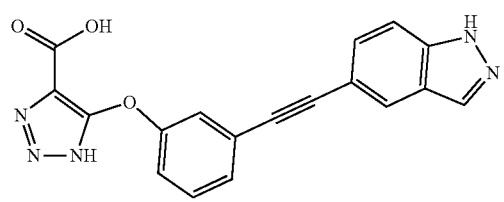 [SMILES: O=C(O)c1nn[nH]c1Oc1cccc(C#Cc2ccc3[nH]ncc3c2)c1]

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 5-bromo-1H-indazole to afford 5-(3-(2-(1H-indazol-5-yl)ethynyl)phenoxy)-1H-1,2,3-triazole-4-carboxylic acid. $^1$H-NMR (400 MHz, DMSO-d$_6$) δ: 8.10 (s, 1H), 8.03 (s, 1H), 7.56 (d, J=8.4 Hz, 1H), 7.48 (dd, J=8.4 Hz, 0.8 Hz, 1H), 7.35 (t, J=8.4 Hz, 1H), 7.21 (d, J=7.6 Hz, 1H), 6.99-6.97 (m, 2H). MS (ESI) m/z 346.1 [M+H]$^+$.

Example 308: 5-(4-(2-(Pyridin-2-yl)ethynyl)phenoxy)-1H-1,2,3-triazole-4-carboxylic Acid

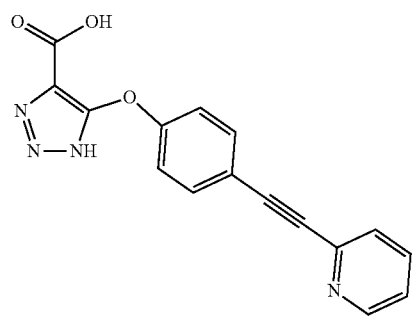 [SMILES: O=C(O)c1nn[nH]c1Oc1ccc(C#Cc2ccccn2)cc1]

The title compound was prepared following procedures described for Example 5 using ethyl 5-chloro-1-(4-methoxybenzyl)-1H-1,2,3-triazole-4-carboxylate, 4-iodophenol and 2-ethynylpyridine to afford 5-(4-(2-(pyridin-2-yl)ethynyl) phenoxy)-1H-1,2,3-triazole-4-carboxylic acid. ¹H-NMR (400 MHz, DMSO-d₆) δ: 15.34 (brs, 1H), 13.33 (brs, 1H), 8.61 (d, J=4.0 Hz, 1H), 7.88-7.84 (m, 1H), 7.65-7.61 (m, 3H), 7.43-7.40 (m, 1H), 7.13 (d, J=8.8 Hz, 2H). MS (ESI) m/z 307.1 [M+H]⁺.

Example 309: 5-(4-(2-(Pyridin-3-yl)ethynyl)phenoxy)-1H-1,2,3-triazole-4-carboxylic Acid

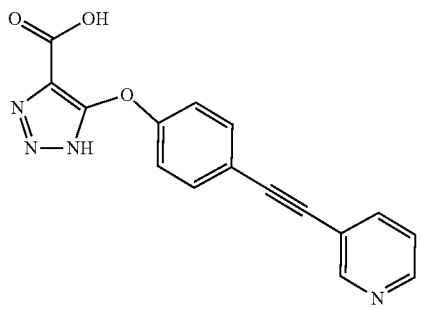 [SMILES: O=C(O)c1nn[nH]c1Oc1ccc(C#Cc2cccnc2)cc1]

The title compound was prepared following procedures described for Example 5 using ethyl 5-chloro-1-(4-methoxybenzyl)-1H-1,2,3-triazole-4-carboxylate, 4-iodophenol and 3-ethynylpyridine to afford 5-(4-(2-(pyridin-3-yl)ethynyl) phenoxy)-1H-1,2,3-triazole-4-carboxylic acid. ¹H-NMR (400 MHz, DMSO-d₆) δ: 8.77 (t, J=0.8 Hz, 1H), 8.60 (dd, J=4.4 Hz, 1.6 Hz, 1H), 8.02-7.99 (m, 1H), 7.61-7.59 (m, 2H), 7.50-7.47 (m, 1H), 7.15-7.12 (m, 2H). MS (ESI) m/z 307.1 [M+H]⁺.

Example 310: 5-(4-(2-(Pyridin-4-yl)ethynyl)phenoxy)-1H-1,2,3-triazole-4-carboxylic Acid

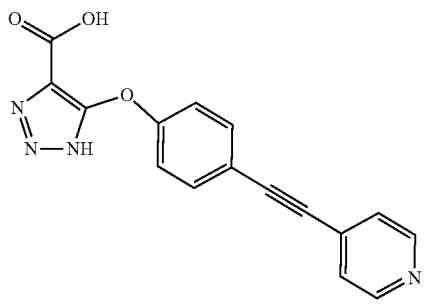 [SMILES: O=C(O)c1nn[nH]c1Oc1ccc(C#Cc2ccncc2)cc1]

The title compound was prepared following procedures described for Example 5 using ethyl 5-chloro-1-(4-methoxybenzyl)-1H-1,2,3-triazole-4-carboxylate, 4-iodophenol and 4-ethynylpyridine hydrochloride to afford 5-(4-(2-(pyridin-4-yl)ethynyl)phenoxy)-1H-1,2,3-triazole-4-carboxylic acid. ¹H-NMR (400 MHz, DMSO-d₆) δ: 15.41 (brs, 1H), 13.27 (brs, 1H), 8.63 (d, J=5.2 Hz, 2H), 7.62 (d, J=8.8 Hz, 2H), 7.54 (d, J=5.6 Hz, 2H), 7.14 (d, J=8.8 Hz, 2H). MS (ESI) m/z 307.1 [M+H]⁺.

Example 311: 5-(3-(2-(Pyridin-2-yl)ethynyl)phenoxy)-1H-1,2,3-triazole-4-carboxylic Acid

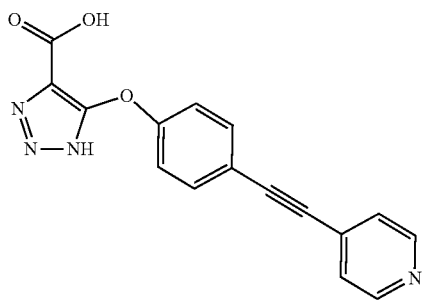 [SMILES: O=C(O)c1nn[nH]c1Oc1ccc(C#Cc2ccncc2)cc1]

The title compound was prepared following procedures described for Example 6 using ethyl 5-chloro-1-(4-methoxybenzyl)-1H-1,2,3-triazole-4-carboxylate, 3-iodophenol and 2-ethynylpyridine to afford 5-(3-(2-(pyridin-2-yl)ethynyl) phenoxy)-1H-1,2,3-triazole-4-carboxylic acid. ¹H-NMR (400 MHz, DMSO-d₆) δ: 15.30 (brs, 1H), 13.26 (brs, 1H), 8.61 (d, J=4.4 Hz, 1H), 7.88-7.84 (m, 1H), 7.66 (d, J=8.0 Hz, 1H), 7.49-7.29 (m, 3H), 7.20 (d, J=2.0 Hz, 1H), 7.19-7.18 (m, 1H). MS (ESI) m/z 307.1 [M+H]⁺.

Example 312: 5-(3-(2-(Pyridin-3-yl)ethynyl)phenoxy)-1H-1,2,3-triazole-4-carboxylic Acid

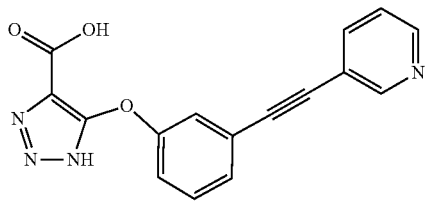 [SMILES: O=C(O)c1nn[nH]c1Oc1cccc(C#Cc2cccnc2)c1]

The title compound was prepared following procedures described for Example 6 using ethyl 5-chloro-1-(4-methoxybenzyl)-1H-1,2,3-triazole-4-carboxylate, 3-iodophenol and 3-ethynylpyridine to afford 5-(3-(2-(pyridin-3-yl)ethynyl) phenoxy)-1H-1,2,3-triazole-4-carboxylic acid. ¹H-NMR (400 MHz, DMSO-d₆) δ: 8.80 (s, 1H), 8.63-8.61 (m, 1H), 8.05-8.02 (m, 1H), 7.52-7.38 (m, 3H), 7.27 (d, J=2.0 Hz, 1H), 7.19 (dd, J=8.0 Hz, 2.0 Hz, 1H), 7.19-7.18 (m, 1H). MS (ESI) m/z 307.1 [M+H]⁺.

Example 313: 5-(3-(2-(Pyridin-4-yl)ethynyl)phenoxy)-1H-1,2,3-triazole-4-carboxylic Acid

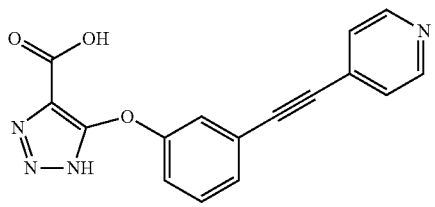 [SMILES: O=C(O)c1nn[nH]c1Oc1cccc(C#Cc2ccncc2)c1]

The title compound was prepared following procedures described for Example 6 using ethyl 5-chloro-1-(4-methoxybenzyl)-1H-1,2,3-triazole-4-carboxylate, 3-iodophenol and 4-ethynylpyridine hydrochloride to afford 5-(3-(2-(pyridin-3-yl)ethynyl)phenoxy)-1H-1,2,3-triazole-4-carboxylic acid. ¹H-NMR (400 MHz, DMSO-d₆) δ: 13.38 (brs, 1H), 8.69 (d, J=6.0 Hz, 2H), 7.65 (d, J=6.0 Hz, 2H), 7.50-7.41 (m, 2H), 7.32 (s, 1H), 7.22 (dd, J=8.0 Hz, 1.6 Hz, 1H). MS (ESI) m/z 307.1 [M+H]⁺.

Example 314: 5-(4-(2-(1-Methyl-1H-indazol-4-yl)ethynyl)phenoxy)-1H-1,2,3-triazole-4-carboxylic Acid

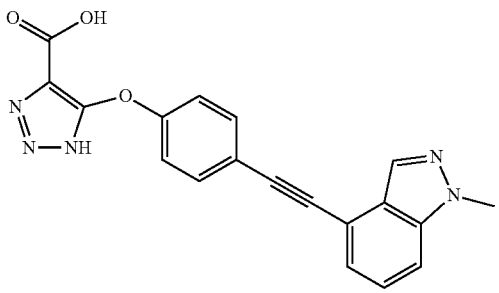 [SMILES: Cn1ncc2c(C#Cc3ccc(Oc4[nH]nnc4C(=O)O)cc3)cccc21]

The title compound was prepared following procedures described for Example 282 using ethyl 5-(4-ethynylphenoxy)-1H-1,2,3-triazole-4-carboxylate and 4-bromo-1-methyl-1H-indazole to afford 5-(4-(2-(1-methyl-1H-indazol-4-yl)ethynyl)phenoxy)-1H-1,2,3-triazole-4-carboxylic acid. ¹H-NMR (400 MHz, DMSO-d₆) δ: 13.27 (brs, 1H), 8.23 (d, J=1.2 Hz, 1H), 7.73-7.67 (m, 3H), 7.45-7.34 (m, 2H), 7.16-7.13 (m, 2H), 4.09 (s, 3H). MS (ESI) m/z 360.1 [M+H]⁺.

Example 315: 5-(3-(2-(1-Methyl-1H-indazol-4-yl)ethynyl)phenoxy)-1H-1,2,3-triazole-4-carboxylic Acid

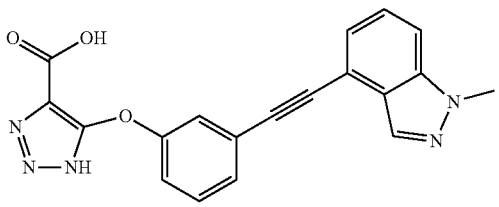 [SMILES: Cn1ncc2c(C#Cc3cccc(Oc4[nH]nnc4C(=O)O)c3)cccc21]

The title compound was prepared following procedures described for Example 282 using ethyl 5-(3-ethynylphenoxy)-1H-1,2,3-triazole-4-carboxylate and 4-bromo-1-methyl-1H-indazole to afford 5-(3-(2-(1-methyl-1H-indazol-4-yl)ethynyl)phenoxy)-1H-1,2,3-triazole-4-carboxylic acid. ¹H-NMR (400 MHz, DMSO-d₆) δ: 13.36 (brs, 1H), 8.26 (s, 1H), 7.73 (t, J=8.4 Hz, 1H), 7.47-7.37 (m, 5H), 7.19-7.16 (m, 1H), 4.07 (s, 3H). MS (ESI) m/z 360.1 [M+H]⁺.

Example 316: 5-(4-(2-(1-Methyl-1H-indazol-5-yl)ethynyl)phenoxy)-1H-1,2,3-triazole-4-carboxylic Acid

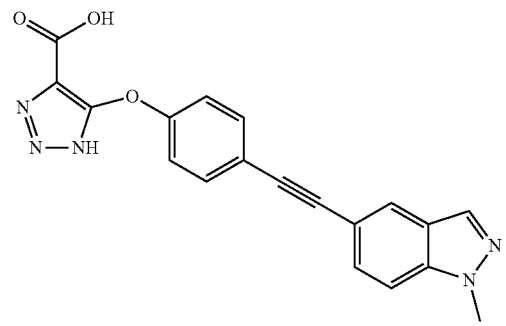 [SMILES: Cn1ncc2cc(C#Cc3ccc(Oc4[nH]nnc4C(=O)O)cc3)ccc21]

The title compound was prepared following procedures described for Example 282 using ethyl 5-(4-ethynylphenoxy)-1H-1,2,3-triazole-4-carboxylate and 5-bromo-1-methyl-1H-indazole to afford 5-(4-(2-(1-methyl-1H-indazol-5-yl)ethynyl)phenoxy)-1H-1,2,3-triazole-4-carboxylic acid. ¹H-NMR (400 MHz, DMSO-d₆) δ: 15.32 (brs, 1H), 13.23 (brs, 1H), 8.09 (s, 1H), 8.00 (s, 1H), 7.70 (d, J=8.8 Hz, 1H), 7.58-7.52 (m, 3H), 7.11 (d, J=8.8 Hz, 1H), 4.07 (s, 3H). MS (ESI) m/z 360.1 [M+H]⁺.

Example 317: 5-(3-(2-(1-Methyl-1H-indazol-5-yl)ethynyl)phenoxy)-1H-1,2,3-triazole-4-carboxylic Acid

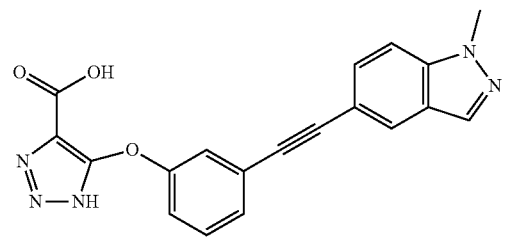 [SMILES: Cn1ncc2cc(C#Cc3cccc(Oc4[nH]nnc4C(=O)O)c3)ccc21]

The title compound was prepared following procedures described for Example 282 using ethyl 5-(3-ethynylphenoxy)-1H-1,2,3-triazole-4-carboxylate and 5-bromo-1-methyl-1H-indazole to afford 5-(3-(2-(1-methyl-1H-indazol-5-yl)ethynyl)phenoxy)-1H-1,2,3-triazole-4-carboxylic acid. ¹H-NMR (400 MHz, DMSO-d₆) δ: 15.29 (brs, 1H), 13.25 (brs, 1H), 8.09 (s, 1H), 8.02 (s, 1H), 7.70 (d, J=8.8 Hz, 1H), 7.54 (d, J=8.8, 1.2 Hz, 1H), 7.43 (t, J=8.0 Hz, 1H), 7.34 (d, J=7.6 Hz, 1H), 7.22 (d, J=2.0 Hz, 1H), 7.15-7.12 (m, 1H), 4.07 (s, 3H). MS (ESI) m/z 360.1 [M+H]⁺.

Example 318: 5-(4-(2-(1-Methyl-1H-indazol-6-yl)ethynyl)phenoxy)-1H-1,2,3-triazole-4-carboxylic Acid

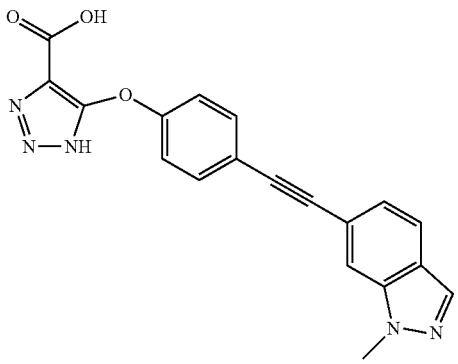 [SMILES: Cn1ncc2ccc(C#Cc3ccc(Oc4[nH]nnc4C(=O)O)cc3)cc21]

The title compound was prepared following procedures described for Example 282 using ethyl 5-(4-ethynylphenoxy)-1H-1,2,3-triazole-4-carboxylate and 6-bromo-1-methyl-1H-indazole to afford 5-(4-(2-(1-methyl-1H-indazol-6-yl)ethynyl)phenoxy)-1H-1,2,3-triazole-4-carboxylic acid. $^1$H-NMR (400 MHz, DMSO-$d_6$) δ: 13.32 (brs, 1H), 8.09 (d, J=1.2 Hz, 1H), 7.93 (d, J=0.8 Hz, 1H), 7.79 (d, J=8.4 Hz, 1H), 7.61-7.57 (m, 2H), 7.26 (dd, J=8.0, 1.2 Hz, 1H), 7.15-7.12 (m, 2H), 4.07 (s, 3H). MS (ESI) m/z 360.1 [M+H]$^+$.

Example 319: 5-(3-(2-(1-Methyl-1H-indazol-6-yl)ethynyl)phenoxy)-1H-1,2,3-triazole-4-carboxylic Acid

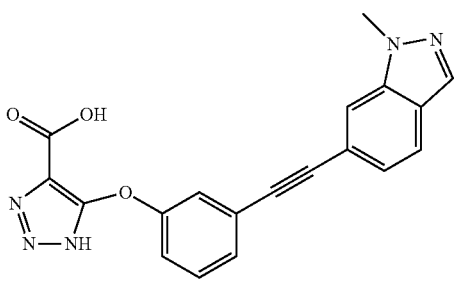 [SMILES: Cn1ncc2ccc(C#Cc3cccc(Oc4[nH]nnc4C(=O)O)c3)cc21]

The title compound was prepared following procedures described for Example 282 using ethyl 5-(3-ethynylphenoxy)-1H-1,2,3-triazole-4-carboxylate and 6-bromo-1-methyl-1H-indazole to afford 5-(3-(2-(1-methyl-1H-indazol-6-yl)ethynyl)phenoxy)-1H-1,2,3-triazole-4-carboxylic acid. $^1$H-NMR (400 MHz, DMSO-$d_6$) δ: 13.35 (brs, 1H), 8.09 (s, 1H), 7.95 (s, 1H), 7.79 (d, J=8.0 Hz, 1H), 7.45 (t, J=8.0 Hz, 1H), 7.37 (d, J=7.6 Hz, 1H), 7.29-7.15 (m, 3H), 4.07 (s, 3H). MS (ESI) m/z 360.1 [M+H]$^+$.

Example 320: 5-(3-(2-(1H-Pyrazol-4-yl)ethynyl)phenoxy)-1H-1,2,3-triazole-4-carboxylic Acid

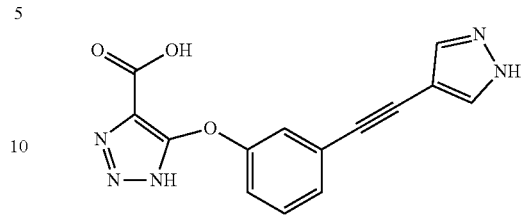

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 4-iodo-1H-pyrazole to afford 5-(3-(2-(1H-pyrazol-4-yl)ethynyl)phenoxy)-1H-1,2,3-triazole-4-carboxylic acid. $^1$H-NMR (400 MHz, DMSO-$d_6$) δ: 13.28 (brs, 2H), 7.94 (brs, 2H), 7.41-7.37 (m, 1H), 7.25 (d, J=7.6 Hz, 1H), 7.10-7.08 (m, 2H). MS (ESI) m/z 296.1 [M+H]$^+$.

Example 321: 5-(4-(2-(1-Methyl-1H-pyrazol-5-yl)ethynyl)phenoxy)-1H-1,2,3-triazole-4-carboxylic Acid

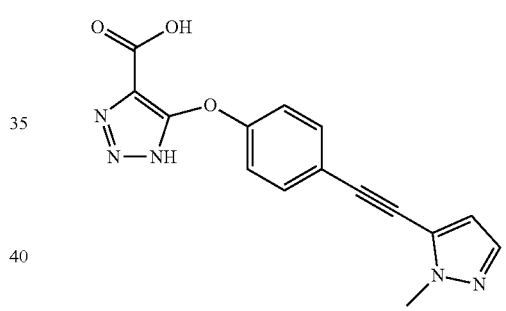

The title compound was prepared following procedures described for Example 282 using ethyl 5-(4-ethynylphenoxy)-1H-1,2,3-triazole-4-carboxylate and 5-bromo-1-methyl-1H-pyrazole to afford 5-(4-(2-(1-methyl-1H-pyrazol-5-yl)ethynyl)phenoxy)-1H-1,2,3-triazole-4-carboxylic acid. $^1$H-NMR (400 MHz, DMSO-$d_6$) δ: 7.61 (d, J=9.2 Hz, 2H), 7.51 (d, J=2.0 Hz, 1H), 7.13 (d, J=8.8 Hz, 2H), 6.61 (d, J=2.0 Hz, 1H), 3.93 (s, 3H). MS (ESI) m/z 310.1 [M+H]$^+$.

Example 322: 5-(3-(2-(1-Methyl-1H-pyrazol-5-yl)ethynyl)phenoxy)-1H-1,2,3-triazole-4-carboxylic Acid

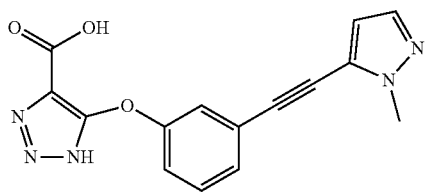 [SMILES: Cn1nccc1C#Cc1cccc(Oc2[nH]nnc2C(=O)O)c1]

The title compound was prepared following procedures described for Example 282 using ethyl 5-chloro-1-(4-methoxybenzyl)-1H-1,2,3-triazole-4-carboxylate, 3-bromophenol, ethynyltrimethylsilane and 5-bromo-1-methyl-1H-pyrazole to afford 5-(3-(2-(1-methyl-1H-pyrazol-5-yl)ethynyl)phenoxy)-1H-1,2,3-triazole-4-carboxylic acid. $^1$H-NMR (400 MHz, DMSO-d$_6$) δ: 7.52-7.39 (m, 3H), 7.32 (s, 1H), 7.18 (d, J=7.6 Hz, 1H), 6.63 (d, J=1.2 Hz, 1H), 3.94 (s, 3H). MS (ESI) m/z 310.1 [M+H]$^+$.

Example 323: 5-(4-(2-(1H-Indazol-7-yl)ethynyl)phenoxy)-1H-1,2,3-triazole-4-carboxylic Acid

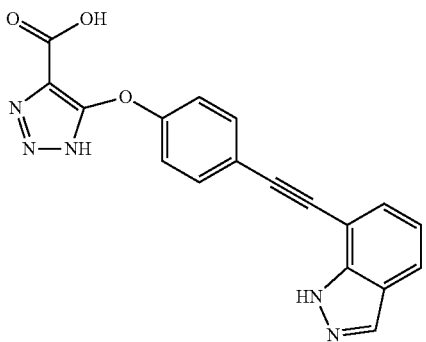 [SMILES: O=C(O)c1nn[nH]c1Oc1ccc(C#Cc2cccc3cn[nH]c23)cc1]

The title compound was prepared following procedures described for Example 282 using ethyl 5-(4-ethynylphenoxy)-1H-1,2,3-triazole-4-carboxylate and 7-bromo-1H-indazole to afford 5-(4-(2-(1H-indazol-7-yl)ethynyl)phenoxy)-1H-1,2,3-triazole-4-carboxylic acid. $^1$H-NMR (400 MHz, DMSO-d$_6$) δ: 13.58 (brs, 1H), 8.19 (s, 1H), 7.83 (dd, J=8.0, 0.4 Hz, 1H), 7.74 (d, J=8.8 Hz, 1H), 7.54 (dd, J=7.2, 0.8 Hz, 1H), 7.18-7.15 (m, 3H), 6.61 (d, J=2.0 Hz, 1H), 3.93 (s, 3H). MS (ESI) m/z 346.1 [M+H]$^+$.

Example 324: 5-(3-(2-(1H-Indazol-7-yl)ethynyl)phenoxy)-1H-1,2,3-triazole-4-carboxylic Acid

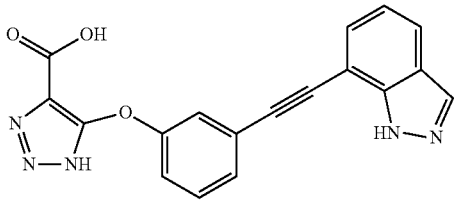 [SMILES: O=C(O)c1nn[nH]c1Oc1cccc(C#Cc2cccc3cn[nH]c23)c1]

The title compound was prepared following procedures described for Example 282 using ethyl 5-(3-ethynylphenoxy)-1H-1,2,3-triazole-4-carboxylate and 7-bromo-1H-indazole to afford 5-(3-(2-(1H-indazol-7-yl)ethynyl)phenoxy)-1H-1,2,3-triazole-4-carboxylic acid. $^1$H-NMR (400 MHz, DMSO-d$_6$) δ: 15.30 (brs, 1H), 13.58 (brs, 1H), 8.20 (s, 1H), 7.85 (d, J=7.6 Hz, 1H), 7.57-7.45 (m, 4H), 7.18-7.15 (m, 2H). MS (ESI) m/z 346.1 [M+H]$^+$.

Example 325: 5-(4-(2-(1-Methyl-1H-indazol-7-yl)ethynyl)phenoxy)-1H-1,2,3-triazole-4-carboxylic Acid

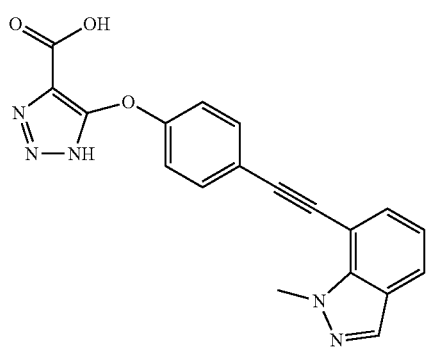 [SMILES: Cn1ncc2cccc(C#Cc3ccc(Oc4[nH]nnc4C(=O)O)cc3)c21]

The title compound was prepared following procedures described for Example 282 using ethyl 5-(4-ethynylphenoxy)-1H-1,2,3-triazole-4-carboxylate and 7-bromo-1-methyl-1H-pyrazole to afford 5-(4-(2-(1-methyl-1H-indazol-7-yl)ethynyl)phenoxy)-1H-1,2,3-triazole-4-carboxylic acid. $^1$H-NMR (400 MHz, DMSO-d$_6$) δ: 13.27 (brs, 1H), 8.15 (s, 1H), 7.83 (dd, J=8.0, 0.8 Hz, 1H), 7.67-7.59 (m, 3H), 7.19-7.15 (m, 3H), 4.42 (s, 3H). MS (ESI) m/z 360.1 [M+H]$^+$.

Example 326: 5-(3-(2-(1-Methyl-1H-indazol-7-yl)ethynyl)phenoxy)-1H-1,2,3-triazole-4-carboxylic Acid

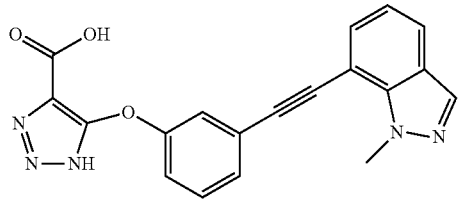 [SMILES: Cn1ncc2cccc(C#Cc3cccc(Oc4[nH]nnc4C(=O)O)c3)c21]

The title compound was prepared following procedures described for Example 326 using ethyl 5-(3-ethynylphenoxy)-1H-1,2,3-triazole-4-carboxylate and 7-bromo-1-methyl-1H-indazole to afford 5-(3-(2-(1-methyl-1H-indazol-7-yl)ethynyl)phenoxy)-1H-1,2,3-triazole-4-carboxylic acid. $^1$H-NMR (400 MHz, DMSO-d$_6$) δ: 8.15 (s, 1H), 7.85 (dd, J=8.0 Hz, 0.8 Hz, 1H), 7.62 (dd, J=7.2 Hz, 0.8 Hz, 1H), 7.47-7.35 (m, 3H), 7.19-7.15 (m, 2H), 4.40 (s, 3H). MS (ESI) m/z 360.1 [M+H]$^+$.

Example 327: 5-(4-(2-(1H-Indazol-4-yl)ethynyl)phenoxy)-1H-1,2,3-triazole-4-carboxylic Acid

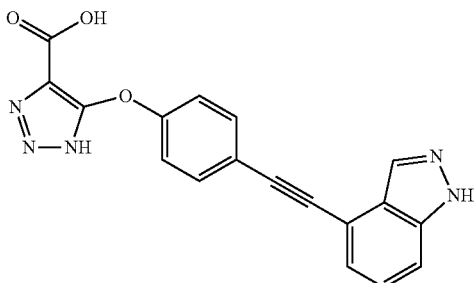

The title compound was prepared following procedures described for Example 282 using ethyl 5-(4-ethynylphenoxy)-1H-1,2,3-triazole-4-carboxylate and 4-bromo-1H-indazole to afford 5-(4-(2-(1H-indazol-4-yl)ethynyl)phenoxy)-1H-1,2,3-triazole-4-carboxylic acid. $^1$H-NMR (400 MHz, DMSO-$d_6$) δ: 13.33 (brs, 1H), 8.25 (d, J=0.8 Hz, 1H), 7.70-7.60 (m, 3H), 7.41-7.32 (m, 2H), 7.16-7.14 (m, 2H). MS (ESI) m/z 346.1 [M+H]$^+$.

Example 328: 5-(3-(2-(1H-Indazol-4-yl)ethynyl)phenoxy)-1H-1,2,3-triazole-4-carboxylic Acid

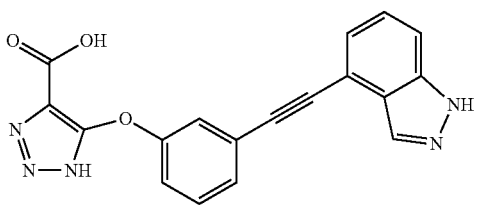 [SMILES: O=C(O)c1nn[nH]c1Oc1cccc(C#Cc2cccc3[nH]ncc23)c1]

The title compound was prepared following procedures described for Example 282 using ethyl 5-(3-ethynylphenoxy)-1H-1,2,3-triazole-4-carboxylate and 4-bromo-1H-indazole to afford 5-(3-(2-(1H-indazol-4-yl)ethynyl)phenoxy)-1H-1,2,3-triazole-4-carboxylic acid. $^1$H-NMR (400 MHz, DMSO-$d_6$) δ: 8.26 (s, 1H), 7.62 (d, J=7.6 Hz, 1H), 7.44-7.34 (m, 4H), 7.26 (s, 1H), 7.10-7.07 (m, 1H). MS (ESI) m/z 346.1 [M+H]$^+$.

Example 329: 5-(4-(2-(1H-Indazol-6-yl)ethynyl)phenoxy)-1H-1,2,3-triazole-4-carboxylic Acid

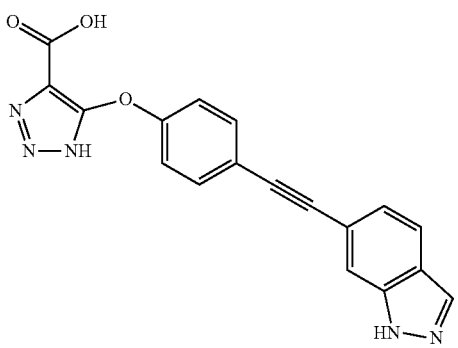 [SMILES: O=C(O)c1nn[nH]c1Oc1ccc(C#Cc2ccc3cn[nH]c3c2)cc1]

The title compound was prepared following procedures described for Example 282 using ethyl 5-(4-ethynylphenoxy)-1H-1,2,3-triazole-4-carboxylate and 6-bromo-1H-indazole to afford 5-(4-(2-(1H-indazol-6-yl)ethynyl)phenoxy)-1H-1,2,3-triazole-4-carboxylic acid. $^1$H-NMR (400 MHz, DMSO-$d_6$) δ: 13.25 (brs, 1H), 8.12 (s, 1H), 7.80 (d, J=8.4 Hz, 1H), 7.73 (s, 1H), 7.59 (d, J=8.8 Hz, 2H), 7.24 (d, J=8.4 Hz, 1H), 7.12 (d, J=9.2 Hz, 2H). MS (ESI) m/z 346.1 [M+H]$^+$.

Example 330: 5-(3-(2-(1H-Indazol-6-yl)ethynyl)phenoxy)-1H-1,2,3-triazole-4-carboxylic Acid

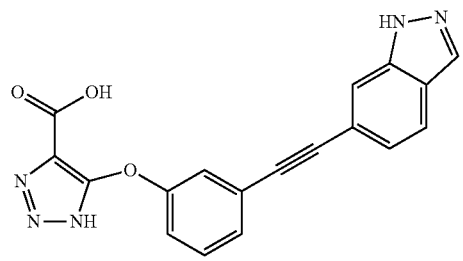 [SMILES: O=C(O)c1nn[nH]c1Oc1cccc(C#Cc2ccc3cn[nH]c3c2)c1]

The title compound was prepared following procedures described for Example 282 using ethyl 5-(3-ethynylphenoxy)-1H-1,2,3-triazole-4-carboxylate and 6-bromo-1H-indazole to afford 5-(3-(2-(1H-indazol-6-yl)ethynyl)phenoxy)-1H-1,2,3-triazole-4-carboxylic acid. $^1$H-NMR (400 MHz, DMSO-$d_6$) δ: 13.25 (brs, 2H), 8.12 (s, 1H), 7.82-7.76 (m, 2H), 7.46-7.37 (m, 2H), 7.27-7.24 (m, 2H), 7.16-7.14 (m, 1H). MS (ESI) m/z 346.1 [M+H]$^+$.

Example 331: 5-(4-(2-(1H-Imidazol-2-yl)ethynyl)phenoxy)-1H-1,2,3-triazole-4-carboxylic Acid

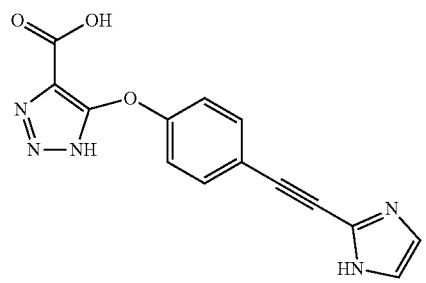 [SMILES: O=C(O)c1nn[nH]c1Oc1ccc(C#Cc2ncc[nH]2)cc1]

The title compound was prepared following procedures described for Example 282 using ethyl 5-(4-ethynylphenoxy)-1H-1,2,3-triazole-4-carboxylate and 2-bromo-1H-imidazole to afford 5-(4-(2-(1H-imidazol-2-yl)ethynyl)phenoxy)-1H-1,2,3-triazole-4-carboxylic acid. $^1$H-NMR (400 MHz, DMSO-$d_6$) δ: 13.15 (brs, 2H), 7.57 (d, J=8.8 Hz, 2H), 7.14-7.15 (m, 3H). MS (ESI) m/z 296.1 [M+H]$^+$.

Example 332: 5-(3-(2-(1H-Imidazol-2-yl)ethynyl)phenoxy)-1H-1,2,3-triazole-4-carboxylic Acid

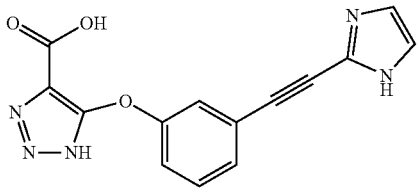 [SMILES: O=C(O)c1nn[nH]c1Oc1cccc(C#Cc2ncc[nH]2)c1]

The title compound was prepared following procedures described for Example 282 using ethyl 5-(3-ethynylphenoxy)-1H-1,2,3-triazole-4-carboxylate and 2-bromo-1H-imidazole to afford 5-(3-(2-(1H-imidazol-2-yl)ethynyl)phenoxy)-1H-1,2,3-triazole-4-carboxylic acid. $^1$H-NMR (400 MHz, DMSO-$d_6$) δ: 13.45 (brs, 1H), 7.52-7.40 (m, 4H), 7.27-7.25 (m, 2H). MS (ESI) m/z 296.1 [M+H]$^+$.

Example 333: 5-(4-(2-(1-Methyl-1H-imidazol-2-yl)ethynyl)phenoxy)-1H-1,2,3-triazole-4-carboxylic Acid

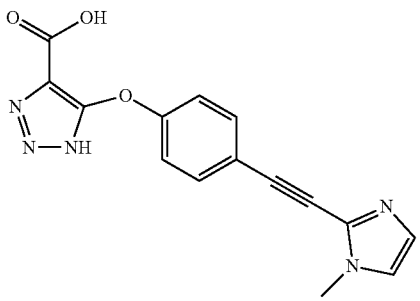 [SMILES: Cn1ccnc1C#Cc1ccc(Oc2[nH]nnc2C(=O)O)cc1]

The title compound was prepared following procedures described for Example 282 using ethyl 5-(4-ethynylphenoxy)-1H-1,2,3-triazole-4-carboxylate and 2-bromo-1-methyl-1H-imidazole to afford 5-(4-(2-(1-methyl-1H-imidazol-2-yl)ethynyl)phenoxy)-1H-1,2,3-triazole-4-carboxylic acid. $^1$H-NMR (400 MHz, DMSO-$d_6$) δ: 7.71-7.69 (m, 2H), 7.62 (s, 1H), 7.44 (s, 1H), 7.20-7.18 (m, 2H), 3.86 (s, 3H). MS (ESI) m/z 310.1 [M+H]$^+$.

Example 334: 5-(3-(2-(1-Methyl-1H-imidazol-2-yl)ethynyl)phenoxy)-1H-1,2,3-triazole-4-carboxylic Acid

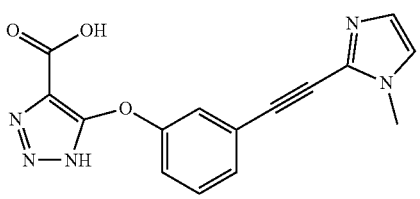 [SMILES: Cn1ccnc1C#Cc1cccc(Oc2[nH]nnc2C(=O)O)c1]

The title compound was prepared following procedures described for Example 282 using ethyl 5-(3-ethynylphenoxy)-1H-1,2,3-triazole-4-carboxylate and 2-bromo-1-methyl-1H-imidazole to afford 5-(3-(2-(1-methyl-1H-imidazol-2-yl)ethynyl)phenoxy)-1H-1,2,3-triazole-4-carboxylic acid. $^1$H-NMR (400 MHz, DMSO-$d_6$) δ: 7.59 (s, 1H), 7.58-7.38 (m, 4H), 7.27-7.25 (m, 1H), 3.84 (s, 3H). MS (ESI) m/z 310.1 [M+H]$^+$.

Example 335: 5-(4-(3,3,3-Trifluoroprop-1-ynyl)phenoxy)-1H-1,2,3-triazole-4-carboxylic Acid

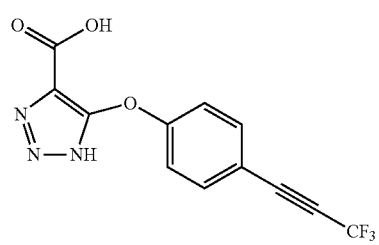 [SMILES: O=C(O)c1nn[nH]c1Oc1ccc(C#CC(F)(F)F)cc1]

Step 1: Ethyl 5-(4-(3,3,3-trifluoroprop-1-ynyl)phenoxy)-1H-1,2,3-triazole-4-carboxylate To a mixture of ethyl 5-(4-ethynylphenoxy)-1H-1,2,3-triazole-4-carboxylate (645 mg, 2.5 mmol, 1.0 eq), 1,10-phenanthroline (180 mg, 1.0 mmol, 0.4 eq), CuI (95 mg, 0.5 mmol, 0.2 eq) and K$_2$CO$_3$ (690 mg, 5.0 mmol, 2.0 eq) in DCM (40 mL) was added 1,3-dihydro-3,3-dimethyl-1-(trifluoromethyl)-1,2-benziodoxole (1.24 g, 3.75 mmol, 1.5 eq) in DCM (20 mL) slowly. The result mixture was stirred at 25° C. for 4 d. The reaction mixture was concentrated to give a crude, which was purified by prep-HPLC (20-95% CH$_3$CN in water) to give the desired (35 mg, yield: 4%) as a white solid. MS (ESI) m/z 326.1 [M+H]$^+$.

Step 2: 5-(4-(3,3,3-trifluoroprop-1-ynyl)phenoxy)-1H-1,2,3-triazole-4-carboxylic Acid A mixture of ethyl 5-(4-(3,3,3-trifluoroprop-1-ynyl)phenoxy)-1H-1,2,3-triazole-4-carboxylate (35 mg, 0.13 mmol, 1.0 eq) in 3N KOH (1 mL, 1 mmol, 7.7 eq) and methanol (3 mL) was stirred at 35° C. for 16 h. The reaction was adjusted to pH ~3 and extracted with EtOAc (3×20 mL). The organic layers were combined, dried over anhydrous sodium sulfate, filtered, and concentrated in vacuo. The crude product was purified by prep-HPLC (10-95% CH$_3$CN in water) to give the desired (3.3 mg, yield: 10%) as a white solid. $^1$H-NMR (400 MHz, DMSO-$d_6$) δ: 7.66 (d, J=8.8 Hz, 2H), 6.98 (d, J=8.8 Hz, 2H). MS (ESI) m/z 298.1 [M+H]$^+$.

Example 336: 5-(4-(2-(Pyrimidin-2-yl)ethynyl)phenoxy)-1H-1,2,3-triazole-4-carboxylic Acid

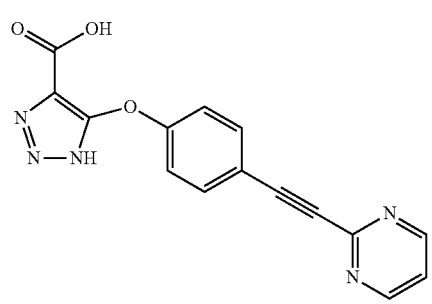 [SMILES: O=C(O)c1nn[nH]c1Oc1ccc(C#Cc2ncccn2)cc1]

The title compound was prepared following procedures described for Example 282 using ethyl 5-(4-ethynylphenoxy)-1H-1,2,3-triazole-4-carboxylate and 2-bromopyrimidine to afford 5-(4-(2-(pyrimidin-2-yl)ethynyl)phenoxy)-1H-1,2,3-triazole-4-carboxylic acid. $^1$H-NMR (400 MHz, DMSO-d$_6$) δ: 13.25 (brs, 1H), 8.84 (d, J=4.8 Hz, 2H), 7.67 (d, J=8.8 Hz, 2H), 7.51 (t, J=4.8 Hz, 1H), 7.15 (d, J=8.8 Hz, 2H). MS (ESI) m/z 308.1 [M+H]$^+$.

Example 337: 5-(4-(2-(Pyrazin-2-yl)ethynyl)phenoxy)-1H-1,2,3-triazole-4-carboxylic Acid

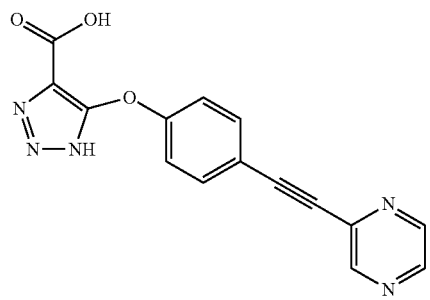 [SMILES: O=C(O)c1nn[nH]c1Oc1ccc(C#Cc2cnccn2)cc1]

The title compound was prepared following procedures described for Example 282 using ethyl 5-(4-ethynylphenoxy)-1H-1,2,3-triazole-4-carboxylate and 2-iodopyrazine to afford 5-(4-(2-(pyrazin-2-yl)ethynyl)phenoxy)-1H-1,2,3-triazole-4-carboxylic acid. $^1$H-NMR (400 MHz, DMSO-d$_6$) δ: 13.32 (brs, 1H), 8.88 (d, J=1.2 Hz, 1H), 8.70-8.63 (m, 2H), 7.67 (d, J=8.8 Hz, 2H), 7.16 (d, J=8.4 Hz, 2H). MS (ESI) m/z 308.1 [M+H]$^+$.

Example 338: 5-(3-(2-(Pyrazin-2-yl)ethynyl)phenoxy)-1H-1,2,3-triazole-4-carboxylic Acid

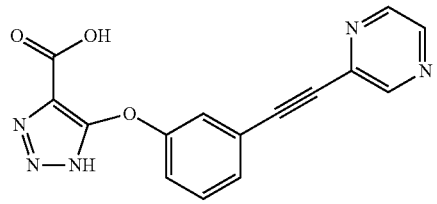 [SMILES: O=C(O)c1nn[nH]c1Oc1cccc(C#Cc2cnccn2)c1]

The title compound was prepared following procedures described for Example 282 using ethyl 5-(3-ethynylphenoxy)-1H-1,2,3-triazole-4-carboxylate and 2-iodopyrazine to afford 5-(3-(2-(pyrazin-2-yl)ethynyl)phenoxy)-1H-1,2,3-triazole-4-carboxylic acid. $^1$H-NMR (400 MHz, DMSO-d$_6$) δ: 13.25 (brs, 1H), 8.90 (d, J=0.8 Hz, 1H), 8.71-8.65 (m, 2H), 7.49-7.44 (m, 2H), 7.34 (d, J=2.0 Hz, 1H), 7.26-7.23 (m, 1H). MS (ESI) m/z 308.1 [M+H]$^+$.

Example 339: 5-(4-(2-(Pyridazin-3-yl)ethynyl)phenoxy)-1H-1,2,3-triazole-4-carboxylic Acid

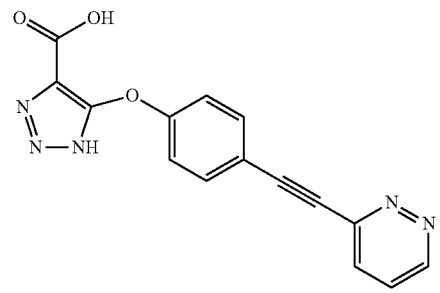 [SMILES: O=C(O)c1nn[nH]c1Oc1ccc(C#Cc2cccnn2)cc1]

The title compound was prepared following procedures described for Example 282 using ethyl 5-(4-ethynylphenoxy)-1H-1,2,3-triazole-4-carboxylate and 3-bromopyridazine to afford 5-(4-(2-(pyridazin-3-yl)ethynyl)phenoxy)-1H-1,2,3-triazole-4-carboxylic acid. $^1$H-NMR (400 MHz, DMSO-d$_6$) δ: 13.42 (brs, 1H), 9.22 (dd, J=4.8 Hz, 1.6 Hz, 1H), 9.22 (dd, J=4.8 Hz, 1.6 Hz, 1H), 7.93 (dd, J=4.8 Hz, 1.6 Hz, 1H), 7.78-7.68 (m, 2H), 7.70-7.68 (m, 2H), 7.18-7.16 (m, 2H). MS (ESI) m/z 308.1 [M+H]$^+$.

Example 340: 5-(3-(2-(Pyridazin-3-yl)ethynyl)phenoxy)-1H-1,2,3-triazole-4-carboxylic Acid

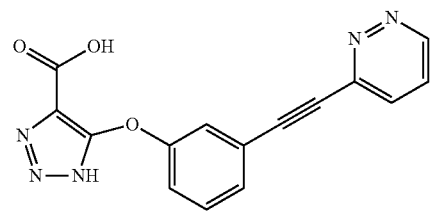 [SMILES: O=C(O)c1nn[nH]c1Oc1cccc(C#Cc2cccnn2)c1]

The title compound was prepared following procedures described for Example 282 using ethyl 5-(3-ethynylphenoxy)-1H-1,2,3-triazole-4-carboxylate and 3-bromopyridazine to afford 5-(3-(2-(pyridazin-3-yl)ethynyl)phenoxy)-1H-1,2,3-triazole-4-carboxylic acid. $^1$H-NMR (400 MHz, DMSO-d$_6$) δ: 12.75 (brs, 1H), 9.24 (dd, J=4.8 Hz, 1.6 Hz, 1H), 7.96 (dd, J=8.4 Hz, 1.6 Hz, 1H), 7.77 (dd, J=8.4 Hz, 5.2 Hz, 1H), 7.50-7.46 (m, 2H), 7.36 (s, 1H), 7.26-7.23 (m, 1H). MS (ESI) m/z 308.1 [M+H]$^+$.

Example 341: 5-(4-(2-(Thiazol-2-yl)ethynyl)phenoxy)-1H-1,2,3-triazole-4-carboxylic Acid

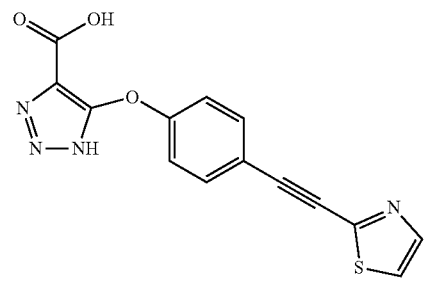 [SMILES: O=C(O)c1nn[nH]c1Oc1ccc(C#Cc2nccs2)cc1]

The title compound was prepared following procedures described for Example 282 using ethyl 5-(4-ethynylphenoxy)-1H-1,2,3-triazole-4-carboxylate and 2-bromothiazole to afford 5-(4-(2-(thiazol-2-yl)ethynyl)phenoxy)-1H-1,2,3-triazole-4-carboxylic acid. $^1$H-NMR (400 MHz, DMSO-$d_6$) δ: 7.96-7.92 (m, 2H), 7.67-7.65 (m, 2H), 7.15-7.12 (m, 2H). MS (ESI) m/z 313.0 [M+H]$^+$.

Example 342: 5-(3-(2-(Thiazol-2-yl)ethynyl)phenoxy)-1H-1,2,3-triazole-4-carboxylic Acid

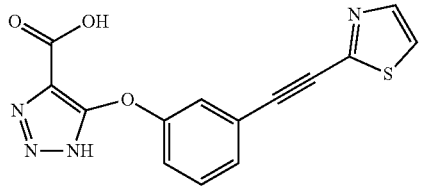 [SMILES: O=C(O)c1nn[nH]c1Oc1cccc(C#Cc2nccs2)c1]

The title compound was prepared following procedures described for Example 282 using ethyl 5-(3-ethynylphenoxy)-1H-1,2,3-triazole-4-carboxylate and 2-bromothiazole to afford 5-(3-(2-(thiazol-2-yl)ethynyl)phenoxy)-1H-1,2,3-triazole-4-carboxylic acid. $^1$H-NMR (400 MHz, DMSO-$d_6$) δ: 13.35 (brs, 1H), 7.99-7.95 (m, 2H), 7.50-7.44 (m, 2H), 7.36 (s, 1H), 7.25-7.22 (m, 1H). MS (ESI) m/z 313.0 [M+H]$^+$.

Example 343: 5-(3-(4-Methylpent-1-ynyl)phenoxy)-1H-1,2,3-triazole-4-carboxylic Acid

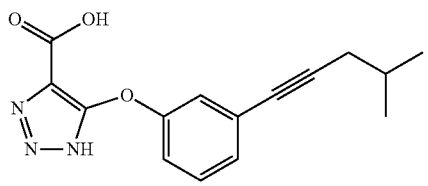

Step 1: Ethyl 5-(3-(4-methylpent-1-ynyl)phenoxy)-1H-1,2,3-triazole-4-carboxylate A mixture of ethyl 5-(3-iodophenoxy)-1H-1,2,3-triazole-4-carboxylate (270 mg, 0.75 mmol, 1.0 eq), 4-methylpent-1-yne (315 mg, 3.75 mmol, 5.0 eq), Pd(PPh$_3$)$_2$Cl$_2$ (52.7 mg, 0.075 mmol, 0.1 eq) and CuI (14.3 mg, 0.075 mmol, 0.1 eq) in DMF/DIEA (1.5 mL/1.5 mL) in a sealed tube was heated at 50° C. under N$_2$ for 2 h. The reaction mixture was concentrated and the residue was purified by silica gel column chromatography (PE:EtOAc=3:1) to give the crude desired (80 mg, yield: 33%) as a colorless oil. MS (ESI) m/z 314.1 [M+H]$^+$.

Step 2: 5-(3-(4-methylpent-1-ynyl)phenoxy)-1H-1,2,3-triazole-4-carboxylic Acid

A mixture of ethyl 5-(3-(4-methylpent-1-ynyl)phenoxy)-1H-1,2,3-triazole-4-carboxylate (80 mg, 0.25 mmol) and 3N KOH (2 mL, 6 mmol, 24 eq) in methanol/THF (2 mL/2 mL) was stirred at room temperature overnight. The reaction was adjusted to pH ~3 by 1N aqueous HCl and extracted with EtOAc (3×30 mL). The organic layers were combined, dried over anhydrous sodium sulfate, filtered and concentrated in vacuo. The crude product was purified by prep-HPLC (10-95% CH$_3$CN in water) to give 5-(3-(4-methylpent-1-ynyl)phenoxy)-1H-1,2,3-triazole-4-carboxylic acid (50 mg, yield: 69%) as a white solid. $^1$H-NMR (400 MHz, DMSO-$d_6$) δ: 13.35 (brs, 1H), 7.36-7.32 (m, 1H), 7.16 (d, J=7.6 Hz, 1H), 7.06-7.04 (m, 2H), 2.31 (d, J=6.8 Hz, 2H), 1.86-1.82 (m, 1H), 0.98 (d, J=6.8 Hz, 6H). MS (ESI) m/z 286.1 [M+H]$^+$.

Example 344: 5-(3-(3-Cyclopentylprop-1-ynyl)phenoxy)-1H-1,2,3-triazole-4-carboxylic Acid

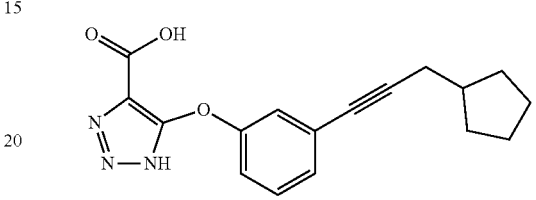

The title compound was prepared following procedures described for Example 343 using ethyl 5-(3-iodophenoxy)-1-(4-methoxybenzyl)-1H-1,2,3-triazole-4-carboxylate and prop-2-ynylcyclopentane to afford 5-(3-(3-cyclopentylprop-1-ynyl)phenoxy)-1H-1,2,3-triazole-4-carboxylic acid. $^1$H-NMR (400 MHz, DMSO-$d_6$) δ: 13.35 (brs, 1H), 7.34 (t, J=8.0 Hz, 1H), 7.16 (d, J=7.6 Hz, 1H), 7.06-7.03 (m, 2H), 2.41 (d, J=6.4 Hz, 2H), 2.11-2.04 (m, 1H), 1.81-1.73 (m, 2H), 1.63-1.49 (m, 4H), 1.33-1.23 (m, 2H). MS (ESI) m/z 312.2 [M+H]$^+$.

Example 345: 5-(3-(3-Cyclobutylprop-1-ynyl)phenoxy)-1H-1,2,3-triazole-4-carboxylic Acid

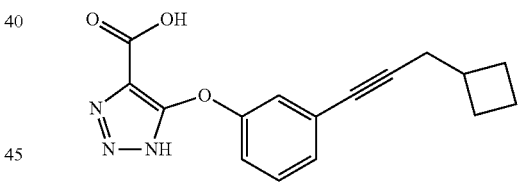

Step 1: Prop-2-ynylcyclobutane

To a solution of lithium acetylide ethylenediamine complex (2.12 g, 23 mmol, 2.3 eq) in DMSO (20 mL)/THF (10 mL) was added (bromomethyl)cyclobutane (1.49 g, 10 mmol, 1.0 eq) slowly at 0° C. The resulting mixture was stirred at room temperature overnight. The reaction was diluted with Et$_2$O (80 mL) and washed with brine (250 mL). The separated organic layer was dried over anhydrous sodium sulfate and concentrated to give the crude desired (2 g) as a pale yellow liquid, which was used directly for next step without further purification.

Step 2: 5-(3-(3-Cyclobutylprop-1-ynyl)phenoxy)-1H-1,2,3-triazole-4-carboxylic Acid The title compound was prepared following procedures described for Example 343 using ethyl 5-(3-iodophenoxy)-1H-1,2,3-triazole-4-carboxylate and prop-2-ynylcyclobutane to afford 5-(3-(3-cyclobutylprop-1-ynyl)phenoxy)-1H-1,2,3-triazole-4-carboxylic acid. $^1$H-NMR (400 MHz, CD$_3$OD) δ: 7.28 (t, J=8.0 Hz, 1H), 7.14 (d, J=7.6 Hz, 1H), 7.08-7.02 (m, 2H), 2.59-2.47 (m, 1H), 2.46 (d, J=6.8 Hz, 2H), 2.15-2.09 (m, 2H), 1.94-1.81 (m, 4H). MS (ESI) m/z 298.1 [M+H]$^+$.

Example 346: 5-(3-(3-Cyclohexylprop-1-ynyl)phenoxy)-1H-1,2,3-triazole-4-carboxylic Acid

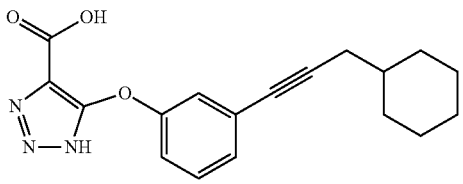

The title compound was prepared following procedures described for Example 343 using ethyl 5-(3-iodophenoxy)-1H-1,2,3-triazole-4-carboxylate and prop-2-ynylcyclopentane to afford 5-(3-(3-cyclohexylprop-1-ynyl)phenoxy)-1H-1,2,3-triazole-4-carboxylic acid. $^1$H-NMR (400 MHz, DMSO-d$_6$) δ: 13.25 (brs, 1H), 7.36-7.31 (m, 1H), 7.16 (d, J=7.6 Hz, 1H), 7.06-7.03 (m, 2H), 2.31 (d, J=6.4 Hz, 2H), 1.78 (d, J=13.2 Hz, 2H), 1.71-1.49 (m, 5H), 1.26-1.01 (m, 5H). MS (ESI) m/z 326.2 [M+H]$^+$.

Example 347: 5-(3-(2-(4,4-Difluorocyclohexyl)ethynyl)phenoxy)-1H-1,2,3-triazole-4-carboxylic Acid

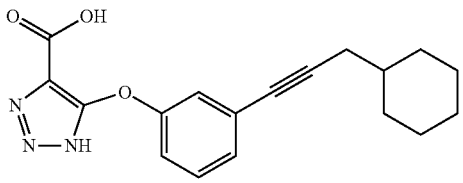 [SMILES: O=C(O)c1nn[nH]c1Oc1cccc(C#CCC2CCCCC2)c1]

Step 1: 4,4-difluorocyclohexanecarbaldehyde

A solution of ethyl 4,4-difluorocyclohexanecarboxylate (5.0 g, 26.0 mmol) in toluene (25 mL) was added DIBAL-H (31.2 mL, 1M in toluene, 31.2 mmol, 1.2 eq) at −70° C. under N$_2$. The reaction mixture was stirred at −70° C. for 30 min. Quenched with methanol and treated with brine. The mixture was extracted with EtOAc (2×300 mL), dried over anhydrous Na$_2$SO$_4$, and concentrated to give the desired (5 g, crude) as a yellow oil. MS (ESI) m/z 149.1 [M+H]$^+$.

Step 2: 4-Ethynyl-1,1-difluorocyclohexane

To a solution of 4,4-difluorocyclohexanecarbaldehyde (2 g, crude, 10.4 mmol) and K$_2$CO$_3$ (5.74 g, 41.6 mmol, 4.0 eq) in methanol (25 ml) was added dimethyl 1-diazoacetonylphosphonate (2.60 g, 13.5 mmol, 1.3 eq) slowly at 0° C. The resulting mixture was stirred at 0° C. for 2 h. The reaction was treated with brine and extracted with Et$_2$O (3×100 mL). The combined organic layers were dried over anhydrous Na$_2$SO$_4$ and concentrated to give the desired (1.94 g, crude) as a yellow oil. MS (ESI) m/z 145.1 [M+H]$^+$.

Step 3: 5-(3-(2-(4,4-Difluorocyclohexyl)ethynyl)phenoxy)-1H-1,2,3-triazole-4-carboxylic Acid The title compound was prepared following procedures described for Example 343 using ethyl 5-(3-iodophenoxy)-1H-1,2,3-triazole-4-carboxylate and 4-ethynyl-1,1-difluorocyclohexane to afford 5-(3-(2-(4,4-difluorocyclohexyl)ethynyl)phenoxy)-1H-1,2,3-triazole-4-carboxylic acid. $^1$H-NMR (400 MHz, DMSO-d$_6$) δ: 13.20 (brs, 1H), 7.37-7.33 (m, 1H), 7.18 (d, J=8.0 Hz, 1H), 7.08-7.05 (m, 2H), 2.90-2.80 (m, 1H), 2.08-1.84 (m, 6H), 1.73-1.65 (m, 2H). MS (ESI) m/z 348.1 [M+H]$^+$.

Example 348: 5-(4-(3-Phenylprop-1-ynyl)phenoxy)-1H-1,2,3-triazole-4-carboxylic Acid

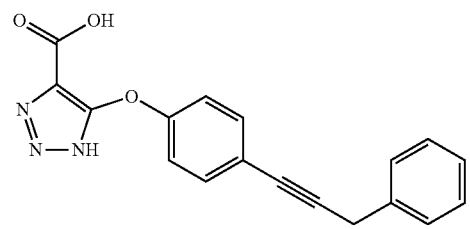 [SMILES: O=C(O)c1nn[nH]c1Oc1ccc(C#CCc2ccccc2)cc1]

The title compound was prepared following procedures described for Example 343 using ethyl 5-(4-iodophenoxy)-1H-1,2,3-triazole-4-carboxylic acid and prop-2-ynylbenzene to afford 5-(4-(3-Phenylprop-1-ynyl)phenoxy)-1H-1,2,3-triazole-4-carboxylic acid. $^1$H-NMR (400 MHz, DMSO-d$_6$) δ: 13.38 (brs, 1H), 7.45-7.24 (m, 7H), 7.04 (d, J=8.8 Hz, 2H), 3.88 (s, 2H). MS (ESI) m/z 320.1 [M+H]$^+$.

Example 349: 5-(3-(3-Phenylprop-1-ynyl)phenoxy)-1H-1,2,3-triazole-4-carboxylic Acid

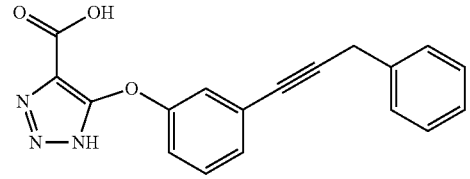 [SMILES: O=C(O)c1nn[nH]c1Oc1cccc(C#CCc2ccccc2)c1]

The title compound was prepared following procedures described for Example 343 using ethyl 5-(3-iodophenoxy)-1H-1,2,3-triazole-4-carboxylic acid and prop-2-ynylbenzene to afford 5-(4-(3-phenylprop-1-ynyl)phenoxy)-1H-1,2,3-triazole-4-carboxylic acid. $^1$H-NMR (400 MHz, DMSO-d$_6$) δ: 13.35 (brs, 1H), 7.41-7.33 (m, 5H), 7.27-7.22 (m, 2H), 7.12-7.06 (m, 2H), 3.89 (s, 2H). MS (ESI) m/z 320.1 [M+H]$^+$.

Example 350: 5-(3-(4-Cyanobut-1-ynyl)phenoxy)-1H-1,2,3-triazole-4-carboxylic Acid

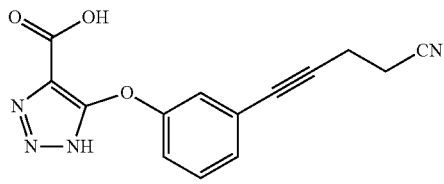 [SMILES: N#CCCC#Cc1cccc(Oc2[nH]nnc2C(=O)O)c1]

The title compound was prepared following procedures described for Example 5 using ethyl 5-chloro-1-(4-methoxybenzyl)-1H-1,2,3-triazole-4-carboxylate, 3-iodophenol and pent-4-ynenitrile to afford 5-(3-(4-cyanobut-1-ynyl)phenoxy)-1H-1,2,3-triazole-4-carboxylic acid. $^1$H-NMR (400 MHz, DMSO-d$_6$) δ: 7.29 (t, J=8.0 Hz, 1H), 7.14 (d, J=7.6 Hz, 1H), 7.10-7.05 (m, 2H), 2.80-2.73 (m, 4H). MS (ESI) m/z 283.0 [M+H]$^+$.

Example 351: 5-(3-(1,4-Dioxaspiro[4.5]decan-8-ylethynyl)phenoxy)-1H-1,2,3-triazole-4-carboxylic Acid

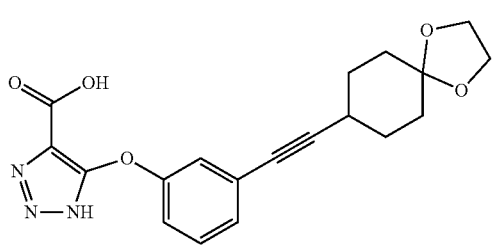 [SMILES: O=C(O)c1nn[nH]c1Oc1cccc(C#CC2CCC3(CC2)OCCO3)c1]

The title compound was prepared following procedures described for Example 5 using ethyl 5-chloro-1-(4-methoxybenzyl)-1H-1,2,3-triazole-4-carboxylate, 3-iodophenol and 8-ethynyl-1,4-dioxaspiro[4.5]decane to afford 5-(3-(1,4-dioxaspiro[4.5]decan-8-ylethynyl)phenoxy)-1H-1,2,3-triazole-4-carboxylic acid. $^1$H-NMR (400 MHz, DMSO-d$_6$) δ: 7.33 (t, J=8.0 Hz, 1H), 7.15 (d, J=7.6 Hz, 1H), 7.05-7.02 (m, 2H), 3.86 (s, 4H), 2.73-2.70 (m, 1H), 1.88-1.82 (m, 2H), 1.74-1.61 (m, 4H), 1.56-1.51 (m, 2H). MS (ESI) m/z 370.1 [M+H]$^+$.

Example 352: 5-(3-((4-Oxocyclohexyl)ethynyl)phenoxy)-1H-1,2,3-triazole-4-carboxylic Acid

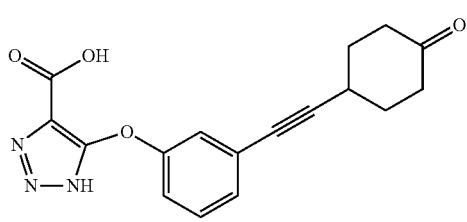 [SMILES: O=C1CCC(C#Cc2cccc(Oc3[nH]nnc3C(=O)O)c2)CC1]

The title compound was prepared following procedures described for Example 5 using ethyl 5-chloro-1-(4-methoxybenzyl)-1H-1,2,3-triazole-4-carboxylate, 3-iodophenol and 4-ethynylcyclohexanone to afford 5-(3-((4-oxocyclohexyl)ethynyl)phenoxy)-1H-1,2,3-triazole-4-carboxylic acid. $^1$H-NMR (400 MHz, DMSO-d$_6$) δ: 13.28 (brs, 1H), 7.35 (t, J=8.0 Hz, 1H), 7.20 (t, J=7.6 Hz, 1H), 7.10-7.06 (m, 2H), 3.12-3.08 (m, 1H), 2.50-2.31 (m, 4H), 2.14-1.92 (m, 2H), 1.90-1.87 (m, 2H). MS (ESI) m/z 326.1 [M+H]$^+$.

Example 353: 5-(4-(3-(4-fluorophenyl)prop-1-ynyl)phenoxy)-1H-1,2,3-triazole-4-carboxylic Acid

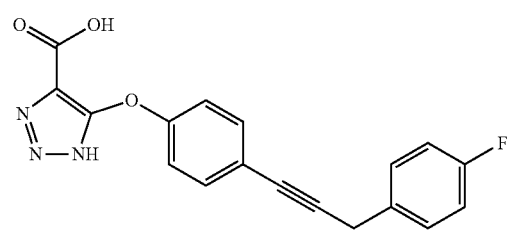 [SMILES: O=C(O)c1nn[nH]c1Oc1ccc(C#CCc2ccc(F)cc2)cc1]

The title compound was prepared following procedures described for Example 343 using ethyl 5-(4-iodophenoxy)-1H-1,2,3-triazole-4-carboxylic acid and 1-fluoro-4-(prop-2-ynyl)benzene to afford 5-(4-(3-(4-fluorophenyl)prop-1-ynyl)phenoxy)-1H-1,2,3-triazole-4-carboxylic acid. $^1$H-NMR (400 MHz, DMSO-d$_6$) δ: 13.25 (brs, 1H), 7.45-7.42 (m, 4H), 7.18 (t, J=8.8 Hz, 2H), 7.04 (d, J=9.2 Hz, 2H), 3.88 (s, 2H). MS (ESI) m/z 338.1 [M+H]$^+$.

Example 354: 5-(3-(3-(4-Fluorophenyl)prop-1-ynyl)phenoxy)-1H-1,2,3-triazole-4-carboxylic Acid

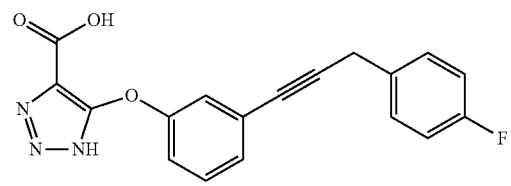 [SMILES: O=C(O)c1nn[nH]c1Oc1cccc(C#CCc2ccc(F)cc2)c1]

The title compound was prepared following procedures described for Example 343 using ethyl 5-(3-iodophenoxy)-1H-1,2,3-triazole-4-carboxylic acid and 1-fluoro-4-(prop-2-ynyl)benzene to afford 5-(3-(3-(4-fluorophenyl)prop-1-ynyl)phenoxy)-1H-1,2,3-triazole-4-carboxylic acid. $^1$H-NMR (400 MHz, DMSO-d$_6$) δ: 7.43-7.40 (m, 2H), 7.27 (t, J=8.0 Hz, 1H), 7.17 (t, J=8.8 Hz, 2H), 7.08 (d, J=8.0 Hz, 1H), 6.91 (dd, J=8.0 Hz, 2.4 Hz, 1H), 6.86 (m, 1H), 3.86 (s, 2H). MS (ESI) m/z 338.1 [M+H]$^+$.

Example 355: 5-(4-(3-Cyclopropylprop-1-ynyl)phenylthio)-1H-1,2,3-triazole-4-carboxylic Acid

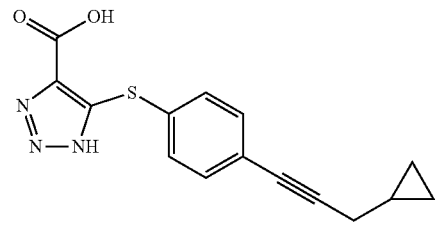 [SMILES: O=C(O)c1nn[nH]c1Sc1ccc(C#CCC2CC2)cc1]

The title compound was prepared following procedures described for Example 5 using ethyl 5-chloro-1-(4-methoxybenzyl)-1H-1,2,3-triazole-4-carboxylate, 4-bromobenzenethiol and (3-cyclopropylprop-1-ynyl)trimethylsilane to afford 5-(4-(3-cyclopropylprop-1-ynyl)phenylthio)-1H-1,2,3-triazole-4-carboxylic acid. $^1$H-NMR (400 MHz, DMSO-$d_6$) δ: 7.25 (d, J=8.4 Hz, 2H), 7.14 (d, J=8.4 Hz, 2H), 2.45 (d, J=6.0 Hz, 2H), 1.01-0.97 (m, 1H), 0.49-0.44 (m, 2H), 0.25-0.22 (m, 2H). MS (ESI) m/z 300.1 [M+H]$^+$.

Example 356: 5-(3-(3-Cyclopropylprop-1-ynyl)phenylthio)-1H-1,2,3-triazole-4-carboxylic Acid

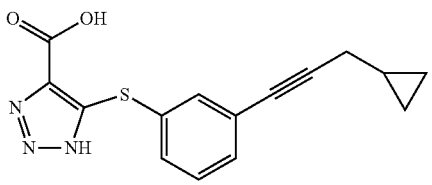

Step 1: Ethyl 5-chloro-1-(4-methoxybenzyl)-1H-1,2,3-triazole-4-carboxylate

To a mixture of ethyl 5-hydroxy-1-(4-methoxybenzyl)-1H-1,2,3-triazole-4-carboxylate (26.0 g, 93.5 mmol, 1.0 eq) in toluene (580 mL) was added PCl$_5$ (49.0 g, 234 mmol, 2.5 eq) portion-wise. The reaction mixture was stirred at 40° C. for under N$_2$ for 3 h. The solvent was removed in vacuo, and the residue was dissolved in diethyl ether (500 mL), washed with saturated sodium bicarbonate (3×100 mL), dried over anhydrous sodium sulfate, filtered and the solvent removed in vacuo. The residue was purified by silica gel column chromatography (PE:EtOAc=15:1) to give the title compound (24.0 g, yield: 63%) as a pale-yellow solid. $^1$H NMR (400 MHz, CDCl$_3$) δ: 7.26 (d, 2H), 6.87 (d, 2H), 5.50 (s, 2H), 4.42 (q, 2H), 3.79 (s, 3H), 1.40 (t, 3H).

Step 2: Ethyl 5-((3-bromophenyl)thio)-1-(4-methoxybenzyl)-1H-1,2,3-triazole-4-carboxylate To a mixture of NaH (60% in mineral oil, 158 mg, 3.96 mmol, 1.2 eq) in DMF (10 mL) was added 4-bromobenzenethiol (811 mg, 4.29 mmol, 1.3 eq) at 0° C. The resulting mixture was stirred at r.t. for 1 h. Ethyl 5-chloro-1-(4-methoxybenzyl)-1H-1,2,3-triazole-4-carboxylate (974 mg, 3.30 mmol, 1.0 eq) was added into the mixture and stirred at 80° C. for 3 h. The reaction was quenched with saturated NH$_4$Cl aqueous solution and extracted with EtOAc (3×100 mL). The combined organic layers were dried over anhydrous sodium sulfate and concentrated. The residue was purified by silica gel column chromatography (PE:EtOAc=20:1) to give the title compound (1.10 g, yield: 74%) as a yellow oil. MS (ESI) m/z 448.0 [M+H]$^+$.

Step 3: Ethyl 5-((3-bromophenyl)thio)-1H-1,2,3-triazole-4-carboxylate

A solution of ethyl 5-((3-bromophenyl)thio)-1-(4-methoxybenzyl)-1H-1,2,3-triazole-4-carboxylate (1.1 g, 2.45 mmol) in TFA (10 mL) was heated at 65° C. for 2 h. The reaction mixture was concentrated under reduced pressure, and the residue was purified by silica gel column chromatography (DCM:MeOH=200:1) to give the desired (780 mg, yield: 97%) as a yellow solid. MS (ESI) m/z 328.0 [M+H]$^+$.

Step 4: Ethyl 5-((3-(3-cyclopropylprop-1-ynyl)phenyl)thio)-1H-1,2,3-triazole-4-carboxylate A mixture of ethyl 5-((3-bromophenyl)thio)-1H-1,2,3-triazole-4-carboxylate (600 mg, 1.67 mmol, 1.0 eq), (3-cyclopropylprop-1-ynyl)trimethylsilane (2.05 g, 12.5 mmol, 7.5 eq), Pd(PPh$_3$)$_2$Cl$_2$ (252 mg, 0.36 mmol, 0.2 eq), CuI (68.4 mg, 0.36 mmol, 0.2 eq) and TBAF (1M in THF, 15 mL, 15 mmol, 9.0 eq) in DIEA/DMF (6 mL/6 mL) in a sealed tube was heated at 70° C. under N$_2$ overnight. The reaction mixture was concentrated and the residue was purified by silica gel column chromatography (PE:EtOAc=5:1) to give the title compound (90 mg, yield: 15%) as a yellow solid. MS (ESI) m/z 328.1 [M+H]$^+$.

Step 5: 5-((4-(3-cyclopropylprop-1-ynyl)phenyl)thio)-1H-1,2,3-triazole-4-carboxylic Acid A mixture of 5-((3-(3-cyclopropylprop-1-ynyl)phenyl)thio)-1H-1,2,3-triazole-4-carboxylic acid (90 mg, 0.27 mmol) and 3N KOH (1 mL, 3 mmol, 11 eq) in MeOH/THF (1 mL/1 mL) was stirred at r.t. overnight. The reaction was adjusted to pH ~3 by 1N HCl and extracted with EtOAc (3×10 mL). The organic layers were combined, dried over anhydrous sodium sulfate, filtered and concentrated in vacuo. The crude product was purified by prep-HPLC (15-95% CH$_3$CN in water) to give the desired (50 mg, yield: 61%) as a white solid. $^1$H NMR (400 MHz, DMSO-$d_6$) δ: 7.30-7.22 (m, 4H), 2.45 (d, J=5.6 Hz, 2H), 1.00-0.96 (m, 1H), 0.48-0.44 (m, 2H), 0.25-0.21 (m, 2H), —NH and CO$_2$H protons not observed. MS (ESI) m/z 300.0 [M+H]$^+$.

Example 357: Ethyl 5-(3-(3-cyclopropylprop-1-ynyl)phenoxy)-1H-1,2,3-triazole-4-carboxylate

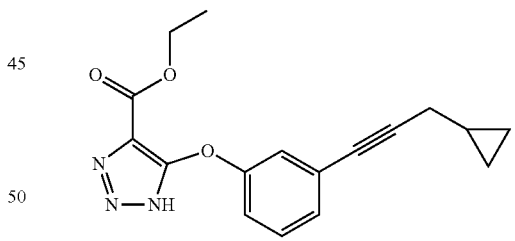

A mixture of ethyl 5-(3-iodophenoxy)-1H-1,2,3-triazole-4-carboxylate (4.5 g, 12.5 mmol, 1.0 eq), (3-cyclopropylprop-1-ynyl)trimethylsilane (8 g, crude), Pd(PPh$_3$)$_2$Cl$_2$ (878 mg, 1.25 mmol, 0.1 eq), CuI (228 mg, 1.25 mmol, 0.1 eq) and TBAF (1M in THF, 150 mL, 150 mmol, 12.0 eq) in DIEA (75 mL) was heated at 70° C. under N$_2$ for 2 h. The reaction mixture was concentrated and the residue was purified by silica gel column chromatography (PE:EtOAc=5:1) to give the desired (1.4 g, yield: 36%) as a white solid. $^1$H-NMR (400 MHz, DMSO-$d_6$) δ: 7.31 (t, J=8.0 Hz, 1H), 7.11 (d, J=7.6 Hz, 1H), 7.03-6.97 (m, 2H), 4.15 (q, J=7.2 Hz, 2H), 2.44 (d, J=5.6 Hz, 2H), 1.13 (t, J=7.2 Hz, 3H), 1.00-0.97 (m, 1H), 0.49-0.44 (m, 2H), 0.25-0.20 (m, 2H). MS (ESI) m/z 312.1 [M+H]$^+$.

Example 358: Ethyl 3-(3-(3-cyclopropylprop-1-ynyl)phenoxy)-5-methyl-1H-pyrazole-4-carboxylate

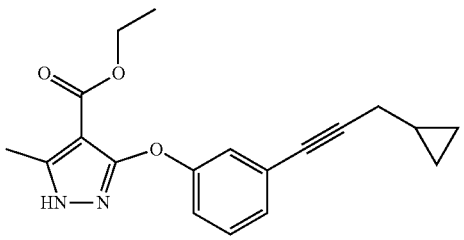 [SMILES: CCOC(=O)c1c(Oc2cccc(C#CCC3CC3)c2)n[nH]c1C]

Step 1: Ethyl 3-chloro-5-methyl-1H-pyrazole-4-carboxylate

To a mixture of ethyl 3-amino-5-methyl-1H-pyrazole-4-carboxylate (10 g, 59 mmol, 1.0 eq) and CuCl (11.7 g, 118 mmol, 2.0 eq) was added t-BuNO$_2$ (7.3 g, 71 mmol, 1.2 eq) slowly at 0° C. The resulting mixture was refluxed for 2 h. Quenched with 4N HCl and extracted with EtOAc (3×200 mL). The combined organic layers were dried over anhydrous Na$_2$SO$_4$ and concentrated to give a crude, which was purified by silica gel column chromatography (PE:EA=3:1) to give the desired (4.7 g, yield: 42%) as a white solid. MS (ESI) m/z 189.0 [M+H]$^+$.

Step 2: Ethyl 3-chloro-5-methyl-1-((2-(trimethylsilyl)ethoxy)methyl)-1H-pyrazole-4-carboxylate To a solution of ethyl 3-chloro-5-methyl-1H-pyrazole-4-carboxylate (4.7 g, 24.9 mmol, 1.0 eq) in DMF (30 mL) was added NaH (60% in mineral oil, 1.2 g, 29.8 mmol, 1.2 eq) in-portion at 0° C. After the resulting mixture was stirred at room temperature for 1 h, SEMCl (4.5 g, 27.4 mmol, 1.1 eq) was added slowly at 0° C. The resulting mixture was stirred at room temperature for 3 h. The reaction mixture was poured into ice-water and extracted with EtOAc (3×200 mL). The combined organic layers were dried over anhydrous sodium sulfate, filtered and the solvent removed in vacuo. The residue was purified by silica gel column chromatography (PE:EtOAc=10:1) to give the desired (6.5 g, yield: 82%) as a colorless oil. MS (ESI) m/z 319.1 [M+H]$^+$.

Step 3: Ethyl 3-(3-iodophenoxy)-5-methyl-1-((2-(trimethylsilyl)ethoxy)methyl)-1H-pyrazole-4-carboxylate To a solution of 3-iodophenol (2.64 g, 12.0 mmol, 1.2 eq) in DMF (26 mL) was added NaH (60% in mineral oil, 480 mg, 12.0 mmol, 1.2 eq) in-portion at 0° C. After the result mixture was stirred at room temperature for 1 h, SEMCl (4.5 g, 27.4 mmol, 1.1 eq) was added ethyl 3-chloro-5-methyl-1-((2-(trimethylsilyl)ethoxy)methyl)-1H-pyrazole-4-carboxylate (3.19 g, 10 mmol, 1.0 eq) at 0° C. The resulting mixture was stirred at 110° C. for 3 days. The reaction mixture was quenched with ice-water (100 mL) and extracted with EtOAc (3×300 mL). The combined organic layers were dried over anhydrous sodium sulfate, filtered and the solvent removed in vacuo. The residue was purified by silica gel column chromatography (PE:EtOAc=5:1) to give the desired (1.1 g, yield: 22%) as a white solid. MS (ESI) m/z 503.1 [M+H]$^+$.

Step 4: Ethyl 3-(3-iodophenoxy)-5-methyl-1H-pyrazole-4-carboxylate

To solution of ethyl 3-(3-iodophenoxy)-5-methyl-1-((2-(trimethylsilyl)ethoxy)methyl)-1H-pyrazole-4-carboxylate (1.1 g, 2.19 mmol) in TFA/DCM (3 mL/3 mL) was stirred at room temperature for 2 h. After the reaction mixture was concentrated under reduced pressure, the residue was treated with water and extracted with EtOAc (3×100 mL). The combined organic layers were dried over anhydrous sodium sulfate, filtered, and the solvent removed in vacuo to give the desired (820 mg, yield: 100%) as a yellow gel. MS (ESI) m/z 373.0 [M+H]$^+$.

Step 5: Ethyl 3-(3-(3-cyclopropylprop-1-ynyl)phenoxy)-5-methyl-1H-pyrazole-4-carboxylate A mixture of ethyl 3-(3-iodophenoxy)-5-methyl-1H-pyrazole-4-carboxylate (410 mg, 1.10 mmol, 1.0 eq), (3-cyclopropylprop-1-ynyl)trimethylsilane (835 mg, 5.5 mmol, 5.0 eq), Pd(PPh$_3$)$_2$Cl$_2$ (77 mg, 0.11 mmol, 0.1 eq), CuI (21 mg, 0.11 mmol, 0.1 eq) and TBAF (1M in THF, 5.5 mL, 5.50 mmol, 5.0 eq) in DIEA/DMF (1.5 mL/3 mL) in a sealed tube was heated at 50° C. under N$_2$ for 3 h. The reaction mixture was concentrated and the residue was purified by silica gel column chromatography (PE:EtOAc=3:1) to give the desired (110 mg, yield: 31%) as a colorless gel. $^1$H-NMR (400 MHz, CDCl$_3$) δ:7.22 (t, J=8.0 Hz, 1H), 7.13-7.08 (m, 2H), 7.00 (dd, J=8.0 Hz, 2.0 Hz, 1H), 4.17 (q, J=7.2 Hz, 2H), 2.50 (s, 3H), 2.44 (d, J=5.6 Hz, 2H), 1.16 (t, J=7.2 Hz, 3H), 1.01-0.97 (m, 1H), 0.52-0.48 (m, 2H), 0.30-0.26 (m, 2H). MS (ESI) m/z 325.2 [M+H]$^+$.

Example 359: 3-(3-(3-Cyclopropylprop-1-ynyl)phenoxy)-5-methyl-1H-pyrazole-4-carboxylic Acid

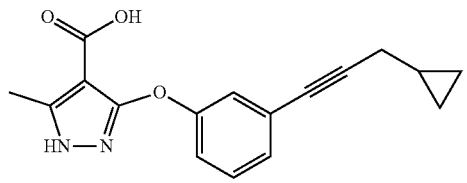

A mixture of ethyl 3-(3-(3-cyclopropylprop-1-ynyl)phenoxy)-5-methyl-1H-pyrazole-4-carboxylate (95 mg, 0.29 mmol, 1.0 eq) in 3N KOH (2 mL, 6 mmol, 20.7 eq) and methanol (3 mL) was stirred at reflux for 30 h. The reaction was adjusted to pH ~3 and extracted with EtOAc (3×50 mL). The organic layers were combined, dried over anhydrous sodium sulfate, filtered and concentrated in vacuo. The crude product was purified by prep-HPLC (10-95% CH$_3$CN in water) to give the desired (43 mg, yield: 50%) as a white solid. $^1$H-NMR (400 MHz, DMSO-d$_6$) δ: 12.75 (brs, 1H), 12.10 (brs, 1H), 7.28 (t, J=8.0 Hz, 1H), 7.07 (d, J=7.6 Hz, 1H), 6.95 (dd, J=8.4 Hz, 2.0 Hz, 1H), 6.88 (t, J=2.0 Hz, 1H), 2.50-2.42 (m, 5H), 1.16 (t, J=7.2 Hz, 3H), 1.01-0.97 (m, 1H), 0.49-0.44 (m, 2H), 0.25-0.20 (m, 2H). MS (ESI) m/z 297.1 [M+H]$^+$.

Example 360: Ethyl 3-(4-(3-cyclopropylprop-1-ynyl)phenoxy)-5-methyl-1H-pyrazole-4-carboxylate

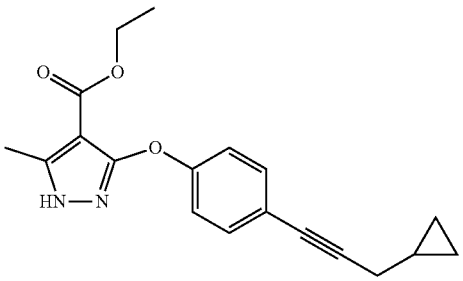 [SMILES: CCOC(=O)c1c(Oc2ccc(C#CCC3CC3)cc2)n[nH]c1C]

The title compound was prepared following procedures described for Example 358 using ethyl 3-chloro-5-methyl-1-((2-(trimethylsilyl)ethoxy)methyl)-1H-pyrazole-4-carboxylate, 4-iodophenol and (3-cyclopropylprop-1-ynyl)trimethylsilane to afford ethyl 3-(4-(3-cyclopropylprop-1-ynyl)phenoxy)-5-methyl-1H-pyrazole-4-carboxylate. $^1$H-NMR (400 MHz, CDCl$_3$) δ:7.34 (d, J=8.8 Hz, 2H), 6.96 (d, J=8.8 Hz, 2H), 4.16 (q, J=7.2 Hz, 2H), 2.49 (s, 3H), 2.44 (d, J=6.0 Hz, 2H), 1.14 (t, J=7.2 Hz, 3H), 1.02-0.97 (m, 1H), 0.52-0.48 (m, 2H), 0.31-0.26 (m, 2H). MS (ESI) m/z 325.2 [M+H]$^+$.

Example 361: 3-(4-(3-Cyclopropylprop-1-ynyl)phenoxy)-5-methyl-1H-pyrazole-4-carboxylic Acid

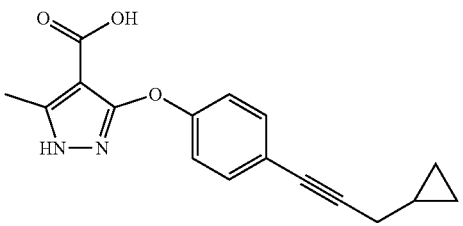 [SMILES: Cc1[nH]nc(Oc2ccc(C#CCC3CC3)cc2)c1C(=O)O]

The title compound was prepared following procedures described for Example 358 using ethyl 3-(4-(3-cyclopropylprop-1-ynyl)phenoxy)-5-methyl-1H-pyrazole-4-carboxylate to afford 3-(4-(3-cyclopropylprop-1-ynyl)phenoxy)-5-methyl-1H-pyrazole-4-carboxylic acid. $^1$H-NMR (400 MHz, CD$_3$OD) δ: 7.20 (d, J=8.8 Hz, 2H), 6.84 (d, J=8.8 Hz, 2H), 2.40 (s, 3H), 2.34 (d, J=6.0 Hz, 2H), 0.92-0.88 (m, 1H), 0.42-0.37 (m, 2H), 0.20-0.16 (m, 2H). MS (ESI) m/z 297.1 [M+H]$^+$.

Example 362: 5-(4-(3-Cyclopropylprop-1-ynyl)phenylamino)-1H-1,2,3-triazole-4-carboxylic Acid

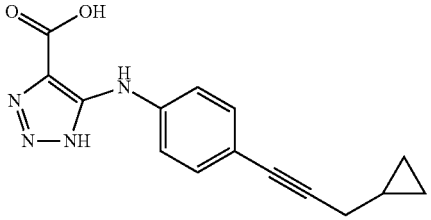

Step 1: Ethyl 5-amino-1-(4-bromophenyl)-1H-1,2,3-triazole-4-carboxylate

To a mixture of 4-bromoaniline (2 g, 59 mmol, 1.0 eq) in TFA (10 mL) was added NaNO$_2$ (4.9 g, 71 mmol, 1.2 eq) portion-wise at 0° C. The resulting mixture was stirred at 0° C. for 0.5 h. sodium azide (4.6 g, 71 mmol, 1.2 eq) in water (5 mL) was added. The mixture was stirred in an ice bath for 1 h and concentrated in vacuo to remove TFA. The residue was diluted with DCM (100 mL), washed with brine, dried over Na$_2$SO$_4$, and concentrated to give the 1-azido-4-bromobenzene (2.2 g, crude), which was dissolved in EtOH (30 mL). Then sodium ethoxide (4.8 g, 71 mmol, 1.2 eq) and ethyl 2-cyanoacetate (10 g, 88.5 mmol, 1.5 eq) were added. The reaction mixture was stirred at room temperature for 3 h. The mixture was diluted with water (100 mL) and extracted with EtOAc (2×100 mL). The combined organic layers were dried over anhydrous sodium sulfate, filtered and the solvent removed in vacuo. The residue was washed with (PE:EtOAc=10:1, 50 mL) to give the desired (3.3 g, yield: 91%) as a yellow solid. MS (ESI) m/z 311.0 [M+H]$^+$.

Step 2: Ethyl 5-((4-bromophenyl)amino)-1H-1,2,3-triazole-4-carboxylate

A solution of ethyl 5-amino-1-(4-bromophenyl)-1H-1,2,3-triazole-4-carboxylate (1 g, 3.22 mmol, 1.0 eq) in pyridine (10 mL) was refluxed overnight. After removed most of pyridine, the residue was washed with (PE:EtOAc=10:1, 20 mL) to give the desired (600 mg, yield: 60%) as a yellow solid. MS (ESI) m/z 311.0 [M+H]$^+$.

Step 3: Ethyl 5-((4-(3-cyclopropylprop-1-ynyl)phenyl)amino)-1H-1,2,3-triazole-4-carboxylate A mixture of ethyl 5-((4-bromophenyl)amino)-1H-1,2,3-triazole-4-carboxylate (400 mg, 1.29 mmol, 1.0 eq), (3-cyclopropylprop-1-ynyl)trimethylsilane (588 mg, 3.87 mmol, 3.0 eq), Pd(PPh$_3$)$_2$Cl$_2$ (181 mg, 0.26 mmol, 0.2 eq), CuI (51 mg, 0.26 mmol, 0.2 eq) and TBAF (1M in THF, 3.87 mL, 3.87 mmol, 3.0 eq) in DIEA/DMF (2 mL/2 mL) in a sealed tube was heated at 90° C. under N$_2$ for 5 h. The reaction mixture was concentrated and the residue was purified by silica gel column chromatography (PE:EtOAc=10:1) to give the desired (400 mg, crude) as a white solid. MS (ESI) m/z 311.1 [M+H]$^+$.

Step 4: 5-((4-(3-cyclopropylprop-1-ynyl)phenyl)amino)-1H-1,2,3-triazole-4-carboxylic Acid A mixture of 5-((4-(3-cyclopropylprop-1-ynyl)phenyl)amino)-1H-1,2,3-triazole-4-carboxylate (200 mg, 0.64 mmol) in 3N KOH (2 mL, 6 mmol, 9.4 eq) and methanol/THF (2 mL/2 mL) was stirred at room temperature overnight. The reaction was adjusted to pH ~3 and extracted with EtOAc (3×50 mL). The organic layers were combined, dried over anhydrous sodium sulfate, filtered and concentrated in vacuo. The crude product was purified by prep-HPLC (10-95% CH$_3$CN in water) to give the desired (13.5 mg, yield: 7%) as a white solid. $^1$H-NMR (400 MHz, DMSO-d$_6$) δ: 15.00 (brs, 1H), 13.45 (brs, 1H), 8.31 (brs, 1H), 7.54 (d, J=8.0 Hz, 2H), 7.29 (d, J=8.0 Hz, 2H), 2.45 (d, J=5.6 Hz, 2H), 1.02-0.98 (m, 1H), 0.51-0.44 (m, 2H), 0.26-0.20 (m, 2H). MS (ESI) m/z 283.1 [M+H]+.

Example 363: 5-(3-(3-Cyclopropylprop-1-ynyl)phenylamino)-1H-1,2,3-triazole-4-carboxylic Acid

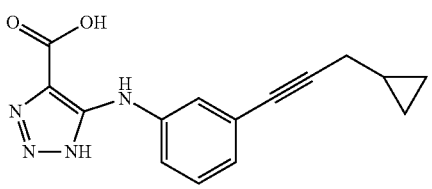 [SMILES: O=C(O)c1nn[nH]c1Nc1cccc(C#CCC2CC2)c1]

The title compound was prepared following procedures described for Example 362 using ethyl 5-((3-bromophenyl)amino)-1H-1,2,3-triazole-4-carboxylate and (3-cyclopropylprop-1-ynyl)trimethylsilane to afford 5-(3-(3-cyclopropylprop-1-ynyl)phenylamino)-1H-1,2,3-triazole-4-carboxylic acid $^1$H-NMR (400 MHz, DMSO-d$_6$) δ: 8.91 (brs, 1H), 7.72 (s, 1H), 7.33 (dd, J=8.0 Hz, 2.0 Hz, 1H), 7.20 (t, J=8.0 Hz, 1H), 6.83 (d, J=7.6 Hz, 1H), 2.47 (d, J=5.6 Hz, 2H), 1.05-0.98 (m, 1H), 0.51-0.46 (m, 2H), 0.28-0.20 (m, 2H). MS (ESI) m/z 283.1 [M+H]+.

Example 364: 5-(4-(3-Cyclopropylprop-1-ynyl)benzyl)-1H-1,2,3-triazole-4-carboxylic Acid

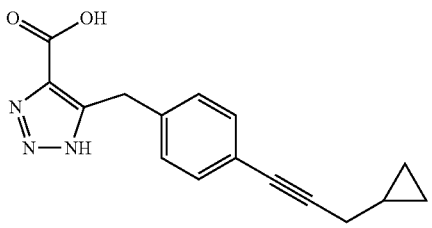

Step 1: Ethyl 4-(4-iodophenyl)-3-oxobutanoate

To a solution of 2-(4-iodophenyl)acetic acid (2.62 g, 10 mmol, 1.0 eq) in EtOAc (30 mL) was added CDI (2.92 g, 18 mmol, 1.8 eq) portion-wise at 0° C. The resulting mixture was stirred at room temperature overnight. Then potassium 3-ethoxy-3-oxopropanoate (1.87 g, 11 mmol, 1.1 eq), MgCl2 (1.05 g, 11 mmol, 1.1. eq) and TEA (1.34 g, 13.2 mmol, 1.3 eq) was added. The resulting mixture was stirred at 45° C. overnight. The reaction mixture was diluted with EtOAc (100 mL), washed with 1N HCl, dried over Na$_2$SO$_4$ and concentrated to give a crude, which was purified by silica gel column chromatography (PE:EtOAc=5:1) to give the desired (1.35 g, yield: 41%) as a colorless oil. MS (ESI) m/z 333.0 [M+H]+.

Step 2: Ethyl 5-(4-iodobenzyl)-1-(4-methoxybenzyl)-1H-1,2,3-triazole-4-carboxylate A mixture of ethyl 4-(4-iodophenyl)-3-oxobutanoate (333 mg, 1 mmol, 1.0 eq), PMBN3 (196 mg, 1.2 mmol, 1.2 eq) and K$_2$CO$_3$ (414 mg, 3 mmol, 3.0 eq) was heated at 80° C. under N$_2$ overnight. The reaction was treated with brine (100 mL) and extracted with Et$_2$O (100 mL). The separated organic layer was dried over Na$_2$SO$_4$ and concentrated to give a crude, which was purified by silica gel column chromatography (PE:EtOAc=5:1) to give the desired (300 mg, yield: 63%) as a yellow oil. MS (ESI) m/z 478.1 [M+H]+.

Step 3: Ethyl 5-(4-iodobenzyl)-1H-1,2,3-triazole-4-carboxylate

A solution of ethyl 5-(4-iodobenzyl)-1-(4-methoxybenzyl)-1H-1,2,3-triazole-4-carboxylate (300 mg, 0.63 mmol, 1.0 eq) in TFA (6 mL) was heated at 60° C. for 2 h. The reaction mixture was concentrated under reduced pressure, and the residue was purified by prep-HPLC (15-95% CH$_3$CN in water, 0.1% TFA) to give the desired (130 mg, yield: 58%) as a yellow solid. MS (ESI) m/z 358.0 [M+H]+.

Step 4: Ethyl 5-(4-(3-cyclopropylprop-1-ynyl)benzyl)-1H-1,2,3-triazole-4-carboxylate A mixture of ethyl 5-(4-iodobenzyl)-1H-1,2,3-triazole-4-carboxylate (130 mg, 0.36 mmol, 1.0 eq), (3-cyclopropylprop-1-ynyl)trimethylsilane (219 mg, 1.44 mmol, 4.0 eq), Pd(PPh$_3$)$_2$Cl$_2$ (26 mg, 0.036 mmol, 0.1 eq), CuI (6.8 mg, 0.036 mmol, 0.1 eq) and TBAF (1M in THF, 1.44 mL, 1.44 mmol, 4.0 eq) in DIEA/DMF (0.5 mL/0.5 mL) in a sealed tube was heated at 50° C. under N$_2$ overnight. The reaction mixture was concentrated and the residue was purified by silica gel column chromatography (PE:EtOAc=5:1) to give the desired (70 mg, yield: 64%) as a yellow solid. MS (ESI) m/z 310.2 [M+H]+.

Step 5: 5-(4-(3-cyclopropylprop-1-ynyl)benzyl)-1H-1,2,3-triazole-4-carboxylic Acid A mixture of ethyl 5-(4-(3-cyclopropylprop-1-ynyl)benzyl)-1H-1,2,3-triazole-4-carboxylate (70 mg, 0.22 mmol) in 3N KOH (1 mL, 3 mmol, 13.6 eq) and methanol/THF (1 mL/1 mL) was stirred at room temperature overnight. The reaction was adjusted to pH ~3 and extracted with EtOAc (3×50 mL). The organic layers were combined, dried over anhydrous sodium sulfate, filtered and concentrated in vacuo. The crude product was purified by prep-HPLC (10-95% CH$_3$CN in water) to give the desired (39 mg, yield: 63%) as a white solid. $^1$H-NMR (400 MHz, DMSO-d$_6$) δ: 7.24 (s, 4H), 4.22 (s, 2H), 2.43 (d, J=6.0 Hz, 2H), 1.00-0.96 (m, 1H), 0.48-0.44 (m, 2H), 0.26-0.21 (m, 2H). MS (ESI) m/z 282.1 [M+H]+.

Example 365: 5-(3-(3-Cyclopropylprop-1-ynyl)benzyl)-1H-1,2,3-triazole-4-carboxylic Acid

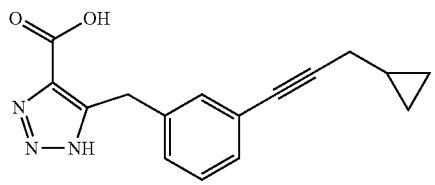 [SMILES: O=C(O)c1nn[nH]c1Cc1cccc(C#CCC2CC2)c1]

The title compound was prepared following procedures described for Example 364 using 2-(3-iodophenyl)acetic acid, potassium 3-ethoxy-3-oxopropanoate, PMBN3 and (3-cyclopropylprop-1-ynyl)trimethylsilane to afford 5-(3-(3-cyclopropylprop-1-ynyl)benzyl)-1H-1,2,3-triazole-4-carboxylic acid. $^1$H-NMR (400 MHz, DMSO-d$_6$) δ: 7.25-7.17 (m, 4H), 4.24 (s, 2H), 2.43 (d, J=6.0 Hz, 2H), 1.02-0.95 (m, 1H), 0.48-0.44 (m, 2H), 0.25-0.21 (m, 2H). MS (ESI) m/z 282.1 [M+H]$^+$.

Example 366: Ethyl 5-(3-(4-methylpent-1-ynyl) phenoxy)-1H-1,2,3-triazole-4-carboxylate

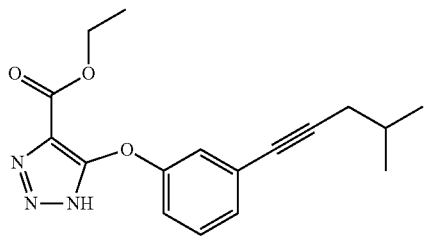

The title compound was prepared following procedures described for Example 343 using ethyl 5-(3-iodophenoxy)-1H-1,2,3-triazole-4-carboxylate and 4-methylpent-1-yne to afford ethyl 5-(3-(4-methylpent-1-ynyl)phenoxy)-1H-1,2,3-triazole-4-carboxylate. $^1$H-NMR (400 MHz, CDCl$_3$) δ: 7.29-7.18 (m, 3H), 7.09-7.07 (m, 1H), 4.38 (q, J=7.2 Hz, 2H), 2.28 (d, J=6.4 Hz, 2H), 1.93-1.85 (m, 1H), 1.32 (t, J=7.2 Hz, 2H), 1.02 (d, J=6.8 Hz, 6H). MS (ESI) m/z 314.1 [M+H]$^+$.

Example 367: 5-(3-(3-(3,3-Difluorocyclobutyl)prop-1-ynyl)phenoxy)-1H-1,2,3-triazole-4-carboxylic Acid

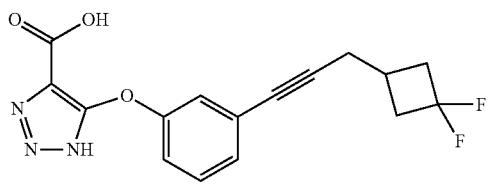 [SMILES: O=C(O)c1nn[nH]c1Oc1cccc(C#CCC2CC(F)(F)C2)c1]

The title compound was prepared following procedures described for Example 343 using ethyl 5-(3-iodophenoxy)-1H-1,2,3-triazole-4-carboxylate and (3-(3,3-difluorocyclobutyl) prop-1-ynyl)trimethylsilane to afford 5-(3-(3-(3,3-difluorocyclobutyl)prop-1-ynyl)phenoxy)-1H-1,2,3-triazole-4-carboxylic acid. $^1$H-NMR (400 MHz, DMSO-d$_6$) δ: 13.20 (brs, 1H), 7.35 (t, J=8.0 Hz, 1H), 7.18 (d, J=7.6 Hz, 1H), 7.08-7.06 (m, 2H), 2.71-2.64 (m, 4H), 2.45-2.38 (m, 3H). MS (ESI) m/z 334.1 [M+H]$^+$.

Example 368: 5-(5-(3-Cyclopropylprop-1-ynyl)-1,6-dihydro-1-methyl-6-oxopyridin-3-yloxy)-1H-1,2,3-triazole-4-carboxylic Acid

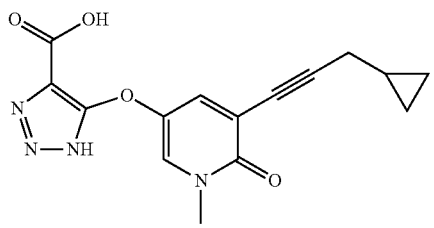 [SMILES: Cn1cc(Oc2[nH]nnc2C(=O)O)cc(C#CCC2CC2)c1=O]

Step 1: 3-bromo-1-methylpyridin-2(1H)-one

A mixture of 3-bromopyridin-2(1H)-one (10 g, 57.5 mmol, 1.0 eq), K$_2$CO$_3$ (15.9 g, 115 mmol, 2.0 eq) and MeI (12.2 g, 86.3 mmol) in DMF (50 mL) was stirred at room temperature overnight. The reaction was treated with water (150 mL) and extracted with EtOAc (4×150 mL). The combined organic layers were dried over anhydrous Na$_2$SO$_4$ and concentrated. The residue was purified by silica gel column chromatography (PE:EtOAc=1:1) to give the desired (8.3 g, yield: 77%) as a yellow oil. MS (ESI) m/z 188.0 [M+H]$^+$.

Step 2: 3-bromo-1-methyl-5-(4,4,5,5-tetramethyl-1,3,2-dioxaborolan-2-yl)pyridin-2(1H)-one A mixture of 3-bromo-1-methylpyridin-2(1H)-one (2.26 g, 12.0 mmol, 1.0 eq), BPD (4.6 g, 18.0 mmol, 1.5 eq), [Ir(OMe)(cod)]$_2$ (150 mg, 0.24 mmol, 0.02 eq) and dtbpy (136 mg, 0.48 mmol, 0.04 eq) in THF (70 mL) was stirred at 45° C. under N$_2$ overnight. The reaction mixture was concentrated to give a crude, which was purified by silica gel column chromatography (PE:EtOAc=2:1) to give the desired (2.06 g, yield: 41%) as a white solid. MS (ESI) m/z 314.1 [M+H]$^+$.

Step 3: 3-bromo-5-hydroxy-1-methylpyridin-2(1H)-one

To a mixture of 3-bromo-1-methyl-5-(4,4,5,5-tetramethyl-1,3,2-dioxaborolan-2-yl)pyridin-2(1H)-one (1.46 g, 4.65 mmol, 1.0 eq) and NaOH (2.0 M, 10 mL, 20 mmol, 4.3 eq) in THF (20 mL) was added hydrogen peroxide (30 wt. %, 2 mL, 22 mmol, 4.7 eq) portion-wise at 0° C. The reaction mixture was stirred at 0° C. for 4 h. After the solvent was removed in vacuo and the residue was diluted with water and extracted with EtOAc (3×200 mL). The combined organic layer was dried over anhydrous sodium sulfate, filtered and the solvent removed in vacuo. The residue was purified by prep-HPLC (10-95% CH$_3$CN in water) to give the desired (900 mg, yield: 95%) as a white solid. MS (ESI) m/z 204.0 [M+H]$^+$.

Step 4: Ethyl 5-((5-bromo-1-methyl-6-oxo-1,6-dihydropyridin-3-yl)oxy)-1-(4-methoxybenzyl)-1H-1,2,3-triazole-4-carboxylate To a mixture of NaH (60% in mineral oil, 212 mg, 5.29 mmol, 1.2 eq) in DMF (25 mL) was added 3-bromo-5-hydroxy-1-methylpyridin-2(1H)-one (900 mg, 4.41 mmol, 1.0 eq) at 0° C. The resulting mixture was stirred at room temperature for 1 h. Ethyl 5-chloro-1-(4-methoxybenzyl)-1H-1,2,3-triazole-4-carboxylate (1.3 g, 4.41 mmol, 1.0 eq) was added into the mixture and stirred at 95° C. for 5 h. The reaction was quenched with saturated NH$_4$Cl aqueous solution and extracted with EtOAc (3×100 mL). The combined organic layers were dried over anhydrous sodium sulfate and concentrated. The residue was purified by silica gel column chromatography (PE:EtOAc=3:1) to give the desired (800 mg, yield: 39%) as a gray solid. MS (ESI) m/z 463.1 [M+H]$^+$.

Step 5—Ethyl 5-((5-bromo-1-methyl-6-oxo-1,6-dihydropyridin-3-yl)oxy)-1H-1,2,3-triazole-4-carboxylate A solution of ethyl 5-((5-bromo-1-methyl-6-oxo-1,6-dihydropyridin-3-yl)oxy)-1-(4-methoxybenzyl)-1H-1,2,3-triazole-4-carboxylate (710 mg, 1.53 mmol) in TFA (17 mL) was heated at 55° C. for 20 h. The reaction mixture was concentrated under reduced pressure and the residue was purified by silica gel column chromatography (PE: EtOAc=3:2) to give the desired (540 mg, yield: 91%) as a gray solid. MS (ESI) m/z 343.0 [M+H]$^+$.

Step 6: Ethyl 5-((5-(3-cyclopropylprop-1-ynyl)-1-methyl-6-oxo-1,6-dihydropyridin-3-yl)oxy)-1H-1,2,3-triazole-4-carboxylate A mixture of ethyl 5-((5-bromo-1-methyl-6-oxo-1,6-dihydropyridin-3-yl)oxy)-1H-1,2,3-triazole-4-carboxylate (470 mg, 1.37 mmol, 1.0 eq), (3-cyclopropylprop-1-ynyl)trimethylsilane (1.04 g, 6.85 mmol, 5.0 eq), Pd(PPh$_3$)$_2$Cl$_2$ (98 mg, 0.14 mmol, 0.1 eq), CuI (27 mg, 0.14 mmol, 0.1 eq) and TBAF (1M in THF, 7 mL, 7 mmol, 5.0 eq) in DIEA/DMF (2.5 mL/5 mL) in a sealed tube was heated at 50° C. under N$_2$ overnight. The reaction mixture was concentrated and the residue was purified by silica gel column chromatography (DCM:methanol=50:1) to give the desired (170 mg, yield: 35%) as a yellow solid. MS (ESI) m/z 343.1 [M+H]$^+$.

Step 7: 5-((5-(3-cyclopropylprop-1-ynyl)-1-methyl-6-oxo-1,6-dihydropyridin-3-yl)oxy)-1H-1,2,3-triazole-4-carboxylic Acid A mixture of ethyl 5-((5-(3-cyclopropylprop-1-ynyl)-1-methyl-6-oxo-1,6-dihydropyridin-3-yl)oxy)-1H-1,2,3-triazole-4-carboxylate (166 mg, 0.48 mmol) and 3N KOH (2 mL, 6 mmol, 12.5 eq) in methanol/THF (2 mL/2 mL) was stirred at 35° C. for 3 h. The reaction was adjusted to pH ~3 by 1N HCl and extracted with EtOAc (3×30 mL). The organic layers were combined, dried over anhydrous sodium sulfate, filtered and concentrated in vacuo. The crude product was purified by prep-HPLC (10-95% CH$_3$CN in water) to give the desired (100 mg, yield: 65%) as a yellow solid. $^1$H-NMR (400 MHz, DMSO-d$_6$) δ: 15.20 (brs, 1H), 13.20 (brs, 1H), 7.90 (d, J=3.2 Hz, 1H), 7.64 (d, J=2.8 Hz, 1H), 3.42 (s, 3H), 2.49 (d, J=6.0 Hz, 2H), 0.98-0.94 (m, 1H), 0.46-0.44 (m, 2H), 0.28-0.21 (m, 2H). MS (ESI) m/z 315.1 [M+H]$^+$.

Example 369: 4-(4-(3-Cyclopropylprop-1-ynyl)phenoxy)-1,2,5-oxadiazole-3-carboxylic Acid

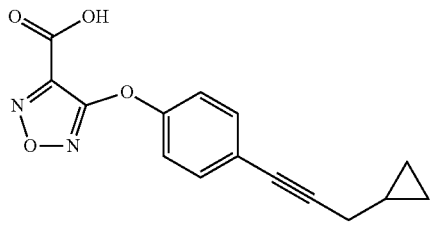 [SMILES: O=C(O)c1nonc1Oc1ccc(C#CCC2CC2)cc1]

Step 1: Ethyl 4-nitro-1,2,5-oxadiazole-3-carboxylate

At 0° C. sulfuric acid (21 mL) was slowly added to hydrogen peroxide (21 mL, 30 wt. %), then sodium tungstate (2.06 g, 7 mmol, 1.0 eq) was added, to which ethyl 4-amino-1,2,5-oxadiazole-3-carboxylate (1.10 g, 17 mmol, 1.00 eq) was added. The resulting mixture was heated to 15° C. and reacted for 3 hours. The reaction was diluted with water (50 mL) and extracted with EtOAc (3×100 mL). The combined organic layers were dried over hydrous Na$_2$SO$_4$ and concentrated under reduced pressure to give the desired (1.3 g, yield: 100%) as a colorless oil. MS (ESI) m/z 188.0 [M+H]$^+$.

Step 2: 4-(3-cyclopropylprop-1-ynyl)phenol

A mixture of 4-iodophenol (660 mg, 3 mmol, 1.0 eq), (3-cyclopropylprop-1-ynyl)trimethylsilane (1.82 g, 12 mmol, 4.0 eq), Pd(PPh$_3$)$_2$Cl$_2$ (210 mg, 0.3 mmol, 0.1 eq), CuI (57 mg, 0.3 mmol, 0.1 eq) and TBAF (1M in THF, 12 mL, 12 mmol, 4.0 eq) in DIEA/DMF (4 mL/4 mL) in a sealed tube was heated at 50° C. under N$_2$ for 5 h. The reaction mixture was concentrated and the residue was purified by silica gel column chromatography (PE: EtOAc=15:1) to give the desired (550 mg, yield: 71%) as a brown oil. MS (ESI) m/z 173.1 [M+H]$^+$.

Step 3: Ethyl 4-(4-(3-cyclopropylprop-1-ynyl)phenoxy)-1,2,5-oxadiazole-3-carboxylate A mixture of ethyl 4-nitro-1,2,5-oxadiazole-3-carboxylate (280 mg, 1.5 mmol, 1.0 eq), 4-(3-cyclopropylprop-1-ynyl)phenol (310 mg, 1.8 mmol, 1.2 eq) and K$_2$CO$_3$ (620 mg, 4.5 mmol, 3.0 eq) in DMSO (6 mL) was stirred at room temperature for 3 h. The reaction mixture was diluted with brine (50 mL) and extracted with extracted with EtOAc (3×100 mL). The combined organic layers were dried over hydrous Na$_2$SO$_4$ and concentrated under reduced pressure to give a crude, which was purified by silica gel column chromatography (PE:EtOAc=50:1) to give the desired (180 mg, yield: 38%) as a yellow oil. $^1$H-NMR (400 MHz, CDCl$_3$) δ: 7.50 (d, J=8.8 Hz, 2H), 7.25 (d, J=8.8 Hz, 2H), 4.51 (q, J=6.8 Hz, 2H), 2.46 (d, J=6.0 Hz, 2H), 1.43 (t, J=6.8 Hz, 3H), 1.03-0.96 (m, 1H), 0.52-0.44 (m, 2H), 0.26-0.21 (m, 2H).

Step 4: 4-(4-(3-cyclopropylprop-1-ynyl)phenoxy)-1,2,5-oxadiazole-3-carboxylic Acid A mixture of ethyl 4-(4-(3-cyclopropylprop-1-ynyl)phenoxy)-1,2,5-oxadiazole-3-carboxylate (110 mg, 0.35 mmol, 1.0 eq) and LiOH.H$_2$O (44 mg, 1.05 mmol, 3.0 eq) in THF/methanol/H$_2$O (5 mL/5 mL/5 mL) was stirred at room temperature for 3 h. The reaction was adjusted to pH ~3 and extracted with EtOAc (3×50 mL). The organic layers were combined, dried over anhydrous sodium sulfate, filtered and concentrated in vacuo. The crude product was purified by prep-HPLC (10-95% CH$_3$CN in water) to give the desired (11.7 mg, yield: 12%) as a white solid. $^1$H-NMR (400 MHz, DMSO-d$_6$) δ: 12.54 (brs, 1H), 7.48-7.44 (m, 2H), 7.27-7.23 (m, 2H), 2.47 (d, J=6.0 Hz, 2H), 1.02-0.96 (m, 1H), 0.50-0.45 (m, 2H), 0.26-0.20 (m, 2H). MS (ESI) m/z 285.1 [M+H]$^+$.

Example 370: 4-(3-(3-Cyclopropylprop-1-ynyl)phenoxy)-1,2,5-oxadiazole-3-carboxylic Acid

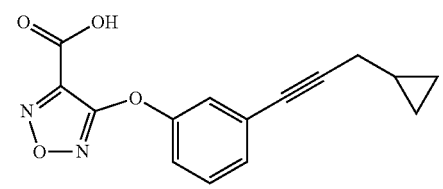

The title compound was prepared following procedures described for Example 369 using ethyl 4-nitro-1,2,5-oxadiazole-3-carboxylate and 3-(3-cyclopropylprop-1-ynyl)phenol to afford 4-(3-(3-cyclopropylprop-1-ynyl)phenoxy)-1,2,5-oxadiazole-3-carboxylic acid. ¹H-NMR (400 MHz, DMSO-d₆) δ: 12.50 (brs, 1H), 7.45-7.25 (m, 4H), 2.48 (d, J=6.0 Hz, 2H), 1.02-0.99 (m, 1H), 0.50-0.46 (m, 2H), 0.26-0.20 (m, 2H). MS (ESI) m/z 285.4 [M+H]⁺.

Example 371: Ethyl 5-(3-(4,4-dimethylpent-1-ynyl)phenoxy)-1H-1,2,3-triazole-4-carboxylate

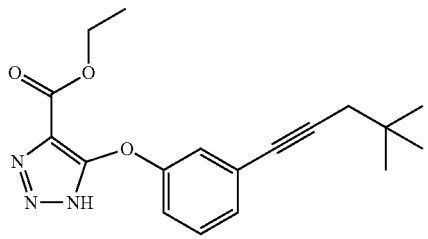 [SMILES: CCOC(=O)c1nn[nH]c1Oc1cccc(C#CCC(C)(C)C)c1]

The title compound was prepared following procedures described for Example 343 using ethyl 5-(3-iodophenoxy)-1H-1,2,3-triazole-4-carboxylate and 4,4-dimethylpent-1-yne to afford ethyl 5-(3-(4,4-dimethylpent-1-ynyl)phenoxy)-1H-1,2,3-triazole-4-carboxylate. ¹H NMR (400 MHz, CDCl₃) δ: 7.29-7.19 (m, 3H), 7.08 (dd, J=8.0 Hz and 1.2 Hz, 1H), 4.38 (q, J=7.2 Hz, 2H), 2.26 (s, 2H), 1.32 (t, J=7.2 Hz, 3H), 1.04 (s, 9H). MS (ESI) m/z 328.1 [M+H]⁺.

Example 372: 5-(3-(4,4-Dimethylpent-1-ynyl)phenoxy)-1H-1,2,3-triazole-4-carboxylic Acid

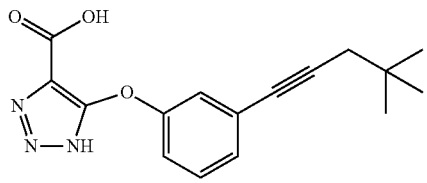

The title compound was prepared following procedures described for Example 343 using ethyl 5-(3-iodophenoxy)-1H-1,2,3-triazole-4-carboxylate and 4,4-dimethylpent-1-yne to afford 5-(3-(4,4-dimethylpent-1-ynyl)phenoxy)-1H-1,2,3-triazole-4-carboxylic acid. ¹H NMR (400 MHz, DMSO-d₆) δ: 13.20 (brs, 1H), 7.36-7.32 (m, 1H), 7.17 (d, J=7.6 Hz, 1H), 7.06-7.04 (m, 2H), 2.30 (s, 2H), 1.01 (s, 9H). MS (ESI) m/z 300.1 [M+H]⁺.

Example 373: Ethyl 5-(3-(4-methylpent-1-ynyl)phenylsulfinyl)-1H-1,2,3-triazole-4-carboxylate

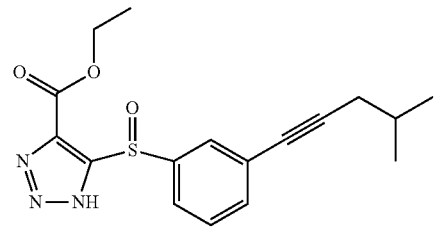 [SMILES: CCOC(=O)c1nn[nH]c1S(=O)c1cccc(C#CCC(C)C)c1]

Step 1: Ethyl 5-((3-bromophenyl)sulfinyl)-1H-1,2,3-triazole-4-carboxylate

To a solution of ethyl 5-((3-bromophenyl)thio)-1H-1,2,3-triazole-4-carboxylate (1.16 g, 3.54 mmol, 1.0 eq) in DCM (50 mL) was added m-CPBA (85%, 611 mg, 3.54 mmol, 1.0 eq) at 0° C. The reaction mixture was stirred at r.t. for 2 h. The reaction was concentrated under reduced pressure and the residue was purified by silica gel column chromatography (DCM:MeOH=60:1) to give the title compound (750 mg, 61%) as a colorless gel. MS (ESI) m/z 344.0 [M+H]⁺.

Step 2: Ethyl 5-((3-(4-methylpent-1-ynyl)phenyl)sulfinyl)-1H-1,2,3-triazole-4-carboxylate A mixture of ethyl 5-((3-bromophenyl)sulfinyl)-1H-1,2,3-triazole-4-carboxylate (320 mg, 0.93 mmol, 1.0 eq), 4-methylpent-1-yne (380 mg, 4.63 mmol, 5.0 eq), Pd(PPh₃)₂Cl₂ (63 mg, 0.09 mmol, 0.1 eq), CuI (18 mg, 0.09 mmol, 0.1 eq) in DIEA/DMF (3 mL/1.5 mL) in a sealed tube was heated at 50° C. under N₂ overnight. The reaction mixture was concentrated and the residue was purified by silica gel column chromatography (DCM:MeOH=40:1) to give the title compound (220 mg, 72%) as a colorless gel. ¹H NMR (400 MHz, CDCl₃) δ: 7.84 (s, 1H), 7.74 (d, J=8.0 Hz, 1H), 7.50 (d, J=8.0 Hz, 1H), 7.41 (t, J=8.0 Hz, 1H), 4.47-4.41 (m, 1H), 2.28 (d, J=6.4 Hz, 2H), 1.93-1.87 (m, 1H), 1.40 (t, J=7.2 Hz, 3H), 1.02 (d, J=6.8 Hz, 6H). MS (ESI) m/z 346.1 [M+H]⁺.

Example 374: 5-(3-(4-Methylpent-1-ynyl)phenylsulfinyl)-1H-1,2,3-triazole-4-carboxylic Acid

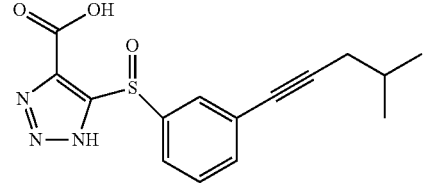 [SMILES: CC(C)CC#Cc1cccc(S(=O)c2[nH]nnc2C(=O)O)c1]

The title compound was prepared following procedures described for Example 343 using ethyl 5-((3-bromophenyl)sulfinyl)-1H-1,2,3-triazole-4-carboxylate and 4-methylpent-1-yne followed by hydrolysis to afford 5-(3-(4-methylpent-1-ynyl)phenylsulfinyl)-1H-1,2,3-triazole-4-carboxylic acid. ¹H NMR (400 MHz, DMSO-d₆) δ 7.72 (s, 1H), 7.68-7.65

(m, 1H), 7.57-7.52 (m, 2H), 2.34 (d, J=6.0 Hz, 2H), 1.89-1.82 (m, 1H), 1.00 (d, J=6.4 Hz, 6H). MS (ESI) m/z 318.1 [M+H]$^+$.

Example 375: Ethyl 5-(3-(4-methylpent-1-ynyl)phenylsulfonyl)-1H-1,2,3-triazole-4-carboxylate

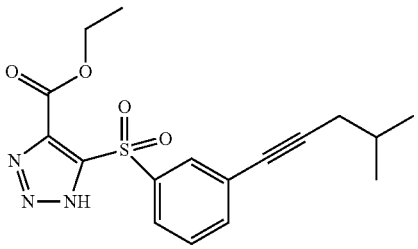 [SMILES: CCOC(=O)c1nn[nH]c1S(=O)(=O)c1cccc(C#CCC(C)C)c1]

The title compound was prepared following procedures described for Example 373 using 5-((3-bromophenyl)thio)-1H-1,2,3-triazole-4-carboxylate, m-CPBA and 4-methylpent-1-yne to afford ethyl 5-(3-(4-methylpent-1-ynyl)phenylsulfonyl)-1H-1,2,3-triazole-4-carboxylate. $^1$H NMR (400 MHz, DMSO-d$_6$) δ: 7.94-7.93 (m, 2H), 7.76 (d, J=7.6 Hz, 1H), 7.65 (t, J=8.0 Hz, 1H), 4.34 (q, J=7.2 Hz, 2H), 2.36 (d, J=6.4 Hz, 2H), 1.91-1.84 (m, 1H), 1.30 (t, J=7.2 Hz, 3H), 1.00 (d, J=6.8 Hz, 6H). MS (ESI) m/z 362.1 [M+H]$^+$.

Example 376: 5-(3-(4-Methylpent-1-ynyl)phenylsulfonyl)-1H-1,2,3-triazole-4-carboxylic Acid

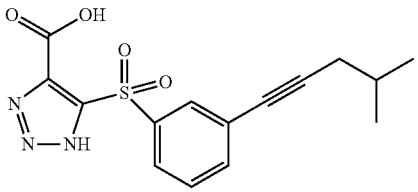 [SMILES: CC(C)CC#Cc1cccc(S(=O)(=O)c2[nH]nnc2C(=O)O)c1]

The title compound was prepared following procedures described for Example 373 using 5-((3-bromophenyl)thio)-1H-1,2,3-triazole-4-carboxylate, m-CPBA and 4-methylpent-1-yne followed by hydrolysis to afford 5-(3-(4-methylpent-1-ynyl)phenylsulfonyl)-1H-1,2,3-triazole-4-carboxylic acid. $^1$H NMR (400 MHz, DMSO-d$_6$) δ: 7.72 (s, 1H), 7.68-7.65 (m, 1H), 7.57-7.52 (m, 2H), 2.34 (d, J=6.0 Hz, 2H), 1.89-1.82 (m, 1H), 1.00 (d, J=6.4 Hz, 6H). MS (ESI) m/z 334.8 [M+H]$^+$.

Example 377: Ethyl 5-(3-(4-fluoro-4-methylpent-1-ynyl)phenoxy)-1H-1,2,3-triazole-4-carboxylate

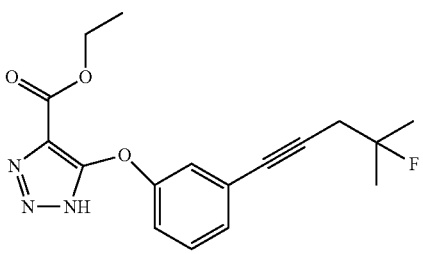 [SMILES: CCOC(=O)c1nn[nH]c1Oc1cccc(C#CCC(C)(C)F)c1]

Step 1: Ethyl 5-(3-(4-hydroxy-4-methylpent-1-ynyl)phenoxy)-1H-1,2,3-triazole-4-carboxylate A mixture of ethyl 5-(3-iodophenoxy)-1H-1,2,3-triazole-4-carboxylate (900 mg, 2.5 mmol, 1.0 eq), 2-methyl-5-(triisopropylsilyl)pent-4-yn-2-ol (3.0 g, 11.8 mmol, 4.7 eq), Pd(PPh$_3$)$_2$Cl$_2$ (176 mg, 0.25 mmol, 0.1 eq), CuI (48 mg, 0.25 mmol, 0.1 eq) and TBAF (1M in THF, 12 mL, 12 mmol, 4.8 eq) in DMF/DIEA (8 mL/4 mL)) in a sealed tube was heated at 50° C. under N$_2$ for 6 h. The reaction mixture was concentrated and the residue was purified by prep-HPLC (15-95% CH$_3$CN in water) to give the desired (340 mg, yield: 41%) as colorless gel. MS (ESI) m/z 330.1 [M+H]$^+$.

Step 2: Ethyl 5-(3-(4-fluoro-4-methylpent-1-ynyl)phenoxy)-1H-1,2,3-triazole-4-carboxylate To a mixture of ethyl 5-(3-(4-hydroxy-4-methylpent-1-ynyl)phenoxy)-1H-1,2,3-triazole-4-carboxylate (183 mg, 0.55 mmol, 1.0 eq) in DCM (15 mL) was added DAST (530 mg, 3.30 mmol, 6.0 eq) at 0° C. The result mixture was stirred at 0° C. for 15 minutes. The reaction mixture was quenched with water (50 mL) and extracted with DCM (2×150 mL). The combined organic layers were dried over anhydrous Na$_2$SO$_4$ and concentrated under reduced pressure to give a crude, which was purified by prep-HPLC (5-95% CH$_3$CN in water) to give the desired (100 mg, yield: 54%) as pale-yellow solid. $^1$H NMR (400 MHz, CDCl$_3$) δ: 7.30-7.19 (m, 3H), 7.11 (dd, J=8.0 Hz and 1.2 Hz, 1H), 4.38 (q, J=7.2 Hz, 2H), 2.73 (d, J=15.2 Hz, 2H), 1.50 (d, J=21.6 Hz, 6H), 2.26 (s, 2H), 1.32 (t, J=7.2 Hz, 3H). MS (ESI) m/z 330.0 [M−H]$^-$.

Example 378: 5-(3-(4-Fluoro-4-methylpent-1-ynyl)phenoxy)-1H-1,2,3-triazole-4-carboxylic Acid

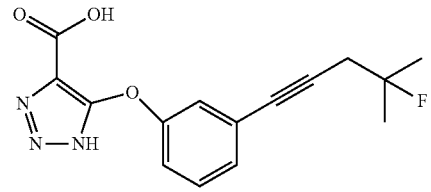 [SMILES: CC(C)(F)CC#Cc1cccc(Oc2[nH]nnc2C(=O)O)c1]

The title compound was prepared following procedures described for Example 377 using 5-(3-(4-fluoro-4-methylpent-1-ynyl)phenoxy)-1H-1,2,3-triazole-4-carboxylate and 3N KOH to afford 5-(3-(4-fluoro-4-methylpent-1-ynyl)phenoxy)-1H-1,2,3-triazole-4-carboxylic acid. $^1$H NMR (400 MHz, CD$_3$OD) δ: 7.21 (t, J=8.0 Hz, 1H), 7.08 (d, J=8.0 Hz, 1H), 7.02 (s, 1H), 6.96 (dd, J=8.0, 1.6 Hz, 1H), 2.64 (d, J=16.0 Hz, 2H), 1.38 (d, J=20.8 Hz, 6H). MS (ESI) m/z 304.1 [M+H]$^+$.

Compounds 1, 2, 5, 6, 9, 10, 13, 16, 17, 20, 21, 24, 25, 28, 29, 36, 37, 40, 41, 108, 138, 139, 146, 147, 149, 165, 178, 187, 190, 191, 208, 209, 215, 220, 221, and 254-378 in Table 1 have been made or prepared using the methods set for above. The other compounds in Table 1 can be prepared by the methods set forth above.

TABLE 1

Example Compounds

| Ex. No. | Structure | IUPAC Name | MW (g/mol) |
|---|---|---|---|
| 1 | 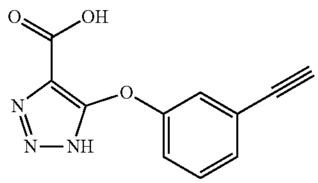 [SMILES: C#Cc1cccc(Oc2[nH]nnc2C(=O)O)c1] | 5-(3-ethynylphenoxy)-1H-1,2,3-triazole-4-carboxylic acid | 229.19 |
| 2 | 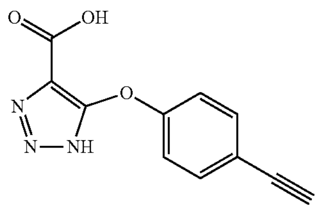 [SMILES: C#Cc1ccc(Oc2[nH]nnc2C(=O)O)cc1] | 5-(4-ethynylphenoxy)-1H-1,2,3-triazole-4-carboxylic acid | 229.19 |
| 3 | 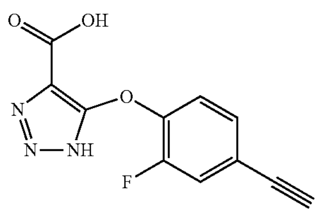 [SMILES: C#Cc1ccc(Oc2[nH]nnc2C(=O)O)c(F)c1] | 5-(4-ethynyl-2-fluorophenoxy)-1H-1,2,3-triazole-4-carboxylic acid | 247.04 |
| 4 | 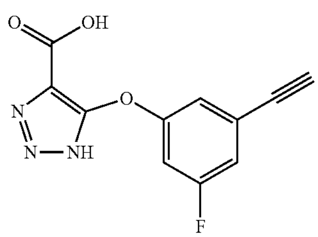 [SMILES: C#Cc1cc(F)cc(Oc2[nH]nnc2C(=O)O)c1] | 5-(4-ethynyl-3-fluorophenoxy)-1H-1,2,3-triazole-4-carboxylic acid | 247.04 |
| 5 | 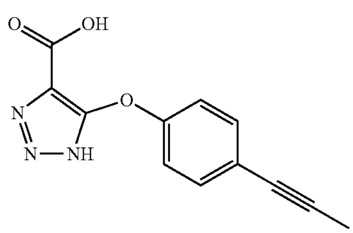 [SMILES: CC#Cc1ccc(Oc2[nH]nnc2C(=O)O)cc1] | 5-(4-(prop-1-ynyl)phenoxy)-1H-1,2,3-triazole-4-carboxylic acid | 243.22 |
| 6 | 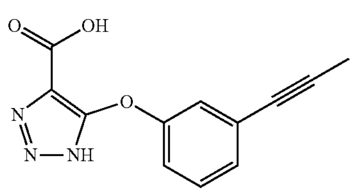 [SMILES: CC#Cc1cccc(Oc2[nH]nnc2C(=O)O)c1] | 5-(3-(prop-1-ynyl)phenoxy)-1H-1,2,3-triazole-4-carboxylic acid | 243.22 |
| 7 | 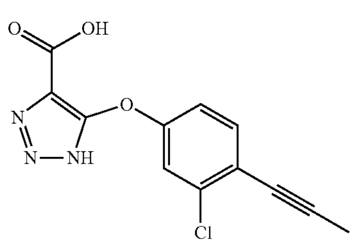 [SMILES: CC#Cc1ccc(Oc2[nH]nnc2C(=O)O)cc1Cl] | 5-(3-chloro-4-(prop-1-ynyl)phenoxy)-1H-1,2,3-triazole-4-carboxylic acid | 277.03 |

TABLE 1-continued

Example Compounds

| Ex. No. | Structure | IUPAC Name | MW (g/mol) |
|---|---|---|---|
| 8 | 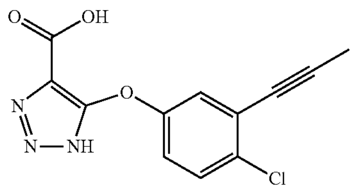 | 5-(4-chloro-3-(prop-1-ynyl)phenoxy)-1H-1,2,3-triazole-4-carboxylic acid | 277.03 |
| 9 | 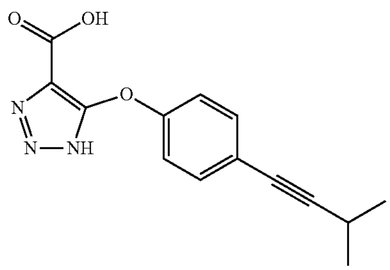 [SMILES: CC(C)C#Cc1ccc(Oc2[nH]nnc2C(=O)O)cc1] | 5-(4-(3-methylbut-1-ynyl)phenoxy)-1H-1,2,3-triazole-4-carboxylic acid | 271.27 |
| 10 | 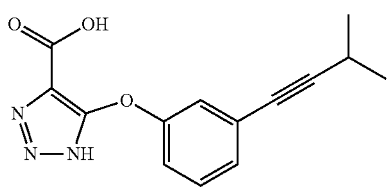 [SMILES: CC(C)C#Cc1cccc(Oc2[nH]nnc2C(=O)O)c1] | 5-(3-(3-methylbut-1-ynyl)phenoxy)-1H-1,2,3-triazole-4-carboxylic acid | 271.10 |
| 11 | 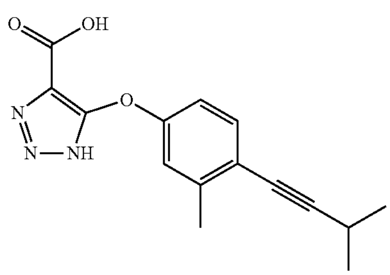 [SMILES: Cc1cc(Oc2[nH]nnc2C(=O)O)ccc1C#CC(C)C] | 5-(3-methyl-4-(3-methylbut-1-ynyl)phenoxy)-1H-1,2,3-triazole-4-carboxylic acid | 285.11 |
| 12 | 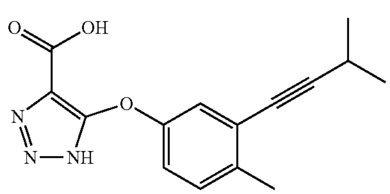 [SMILES: Cc1ccc(Oc2[nH]nnc2C(=O)O)cc1C#CC(C)C] | 5-(4-methyl-3-(3-methylbut-1-ynyl)phenoxy)-1H-1,2,3-triazole-4-carboxylic acid | 285.11 |
| 13 | 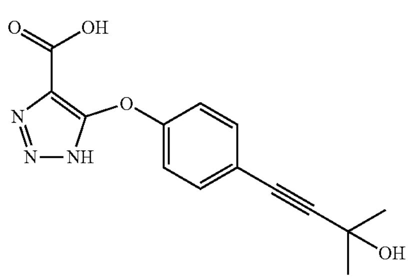 [SMILES: CC(C)(O)C#Cc1ccc(Oc2[nH]nnc2C(=O)O)cc1] | 5-(4-(3-hydroxy-3-methylbut-1-ynyl)phenoxy)-1H-1,2,3-triazole-4-carboxylic acid | 287.27 |

TABLE 1-continued

Example Compounds

| Ex. No. | Structure | IUPAC Name | MW (g/mol) |
|---|---|---|---|
| 14 | 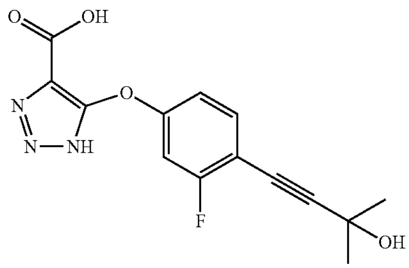 [SMILES: CC(C)(O)C#Cc1ccc(Oc2[nH]nnc2C(=O)O)cc1F] | 5-(3-fluoro-4-(3-hydroxy-3-methylbut-1-ynyl)phenoxy)-1H-1,2,3-triazole-4-carboxylic acid | 305.27 |
| 15 | 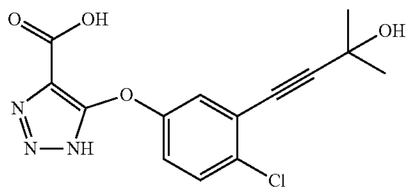 [SMILES: CC(C)(O)C#Cc1cc(Oc2[nH]nnc2C(=O)O)ccc1Cl] | 5-(4-chloro-3-(3-hydroxy-3-methylbut-1-ynyl)phenoxy)-1H-1,2,3-triazole-4-carboxylic acid | 321.05 |
| 16 | 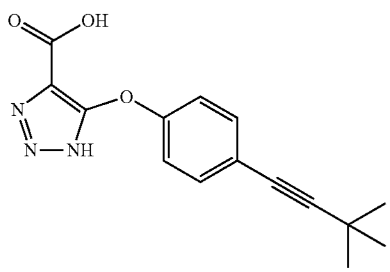 [SMILES: CC(C)(C)C#Cc1ccc(Oc2[nH]nnc2C(=O)O)cc1] | 5-(4-(3,3-dimethylbut-1-ynyl)phenoxy)-1H-1,2,3-triazole-4-carboxylic acid | 285.30 |
| 17 | 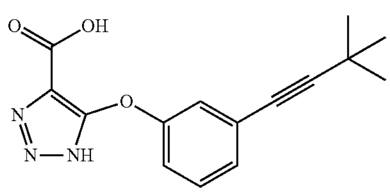 [SMILES: CC(C)(C)C#Cc1cccc(Oc2[nH]nnc2C(=O)O)c1] | 5-(3-(3,3-dimethylbut-1-ynyl)phenoxy)-1H-1,2,3-triazole-4-carboxylic acid | 285.30 |
| 18 | 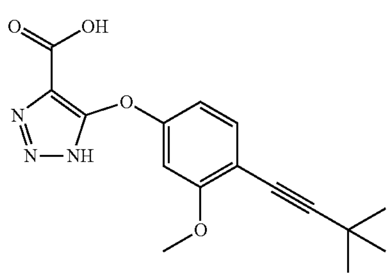 [SMILES: COc1cc(Oc2[nH]nnc2C(=O)O)ccc1C#CC(C)(C)C] | 5-(4-(3,3-dimethylbut-1-ynyl)-3-methoxyphenoxy)-1H-1,2,3-triazole-4-carboxylic acid | 315.12 |
| 19 | 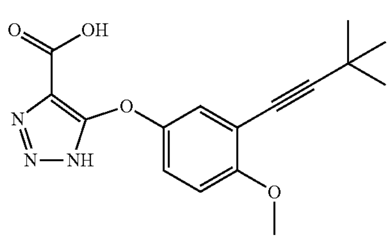 [SMILES: COc1ccc(Oc2[nH]nnc2C(=O)O)cc1C#CC(C)(C)C] | 5-(3-(3,3-dimethylbut-1-ynyl)-3-methoxyphenoxy)-1H-1,2,3-triazole-4-carboxylic acid | 315.12 |

TABLE 1-continued

Example Compounds

| Ex. No. | Structure | IUPAC Name | MW (g/mol) |
|---|---|---|---|
| 20 | 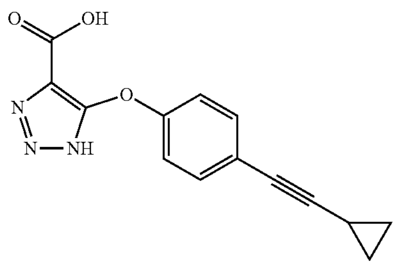 [SMILES: O=C(O)c1nn[nH]c1Oc1ccc(C#CC2CC2)cc1] | 5-(4-(cyclopropyl-ethynyl)phenoxy)-1H-1,2,3-triazole-4-carboxylic acid | 269.26 |
| 21 | 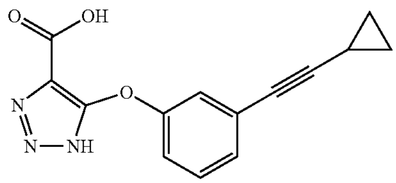 [SMILES: O=C(O)c1nn[nH]c1Oc1cccc(C#CC2CC2)c1] | 5-(3-(cyclopropyl-ethynyl)phenoxy)-1H-1,2,3-triazole-4-carboxylic acid | 269.26 |
| 22 | 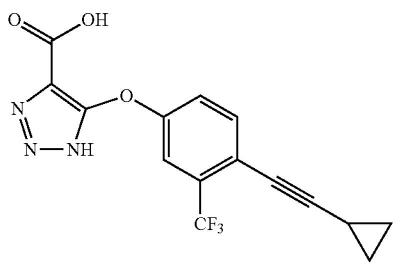 [SMILES: O=C(O)c1nn[nH]c1Oc1ccc(C#CC2CC2)c(C(F)(F)F)c1] | 5-(4-(cyclopropylethynyl)-3-(trifluoromethyl)phenoxy)-1H-1,2,3-triazole-4-carboxylic acid | 337.07 |
| 23 | 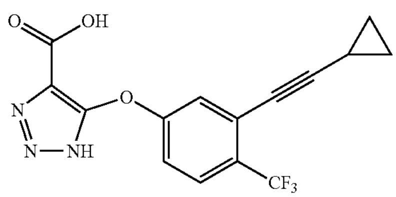 [SMILES: O=C(O)c1nn[nH]c1Oc1ccc(C(F)(F)F)c(C#CC2CC2)c1] | 5-(3-(cyclopropylethynyl)-4-(trifluoromethyl)phenoxy)-1H-1,2,3-triazole-4-carboxylic acid | 337.07 |
| 24 | 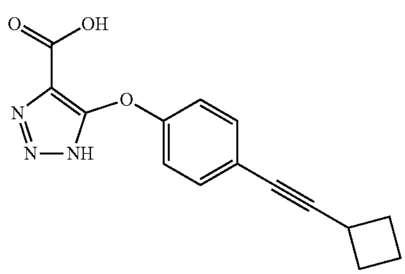 [SMILES: O=C(O)c1nn[nH]c1Oc1ccc(C#CC2CCC2)cc1] | 5-(4-(cyclobutyl-ethynyl)phenoxy)-1H-1,2,3-triazole-4-carboxylic acid | 283.28 |
| 25 | 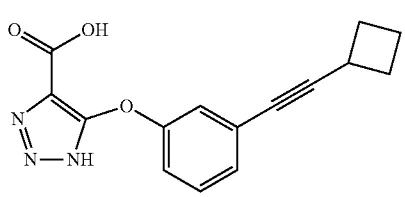 [SMILES: O=C(O)c1nn[nH]c1Oc1cccc(C#CC2CCC2)c1] | 5-(3-(cyclobutyl-ethynyl)phenoxy)-1H-1,2,3-triazole-4-carboxylic acid | 283.28 |

TABLE 1-continued

Example Compounds

| Ex. No. | Structure | IUPAC Name | MW (g/mol) |
|---|---|---|---|
| 26 | 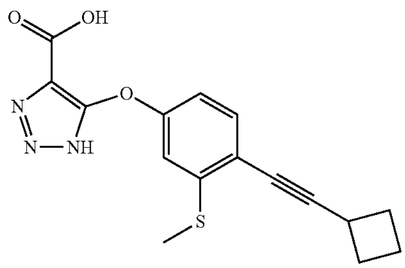 [SMILES: CSc1cc(Oc2[nH]nnc2C(=O)O)ccc1C#CC1CCC1] | 5-(4-(cyclobutylethynyl)-3-(methylthio)phenoxy)-1H-1,2,3-triazole-4-carboxylic acid | 329.08 |
| 27 | 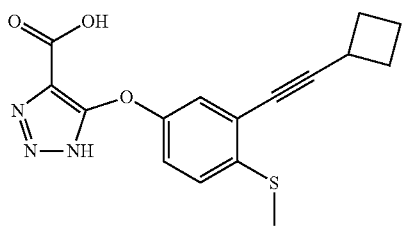 [SMILES: CSc1ccc(Oc2[nH]nnc2C(=O)O)cc1C#CC1CCC1] | 5-(3-(cyclobutylethynyl)-4-(methylthio)phenoxy)-1H-1,2,3-triazole-4-carboxylic acid | 329.08 |
| 28 | 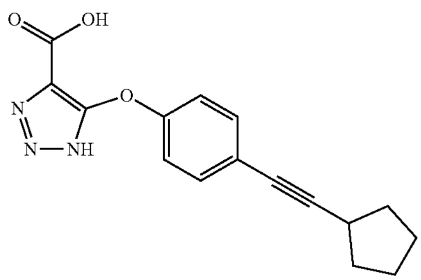 [SMILES: O=C(O)c1nn[nH]c1Oc1ccc(C#CC2CCCC2)cc1] | 5-(3-(cyclopentylethynyl)phenoxy)-1H-1,2,3-triazole-4-carboxylic acid | 297.31 |
| 29 | 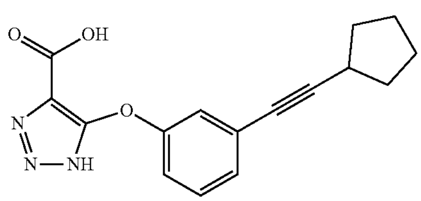 [SMILES: O=C(O)c1nn[nH]c1Oc1cccc(C#CC2CCCC2)c1] | 5-(4-(cyclopentyl ethynyl)phenoxy)-1H-1,2,3-triazole-4-carboxylic acid | 297.31 |
| 30 | 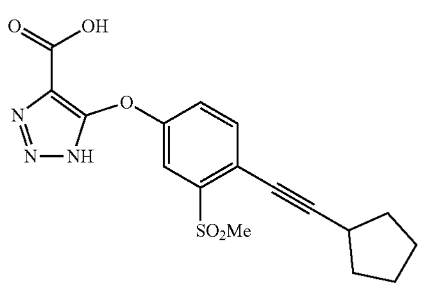 [SMILES: CS(=O)(=O)c1cc(Oc2[nH]nnc2C(=O)O)ccc1C#CC1CCCC1] | 5-(4-(cyclopentylethynyl)-3-(methylsulfonyl) phenoxy)-1H-1,2,3-triazole-4-carboxylic acid | 375.09 |
| 31 | 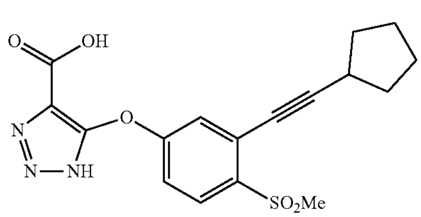 [SMILES: CS(=O)(=O)c1ccc(Oc2[nH]nnc2C(=O)O)cc1C#CC1CCCC1] | 5-(3-(cyclopentylethynyl)-4-(methylsulfonyl) phenoxy)-1H-1,2,3-triazole-4-carboxylic acid | 375.09 |

TABLE 1-continued

Example Compounds

| Ex. No. | Structure | IUPAC Name | MW (g/mol) |
|---|---|---|---|
| 32 | 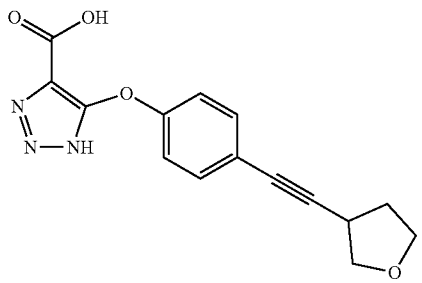 [SMILES: O=C(O)c1nn[nH]c1Oc1ccc(C#CC2CCOC2)cc1] | 5-(4-((tetrahydrofuran-3-yl)ethynyl) phenoxy)-1H-1,2,3-triazole-4-carboxylic acid | 299.09 |
| 33 | 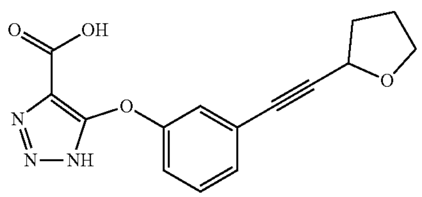 [SMILES: O=C(O)c1nn[nH]c1Oc1cccc(C#CC2CCCO2)c1] | 5-(3-((tetrahydrofuran-2-yl)ethynyl) phenoxy)-1H-1,2,3-triazole-4-carboxylic acid | 299.09 |
| 34 | 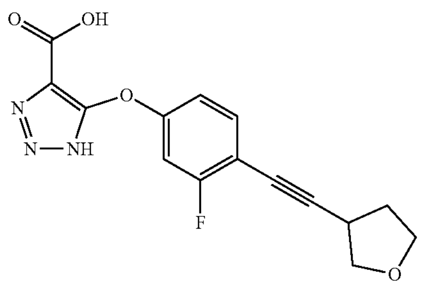 [SMILES: O=C(O)c1nn[nH]c1Oc1ccc(C#CC2CCOC2)c(F)c1] | 5-(3-fluoro-4-((tetrahydrofuran-3-yl)ethynyl)phenoxy)-1H-1,2,3-triazole-4-carboxylic acid | 317.08 |
| 35 | 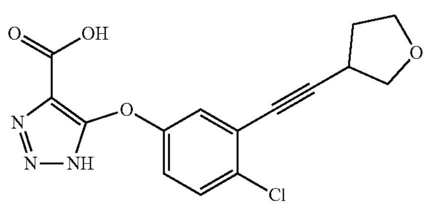 [SMILES: O=C(O)c1nn[nH]c1Oc1ccc(Cl)c(C#CC2CCOC2)c1] | 5-(4-chloro-3-((tetrahydro-furan-3-yl)ethynyl)phenoxy)-1H-1,2,3-triazole-4-carboxylic acid | 333.05 |
| 36 | 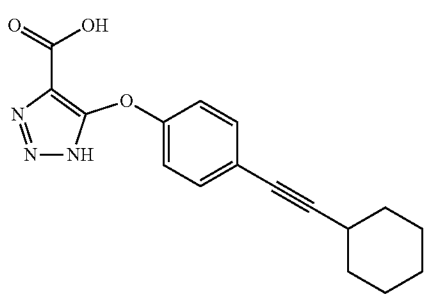 [SMILES: O=C(O)c1nn[nH]c1Oc1ccc(C#CC2CCCCC2)cc1] | 5-(4-(cyclohexylethynyl) phenoxy)-1H-1,2,3-triazole-4-carboxylic acid | 311.34 |
| 37 | 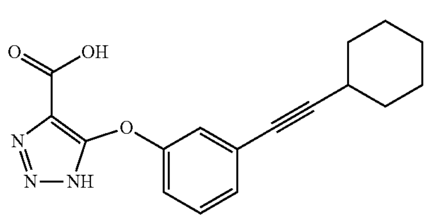 [SMILES: O=C(O)c1nn[nH]c1Oc1cccc(C#CC2CCCCC2)c1] | 5-(3-(cyclohexylethynyl) phenoxy)-1H-1,2,3-triazole-4-carboxylic acid | 311.34 |

TABLE 1-continued

Example Compounds

| Ex. No. | Structure | IUPAC Name | MW (g/mol) |
|---|---|---|---|
| 38 | 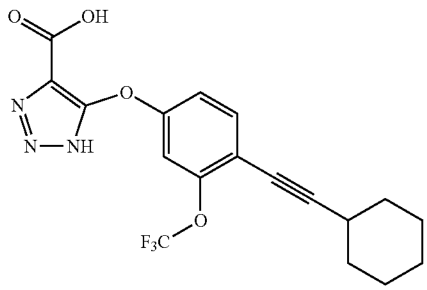 [SMILES: O=C(O)c1nn[nH]c1Oc1ccc(C#CC2CCCCC2)c(OC(F)(F)F)c1] | 5-(4-(cyclohexylethynyl)-3-(trifluoromethoxy)phenoxy)-1H-1,2,3-triazole-4-carboxylic acid | 395.11 |
| 39 | 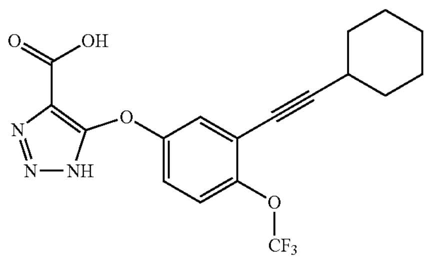 [SMILES: O=C(O)c1nn[nH]c1Oc1ccc(OC(F)(F)F)c(C#CC2CCCCC2)c1] | 5-(3-(cyclohexylethynyl)-4-(trifluoromethoxy)phenoxy)-1H-1,2,3-triazole-4-carboxylic acid | 395.11 |
| 40 | 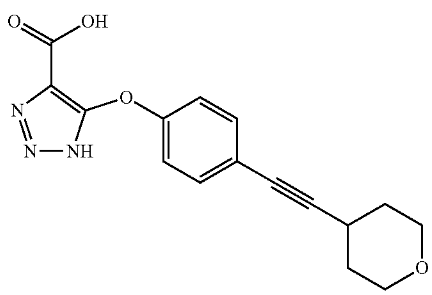 [SMILES: O=C(O)c1nn[nH]c1Oc1ccc(C#CC2CCOCC2)cc1] | 5-(4-((tetrahydro-2H-pyran-4-yl)ethynyl)phenoxy)-1H-1,2,3-triazole-4-carboxylic acid | 313.31 |
| 41 | 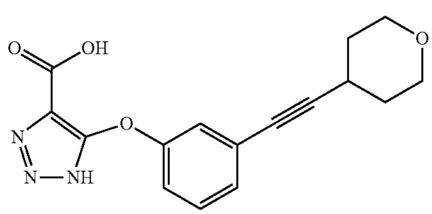 [SMILES: O=C(O)c1nn[nH]c1Oc1cccc(C#CC2CCOCC2)c1] | 5-(3-((tetrahydro-2H-pyran-4-yl)ethynyl)phenoxy)-1H-1,2,3-triazole-4-carboxylic acid | 313.31 |
| 42 | 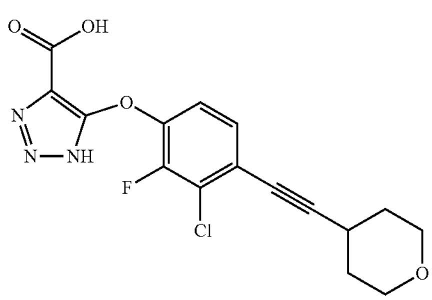 [SMILES: O=C(O)c1nn[nH]c1Oc1ccc(C#CC2CCOCC2)c(Cl)c1F] | 5-(3-chloro-2-fluoro-4-((tetrahydro-2H-pyran-4-yl)ethynyl) phenoxy)-1H-1,2,3-triazole-4-carboxylic acid | 365.06 |

TABLE 1-continued

Example Compounds

| Ex. No. | Structure | IUPAC Name | MW (g/mol) |
|---|---|---|---|
| 43 | 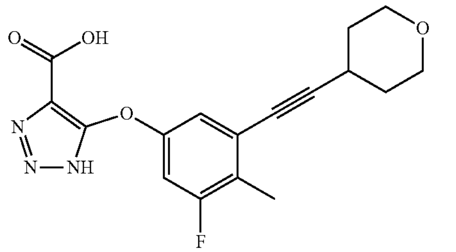 [SMILES: Cc1c(F)cc(Oc2[nH]nnc2C(=O)O)cc1C#CC1CCOCC1] | 5-(3-fluoro-4-methyl-5-((tetrahydro-2H-pyran-4-yl)ethynyl)phenoxy)-1H-1,2,3-triazole-4-carboxylic acid | 345.11 |
| 44 | 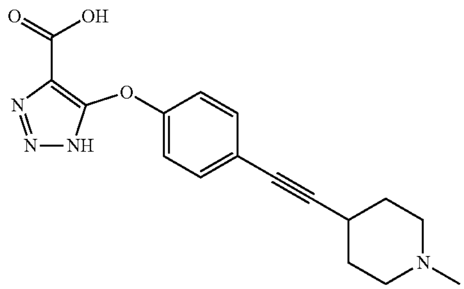 [SMILES: CN1CCC(C#Cc2ccc(Oc3[nH]nnc3C(=O)O)cc2)CC1] | 5-(4-((1-methylpiperidin-4-yl)ethynyl)phenoxy)-1H-1,2,3-triazole-4-carboxylic acid | 326.14 |
| 45 | 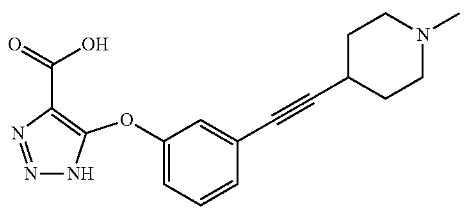 [SMILES: CN1CCC(C#Cc2cccc(Oc3[nH]nnc3C(=O)O)c2)CC1] | 5-(3-((1-methylpiperidin-4-yl)ethynyl)phenoxy)-1H-1,2,3-triazole-4-carboxylic acid | 326.14 |
| 46 | 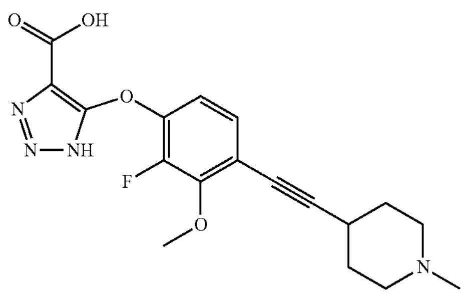 [SMILES: COc1c(C#CC2CCN(C)CC2)ccc(Oc2[nH]nnc2C(=O)O)c1F] | 5-(2-fluoro-3-methoxy-4-((1-methylpiperidin-4-yl)ethynyl)phenoxy)-1H-1,2,3-triazole-4-carboxylic acid | 374.14 |
| 47 | 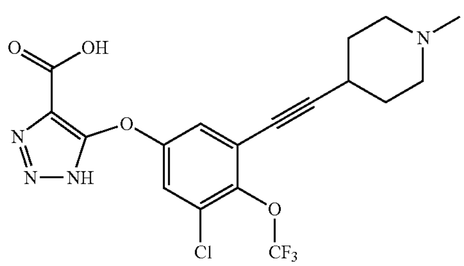 [SMILES: CN1CCC(C#Cc2cc(Oc3[nH]nnc3C(=O)O)cc(Cl)c2OC(F)(F)F)CC1] | 5-(3-chloro-5-((1-methylpiperidin-4-yl)ethynyl)-4-(trifluoromethoxy)phenoxy)-1H-1,2,3-triazole-4-carboxylic acid | 444.08 |
| 48 | 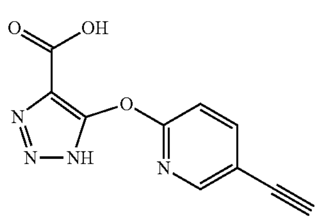 [SMILES: C#Cc1ccc(Oc2[nH]nnc2C(=O)O)nc1] | 5-((5-ethynylpyridin-2-yl)oxy)-1H-1,2,3-triazole-4-carboxylic acid | 230.04 |

TABLE 1-continued

Example Compounds

| Ex. No. | Structure | IUPAC Name | MW (g/mol) |
|---|---|---|---|
| 49 | 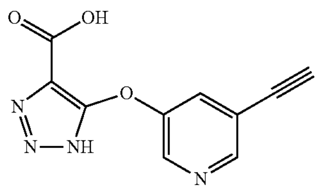 [SMILES: C#Cc1cncc(Oc2[nH]nnc2C(=O)O)c1] | 5-((5-ethynylpyridin-3-yl)oxy)-1H-1,2,3-triazole-4-carboxylic acid | 230.04 |
| 50 | 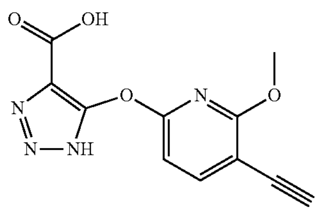 [SMILES: C#Cc1ccc(Oc2[nH]nnc2C(=O)O)nc1OC] | 5-((5-ethynyl-6-methoxypyridin-2-yl)oxy)-1H-1,2,3-triazole-4-carboxylic acid | 260.05 |
| 51 | 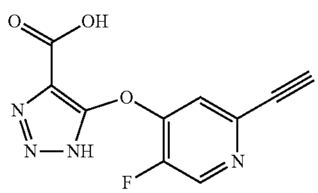 [SMILES: C#Cc1cc(Oc2[nH]nnc2C(=O)O)c(F)cn1] | 5-((2-ethynyl-5-fluoropyridin-4-yl)oxy)-1H-1,2,3-triazole-4-carboxylic acid | 248.03 |
| 52 | 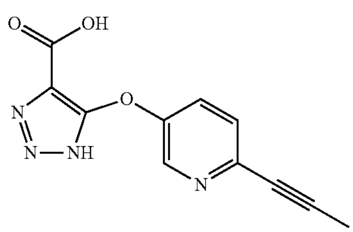 [SMILES: CC#Cc1ccc(Oc2[nH]nnc2C(=O)O)cn1] | 5-((2-(prop-1-ynyl)pyridin-4-yl)oxy)-1H-1,2,3-triazole-4-carboxylic acid | 244.06 |
| 53 | 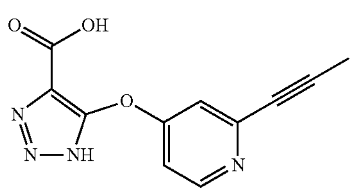 [SMILES: CC#Cc1cc(Oc2[nH]nnc2C(=O)O)ccn1] | 5-((6-(prop-1-ynyl)pyridin-3-yl)oxy)-1H-1,2,3-triazole-4-carboxylic acid | 244.06 |
| 54 | 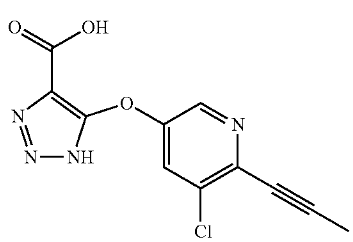 [SMILES: CC#Cc1ncc(Oc2[nH]nnc2C(=O)O)cc1Cl] | 5-((5-chloro-6-(prop-1-ynyl)pyridin-3-yl)oxy)-1H-1,2,3-triazole-4-carboxylic acid | 278.02 |
| 55 | 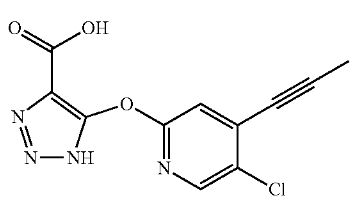 [SMILES: CC#Cc1cc(Oc2[nH]nnc2C(=O)O)ncc1Cl] | 5-((5-chloro-4-(prop-1-ynyl)pyridin-2-yl)oxy)-1H-1,2,3-triazole-4-carboxylic acid | 278.02 |

TABLE 1-continued

Example Compounds

| Ex. No. | Structure | IUPAC Name | MW (g/mol) |
|---|---|---|---|
| 56 | 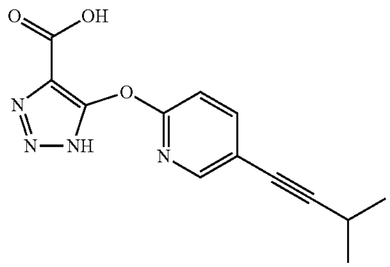 [SMILES: CC(C)C#Cc1ccc(Oc2[nH]nnc2C(=O)O)nc1] | 5-((2-(3-methylbut-1-ynyl)pyridin-4-yl)oxy)-1H-1,2,3-triazole-4-carboxylic acid | 272.09 |
| 57 | 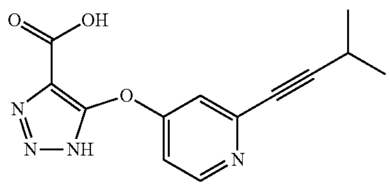 [SMILES: CC(C)C#Cc1cc(Oc2[nH]nnc2C(=O)O)ccn1] | 5-((6-methyl-5-(3-methylbut-1-ynyl)pyridin-2-yl)oxy)-1H-1,2,3-triazole-4-carboxylic acid | 286.11 |
| 58 | 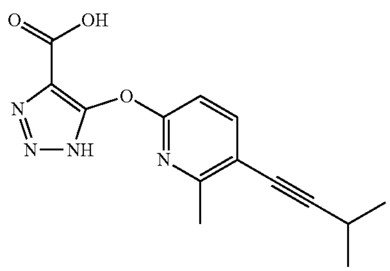 [SMILES: Cc1nc(Oc2[nH]nnc2C(=O)O)ccc1C#CC(C)C] | 5-((5-(3-methylbut-1-ynyl)pyridin-2-yl)oxy)-1H-1,2,3-triazole-4-carboxylic acid | 272.09 |
| 59 | 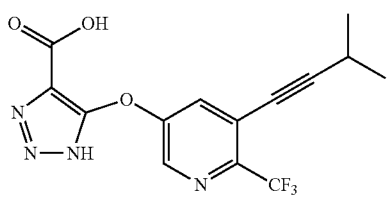 [SMILES: CC(C)C#Cc1cc(Oc2[nH]nnc2C(=O)O)cnc1C(F)(F)F] | 5-((5-(3-methylbut-1-ynyl)-6-(trifluoromethyl)pyridin-3-yl)oxy)-1H-1,2,3-triazole-4-carboxylic acid | 340.08 |
| 60 | 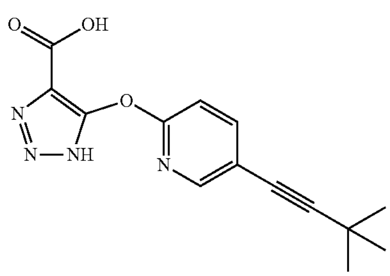 [SMILES: CC(C)(C)C#Cc1ccc(Oc2[nH]nnc2C(=O)O)nc1] | 5-((5-(3,3-dimethylbut-1-ynyl)pyridin-2-yl)oxy)-1H-1,2,3-triazole-4-carboxylic acid | 286.11 |
| 61 | 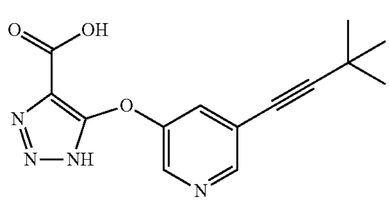 [SMILES: CC(C)(C)C#Cc1cncc(Oc2[nH]nnc2C(=O)O)c1] | 5-((5-(3,3-dimethylbut-1-ynyl)pyridin-3-yl)oxy)-1H-1,2,3-triazole-4-carboxylic acid | 286.11 |

TABLE 1-continued

Example Compounds

| Ex. No. | Structure | IUPAC Name | MW (g/mol) |
|---|---|---|---|
| 62 | 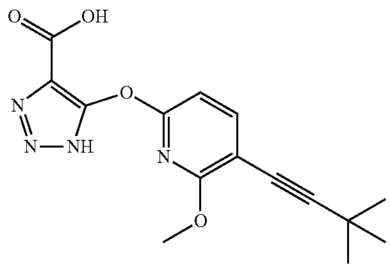 [SMILES: COc1nc(Oc2[nH]nnc2C(=O)O)ccc1C#CC(C)(C)C] | 5-((5-(3,3-dimethylbut-1-ynyl)-6-methoxypyridin-2-yl)oxy)-1H-1,2,3-triazole-4-carboxylic acid | 316.12 |
| 63 | 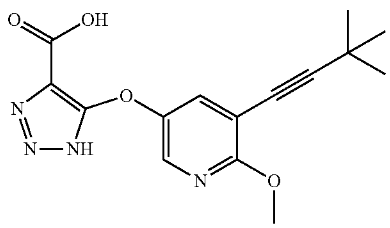 [SMILES: COc1ncc(Oc2[nH]nnc2C(=O)O)cc1C#CC(C)(C)C] | 5-((5-(3,3-dimethylbut-1-ynyl)-6-methoxypyridin-3-yl)oxy)-1H-1,2,3-triazole-4-carboxylic acid | 316.12 |
| 64 | 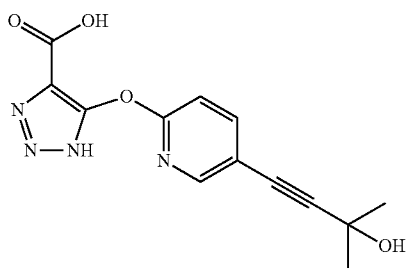 [SMILES: CC(C)(O)C#Cc1ccc(Oc2[nH]nnc2C(=O)O)nc1] | 5-((5-(3-hydroxy-3-methylbut-1-ynyl)pyridin-2-yl)oxy)-1H-1,2,3-triazole-4-carboxylic acid | 288.09 |
| 65 | 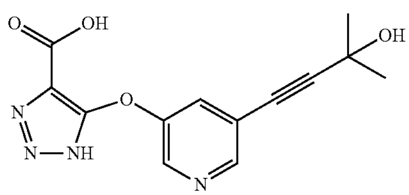 [SMILES: CC(C)(O)C#Cc1cncc(Oc2[nH]nnc2C(=O)O)c1] | 5-((5-(3-hydroxy-3-methylbut-1-ynyl)pyridin-3-yl)oxy)-1H-1,2,3-triazole-4-carboxylic acid | 288.09 |
| 66 | 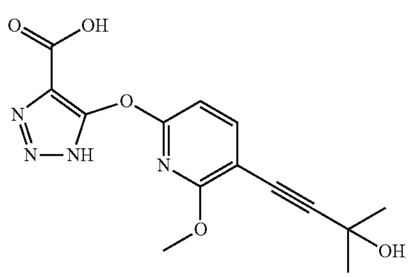 [SMILES: COc1nc(Oc2[nH]nnc2C(=O)O)ccc1C#CC(C)(C)O] | 5-((5-(3-hydroxy-3-methylbut-1-ynyl)-6-methoxypyridin-2-yl)oxy)-1H-1,2,3-triazole-4-carboxylic acid | 318.10 |
| 67 | 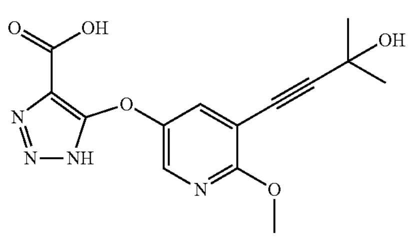 [SMILES: COc1ncc(Oc2[nH]nnc2C(=O)O)cc1C#CC(C)(C)O] | 5-((5-(3-hydroxy-3-methylbut-1-ynyl)-6-methoxypyridin-3-yl)oxy)-1H-1,2,3-triazole-4-carboxylic acid | 318.10 |

TABLE 1-continued

Example Compounds

| Ex. No. | Structure | IUPAC Name | MW (g/mol) |
|---|---|---|---|
| 68 | 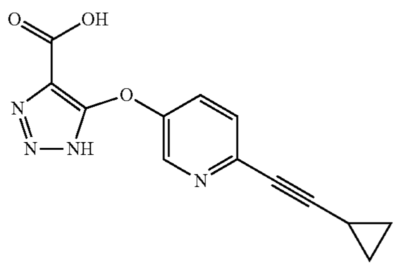 [SMILES: O=C(O)c1nn[nH]c1Oc1ccc(C#CC2CC2)nc1] | 5-((6-(cyclopropylethynyl)pyridin-3-yl)oxy)-1H-1,2,3-triazole-4-carboxylic acid | 270.08 |
| 69 | 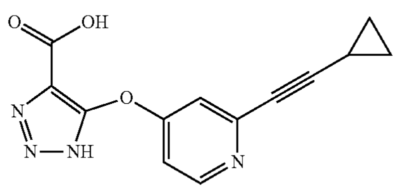 [SMILES: O=C(O)c1nn[nH]c1Oc1ccnc(C#CC2CC2)c1] | 5-((2-(cyclopropylethynyl)pyridin-4-yl)oxy)-1H-1,2,3-triazole-4-carboxylic acid | 270.08 |
| 70 | 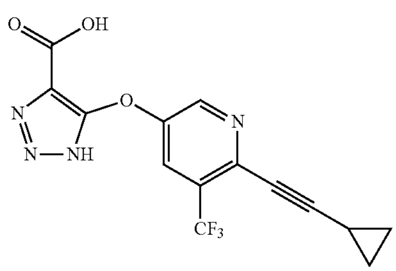 [SMILES: O=C(O)c1nn[nH]c1Oc1cnc(C#CC2CC2)c(C(F)(F)F)c1] | 5-((6-(cyclopropylethynyl)-4-(trifluoromethyl) pyridin-3-yl)oxy)-1H-1,2,3-triazole-4-carboxylic acid | 338.06 |
| 71 | 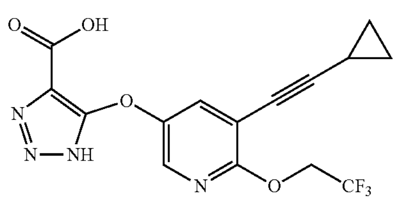 [SMILES: O=C(O)c1nn[nH]c1Oc1cnc(OCC(F)(F)F)c(C#CC2CC2)c1] | 5-((5-(cyclopropyl ethynyl)-6-(2,2,2-trifluoroethoxy) pyridin-3-yl)oxy)-1H-1,2,3-triazole-4-carboxylic acid | 368.07 |
| 72 | 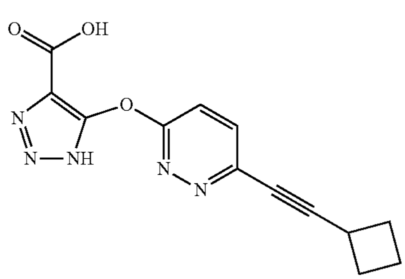 [SMILES: O=C(O)c1nn[nH]c1Oc1ccc(C#CC2CCC2)nn1] | 5-((6-(cyclobutylethynyl) pyridazin-3-yl)oxy)-1H-1,2,3-triazole-4-carboxylic acid | 285.09 |
| 73 | 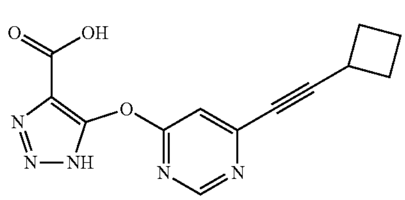 [SMILES: O=C(O)c1nn[nH]c1Oc1cc(C#CC2CCC2)ncn1] | 5-((6-(cyclobutylethynyl) pyrimidin-4-yl)oxy)-1H-1,2,3-triazole-4-carboxylic acid | 285.09 |

TABLE 1-continued

Example Compounds

| Ex. No. | Structure | IUPAC Name | MW (g/mol) |
|---|---|---|---|
| 74 | 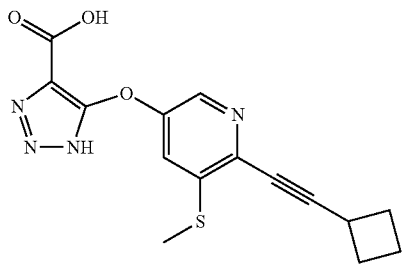 [SMILES: CSc1cc(Oc2[nH]nnc2C(=O)O)cnc1C#CC1CCC1] | 5-((6-(cyclobutylethynyl)-5-(methylthio)pyridin-3-yl)oxy)-1H-1,2,3-triazole-4-carboxylic acid | 330.08 |
| 75 | 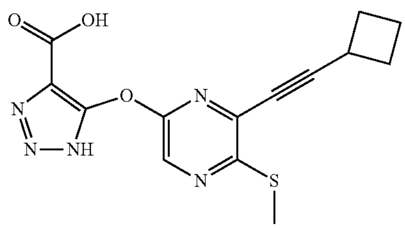 [SMILES: CSc1ncc(Oc2[nH]nnc2C(=O)O)nc1C#CC1CCC1] | 5-((6-(cyclobutylethynyl)-5-(methylthio)pyrazin-2-yl)oxy)-1H-1,2,3-triazole-4-carboxylic acid | 331.07 |
| 76 | 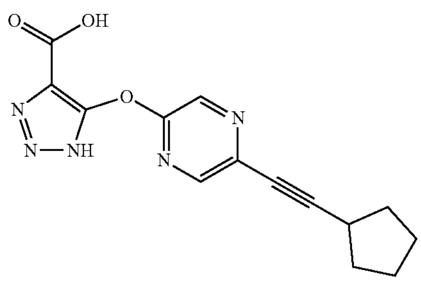 [SMILES: O=C(O)c1nn[nH]c1Oc1cnc(C#CC2CCCC2)cn1] | 5-((5-(cyclopentylethynyl)pyrazin-2-yl)oxy)-1H-1,2,3-triazole-4-carboxylic acid | 299.10 |
| 77 | 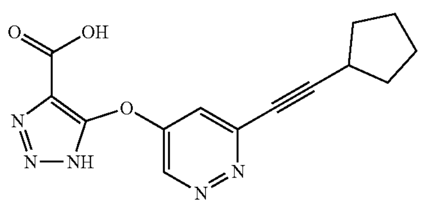 [SMILES: O=C(O)c1nn[nH]c1Oc1cnnc(C#CC2CCCC2)c1] | 5-((6-(cyclopentylethynyl)pyridazin-4-yl)oxy)-1H-1,2,3-triazole-4-carboxylic acid | 299.10 |
| 78 | 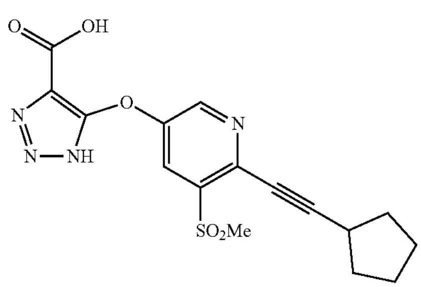 [SMILES: CS(=O)(=O)c1cc(Oc2[nH]nnc2C(=O)O)cnc1C#CC1CCCC1] | 5-((6-(cyclopentylethynyl)-5-(methylsulfonyl) pyridin-3-yl)oxy)-1H-1,2,3-triazole-4-carboxylic acid | 376.08 |
| 79 | 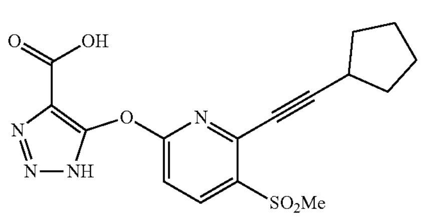 [SMILES: CS(=O)(=O)c1ccc(Oc2[nH]nnc2C(=O)O)nc1C#CC1CCCC1] | 5-((6-(cyclopentylethynyl)-5-(methylsulfonyl) pyridin-2-yl)oxy)-1H-1,2,3-triazole-4-carboxylic acid | 376.08 |

TABLE 1-continued

Example Compounds

| Ex. No. | Structure | IUPAC Name | MW (g/mol) |
|---|---|---|---|
| 80 | 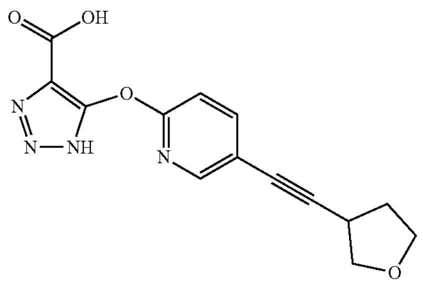 [SMILES: O=C(O)c1nn[nH]c1Oc1ccc(C#CC2CCOC2)cn1] | 5-((5-((tetrahydrofuran-3-yl)ethynyl)pyridin-2-yl)oxy)-1H-1,2,3-triazole-4-carboxylic acid | 300.09 |
| 81 | 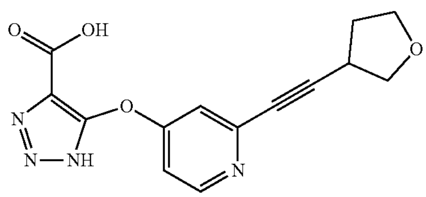 [SMILES: O=C(O)c1nn[nH]c1Oc1ccnc(C#CC2CCOC2)c1] | 5-((2-((tetrahydrofuran-3-yl)ethynyl)pyridin-4-yl)oxy)-1H-1,2,3-triazole-4-carboxylic acid | 300.09 |
| 82 | 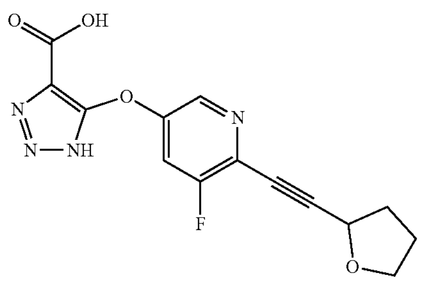 [SMILES: O=C(O)c1nn[nH]c1Oc1cnc(C#CC2CCCO2)c(F)c1] | 5-((5-fluoro-6-((tetrahydrofuran-2-yl)ethynyl)pyridin-3-yl)oxy)-1H-1,2,3-triazole-4-carboxylic acid | 318.08 |
| 83 | 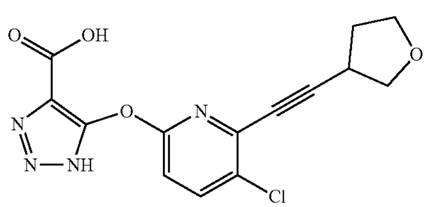 [SMILES: O=C(O)c1nn[nH]c1Oc1ccc(Cl)c(C#CC2CCOC2)n1] | 5-((5-chloro-6-((tetrahydrofuran-3-yl)ethynyl)pyridin-2-yl)oxy)-1H-1,2,3-triazole-4-carboxylic acid | 334.05 |
| 84 | 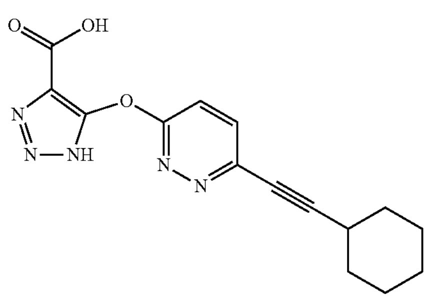 [SMILES: O=C(O)c1nn[nH]c1Oc1ccc(C#CC2CCCCC2)nn1] | 5-((6-(cyclohexylethynyl)pyridazin-3-yl)oxy)-1H-1,2,3-triazole-4-carboxylic acid | 313.12 |
| 85 | 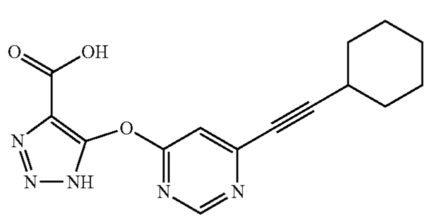 [SMILES: O=C(O)c1nn[nH]c1Oc1cc(C#CC2CCCCC2)ncn1] | 5-((6-(cyclohexylethynyl)pyrimidin-4-yl)oxy)-1H-1,2,3-triazole-4-carboxylic acid | 313.12 |

TABLE 1-continued

Example Compounds

| Ex. No. | Structure | IUPAC Name | MW (g/mol) |
|---|---|---|---|
| 86 | 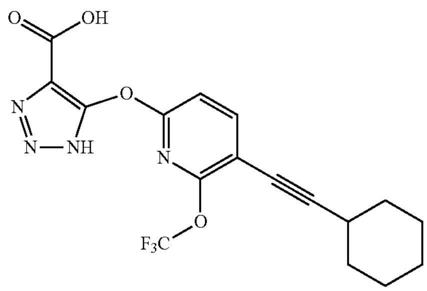 [SMILES: O=C(O)c1nn[nH]c1Oc1ccc(C#CC2CCCCC2)c(OC(F)(F)F)n1] | 5-((5-(cyclohexylethynyl)-6-(trifluoromethoxy)pyridin-2-yl)oxy)-1H-1,2,3-triazole-4-carboxylic acid | 396.10 |
| 87 | 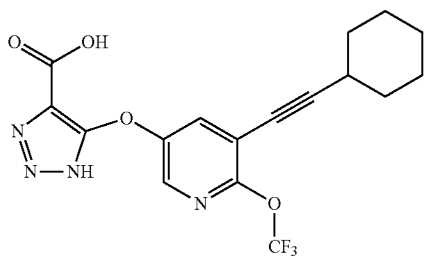 [SMILES: O=C(O)c1nn[nH]c1Oc1cnc(OC(F)(F)F)c(C#CC2CCCCC2)c1] | 5-((5-(cyclohexylethynyl)-6-(trifluoromethoxy)pyridin-3-yl)oxy)-1H-1,2,3-triazole-4-carboxylic acid | 396.10 |
| 88 | 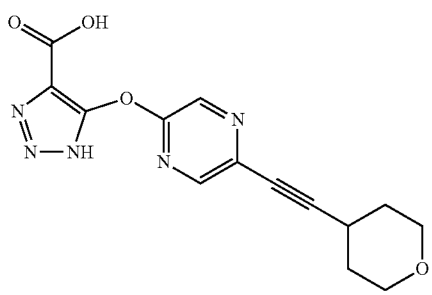 [SMILES: O=C(O)c1nn[nH]c1Oc1cnc(C#CC2CCOCC2)cn1] | 5-((5-((tetrahydro-2H-pyran-4-yl)ethynyl) pyrazin-2-yl)oxy)-1H-1,2,3-triazole-4-carboxylic acid | 315.10 |
| 89 | 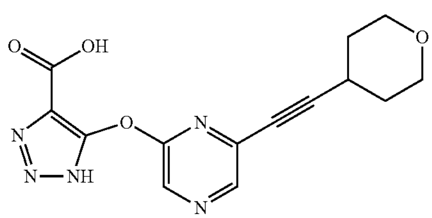 [SMILES: O=C(O)c1nn[nH]c1Oc1cncc(C#CC2CCOCC2)n1] | 5-((6-((tetrahydro-2H-pyran-4-yl)ethynyl) pyrazin-2-yl)oxy)-1H-1,2,3-triazole-4-carboxylic acid | 315.10 |
| 90 | 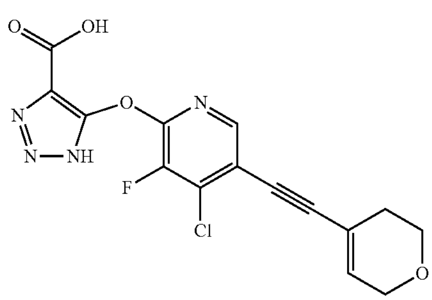 [SMILES: O=C(O)c1nn[nH]c1Oc1ncc(C#CC2=CCOCC2)c(Cl)c1F] | 5-((4-chloro-5-((3,6-dihydro-2H-pyran-4-yl)ethynyl)-3-fluoropyridin-2-yl)oxy)-1H-1,2,3-triazole-4-carboxylic acid | 364.04 |

TABLE 1-continued

Example Compounds

| Ex. No. | Structure | IUPAC Name | MW (g/mol) |
|---|---|---|---|
| 91 | 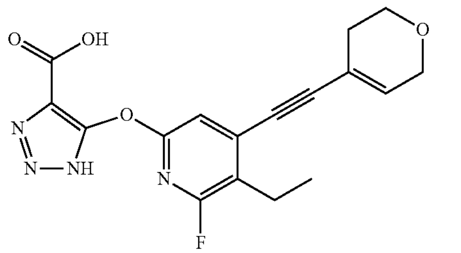 [SMILES: CCc1c(C#CC2=CCOCC2)cc(Oc2[nH]nnc2C(=O)O)nc1F] | 5-((4-((3,6-dihydro-2H-pyran-4-yl)ethynyl)-5-ethyl-6-fluoropyridin-2-yl)oxy)-1H-1,2,3-triazole-4-carboxylic acid | 358.11 |
| 92 | 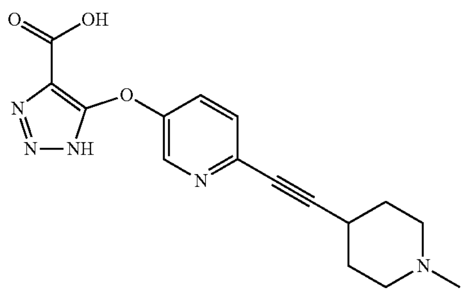 [SMILES: CN1CCC(C#Cc2ccc(Oc3[nH]nnc3C(=O)O)cn2)CC1] | 5-((6-((1-methylpiperidin-4-yl)ethynyl) pyridin-3-yl)oxy)-1H-1,2,3-triazole-4-carboxylic acid | 327.13 |
| 93 | 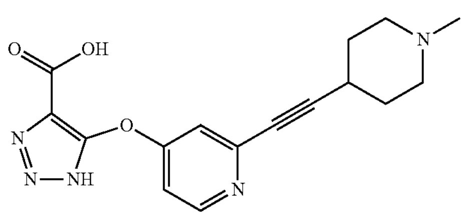 [SMILES: CN1CCC(C#Cc2cc(Oc3[nH]nnc3C(=O)O)ccn2)CC1] | 5-((2-((1-methylpiperidin-4-yl)ethynyl) pyridin-4-yl)oxy)-1H-1,2,3-triazole-4-carboxylic acid | 327.13 |
| 94 | 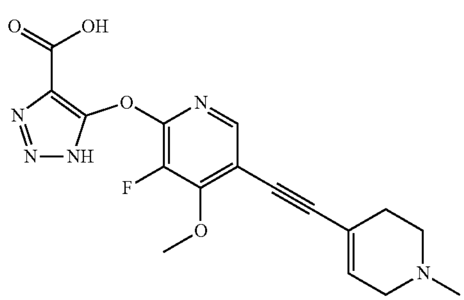 [SMILES: COc1c(C#CC2=CCN(C)CC2)cnc(Oc2[nH]nnc2C(=O)O)c1F] | 5-((3-fluoro-4-methoxy-5-((1-methyl-1,2,3,6-tetrahydropyridin-4-yl)ethynyl)pyridin-2-yl)oxy)-1H-1,2,3-triazole-4-carboxylic acid | 373.12 |
| 95 | 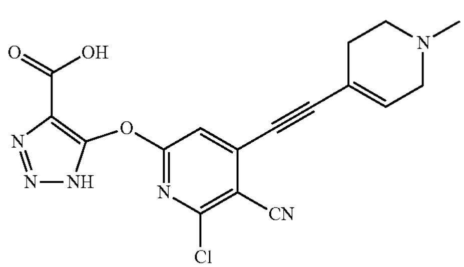 [SMILES: CN1CC=C(C#Cc2cc(Oc3[nH]nnc3C(=O)O)nc(Cl)c2C#N)CC1] | 5-((6-chloro-5-cyano-4-((1-methyl-1,2,3,6-tetrahydropyridin-4-yl)ethynyl)pyridin-2-yl)oxy)-1H-1,2,3-triazole-4-carboxylic acid | 384.07 |

TABLE 1-continued

Example Compounds

| Ex. No. | Structure | IUPAC Name | MW (g/mol) |
|---|---|---|---|
| 96 | 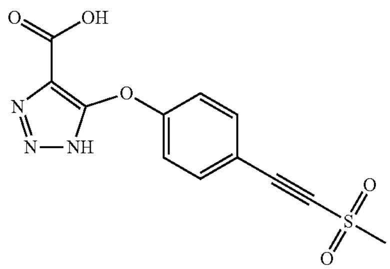 [SMILES: CS(=O)(=O)C#Cc1ccc(Oc2[nH]nnc2C(=O)O)cc1] | 5-(4-((methylsulfonyl)ethynyl)phenoxy)-1H-1,2,3-triazole-4-carboxylic acid | 307.03 |
| 97 | 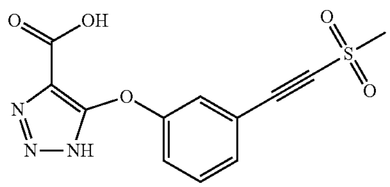 [SMILES: CS(=O)(=O)C#Cc1cccc(Oc2[nH]nnc2C(=O)O)c1] | 5-(3-((methylsulfonyl)ethynyl)phenoxy)-1H-1,2,3-triazole-4-carboxylic acid | 307.03 |
| 98 | 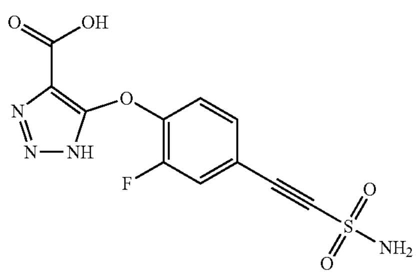 [SMILES: NS(=O)(=O)C#Cc1ccc(Oc2[nH]nnc2C(=O)O)c(F)c1] | 5-(2-fluoro-4-(sulfamoylethynyl)phenoxy)-1H-1,2,3-triazole-4-carboxylic acid | 326.01 |
| 99 | 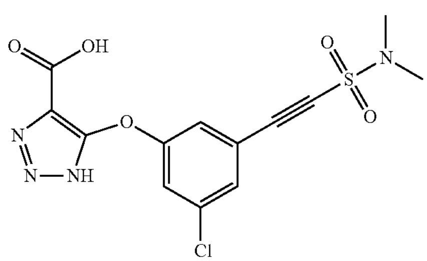 [SMILES: CN(C)S(=O)(=O)C#Cc1cc(Cl)cc(Oc2[nH]nnc2C(=O)O)c1] | 5-(3-chloro-5-((N,N-dimethylsulfamoyl)ethynyl)phenoxy)-1H-1,2,3-triazole-4-carboxylic acid | 370.01 |
| 100 | 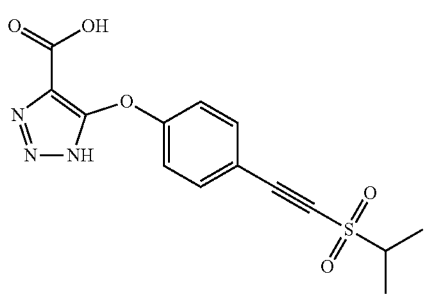 [SMILES: CC(C)S(=O)(=O)C#Cc1ccc(Oc2[nH]nnc2C(=O)O)cc1] | 5-(4-((isopropylsulfonyl)ethynyl)phenoxy)-1H-1,2,3-triazole-4-carboxylic acid | 335.06 |
| 101 | 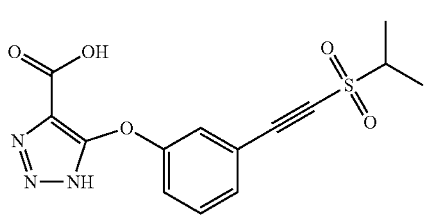 [SMILES: CC(C)S(=O)(=O)C#Cc1cccc(Oc2[nH]nnc2C(=O)O)c1] | 5-(3-((isopropylsulfonyl)ethynyl)phenoxy)-1H-1,2,3-triazole-4-carboxylic acid | 335.06 |

TABLE 1-continued

Example Compounds

| Ex. No. | Structure | IUPAC Name | MW (g/mol) |
|---|---|---|---|
| 102 | 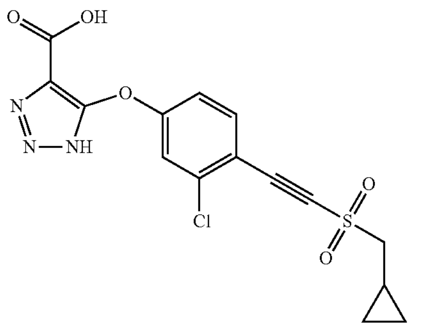 [SMILES: O=C(O)c1nn[nH]c1Oc1ccc(C#CS(=O)(=O)CC2CC2)c(Cl)c1] | 5-(3-chloro-4-(((cyclopropylmethyl)sulfonyl)ethynyl) phenoxy)-1H-1,2,3-triazole-4-carboxylic acid | 381.02 |
| 103 | 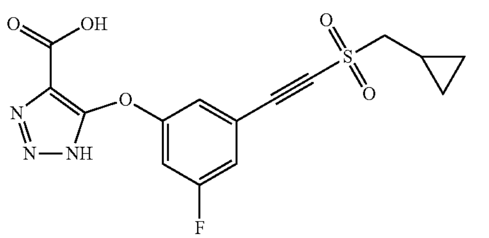 [SMILES: O=C(O)c1nn[nH]c1Oc1cc(F)cc(C#CS(=O)(=O)CC2CC2)c1] | 5-(3-(((cyclopropylmethyl)sulfonyl)ethynyl)-5-fluorophenoxy)-1H-1,2,3-triazole-4-carboxylic acid | 365.05 |
| 104 | 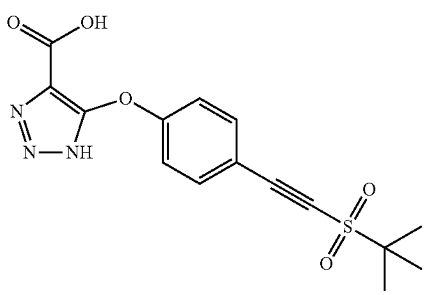 [SMILES: CC(C)(C)S(=O)(=O)C#Cc1ccc(Oc2[nH]nnc2C(=O)O)cc1] | 5-(4-((tert-butylsulfonyl)ethynyl)phenoxy)-1H-1,2,3-triazole-4-carboxylic acid | 349.07 |
| 105 | 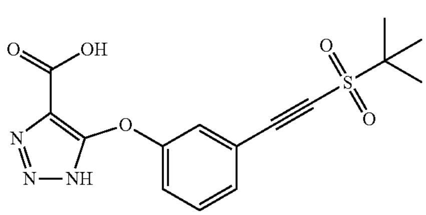 [SMILES: CC(C)(C)S(=O)(=O)C#Cc1cccc(Oc2[nH]nnc2C(=O)O)c1] | 5-(3-((tert-butylsulfonyl)ethynyl)phenoxy)-1H-1,2,3-triazole-4-carboxylic acid | 349.07 |
| 106 | 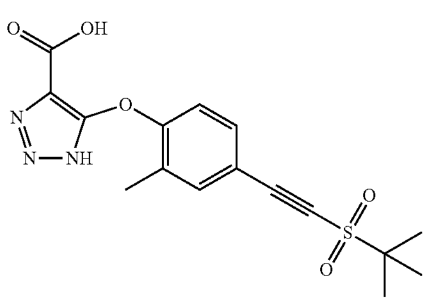 [SMILES: Cc1cc(C#CS(=O)(=O)C(C)(C)C)ccc1Oc1[nH]nnc1C(=O)O] | 5-(4-((tert-butylsulfonyl)ethynyl)-2-methylphenoxy)-1H-1,2,3-triazole-4-carboxylic acid | 363.09 |

TABLE 1-continued

Example Compounds

| Ex. No. | Structure | IUPAC Name | MW (g/mol) |
|---|---|---|---|
| 107 | 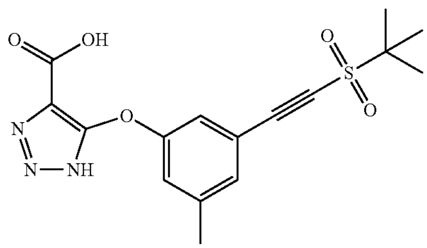 [SMILES: Cc1cc(C#CS(=O)(=O)C(C)(C)C)cc(Oc2[nH]nnc2C(=O)O)c1] | 5-(3-((tert-butylsulfonyl)ethynyl)-5-methylphenoxy)-1H-1,2,3-triazole-4-carboxylic acid | 363.09 |
| 108 | 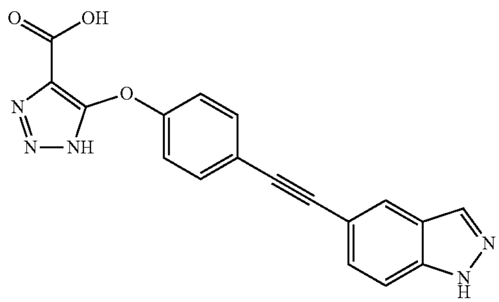 [SMILES: O=C(O)c1nn[nH]c1Oc1ccc(C#Cc2ccc3[nH]ncc3c2)cc1] | 5-(4-(()ethynyl)phenoxy)-1H-1,2,3-triazole-4-carboxylic acid | 345.31 |
| 109 | 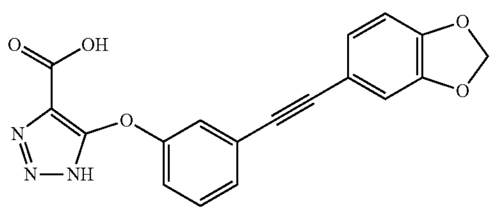 [SMILES: O=C(O)c1nn[nH]c1Oc1cccc(C#Cc2ccc3c(c2)OCO3)c1] | 5-(3-(benzo[d][1,3]dioxol-5-ylethynyl)phenoxy)-1H-1,2,3-triazole-4-carboxylic acid | 349.07 |
| 110 | 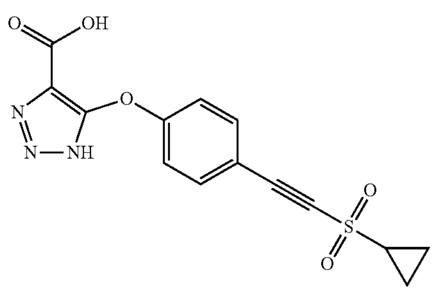 [SMILES: O=C(O)c1nn[nH]c1Oc1ccc(C#CS(=O)(=O)C2CC2)cc1] | 5-(4-((cyclopropylsulfonyl)ethynyl)phenoxy)-1H-1,2,3-triazole-4-carboxylic acid | 333.04 |
| 111 | 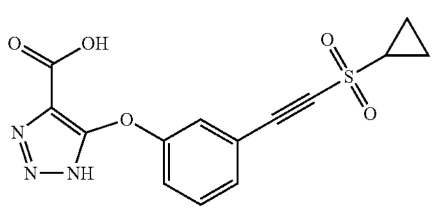 [SMILES: O=C(O)c1nn[nH]c1Oc1cccc(C#CS(=O)(=O)C2CC2)c1] | 5-(3-((cyclopropylsulfonyl)ethynyl)phenoxy)-1H-1,2,3-triazole-4-carboxylic acid | 333.04 |
| 112 | 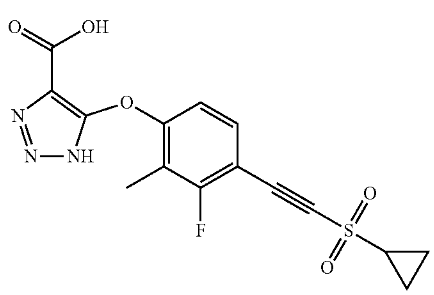 [SMILES: Cc1c(Oc2[nH]nnc2C(=O)O)ccc(C#CS(=O)(=O)C2CC2)c1F] | 5-(4-((cyclopropylsulfonyl)ethynyl)-3-fluoro-2-methylphenoxy)-1H-1,2,3-triazole-4-carboxylic acid | 365.05 |

TABLE 1-continued

Example Compounds

| Ex. No. | Structure | IUPAC Name | MW (g/mol) |
|---|---|---|---|
| 113 | 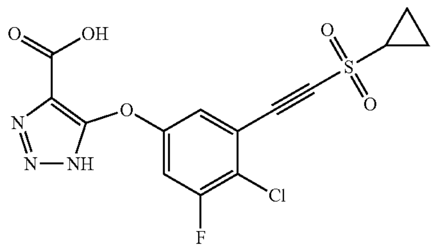 [SMILES: O=C(O)c1nn[nH]c1Oc1cc(F)c(Cl)c(C#CS(=O)(=O)C2CC2)c1] | 5-(4-chloro-3-((cyclopropylsulfonyl)ethynyl)-5-fluorophenoxy)-1H-1,2,3-triazole-4-carboxylic acid | 384.99 |
| 114 | 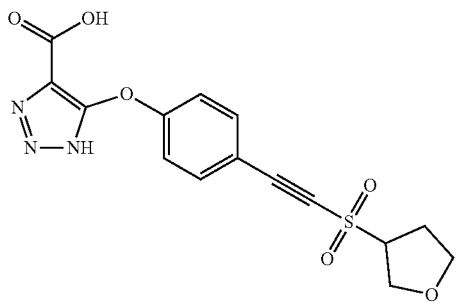 [SMILES: O=C(O)c1nn[nH]c1Oc1ccc(C#CS(=O)(=O)C2CCOC2)cc1] | 5-(4-(((tetrahydrofuran-3-yl)sulfonyl)ethynyl) phenoxy)-1H-1,2,3-triazole-4-carboxylic acid | 363.05 |
| 115 | 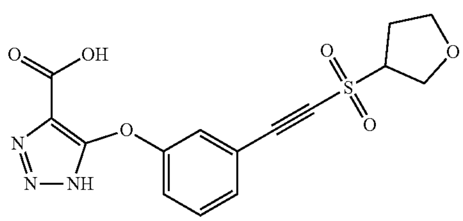 [SMILES: O=C(O)c1nn[nH]c1Oc1cccc(C#CS(=O)(=O)C2CCOC2)c1] | 5-(3-(((tetrahydrofuran-3-yl)sulfonyl)ethynyl) phenoxy)-1H-1,2,3-triazole-4-carboxylic acid | 363.05 |
| 116 | 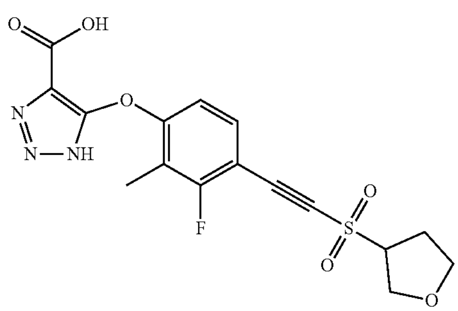 [SMILES: Cc1c(Oc2[nH]nnc2C(=O)O)ccc(C#CS(=O)(=O)C2CCOC2)c1F] | 5-(3-fluoro-2-methyl-4-(((tetrahydrofuran-3-yl)sulfonyl)ethynyl)phenoxy)-1H-1,2,3-triazole-4-carboxylic acid | 395.06 |
| 117 | 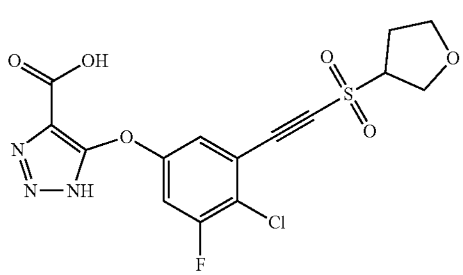 [SMILES: O=C(O)c1nn[nH]c1Oc1cc(F)c(Cl)c(C#CS(=O)(=O)C2CCOC2)c1] | 5-(4-chloro-3-fluoro-5-(((tetrahydrofuran-3-yl)sulfonyl)ethynyl)phenoxy)-1H-1,2,3-triazole-4-carboxylic acid | 415.00 |

TABLE 1-continued

Example Compounds

| Ex. No. | Structure | IUPAC Name | MW (g/mol) |
|---|---|---|---|
| 118 | 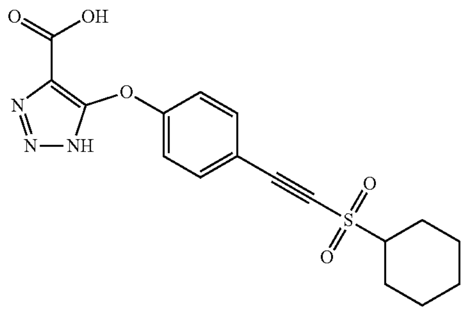 [SMILES: O=C(O)c1nn[nH]c1Oc1ccc(C#CS(=O)(=O)C2CCCCC2)cc1] | 5-(4-((cyclohexylsulfonyl)ethynyl)phenoxy)-1H-1,2,3-triazole-4-carboxylic acid | 375.09 |
| 119 | 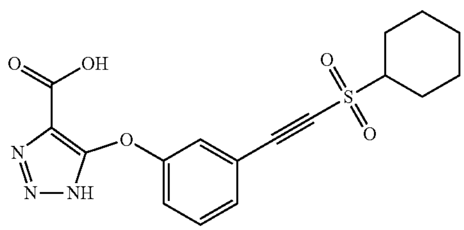 [SMILES: O=C(O)c1nn[nH]c1Oc1cccc(C#CS(=O)(=O)C2CCCCC2)c1] | 5-(3-((cyclohexylsulfonyl)ethynyl)phenoxy)-1H-1,2,3-triazole-4-carboxylic acid | 375.09 |
| 120 | 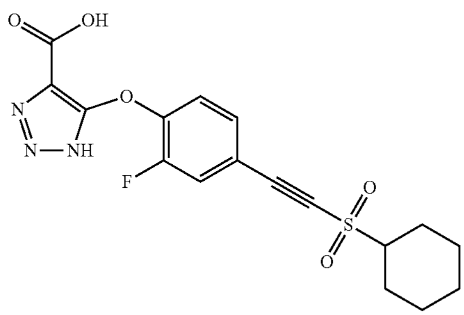 [SMILES: O=C(O)c1nn[nH]c1Oc1ccc(C#CS(=O)(=O)C2CCCCC2)cc1F] | 5-(4-((cyclohexylsulfonyl)ethynyl)-2-fluorophenoxy)-1H-1,2,3-triazole-4-carboxylic acid | 393.08 |
| 121 | 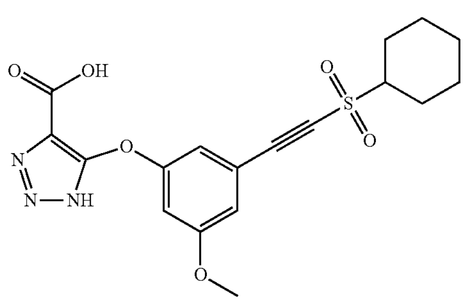 [SMILES: COc1cc(C#CS(=O)(=O)C2CCCCC2)cc(Oc2[nH]nnc2C(=O)O)c1] | 5-(3-((cyclohexylsulfonyl)ethynyl)-5-methoxyphenoxy)-1H-1,2,3-triazole-4-carboxylic acid | 405.10 |
| 122 | 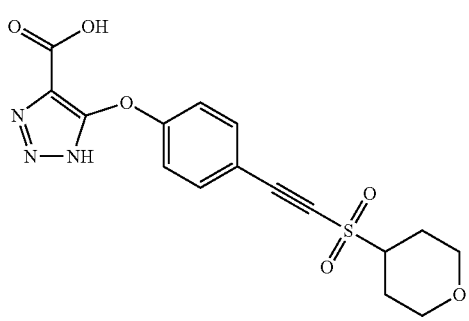 [SMILES: O=C(O)c1nn[nH]c1Oc1ccc(C#CS(=O)(=O)C2CCOCC2)cc1] | 5-(4-(((tetrahydro-2H-pyran-4-yl)sulfonyl)ethynyl)phenoxy)-1H-1,2,3-triazole-4-carboxylic acid | 377.07 |

TABLE 1-continued

Example Compounds

| Ex. No. | Structure | IUPAC Name | MW (g/mol) |
|---|---|---|---|
| 123 | 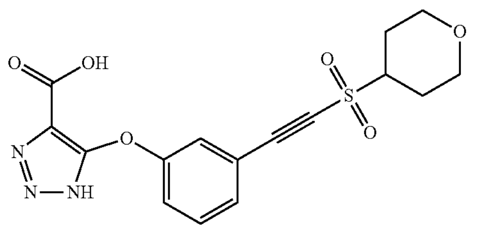 [SMILES: O=C(O)c1nn[nH]c1Oc1cccc(C#CS(=O)(=O)C2CCOCC2)c1] | 5-(3-(((tetrahydro-2H-pyran-4-yl)sulfonyl) ethynyl)phenoxy)-1H-1,2,3-triazole-4-carboxylic acid | 377.07 |
| 124 | 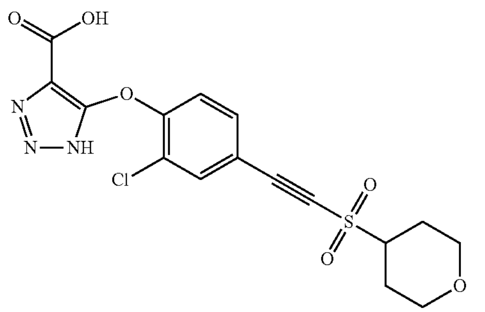 [SMILES: O=C(O)c1nn[nH]c1Oc1ccc(C#CS(=O)(=O)C2CCOCC2)cc1Cl] | 5-(2-chloro-4-(((tetrahydro-2H-pyran-4-yl)sulfonyl) ethynyl)phenoxy)-1H-1,2,3-triazole-4-carboxylic acid | 411.03 |
| 125 | 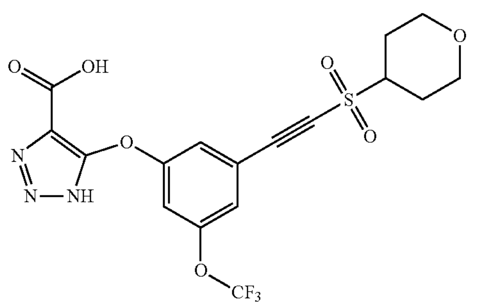 [SMILES: O=C(O)c1nn[nH]c1Oc1cc(C#CS(=O)(=O)C2CCOCC2)cc(OC(F)(F)F)c1] | 5-(3-(((tetrahydro-2H-pyran-4-yl)sulfonyl) ethynyl)-5-(trifluoro methoxy)phenoxy)-1H-1,2,3-triazole-4-carboxylic acid | 461.05 |
| 126 | 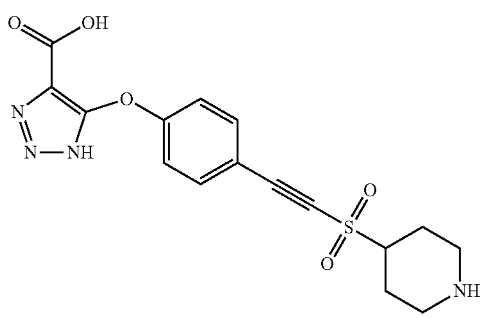 [SMILES: O=C(O)c1nn[nH]c1Oc1ccc(C#CS(=O)(=O)C2CCNCC2)cc1] | 5-(4-((piperidin-4-ylsulfonyl)ethynyl)phenoxy)-1H-1,2,3-triazole-4-carboxylic acid | 376.08 |
| 127 | 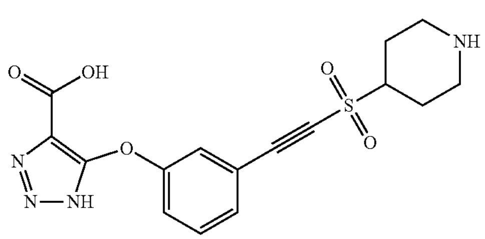 [SMILES: O=C(O)c1nn[nH]c1Oc1cccc(C#CS(=O)(=O)C2CCNCC2)c1] | 5-(3-((piperidin-4-ylsulfonyl)ethynyl) phenoxy)-1H-1,2,3-triazole-4-carboxylic acid | 376.08 |

TABLE 1-continued

Example Compounds

| Ex. No. | Structure | IUPAC Name | MW (g/mol) |
|---|---|---|---|
| 128 | 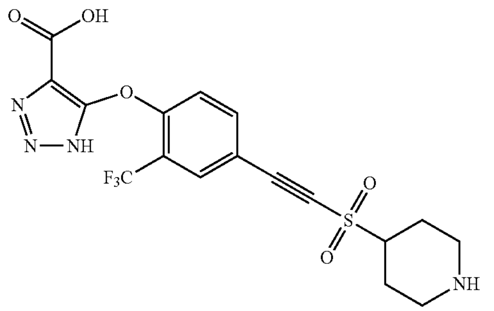 [SMILES: O=C(O)c1nn[nH]c1Oc1ccc(C#CS(=O)(=O)C2CCNCC2)cc1C(F)(F)F] | 5-(4-((piperidin-4-ylsulfonyl)ethynyl)-2-(trifluoromethyl)phenoxy)-1H-1,2,3-triazole-4-carboxylic acid | 444.07 |
| 129 | 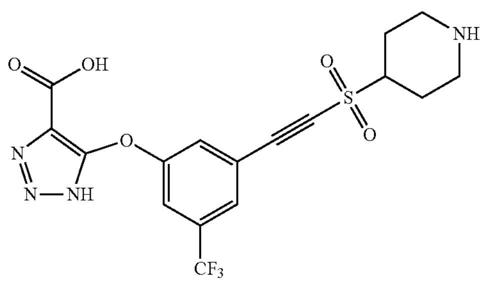 [SMILES: O=C(O)c1nn[nH]c1Oc1cc(C#CS(=O)(=O)C2CCNCC2)cc(C(F)(F)F)c1] | 5-(3-((piperidin-4-ylsulfonyl)ethynyl)-5-(trifluoromethyl)phenoxy)-1H-1,2,3-triazole-4-carboxylic acid | 444.07 |
| 130 | 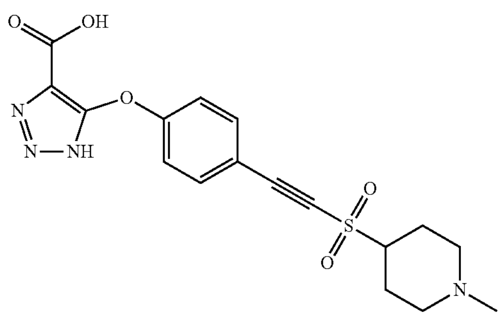 [SMILES: CN1CCC(S(=O)(=O)C#Cc2ccc(Oc3[nH]nnc3C(=O)O)cc2)CC1] | 5-(4-(((1-methylpiperidin-4-yl)sulfonyl)ethynyl)phenoxy)-1H-1,2,3-triazole-4-carboxylic acid | 390.10 |
| 131 | 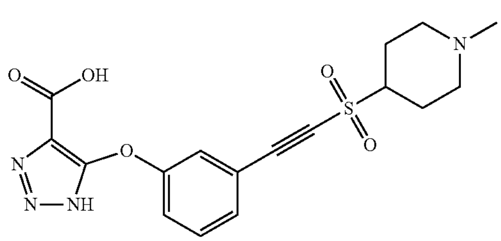 [SMILES: CN1CCC(S(=O)(=O)C#Cc2cccc(Oc3[nH]nnc3C(=O)O)c2)CC1] | 5-(3-(((1-methylpiperidin-4-yl)sulfonyl)ethynyl)phenoxy)-1H-1,2,3-triazole-4-carboxylic acid | 390.10 |
| 132 | 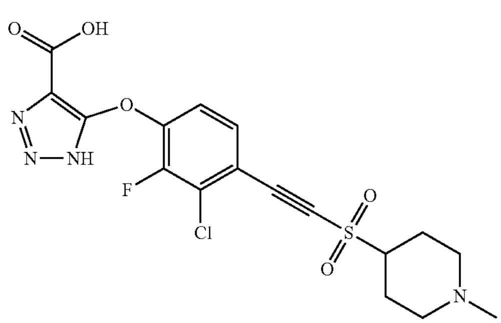 [SMILES: CN1CCC(S(=O)(=O)C#Cc2ccc(Oc3[nH]nnc3C(=O)O)c(F)c2Cl)CC1] | 5-(3-chloro-2-fluoro-4-(((1-methylpiperidin-4-yl)sulfonyl)ethynyl) phenoxy)-1H-1,2,3-triazole-4-carboxylic acid | 442.05 |

TABLE 1-continued

Example Compounds

| Ex. No. | Structure | IUPAC Name | MW (g/mol) |
|---|---|---|---|
| 133 | 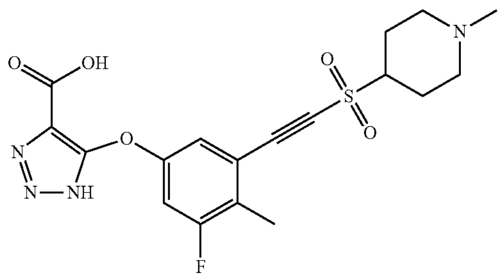 [SMILES: Cc1c(F)cc(Oc2[nH]nnc2C(=O)O)cc1C#CS(=O)(=O)C1CCN(C)CC1] | 5-(3-fluoro-4-methyl-5-(((1-methylpiperidin-4-yl)sulfonyl)ethynyl) phenoxy)-1H-1,2,3-triazole-4-carboxylic acid | 422.11 |
| 134 | 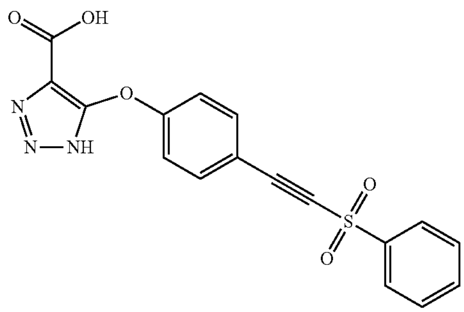 [SMILES: O=C(O)c1nn[nH]c1Oc1ccc(C#CS(=O)(=O)c2ccccc2)cc1] | 5-(4-((phenylsulfonyl) ethynyl)phenoxy)-1H-1,2,3-triazole-4-carboxylic acid | 369.04 |
| 135 | 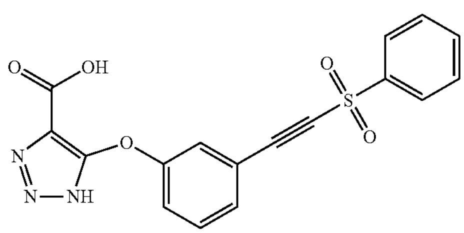 [SMILES: O=C(O)c1nn[nH]c1Oc1cccc(C#CS(=O)(=O)c2ccccc2)c1] | 5-(3-((phenylsulfonyl) ethynyl)phenoxy)-1H-1,2,3-triazole-4-carboxylic acid | 369.04 |
| 136 | 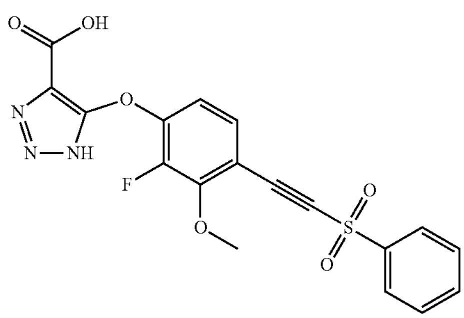 [SMILES: COc1c(C#CS(=O)(=O)c2ccccc2)ccc(Oc2[nH]nnc2C(=O)O)c1F] | 5-(2-fluoro-3-methoxy-4-((phenylsulfonyl) ethynyl)phenoxy)-1H-1,2,3-triazole-4-carboxylic acid | 417.04 |
| 137 | 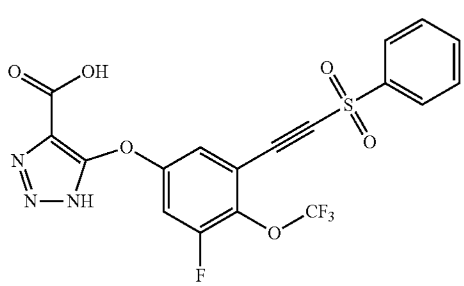 [SMILES: O=C(O)c1nn[nH]c1Oc1cc(F)c(OC(F)(F)F)c(C#CS(=O)(=O)c2ccccc2)c1] | 5-(3-fluoro-5-((phenylsulfonyl) ethynyl)-4-(trifluoro methoxy) phenoxy)-1H-1,2,3-triazole-4-carboxylic acid | 471.01 |

TABLE 1-continued

Example Compounds

| Ex. No. | Structure | IUPAC Name | MW (g/mol) |
|---|---|---|---|
| 138 | 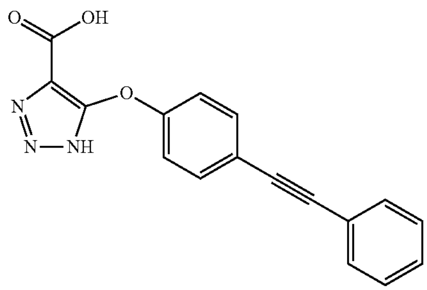 [SMILES: O=C(O)c1nn[nH]c1Oc1ccc(C#Cc2ccccc2)cc1] | 5-(4-(phenyl ethynyl)phenoxy)-1H-1,2,3-triazole-4-carboxylic acid | 305.29 |
| 139 | 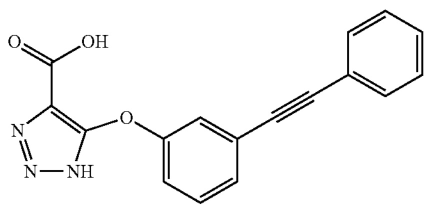 [SMILES: O=C(O)c1nn[nH]c1Oc1cccc(C#Cc2ccccc2)c1] | 5-(3-(phenylethynyl) phenoxy)-1H-1,2,3-triazole-4-carboxylic acid | 305.29 |
| 140 | 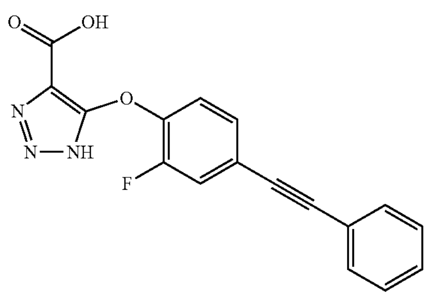 [SMILES: O=C(O)c1nn[nH]c1Oc1ccc(C#Cc2ccccc2)cc1F] | 5-(2-fluoro-4-(phenylethynyl) phenoxy)-1H-1,2,3-triazole-4-carboxylic acid | 323.07 |
| 141 | 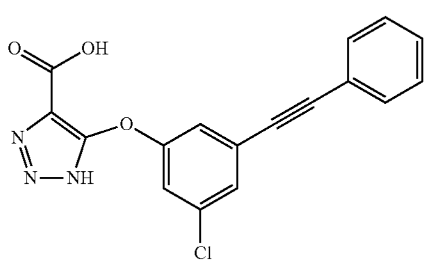 [SMILES: O=C(O)c1nn[nH]c1Oc1cc(Cl)cc(C#Cc2ccccc2)c1] | 5-(3-chloro-5-(phenylethynyl)phenoxy)-1H-1,2,3-triazole-4-carboxylic acid | 339.04 |
| 142 | 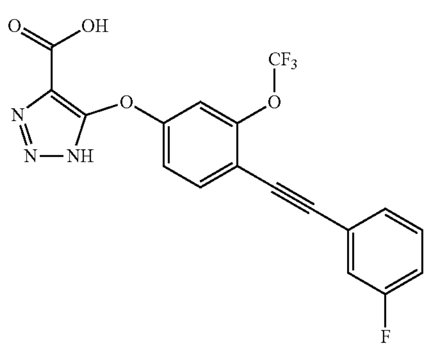 [SMILES: O=C(O)c1nn[nH]c1Oc1ccc(C#Cc2cccc(F)c2)c(OC(F)(F)F)c1] | 5-(4-((3-fluorophenyl)ethynyl)-3-(trifluoromethoxy) phenoxy)-1H-1,2,3-triazole-4-carboxylic acid | 407.05 |

TABLE 1-continued

Example Compounds

| Ex. No. | Structure | IUPAC Name | MW (g/mol) |
|---|---|---|---|
| 143 | 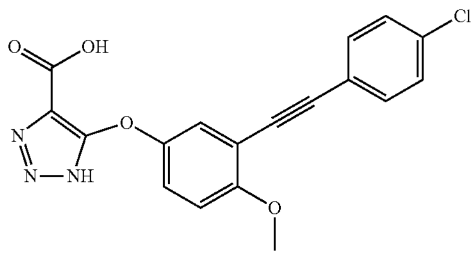 [SMILES: COc1ccc(Oc2[nH]nnc2C(=O)O)cc1C#Cc1ccc(Cl)cc1] | 5-(3-((4-chlorophenyl)ethynyl)-4-methoxyphenoxy)-1H-1,2,3-triazole-4-carboxylic acid | 369.05 |
| 144 | 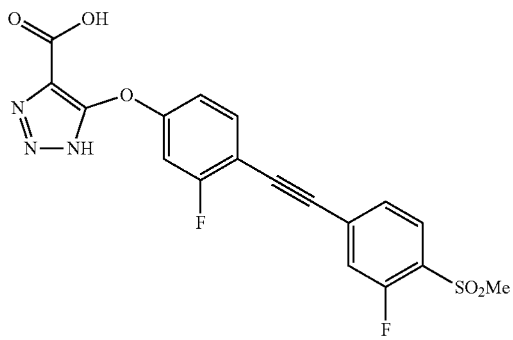 [SMILES: CS(=O)(=O)c1ccc(C#Cc2ccc(Oc3[nH]nnc3C(=O)O)cc2F)cc1F] | 5-(3-fluoro-4-((3-fluoro-4-(methyl sulfonyl)phenyl)ethynyl)phenoxy)-1H-1,2,3-triazole-4-carboxylic acid | 419.04 |
| 145 | 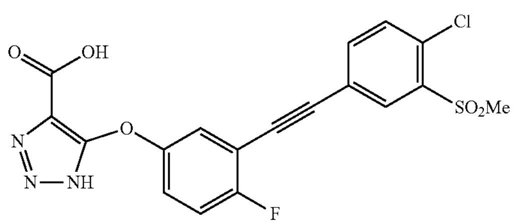 [SMILES: CS(=O)(=O)c1cc(C#Cc2cc(Oc3[nH]nnc3C(=O)O)ccc2F)ccc1Cl] | 5-(3-((4-chloro-3-(methylsulfonyl)phenyl)ethynyl)-4-fluorophenoxy)-1H-1,2,3-triazole-4-carboxylic acid | 435.01 |
| 146 | 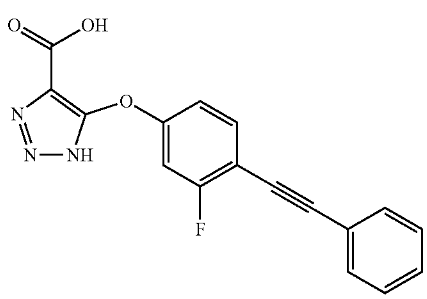 [SMILES: O=C(O)c1nn[nH]c1Oc1ccc(C#Cc2ccccc2)c(F)c1] | 5-(3-fluoro-4-(phenylethynyl)phenoxy)-1H-1,2,3-triazole-4-carboxylic acid | 323.28 |
| 147 | 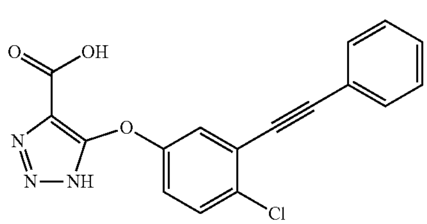 [SMILES: O=C(O)c1nn[nH]c1Oc1ccc(Cl)c(C#Cc2ccccc2)c1] | 5-(4-chloro-3-(phenylethynyl)phenoxy)-1H-1,2,3-triazole-4-carboxylic acid | 339.73 |

TABLE 1-continued

Example Compounds

| Ex. No. | Structure | IUPAC Name | MW (g/mol) |
|---|---|---|---|
| 148 | 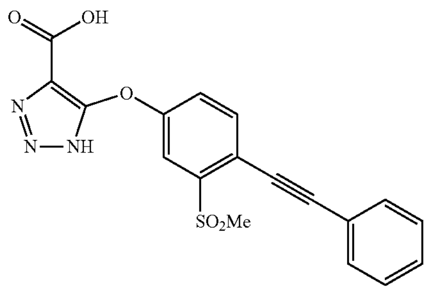 [SMILES: CS(=O)(=O)c1cc(Oc2[nH]nnc2C(=O)O)ccc1C#Cc1ccccc1] | 5-(3-(methylsulfonyl)-4-(phenylethynyl) phenoxy)-1H-1,2,3-triazole-4-carboxylic acid | 383.06 |
| 149 | 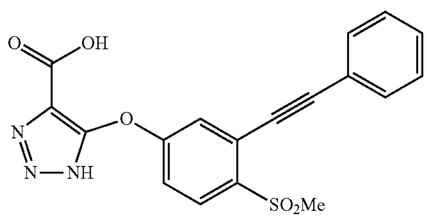 [SMILES: CS(=O)(=O)c1ccc(Oc2[nH]nnc2C(=O)O)cc1C#Cc1ccccc1] | 5-(4-(methylsulfonyl)-3-(phenylethynyl) phenoxy)-1H-1,2,3-triazole-4-carboxylic acid | 383.38 |
| 150 | 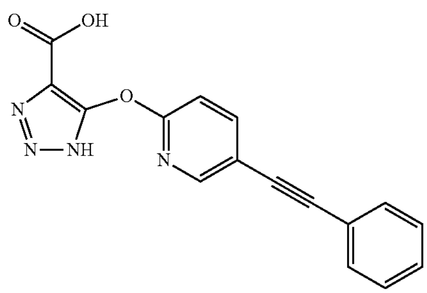 [SMILES: O=C(O)c1nn[nH]c1Oc1ccc(C#Cc2ccccc2)cn1] | 5-((5-(phenylethynyl)pyridin-2-yl)oxy)-1H-1,2,3-triazole-4-carboxylic acid | 306.08 |
| 151 | 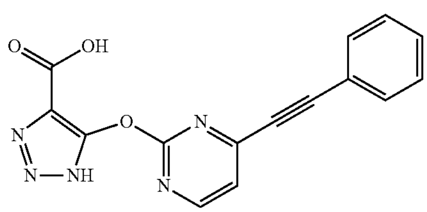 [SMILES: O=C(O)c1nn[nH]c1Oc1nccc(C#Cc2ccccc2)n1] | 5-((4-(phenylethynyl) pyrimidin-2-yl)oxy)-1H-1,2,3-triazole-4-carboxylic acid | 307.07 |
| 152 | 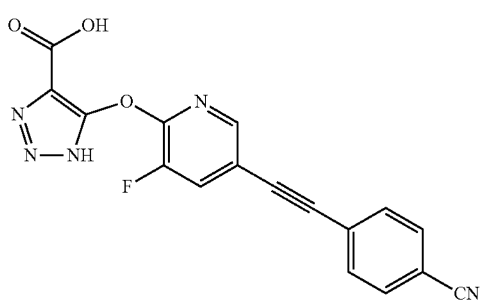 [SMILES: N#Cc1ccc(C#Cc2cnc(Oc3[nH]nnc3C(=O)O)c(F)c2)cc1] | 5-((5-((4-cyanophenyl)ethynyl)-3-fluoropyridin-2-yl)oxy)-1H-1,2,3-triazole-4-carboxylic acid | 349.06 |
| 153 | 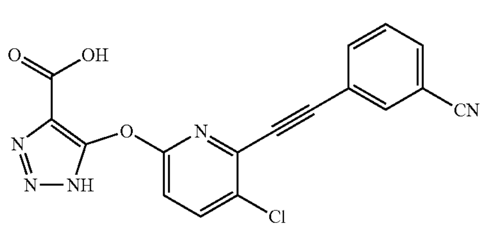 [SMILES: N#Cc1cccc(C#Cc2nc(Oc3[nH]nnc3C(=O)O)ccc2Cl)c1] | 5-((5-chloro-6-((3-cyanophenyl)ethynyl)pyridin-2-yl)oxy)-1H-1,2,3-triazole-4-carboxylic acid | 365.03 |

TABLE 1-continued

Example Compounds

| Ex. No. | Structure | IUPAC Name | MW (g/mol) |
|---|---|---|---|
| 154 | 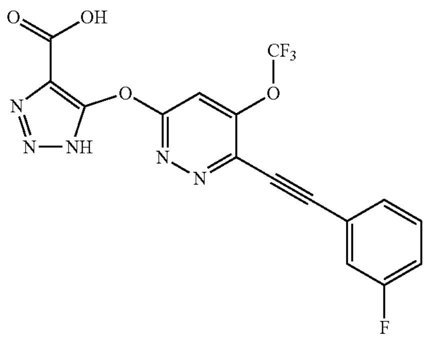 [SMILES: O=C(O)c1nn[nH]c1Oc1cc(OC(F)(F)F)c(C#Cc2cccc(F)c2)nn1] | 5-((6-((3-fluorophenyl)ethynyl)-5-(trifluoromethoxy) pyridazin-3-yl)oxy)-1H-1,2,3-triazole-4-carboxylic acid | 409.04 |
| 155 | 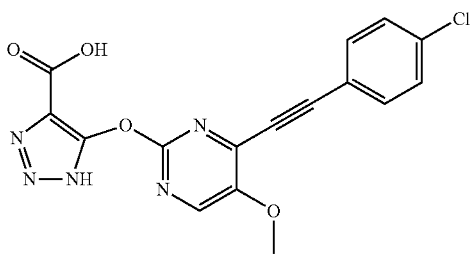 [SMILES: COc1cnc(Oc2[nH]nnc2C(=O)O)nc1C#Cc1ccc(Cl)cc1] | 5-((4-((4-chlorophenyl)ethynyl)-5-methoxypyrimidin-2-yl)oxy)-1H-1,2,3-triazole-4-carboxylic acid | 371.04 |
| 156 | 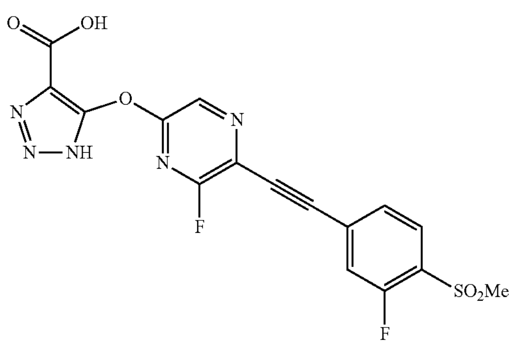 [SMILES: CS(=O)(=O)c1ccc(C#Cc2ncc(Oc3[nH]nnc3C(=O)O)nc2F)cc1F] | 5-((6-fluoro-5-((3-fluoro-4-(methylsulfonyl)phenyl)ethynyl) pyrazin-2-yl)oxy)-1H-1,2,3-triazole-4-carboxylic acid | 421.03 |
| 157 | 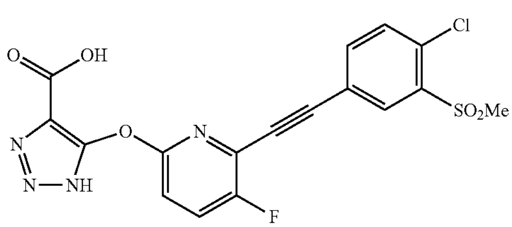 [SMILES: CS(=O)(=O)c1cc(C#Cc2nc(Oc3[nH]nnc3C(=O)O)ccc2F)ccc1Cl] | 5-((6-((4-chloro-3-(methylsulfonyl)phenyl)ethynyl)-5-fluoropyridin-2-yl)oxy)-1H-1,2,3-triazole-4-carboxylic acid | 436.00 |
| 158 | 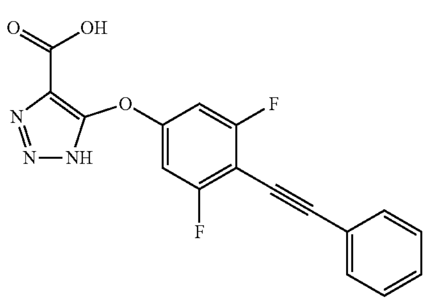 [SMILES: O=C(O)c1nn[nH]c1Oc1cc(F)c(C#Cc2ccccc2)c(F)c1] | 5-(3,5-difluoro-4-(phenylethynyl)phenoxy)-1H-1,2,3-triazole-4-carboxylic acid | 341.06 |

TABLE 1-continued

Example Compounds

| Ex. No. | Structure | IUPAC Name | MW (g/mol) |
|---|---|---|---|
| 159 | 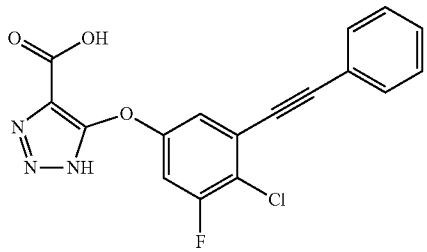 [SMILES: O=C(O)c1nn[nH]c1Oc1cc(F)c(Cl)c(C#Cc2ccccc2)c1] | 5-(4-chloro-3-fluoro-5-(phenylethynyl) phenoxy)-1H-1,2,3-triazole-4-carboxylic acid | 357.03 |
| 160 | 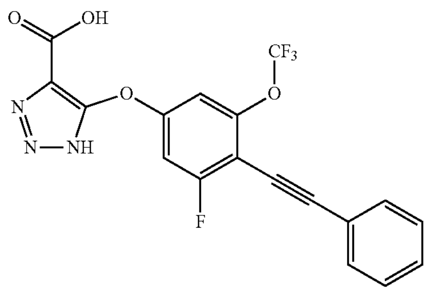 [SMILES: O=C(O)c1nn[nH]c1Oc1cc(F)c(C#Cc2ccccc2)c(OC(F)(F)F)c1] | 5-(3-fluoro-4-(phenylethynyl)-5-(trifluoromethoxy)phenoxy)-1H-1,2,3-triazole-4-carboxylic acid | 407.05 |
| 161 | 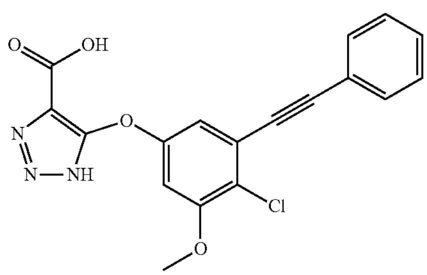 [SMILES: COc1cc(Oc2[nH]nnc2C(=O)O)cc(C#Cc2ccccc2)c1Cl] | 5-(4-chloro-3-methoxy-5-(phenylethynyl)phenoxy)-1H-1,2,3-triazole-4-carboxylic acid | 369.05 |
| 162 | 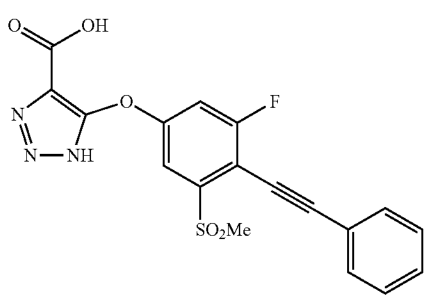 [SMILES: CS(=O)(=O)c1cc(Oc2[nH]nnc2C(=O)O)cc(F)c1C#Cc1ccccc1] | 5-(3-fluoro-5-(methylsulfonyl)-4-(phenylethynyl) phenoxy)-1H-1,2,3-triazole-4-carboxylic acid | 401.05 |
| 163 | 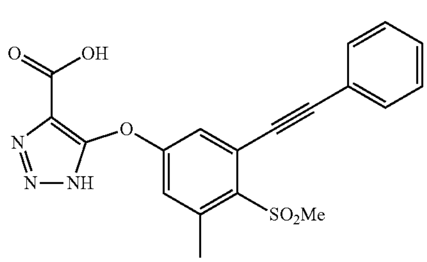 [SMILES: Cc1cc(Oc2[nH]nnc2C(=O)O)cc(C#Cc2ccccc2)c1S(C)(=O)=O] | 5-(3-methyl-4-(methylsulfonyl)-5-(phenylethynyl)phenoxy)-1H-1,2,3-triazole-4-carboxylic acid | 397.07 |

TABLE 1-continued

Example Compounds

| Ex. No. | Structure | IUPAC Name | MW (g/mol) |
|---|---|---|---|
| 164 | 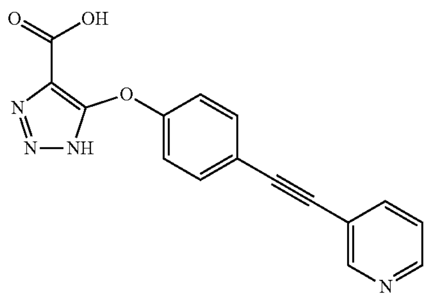 [SMILES: O=C(O)c1nn[nH]c1Oc1ccc(C#Cc2cccnc2)cc1] | 5-(4-(pyridin-3-ylethynyl)phenoxy)-1H-1,2,3-triazole-4-carboxylic acid | 306.08 |
| 165 | 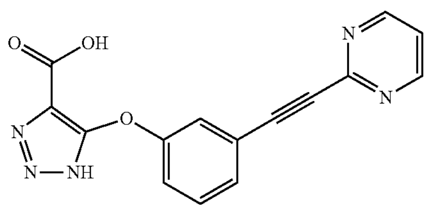 [SMILES: O=C(O)c1nn[nH]c1Oc1cccc(C#Cc2ncccn2)c1] | 5-(3-(pyrimidin-2-ylethynyl)phenoxy)-1H-1,2,3-triazole-4-carboxylic acid | 307.26 |
| 166 | 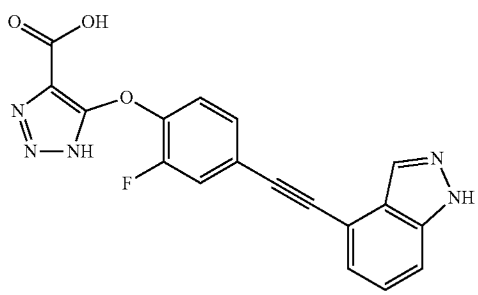 [SMILES: O=C(O)c1nn[nH]c1Oc1ccc(C#Cc2cccc3[nH]ncc23)cc1F] | 5-(4-((1H-indazol-4-yl)ethynyl)-2-fluorophenoxy)-1H-1,2,3-triazole-4-carboxylic acid | 363.08 |
| 167 | 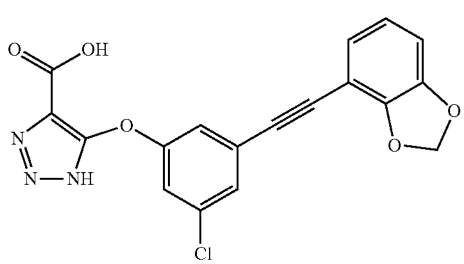 [SMILES: O=C(O)c1nn[nH]c1Oc1cc(Cl)cc(C#Cc2cccc3c2OCO3)c1] | 5-(3-(benzo[d][1,3]dioxol-4-ylethynyl)-5-chlorophenoxy)-1H-1,2,3-triazole-4-carboxylic acid | 383.03 |
| 168 | 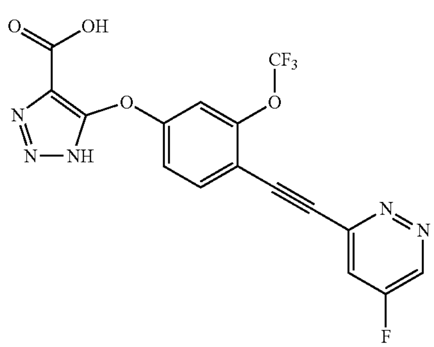 [SMILES: O=C(O)c1nn[nH]c1Oc1ccc(C#Cc2cc(F)cnn2)c(OC(F)(F)F)c1] | 5-(4-((5-fluoropyridazin-3-yl)ethynyl)-3-(trifluoromethoxy)phenoxy)-1H-1,2,3-triazole-4-carboxylic acid | 409.04 |

TABLE 1-continued

Example Compounds

| Ex. No. | Structure | IUPAC Name | MW (g/mol) |
|---|---|---|---|
| 169 | 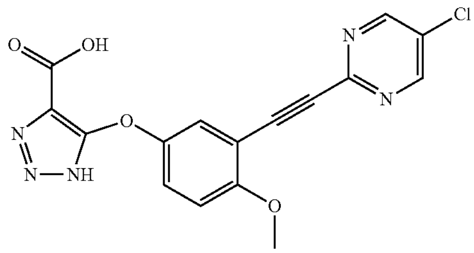 [SMILES: COc1ccc(Oc2[nH]nnc2C(=O)O)cc1C#Cc1ncc(Cl)cn1] | 5-(3-((5-chloropyrimidin-2-yl)ethynyl)-4-methoxyphenoxy)-1H-1,2,3-triazole-4-carboxylic acid | 371.04 |
| 170 | 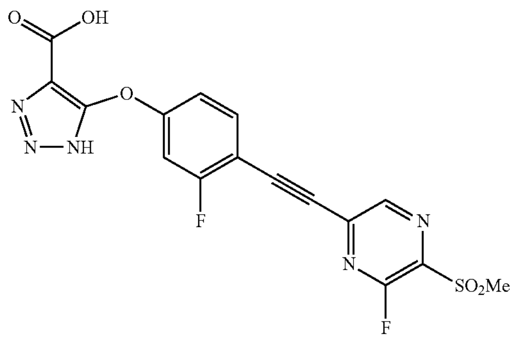 [SMILES: CS(=O)(=O)c1ncc(C#Cc2ccc(Oc3[nH]nnc3C(=O)O)cc2F)nc1F] | 5-(3-fluoro-4-((6-fluoro-5-(methylsulfonyl) pyrazin-2-yl)ethynyl) phenoxy)-1H-1,2,3-triazole-4-carboxylic acid | 421.03 |
| 171 | 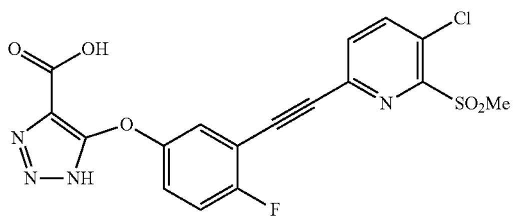 [SMILES: CS(=O)(=O)c1nc(C#Cc2cc(Oc3[nH]nnc3C(=O)O)ccc2F)ccc1Cl] | 5-(3-((5-chloro-6-(methylsulfonyl)pyridin-2-yl)ethynyl)-4-fluorophenoxy)-1H-1,2,3-triazole-4-carboxylic acid | 436.00 |
| 172 | 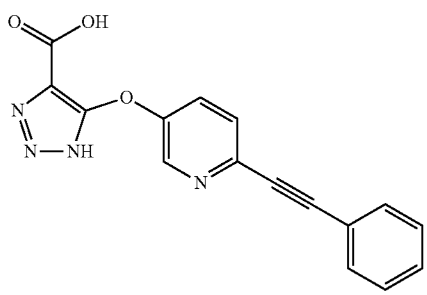 [SMILES: O=C(O)c1nn[nH]c1Oc1ccc(C#Cc2ccccc2)nc1] | 5-((6-(phenylethynyl) pyridin-3-yl)oxy)-1H-1,2,3-triazole-4-carboxylic acid | 306.08 |
| 173 | 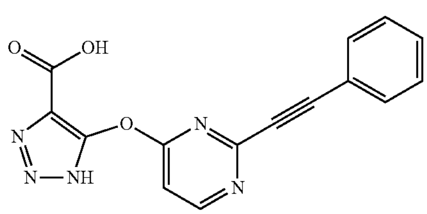 [SMILES: O=C(O)c1nn[nH]c1Oc1ccnc(C#Cc2ccccc2)n1] | 5-((2-(phenylethynyl) pyrimidin-4-yl)oxy)-1H-1,2,3-triazole-4-carboxylic acid | 307.07 |

TABLE 1-continued

Example Compounds

| Ex. No. | Structure | IUPAC Name | MW (g/mol) |
|---|---|---|---|
| 174 | 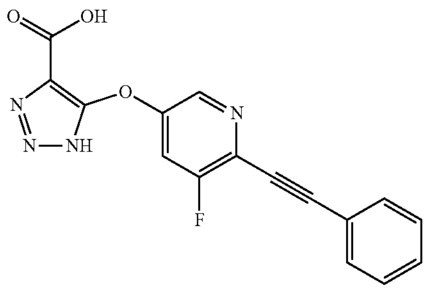 [SMILES: O=C(O)c1nn[nH]c1Oc1cnc(C#Cc2ccccc2)c(F)c1] | 5-((5-fluoro-6-(phenylethynyl)pyridin-3-yl)oxy)-1H-1,2,3-triazole-4-carboxylic acid | 324.07 |
| 175 | 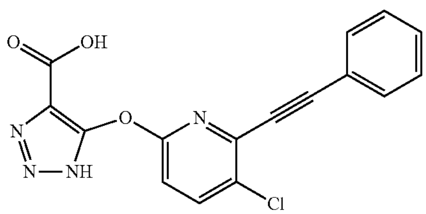 | 5-((5-chloro-6-(phenylethynyl)pyridin-2-yl)oxy)-1H-1,2,3-triazole-4-carboxylic acid | 340.04 |
| 176 | 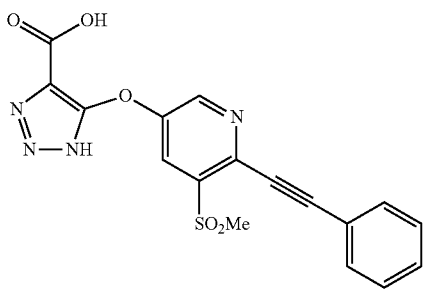 [SMILES: CS(=O)(=O)c1cc(Oc2[nH]nnc2C(=O)O)cnc1C#Cc1ccccc1] | 5-((5-(methylsulfonyl)-6-(phenylethynyl) pyridin-3-yl)oxy)-1H-1,2,3-triazole-4-carboxylic acid | 384.05 |
| 177 | 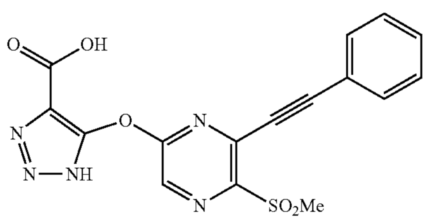 [SMILES: CS(=O)(=O)c1ncc(Oc2[nH]nnc2C(=O)O)nc1C#Cc1ccccc1] | 5-((5-(methylsulfonyl)-6-(phenylethynyl)pyrazin-2-yl)oxy)-1H-1,2,3-triazole-4-carboxylic acid | 385.05 |
| 178 | 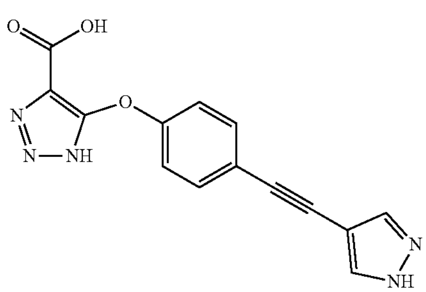 [SMILES: O=C(O)c1nn[nH]c1Oc1ccc(C#Cc2cn[nH]c2)cc1] | 5-(4-((1H-pyrazol-4-yl)ethynyl)phenoxy)-1H-1,2,3-triazole-4-carboxylic acid | 295.25 |
| 179 | 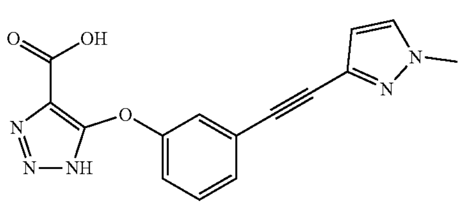 [SMILES: Cn1ccc(C#Cc2cccc(Oc3[nH]nnc3C(=O)O)c2)n1] | 5-(3-((1-methyl-1H-pyrazol-3-yl)ethynyl)phenoxy)-1H-1,2,3-triazole-4-carboxylic acid | 309.09 |

TABLE 1-continued

Example Compounds

| Ex. No. | Structure | IUPAC Name | MW (g/mol) |
|---|---|---|---|
| 180 | 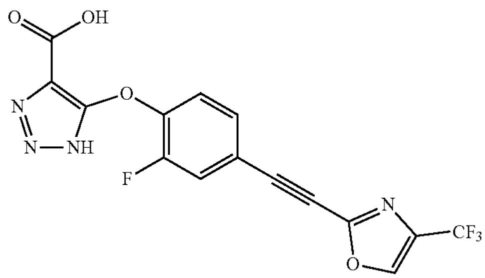 [SMILES: O=C(O)c1nn[nH]c1Oc1ccc(C#Cc2nc(C(F)(F)F)co2)cc1F] | 5-(2-fluoro-4-((4-(trifluoromethyl)oxazol-2-yl)ethynyl)phenoxy)-1H-1,2,3-triazole-4-carboxylic acid | 382.03 |
| 181 | 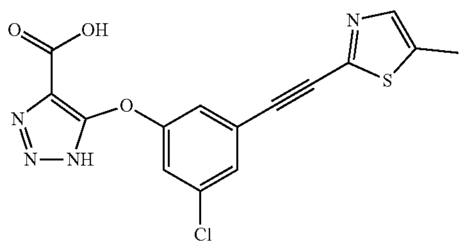 [SMILES: Cc1cnc(C#Cc2cc(Cl)cc(Oc3[nH]nnc3C(=O)O)c2)s1] | 5-(3-chloro-5-((5-methylthiazol-2-yl)ethynyl)phenoxy)-1H-1,2,3-triazole-4-carboxylic acid | 360.01 |
| 182 | 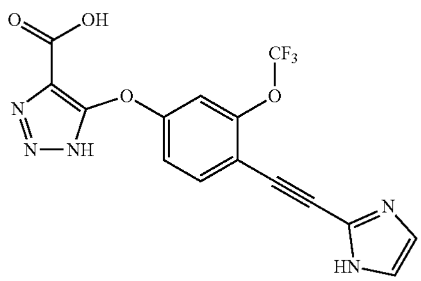 [SMILES: O=C(O)c1nn[nH]c1Oc1ccc(C#Cc2ncc[nH]2)c(OC(F)(F)F)c1] | 5-(4-((1H-imidazol-2-yl)ethynyl)-3-(trifluoromethoxy)phenoxy)-1H-1,2,3-triazole-4-carboxylic acid | 379.05 |
| 183 | 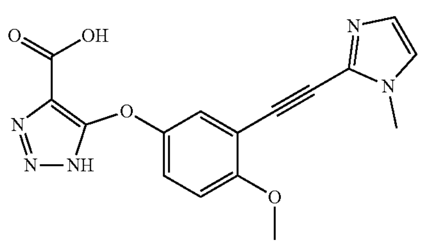 [SMILES: COc1ccc(Oc2[nH]nnc2C(=O)O)cc1C#Cc1nccn1C] | 5-(4-methoxy-3-((1-methyl-1H-imidazol-2-yl)ethynyl)phenoxy)-1H-1,2,3-triazole-4-carboxylic acid | 339.10 |
| 184 | 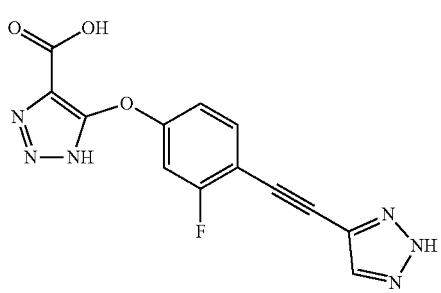 [SMILES: O=C(O)c1nn[nH]c1Oc1ccc(C#Cc2cn[nH]n2)c(F)c1] | 5-(4-((2H-1,2,3-triazol-4-yl)ethynyl)-3-fluorophenoxy)-1H-1,2,3-triazole-4-carboxylic acid | 314.06 |
| 185 | 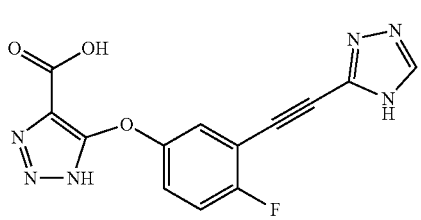 [SMILES: O=C(O)c1nn[nH]c1Oc1ccc(F)c(C#Cc2nnc[nH]2)c1] | 5-(3-((4H-1,2,4-triazol-3-yl)ethynyl)-4-fluorophenoxy)-1H-1,2,3-triazole-4-carboxylic acid | 314.06 |

TABLE 1-continued

Example Compounds

| Ex. No. | Structure | IUPAC Name | MW (g/mol) |
|---|---|---|---|
| 186 | 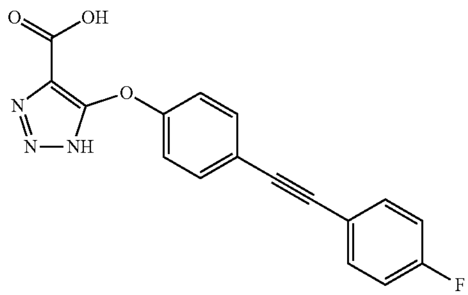 [SMILES: O=C(O)c1nn[nH]c1Oc1ccc(C#Cc2ccc(F)cc2)cc1] | 5-(4-((4-fluorophenyl)ethynyl)phenoxy)-1H-1,2,3-triazole-4-carboxylic acid | 323.07 |
| 187 | 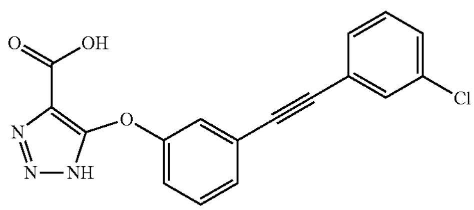 [SMILES: O=C(O)c1nn[nH]c1Oc1cccc(C#Cc2cccc(Cl)c2)c1] | 5-(3-((3-chlorophenyl)ethynyl)phenoxy)-1H-1,2,3-triazole-4-carboxylic acid | 339.73 |
| 188 | 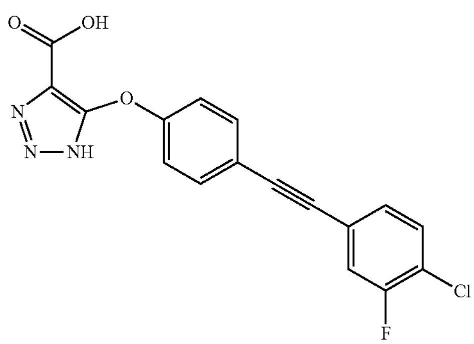 [SMILES: O=C(O)c1nn[nH]c1Oc1ccc(C#Cc2ccc(Cl)c(F)c2)cc1] | 5-(4-((4-chloro-3-fluorophenyl)ethynyl)phenoxy)-1H-1,2,3-triazole-4-carboxylic acid | 357.03 |
| 189 | 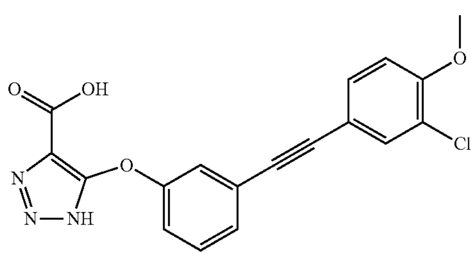 [SMILES: COc1ccc(C#Cc2cccc(Oc3[nH]nnc3C(=O)O)c2)cc1Cl] | 5-(3-((3-chloro-4-methoxyphenyl)ethynyl)phenoxy)-1H-1,2,3-triazole-4-carboxylic acid | 369.05 |
| 190 | 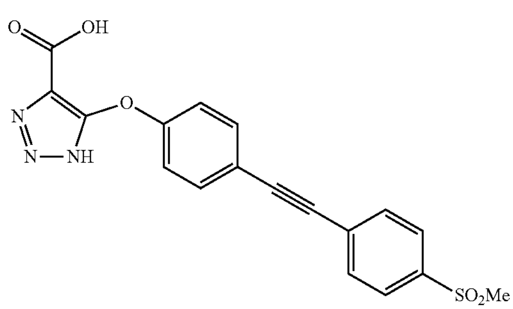 [SMILES: CS(=O)(=O)c1ccc(C#Cc2ccc(Oc3[nH]nnc3C(=O)O)cc2)cc1] | 5-(4-((4-(methylsulfonyl)phenyl)ethynyl)phenoxy)-1H-1,2,3-triazole-4-carboxylic acid | 383.38 |

TABLE 1-continued

Example Compounds

| Ex. No. | Structure | IUPAC Name | MW (g/mol) |
|---|---|---|---|
| 191 | 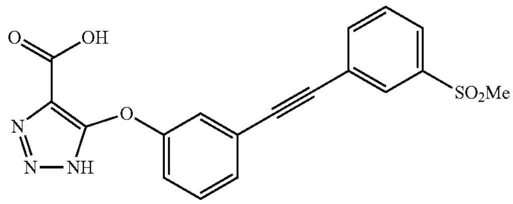 [SMILES: CS(=O)(=O)c1cccc(C#Cc2cccc(Oc3[nH]nnc3C(=O)O)c2)c1] | 5-(3-((3-(methylsulfonyl)phenyl)ethynyl)phenoxy)-1H-1,2,3-triazole-4-carboxylic acid | 383.38 |
| 192 | 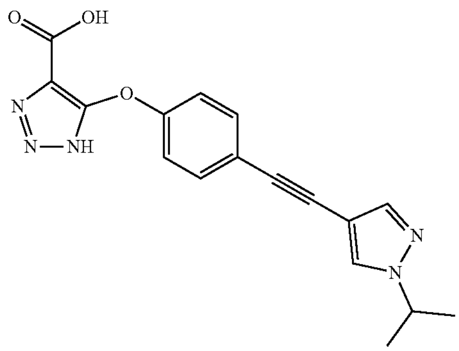 [SMILES: CC(C)n1cc(C#Cc2ccc(Oc3[nH]nnc3C(=O)O)cc2)cn1] | 5-(4-((1-isopropyl-1H-pyrazol-4-yl)ethynyl)phenoxy)-1H-1,2,3-triazole-4-carboxylic acid | 337.12 |
| 193 | 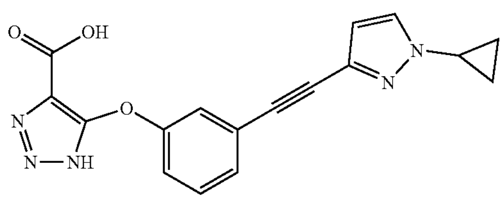 [SMILES: O=C(O)c1nn[nH]c1Oc1cccc(C#Cc2ccn(C3CC3)n2)c1] | 5-(3-((1-cyclopropyl-1H-pyrazol-3-yl)ethynyl)phenoxy)-1H-1,2,3-triazole-4-carboxylic acid | 335.10 |
| 194 | 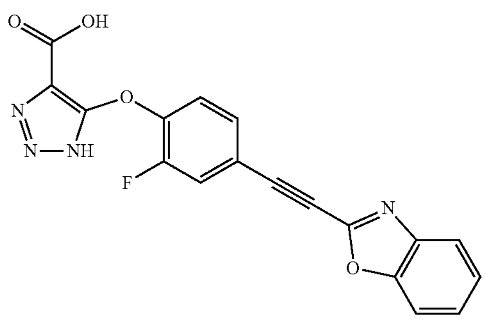 [SMILES: O=C(O)c1nn[nH]c1Oc1ccc(C#Cc2nc3ccccc3o2)cc1F] | 5-(4-(benzo[d]oxazol-2-ylethynyl)-2-fluorophenoxy)-1H-1,2,3-triazole-4-carboxylic acid | 335.10 |
| 195 | 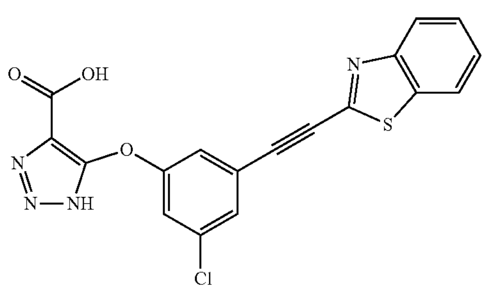 [SMILES: O=C(O)c1nn[nH]c1Oc1cc(Cl)cc(C#Cc2nc3ccccc3s2)c1] | 5-(3-(benzo[d]thiazol-2-ylethynyl)-5-chlorophenoxy)-1H-1,2,3-triazole-4-carboxylic acid | 396.01 |

TABLE 1-continued

Example Compounds

| Ex. No. | Structure | IUPAC Name | MW (g/mol) |
|---|---|---|---|
| 196 | 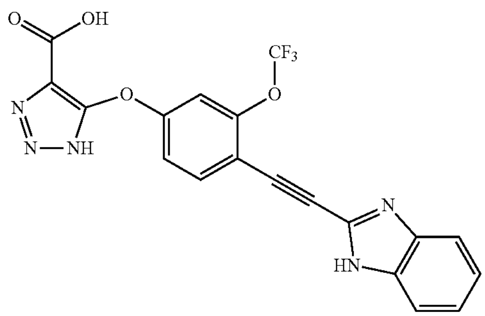 [SMILES: O=C(O)c1nn[nH]c1Oc1ccc(C#Cc2nc3ccccc3[nH]2)c(OC(F)(F)F)c1] | 5-(4-((1H-benzo[d]imidazol-2-yl)ethynyl)-3-(trifluoromethoxy)phenoxy)-1H-1,2,3-triazole-4-carboxylic acid | 429.07 |
| 197 | 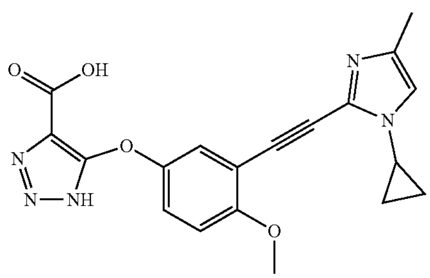 [SMILES: COc1ccc(Oc2[nH]nnc2C(=O)O)cc1C#Cc1nc(C)cn1C1CC1] | 5-(3-((1-cyclopropyl-4-methyl-1H-imidazol-2-yl) ethynyl)-4-methoxy phenoxy)-1H-1,2,3-triazole-4-carboxylic acid | 379.13 |
| 198 | 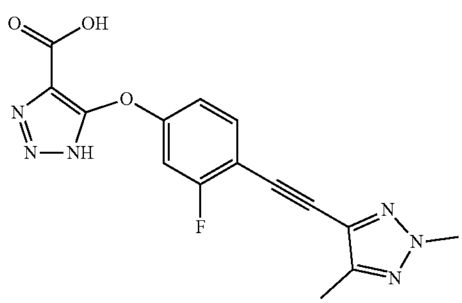 [SMILES: Cc1nn(C)nc1C#Cc1ccc(Oc2[nH]nnc2C(=O)O)cc1F] | 5-(4-((2,5-dimethyl-2H-1,2,3-triazol-4-yl)ethynyl)-3-fluorophenoxy)-1H-1,2,3-triazole-4-carboxylic acid | 342.09 |
| 199 | 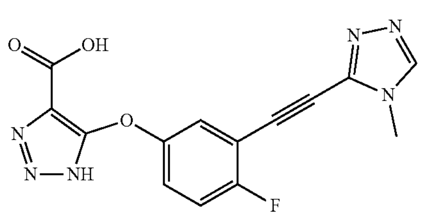 [SMILES: Cn1cnnc1C#Cc1cc(Oc2[nH]nnc2C(=O)O)ccc1F] | 5-(4-fluoro-3-((4-methyl-4H-1,2,4-triazol-3-yl)ethynyl) phenoxy)-1H-1,2,3-triazole-4-carboxylic acid | 328.07 |
| 200 | 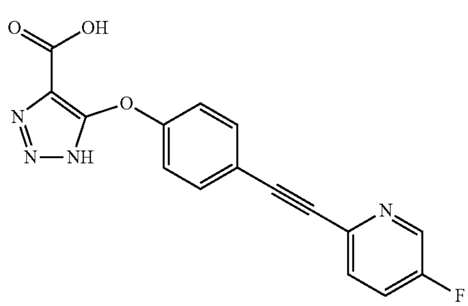 [SMILES: O=C(O)c1nn[nH]c1Oc1ccc(C#Cc2ccc(F)cn2)cc1] | 5-(4-((5-fluoropyridin-2-yl)ethynyl) phenoxy)-1H-1,2,3-triazole-4-carboxylic acid | 324.07 |

TABLE 1-continued

Example Compounds

| Ex. No. | Structure | IUPAC Name | MW (g/mol) |
|---|---|---|---|
| 201 | 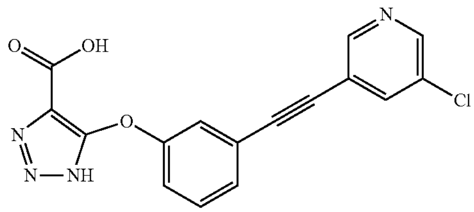 [SMILES: O=C(O)c1nn[nH]c1Oc1cccc(C#Cc2cncc(Cl)c2)c1] | 5-(3-((5-chloropyridin-3-yl)ethynyl)phenoxy)-1H-1,2,3-triazole-4-carboxylic acid | 340.04 |
| 202 | 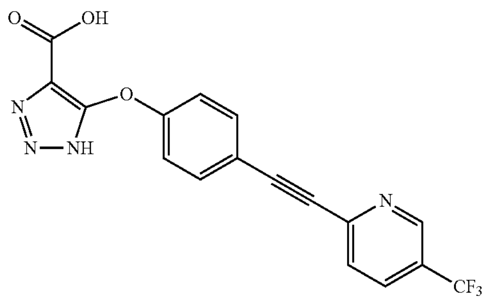 [SMILES: O=C(O)c1nn[nH]c1Oc1ccc(C#Cc2ccc(C(F)(F)F)cn2)cc1] | 5-(4-((5-(trifluoromethyl)pyridin-2-yl)ethynyl)phenoxy)-1H-1,2,3-triazole-4-carboxylic acid | 374.06 |
| 203 | 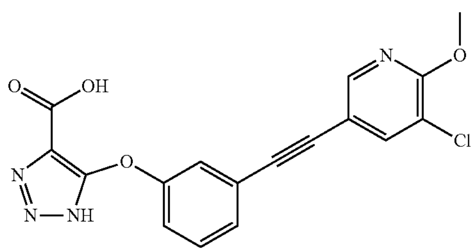 [SMILES: COc1ncc(C#Cc2cccc(Oc3[nH]nnc3C(=O)O)c2)cc1Cl] | 5-(3-((5-chloro-6-methoxypyridin-3-yl)ethynyl)phenoxy)-1H-1,2,3-triazole-4-carboxylic acid | 370.05 |
| 204 | 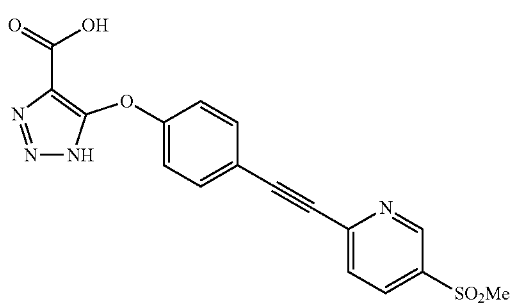 [SMILES: CS(=O)(=O)c1ccc(C#Cc2ccc(Oc3[nH]nnc3C(=O)O)cc2)nc1] | 5-(4-((5-(methylsulfonyl)pyridin-2-yl)ethynyl)phenoxy)-1H-1,2,3-triazole-4-carboxylic acid | 384.05 |
| 205 | 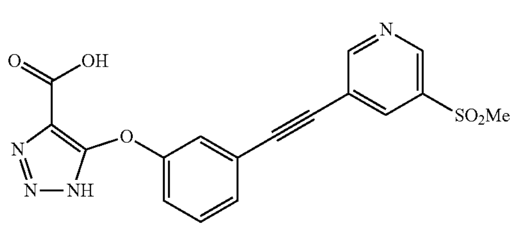 [SMILES: CS(=O)(=O)c1cncc(C#Cc2cccc(Oc3[nH]nnc3C(=O)O)c2)c1] | 5-(3-((5-(methylsulfonyl)pyridin-3-yl)ethynyl)phenoxy)-1H-1,2,3-triazole-4-carboxylic acid | 384.05 |

TABLE 1-continued

Example Compounds

| Ex. No. | Structure | IUPAC Name | MW (g/mol) |
|---|---|---|---|
| 206 | 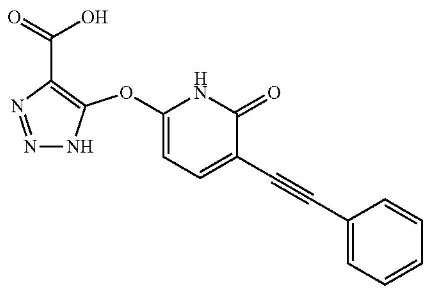 [SMILES: O=C(O)c1nn[nH]c1Oc1ccc(C#Cc2ccccc2)c(=O)[nH]1] | 5-((6-oxo-5-(phenylethynyl)-1,6-dihydropyridin-2-yl)oxy)-1H-1,2,3-triazole-4-carboxylic acid | 337.09 |
| 207 | 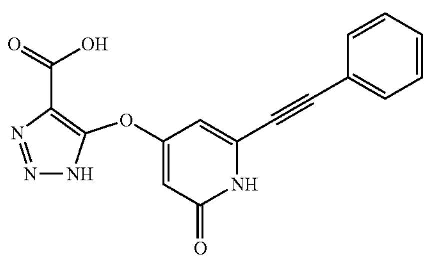 [SMILES: O=C(O)c1nn[nH]c1Oc1cc(C#Cc2ccccc2)[nH]c(=O)c1] | 5-((2-oxo-6-(phenylethynyl)-1,2-dihydropyridin-4-yl)oxy)-1H-1,2,3-triazole-4-carboxylic acid | 322.07 |
| 208 | 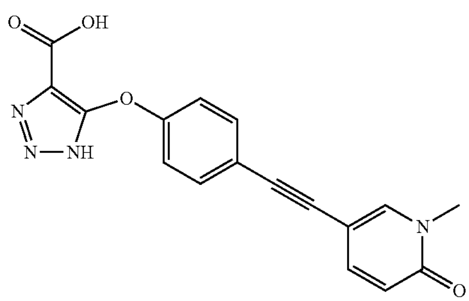 [SMILES: Cn1cc(C#Cc2ccc(Oc3[nH]nnc3C(=O)O)cc2)ccc1=O] | 5-(4-((1-methyl-6-oxo-1,6-dihydropyridin-3-yl)ethynyl)phenoxy)-1H-1,2,3-triazole-4-carboxylic acid | 336.30 |
| 209 | 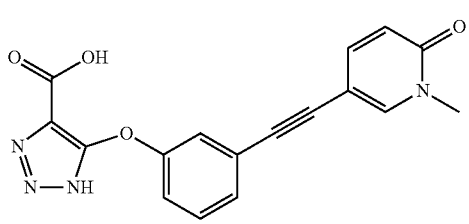 [SMILES: Cn1cc(C#Cc2cccc(Oc3[nH]nnc3C(=O)O)c2)ccc1=O] | 5-(3-((1-methyl-6-oxo-1,6-dihydropyridin-3-yl)ethynyl)phenoxy)-1H-1,2,3-triazole-4-carboxylic acid | 336.30 |
| 210 | 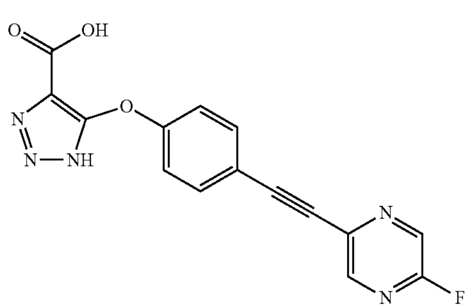 [SMILES: O=C(O)c1nn[nH]c1Oc1ccc(C#Cc2cnc(F)cn2)cc1] | 5-(4-((5-fluoropyrazin-2-yl)ethynyl)phenoxy)-1H-1,2,3-triazole-4-carboxylic acid | 325.06 |

TABLE 1-continued

Example Compounds

| Ex. No. | Structure | IUPAC Name | MW (g/mol) |
|---|---|---|---|
| 211 | 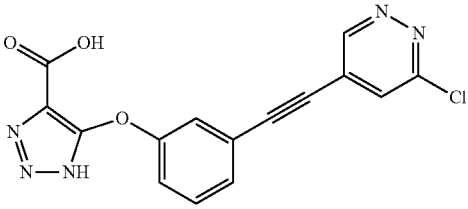 [SMILES: O=C(O)c1nn[nH]c1Oc1cccc(C#Cc2cnnc(Cl)c2)c1] | 5-(3-((6-chloropyridazin-4-yl)ethynyl)phenoxy)-1H-1,2,3-triazole-4-carboxylic acid | 341.03 |
| 212 | 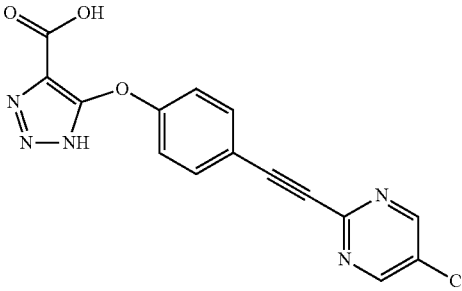 | 5-(4-((5-(trifluoromethyl)pyrimidin-2-yl)ethynyl)phenoxy)-1H-1,2,3-triazole-4-carboxylic acid | 375.06 |
| 213 | 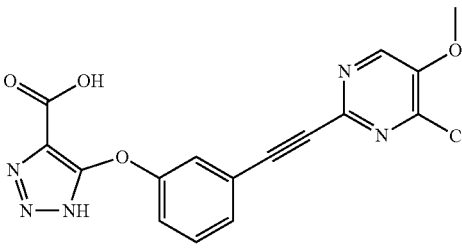 | 5-(3-((4-chloro-5-methoxypyrimidin-2-yl)ethynyl)phenoxy)-1H-1,2,3-triazole-4-carboxylic acid | 371.04 |
| 214 | 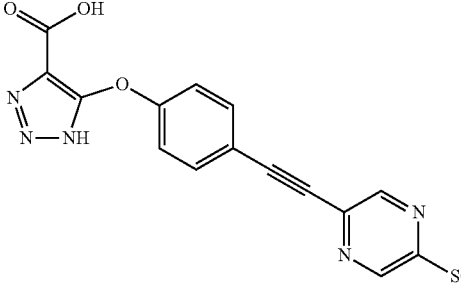 | 5-(4-((5-(methylsulfonyl)pyrazin-2-yl)ethynyl)phenoxy)-1H-1,2,3-triazole-4-carboxylic acid | 385.05 |
| 215 | 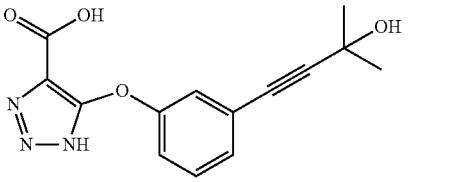 [SMILES: CC(C)(O)C#Cc1cccc(Oc2[nH]nnc2C(=O)O)c1] | 5-(3-(3-hydroxy-3-methylbut-1-ynyl)phenoxy)-1H-1,2,3-triazole-4-carboxylic acid | 287.27 |

TABLE 1-continued

Example Compounds

| Ex. No. | Structure | IUPAC Name | MW (g/mol) |
|---|---|---|---|
| 216 | 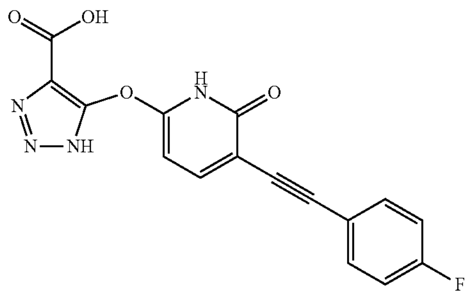 [SMILES: O=C(O)c1nn[nH]c1Oc1ccc(C#Cc2ccc(F)cc2)c(=O)[nH]1] | 5-((5-((4-fluorophenyl)ethynyl)-6-oxo-1,6-dihydropyridin-2-yl)oxy)-1H-1,2,3-triazole-4-carboxylic acid | 355.08 |
| 217 | 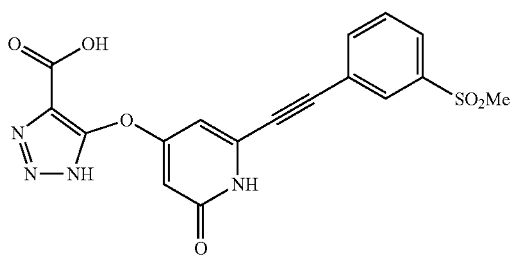 [SMILES: CS(=O)(=O)c1cccc(C#Cc2cc(Oc3[nH]nnc3C(=O)O)cc(=O)[nH]2)c1] | 5-((6-((3-(methylsulfonyl)phenyl)ethynyl)-2-oxo-1,2-dihydropyridin-4-yl)oxy)-1H-1,2,3-triazole-4-carboxylic acid | 400.05 |
| 218 | 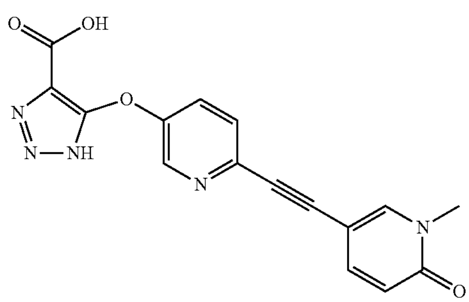 [SMILES: Cn1cc(C#Cc2ccc(Oc3[nH]nnc3C(=O)O)cn2)ccc1=O] | 5-((6-((1-methyl-6-oxo-1,6-dihydropyridin-3-yl)ethynyl)pyridin-3-yl)oxy)-1H-1,2,3-triazole-4-carboxylic acid | 337.08 |
| 219 | 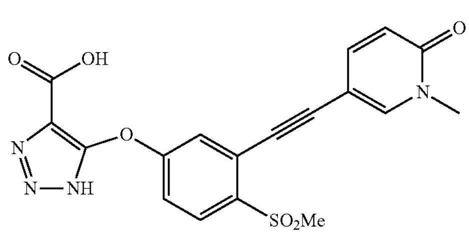 [SMILES: Cn1cc(C#Cc2cc(Oc3[nH]nnc3C(=O)O)ccc2S(C)(=O)=O)ccc1=O] | 5-(3-((1-methyl-6-oxo-1,6-dihydropyridin-3-yl)ethynyl)-4-(methylsulfonyl)phenoxy)-1H-1,2,3-triazole-4-carboxylic acid | 414.4 |
| 220 | 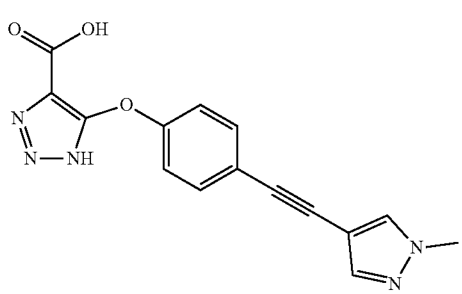 [SMILES: Cn1cc(C#Cc2ccc(Oc3[nH]nnc3C(=O)O)cc2)cn1] | 5-(4-(2-(1-methyl-1H-pyrazol-4-yl)ethynyl)phenoxy)-1H-1,2,3-triazole-4-carboxylic acid | 309.28 |

TABLE 1-continued

Example Compounds

| Ex. No. | Structure | IUPAC Name | MW (g/mol) |
|---|---|---|---|
| 221 | 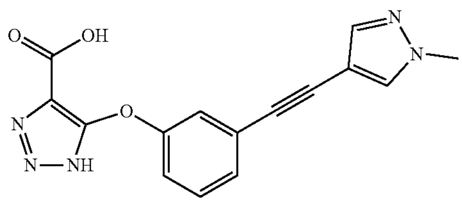 [SMILES: Cn1cc(C#Cc2cccc(Oc3[nH]nnc3C(=O)O)c2)cn1] | 5-(3-(2-(1-methyl-1H-pyrazol-4-yl)ethynyl)phenoxy)-1H-1,2,3-triazole-4-carboxylic acid | 309.28 |
| 222 | 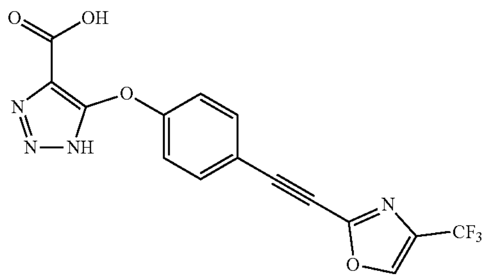 [SMILES: O=C(O)c1nn[nH]c1Oc1ccc(C#Cc2nc(C(F)(F)F)co2)cc1] | 5-(4-((4-(trifluoromethyl)oxazol-2-yl)ethynyl) phenoxy)-1H-1,2,3-triazole-4-carboxylic acid | 364.04 |
| 223 | 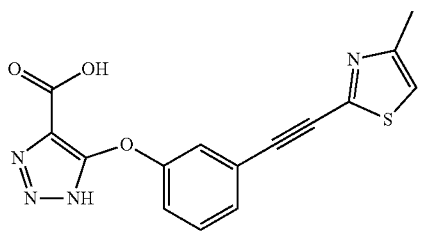 [SMILES: Cc1csc(C#Cc2cccc(Oc3[nH]nnc3C(=O)O)c2)n1] | 5-(3-((4-methylthiazol-2-yl)ethynyl)phenoxy)-1H-1,2,3-triazole-4-carboxylic acid | 326.05 |
| 224 | 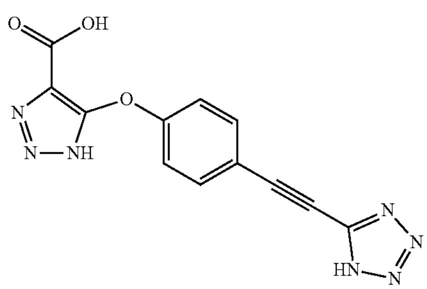 [SMILES: O=C(O)c1nn[nH]c1Oc1ccc(C#Cc2nnn[nH]2)cc1] | 5-(4-((1H-tetrazol-5-yl)ethynyl)phenoxy)-1H-1,2,3-triazole-4-carboxylic acid | 297.06 |
| 225 | 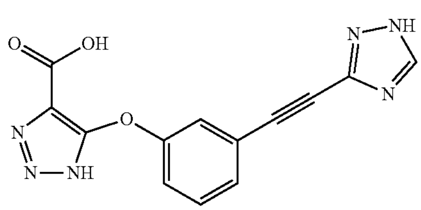 [SMILES: O=C(O)c1nn[nH]c1Oc1cccc(C#Cc2nc[nH]n2)c1] | 5-(3-((1H-1,2,4-triazol-3-yl)ethynyl)phenoxy)-1H-1,2,3-triazole-4-carboxylic acid | 296.07 |
| 226 | 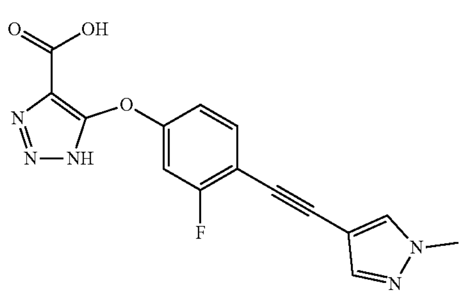 [SMILES: Cn1cc(C#Cc2ccc(Oc3[nH]nnc3C(=O)O)cc2F)cn1] | 5-(3-fluoro-4-((1-methyl-1H-pyrazol-4-yl)ethynyl)phenoxy)-1H-1,2,3-triazole-4-carboxylic acid | 327.08 |

TABLE 1-continued

Example Compounds

| Ex. No. | Structure | IUPAC Name | MW (g/mol) |
|---|---|---|---|
| 227 | 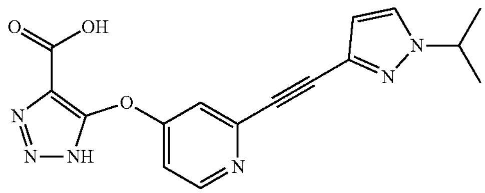 [SMILES: CC(C)n1ccc(C#Cc2cc(Oc3[nH]nnc3C(=O)O)ccn2)n1] | 5-((2-((1-isopropyl-1H-pyrazol-3-yl)ethynyl)pyridin-4-yl)oxy)-1H-1,2,3-triazole-4-carboxylic acid | 338.11 |
| 228 | 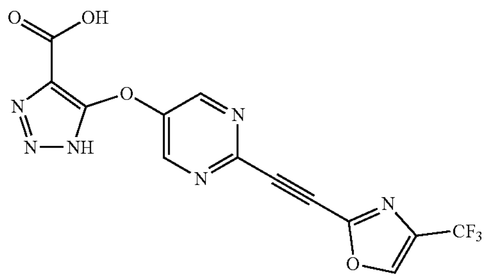 [SMILES: O=C(O)c1nn[nH]c1Oc1cnc(C#Cc2nc(C(F)(F)F)co2)nc1] | 5-((2-((4-(trifluoromethyl)oxazol-2-yl)ethynyl) pyrimidin-5-yl)oxy)-1H-1,2,3-triazole-4-carboxylic acid | 366.03 |
| 229 | 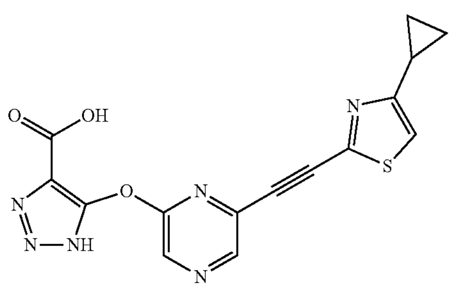 [SMILES: O=C(O)c1nn[nH]c1Oc1cncc(C#Cc2nc(C3CC3)cs2)n1] | 5-((6-((4-cyclopropylthiazol-2-yl)ethynyl)pyrazin-2-yl)oxy)-1H-1,2,3-triazole-4-carboxylic acid | 354.05 |
| 230 | 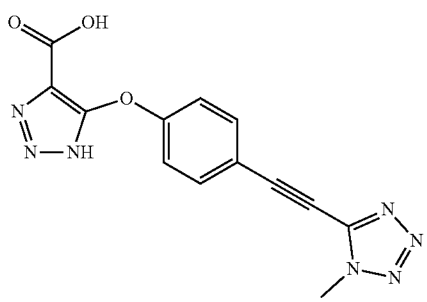 [SMILES: Cn1nnnc1C#Cc1ccc(Oc2[nH]nnc2C(=O)O)cc1] | 5-(4-((1-methyl-1H-tetrazol-5-yl)ethynyl)phenoxy)-1H-1,2,3-triazole-4-carboxylic acid | 311.08 |
| 231 | 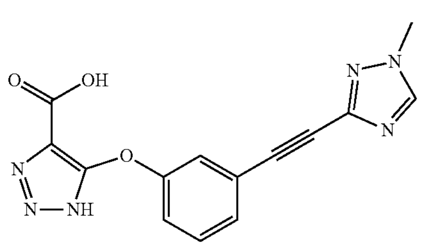 [SMILES: Cn1cnc(C#Cc2cccc(Oc3[nH]nnc3C(=O)O)c2)n1] | 5-(3-((1-methyl-1H-1,2,4-triazol-3-yl)ethynyl)phenoxy)-1H-1,2,3-triazole-4-carboxylic acid | 310.08 |

TABLE 1-continued

Example Compounds

| Ex. No. | Structure | IUPAC Name | MW (g/mol) |
|---|---|---|---|
| 232 | 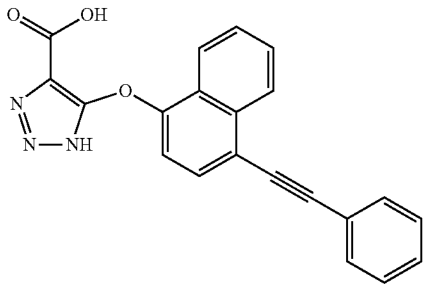 [SMILES: O=C(O)c1nn[nH]c1Oc1ccc(C#Cc2ccccc2)c2ccccc12] | 5-((4-(phenylethynyl)naphthalen-1-yl)oxy)-1H-1,2,3-triazole-4-carboxylic acid | 355.10 |
| 233 | 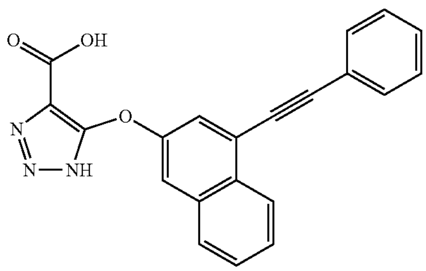 [SMILES: O=C(O)c1nn[nH]c1Oc1cc(C#Cc2ccccc2)c2ccccc2c1] | 5-((4-(phenylethynyl)naphthalen-2-yl)oxy)-1H-1,2,3-triazole-4-carboxylic acid | 355.10 |
| 234 | 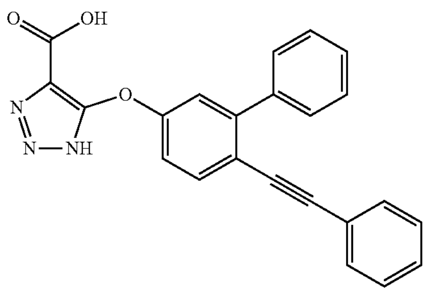 [SMILES: O=C(O)c1nn[nH]c1Oc1ccc(C#Cc2ccccc2)c(-c2ccccc2)c1] | 5-((6-(phenylethynyl)-[1,1'-biphenyl]-3-yl)oxy)-1H-1,2,3-triazole-4-carboxylic acid | 381.11 |
| 235 | 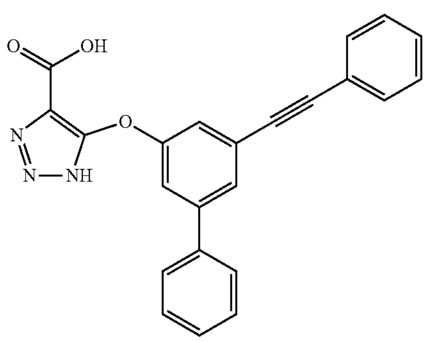 [SMILES: O=C(O)c1nn[nH]c1Oc1cc(C#Cc2ccccc2)cc(-c2ccccc2)c1] | 5-((5-(phenylethynyl)-[1,1'-biphenyl]-3-yl)oxy)-1H-1,2,3-triazole-4-carboxylic acid | 381.11 |
| 236 | 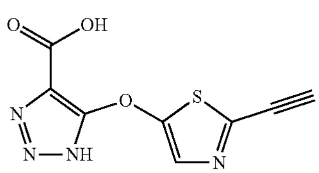 [SMILES: C#Cc1ncc(Oc2[nH]nnc2C(=O)O)s1] | 5-((2-ethynylthiazol-5-yl)oxy)-1H-1,2,3-triazole-4-carboxylic acid | 236.00 |
| 237 | 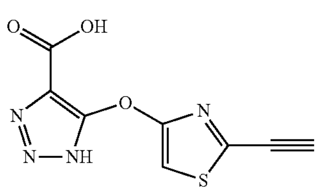 [SMILES: C#Cc1nc(Oc2[nH]nnc2C(=O)O)cs1] | 5-((2-ethynylthiazol-4-yl)oxy)-1H-1,2,3-triazole-4-carboxylic acid | 236.00 |

TABLE 1-continued

Example Compounds

| Ex. No. | Structure | IUPAC Name | MW (g/mol) |
|---|---|---|---|
| 238 | 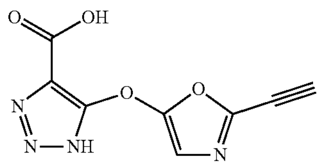 [SMILES: C#Cc1ncc(Oc2[nH]nnc2C(=O)O)o1] | 5-((2-ethynyloxazol-5-yl)oxy)-1H-1,2,3-triazole-4-carboxylic acid | 220.02 |
| 239 | 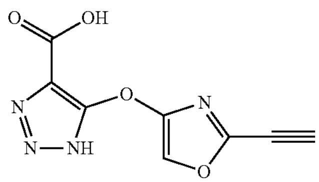 [SMILES: C#Cc1nc(Oc2[nH]nnc2C(=O)O)co1] | 5-((2-ethynyloxazol-4-yl)oxy)-1H-1,2,3-triazole-4-carboxylic acid | 220.02 |
| 240 | 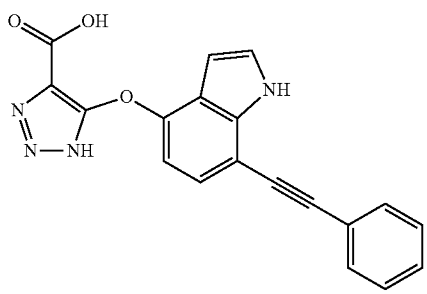 [SMILES: O=C(O)c1nn[nH]c1Oc1ccc(C#Cc2ccccc2)c2[nH]ccc12] | 5-((7-(phenylethynyl)-1H-indol-4-yl)oxy)-1H-1,2,3-triazole-4-carboxylic acid | 344.09 |
| 241 | 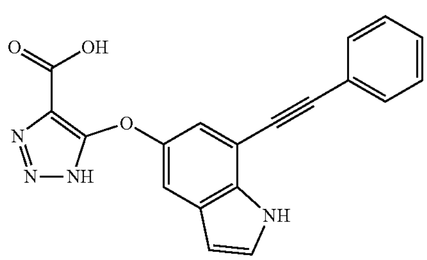 [SMILES: O=C(O)c1nn[nH]c1Oc1cc(C#Cc2ccccc2)c2[nH]ccc2c1] | 5-((7-(phenylethynyl)-1H-indol-5-yl)oxy)-1H-1,2,3-triazole-4-carboxylic acid | 344.09 |
| 242 | 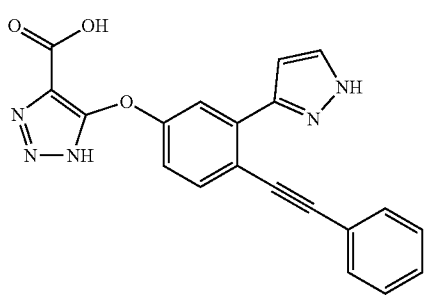 [SMILES: O=C(O)c1nn[nH]c1Oc1ccc(C#Cc2ccccc2)c(-c2cc[nH]n2)c1] | 5-(4-(phenylethynyl)-3-(1H-pyrazol-3-yl)phenoxy)-1H-1,2,3-triazole-4-carboxylic acid | 371.10 |
| 243 | 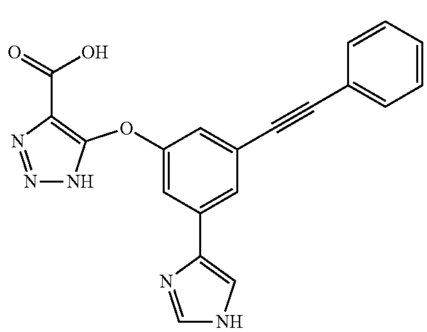 [SMILES: O=C(O)c1nn[nH]c1Oc1cc(C#Cc2ccccc2)cc(-c2c[nH]cn2)c1] | 5-(3-(1H-imidazol-4-yl)-5-(phenylethynyl) phenoxy)-1H-1,2,3-triazole-4-carboxylic acid | 371.10 |

TABLE 1-continued

Example Compounds

| Ex. No. | Structure | IUPAC Name | MW (g/mol) |
|---|---|---|---|
| 244 | 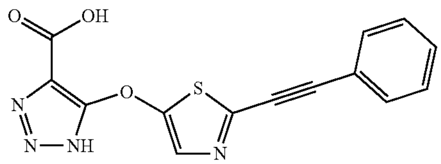 | 5-((2-(phenylethynyl)thiazol-5-yl)oxy)-1H-1,2,3-triazole-4-carboxylic acid | 312.03 |
| 245 | 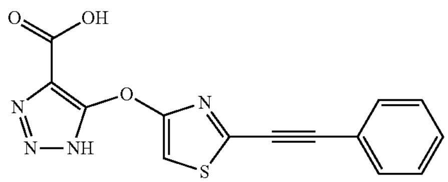 [SMILES: O=C(O)c1nn[nH]c1Oc1csc(C#Cc2ccccc2)n1] | 5-((2-(phenylethynyl)thiazol-4-yl)oxy)-1H-1,2,3-triazole-4-carboxylic acid | 312.03 |
| 246 | 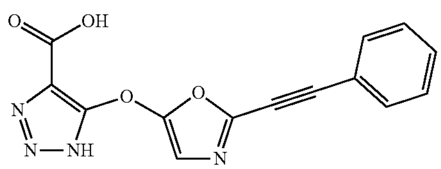 [SMILES: O=C(O)c1nn[nH]c1Oc1cnc(C#Cc2ccccc2)o1] | 5-((2-(phenylethynyl)oxazol-5-yl)oxy)-1H-1,2,3-triazole-4-carboxylic acid | 296.05 |
| 247 | 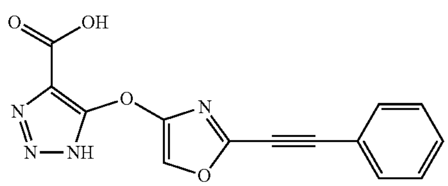 [SMILES: O=C(O)c1nn[nH]c1Oc1coc(C#Cc2ccccc2)n1] | 5-((2-(phenylethynyl)oxazol-4-yl)oxy)-1H-1,2,3-triazole-4-carboxylic acid | 296.05 |
| 248 | 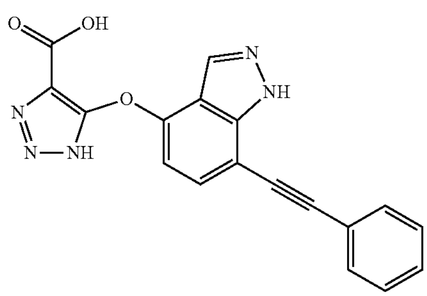 [SMILES: O=C(O)c1nn[nH]c1Oc1ccc(C#Cc2ccccc2)c2[nH]ncc12] | 5-((7-(phenylethynyl)-1H-indazol-4-yl)oxy)-1H-1,2,3-triazole-4-carboxylic acid | 345.09 |
| 249 | 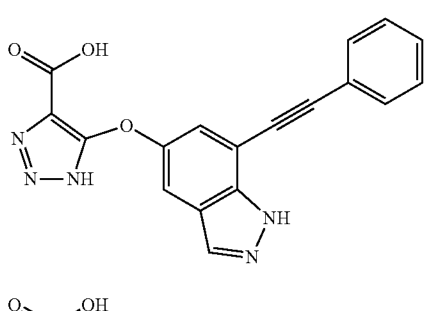 | 5-((7-(phenylethynyl)-1H-indazol-5-yl)oxy)-1H-1,2,3-triazole-4-carboxylic acid | 345.09 |
| 250 | 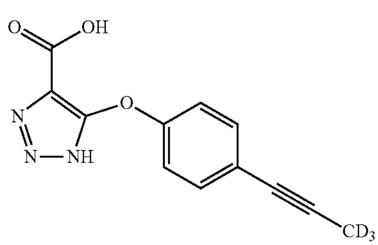 [SMILES: [2H]C([2H])([2H])C#Cc1ccc(Oc2[nH]nnc2C(=O)O)cc1] | 5-(4-(prop-1-ynyl-$d_3$)phenoxy)-1H-1,2,3-triazole-4-carboxylic acid | 246.08 |

TABLE 1-continued

Example Compounds

| Ex. No. | Structure | IUPAC Name | MW (g/mol) |
|---|---|---|---|
| 251 | 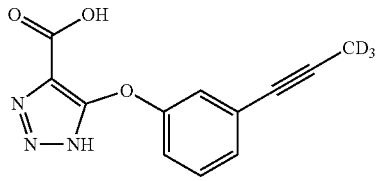 [SMILES: [2H]C([2H])([2H])C#Cc1cccc(Oc2[nH]nnc2C(=O)O)c1] | 5-(3-(prop-1-ynyl-$d_3$)phenoxy)-1H-1,2,3-triazole-4-carboxylic acid | 246.08 |
| 252 | 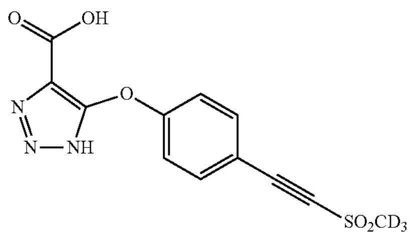 | 5-(4-(((methyl-$d_3$)sulfonyl)ethynyl)phenoxy)-1H-1,2,3-triazole-4-carboxylic acid | 310.05 |
| 253 | 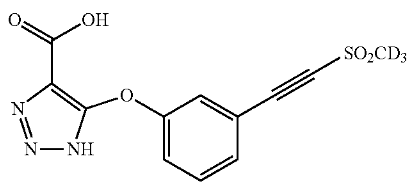 | 5-(3-(((methyl-$d_3$)sulfonyl)ethynyl) phenoxy)-1H-1,2,3-triazole-4-carboxylic acid | 310.05 |
| 254 | 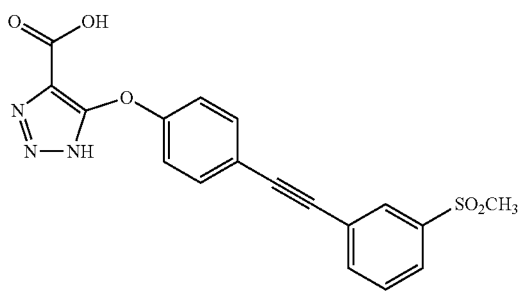 [SMILES: CS(=O)(=O)c1cccc(C#Cc2ccc(Oc3[nH]nnc3C(=O)O)cc2)c1] | 5-(4-(2-(3-(methylsulfonyl)phenyl)ethynyl)phenoxy)-1H-1,2,3-triazole-4-carboxylic acid | 383.38 |
| 255 | 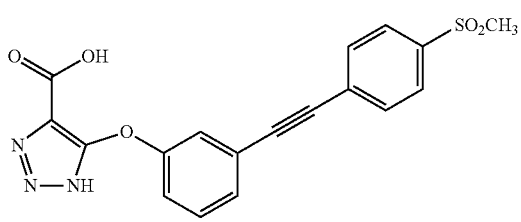 [SMILES: CS(=O)(=O)c1ccc(C#Cc2cccc(Oc3[nH]nnc3C(=O)O)c2)cc1] | 5-(3-(2-(4-(methylsulfonyl)phenyl)ethynyl)phenoxy)-1H-1,2,3-triazole-4-carboxylic acid | 383.38 |
| 256 | 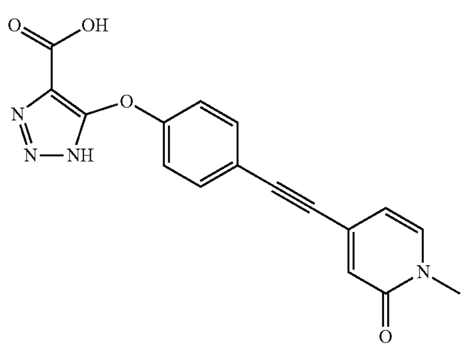 [SMILES: Cn1ccc(C#Cc2ccc(Oc3[nH]nnc3C(=O)O)cc2)cc1=O] | 5-(4-((1-methyl-2-oxo-1,2-dihydropyridin-4-yl)ethynyl)phenoxy)-1H-1,2,3-triazole-4-carboxylic acid | 336.3 |

TABLE 1-continued

Example Compounds

| Ex. No. | Structure | IUPAC Name | MW (g/mol) |
|---|---|---|---|
| 257 | 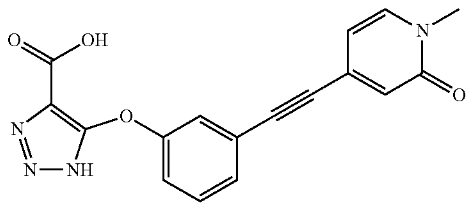 [SMILES: Cn1ccc(C#Cc2cccc(Oc3[nH]nnc3C(=O)O)c2)cc1=O] | 5-(3-((1-methyl-2-oxo-1,2-dihydropyridin-4-yl)ethynyl)phenoxy)-1H-1,2,3-triazole-4-carboxylic acid | 336.3 |
| 258 | 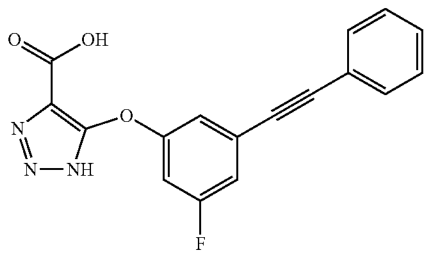 | 5-(3-fluoro-5-(2-phenylethynyl)phenoxy)-1H-1,2,3-triazole-4-carboxylic acid | 323.28 |
| 259 | 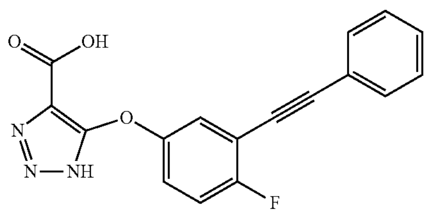 [SMILES: O=C(O)c1nn[nH]c1Oc1ccc(F)c(C#Cc2ccccc2)c1] | 5-(4-fluoro-3-(2-phenylethynyl)phenoxy)-1H-1,2,3-triazole-4-carboxylic acid | 323.28 |
| 260 | 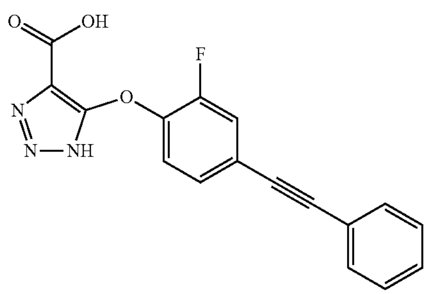 [SMILES: O=C(O)c1nn[nH]c1Oc1ccc(C#Cc2ccccc2)cc1F] | 5-(2-fluoro-4-(2-phenylethynyl)phenoxy)-1H-1,2,3-triazole-4-carboxylic acid | 323.28 |
| 261 | 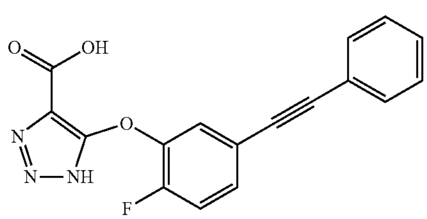 [SMILES: O=C(O)c1nn[nH]c1Oc1cc(C#Cc2ccccc2)ccc1F] | 5-(2-fluoro-5-(2-phenylethynyl)phenoxy)-1H-1,2,3-triazole-4-carboxylic acid | 323.28 |
| 262 | 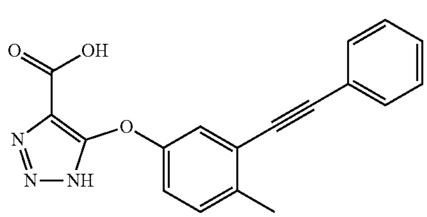 [SMILES: Cc1ccc(Oc2[nH]nnc2C(=O)O)cc1C#Cc1ccccc1] | 5-(4-methyl-3-(2-phenylethynyl)phenoxy)-1H-1,2,3-triazole-4-carboxylic acid | 319.31 |

TABLE 1-continued

Example Compounds

| Ex. No. | Structure | IUPAC Name | MW (g/mol) |
|---|---|---|---|
| 263 | 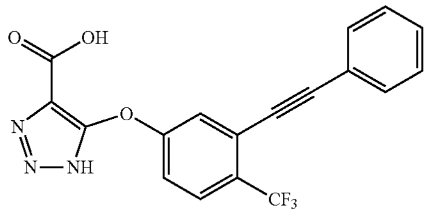 [SMILES: O=C(O)c1nn[nH]c1Oc1ccc(C(F)(F)F)c(C#Cc2ccccc2)c1] | 5-(4-(trifluoromethyl)-3-(2-phenylethynyl)phenoxy)-1H-1,2,3-triazole-4-carboxylic acid | 373.29 |
| 264 | 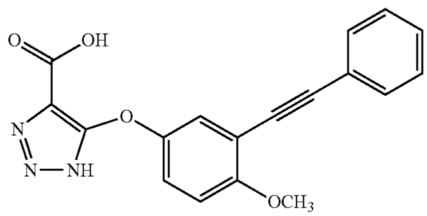 [SMILES: COc1ccc(Oc2[nH]nnc2C(=O)O)cc1C#Cc1ccccc1] | 5-(4-methoxy-3-(2-phenylethynyl)phenoxy)-1H-1,2,3-triazole-4-carboxylic acid | 335.31 |
| 265 | 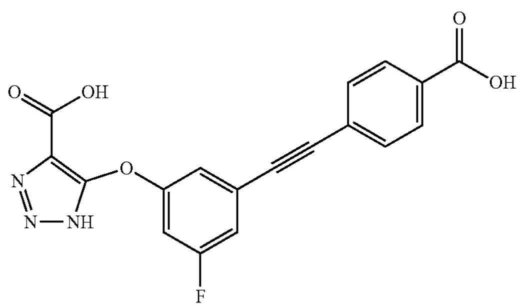 [SMILES: O=C(O)c1ccc(C#Cc2cc(F)cc(Oc3[nH]nnc3C(=O)O)c2)cc1] | 5-(3-fluoro-5-(2-(4-carboxyphenyl)ethynyl)phenoxy)-1H-1,2,3-triazole-4-carboxylic acid | 367.29 |
| 266 | 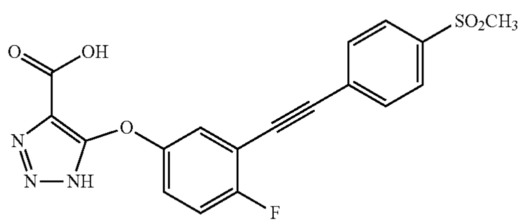 [SMILES: CS(=O)(=O)c1ccc(C#Cc2cc(Oc3[nH]nnc3C(=O)O)ccc2F)cc1] | 5-(4-fluoro-3-(2-(4-(methylsulfonyl)phenyl)ethynyl)phenoxy)-1H-1,2,3-triazole-4-carboxylic acid | 401.37 |
| 267 | 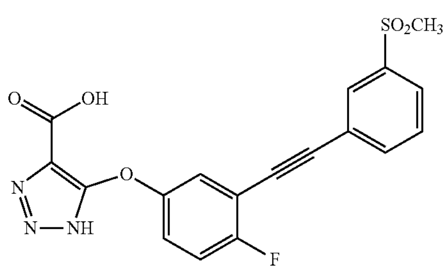 [SMILES: CS(=O)(=O)c1cccc(C#Cc2cc(Oc3[nH]nnc3C(=O)O)ccc2F)c1] | 5-(4-fluoro-3-(2-(3-(methylsulfonyl)phenyl)ethynyl)phenoxy)-1H-1,2,3-triazole-4-carboxylic acid | 401.37 |
| 268 | 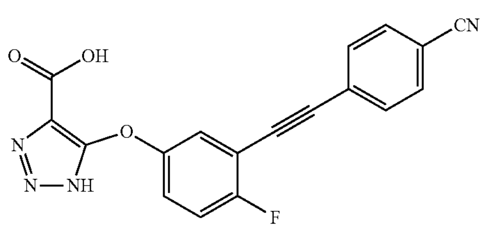 [SMILES: N#Cc1ccc(C#Cc2cc(Oc3[nH]nnc3C(=O)O)ccc2F)cc1] | 5-(3-((4-cyanophenyl)ethynyl)-4-fluorophenoxy)-1H-1,2,3-triazole-4-carboxylic acid | 348.29 |

TABLE 1-continued

Example Compounds

| Ex. No. | Structure | IUPAC Name | MW (g/mol) |
|---|---|---|---|
| 269 | 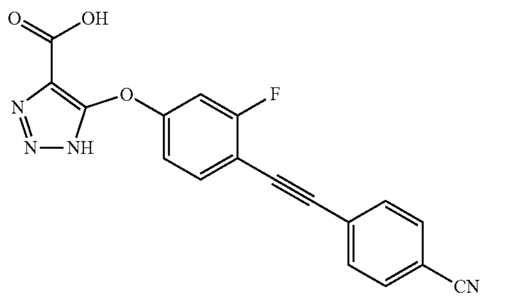 [SMILES: N#Cc1ccc(C#Cc2ccc(Oc3[nH]nnc3C(=O)O)cc2F)cc1] | 5-(4-((4-cyanophenyl)ethynyl)-3-fluorophenoxy)-1H-1,2,3-triazole-4-carboxylic acid | 348.29 |
| 270 | 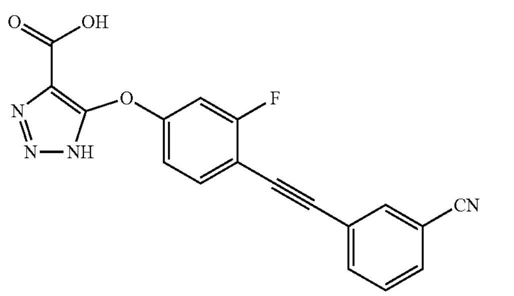 [SMILES: N#Cc1cccc(C#Cc2ccc(Oc3[nH]nnc3C(=O)O)cc2F)c1] | 5-(4-((3-cyanophenyl)ethynyl)-3-fluorophenoxy)-1H-1,2,3-triazole-4-carboxylic acid | 348.29 |
| 271 | 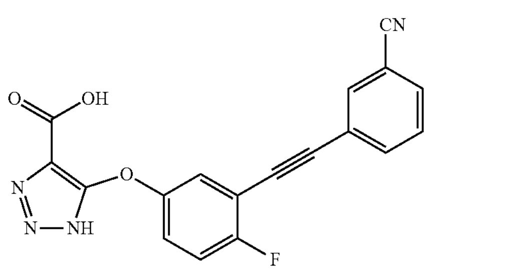 [SMILES: N#Cc1cccc(C#Cc2cc(Oc3[nH]nnc3C(=O)O)ccc2F)c1] | 5-(4-((3-cyanophenyl)ethynyl)-3-fluorophenoxy)-1H-1,2,3-triazole-4-carboxylic acid | 348.29 |
| 272 | 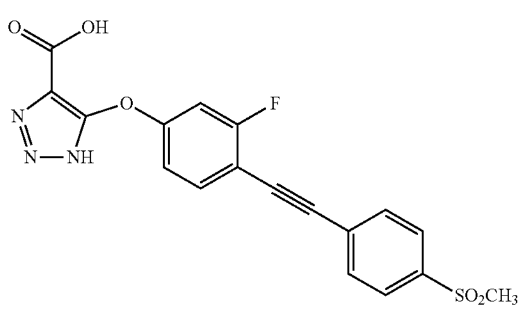 | 5-(3-fluoro-4-(2-(4-(methylsulfonyl)phenyl)ethynyl)phenoxy)-1H-1,2,3-triazole-4-carboxylic acid | 401.37 |
| 273 | 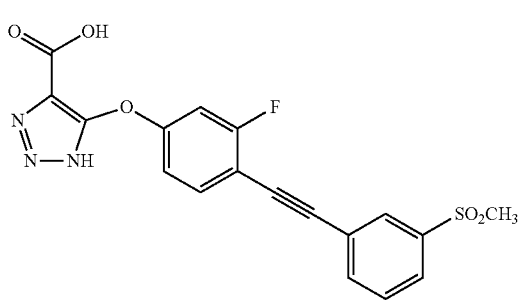 [SMILES: CS(=O)(=O)c1cccc(C#Cc2ccc(Oc3[nH]nnc3C(=O)O)cc2F)c1] | 5-(3-fluoro-4-(2-(3-(methylsulfonyl)phenyl)ethynyl)phenoxy)-1H-1,2,3-triazole-4-carboxylic acid | 401.37 |

TABLE 1-continued

Example Compounds

| Ex. No. | Structure | IUPAC Name | MW (g/mol) |
|---|---|---|---|
| 274 | 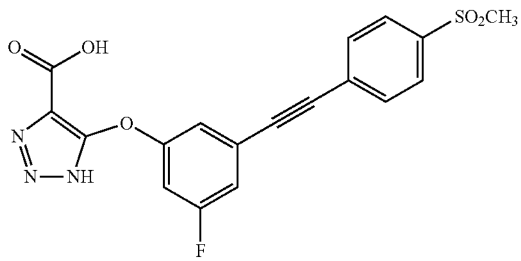 [SMILES: CS(=O)(=O)c1ccc(C#Cc2cc(F)cc(Oc3[nH]nnc3C(=O)O)c2)cc1] | 5-(3-fluoro-5-(2-(4-(methylsulfonyl)phenyl)ethynyl)phenoxy)-1H-1,2,3-triazole-4-carboxylic acid | 401.37 |
| 275 | 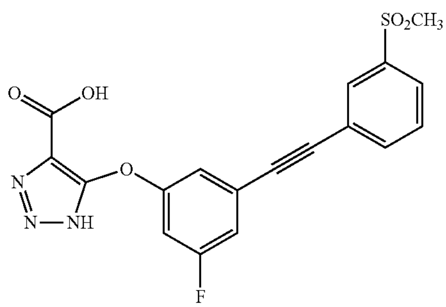 [SMILES: CS(=O)(=O)c1cccc(C#Cc2cc(F)cc(Oc3[nH]nnc3C(=O)O)c2)c1] | 5-(3-fluoro-5-(2-(3-(methylsulfonyl)phenyl)ethynyl)phenoxy)-1H-1,2,3-triazole-4-carboxylic acid | 401.37 |
| 276 | 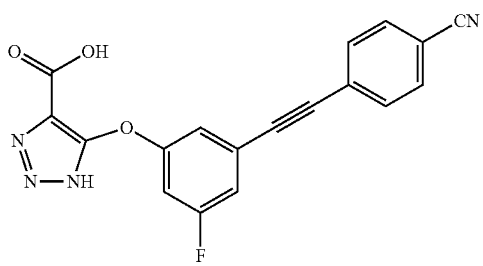 [SMILES: N#Cc1ccc(C#Cc2cc(F)cc(Oc3[nH]nnc3C(=O)O)c2)cc1] | 4-(3-((4-cyanophenyl)ethynyl)-5-fluorophenoxy)-1H-1,2,3-triazole-4-carboxylic acid | 348.29 |
| 277 | 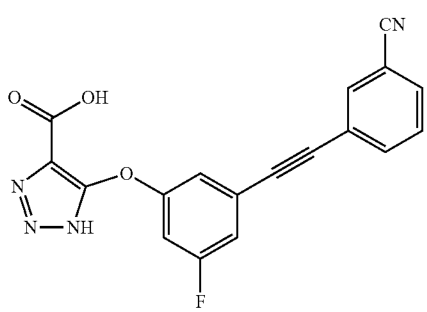 [SMILES: N#Cc1cccc(C#Cc2cc(F)cc(Oc3[nH]nnc3C(=O)O)c2)c1] | 4-(3-((3-cyanophenyl)ethynyl)-5-fluorophenoxy)-1H-1,2,3-triazole-4-carboxylic acid | 348.29 |
| 278 | 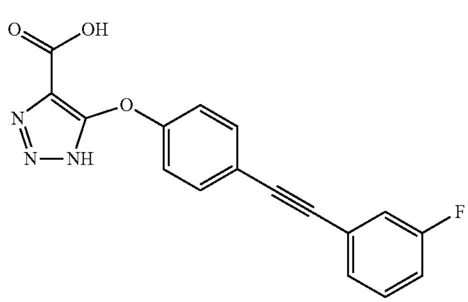 [SMILES: O=C(O)c1nn[nH]c1Oc1ccc(C#Cc2cccc(F)c2)cc1] | 5-(4-(2-(3-fluorophenyl)ethynyl)phenoxy)-1H-1,2,3-triazole-4-carboxylic acid | 323.28 |

TABLE 1-continued

Example Compounds

| Ex. No. | Structure | IUPAC Name | MW (g/mol) |
|---|---|---|---|
| 279 | 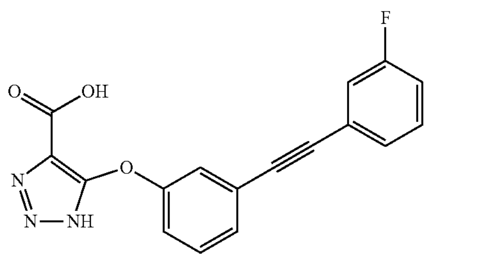 [SMILES: O=C(O)c1nn[nH]c1Oc1cccc(C#Cc2cccc(F)c2)c1] | 5-(3-(2-(3-fluorophenyl)ethynyl)phenoxy)-1H-1,2,3-triazole-4-carboxylic acid | 323.28 |
| 280 | 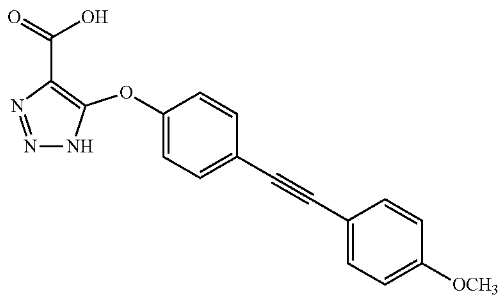 [SMILES: COc1ccc(C#Cc2ccc(Oc3[nH]nnc3C(=O)O)cc2)cc1] | 5-(4-(2-(4-methoxyphenyl)ethynyl)phenoxy)-1H-1,2,3-triazole-4-carboxylic acid | 335.31 |
| 281 | 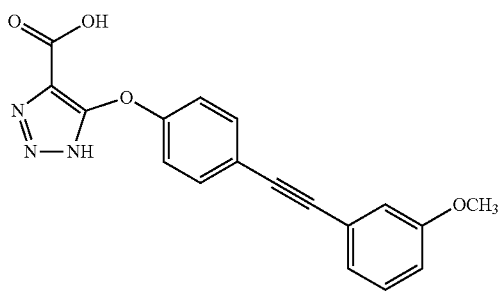 [SMILES: COc1cccc(C#Cc2ccc(Oc3[nH]nnc3C(=O)O)cc2)c1] | 5-(4-(2-(3-methoxyphenyl)ethynyl)phenoxy)-1H-1,2,3-triazole-4-carboxylic acid | 335.31 |
| 282 | 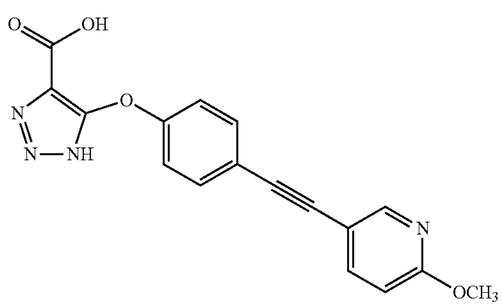 | 5-(4-(2-(6-methoxypyridin-3-yl)ethynyl)phenoxy)-1H-1,2,3-triazole-4-carboxylic acid | 336.3 |
| 283 | 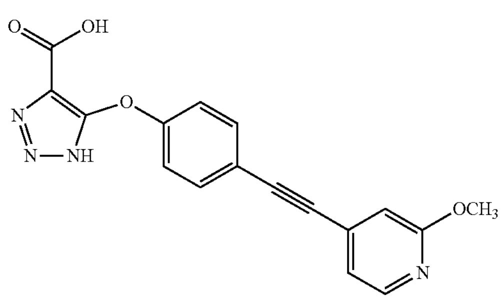 [SMILES: COc1cc(C#Cc2ccc(Oc3[nH]nnc3C(=O)O)cc2)ccn1] | 5-(4-(2-(2-methoxypyridin-4-yl)ethynyl)phenoxy)-1H-1,2,3-triazole-4-carboxylic acid | 336.3 |

TABLE 1-continued

Example Compounds

| Ex. No. | Structure | IUPAC Name | MW (g/mol) |
|---|---|---|---|
| 284 | 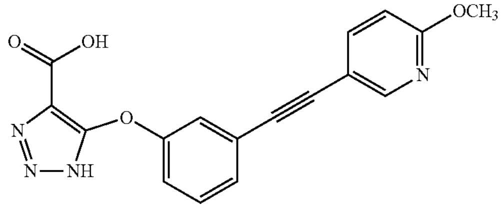 [SMILES: COc1ccc(C#Cc2cccc(Oc3[nH]nnc3C(=O)O)c2)cn1] | 5-(3-(2-(6-methoxypyridin-3-yl)ethynyl)phenoxy)-1H-1,2,3-triazole-4-carboxylic acid | 336.3 |
| 285 | 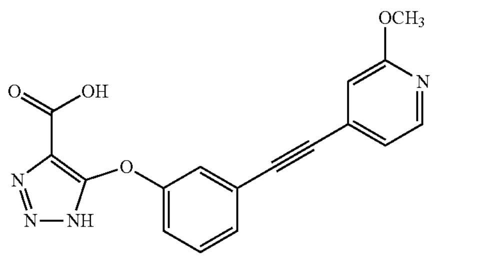 [SMILES: COc1cc(C#Cc2cccc(Oc3[nH]nnc3C(=O)O)c2)ccn1] | 5-(3-(2-(2-methoxypyridin-4-yl)ethynyl)phenoxy)-1H-1,2,3-triazole-4-carboxylic acid | 336.3 |
| 286 | 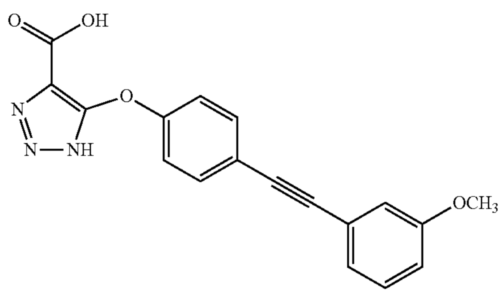 [SMILES: COc1cccc(C#Cc2ccc(Oc3[nH]nnc3C(=O)O)cc2)c1] | 5-(4-(2-(3-methoxyphenyl)ethynyl)phenoxy)-1H-1,2,3-triazole-4-carboxylic acid | 335.31 |
| 287 | 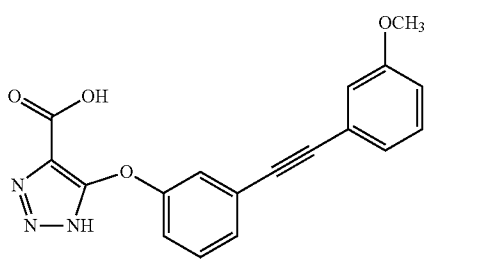 [SMILES: COc1cccc(C#Cc2cccc(Oc3[nH]nnc3C(=O)O)c2)c1] | 5-(3-(2-(3-methoxyphenyl)ethynyl)phenoxy)-1H-1,2,3-triazole-4-carboxylic acid | 335.31 |
| 288 | 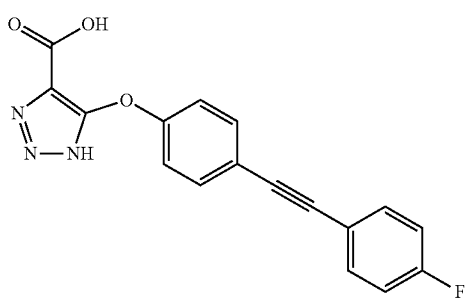 [SMILES: O=C(O)c1nn[nH]c1Oc1ccc(C#Cc2ccc(F)cc2)cc1] | 5-(4-(2-(4-fluorophenyl)ethynyl)phenoxy)-1H-1,2,3-triazole-4-carboxylic acid | 323.28 |
| 289 | 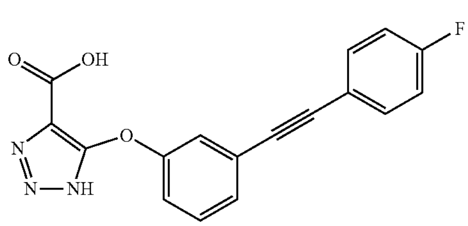 [SMILES: O=C(O)c1nn[nH]c1Oc1cccc(C#Cc2ccc(F)cc2)c1] | 5-(3-(2-(4-fluorophenyl)ethynyl)phenoxy)-1H-1,2,3-triazole-4-carboxylic acid | 323.28 |

TABLE 1-continued

Example Compounds

| Ex. No. | Structure | IUPAC Name | MW (g/mol) |
|---|---|---|---|
| 290 | 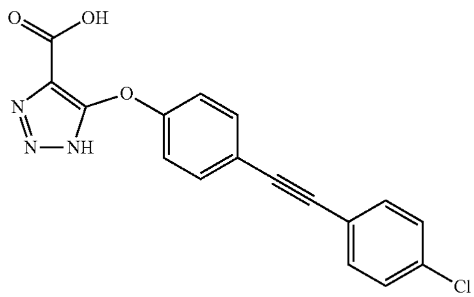 [SMILES: O=C(O)c1nn[nH]c1Oc1ccc(C#Cc2ccc(Cl)cc2)cc1] | 5-(4-(2-(4-chlorophenyl)ethynyl)phenoxy)-1H-1,2,3-triazole-4-carboxylic acid | 339.73 |
| 291 | 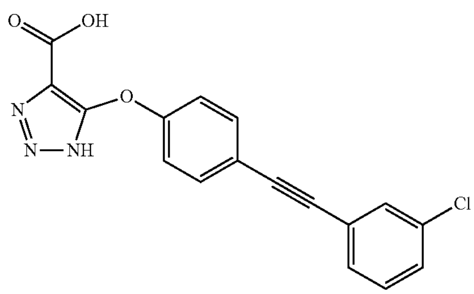 [SMILES: O=C(O)c1nn[nH]c1Oc1ccc(C#Cc2cccc(Cl)c2)cc1] | 5-(4-(2-(3-chlorophenyl)ethynyl)phenoxy)-1H-1,2,3-triazole-4-carboxylic acid | 339.73 |
| 292 | 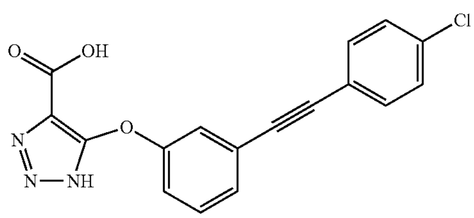 [SMILES: O=C(O)c1nn[nH]c1Oc1cccc(C#Cc2ccc(Cl)cc2)c1] | 5-(3-(2-(4-chlorophenyl)ethynyl)phenoxy)-1H-1,2,3-triazole-4-carboxylic acid | 339.73 |
| 293 | 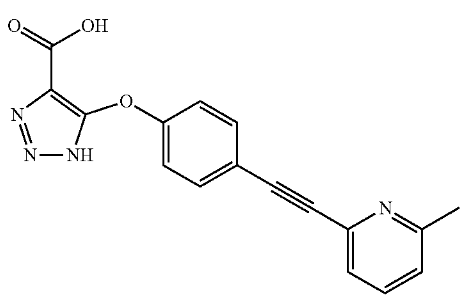 [SMILES: Cc1cccc(C#Cc2ccc(Oc3[nH]nnc3C(=O)O)cc2)n1] | 5-(4-(2-(6-methylpyridin-2-yl)ethynyl)phenoxy)-1H-1,2,3-triazole-4-carboxylic acid | 320.3 |
| 294 | 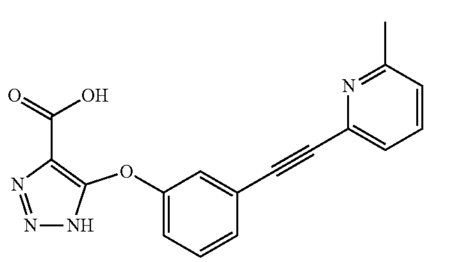 [SMILES: Cc1cccc(C#Cc2cccc(Oc3[nH]nnc3C(=O)O)c2)n1] | 5-(3-(2-(6-methylpyridin-2-yl)ethynyl)phenoxy)-1H-1,2,3-triazole-4-carboxylic acid | 320.3 |

TABLE 1-continued

Example Compounds

| Ex. No. | Structure | IUPAC Name | MW (g/mol) |
|---|---|---|---|
| 295 | 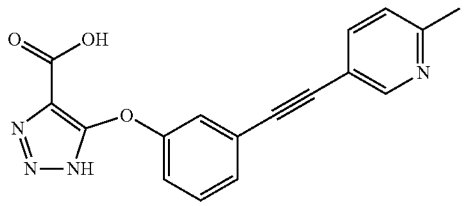 [SMILES: Cc1ccc(C#Cc2cccc(Oc3[nH]nnc3C(=O)O)c2)cn1] | 5-(3-(2-(6-methylpyridin-3-yl)ethynyl)phenoxy)-1H-1,2,3-triazole-4-carboxylic acid | 320.3 |
| 296 | 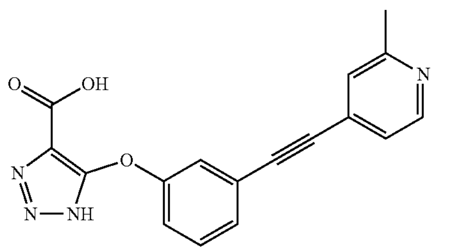 [SMILES: Cc1cc(C#Cc2cccc(Oc3[nH]nnc3C(=O)O)c2)ccn1] | 5-(3-(2-(2-methylpyridin-4-yl)ethynyl)phenoxy)-1H-1,2,3-triazole-4-carboxylic acid | 320.3 |
| 297 | 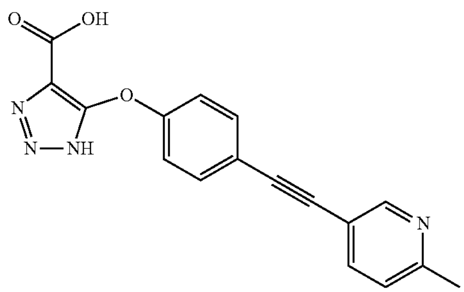 [SMILES: Cc1ccc(C#Cc2ccc(Oc3[nH]nnc3C(=O)O)cc2)cn1] | 5-(4-(2-(6-methylpyridin-3-yl)ethynyl)phenoxy)-1H-1,2,3-triazole-4-carboxylic acid | 320.3 |
| 298 | 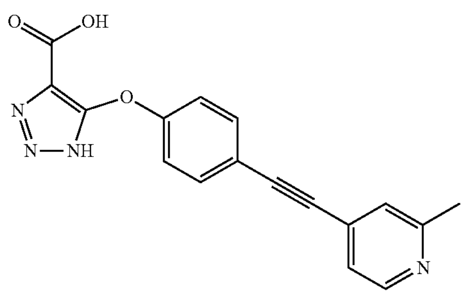 [SMILES: Cc1cc(C#Cc2ccc(Oc3[nH]nnc3C(=O)O)cc2)ccn1] | 5-(4-(2-(2-methylpyridin-4-yl)ethynyl)phenoxy)-1H-1,2,3-triazole-4-carboxylic acid | 320.3 |
| 299 | 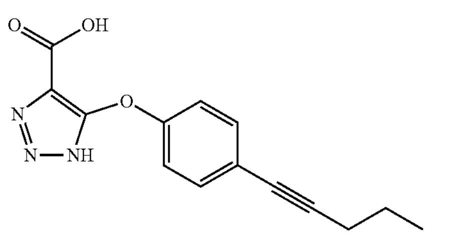 [SMILES: CCCC#Cc1ccc(Oc2[nH]nnc2C(=O)O)cc1] | 5-(4-(pent-1-ynyl)phenoxy)-1H-1,2,3-triazole-4-carboxylic acid | 271.27 |
| 300 | 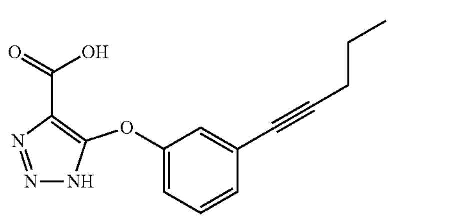 [SMILES: CCCC#Cc1cccc(Oc2[nH]nnc2C(=O)O)c1] | 5-(3-(pent-1-ynyl)phenoxy)-1H-1,2,3-triazole-4-carboxylic acid | 271.27 |

… 287 …

TABLE 1-continued

Example Compounds

| Ex. No. | Structure | IUPAC Name | MW (g/mol) |
|---|---|---|---|
| 301 | 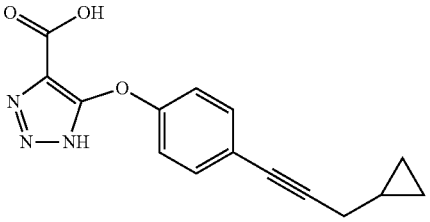 [SMILES: O=C(O)c1nn[nH]c1Oc1ccc(C#CCC2CC2)cc1] | 5-(4-(3-cyclopropylprop-1-ynyl)phenoxy)-1H-1,2,3-triazole-4-carboxylic acid | 283.28 |
| 302 | 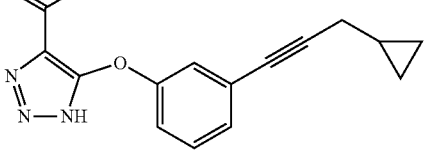 | 5-(3-(3-cyclopropylprop-1-ynyl)phenoxy)-1H-1,2,3-triazole-4-carboxylic acid | 283.28 |
| 303 | 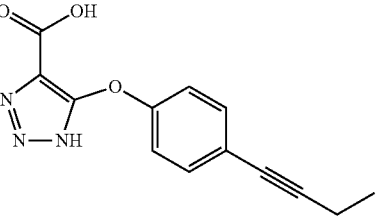 | 5-(4-(but-1-ynyl)phenoxy)-1H-1,2,3-triazole-4-carboxylic acid | 257.24 |
| 304 | 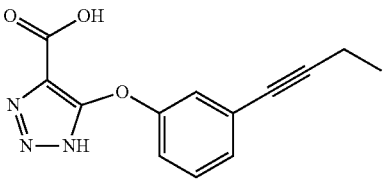 [SMILES: CCC#Cc1cccc(Oc2[nH]nnc2C(=O)O)c1] | 5-(3-(but-1-ynyl)phenoxy)-1H-1,2,3-triazole-4-carboxylic acid | 257.24 |
| 305 | 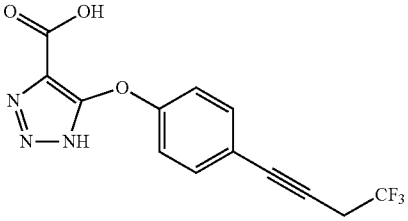 [SMILES: O=C(O)c1nn[nH]c1Oc1ccc(C#CCC(F)(F)F)cc1] | 5-(4-(4,4,4-trifluorobut-1-ynyl)phenoxy)-1H-1,2,3-triazole-4-carboxylic acid | 311.05 |
| 306 | 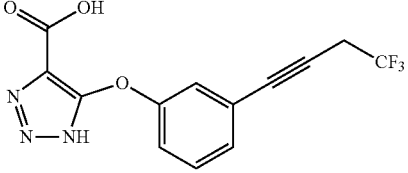 [SMILES: O=C(O)c1nn[nH]c1Oc1cccc(C#CCC(F)(F)F)c1] | 5-(3-(4,4,4-trifluorobut-1-ynyl)phenoxy)-1H-1,2,3-triazole-4-carboxylic acid | 311.22 |
| 307 | 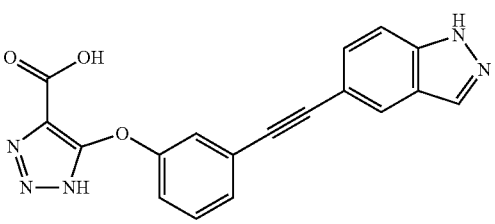 [SMILES: O=C(O)c1nn[nH]c1Oc1cccc(C#Cc2ccc3[nH]ncc3c2)c1] | 5-(3-(2-(1H-indazol-5-yl)ethynyl)phenoxy)-1H-1,2,3-triazole-4-carboxylic acid | 345.31 |

TABLE 1-continued

Example Compounds

| Ex. No. | Structure | IUPAC Name | MW (g/mol) |
|---|---|---|---|
| 308 | 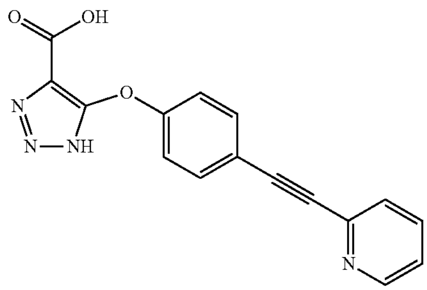 [SMILES: O=C(O)c1nn[nH]c1Oc1ccc(C#Cc2ccccn2)cc1] | 5-(4-(2-(pyridin-2-yl)ethynyl)phenoxy)-1H-1,2,3-triazole-4-carboxylic acid | 306.28 |
| 309 | 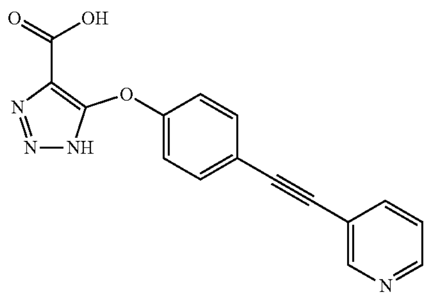 [SMILES: O=C(O)c1nn[nH]c1Oc1ccc(C#Cc2cccnc2)cc1] | 5-(4-(2-(pyridin-3-yl)ethynyl)phenoxy)-1H-1,2,3-triazole-4-carboxylic acid | 306.28 |
| 310 | 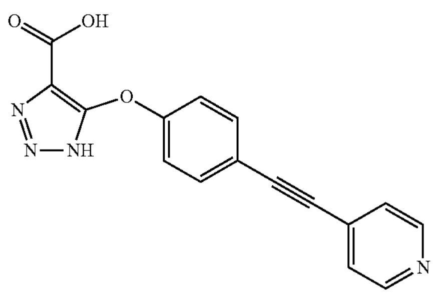 [SMILES: O=C(O)c1nn[nH]c1Oc1ccc(C#Cc2ccncc2)cc1] | 5-(4-(2-(pyridin-4-yl)ethynyl)phenoxy)-1H-1,2,3-triazole-4-carboxylic acid | 306.28 |
| 311 | 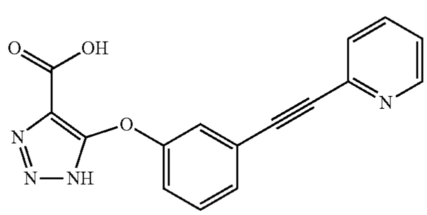 | 5-(3-(2-(pyridin-2-yl)ethynyl)phenoxy)-1H-1,2,3-triazole-4-carboxylic acid | 306.28 |
| 312 | 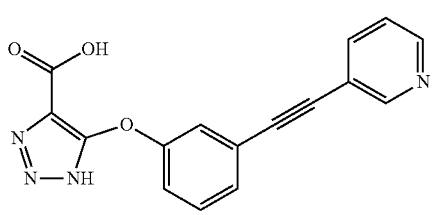 [SMILES: O=C(O)c1nn[nH]c1Oc1cccc(C#Cc2cccnc2)c1] | 5-(3-(2-(pyridin-3-yl)ethynyl)phenoxy)-1H-1,2,3-triazole-4-carboxylic acid | 306.28 |
| 313 | 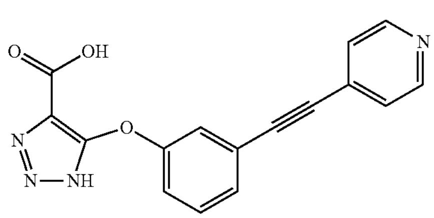 [SMILES: O=C(O)c1nn[nH]c1Oc1cccc(C#Cc2ccncc2)c1] | 5-(3-(2-(pyridin-4-yl)ethynyl)phenoxy)-1H-1,2,3-triazole-4-carboxylic acid | 306.28 |

TABLE 1-continued

Example Compounds

| Ex. No. | Structure | IUPAC Name | MW (g/mol) |
|---|---|---|---|
| 314 | 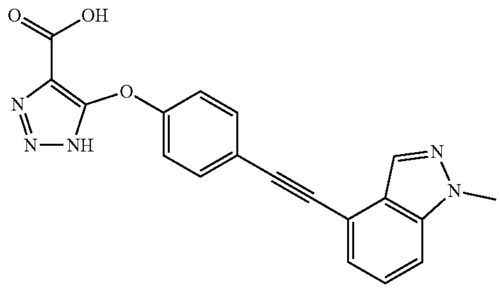 [SMILES: Cn1ncc2c(C#Cc3ccc(Oc4[nH]nnc4C(=O)O)cc3)cccc21] | 5-(4-(2-(1-methyl-1H-indazol-4-yl)ethynyl)phenoxy)-1H-1,2,3-triazole-4-carboxylic acid | 359.34 |
| 315 | 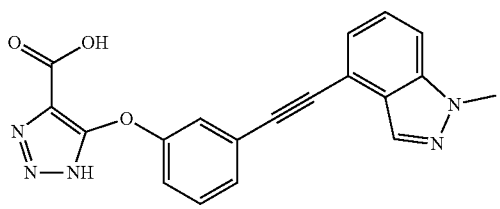 [SMILES: Cn1ncc2c(C#Cc3cccc(Oc4[nH]nnc4C(=O)O)c3)cccc21] | 5-(3-(2-(1-methyl-1H-indazol-4-yl)ethynyl)phenoxy)-1H-1,2,3-triazole-4-carboxylic acid | 359.34 |
| 316 | 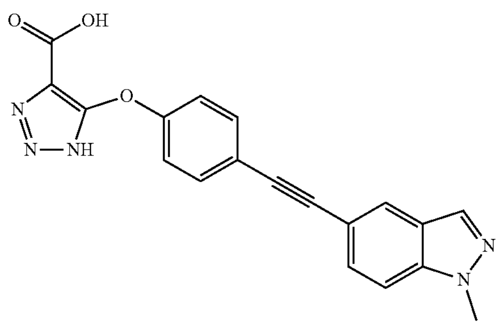 [SMILES: Cn1ncc2cc(C#Cc3ccc(Oc4[nH]nnc4C(=O)O)cc3)ccc21] | 5-(4-(2-(1-methyl-1H-indazol-5-yl)ethynyl)phenoxy)-1H-1,2,3-triazole-4-carboxylic acid | 359.34 |
| 317 | 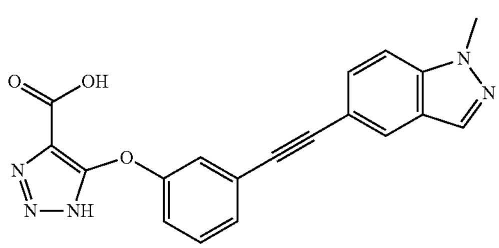 [SMILES: Cn1ncc2cc(C#Cc3cccc(Oc4[nH]nnc4C(=O)O)c3)ccc21] | 5-(3-(2-(1-methyl-1H-indazol-5-yl)ethynyl)phenoxy)-1H-1,2,3-triazole-4-carboxylic acid | 359.34 |
| 318 | 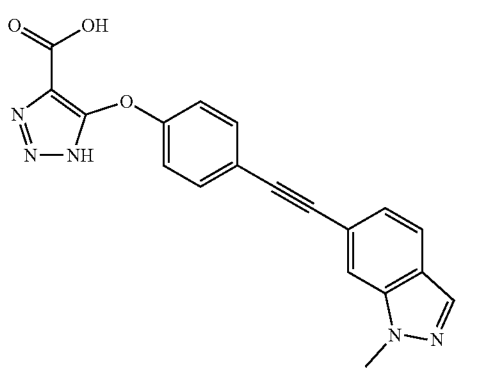 [SMILES: Cn1ncc2ccc(C#Cc3ccc(Oc4[nH]nnc4C(=O)O)cc3)cc21] | 5-(4-(2-(1-methyl-1H-indazol-6-yl)ethynyl)phenoxy)-1H-1,2,3-triazole-4-carboxylic acid | 359.34 |

TABLE 1-continued

Example Compounds

| Ex. No. | Structure | IUPAC Name | MW (g/mol) |
|---|---|---|---|
| 319 | 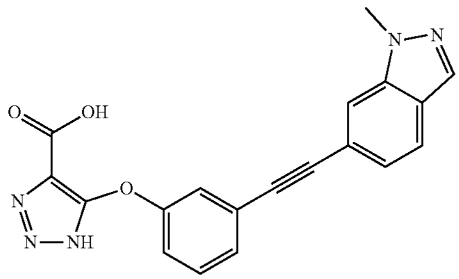 [SMILES: Cn1ncc2ccc(C#Cc3cccc(Oc4[nH]nnc4C(=O)O)c3)cc21] | 5-(3-(2-(1-methyl-1H-indazol-6-yl)ethynyl)phenoxy)-1H-1,2,3-triazole-4-carboxylic acid | 359.34 |
| 320 | 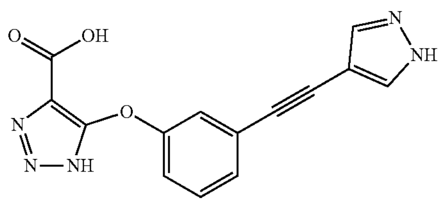 [SMILES: O=C(O)c1nn[nH]c1Oc1cccc(C#Cc2cn[nH]c2)c1] | 5-(3-(2-(1H-pyrazol-4-yl)ethynyl)phenoxy)-1H-1,2,3-triazole-4-carboxylic acid | 295.25 |
| 321 | 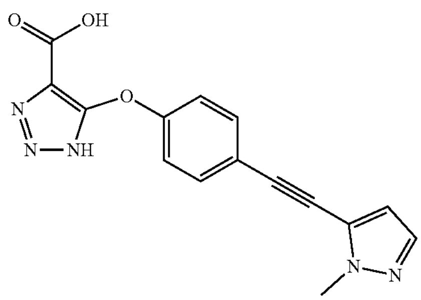 [SMILES: Cn1nccc1C#Cc1ccc(Oc2[nH]nnc2C(=O)O)cc1] | 5-(4-(2-(1-methyl-1H-pyrazol-5-yl)ethynyl)phenoxy)-1H-1,2,3-triazole-4-carboxylic acid | 309.28 |
| 322 | 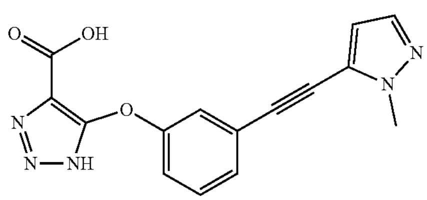 [SMILES: Cn1nccc1C#Cc1cccc(Oc2[nH]nnc2C(=O)O)c1] | 5-(3-(2-(1-methyl-1H-pyrazol-5-yl)ethynyl)phenoxy)-1H-1,2,3-triazole-4-carboxylic acid | 309.28 |
| 323 | 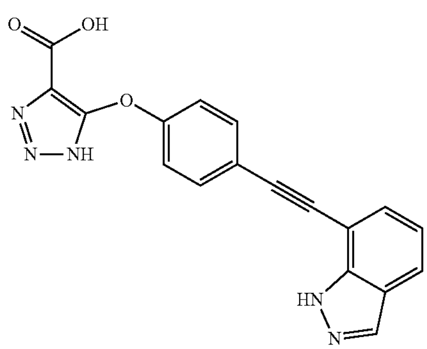 [SMILES: O=C(O)c1nn[nH]c1Oc1ccc(C#Cc2cccc3cn[nH]c23)cc1] | 5-(4-(2-(1H-indazol-7-yl)ethynyl)phenoxy)-1H-1,2,3-triazole-4-carboxylic acid | 345.31 |
| 324 | 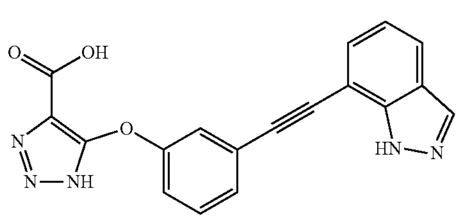 [SMILES: O=C(O)c1nn[nH]c1Oc1cccc(C#Cc2cccc3cn[nH]c23)c1] | 5-(3-(2-(1H-indazol-7-yl)ethynyl)phenoxy)-1H-1,2,3-triazole-4-carboxylic acid | 345.31 |

TABLE 1-continued

Example Compounds

| Ex. No. | Structure | IUPAC Name | MW (g/mol) |
|---|---|---|---|
| 325 | 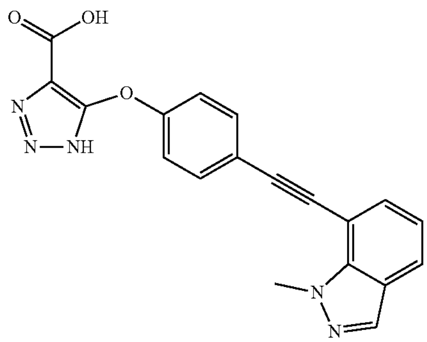 [SMILES: Cn1ncc2cccc(C#Cc3ccc(Oc4[nH]nnc4C(=O)O)cc3)c21] | 5-(4-(2-(1-methyl-1H-indazol-7-yl)ethynyl)phenoxy)-1H-1,2,3-triazole-4-carboxylic acid | 359.34 |
| 326 | 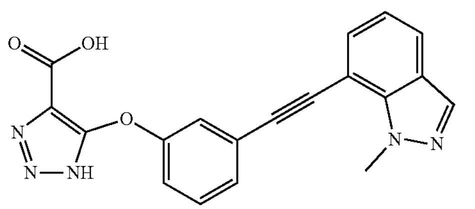 [SMILES: Cn1ncc2cccc(C#Cc3cccc(Oc4[nH]nnc4C(=O)O)c3)c21] | 5-(3-(2-(1-methyl-1H-indazol-7-yl)ethynyl)phenoxy)-1H-1,2,3-triazole-4-carboxylic acid | 359.34 |
| 327 | 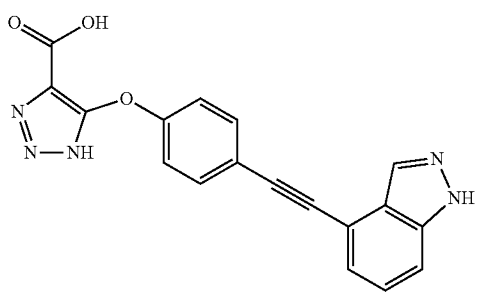 [SMILES: O=C(O)c1nn[nH]c1Oc1ccc(C#Cc2cccc3[nH]ncc23)cc1] | 5-(4-(2-(1H-indazol-4-yl)ethynyl)phenoxy)-1H-1,2,3-triazole-4-carboxylic acid | 345.31 |
| 328 | 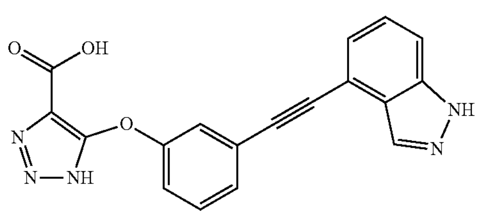 [SMILES: O=C(O)c1nn[nH]c1Oc1cccc(C#Cc2cccc3[nH]ncc23)c1] | 5-(3-(2-(1H-indazol-4-yl)ethynyl)phenoxy)-1H-1,2,3-triazole-4-carboxylic acid | 345.31 |
| 329 | 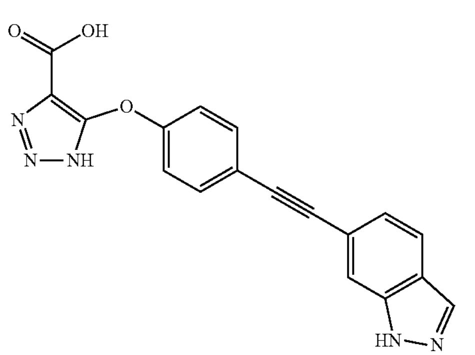 [SMILES: O=C(O)c1nn[nH]c1Oc1ccc(C#Cc2ccc3cn[nH]c3c2)cc1] | 5-(4-(2-(1H-indazol-6-yl)ethynyl)phenoxy)-1H-1,2,3-triazole-4-carboxylic acid | 345.31 |

TABLE 1-continued

Example Compounds

| Ex. No. | Structure | IUPAC Name | MW (g/mol) |
|---|---|---|---|
| 330 | 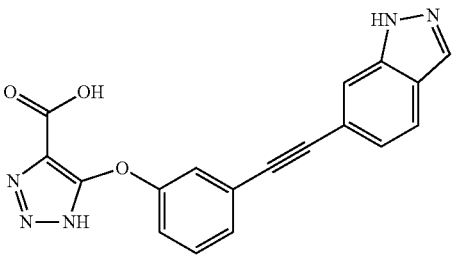 [SMILES: O=C(O)c1nn[nH]c1Oc1cccc(C#Cc2ccc3cn[nH]c3c2)c1] | 5-(3-(2-(1H-indazol-6-yl)ethynyl)phenoxy)-1H-1,2,3-triazole-4-carboxylic acid | 345.31 |
| 331 | 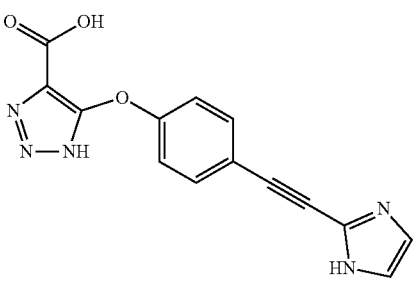 [SMILES: O=C(O)c1nn[nH]c1Oc1ccc(C#Cc2ncc[nH]2)cc1] | 5-(4-(2-(1H-imidazol-2-yl)ethynyl)phenoxy)-1H-1,2,3-triazole-4-carboxylic acid | 295.25 |
| 332 | 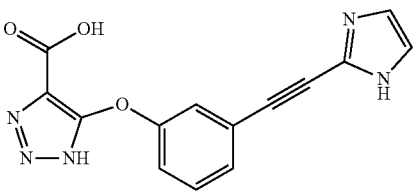 [SMILES: O=C(O)c1nn[nH]c1Oc1cccc(C#Cc2ncc[nH]2)c1] | 5-(3-(2-(1H-imidazol-2-yl)ethynyl)phenoxy)-1H-1,2,3-triazole-4-carboxylic acid | 295.25 |
| 333 | 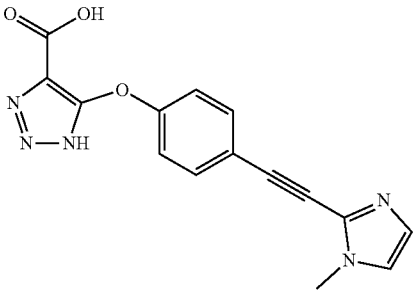 [SMILES: Cn1ccnc1C#Cc1ccc(Oc2[nH]nnc2C(=O)O)cc1] | 5-(4-(2-(1-methyl-1H-imidazol-2-yl)ethynyl)phenoxy)-1H-1,2,3-triazole-4-carboxylic acid | 309.28 |
| 334 | 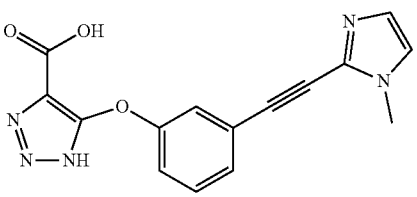 [SMILES: Cn1ccnc1C#Cc1cccc(Oc2[nH]nnc2C(=O)O)c1] | 5-(3-(2-(1-methyl-1H-imidazol-2-yl)ethynyl)phenoxy)-1H-1,2,3-triazole-4-carboxylic acid | 309.28 |
| 335 | 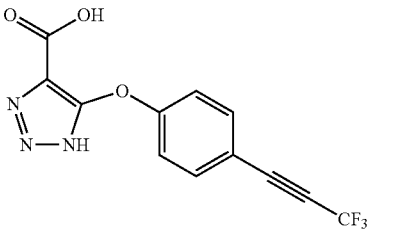 | 5-(4-(3,3,3-trifluoroprop-1-ynyl)phenoxy)-1H-1,2,3-triazole-4-carboxylic acid | 297.19 |

TABLE 1-continued

Example Compounds

| Ex. No. | Structure | IUPAC Name | MW (g/mol) |
|---|---|---|---|
| 336 | 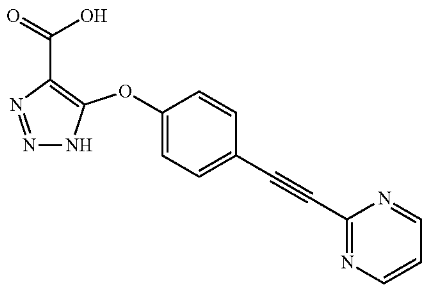 [SMILES: O=C(O)c1nn[nH]c1Oc1ccc(C#Cc2ncccn2)cc1] | 5-(4-(2-(pyrimidin-2-yl)ethynyl)phenoxy)-1H-1,2,3-triazole-4-carboxylic acid | 307.26 |
| 337 | 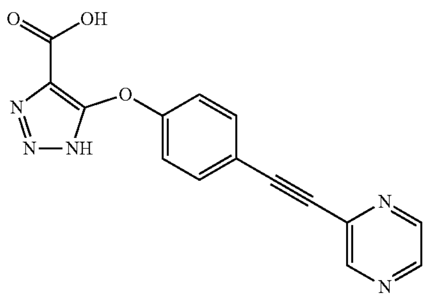 [SMILES: O=C(O)c1nn[nH]c1Oc1ccc(C#Cc2cnccn2)cc1] | 5-(4-(2-(pyrazin-2-yl)ethynyl)phenoxy)-1H-1,2,3-triazole-4-carboxylic acid | 307.26 |
| 338 | 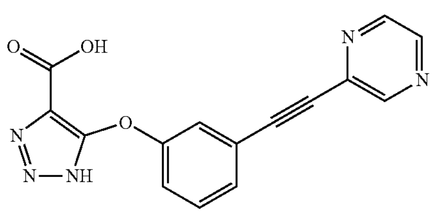 [SMILES: O=C(O)c1nn[nH]c1Oc1cccc(C#Cc2cnccn2)c1] | 5-(3-(2-(pyrazin-2-yl)ethynyl)phenoxy)-1H-1,2,3-triazole-4-carboxylic acid | 307.26 |
| 339 | 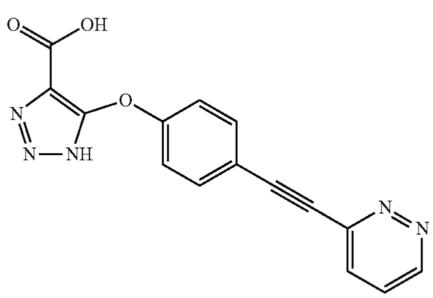 [SMILES: O=C(O)c1nn[nH]c1Oc1ccc(C#Cc2cccnn2)cc1] | 5-(4-(2-(pyridazin-3-yl)ethynyl)phenoxy)-1H-1,2,3-triazole-4-carboxylic acid | 307.26 |
| 340 | 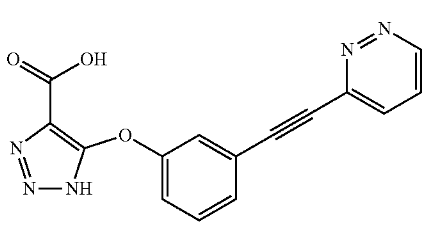 [SMILES: O=C(O)c1nn[nH]c1Oc1cccc(C#Cc2cccnn2)c1] | 5-(3-(2-(pyridazin-3-yl)ethynyl)phenoxy)-1H-1,2,3-triazole-4-carboxylic acid | 307.26 |

TABLE 1-continued

Example Compounds

| Ex. No. | Structure | IUPAC Name | MW (g/mol) |
|---|---|---|---|
| 341 | 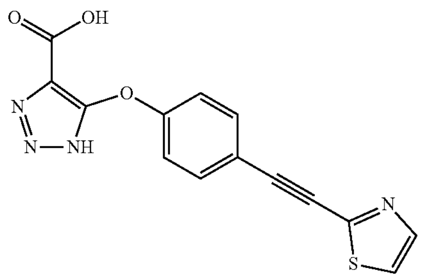 [SMILES: O=C(O)c1nn[nH]c1Oc1ccc(C#Cc2nccs2)cc1] | 5-(4-(2-(thiazol-2-yl)ethynyl)phenoxy)-1H-1,2,3-triazole-4-carboxylic acid | 312.3 |
| 342 | 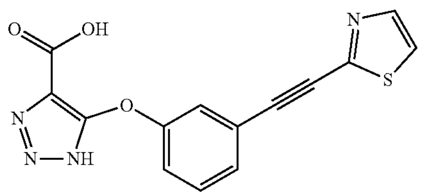 [SMILES: O=C(O)c1nn[nH]c1Oc1cccc(C#Cc2nccs2)c1] | 5-(3-(2-(thiazol-2-yl)ethynyl)phenoxy)-1H-1,2,3-triazole-4-carboxylic acid | 312.3 |
| 343 | 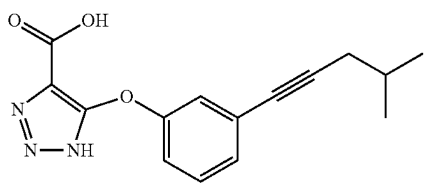 [SMILES: CC(C)CC#Cc1cccc(Oc2[nH]nnc2C(=O)O)c1] | 5-(3-(4-methylpent-1-ynyl)phenoxy)-1H-1,2,3-triazole-4-carboxylic acid | 285.3 |
| 344 | 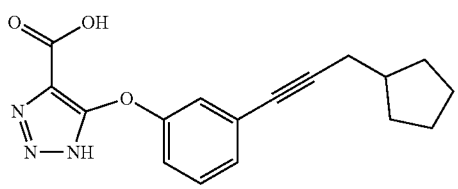 [SMILES: O=C(O)c1nn[nH]c1Oc1cccc(C#CCC2CCCC2)c1] | 5-(3-(3-cyclopentylprop-1-ynyl)phenoxy)-1H-1,2,3-triazole-4-carboxylic acid | 311.34 |
| 345 | 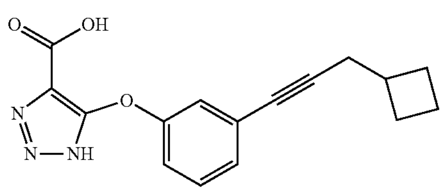 [SMILES: O=C(O)c1nn[nH]c1Oc1cccc(C#CCC2CCC2)c1] | 5-(3-(3-cyclobutylprop-1-ynyl)phenoxy)-1H-1,2,3-triazole-4-carboxylic acid | 297.31 |
| 346 | 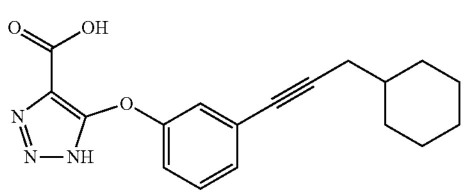 [SMILES: O=C(O)c1nn[nH]c1Oc1cccc(C#CCC2CCCCC2)c1] | 5-(3-(3-cyclohexylprop-1-ynyl)phenoxy)-1H-1,2,3-triazole-4-carboxylic acid | 325.36 |
| 347 | 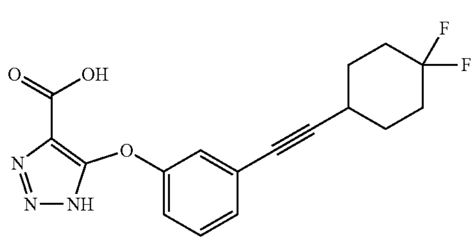 [SMILES: O=C(O)c1nn[nH]c1Oc1cccc(C#CC2CCC(F)(F)CC2)c1] | 5-(3-(2-(4,4-difluorocyclohexyl)ethynyl)phenoxy)-1H-1,2,3-triazole-4-carboxylic acid | 347.32 |

TABLE 1-continued

Example Compounds

| Ex. No. | Structure | IUPAC Name | MW (g/mol) |
|---|---|---|---|
| 348 | 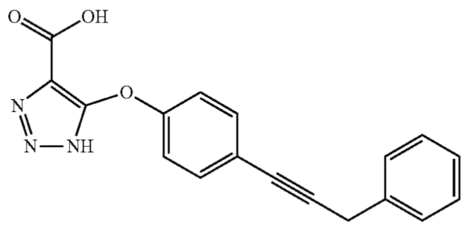 [SMILES: O=C(O)c1nn[nH]c1Oc1ccc(C#CCc2ccccc2)cc1] | 5-(4-(3-phenylprop-1-ynyl)phenoxy)-1H-1,2,3-triazole-4-carboxylic acid | 319.31 |
| 349 | 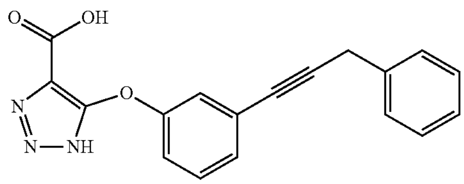 [SMILES: O=C(O)c1nn[nH]c1Oc1cccc(C#CCc2ccccc2)c1] | 5-(3-(3-phenylprop-1-ynyl)phenoxy)-1H-1,2,3-triazole-4-carboxylic acid | 319.31 |
| 350 | 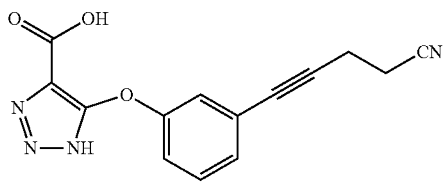 [SMILES: N#CCCC#Cc1cccc(Oc2[nH]nnc2C(=O)O)c1] | 5-(3-(4-cyanobut-1-ynyl)phenoxy)-1H-1,2,3-triazole-4-carboxylic acid | 282.25 |
| 351 | 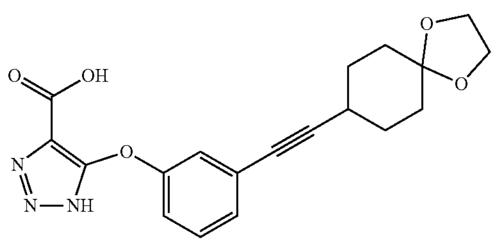 [SMILES: O=C(O)c1nn[nH]c1Oc1cccc(C#CC2CCC3(CC2)OCCO3)c1] | 5-(3-(1,4-dioxaspiro[4.5]decan-8-ylethynyl)phenoxy)-1H-1,2,3-triazole-4-carboxylic acid | 369.37 |
| 352 | 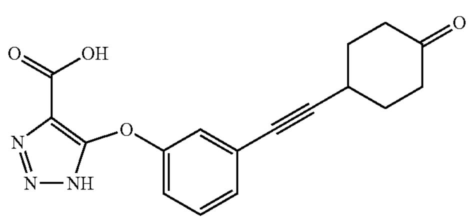 [SMILES: O=C1CCC(C#Cc2cccc(Oc3[nH]nnc3C(=O)O)c2)CC1] | 5-(3-((4-oxocyclohexyl)ethynyl)phenoxy)-1H-1,2,3-triazole-4-carboxylic acid | 325.32 |
| 353 | 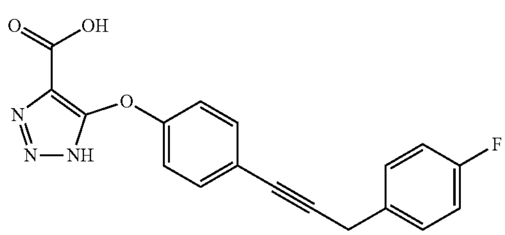 [SMILES: O=C(O)c1nn[nH]c1Oc1ccc(C#CCc2ccc(F)cc2)cc1] | 5-(4-(3-(4-fluorophenyl)prop-1-ynyl)phenoxy)-1H-1,2,3-triazole-4-carboxylic acid | 337.3 |
| 354 | 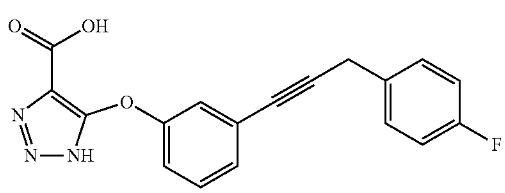 [SMILES: O=C(O)c1nn[nH]c1Oc1cccc(C#CCc2ccc(F)cc2)c1] | 5-(3-(3-(4-fluorophenyl)prop-1-ynyl)phenoxy)-1H-1,2,3-triazole-4-carboxylic acid | 337.3 |

TABLE 1-continued

Example Compounds

| Ex. No. | Structure | IUPAC Name | MW (g/mol) |
|---|---|---|---|
| 355 | 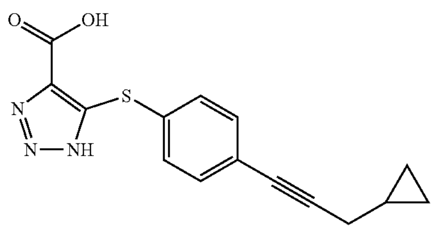 | 5-(4-(3-cyclopropylprop-1-ynyl)phenylthio)-1H-1,2,3-triazole-4-carboxylic acid | 299.35 |
| 356 | 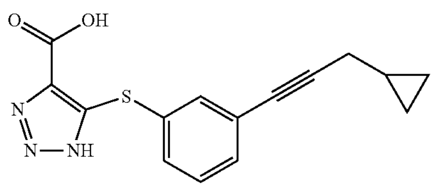 [SMILES: O=C(O)c1nn[nH]c1Sc1cccc(C#CCC2CC2)c1] | 5-(3-(3-cyclopropylprop-1-ynyl)phenylthio)-1H-1,2,3-triazole-4-carboxylic acid | 299.35 |
| 357 | 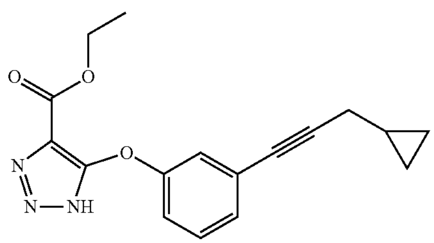 [SMILES: CCOC(=O)c1nn[nH]c1Oc1cccc(C#CCC2CC2)c1] | ethyl 5-(3-(3-cyclopropylprop-1-ynyl)phenoxy)-1H-1,2,3-triazole-4-carboxylate | 311.34 |
| 358 | 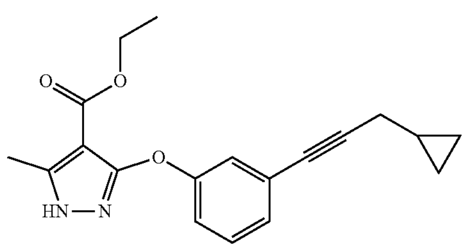 [SMILES: CCOC(=O)c1c(Oc2cccc(C#CCC3CC3)c2)n[nH]c1C] | ethyl 3-(3-(3-cyclopropylprop-1-ynyl)phenoxy)-5-methyl-1H-pyrazole-4-carboxylate | 324.37 |
| 359 | 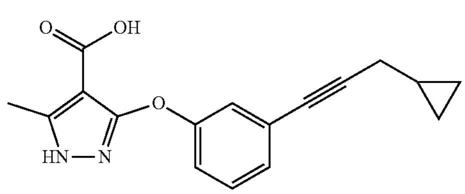 [SMILES: Cc1[nH]nc(Oc2cccc(C#CCC3CC3)c2)c1C(=O)O] | 3-(3-(3-cyclopropylprop-1-ynyl)phenoxy)-5-methyl-1H-pyrazole-4-carboxylic acid | 296.32 |
| 360 | 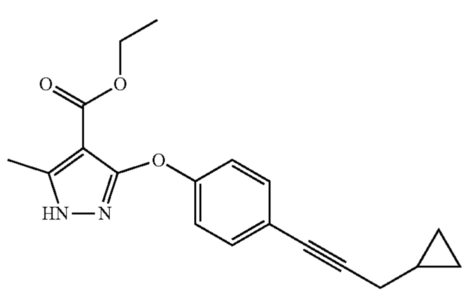 [SMILES: CCOC(=O)c1c(Oc2ccc(C#CCC3CC3)cc2)n[nH]c1C] | ethyl 3-(4-(3-cyclopropylprop-1-ynyl)phenoxy)-5-methyl-1H-pyrazole-4-carboxylate | 324.37 |

TABLE 1-continued

Example Compounds

| Ex. No. | Structure | IUPAC Name | MW (g/mol) |
|---|---|---|---|
| 361 | 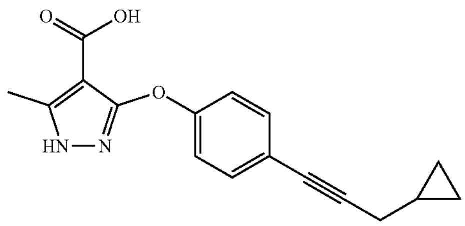 [SMILES: Cc1[nH]nc(Oc2ccc(C#CCC3CC3)cc2)c1C(=O)O] | 3-(4-(3-cyclopropylprop-1-ynyl)phenoxy)-5-methyl-1H-pyrazole-4-carboxylic acid | 296.32 |
| 362 | 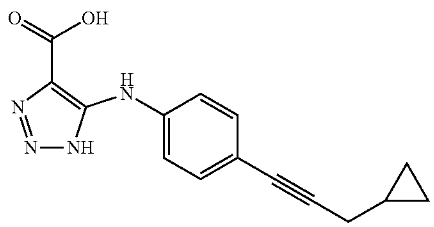 [SMILES: O=C(O)c1nn[nH]c1Nc1ccc(C#CCC2CC2)cc1] | 5-(4-(3-cyclopropylprop-1-ynyl)phenylamino)-1H-1,2,3-triazole-4-carboxylic acid | 282.3 |
| 363 | 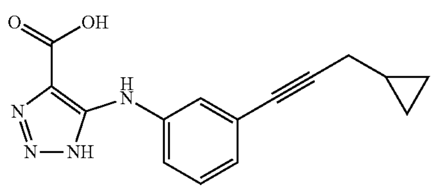 [SMILES: O=C(O)c1nn[nH]c1Nc1cccc(C#CCC2CC2)c1] | 5-(3-(3-cyclopropylprop-1-ynyl)phenylamino)-1H-1,2,3-triazole-4-carboxylic acid | 282.3 |
| 364 | 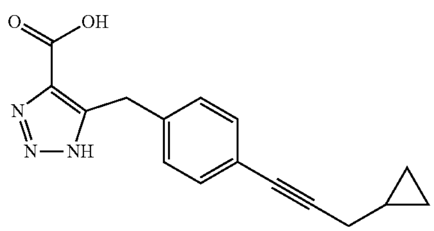 [SMILES: O=C(O)c1nn[nH]c1Cc1ccc(C#CCC2CC2)cc1] | 5-(4-(3-cyclopropylprop-1-ynyl)benzyl)-1H-1,2,3-triazole-4-carboxylic acid | 281.31 |
| 365 | 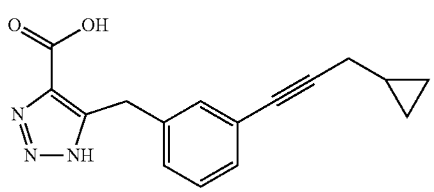 [SMILES: O=C(O)c1nn[nH]c1Cc1cccc(C#CCC2CC2)c1] | 5-(3-(3-cyclopropylprop-1-ynyl)benzyl)-1H-1,2,3-triazole-4-carboxylic acid | 281.31 |
| 366 | 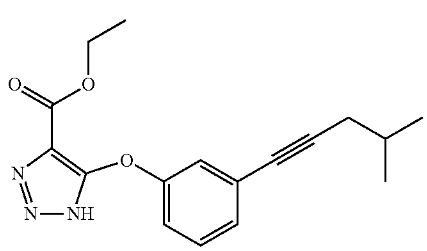 [SMILES: CCOC(=O)c1nn[nH]c1Oc1cccc(C#CCC(C)C)c1] | ethyl 5-(3-(4-methylpent-1-ynyl)phenoxy)-1H-1,2,3-triazole-4-carboxylate | 313.35 |
| 367 | 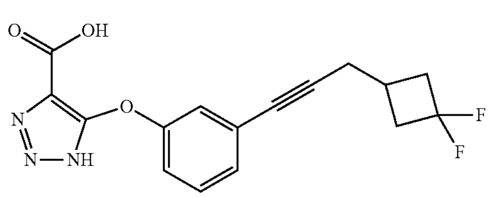 [SMILES: O=C(O)c1nn[nH]c1Oc1cccc(C#CCC2CC(F)(F)C2)c1] | 5-(3-(3-(3,3-difluorocyclobutyl)prop-1-ynyl)phenoxy)-1H-1,2,3-triazole-4-carboxylic acid | 333.29 |

TABLE 1-continued

Example Compounds

| Ex. No. | Structure | IUPAC Name | MW (g/mol) |
|---|---|---|---|
| 368 | 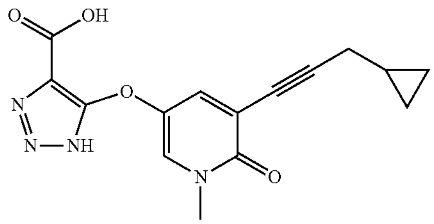 [SMILES: Cn1cc(Oc2[nH]nnc2C(=O)O)cc(C#CCC2CC2)c1=O] | 5-(5-(3-cyclopropylprop-1-ynyl)-1,6-dihydro-1-methyl-6-oxopyridin-3-yloxy)-1H-1,2,3-triazole-4-carboxylic acid | 314.3 |
| 369 | 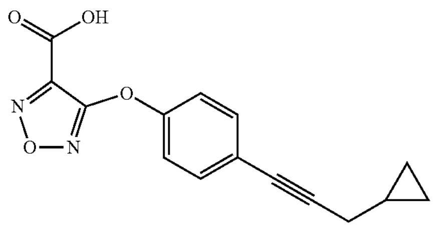 | 4-(4-(3-cyclopropylprop-1-ynyl)phenoxy)-1,2,5-oxadiazole-3-carboxylic acid | 284.27 |
| 370 | 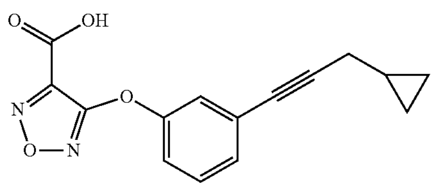 | 4-(3-(3-cyclopropylprop-1-ynyl)phenoxy)-1,2,5-oxadiazole-3-carboxylic acid | 284.27 |
| 371 | 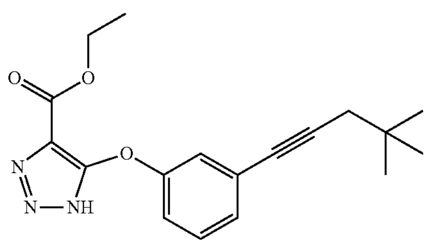 [SMILES: CCOC(=O)c1nn[nH]c1Oc1cccc(C#CCC(C)(C)C)c1] | ethyl 5-(3-(4,4-dimethylpent-1-ynyl)phenoxy)-1H-1,2,3-triazole-4-carboxylate | 327.38 |
| 372 | 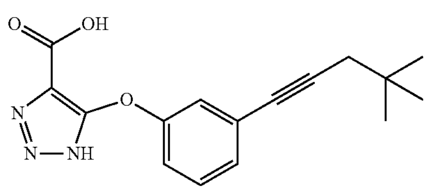 [SMILES: CC(C)(C)CC#Cc1cccc(Oc2[nH]nnc2C(=O)O)c1] | 5-(3-(4,4-dimethylpent-1-ynyl)phenoxy)-1H-1,2,3-triazole-4-carboxylic acid | 299.32 |
| 373 | 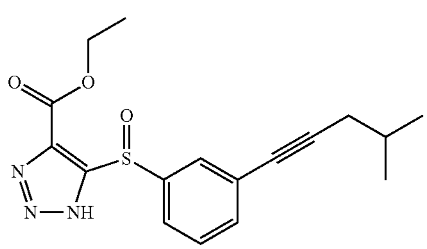 [SMILES: CCOC(=O)c1nn[nH]c1S(=O)c1cccc(C#CCC(C)C)c1] | ethyl 5-(3-(4-methylpent-1-ynyl)phenylsulfinyl)-1H-1,2,3-triazole-4-carboxylate | 345.42 |
| 374 | 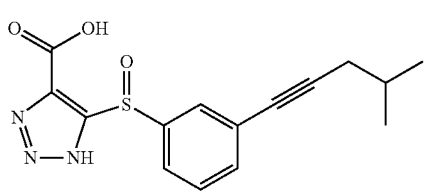 [SMILES: CC(C)CC#Cc1cccc(S(=O)c2[nH]nnc2C(=O)O)c1] | 5-(3-(4-methylpent-1-ynyl)phenylsulfinyl)-1H-1,2,3-triazole-4-carboxylic acid | 317.36 |

TABLE 1-continued

Example Compounds

| Ex. No. | Structure | IUPAC Name | MW (g/mol) |
|---|---|---|---|
| 375 | 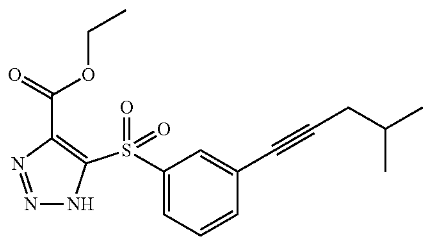 [SMILES: CCOC(=O)c1nn[nH]c1S(=O)(=O)c1cccc(C#CCC(C)C)c1] | ethyl 5-(3-(4-methylpent-1-ynyl)phenylsulfonyl)-1H-1,2,3-triazole-4-carboxylate | 361.42 |
| 376 | 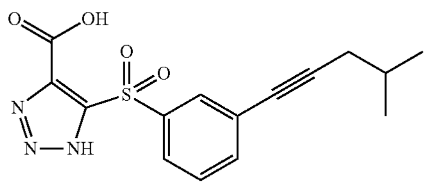 [SMILES: CC(C)CC#Cc1cccc(S(=O)(=O)c2[nH]nnc2C(=O)O)c1] | 5-(3-(4-methylpent-1-ynyl)phenylsulfonyl)-1H-1,2,3-triazole-4-carboxylic acid | 333.36 |
| 377 | 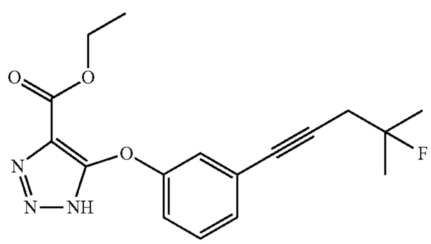 [SMILES: CCOC(=O)c1nn[nH]c1Oc1cccc(C#CCC(C)(C)F)c1] | ethyl 5-(3-(4-fluoro-4-methylpent-1-ynyl)phenoxy)-1H-1,2,3-triazole-4-carboxylate | 331.34 |
| 378 | 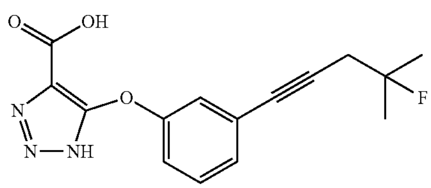 [SMILES: CC(C)(F)CC#Cc1cccc(Oc2[nH]nnc2C(=O)O)c1] | 5-(3-(4-fluoro-4-methylpent-1-ynyl)phenoxy)-1H-1,2,3-triazole-4-carboxylic acid | 303.29 |
| 379 | 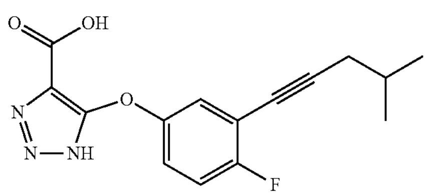 [SMILES: CC(C)CC#Cc1cc(Oc2[nH]nnc2C(=O)O)ccc1F] | 5-(4-fluoro-3-(4-methylpent-1-ynyl)phenoxy)-1H-1,2,3-triazole-4-carboxylic acid | 303.29 |
| 380 | 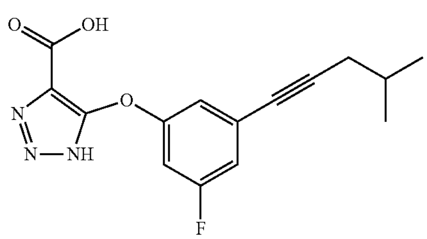 [SMILES: CC(C)CC#Cc1cc(F)cc(Oc2[nH]nnc2C(=O)O)c1] | 5-(3-fluoro-5-(4-methylpent-1-ynyl)phenoxy)-1H-1,2,3-triazole-4-carboxylic acid | 303.29 |
| 381 | 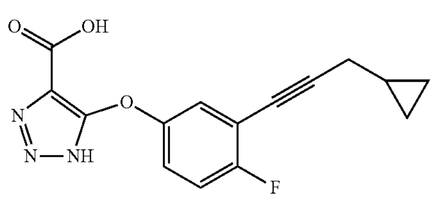 [SMILES: O=C(O)c1nn[nH]c1Oc1ccc(F)c(C#CCC2CC2)c1] | 5-(3-(3-cyclopropylprop-1-ynyl)-4-fluorophenoxy)-1H-1,2,3-triazole-4-carboxylic acid | 301.27 |

TABLE 1-continued

Example Compounds

| Ex. No. | Structure | IUPAC Name | MW (g/mol) |
|---|---|---|---|
| 382 | 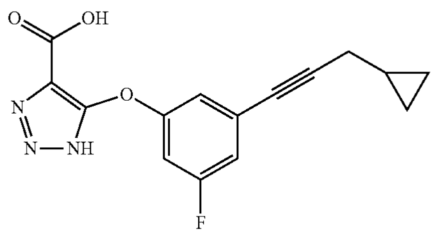 [SMILES: O=C(O)c1nn[nH]c1Oc1cc(F)cc(C#CCC2CC2)c1] | 5-(3-(3-cyclopropylprop-1-ynyl)-5-fluorophenoxy)-1H-1,2,3-triazole-4-carboxylic acid | 301.27 |
| 383 | 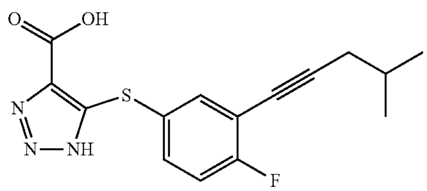 [SMILES: CC(C)CC#Cc1cc(Sc2[nH]nnc2C(=O)O)ccc1F] | 5-(4-fluoro-3-(4-methylpent-1-ynyl)phenylthio)-1H-1,2,3-triazole-4-carboxylic acid | 319.35 |
| 384 | 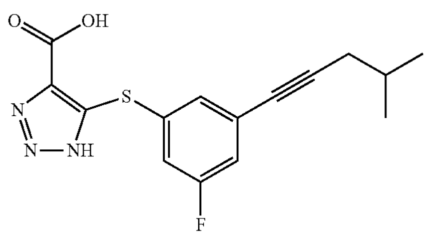 [SMILES: CC(C)CC#Cc1cc(F)cc(Sc2[nH]nnc2C(=O)O)c1] | 5-(3-fluoro-5-(4-methylpent-1-ynyl)phenylthio)-1H-1,2,3-triazole-4-carboxylic acid | 319.35 |
| 385 | 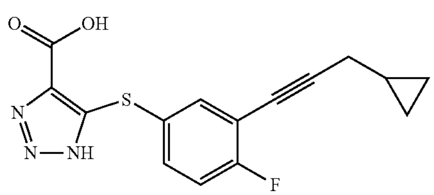 [SMILES: O=C(O)c1nn[nH]c1Sc1ccc(F)c(C#CCC2CC2)c1] | 5-(3-(3-cyclopropylprop-1-ynyl)-4-fluorophenylthio)-1H-1,2,3-triazole-4-carboxylic acid | 317.34 |
| 386 | 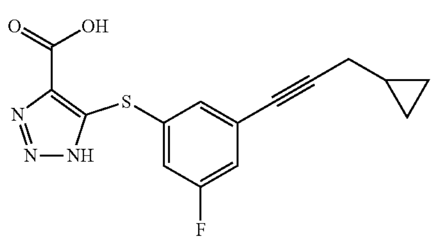 [SMILES: O=C(O)c1nn[nH]c1Sc1cc(F)cc(C#CCC2CC2)c1] | 5-(3-(3-cyclopropylprop-1-ynyl)-5-fluorophenylthio)-1H-1,2,3-triazole-4-carboxylic acid | 317.34 |
| 387 | 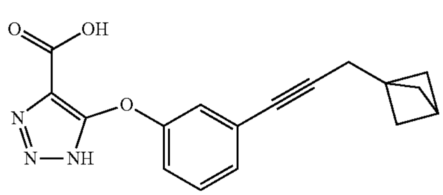 [SMILES: O=C(O)c1nn[nH]c1Oc1cccc(C#CCC23CC(C2)C3)c1] | 5-(3-(3-(bicyclo[1.1.1]pentan-1-yl)prop-1-ynyl)phenoxy)-1H-1,2,3-triazole-4-carboxylic acid | 309.32 |
| 388 | 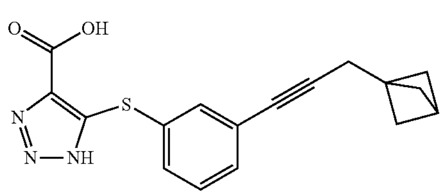 [SMILES: O=C(O)c1nn[nH]c1Sc1cccc(C#CCC23CC(C2)C3)c1] | 5-(3-(3-(bicyclo[1.1.1]pentan-1-yl)prop-1-ynyl)phenylthio)-1H-1,2,3-triazole-4-carboxylic acid | 325.38 |

TABLE 1-continued

Example Compounds

| Ex. No. | Structure | IUPAC Name | MW (g/mol) |
|---|---|---|---|
| 389 | 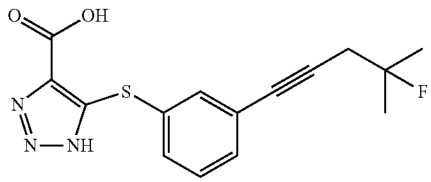 [SMILES: CC(C)(F)CC#Cc1cccc(Sc2[nH]nnc2C(=O)O)c1] | 5-(3-(4-fluoro-4-methylpent-1-ynyl)phenylthio)-1H-1,2,3-triazole-4-carboxylic acid | 319.35 |
| 390 | 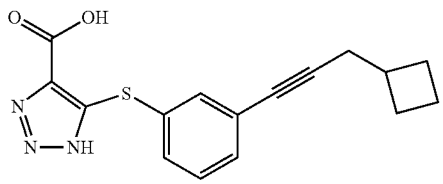 | 5-(3-(3-cyclobutylprop-1-ynyl)phenylthio)-1H-1,2,3-triazole-4-carboxylic acid | 313.37 |
| 391 | 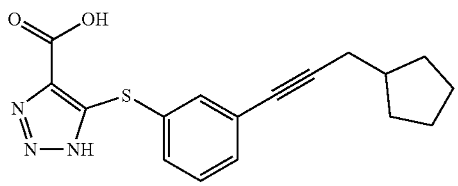 | (5-(3-(3-cyclopentylprop-1-ynyl)phenylthio)-1H-1,2,3-triazole-4-carboxylic acid | 327.4 |
| 392 | 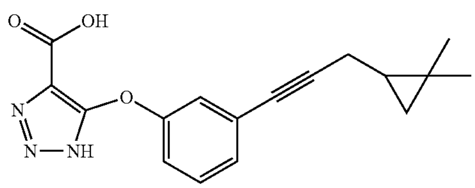 [SMILES: CC1(C)CC1CC#Cc1cccc(Oc2[nH]nnc2C(=O)O)c1] | 5-(3-(3-(2,2-dimethylcyclopropyl)prop-1-ynyl)phenoxy)-1H-1,2,3-triazole-4-carboxylic acid | 311.34 |
| 393 | 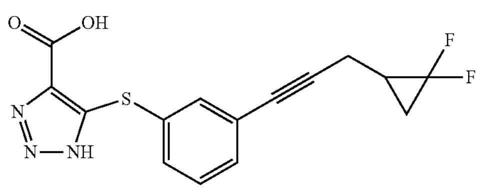 [SMILES: O=C(O)c1nn[nH]c1Sc1cccc(C#CCC2CC2(F)F)c1] | 5-(3-(3-(2,2-difluorocyclopropyl)prop-1-ynyl)phenylthio)-1H-1,2,3-triazole-4-carboxylic acid | 335.33 |
| 394 | 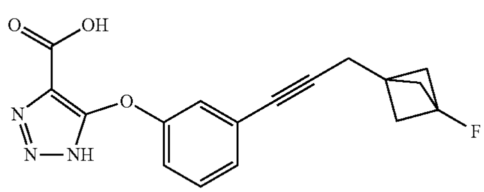 [SMILES: O=C(O)c1nn[nH]c1Oc1cccc(C#CCC23CC(F)(C2)C3)c1] | 5-(3-(3-(3-fluorobicyclo[1.1.1]pentan-1-yl)prop-1-ynyl)phenoxy)-1H-1,2,3-triazole-4-carboxylic acid | 327.31 |
| 395 | 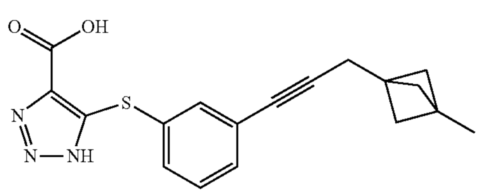 [SMILES: CC12CC(CC#Cc3cccc(Sc4[nH]nnc4C(=O)O)c3)(C1)C2] | 5-(3-(3-(3-methylbicyclo[1.1.1]pentan-1-yl)prop-1-ynyl)phenylthio)-1H-1,2,3-triazole-4-carboxylic acid | 339.41 |
| 396 | 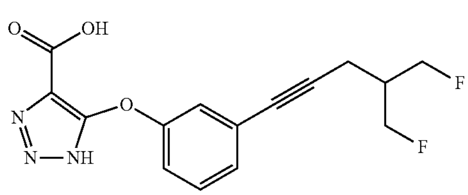 [SMILES: O=C(O)c1nn[nH]c1Oc1cccc(C#CCC(CF)CF)c1] | 5-(3-(5-fluoro-4-(fluoromethyl)pent-1-ynyl)phenoxy)-1H-1,2,3-triazole-4-carboxylic acid | 321.28 |

TABLE 1-continued

Example Compounds

| Ex. No. | Structure | IUPAC Name | MW (g/mol) |
|---|---|---|---|
| 397 | 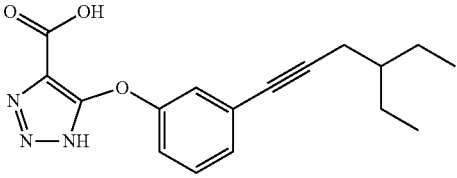 [SMILES: CCC(CC)CC#Cc1cccc(Oc2[nH]nnc2C(=O)O)c1] | 5-(3-(4-ethylhex-1-ynyl)phenoxy)-1H-1,2,3-triazole-4-carboxylic acid | 313.35 |
| 398 | 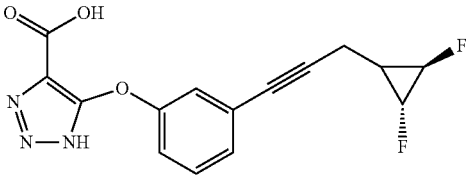 [SMILES: O=C(O)c1nn[nH]c1Oc1cccc(C#CCC2[C@@H](F)[C@@H]2F)c1] | 5-(3-(3-((2R,3R)-2,3-difluorocyclopropyl)prop-1-ynyl)phenoxy)-1H-1,2,3-triazole-4-carboxylic acid | 319.26 |
| 399 | 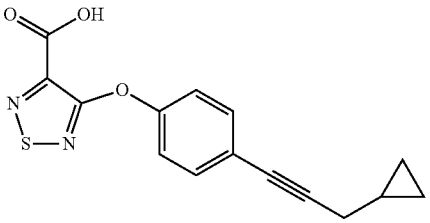 | 4-(4-(3-cyclopropylprop-1-ynyl)phenoxy)-1,2,5-thiadiazole-3-carboxylic acid | 300.33 |
| 400 | 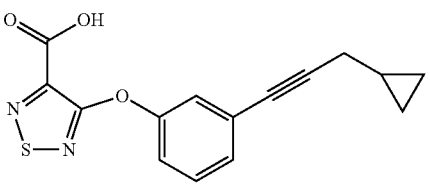 [SMILES: O=C(O)c1nsnc1Oc1cccc(C#CCC2CC2)c1] | 4-(3-(3-cyclopropylprop-1-ynyl)phenoxy)-1,2,5-thiadiazole-3-carboxylic acid | 330.33 |
| 401 | 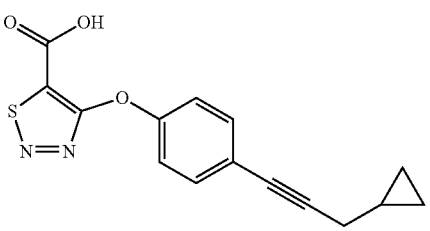 [SMILES: O=C(O)c1snnc1Oc1ccc(C#CCC2CC2)cc1] | 4-(4-(3-cyclopropylprop-1-ynyl)phenoxy)-1,2,3-thiadiazole-5-carboxylic acid | 330.33 |
| 402 | 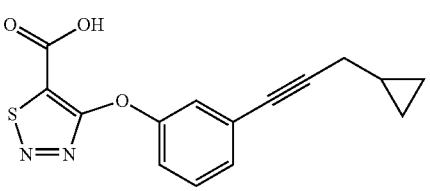 [SMILES: O=C(O)c1snnc1Oc1cccc(C#CCC2CC2)c1] | 4-(3-(3-cyclopropylprop-1-ynyl)phenoxy)-1,2,3-thiadiazole-5-carboxylic acid | 330.33 |
| 403 | 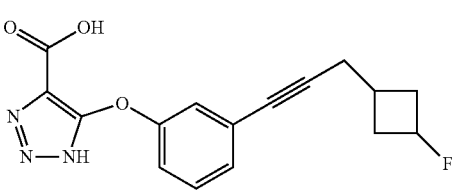 [SMILES: O=C(O)c1nn[nH]c1Oc1cccc(C#CCC2CC(F)C2)c1] | 5-(3-(3-(3-fluorocyclobutyl)prop-1-ynyl)phenoxy)-1H-1,2,3-triazole-4-carboxylic acid | 315.30 |

TABLE 1-continued

Example Compounds

| Ex. No. | Structure | IUPAC Name | MW (g/mol) |
|---|---|---|---|
| 404 | 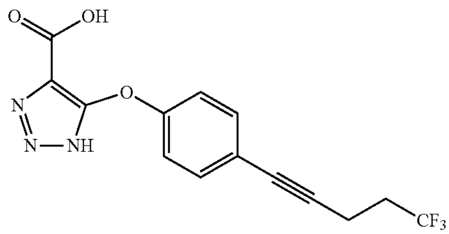 [SMILES: O=C(O)c1nn[nH]c1Oc1ccc(C#CCCC(F)(F)F)cc1] | 5-(4-(5,5,5-trifluoropent-1-ynyl)phenoxy)-1H-1,2,3-triazole-4-carboxylic acid | 325.25 |
| 405 | 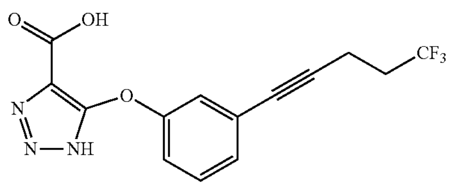 [SMILES: O=C(O)c1nn[nH]c1Oc1cccc(C#CCCC(F)(F)F)c1] | 5-(3-(5,5,5-trifluoropent-1-ynyl)phenoxy)-1H-1,2,3-triazole-4-carboxylic acid | 325.25 |
| 406 | 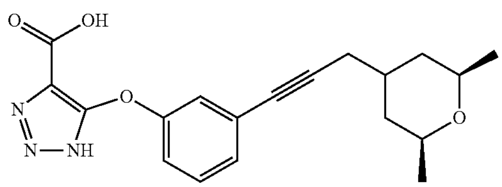 [SMILES: C[C@@H]1CC(CC#Cc2cccc(Oc3[nH]nnc3C(=O)O)c2)C[C@H](C)O1] | 5-(3-(3-((2R,6S)-2,6-dimethyltetrahydro-2H-pyran-4-yl)prop-1-ynyl)phenoxy)-1H-1,2,3-triazole-4-carboxylic acid | 355.39 |
| 407 | 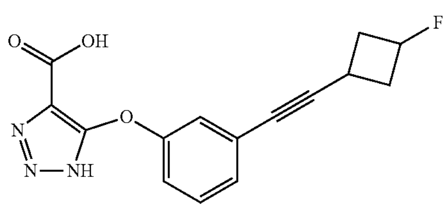 [SMILES: O=C(O)c1nn[nH]c1Oc1cccc(C#CC2CC(F)C2)c1] | 5-(3-((3-fluorocyclobutyl)ethynyl)phenoxy)-1H-1,2,3-triazole-4-carboxylic acid | 301.28 |
| 408 | 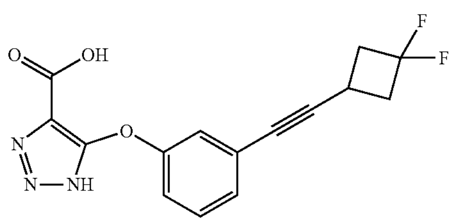 [SMILES: O=C(O)c1nn[nH]c1Oc1cccc(C#CC2CC(F)(F)C2)c1] | 5-(3-((3,3-difluorocyclobutyl)ethynyl)phenoxy)-1H-1,2,3-triazole-4-carboxylic acid | 319.27 |
| 409 | 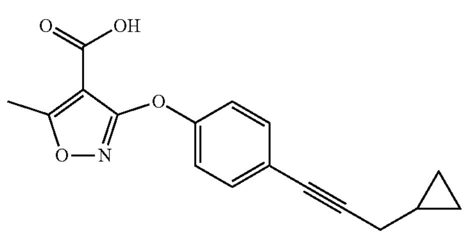 [SMILES: Cc1onc(Oc2ccc(C#CCC3CC3)cc2)c1C(=O)O] | 3-(4-(3-cyclopropylprop-1-ynyl)phenoxy)-5-methylisoxazole-4-carboxylic acid | 297.31 |
| 410 | 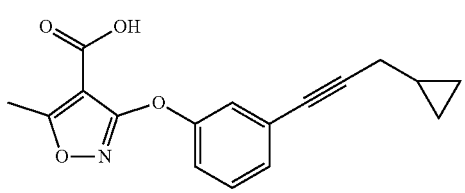 [SMILES: Cc1onc(Oc2cccc(C#CCC3CC3)c2)c1C(=O)O] | 3-(3-(3-cyclopropylprop-1-ynyl)phenoxy)-5-methylisoxazole-4-carboxylic acid | 297.31 |

TABLE 1-continued

Example Compounds

| Ex. No. | Structure | IUPAC Name | MW (g/mol) |
|---|---|---|---|
| 411 | 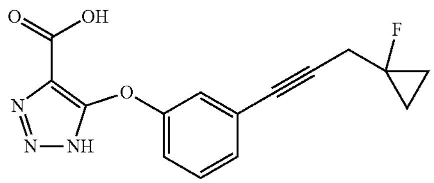 [SMILES: O=C(O)c1nn[nH]c1Oc1cccc(C#CCC2(F)CC2)c1] | 5-(3-(3-(1-fluorocyclopropyl)prop-1-ynyl)phenoxy)-1H-1,2,3-triazole-4-carboxylic acid | 301.27 |
| 412 | 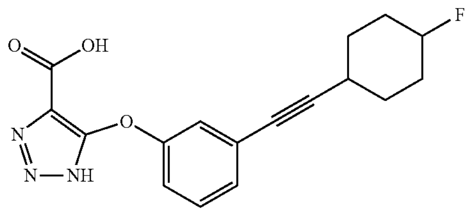 [SMILES: O=C(O)c1nn[nH]c1Oc1cccc(C#CC2CCC(F)CC2)c1] | 5-(3-(2-(4-fluorocyclohexyl)ethynyl)phenoxy)-1H-1,2,3-triazole-4-carboxylic acid | 329.33 |
| 413 | 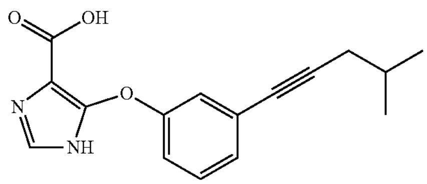 [SMILES: CC(C)CC#Cc1cccc(Oc2[nH]cnc2C(=O)O)c1] | 5-(3-(4-methylpent-1-ynyl)phenoxy)-1H-imidazole-4-carboxylic acid | 284.32 |
| 414 | 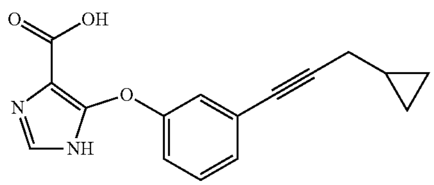 [SMILES: O=C(O)c1nc[nH]c1Oc1cccc(C#CCC2CC2)c1] | 5-(3-(3-cyclopropylprop-1-ynyl)phenoxy)-1H-imidazole-4-carboxylic acid | 282.30 |

Also provided are alkyl esters of the compounds disclosed above, which can be made by the methods above and may be useful as, among other things, prodrugs. Ethyl esters are shown, and other esters, such as methyl, n-propyl, isopropyl, and so on, are also provided herein. Such alkyl esters may be used as prodrugs of the compounds disclosed herein, and as disclosed above, are often made in route to the carboxylic acid compounds disclosed herein. Similarly, de-esterification may be used to produce the carboxylic acid analog of esters disclosed herein.

Biological Activity Assays

In-Vitro Human Glycolate Oxidase (hGOX) Assay

The in-vitro glycolate oxidase assay was performed using recombinant full-length human hydroxyacid oxidase 1 (HAO1), the equivalents of hGOX. The enzyme was obtained from AbCam (Catalog #ab113144) and was purified using conventional chromatography to >95% purity. Purified HAO1 was dissolved in assay buffer consisting of 10 mM NaCl, 110 mM KCl, 2 mM MgCl2, 50 mM HEPES (pH 7.4), and 0.01% Triton™ X-100. The assay used Corning 3575 384-well flat bottom, low flange, non-binding surface, black polystyrene plates.

Test compounds in DMSO were preincubated at different concentrations with purified recombinant human GO (6 nM) for 10 min, followed by the addition of glycolate substrate (85 µM) to start the reaction. The plates were incubated for 10 min at room temperature, at which point Amplex red reagent (50 µM) was added.

The fluorescence intensity signal was measured on a VarioskKan LUX instrument using an excitation of 560 nm and an emission of 590 nm. The $IC_{50}$ values were calculated using Graphpad Prism. The fluorescence signal of wells containing only DMSO was defined as 100% GO activity, while the fluorescence signal without the glycolate substrate was defined as 0% GO activity. Table 2 shows the $IC_{50}$ values for the compounds tested in this in-vitro assay.

TABLE 2

Results from In-Vitro Human Glycolate Oxidase (hGOX) Assay

| Ex. No. | IC50 (nM) |
|---|---|
| 1 | 21 |
| 2 | 90 |
| 5 | 12 |
| 6 | 7 |
| 9 | 62 |
| 10 | 28 |
| 13 | 440 |
| 16 | 210 |
| 17 | 42 |
| 20 | 11 |
| 21 | 9 |
| 24 | 16 |
| 25 | 18 |
| 28 | 18 |
| 29 | 10 |

TABLE 2-continued

Results from In-Vitro
Human Glycolate Oxidase (hGOX) Assay

| Ex. No. | IC50 (nM) |
|---|---|
| 36 | 9 |
| 37 | 8 |
| 40 | 40 |
| 41 | 13 |
| 108 | 1 |
| 138 | 7 |
| 139 | 10 |
| 146 | 1 |
| 147 | 4 |
| 149 | 14 |
| 165 | 6 |
| 178 | 6 |
| 187 | 1 |
| 190 | 3 |
| 191 | 6 |
| 208 | 2 |
| 209 | 8 |
| 215 | 48 |
| 220 | 4 |
| 221 | 1 |
| 254 | 3 |
| 255 | 8 |
| 256 | 2 |
| 257 | 1 |
| 258 | 2 |
| 259 | 1 |
| 260 | 5 |
| 261 | 4 |
| 262 | 1 |
| 263 | 2 |
| 264 | 20 |
| 265 | 3 |
| 266 | 2 |
| 267 | 2 |
| 268 | 1 |
| 269 | 1 |
| 270 | 1 |
| 271 | 2 |
| 272 | 2 |
| 273 | 2 |
| 274 | 5 |
| 275 | 3 |
| 276 | 3 |
| 277 | 2 |
| 278 | 1 |
| 279 | 2 |
| 280 | 4 |
| 281 | 3 |
| 282 | 3 |
| 283 | 3 |
| 284 | 5 |
| 285 | 3 |
| 286 | 2 |
| 287 | 4 |
| 288 | 1 |
| 289 | 1 |
| 290 | 0.4 |
| 291 | 0.3 |
| 292 | 2 |
| 293 | 5 |
| 294 | 3 |
| 295 | 1 |
| 296 | 1 |
| 297 | 3 |
| 298 | 3 |
| 299 | 15 |
| 300 | 9 |
| 301 | 15 |
| 302 | 13 |
| 303 | 36 |
| 304 | 12 |
| 305 | 18 |
| 306 | 16 |
| 307 | 1 |
| 308 | 10 |
| 309 | 3 |
| 310 | 4 |
| 311 | 3 |
| 312 | 3 |
| 313 | 3 |
| 314 | 3 |
| 315 | 2 |
| 316 | 2 |
| 317 | 2 |
| 318 | 2 |
| 319 | 2 |
| 320 | 6 |
| 321 | 5 |
| 322 | 4 |
| 323 | 5 |
| 324 | 4 |
| 325 | 2 |
| 326 | 2 |
| 327 | 2 |
| 328 | 1 |
| 329 | 2 |
| 330 | 1 |
| 331 | 20 |
| 332 | 7 |
| 333 | 10 |
| 334 | 5 |
| 335 | 23 |
| 336 | 25 |
| 337 | 7 |
| 338 | 4 |
| 339 | 4 |
| 340 | 3 |
| 341 | 28 |
| 342 | 2 |
| 343 | 10 |
| 344 | 4 |
| 345 | 8 |
| 346 | 3 |
| 347 | 21 |
| 348 | 5 |
| 349 | 5 |
| 350 | 10 |
| 351 | 20 |
| 352 | 34 |
| 353 | 3 |
| 354 | 5 |
| 355 | 6 |
| 356 | 6 |
| 357 | >1000 |
| 358 | >1000 |
| 359 | >1000 |
| 360 | >1000 |
| 361 | >1000 |
| 362 | 230 |
| 363 | 110 |
| 364 | 94 |
| 365 | 98 |
| 366 | >1000 |
| 367 | 9 |
| 368 | >1000 |
| 369 | >1000 |
| 370 | >1000 |
| 371 | >1000 |
| 372 | >1000 |
| 373 | >1000 |
| 374 | >1000 |
| 375 | >1000 |
| 376 | 4700 |
| 377 | >1000 |
| 378 | 40 |

It is expected that these compounds and the other compounds disclosed herein will be effective in inhibiting human glycolate oxidase, encoded by human hydroxyacid oxidase 1 gene (HAO1), and thus would be effective in treating diseases related to oxalate accumulation, for example, hyperoxaluria.

HepaRG-CAR Cell-Based Assay for Quantitation of Glycolate Oxidase Inhibition

A HepaRG human hepatic cell line was transfected for stable overexpression of the constitutive androstane receptor (i.e., HepaRG-CAR cells), as reported by van der Mark et al. (Drug Metab. Dispos., 2017, 45:56-67. Overexpression of CAR in these cells resulted in higher levels of glycolate oxidase (GOX) expression compared to the parental HepaRG cells. HepaRG-CAR cells were plated in a 12-wells plate and incubated for 4 weeks until fully differentiated.

To measure cellular glycolate flux, the HepaRG-CAR cells were incubated in Williams medium supplemented with 10% fetal bovine serum (FBS), 5 µg/mL insulin, 50 µM hydrocortisone hemisuccinate, 2 mM glutamine, 5000 U/mL penicillin and 5 mg/mL streptomycin. Test compounds were added to the medium at 0, 0.3, 1, 3, or 10 µM and incubated for 30 minutes, after which 500 µM glycolate was also added. After incubation for 48 hours, 400 medium was taken from the culture plate and added to 60 µL 37% HCl.

Internal standards (2,2-$d_2$ glycolate, 1,2-$^{13}C_2$ oxalate, and $^{13}C_2$-glyoxylate) and hydroxylamine were added, followed by another 30-minute incubation at 80° C. The acids were extracted using ethyl acetate with NaCl. The organic phase was dried under nitrogen and derivatized with N-tert-butyldimethylsilyl-N-methyl trifluoroacetamide (MTB-STFA) for 30 minutes at 80° C. The amounts of glycolate, glyoxylate, and oxalate were determined by gas chromatography-mass spectrometry (GC-MS) analysis, using a 25-meter CP-Sil 5 CB low bleed column. A standard curve was used to calculate the concentrations of each acid in the culture medium.

TABLE 3

Results of HepaRG-CAR Cell-Based Assay

| Ex. No. | $IC_{50}$ (µM) |
|---|---|
| 1 | 2.5 |

Solubility, Metabolic Stability, and Protein Binding Assays

Solubility at relevant physiologic conditions and metabolic stability of compounds are both properties that can be important for suitability of use as a pharmaceutical composition and medicament without resort to complicated formulation. Accordingly, representative compounds disclosed herein were tested for aqueous and saline solubility, for metabolic stability in liver microsomes and human plasma, and, as disclosed below.

Solubility. For testing compound solubility in phosphate-buffered saline (PBS), compound stock solutions were prepared at 10 mM in 100% DMSO. For testing in aqueous solution, the phosphate buffer was replaced with deionized, distilled water. Eleven grams $Na_2HPO_4$ (FW: 141.96 g/mol) and 3.5 g $NaH_2PO_4.2H_2O$ (FW: 156.03 g/mol) was added to 1 L Milli-Q water and adjusted to a pH to 7.4 with phosphoric acid or sodium hydroxide. For incubation, the media were preheated to 37° C. Eight µL aliquots of reference and test compound stock solutions (10 mM) were added into 792 µL of 100 mM phosphate buffer (pH 7.4). The final DMSO concentration was 1%. Sample tubes were shaken for 1 hour at 1000 rpm at room temperature.

The calibration curve was prepared with a 300-µM spiking solution (SS) in MeOH:acetonitrile (4:1). Six µL of 10 mM compound was added in 194 µL MeOH/acetonitrile (4:1). Samples were centrifuged for 10 minutes at 12,000 rpm to precipitate undissolved particles. Supernatants were transferred to a new tube or plate and dilute 10-fold and 100-fold with 100 mM buffer. Samples were prepared for LC-MS/MS analysis by adding 5 µL each sample (undiluted, 10-fold diluted, and 100-fold diluted) and 5 µL of standard curve samples to 95 µL of acetonitrile (containing internal standard).

Metabolic stability. For evaluating the metabolic stability in human liver microsomal preparation, three buffers were prepared. Buffer A had a 1.0 L of 0.1 M monobasic potassium phosphate buffer containing 1.0 mM EDTA. Buffer B had 1.0 L of 0.1 M dibasic potassium phosphate buffer containing 1.0 mM EDTA. Buffer C had 0.1 M potassium phosphate buffer, 1.0 mM EDTA, adjusted to a pH 7.4 via titrating 700 mL buffer B with buffer A. Reference compound (ketanserin) and test compounds spiking solutions (500 µM) were prepared by adding 10 µL of 10 mM DMSO stock compound solution into 190 µL acetonitrile. A volume of 1.5 µL 500 µM spiking solution and 18.75 µL 20 mg/mL human liver microsomes were added into 479.75 µL of Buffer C on ice. A stock solution of 6 mM NADPH was prepared by dissolving NADPH into Buffer C.

Wells on an assay plate were iced and filled with 30 µL 1.5-µM spiking solution containing 0.75 mg/mL microsomes solution and designated for different time points (0-, 5-, 15-, 30-, 45-min). For the 0-min time point, 135 µL acetonitrile containing internal standard was added, followed by 15 µL of NADPH stock solution (6 mM). All other plates were preincubated at 37° C. for 5 minutes, and 15 µL NADPH stock solution (6 mM) was added to the plates to start the reaction. At 5-min, 15-min, 30-min, and 45-min, 135 µL acetonitrile containing internal standard were added to the wells of corresponding plates, respectively, to stop the reaction. After quenching, the plates were shaken on the vibrator (IKA, MTS 2/4) for 10 min at 600 rpm and then centrifuged at 5594×g for 15 minutes (Thermo Multifuge× 3R). Fifty µL supernatant from each well was transported into a 96-well sample plate containing 50 µL of ultra-pure water (Millipore, ZMQS50F01) for LC/MS analysis.

Table 4 shows the in vitro Drug Metabolism-Pharmacokinetic (DMPK) results, including aqueous solubility (µM) of the compound in PBS and water (µM), human liver microsome metabolic stability half-life ($t_{1/2}$ in min), metabolic stability Clint (mL/min/kg).

TABLE 4

In-vitro DMPK results for human glycolate oxidase inhibitors

| Ex. No. | Aqueous Solubility PBS (µM) | Aqueous Solubility $H_2O$ (µM) | Metabolic Stability $t_{1/2}$ (min) | Metabolic Stability $Cl_{int}$ (mL/min/kg) |
|---|---|---|---|---|
| 1 | 92.40 | 80.60 | 558.60 | 3.11 |

Stability in Human Plasma. Stock compounds were prepared for testing the stability in human plasma. First, 0.05 M sodium phosphate, and 0.07 M NaCl buffer, pH 7.4, were pre-heated. In deionized water, 14.505 g/L $Na_2HPO_4.12H_2O$, 1.483 g/L $NaH_2PO_4.2H_2O$, and 4.095 g/L NaCl were dissolved. The basic solution was titrated with the phosphoric acid to pH 7.40. Frozen plasma was quickly thawed at 37° C. The plasma was centrifuged at 3,000 rpm for 8 minutes to remove clots, then pipetted and pooled as the plasma stock for the experiment. Only plasma within the range of pH 7.4 to pH 8 was used. If higher than pH 8, the plasma was discarded. The initial pH of the plasma was not adjusted to pH 7.4 with acid or by bubbling with carbon dioxide. By using a 5% carbon dioxide incubator and PBS buffer, a pH of 7.4 is reached after the 4-hour equilibrium dialysis time. Plasma was iced until use.

Spiking solution A with 0.5 mM testing compounds was prepared by adding 10 μL of 10 mM stock solution of test compounds to 190 μL DMSO. Spiking solution B with 0.02 mM testing compound was prepared by adding 40 μL of spiking solution A to 960 μL of 0.05 mM sodium phosphate buffer with 0.5% BSA. The plasma and spiking solution B were prewarmed at 37° C. for 5 minutes. Ten μL of pre-warmed spiking solution B was added into the wells designated for all the time points (5, 15, 30, 45, 60 minutes). For the 0-minute time point, 400 μL acetonitrile containing internal standard was added to the wells of the 0-minute plate, and then 90 μL plasma were added. For the other time points, 90 μL of pre-warmed plasma were added into the wells (0, 5, 15, 30, 45, 60 minutes), and the timing was started. At 5, 15, 30, 45, 60 minutes, 400 μL acetonitrile containing internal standard were added to the wells of corresponding plates, respectively, to stop the reaction. After quenching, the plates were shaken on a vibrator (IKA, MTS 2/4) for 10 minutes at 600 rpm and then centrifuged at 5594×g for 15 minutes (Thermo Multifuge×3R). Fifty μL of supernatant was transferred from each well into a 96-well sample plate containing 50 μL ultra-pure water (Millipore, ZMQS50F01) for LC/MS analysis.

The methods disclosed above yielded the data disclosed below in Table 6 for Example 1. Other compounds disclosed herein have been tested and can be tested, using the alternative protocol below.

Metabolic Stability. For evaluating the metabolic stability in liver microsomal preparations, two buffers were prepared. Buffer A consisted of 10 mM NADPH and 0.5 mg/mL microsomes in 100 mM of phosphate buffer. Buffer B consisted of 0.5 mg/mL microsomes in 100 mM of phosphate buffer. The reference compound (verapamil) and test compound were prepared as 100 μM DMSO stocks. The source of liver microsomes was as follows: Human (BD Gentest, #452117), monkey (RILD, #LM-SXH-02M), dog (BD, #452601), Rat (BioIVT, #M00001), and mouse (BioIVT, #M00501).

The reaction was started by adding 2.5 μL of 100 μM control compound or test compound solutions to 216.25 μL of prewarmed (37° C.) assay buffer. The final concentration of the control compound and test compounds were 1 μM. Aliquots of 30 μL were taken from the reaction solution at 0.5 and 60 minutes. The reaction was stopped by adding 5 volumes of cold acetonitrile with internal standards (100 nM alprazolam, 200 nM caffeine, and 100 nM tolbutamide). Samples were centrifuged at 3,220 g for 30 minutes. An aliquot of 100 μL of the supernatant was mixed with 100 μL of ultra-pure water and then used for LC-MS/MS analysis.

Plasma stability. Stock compounds were prepared for testing the stability in human (BioIVT, #BRH1589665), dog (BioIVT, #BGL102122) and mouse (BioIVT, #MSE37887) plasma. 1 mM test compound working solution was prepared in DMSO. A one mM propantheline working solution was prepared in acetonitrile. Propantheline was used as a positive control for human, dog, and mouse plasma in this assay.

Plasma (398 μL) for each compound was added into an incubation plate, and the plate was pre-warmed for 15 minutes at 37° C. The reaction was initiated upon addition of 2 μL of 1 mM working solution (test compounds or control compound) to the plasma to reach a final concentration of 5 μM. The reaction was incubated at 37° C. Aliquots of 50 μL were taken from the reaction samples at 0 and 60 minutes. Adding 450 μL cold acetonitrile containing internal standards stopped the reaction. Once the reaction was stopped, the samples were vortexed for 10 minutes, followed by centrifugation at 3,220 g for 40 minutes to precipitate proteins. The supernatant (100 μL) was transferred to a new plate and diluted with ultrapure water according to the LC-MS signal response and peak shape. Samples were analyzed by LC-MS/MS.

Other compounds disclosed herein (e.g., Examples 255, 302, and 343) were tested in the alternate liver microsome metabolic stability assay above. They were found to exhibit a strong stability profile in which 100% and 45%-97% of compounds remained intact at 30 minutes and 60 minutes, respectively in all species tested.

Caco-2 Permeability. Stock compounds solubilized in dimethyl sulfoxide (DMSO) were tested using luciferase yellow (LY) dye. For donor solutions in the apical to basolateral (A-to-B) direction, Hanks Balanced Salt Solution (HBSS) buffer with 0.3% DMSO and 5 μM LY was prepared by adding 150 μL DMSO and 50 μL LY (5 mM) into 50 mL HBSS buffer (pH 7.4). HBSS buffer with 0.1% DMSO and 5 μM LY was prepared by adding 50 μL DMSO and 50 μL LY (5 mM) into 50 mL HBSS buffer (pH 7.4). For donor solutions in the basolateral to apical (B-to-A) direction, HBSS buffer with 0.3% DMSO was prepared by adding 150 μL DMSO into 50 mL HBSS buffer (pH 7.4). HBSS buffer with 0.1% DMSO was prepared by adding 50 μL DMSO into 50 mL HBSS buffer (pH 7.4).

The receiver solution buffer for the A-to-B direction used HBSS buffer with 0.4% DMSO prepared by adding 200 μL DMSO into 50 mL HBSS buffer (pH 7.4). For B-to-A direction, HBSS buffer with 0.4% DMSO and 5 μM LY was prepared by adding 200 μL DMSO and 50 μL LY (5 mM) into 50 mL HBSS buffer (pH 7.4)

Transepithelial electrical resistance (TEER) was measured at room temperature after cell culture plates were removed from the incubator, cell monolayers were washed with HBSS buffer. The compound solution was centrifuged at 4000 rpm for 5 minutes before loading samples to donor chambers. Solutions were added, as shown in Table 5.

TABLE 5

Donor and Receiver Chamber Solutions

| Position | Transport Direction | Volume added | Final volume |
|---|---|---|---|
| Apical | A--B (Donor chamber) | 600 μL of A-to-B dosing solution (100 μL for LY measurement and 100 μL for Backup) | 400 μL |
| Basolateral | A--B (Receiver chamber) | 800 μL 0.4% DMSO HBSS | 800 μL |

TABLE 5-continued

Donor and Receiver Chamber Solutions

| Position | Transport Direction | Volume added | Final volume |
|---|---|---|---|
| Basolateral | B--A (Donor chamber) | 900 µL B-to-A dosing solution (100 µL for Backup) | 800 µL |
| Apical | B--A (Receiver chamber) | 500 µL 0.4% DMSO HBSS + LY (100 µL for LY measurement) | 400 |

To determine LY concentration in the apical chamber, a 100 µL sample was transferred from apical chambers and into an opaque plate for LYT0. Apical and basolateral plates were warmed to 37° C. for about 5 minutes, and the apical plate was placed onto the basolateral plate. The assembled plates were incubated at 37° C. for 90 minutes.

For the standard curve, a 20× solution of the compound was prepared. For a 300 µM compound solution, 6 µL of compound stock solution was added into 192 µL of MeOH/H$_2$O (1:1). After 90 minutes of incubation, the apical plate was separated from the basolateral plate after. One hundred µL samples were transferred from the basolateral plate to an opaque plate as LYT90. The LY concentrations were measured for LYT0 and LYT90 using a fluorometer at an excitation of 485 nm and an emission of 535 nm. Samples for LC-MS/MS analysis were prepared from the donor and receiver chambers by diluting with 0.4% DMSO HBSS, then mixing with acetonitrile containing an internal standard of either osalmid or imipramine.

The methods disclosed above yielded the data disclosed below in Table 6 for Example 1. Example 1 and other compounds disclosed herein have been tested, and can be tested, using the alternative protocol below. The data for Example 1 was consistent between protocols.

A working solution for the Caco-2 permeability assay was prepared by diluting test compound stock solutions (2 mM in DMSO) with HBSS (10 mM, pH 7.4) to 10 µM working solution. Metoprolol, erythromycin, and cimetidine were used as the control compounds.

To determine the rate of drug transport in the apical-to-basolateral direction (A-B), 125 µL of the working solution was added to the Transwell insert (apical compartment). 50 µL of each sample was immediately transferred from the apical compartment to 200 µL of acetonitrile containing internal standards (100 nM alprazolam, 200 nM caffeine, and 100 nM tolbutamide) in a new 96-well plate as the initial donor sample (A-B). Samples were vortexed at 1000 rpm for 10 minutes, and the wells in the receiver plate (basolateral compartment) were subsequently filled with 235 µL of transport buffer. Plates were incubated at 37° C. for 2 hours.

To determine the rate of drug transport in the basolateral-to-apical direction (B-A), 285 µL of the working solution was added to the receiver plate wells (basolateral compartment). 50 µL of each sample was transferred immediately from the basolateral compartment to 200 µL of acetonitrile containing internal standards (100 nM alprazolam, 200 nM Caffeine, and 100 nM tolbutamide) in a new 96-well plate as the initial donor sample (B-A). Samples were vortexed at 1000 rpm for 10 minutes, and 75 µL of transport buffer was added to the Transwell insert (apical compartment). Plates were incubated at 37° C. for 2 hours.

At the end of the 2-hour incubation, 50 µL from donor sides (apical compartment for A→B flux and basolateral for B→A flux) were transferred to wells of a new 96-well plate followed by the addition of 4 volume of acetonitrile containing internal standards (100 nM alprazolam, 200 nM Caffeine and 100 nM tolbutamide). Samples were vortexed for 10 minutes, 50 µL samples were transferred to wells of a new 96-well plate, followed by the addition of 50 µL Hepes and 200 µL internal standards. All samples were vortexed for 10 minutes and then centrifuged at 3,220 g for 40 minutes. An aliquot of 150 µL of the supernatant was mixed with an appropriate volume of ultra-pure water before LC-MS/MS analysis.

To determine the Lucifer Yellow leakage after 2 hour transport period, the stock solution of Lucifer yellow was prepared in DMSO and diluted with HBSS (10 mM HEPES, pH 7.4) to reach the final concentration of 100 µM. 100 µL of the Lucifer yellow solution was added to each Transwell insert (apical compartment), followed by filling the wells in the receiver plate (basolateral compartment) with 300 µL of HBSS (10 mM HEPES, pH 7.4). The plates were Incubated at 37° C. for 30 mins. 80 µL samples were removed directly from the apical and basolateral wells (using the basolateral access holes) and transferred to wells of new 96 wells plates. The Lucifer Yellow fluorescence (to monitor monolayer integrity) signal was measured in a fluorescence plate reader at 480 nM excitation and 530 nM emission.

Protein Binding. For testing protein binding of stock compounds solubilized in DMSO, spiking solutions of test and reference compounds were prepared. Solution A (0.5 mM) was prepared by adding 10 µL of 10 mM stock solution into 190 µL of DMSO. Solution B (0.02 mM) was prepared by adding 8 µL of Solution A into 192 µL of 0.05 M sodium phosphate buffer. The final DMSO concentration in Solution B was 4%.

To prepare test and reference compounds in plasma, a 96-well plate with 380 µL aliquots of plasma in the wells designed for plasma and buffer, respectively. Twenty µL of Solution B (0.02 mM of test and reference compounds) were spiked into the pre-loaded plasma in the 96-well plate. The final test concentration is 1 µM containing 0.2% DMSO.

For dialysis sample loading a plasma again, the buffer system was prepared by applying aliquots of 100 µL of new dialysis buffer to the receiver side of dialysis chambers and then applying aliquots of 100 µL of the plasma spiked with test and reference compounds to the donor side of the dialysis chamber. A 25-µL aliquot of the plasma spiked with test and reference compounds was added into a 96-well sample preparation plate as T"0" plasma samples. Aliquots were mixed with the same volume of new buffer (50:50, volume:volume). Samples were quenched with 200 µL of acetonitrile containing internal standard. The dialysis block was covered and shaken at 60 rpm for 5 hours at 37° C.

After a 5-hour incubation, dialyzed samples were prepared from 25-µL aliquots from both the donor and receiver sides of the dialysis apparatus into new sample preparation plates. The aliquots were mixed with the same volume of different matrixes. The samples were quenched with 200 µL acetonitrile containing internal standard. All 0-hour and 5-hour samples were vortexed at 600 rpm for 10 min, followed by centrifugation at 5594×g for 15 minutes (Thermo Multifugex3R). Fifty µL of the supernatants were transferred to a new 96-well plate and mixed with 50 µL Milli-Q water. The sample plate was covered and frozen at −20° C. until LC/MS/MS analysis.

The methods disclosed above yielded the data disclosed below in Table 6 for Example 1. Other compounds disclosed herein have been tested, and can be tested, using the alternative protocol below.

For testing protein binding of stock compounds solubilized in DMSO, spiking solutions of test and reference compounds were prepared. A basic solution was prepared by dissolving 14.2 g/L $Na_2HPO_4$ and 8.77 g/L NaCl in deionized water. An acidic solution was prepared by dissolving 12.0 g/L $NaH2PO4$ and 8.77 g/L NaCl in deionized water. The basic solution was titrated with the acidic solution to pH 7.4. Frozen plasma was quickly thawed at 37° C. Dialysis membranes were prepared by soaking them in ultrapure water for 60 minutes, followed by 20% ethanol (20 minutes), and finally, dialysis buffer for 20 minutes. The membranes were loaded onto the dialysis device and prewarmed to 37° C.

Control samples at the 0-hour were prepared by adding 597 µL of blank plasma solution into each vial of a new plastic plate followed by adding 3 µL of the working solution of the test compound. Solutions were quickly vortexed at 1000 rpm for 2 minutes. The final concentration for test compounds was 5 µM. Fifty µL of the spiked plasma solution was immediately transferred to a 96-well plate to act as a T=0 control sample. All of the remaining spiked plasma solutions were held at 37° C. for the remainder of the experiment. The remaining spiked plasma solution sample in the plastic plate was incubated for 6 hours at 37° C. with 5% $CO_2$ in the $CO_2$ incubator. At T=6 hours, 50 µL of the original spiked plasma solution was transferred to a 96-well plate for analysis.

Compound stability in the plasma samples was determined by equilibrium dialysis. Cells were loaded with 120 µL of each plasma sample and dialyzed against an equal volume of dialysis buffer (PBS). Stability reactions were incubated for 6 hours at 37° C. at 100 rpm with 5% $CO_2$ on an orbital shaker in the $CO_2$ incubator. At the end of incubation, 50 µL of post-dialysis samples from both buffer and plasma solution chambers was transferred into a separated 96-well plate for analysis, respectively.

Stability was analyzed by adding 50 µL of plasma solution to the buffer samples, and an equal volume of PBS to the collected plasma solution samples. The resulting mixtures were shaken at 1000 rpm for 2 minutes before adding 400 µL of acetonitrile containing an appropriate internal standard (IS) to precipitate protein and release compound. Samples were vortexed at 1000 rpm for 10 minutes and then centrifuged for 30 minutes at 3,220 g. 250 µL of the supernatant was transferred to a new 96-well plate and centrifuged again (3,220 g, 30 minutes). 100 µL of the supernatant was transferred to a new 96-well plate and was mixed with 100 µL of distilled water and analyzed by LC-MS/MS.

Table 6 shows the further DMPK results for plasma stability half-life ($T_{1/2}$ in min), Caco-2 permeability ($P_{app}$; B-A/A-B), and protein binding fraction bound (%), and protein binding recovery (%).

TABLE 6

Additional in-vitro DMPK results for human glycolate oxidase inhibitors

| Ex. No. | Plasma Stability $T_{1/2}$ (min) | Caco-2 Permeability $P_{app}$ (basal-apical/apical-basal) | Protein Binding Fraction Bound (%) | Protein Binding Recovery (%) |
|---|---|---|---|---|
| 1 | 117.62 | 2.64 | 97.5 | 109.9 |

Other compounds disclosed herein (e.g., Examples 190, 255, 302, and 343) were tested in the alternate plasma stability assay above and were found to have similarly long or longer half-lives. Other compounds disclosed herein were tested in the alternate Caco-2 permeability assay, and a general trend was noted wherein compounds substituted with an aryl group at $R^3$ had high $P_{app}$ Efflux Ratio values, but Examples 302, 343, and 356 all had $P_{app}$ Efflux Ratio values in the single digits. Other compounds disclosed herein were tested in the alternate protein binding assays and were found to have bound fractions of between 95% and >99%, and % recovery of between 97% and 113%.

In-Vivo Pharmacokinetic Evaluation

In-vivo exposure of test compounds was determined in 5-6 week old male CD-1 mice. Mice (n=2/compound) received 10 mg/kg of each compound formulated in 20% (2-Hydroxypropyl)-β-cyclodextrin (10 µL/g) by oral gavage. At 0.5 hours, 2 hours, and 6 hours post-dose, blood samples were collected from the submandibular vein using EDTA as an anticoagulant and stored on ice. Plasma samples were obtained by centrifugation at 4° C. and were analyzed immediately or stored at −20° C. until analysis. Compounds were extracted from mouse plasma with acetonitrile and quantified by LC-MS-MS in the negative ion mode using a standard curve.

Table 7 shows the results of the preceding study expressed as fold-over Example 1 in AUC.

TABLE 7

Results of Pharmacokinetic Assay

| Ex. No. | AUC Fold over Ex. 1 |
|---|---|
| 1 | 1.0 |
| 6 | 0.8 |
| 10 | 1.6 |
| 16 | 0.2 |
| 17 | 1.3 |
| 20 | 0.8 |
| 21 | 2.5 |
| 24 | 0.3 |
| 25 | 2.9 |
| 28 | 0.3 |
| 29 | 2.5 |
| 41 | 0.1 |
| 139 | 1.1 |
| 221 | 0.1 |
| 255 | 0.1 |
| 268 | 0.3 |
| 282 | 0.5 |
| 284 | 0.2 |
| 293 | 0.1 |
| 295 | 0.2 |
| 299 | 0.9 |
| 300 | 2.5 |
| 301 | 0.7 |
| 302 | 4.1 |
| 303 | 1.5 |
| 304 | 1.6 |
| 305 | 0.3 |
| 306 | 0.7 |
| 307 | 0.0 |
| 312 | 0.2 |
| 315 | 0.3 |
| 324 | 1.7 |
| 342 | 0.4 |
| 343 | 4.3 |
| 344 | 1.9 |
| 345 | 2.6 |
| 346 | 0.7 |
| 347 | 0.7 |
| 354 | 2.4 |
| 356 | 7.4 |

As can be seen, a trend toward increased AUC was noted amongst compounds having a phenyl A ring meta-substituted with $R^3$ as alkyl (particularly $C_2$-$C_6$ alkyl), cycloalkyl, and cycloalkylalkyl.

In Vivo Efficacy of hGOX Inhibitors

The in-vivo activity of test compounds was evaluated using alanine-glyoxylate aminotransferase (AGXT) knock-out mice from Jackson Laboratory (Bar Harbor, Me.), as reported by Martin-Higueras et al., *Molecular Therapy*, vol. 24 no. 4, 719-725, 2016. Ten to 15-week-old male AGXT knock-out mice (Agxt-/-) were used to assess the in-vivo activity of test compounds on urinary oxalate and glycolate.

Male Agxt-/- mice were housed under standard conditions (five animals per cage) and allowed free access to food and water. Upon study initiation, animals were treated with test compounds by oral gavage formulated in 20% (2-hydroxypropyl)-β-cyclodextrin (10 µL/g). Before administering the compound and at multiple times throughout the study, mice were housed individually in metabolic cages overnight to collect urine samples. The collection chambers were chilled to 4-7° C. to minimize evaporation. Age-matched wild type male C57B1/6 mice served as controls.

Urine samples were collected and handled, as described by Liebow et al., "An Investigational RNAi Therapeutic Targeting Glycolate Oxidase Reduces Oxalate Production in Models of Primary Hyperoxaluria." *J Am Soc Nephrol*, 28:494-503 (2017). To determine oxalate levels, part of the collected urine was charcoal-stripped and acidified to pH 1 with 6 N hydrochloric acid (5% v/v) before storage at -20° C. to prevent potential oxalate crystallization and oxalogenesis. The acidified urine was neutralized by the addition of 6 N sodium hydroxide (5% v/v) immediately before measuring oxalate concentration. The remaining nonacidified urine was frozen at -20° C. for the measurement of other urinary parameters. Blood samples were collected from the submandibular vein using EDTA as an anticoagulant and stored on ice. Plasma samples were obtained by centrifugation at 10,000 rpm for 5 minutes at 4° C. and were stored at -20° C. until analysis.

To determine the effect of test compounds on plasma glycolate, 5-6 week old male C57B1/6 mice were treated by oral gavage with compounds formulated in 20% (2-hydroxypropyl)-β-cyclodextrin (10 µL/g). At different times, blood samples were collected from the submandibular vein using EDTA as an anticoagulant and stored on ice. Plasma samples were obtained by centrifugation at 10,000 rpm for 5 minutes at 4° C. and were analyzed immediately or stored at -20° C. until analysis.

Urine oxalate was measured using a commercially available clinical oxalate oxidase assay (Trinity Biotech, Wicklow, Ireland) following the manufacturer's instructions.

Plasma and urine glycolate were determined by methods described in Dutta et al., "Inhibition of Glycolate Oxidase with Dicer-substrate siRNA Reduces Calcium Oxalate Deposition in a Mouse Model of Primary Hyperoxaluria Type 1." *Mol Ther.*, 24(4) 770-778 (2016) using liquid chromatography combined with mass spectrometry detection (LC/MS) on a triple-quadrupole instrument by electrospray ionization and multiple reaction monitoring. Urine samples were analyzed after sample dilution by hydrophilic interaction liquid chromatography (HILIC) and MS detection in the negative electrospray ionization mode. A two-step protein precipitation determined plasma glycolate. The analysis was done by HILIC LC/MS/MS detection in the negative ion electrospray ionization mode with multiple reaction monitoring. Calibration curves of the stable-label internal standard, $^{13}C2$-glycolate, in the appropriate surrogate matrix, were used for quantification.

Urine creatinine was measured using a commercially available creatinine detection kit (Enzo Life Sciences AG, Lausen, Switzerland), following the manufacturer's recommendations.

The in-vivo pharmacokinetics/exposure of test compounds was determined in 5-6 week old male CD-1 mice. Mice were divided into groups of three and received a single dose of 10 mg/kg of each compound formulated in 20% (2-hydroxypropyl)-β-cyclodextrin (10 µL/g) by oral gavage.

At multiple times in the first 24 hours, blood samples were collected from the submandibular vein using EDTA as an anticoagulant and stored on ice. Plasma samples were obtained by centrifugation at 4° C. and were analyzed immediately or stored at -20° C. until analysis. Compounds were extracted from mouse plasma with acetonitrile and quantified by LC-MS-MS in the negative ion mode using a standard curve.

Figure 2:
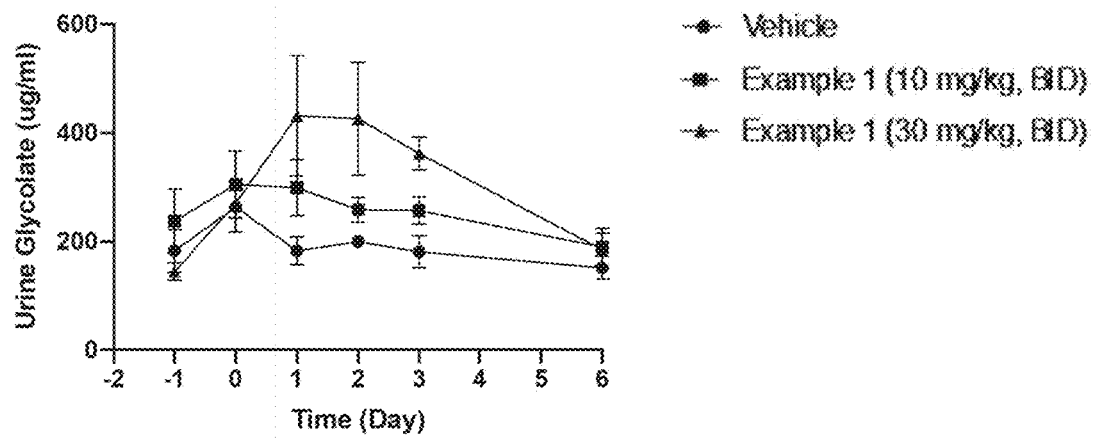
FIG. 2 shows urine glycolate (μg/mL) over time in days for compound 1 dosed twice daily at 10 and 30 mg/kg to Agxt−/− mice.

Unsubstituted alkynes exhibited marginal activity in the primary hyperoxaluria 1 (PH-1) alanine-glyoxylate aminotransferase Agxt-/- mouse model. FIG. 1 shows urine oxalate over time in days for compound 1 dosed at 10, and 30 mg/kg to the Agxt-/- mice expressed as a percentage of the vehicle-treated control values. FIG. 2 shows urine glycolate (m/mL) over time in days for these same mice. The unsubstituted alkyne compound 1 inhibited urine oxalate by about 30%, with a concomitant increase in urine glycolate. This activity reversed upon the compound washout.

Figure 3:
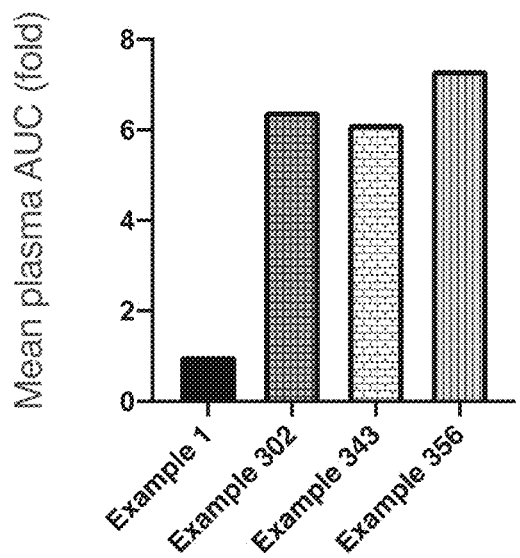
FIG. 3 shows the mean plasma 24-h AUC (fold) for compounds 1, 302, 343, and 356 in CD-1 mice at a dose of 10 mg/kg.

Substituted alkynes possessed a superior mouse pharmacokinetic profile. FIG. 3 shows the mean plasma AUC during the first 24 hours post-dose (fold) for compounds 1, 302, 343, and 356 in CD-1 mice dosed at 10 mg/kg. The substituted alkyne compounds 302, 343, and 356 had a mean plasma AUC that was 6 to 7 times higher than that of the unsubstituted alkyne compound 1.

Figure 4:
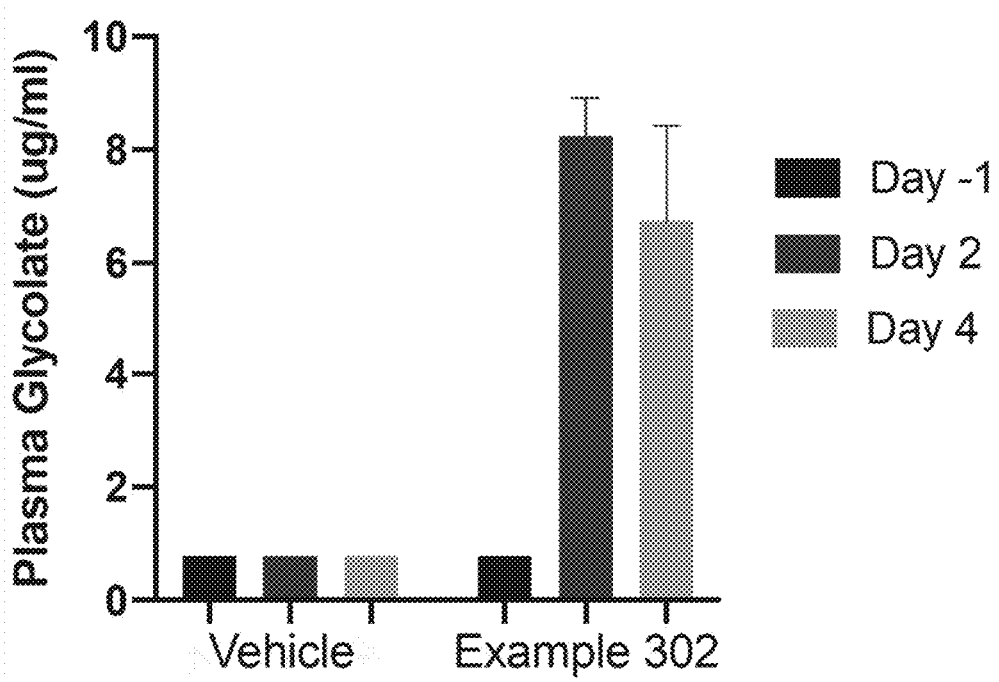
FIG. 4 shows the plasma glycolate concentration (μg/mL) at study Days −1, 2, and 4 for vehicle and compound 302. Male C57B1/6 mice were dosed orally with 30 mg/kg of compound 302 twice daily on Days 1 to 4.

Substituted alkynes also increased plasma glycolate in wild-type mice. FIG. 4 shows the plasma glycolate concentration (m/mL) at study Days -1, 2, and 4 for vehicle and compound 302. Male C57B1/6 mice were dosed orally with 30 mg/kg of compound 302 twice daily on Days -1 to 4.

Figure 5:
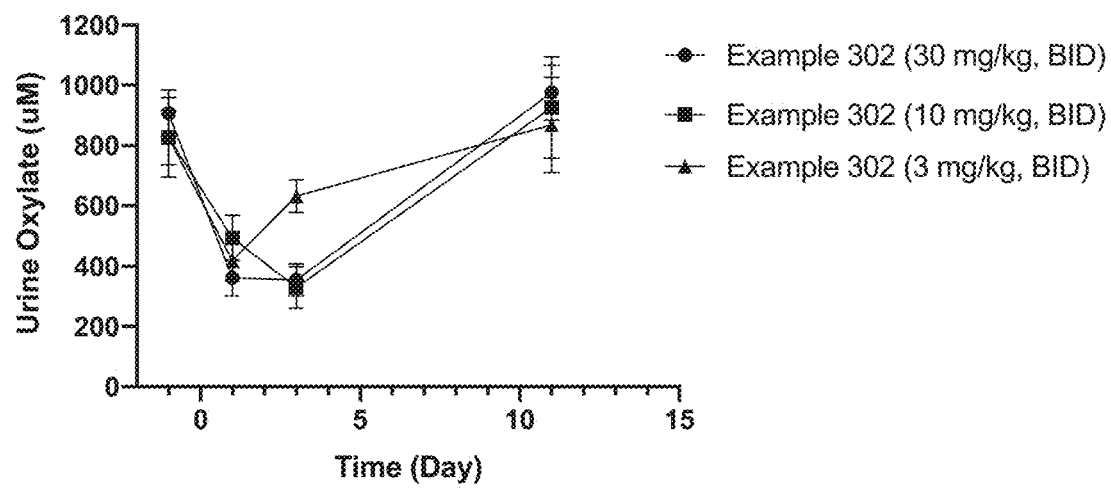
FIG. 5 shows urine oxalate (μM) over time in days for compound 302 orally dosed twice daily at 3, 10, and 30 mg/kg to Agxt−/− mice on study Days 0 to 4.
Figure 6:
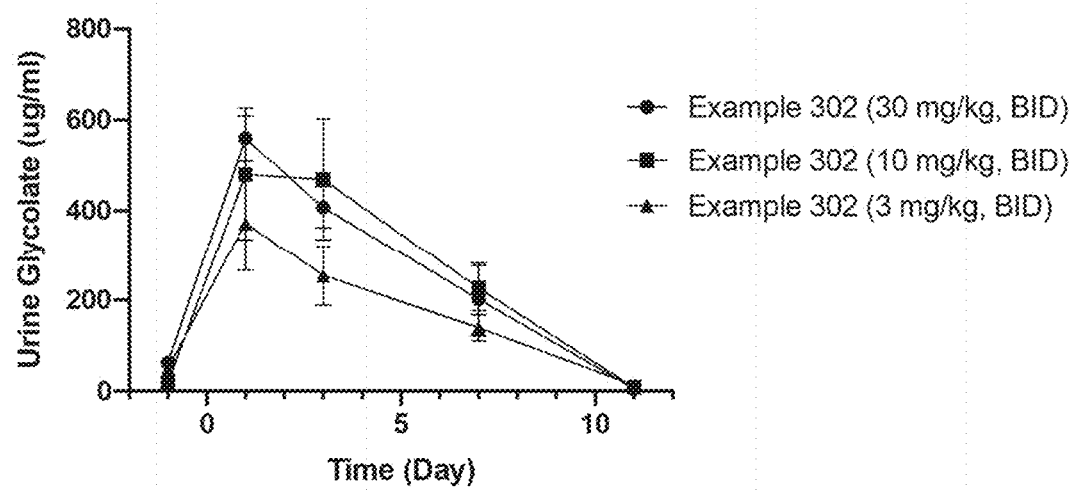
FIG. 6 shows urine glycolate (μg/mL) over time in days for compound 302 orally dosed twice daily at 3, 10, and 30 mg/kg to Agxt−/− mice on study Days 0 to 4.

Substituted alkynes exhibited superior activity in the Agxt-/- mouse model. FIG. 5 shows urine oxalate (µM) over time in days for compound 302 orally dosed twice daily at 3, 10, and 30 mg/kg to Agxt-/- mice on study Days -1 to 3. FIG. 6 shows the urine glycolate concentration (µg/mL) over time in days for these same mice. Substituted alkynes inhibited urine oxalate by about 60%, with a concomitant increase of urine glycolate. This activity reversed upon washout of the compounds.

Figure 7:
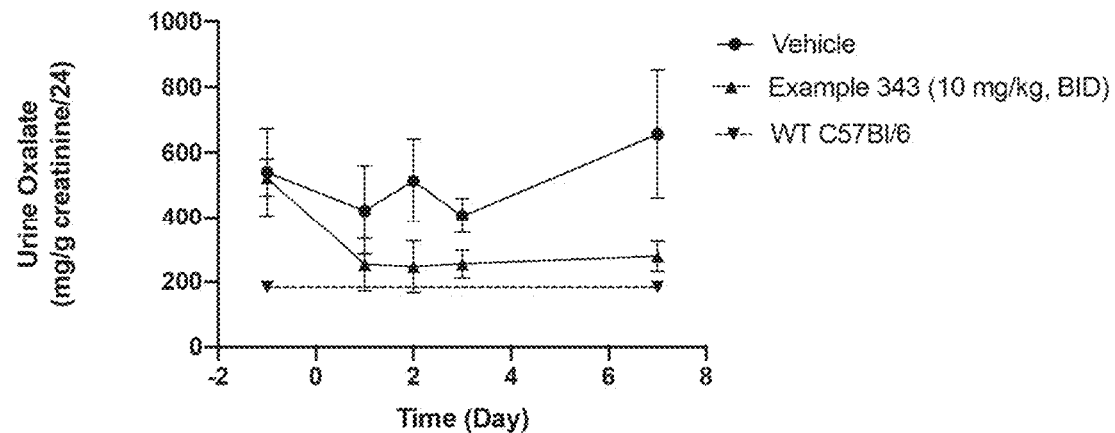
FIG. 7 shows the urine oxalate concentrations indicated by mg/g creatinine over 24 hours. These concentrations are plotted against time in days for compound 343 orally dosed twice daily at 10 mg/kg to Agxt−/− mice compared to vehicle in Agxt−/− mice and wild-type C57B1/6 mice.
Figure 8:
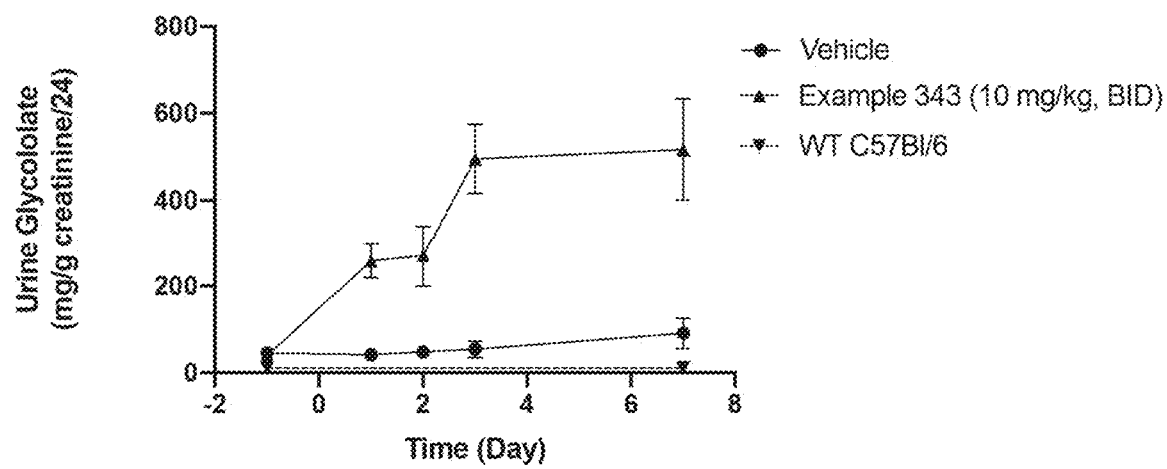
FIG. 8 shows the urine glycolate concentrations indicated by mg/g creatinine over 24 hours. These concentrations are plotted against time in days for compound 343 orally dosed twice daily at 10 mg/kg mg/kg to Agxt−/− mice compared to vehicle in Agxt−/− mice and wild-type C57B1/6 mice.

Substituted alkynes also induced rapid and sustained activity in the Agxt-/- mouse model. FIG. 7 shows the urine oxalate concentrations indicated by mg/g creatinine over 24 hours. These concentrations are plotted against time in days for compound 343 orally dosed twice daily at 10 mg/kg to Agxt-/- mice compared to vehicle in Agxt-/- mice and wild-type C57B1/6 mice. FIG. 8 shows the urine glycolate concentrations for these same mice.

Figure 9:
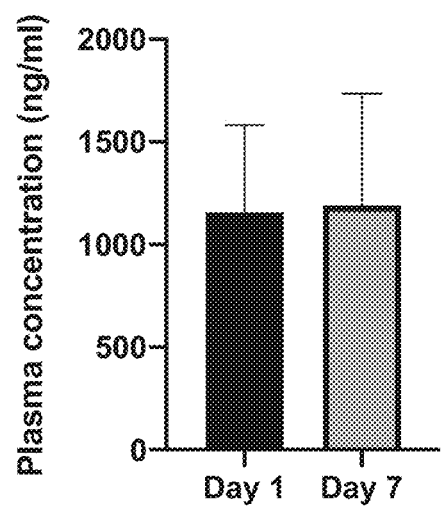
FIG. 9 shows the plasma concentration (ng/mL) of compound 343 measured 6-hours post first dose (Day 1) and last dose (Day 7) in a 7-day dosing experiment in Agxt−/− mice.

FIG. 9 shows plasma compound concentrations measured six hours after the first dose (Day 1) and last dose (Day 7). These concentrations were essentially identical, confirming that chronic dosing of the compound did not inhibit or activate the natural metabolic pathways responsible for its metabolism. This feature is important to ensure that the compound does not accumulate with time (which could be a safety liability) or get metabolized rapidly (which could cause the loss of biological activity).

Figure 10:
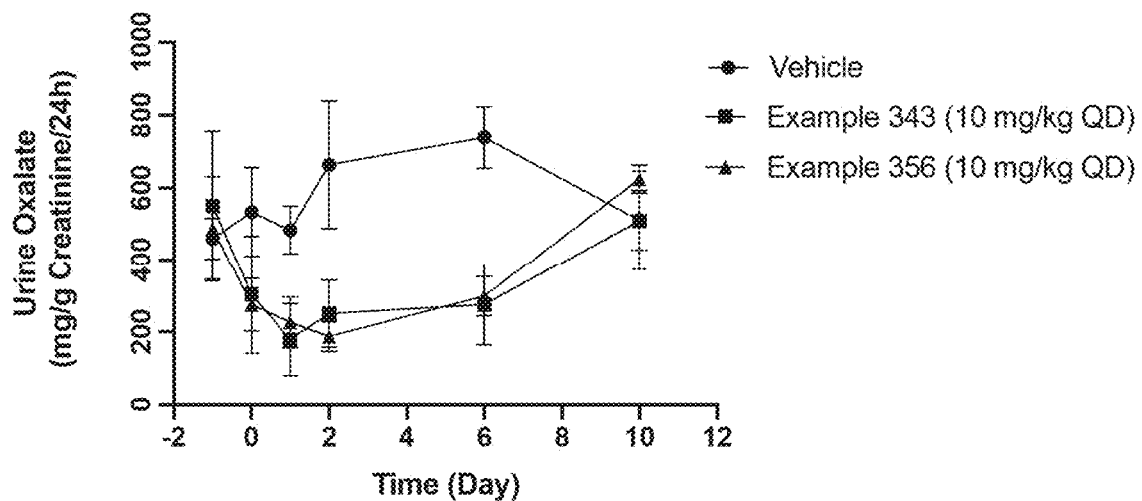
FIG. 10 shows urine oxalate concentrations indicated by mg/g creatinine over 24 hours. These concentrations were plotted against time in days for the vehicle. Compounds 343 and 356 were each orally dosed once daily at 10 mg/kg to Agxt−/− mice on study Days 0 to 6.
Figure 11:
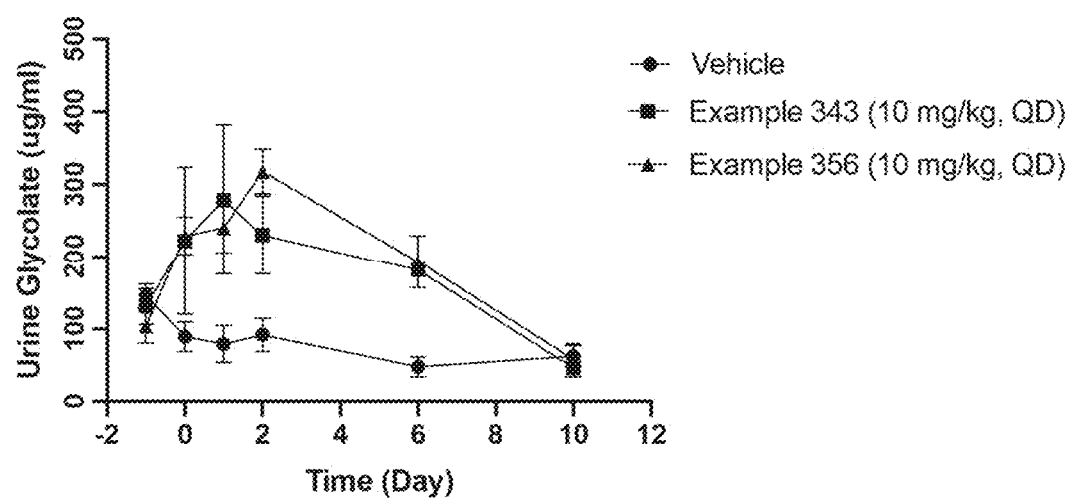
FIG. 11 shows urine glycolate concentrations (μg/mL) plotted against time in days for vehicle and compounds 343 and 356, each orally dosed once daily at 10 mg/kg to Agxt−/− mice on study Days 0 to 6.

The rapid, sustained, and reversible activity of the substituted alkynes was observed upon once-daily dosing in the Agxt−/− mouse model. FIG. 10 shows urine oxalate concentrations indicated by mg/g creatinine over 24 hours. These concentrations are plotted against time in days for vehicle and compounds 343 and 356, each orally dosed once daily at 10 mg/kg to Agxt−/− mice on study Days −1 to 6 and washed out for 4 days. FIG. 11 shows the urine glycolate concentrations (μg/mL) for these same mice.

The compounds described herein are effective in reducing urinary oxalate in this model of hyperoxaluria, essentially by the same magnitude as treatments that focus on selectively knocking out glycolate oxidase by oligonucleotides as described by Liebow et al., "An Investigational RNAi Therapeutic Targeting Glycolate Oxidase Reduces Oxalate Production in Models of Primary Hyperoxaluria." *J Am Soc Nephrol*, 28:494-503 (2017), and thus would be effective in treating diseases related to oxalate accumulation, for example hyperoxaluria.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:
1. A compound of Formula III,

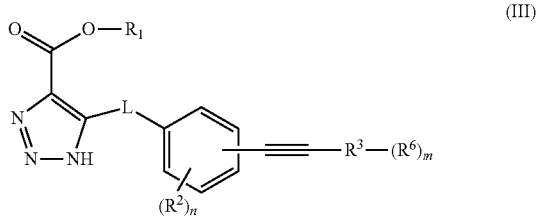

or a salt, polymorph, or tautomer thereof, wherein:
$R^1$ is chosen from hydrogen, $C_1$-$C_6$ alkyl, and $C_1$-$C_6$ cycloalkyl;
L is chosen from O, S, $CH_2$, NH, $NR^4$, S(O), $SO_2$, and $CR^4$=$CR^5$;
each $R^2$ is independently chosen from 5-10-membered heteroaryl, $C_1$-$C_6$ alkoxy, $C_1$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, $C_6$-$C_{10}$ aryl, cyano, and halogen;
n is 0, 1, or 2;
$R^3$ is chosen from 3-10-membered heterocycloalkyl, 5-10-membered heteroaryl, $C_1$-$C_6$ alkyl, $C_1$-$C_6$ sulfonyl, $C_3$-$C_6$ cycloalkyl, $C_3$-$C_6$ cycloalkylalkyl, $C_6$-$C_{10}$ aryl, and $C_6$-$C_{10}$ arylalkyl;
$R^4$ and $R^5$ are each independently chosen from hydrogen and $C_1$-$C_6$ alkyl, or $R^4$ and $R^5$, together with the atoms to which they are attached, form a cycloalkenyl; and
each $R^6$ is independently chosen from 4-6-membered heterocycloalkyl, 5-10-membered heteroaryl, amino, $C_1$-$C_6$ alkoxy, $C_1$-$C_6$ alkyl, $C_1$-$C_6$ alkylsulfonyl, $C_1$-$C_6$ haloalkyl, $C_3$-$C_6$ cycloalkyl, $C_3$-$C_6$ cycloalkylalkyl, carboxyl, cyano, halogen, hydroxyl, methyl-4-6-membered heterocycloalkyl, and phenyl; and
m is 0, 1, 2, or 3.

2. The compound of claim 1, wherein $R^3$ is chosen from methyl, propyl, cyclopropyl, cyclobutyl, cyclopentyl, tetrahydrofuranyl, cyclohexyl, tetrahydropyranyl, piperidinyl, dihydropyranyl, indazolyl, benzodioxolyl, phenyl, pyridinyl, pyrimidinyl, pyridazinyl, pyrazolyl, oxazolyl, thiazolyl, imidazolyl, triazolyl, benzoxazolyl, oxodihydropyridinyl, thiazolyl, tetrazolyl, cyclopropylmethyl, cyclobutylmethyl, cyclopentylmethyl, cyclohexylmethyl, benzyl, dioxaspirodecanyl, oxocyclohexyl, and bicyclo[1.1.1]pentyl, any of which is optionally substituted with 1, 2, or 3 $R^6$ groups.

3. The compound of claim 1, wherein $R^3$ is chosen from $C_1$-$C_6$ alkyl, $C_3$-$C_6$ cycloalkyl, and $C_3$-$C_6$ cycloalkylalkyl, any of which is optionally substituted with 1, 2, or 3 $R^6$ groups.

4. The compound of claim 1, wherein $R^3$ is chosen from propyl and cyclopropylmethyl.

5. The compound of claim 1, wherein $R^6$ is chosen from methyl, hydroxyl, amino, dimethylamino, propyl, cyclopropylmethyl, indazolyl, benzodioxolyl, cyclopropyl, tetrahydrofuranyl, cyclohexyl, tetrahydropyranyl, piperidinyl, methylpiperidinyl, phenyl, fluoro, chloro, methylsulfonyl, cyano, trifluoromethyl, methoxy, carboxyl, and fluoromethyl.

6. The compound of claim 5, wherein $R^6$ is chosen from chloro, methyl, cyano, fluoro, methylsulfonyl, methoxy, carboxyl, trifluoromethyl.

7. The compound of claim 1, wherein m is 0.

8. A compound of claim 1, having structural Formula V,

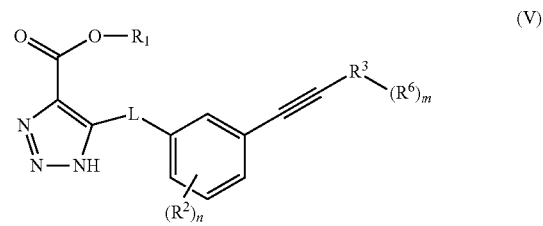

or a salt, polymorph, or tautomer thereof, wherein:
$R^1$ is chosen from hydrogen, $C_1$-$C_6$ alkyl, and $C_1$-$C_6$ cycloalkyl;
L is chosen from O and S;
each $R^2$ is independently chosen from 5-10-membered heteroaryl, $C_1$-$C_6$ alkoxy, $C_1$-$C_6$ alkyl, $C_1$-$C_6$ alkylsulfonyl, $C_1$-$C_6$ alkylthio, $C_1$-$C_6$ haloalkoxy, $C_1$-$C_6$ haloalkyl, $C_6$-$C_{10}$ aryl, cyano, and halogen;
n is 0, 1, or 2;
$R^3$ is chosen from $C_2$-$C_6$ alkyl, $C_3$-$C_6$ cycloalkyl, and $C_3$-$C_6$ cycloalkylalkyl;
and
each $R^6$ is $C_1$-$C_6$ alkoxy, $C_1$-$C_6$ alkyl, $C_1$-$C_6$ haloalkyl, $C_3$-$C_6$ cycloalkyl, cyano, halogen, and hydroxyl; and
m is 0, 1, 2, or 3.

9. The compound of claim 8, wherein $R^1$ is hydrogen.

10. The compound of claim 8, wherein n is 0.

11. The compound claim 8, wherein n is 0 or 1; and $R^6$, if present, is halogen.

12. The compound of claim 8, wherein $R^3$ is chosen from $C_2$-$C_6$ alkyl, $C_3$-$C_6$ cycloalkyl, and $C_3$-$C_6$ cycloalkylmethyl.

13. The compound of claim 8, wherein $R^3$ is chosen from ethyl, propyl, isopropyl, isobutyl, sec-butyl, Cert-butyl, cyclopropyl, cyclobutyl, cyclopentyl, cyclohexyl, bicyclo [1.1.1]pentyl, cyclopropylmethyl, cyclobutylmethyl, cyclopentylmethyl, cyclohexylmethyl, and bicyclo[1.1.1]pentylmethyl.

14. The compound of claim 8, wherein R³ is chosen from ethyl, propyl, isopropyl, isobutyl, sec-butyl, Cert-butyl, cyclopropyl, cyclobutyl, cyclopentyl, cyclohexyl, cyclopropylmethyl, cyclobutylmethyl, cyclopentylmethyl, and cyclohexylmethyl.

15. The compound of claim 8, wherein R³ is chosen from isobutyl and cyclopropylmethyl.

16. A compound of claim 1, having structural Formula VI,

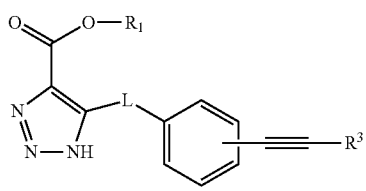

(VI)

or a salt, polymorph, or tautomer thereof, wherein:
R¹ is chosen from hydrogen, C₁-C₆ alkyl, and C₁-C₆ cycloalkyl;
L is chosen from O, S, CH₂, and NH; and
R³ is chosen from C₂-C₆ alkyl, C₃-C₆ cycloalkyl, and C₃-C₆ cycloalkylalkyl.

17. The compound of claim 16, wherein R¹ is chosen from methyl, ethyl, isopropyl, t-butyl, and hydrogen.

18. The compound of claim 17, wherein R¹ is hydrogen.

19. The compound of claim 16, wherein L is O or S.

20. The compound of claim 16, wherein R³ is chosen from isobutyl and cyclopropylmethyl.

21. A compound chosen from

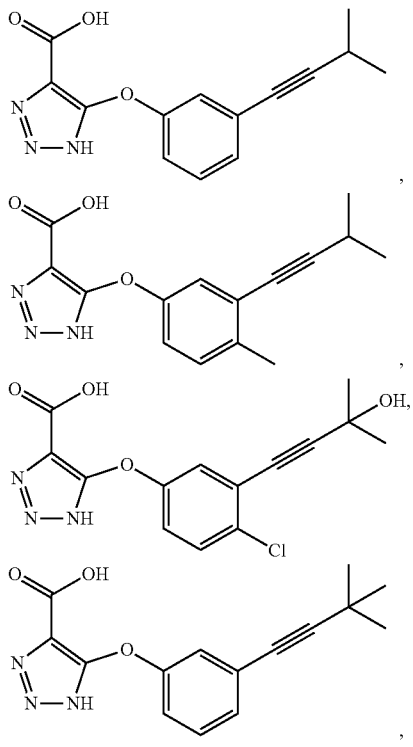

-continued

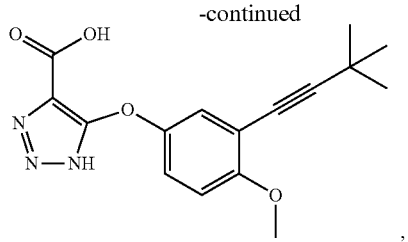

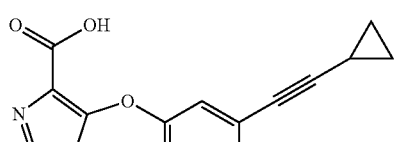

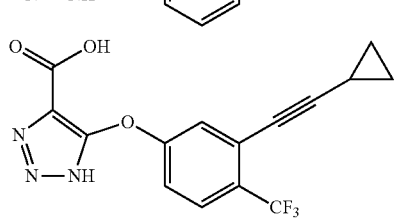

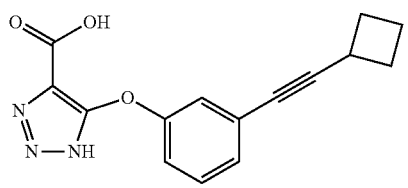

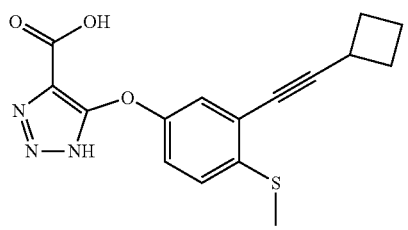

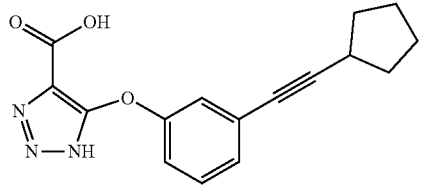

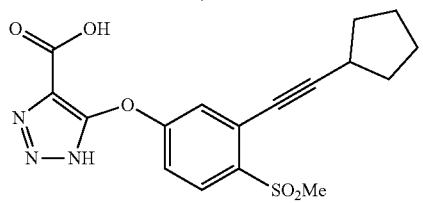

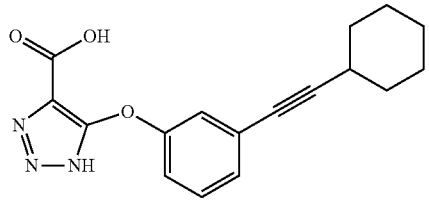

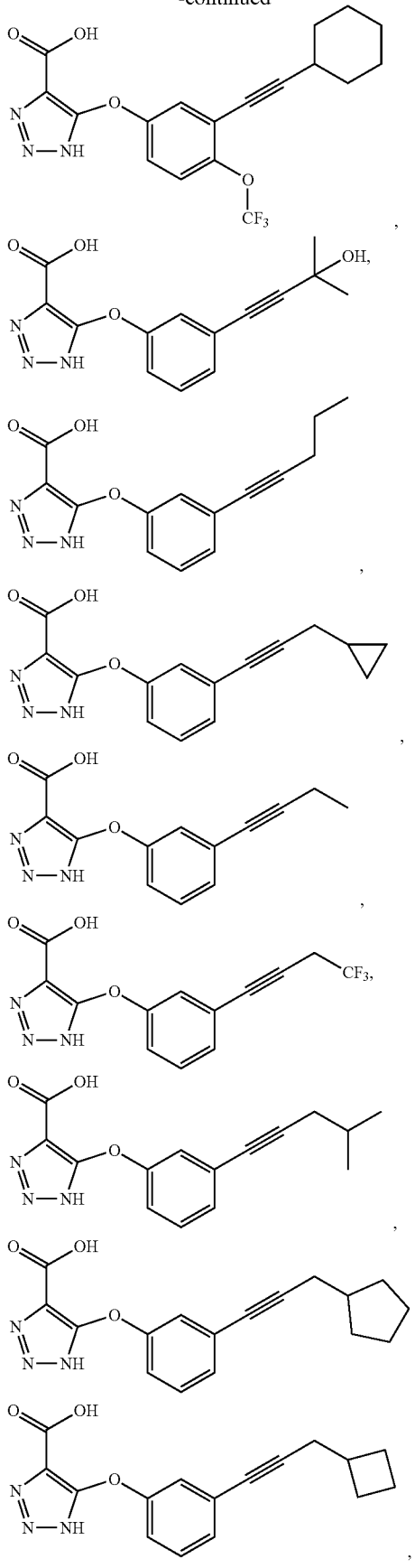
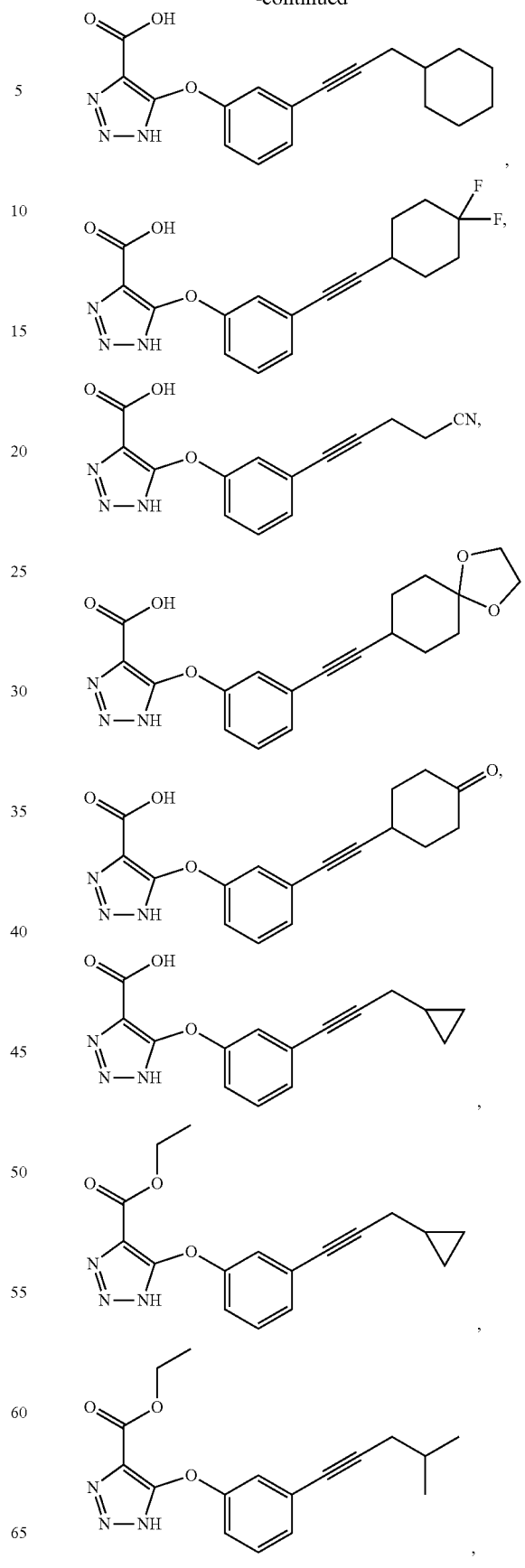

-continued
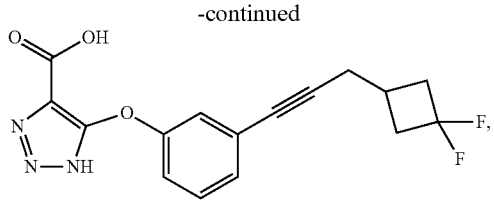
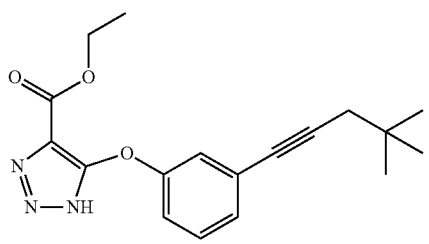
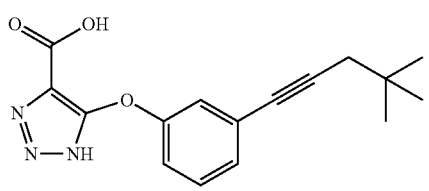
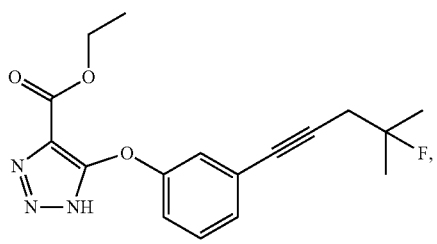
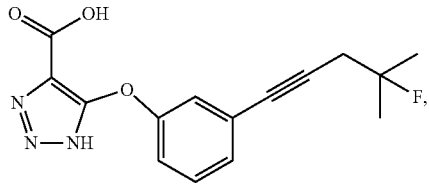
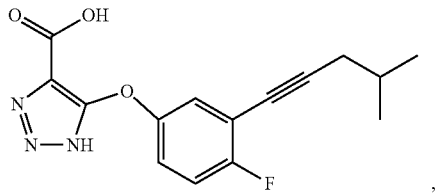
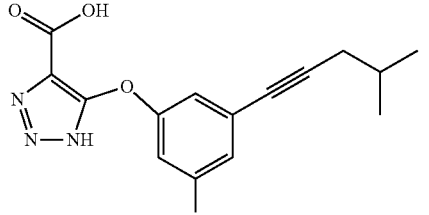
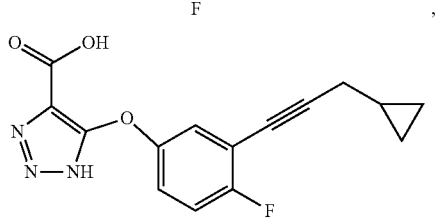
-continued
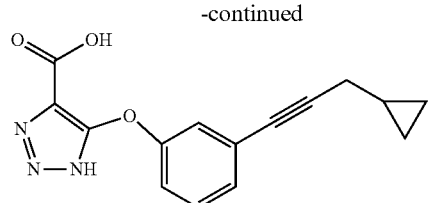
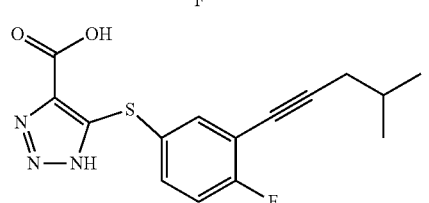
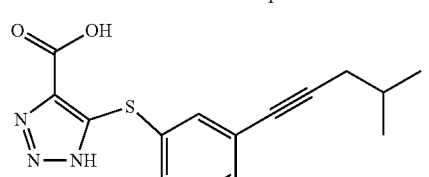
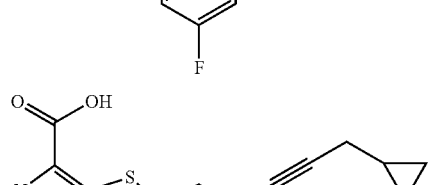
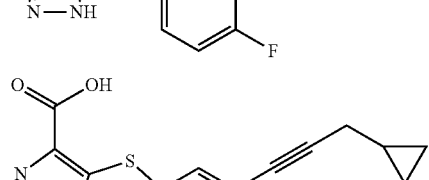
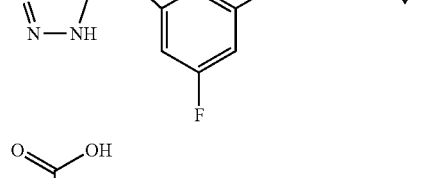
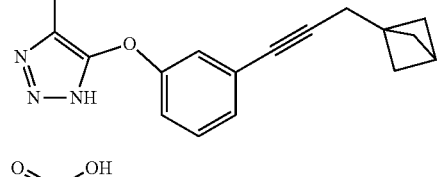
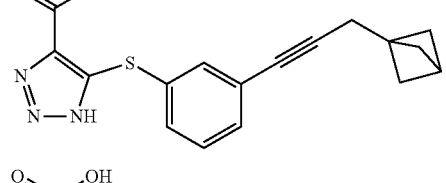
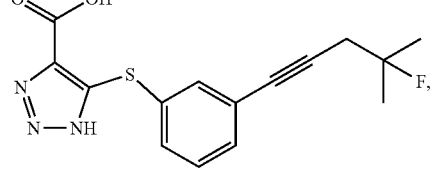

-continued

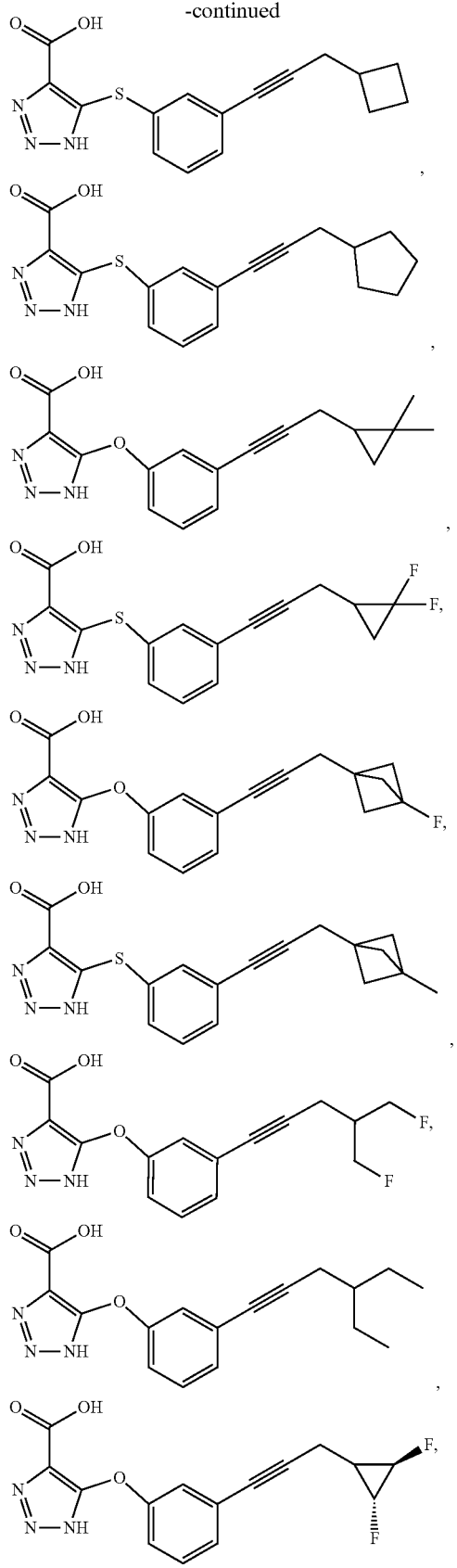

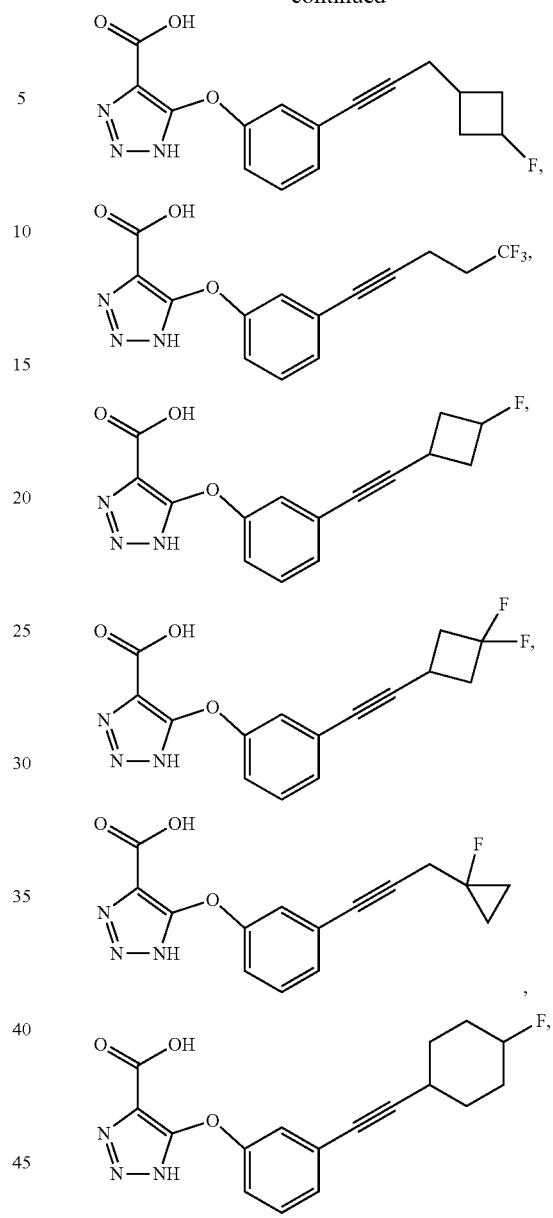

or a salt, polymorph, or tautomer thereof.

22. A pharmaceutical composition comprising a compound of claim 1, or a salt, polymorph, or tautomer thereof, together with a pharmaceutically acceptable carrier.

23. A pharmaceutical composition comprising a compound of claim 8, or a salt, polymorph, or tautomer thereof, together with a pharmaceutically acceptable carrier.

24. A pharmaceutical composition comprising a compound of claim 16, or a salt, polymorph, or tautomer thereof, together with a pharmaceutically acceptable carrier.

25. A pharmaceutical composition comprising a compound of claim 21, or a salt, polymorph, or tautomer thereof, together with a pharmaceutically acceptable carrier.

* * * * *